US011149086B2

(12) United States Patent
Van Hoorick et al.

(10) Patent No.: US 11,149,086 B2
(45) Date of Patent: Oct. 19, 2021

(54) KV1.3 BINDING IMMUNOGLOBULINS

(71) Applicant: Ablynx N.V., Zwijnaarde (BE)

(72) Inventors: Diane Van Hoorick, Laarne (BE); Erik Depla, Destelbergen (BE); Frank Kamiel Delphina Verdonck, Sint-Gillis-Waas (BE); Veerle Delanote, Sint-Kruis (BE); Daniel Janssen, Mortsel (BE); Francis Descamps, Roeselare (BE); Mark Edward Labadia, Ridgefield, CT (US); Ann Mikhail, Ridgefield, CT (US); Alisa K. Waterman, Ridgefield, CT (US)

(73) Assignee: Ablynx N.V., Ghent-Zwijnaarde (BE)

( * ) Notice: Subject to any disclaimer, the term of this patent is extended or adjusted under 35 U.S.C. 154(b) by 276 days.

(21) Appl. No.: 15/319,737

(22) PCT Filed: Jun. 18, 2015

(86) PCT No.: PCT/EP2015/063748
§ 371 (c)(1),
(2) Date: Dec. 16, 2016

(87) PCT Pub. No.: WO2015/193452
PCT Pub. Date: Dec. 23, 2015

(65) Prior Publication Data
US 2017/0137512 A1    May 18, 2017

Related U.S. Application Data

(60) Provisional application No. 62/133,624, filed on Mar. 16, 2015, provisional application No. 62/014,023, filed on Jun. 18, 2014.

(30) Foreign Application Priority Data

Oct. 21, 2014    (NL) ...................................... 2013661

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC ........ *C07K 16/28* (2013.01); *A61K 39/39541* (2013.01); *A61K 45/06* (2013.01); *A61K 2039/505* (2013.01); *C07K 2317/14* (2013.01); *C07K 2317/22* (2013.01); *C07K 2317/31* (2013.01); *C07K 2317/33* (2013.01); *C07K 2317/35* (2013.01); *C07K 2317/569* (2013.01); *C07K 2317/626* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

CN    102180950 A    9/2011

OTHER PUBLICATIONS

MacCallum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Skolnick and Fetrow. From genes to protein structure and function: novel applications of computational approaches in the genomic era. Trends in Biotechnology, 2000. vol. 18, pp. 34-39.*
Wu, Nie, Huse, and Watkins. Humanization of a murine monoclonal antibody by simultaneous optimization of framework and CDR residues. Journal of Molecular Biology, 1999. vol. 294, pp. 151-162.*
Bergeron et al., Scorpion toxins specific for potassium (K+) channels: a historical overview of peptide bioengineering. Toxins (Basel). Nov. 1, 2012;4(11):1082-119. doi: 10.3390/toxins4111082.
Berkut et al., Structural similarity between defense peptide from wheat and scorpion neurotoxin permits rational functional design. J Biol Chem. May 16, 2014;289(20):14331-40. doi: 10.1074/jbc.M113.530477.
Bittner et al., Targeting ion channels for the treatment of autoimmune neuroinflammation. Ther Adv Neurol Disord. Sep. 2013;6(5):322-36. doi:10.1177/1756285613487782.
Chi et al., Development of a sea anemone toxin as an immunomodulator for therapy of autoimmune diseases. Toxicon. Mar. 15, 2012;59(4):529-46. doi: 10.1016/j.toxicon.2011.07.016.
Duque et al., Expression of Kv1.3 potassium channels regulates density of cortical interneurons. Dev Neurobiol. Nov. 2013;73(11):841-55. doi: 10.1002/dneu.22105.
Hoshi et al., C-type inactivation of voltage-gated K+ channels: pore constriction or dilation? J Gen Physiol. Feb. 2013;141(2):151-60. doi:10.1085/jgp.201210888.
Kurata et al., A structural interpretation of voltage-gated potassium channel inactivation. Prog Biophys Mol Biol. Oct. 2006;92(2):185-208.
Morais-Cabral et al., Energetic optimization of ion conduction rate by the K+ selectivity filter. Nature. Nov. 1, 2001;414(6859):37-42.
Naylor et al., Generation of antibodies that are externally acting isoform-specific inhibitors of ion channels. Methods Mol Biol. 2013;998:245-56. doi: 10.1007/978-1-62703-351-0_19.
Takacs et al., A designer ligand specific for Kv1.3 channels from a scorpion neurotoxin-based library. Proc Natl Acad Sci U S A. Dec. 29, 2009;106(52):22211-6. doi:10.1073/pnas.0910123106.

(Continued)

*Primary Examiner* — Michael D Pak
(74) *Attorney, Agent, or Firm* — Wolf, Greenfield & Sacks, P.C.

(57) ABSTRACT

The present invention relates to immunoglobulins that specifically bind Kv1.3 and more in particular to polypeptides, nucleic acids encoding such polypeptides; to methods for preparing such polypeptides; to compositions and in particular to pharmaceutical compositions that comprise such polypeptides, for prophylactic, therapeutic or diagnostic purposes. In particular, the immunoglobulins of the present invention inhibit the activity of Kv1.3.

Figure 1:
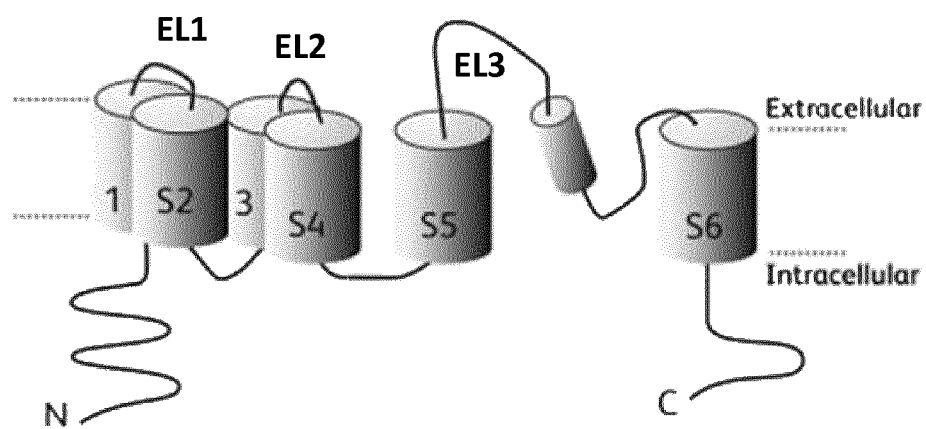

11 Claims, 49 Drawing Sheets
Specification includes a Sequence Listing.

(56) References Cited

OTHER PUBLICATIONS

Yang et al., Specific Kv1.3 blockade modulates key cholesterol-metabolism-associated molecules in human macrophages exposed to ox-LDL. J Lipid Res. Jan. 2013;54(1):34-43. doi: 10.1194/jlr.M023846.

Yang et al., The antibody targeting the E314 peptide of human Kv1.3 pore region serves as a novel, potent and specific channel blocker. PLoS One. 2012;7(4):e36379. doi: 10.1371/journal.pone.0036379.

Yellen, The moving parts of voltage-gated ion channels. Q Rev Biophys. Aug. 1998;31(3):239-95.

Yu et al., Overview of molecular relationships in the voltage-gated ion channel superfamily. Pharmacol Rev. Dec. 2005;57(4):387-95.

Zhu et al., Allowed N-glycosylation sites on the Kv1.2 potassium channel S1-S2 linker: implications for linker secondary structure and the glycosylation effect on channel function. Biochem J. Nov. 1, 2003;375(Pt 3):769-75.

Zhu et al., Molecular diversity and functional evolution of scorpion potassium channel toxins. Mol Cell Proteomics. Feb. 2011;10(2):M110.002832. doi: 10.1074/mcp.M110.002832.

PCT/EP2015/063748, Aug. 28, 2015, International Search Report and Written Opinion.

PCT/EP2015/063748, Dec. 29, 2016, International Preliminary Report on Patentability.

Bakhtiar et al., Observation of noncovalent complexes between margatoxin and the Kv1.3 peptide ligands: A model investigation using ion-spray mass spectrometry. J Am Soc Mass Spectrom. 1996;7(10):1075-1080. doi: 10.1016/1044-0305(96)00108-0.

Feng et al., Kv Channel S1-S2 Linker Working as a Binding Site of Human β-Defensin 2 for Channel Activation Modulation. J Biol Chem. 2015;290(25): 15487-15495. doi:10.1074/jbc.M115.639500.

Grgic et al., Blockade of T-lymphocyte KCa3.1 and Kv1.3 channels as novel immunosuppression strategy to prevent kidney allograft rejection. Transplant Proc. 2009;41(6):2601-2606. doi:10.1016/j.transproceed.2009.06.025.

Hyodo et al., Voltage-gated potassium channel Kv1.3 blocker as a potential treatment for rat anti-glomerular basement membrane glomerulonephritis. Am J Physiol Renal Physiol. 2010;299(6):F1258-F1269. doi:10.1152/ajprenal.00374.2010.

Ishii et al., Sequestosome1/p62: a regulator of redox-sensitive voltage-activated potassium channels, arterial remodeling, inflammation, and neurite outgrowth. Free Radic Biol Med. 2013;65:102-116. doi:10.1016/j.freeradbiomed.2013.06.019.

Kazama et al., Lymphocyte Kv1.3—channels in the pathogenesis of chronic obstructive pulmonary disease: novel therapeutic implications of targeting the channels by commonly used drugs. Allergy Asthma Clin Immunol. 2016;12:60. 6 pages.

Kazama et al., Overexpression of Delayed Rectifier K+ Channels Promotes in situ Proliferation of Leukocytes in Rat Kidneys with Advanced Chronic Renal Failure. Int J Nephrol. 2012; 2012:581581. EPubMay 31, 2012. doi: 10.1155/2012/581581. 8 pages.

Kineta, Dalazatide, first-in-class Kv1.3 channel blocker, an immunomodulators journey from sea to clinic. Aurora Biomed Ion Channels Retreat 2015 Shawn Iadonato. Retrieved from https://www.aurorabiomed.com/wp-content/uploads/2015/07/Dalazatide-ICR-2015.pdf on Feb. 26, 2020. 25 pages.

Koch Hansen et al., Expression of T-cell KV 1.3 potassium channel correlates with pro-inflammatory cytokines and disease activity in ulcerative colitis☆. J Crohns Colitis. Nov. 1, 2014; 8(11): 1378-1391. EPub May 3, 2014. doi: 10.1016/j.crohns.2014.04.003. Author Manuscript.

Koshy et al., Blocking KV1.3 channels inhibits Th2 lymphocyte function and treats a rat model of asthma. J Biol Chem. 2014;289(18):12623-12632. doi:10.1074/jbc.M113.517037.

Kumar Upadhyay et al., Selective Kv1.3 channel blocker as therapeutic for obesity and insulin resistance. PNAS. Jun. 11, 2013; 110(24):E2239-48. https://doi.org/10.1073/pnas.1221206110.

Kundu-Raychaudhuri et al., Kv1.3 in psoriatic disease: PAP-1, a small molecule inhibitor of Kv1.3 is effective in the SCID mouse psoriasis—xenograft model. J Autoimmun. 2014;55:63-72. doi:10.1016/j.jaut.2014.07.003.

Lam et al., The Lymphocyte Potassium Channels Kv1.3 and KCa3.1 as Targets for Immunosuppression. Drug Dev Res. 2011;72(7):573-584. doi:10.1002/ddr.20467.

Lintermans et al., T cells in vascular inflammatory diseases. Front Immunol. 2014;5:504. Published Oct. 14, 2014. doi:10.3389/fimmu.2014.00504.

Poulopoulou et al., Glutamate levels and activity of the T cell voltage-gated potassium Kv1.3 channel in patients with systemic lupus erythematosus. Arthritis Rheum. 2008;58(5): 1445-1450. doi:10.1002/art.23446.

Rus et al., The voltage-gated potassium channel Kv1.3 is highly expressed on inflammatory infiltrates in multiple sclerosis brain. Proc Natl Acad Sci U S A. 2005; 102(31):11094-11099. doi:10.1073/pnas.0501770102.

Schilling et al., Amyloid-β-induced reactive oxygen species production and priming are differentially regulated by ion channels in microglia. J Cell Physiol. 2011;226(12):3295-3302. doi:10.1002/jcp.22675.

Tarcha et al., Durable pharmacological responses from the peptide ShK-186, a specific Kv1.3 channel inhibitor that suppresses T cell mediators of autoimmune disease. J Pharmacol Exp Ther. 2012;342(3):642-653. doi:10.1124/jpet.112.191890.

Valverde et al., Selective blockade of voltage-gated potassium channels reduces inflammatory bone resorption in experimental periodontal disease. J Bone Miner Res. 2004;19(1):155-164. doi:10.1359/JBMR.0301213.

Varga et al., Vm24, a natural immunosuppressive peptide, potently and selectively blocks Kv1.3 potassium channels of human T cells. Mol Pharmacol. 2012;82(3):372-382. doi:10.1124/mol.112.078006.

* cited by examiner

A

B

A

B

A

B

C

A

B

C

A

B

C

A

B

SEQUENCE LISTING

<160> NUMBER OF SEQ ID NOS: 559

<210> SEQ ID NO 1
<211> LENGTH: 116
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Ala Gly Gly

```
1               5                   10                  15
Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
            35                  40                  45

Ala Arg Ile Arg Ser Gly Gly Ser Thr Asn Tyr Ala Asp Ser Val Lys
            50                  55                  60

Gly Arg Phe Thr Ile Ser Arg Asp Lys Ala Thr Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Ala Tyr Glu Tyr Trp Gly Gln Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
            35                  40                  45

Ala Arg Ile Arg Ser Gly Gly Ser Thr Asn Tyr Ala Asp Ser Val Lys
            50                  55                  60

Gly Arg Phe Thr Ile Ser Arg Asp Lys Ala Thr Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Ala Tyr Glu Tyr Trp Gly Gln Gly Thr Gln Val
            100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Ala Asp Thr Val Lys
            50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ser
                 85                  90                  95

Ser Trp Arg Thr Gly Phe Tyr Glu Tyr Trp Gly Gln Gly Thr Gln Val
                100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Ala Gly Gly
 1               5                  10                  15

Ser Leu Arg Leu Ser Cys Ser Ala Ser Gly Leu Leu Phe Ser Val Asn
                 20                  25                  30

Ser Ala Gly Trp Tyr Arg Gln Ala Pro Gly Lys Gln Arg Asp Phe Val
             35                  40                  45

Ala Arg Ile Arg Ser Gly Gly Ser Thr Asn Tyr Ala Asp Ser Val Lys
 50                  55                  60

Gly Arg Phe Thr Ile Ser Arg Asp Lys Ala Thr Asn Thr Val His Leu
 65                  70                  75                  80

Gln Met Asn Ser Leu Lys Pro Glu Asp Thr Ala Val Tyr Tyr Cys Gly
                 85                  90                  95

Ser Trp Arg Thr Gly Ala Tyr Glu Tyr Trp Gly Gln Gly Thr Leu Val
                100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Ala Gly Gly
 1               5                  10                  15

Ser Leu Arg Leu Ser Cys Ser Ala Ser Gly Leu Leu Phe Ser Val Asn
                 20                  25                  30

Ser Ala Gly Trp Tyr Arg Gln Ala Pro Gly Lys Gln Arg Asp Phe Val
             35                  40                  45

Ala Arg Ile Arg Ser Gly Gly Ser Thr Asn Tyr Ala Asp Ser Val Lys
 50                  55                  60

Gly Arg Phe Thr Ile Ser Arg Asp Lys Ala Thr Asn Thr Leu Tyr Leu
 65                  70                  75                  80

Gln Met Asn Asn Leu Lys Pro Glu Asp Thr Ala Val Tyr Tyr Cys Ser
                 85                  90                  95

Ser Trp Arg Thr Glu Ala Tyr Glu Tyr Trp Gly Arg Gly Thr Leu Val
                100                 105                 110

Thr Val Ser Ser
        115
```

<210> SEQ ID NO 6
<211> LENGTH: 116
<212> TYPE: PRT
<213> ORGANISM: Artificial Sequence
<220> FEATURE:
<223> OTHER INFORMATION: Nanobody sequence

<400> SEQUENCE: 6

```
Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Ser Gly Gly Ser Thr Asn Tyr Ala Asp Ser Val Lys
    50                  55                  60

Gly Arg Phe Thr Ile Ser Arg Asp Lys Ala Thr Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Ala Tyr Glu His Trp Gly Gln Gly Thr Leu Val
            100                 105                 110

Thr Val Ser Ser
        115
```

<210> SEQ ID NO 7
<211> LENGTH: 116
<212> TYPE: PRT
<213> ORGANISM: Artificial Sequence
<220> FEATURE:
<223> OTHER INFORMATION: Nanobody sequence

<400> SEQUENCE: 7

```
Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Ser Gly Gly Ser Thr Asn Tyr Ala Asp Ser Val Lys
    50                  55                  60

Gly Arg Phe Thr Ile Ser Arg Asp Lys Ala Thr Asn Thr Leu Tyr Leu
65                  70                  75                  80

Gln Val Asn Asn Leu Lys Pro Glu Asp Thr Ala Val Tyr Tyr Cys Ser
                85                  90                  95

Ser Trp Arg Thr Glu Ala Tyr Glu Tyr Trp Gly Arg Gly Thr Leu Val
            100                 105                 110

Thr Val Ser Ser
        115
```

<210> SEQ ID NO 8
<211> LENGTH: 116
<212> TYPE: PRT
<213> ORGANISM: Artificial Sequence
<220> FEATURE:
<223> OTHER INFORMATION: Nanobody sequence

<400> SEQUENCE: 8

-continued

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Ser Ser Gly Ser Thr Asn Tyr Ala Asp Ser Val Lys
    50                  55                  60

Gly Arg Phe Thr Ile Ser Arg Asp Lys Ala Thr Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Ala Tyr Glu Tyr Trp Gly Gln Gly Ala Gln Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Ser Gly Gly Ser Thr Asn Tyr Ala Asp Ser Val Lys
    50                  55                  60

Gly Arg Phe Thr Ile Ser Arg Asp Lys Ala Thr Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Ala Tyr Glu Tyr Trp Gly Gln Gly Thr Gln Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Leu Val
        35                  40                  45

Ala Arg Ile Arg Ser Gly Gly Ser Thr Asn Tyr Ala Asp Ser Val Lys
    50                  55                  60

Gly Arg Phe Thr Ile Ser Arg Asp Lys Ala Thr Asn Thr Leu Tyr Leu
65                  70                  75                  80

Gln Met Asn Asn Leu Lys Pro Glu Asp Thr Ala Val Tyr Tyr Cys Ser
                85                  90                  95

Ser Trp Arg Thr Glu Ala Tyr Glu Tyr Trp Gly Arg Gly Thr Gln Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Ala Gly Gly
1               5                   10                  15

Ser Leu Glu Leu Ser Cys Ser Ala Ser Gly Leu Leu Phe Ser Arg Asn
                20                  25                  30

Ser Val Gly Trp Tyr Arg Gln Ala Pro Gly Lys Lys Arg Asp Phe Val
            35                  40                  45

Ala Arg Ile Arg Ser Gly Gly Ser Thr Asn Tyr Ala Asp Ser Val Lys
        50                  55                  60

Gly Arg Phe Ile Ile Ser Arg Asp Asn Ala Lys Asn Thr Leu Tyr Leu
65                  70                  75                  80

Gln Met Asn Ala Leu Lys Pro Glu Asp Thr Gly Val Tyr Tyr Cys Ser
                85                  90                  95

Ser Trp Arg Thr Gly Ala Tyr Glu Tyr Trp Gly Gln Gly Thr Leu Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Ala Asn
                20                  25                  30

Ser Ala Gly Trp Tyr Arg Gln Ala Pro Gly Lys Gln Arg Asp Phe Val
            35                  40                  45

Ala Arg Ile Arg Ser Gly Gly Ser Thr Asn Tyr Ala Asp Ser Val Lys
        50                  55                  60

Gly Arg Phe Thr Val Ser Arg Asp Asn Ala Lys Asn Thr Met Tyr Leu
65                  70                  75                  80

Gln Met Asn Gly Leu Lys Pro Glu Asp Thr Ala Val Tyr Tyr Cys Ser
                85                  90                  95

Ser Trp Arg Thr Gly Ala Tyr Glu Tyr Trp Gly Gln Gly Thr Gln Val
            100                 105                 110

Thr Val Ser Ser

<210> SEQ ID NO 13
<211> LENGTH: 116
<212> TYPE: PRT
<213> ORGANISM: Artificial Sequence
<220> FEATURE:
<223> OTHER INFORMATION: Nanobody sequence

<400> SEQUENCE: 13

```
Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser
            115
```

<210> SEQ ID NO 14
<211> LENGTH: 116
<212> TYPE: PRT
<213> ORGANISM: Artificial Sequence
<220> FEATURE:
<223> OTHER INFORMATION: Nanobody sequence

<400> SEQUENCE: 14

```
Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Arg Ala Pro Gly Lys Gln Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Thr Ser Arg Asp Asn Ala Lys Asn Thr Ile Tyr Leu
65                  70                  75                  80

Gln Met Asn Ser Leu Lys Pro Glu Asp Thr Ala Val Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
            115
```

<210> SEQ ID NO 15
<211> LENGTH: 116
<212> TYPE: PRT
<213> ORGANISM: Artificial Sequence
<220> FEATURE:
<223> OTHER INFORMATION: Nanobody sequence

<400> SEQUENCE: 15

```
Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Val Gly Trp Tyr Arg Arg Ala Pro Gly Lys Gln Arg Glu Phe Val
            35                  40                  45

Ala Arg Leu Arg Thr Thr Gly Ser Thr Asn Tyr Ala Gln Ser Val Lys
        50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Ser
                85                  90                  95

Ala Trp Arg Ile Glu Ala Tyr Glu Tyr Trp Gly Gln Gly Thr Gln Val
            100                 105                 110

Thr Val Ser Ser
        115
```

<210> SEQ ID NO 16
<211> LENGTH: 116
<212> TYPE: PRT
<213> ORGANISM: Artificial Sequence
<220> FEATURE:
<223> OTHER INFORMATION: Nanobody sequence

<400> SEQUENCE: 16

```
Glu Val Gln Leu Val Glu Ser Gly Gly Gly Leu Val Gln Pro Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Ala Asp Ser Val Lys
        50                  55                  60

Gly Arg Phe Thr Thr Ser Arg Asp Asn Ala Lys Asn Thr Ile Tyr Leu
65                  70                  75                  80

Gln Met Asn Ser Leu Lys Pro Glu Asp Thr Ala Val Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115
```

<210> SEQ ID NO 17
<211> LENGTH: 116
<212> TYPE: PRT
<213> ORGANISM: Artificial Sequence
<220> FEATURE:
<223> OTHER INFORMATION: Nanobody sequence

<400> SEQUENCE: 17

```
Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Gly Asp Ser Val Lys
```

```
                50                  55                  60
Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Lys Tyr Phe Cys Ser
                85                  90                  95

Ser Trp Arg Glu Gly Phe Tyr Glu Tyr Trp Gly Gln Gly Thr Leu Val
                100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
                35                  40                  45

Ala Arg Ile Arg Met Gly Gly Ser Ile Asn Tyr Ala Asp Ser Val Lys
            50                  55                  60

Gly Arg Phe Thr Thr Ser Arg Asp Asn Ala Lys Asn Thr Ile Tyr Leu
65                  70                  75                  80

Gln Met Asn Ser Leu Lys Pro Glu Asp Thr Ala Val Tyr Tyr Cys Ser
                85                  90                  95

Ser Trp Arg Glu Gly Phe Tyr Glu Tyr Trp Gly Gln Gly Thr Gln Val
                100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Val Glu Ser Ala Gly Gly Leu Val Gln Ala Gly Gly
1               5                   10                  15

Ser Pro Gly Leu Ser Ser Ser Asp Ser Gly Leu Leu Phe Ser Arg His
                20                  25                  30

Ser Ala Gly Trp Tyr Arg Pro Ala Pro Gly Lys Arg Arg Glu Phe Val
                35                  40                  45

Ala Arg Ile Arg Met Gly Gly Ser Ile Asn Tyr Ala Asp Ser Val Lys
            50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Gln Val
                100                 105                 110
```

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Leu Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Leu Met Asn Asp Leu Asn Arg Glu Tyr Thr Ala Val Tyr Phe Cys Ser
                85                  90                  95

Gly Trp Arg Glu Gly Phe Phe Glu Tyr Trp Gly Gln Gly Thr Gln Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Nanobody sequence

<400> SEQUENCE: 21

Glu Val Gln Leu Val Glu Ser Gly Gly Gly Leu Val Gln Ala Gly Gly
1               5                   10                  15

Ala Leu Gly Leu Pro Cys Ser Ala Ser Gly Leu Leu Phe Ile Arg Asn
            20                  25                  30

Ser Ala Ser Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Ile Asp Leu Lys Pro Glu Asp Thr Thr Val Tyr Cys Cys Ser
                85                  90                  95

Gly Trp Arg Glu Gly Phe Tyr Glu Tyr Trp Gly Gln Gly Thr Gln Val
            100                 105                 110

Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: Nanobody sequence

```
<400> SEQUENCE: 22

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Thr Ser Arg Asp Asn Ala Lys Asn Thr Ile Tyr Leu
65                  70                  75                  80

Gln Met Asn Ser Leu Lys Pro Glu Asp Thr Ala Val Tyr Tyr Cys Ser
                85                  90                  95

Ser Trp Arg Glu Gly Phe Tyr Glu Tyr Trp Gly Gln Val Thr Gln Val
            100                 105                 110

Thr Val Ser Ser
            115

<210> SEQ ID NO 23
<211> LENGTH: 116
<212> TYPE: PRT
<213> ORGANISM: Artificial Sequence
<220> FEATURE:
<223> OTHER INFORMATION: Nanobody sequence

<400> SEQUENCE: 23

Glu Val Gln Leu Val Glu Ser Gly Gly Gly Leu Ala Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Arg Tyr Arg Gln Ala Pro Gly Lys Arg Pro Glu Phe Phe
        35                  40                  45

Ala Arg Val Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Ser Gly Gln Gly Thr Gln Val
            100                 105                 110

Thr Val Ser Ser
            115

<210> SEQ ID NO 24
<211> LENGTH: 116
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Phe Val Gln Ala Gly Gly
1               5                   10                  15

Ser Leu Gly His Ser Cys Ser Ala Ser Gly Leu Leu Ser Ser Cys Asn
            20                  25                  30

Thr Ala Gly Trp Tyr Arg Gln Ala Pro Gly Lys Arg Arg Glu Phe Val
        35                  40                  45
```

```
Ala Arg Ile Arg Met Val Gly Ser Ile Asn Tyr Ala Asp Ser Val Lys
 50                  55                  60

Gly Arg Phe Thr Val Ser Arg Asp Asn Ala Lys Asn Met Met Tyr Leu
 65                  70                  75                  80

Gln Met Asn Asp Leu Lys Pro Glu Asp Thr Ala Val Tyr Phe Cys Ser
                 85                  90                  95

Gly Trp Arg Glu Gly Phe Tyr Gly Tyr Trp Gly Gln Gly Thr Gln Val
                100                 105                 110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Leu Val Gln Ala Gly Gly
 1               5                  10                  15

Ser Leu Gly Ala Ser Arg Ser Ala Ser Gly Leu Pro Leu Ser Arg Asn
                 20                  25                  30

Ser Ala Gly Trp Tyr Arg Gln Gly Pro Gly Lys Arg Arg Glu Phe Val
                 35                  40                  45

Ala Arg Ile Arg Met Gly Gly Ser Ile Asn Tyr Ala Asp Ser Val Lys
 50                  55                  60

Gly Arg Phe Thr Val Ser Gly Asp Asn Ala Lys Asn Met Met Tyr Leu
 65                  70                  75                  80

Gln Met Asn Asp Leu Lys Pro Glu Asp Thr Ala Gly Tyr Phe Cys Ser
                 85                  90                  95

Gly Trp Arg Glu Gly Phe Tyr Glu Tyr Trp Gly Gln Gly Thr Gln Val
                100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Nanobody sequence

<400> SEQUENCE: 26

Glu Val Gln Leu Val Glu Ser Gly Gly Gly Leu Val Gln Ala Gly Gly
 1               5                  10                  15

Ser Leu Gly Leu Ser Cys Ser Ala Pro Gly Leu Leu Phe Ser Arg Asn
                 20                  25                  30

Ser Ala Gly Trp Cys Arg Gln Ala Pro Gly Lys Arg Arg Glu Phe Val
                 35                  40                  45

Ala Arg Thr Arg Met Gly Gly Ser Ile Asn Tyr Ala Asp Ser Val Lys
 50                  55                  60

Gly Arg Phe Thr Val Ser Arg Asp Asn Ala Lys Asn Met Met Tyr Leu
 65                  70                  75                  80

Gln Met Asn Gly Leu Lys Pro Glu Asp Thr Ala Val Cys Leu Cys Ser
                 85                  90                  95

Gly Trp Arg Glu Gly Phe Tyr Glu Tyr Trp Arg Gln Gly Thr Gln Val
                100                 105                 110
```

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Nanobody sequence

<400> SEQUENCE: 27

Glu Val Gln Leu Val Glu Ser Gly Gly Cys Leu Val Gln Ala Gly Gly
1               5                   10                  15

Ser Leu Gly Leu Ser Cys Ser Ala Ser Leu Leu Phe Phe Ser Arg Asn
            20                  25                  30

Ser Ala Arg Trp Tyr Arg Gln Ala Pro Val Lys Arg Arg Glu Phe Val
        35                  40                  45

Gly Arg Ile Arg Met Gly Gly Ser Ile Asn Tyr Ala Asp Ser Gly Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Gln Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Nanobody sequence

<400> SEQUENCE: 28

Glu Val Gln Leu Val Glu Ser Gly Gly Gly Leu Val Gln Ala Gly Gly
1               5                   10                  15

Ser Leu Gly Leu Ala Cys Ser Ala Ser Gly Leu Leu Ile Ser Arg Asn
            20                  25                  30

Ser Ala Gly Trp Tyr Arg His Ala Pro Gly Lys Gln Arg Ala Phe Val
        35                  40                  45

Ala Arg Val Arg Met Gly Gly Ser Ile Asn Tyr Gly Asp Ala Val Lys
    50                  55                  60

Gly Arg Phe Thr Ala Ser Arg Asp Ile Ala Lys Asn Thr Met Tyr Leu
65                  70                  75                  80

Gln Met Asn Asp Leu Lys Pro Glu Asp Thr Ala Ile Tyr Phe Cys Ser
                85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 29
<211> LENGTH: 116
<212> TYPE: PRT
<213> ORGANISM: Artificial Sequence
<220> FEATURE:
<223> OTHER INFORMATION: Nanobody sequence

<400> SEQUENCE: 29

Glu Val Gln Leu Val Glu Ser Gly Gly Gly Leu Val Gln Ala Gly Gly
1               5                   10                  15

Ala Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Lys Arg Asp Phe Val
        35                  40                  45

Ala Arg Ile Arg Met Gly Gly Ser Ile Asn Tyr Gly Ser Val Lys
50                  55                  60

Gly Arg Phe Thr Val Ser Arg Asp Ile Ala Lys Asn Thr Met Tyr Pro
65                  70                  75                  80

Gln Met Asn Asp Leu Lys Pro Glu Asp Ala Ala Lys Tyr Phe Cys Ser
                85                  90                  95

Ser Trp Arg Lys Gly Phe Tyr Glu Tyr Trp Gly Gln Gly Thr Gln Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: Nanobody sequence

<400> SEQUENCE: 30

Glu Val Gln Leu Val Glu Ser Gly Gly Gly Ser Ala Gln Pro Gly Glu
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Gly Asp Ser Val Lys
50                  55                  60

Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Lys Tyr Phe Cys Ser
                85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Nanobody sequence

<400> SEQUENCE: 31

Glu Val Gln Leu Val Glu Ser Gly Gly Gly Leu Val Gln Ala Gly Gly
1               5                   10                  15

Ala Leu Gly Phe Thr Cys Ser Asp Ser Arg Leu Leu Phe Ser Arg Asn
            20                  25                  30

Ser Ala Gly Trp Tyr Arg Gln Ala Ala Gly Lys Gln Arg Glu Phe Val
        35                  40                  45

```
Ala Arg Ile Arg Met Gly Gly Ser Ile Asn Tyr Gly Asp Ser Val Lys
        50                  55                  60

Gly Arg Phe Thr Val Ser Arg Asp Ile Ala Lys Asn Thr Met Tyr Leu
 65                  70                  75                  80

Arg Met Asn Asp Leu Lys Pro Glu Asp Thr Ala Ile Tyr Phe Cys Ser
                 85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Nanobody sequence

<400> SEQUENCE: 32

Glu Val Gln Leu Val Glu Ser Gly Gly Ala Leu Val Gln Ala Gly Gly
 1                   5                  10                  15

Ser Leu Gly Leu Pro Cys Ser Ala Pro Gly Leu Leu Phe Ser Arg Asn
                 20                  25                  30

Ser Ala Gly Trp Tyr Arg Gln Ala Pro Gly Lys Gln Arg Glu Phe Val
            35                  40                  45

Ala Gly Val Arg Met Gly Gly Ser Ile Asn Tyr Gly Gly Ser Val Lys
        50                  55                  60

Gly Arg Phe Thr Val Ser Arg Asp Ile Ala Lys Asn Thr Met Tyr Leu
 65                  70                  75                  80

Gln Met Asn Asp Leu Lys Pro Glu Asp Thr Ala Val Tyr Phe Cys Ser
                 85                  90                  95

Ser Trp Arg Gly Gly Phe Tyr Glu Tyr Trp Gly Gln Gly Thr Gln Val
            100                 105                 110

Thr Val Ser Ser
        115

<210> SEQ ID NO 33
<211> LENGTH: 116
<212> TYPE: PRT
<213> ORGANISM: Artificial Sequence
<220> FEATURE:
<223> OTHER INFORMATION: Nanobody sequence

<400> SEQUENCE: 33

Glu Val Gln Leu Val Glu Ser Gly Gly Phe Asp Gln Ala Gly Gly
 1                   5                  10                  15

Ser Leu Gly Leu Pro Cys Ser Ala Pro Gly Leu Leu Phe Ser Arg Asn
                 20                  25                  30

Arg Val Gly Trp Tyr Arg Gln Ala Pro Gly Lys Gln Arg Asp Phe Val
            35                  40                  45

Ala Arg Ile Arg Met Gly Gly Ser Thr Asn Tyr Ala Asp Ser Val Lys
        50                  55                  60

Gly Arg Phe Thr Ile Ser Arg Asp Asn Ala Lys Asn Met Val Tyr Leu
 65                  70                  75                  80

Gln Met Asn Ser Leu Lys Pro Glu Asp Thr Ala Val Tyr Tyr Cys Ser
                 85                  90                  95

Ser Trp Arg Thr Gly Phe Tyr Glu Tyr Trp Gly Gln Gly Thr Gln Val
```

Thr Val Ser Ser
        115

<210> SEQ ID NO 34
<211> LENGTH: 116
<212> TYPE: PRT
<213> ORGANISM: Artificial Sequence
<220> FEATURE:
<223> OTHER INFORMATION: Nanobody sequence

<400> SEQUENCE: 34

Glu Val Gln Leu Val Glu Ser Gly Gly Asp Leu Val Gln Ala Gly Gly
1               5                   10                  15

Ala Leu Gly Leu Ser Cys Pro Ala Ser Gly Leu Leu Phe Ser Arg Asn
            20                  25                  30

Ser Ala Gly Trp Tyr Arg Gln Ala Pro Gly Lys Gln Arg Glu Leu Val
        35                  40                  45

Ala Cys Ile Arg Met Gly Gly Ser Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Val Asp Asp Leu Lys Pro Glu Asp Thr Ala Ile Tyr Phe Cys Ser
                85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: Nanobody sequence

<400> SEQUENCE: 35

Glu Val Gln Leu Val Glu Ser Gly Gly Gly Leu Val Lys Ala Gly Gly
1               5                   10                  15

Ser Leu Gly Leu Ser Cys Ser Ala Ser Gly Leu Leu Phe Ser Arg Asn
            20                  25                  30

Ser Val Gly Trp Tyr Arg Gln Ala Pro Gly Lys Gln Arg Glu Phe Val
        35                  40                  45

Ala Arg Ile Arg Met Gly Gly Ser Ile Asn Tyr Gly Gly Ser Val Lys
    50                  55                  60

Gly Arg Phe Thr Val Ser Arg Asp Ile Ala Lys Asn Thr Met Tyr Leu
65                  70                  75                  80

Gln Met Asn Asp Leu Lys Pro Glu Glu Thr Ala Trp Tyr Phe Cys Ser
                85                  90                  95

Ser Trp Arg Glu Gly Phe Tyr Glu Tyr Trp Ser Gln Arg Thr Gln Val
            100                 105                 110

Thr Val Ser Ser
        115

<210> SEQ ID NO 36
<211> LENGTH: 116
<212> TYPE: PRT
<213> ORGANISM: Artificial Sequence
<220> FEATURE:

<223> OTHER INFORMATION: Nanobody sequence

<400> SEQUENCE: 36

Glu Val Gln Leu Val Glu Ser Ala Gly Gly Leu Val Gln Ala Gly Gly
1               5                   10                  15

Ser Leu Gly Leu Ser Cys Ser Ala Ser Gly Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Gly Asp Ser Val Lys
50                      55                  60

Gly Arg Phe Thr Val Ser Arg Asp Ile Ala Lys Asp Thr Arg Tyr Met
65                  70                  75                  80

Gln Ile Asn Asp Leu Lys Pro Glu Asp Thr Ala Lys Tyr Phe Cys Arg
                85                  90                  95

Ser Trp Arg Glu Gly Leu Tyr Glu Tyr Trp Gly Gln Gly Thr Gln Val
            100                 105                 110

Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: Nanobody sequence

<400> SEQUENCE: 37

Glu Val Gln Leu Val Glu Ser Gly Gly Gly Leu Leu Gln Ala Gly Gly
1               5                   10                  15

Ser Leu Gly Leu Ser Cys Ser Ala Ser Gly Leu Leu Ser Arg Asn
            20                  25                  30

Arg Ala Arg Trp Tyr Arg Gln Ala Pro Gly Lys Gln Arg Glu Phe Val
            35                  40                  45

Ala Arg Ile Arg Met Gly Gly Ser Met Asn Asp Gly Asp Ser Val Lys
50                      55                  60

Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Ile Tyr Phe Cys Arg
                85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 38
<211> LENGTH: 116
<212> TYPE: PRT
<213> ORGANISM: Artificial Sequence
<220> FEATURE:
<223> OTHER INFORMATION: Nanobody sequence

<400> SEQUENCE: 38

Glu Val Gln Leu Val Glu Ser Gly Gly Gly Leu Val Gln Ala Gly Gly
1               5                   10                  15

Ala Leu Gly Leu Ser Cys Ser Ala Ser Gly Leu Leu Phe Ser Arg Asn
            20                  25                  30

Ser Ala Gly Trp His Arg Gln Ala Pro Gly Lys Gln Arg Glu Phe Val

```
            35                  40                  45

Ala Arg Ile Arg Met Gly Gly Ser Ile Asn Tyr Gly Asp Ser Val Lys
 50                  55                  60

Gly Arg Phe Thr Val Ser Arg Asp Ile Ala Lys Asn Thr Met Tyr Leu
 65                  70                  75                  80

Gln Met Asn Glu Leu Lys Pro Glu Asp Thr Ala Lys Tyr Leu Cys Arg
                 85                  90                  95

Ser Trp Arg Glu Gly Phe Tyr Glu Ser Trp Gly Arg Gly Thr Gln Val
                100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Nanobody sequence

<400> SEQUENCE: 39

Glu Val Gln Leu Val Glu Ser Gly Gly Gly Leu Val Gln Ala Gly Gly
 1               5                  10                  15

Ser Leu Gly Leu Ser Cys Ser Ala Ser Gly Leu Leu Phe Ser Arg Asn
                20                  25                  30

Ser Ala Gly Trp Tyr Arg Pro Ala Pro Gly Lys Gln Arg Glu Phe Val
            35                  40                  45

Ala Arg Ile Arg Met Gly Gly Ser Ile Asn Tyr Gly Asp Ser Val Lys
 50                  55                  60

Gly Arg Phe Thr Val Ala Arg Asp Ile Ala Lys Asn Thr Met Tyr Leu
 65                  70                  75                  80

Gln Met Asn Asp Leu Lys Pro Glu Thr Ala Ile Tyr Phe Cys Ser
                 85                  90                  95

Ser Trp Arg Glu Gly Val Tyr Lys Tyr Gly Gly Lys Gly Thr Gln Val
                100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Nanobody sequence

<400> SEQUENCE: 40

Glu Val Gln Leu Val Glu Ser Gly Gly Gly Leu Val Gln Ala Gly Gly
 1               5                  10                  15

Arg Arg Gly Leu Ser Cys Ser Ala Ser Gly Phe Leu Phe Arg Arg Pro
                20                  25                  30

Ser Ala Gly Trp Tyr Arg Gln Asp Pro Gly Lys Gln Arg Glu Phe Val
            35                  40                  45

Ala Arg Ile Arg Met Gly Gly Ser Ile Asn Tyr Gly Asp Ser Val Lys
 50                  55                  60

Gly Arg Phe Thr Val Ser Arg Asp Ile Ala Lys Asn Thr Met Tyr Leu
 65                  70                  75                  80

Gln Met Asn Asp Val Lys Pro Glu Asp Thr Ala Lys Tyr Phe Cys Ser
                 85                  90                  95
```

-continued

Ser Trp Arg Glu Gly Phe Tyr Glu Tyr Trp Gly Gln Gly Thr Gln Val
            100                 105                 110
Thr Val Ser Ser
        115

<210> SEQ ID NO 41
<211> LENGTH: 116
<212> TYPE: PRT
<213> ORGANISM: Artificial Sequence
<220> FEATURE:
<223> OTHER INFORMATION: Nanobody sequence

<400> SEQUENCE: 41

Glu Val Gln Leu Val Glu Ser Gly Gly Ala Leu Val Gln Ala Gly Gly
1               5                   10                  15
Ser Leu Gly Leu Ser Cys Ser Ala Ser Gly Leu Leu Phe Ile Arg Asn
            20                  25                  30
Ser Ala Gly Cys Tyr Arg Gln Ala Pro Gly Lys His Arg Glu Phe Val
        35                  40                  45
Ala Arg Ile Arg Met Gly Gly Ser Ile Asn Tyr Gly Asp Ser Val Lys
    50                  55                  60
Gly Arg Phe Thr Val Ser Arg Asp Ile Ala Lys Asn Thr Val Tyr Leu
65                  70                  75                  80
Gln Met Asn Asp Leu Lys Pro Glu Tyr Thr Ala Ile Tyr Phe Cys Ser
                85                  90                  95
Ser Trp Arg Glu Gly Tyr Tyr Glu Tyr Trp Gly Gln Gly Thr Gln Val
            100                 105                 110
Thr Val Ser Ser
        115

<210> SEQ ID NO 42
<211> LENGTH: 116
<212> TYPE: PRT
<213> ORGANISM: Artificial Sequence
<220> FEATURE:
<223> OTHER INFORMATION: Nanobody sequence

<400> SEQUENCE: 42

Glu Val Gln Leu Val Glu Ser Gly Gly Gly Leu Val Glu Ala Gly Gly
1               5                   10                  15
Ser Leu Gly Leu Ser Cys Ser Ala Ser Gly Leu Leu Phe Ser Arg Ile
            20                  25                  30
Ser Ala Gly Trp Tyr Arg Glu Ala Pro Gly Gln Gln Arg Glu Cys Val
        35                  40                  45
Ala Arg Ile Arg Met Gly Gly Ser Ile Asn Tyr Gly Asp Ser Val Lys
    50                  55                  60
Gly Arg Phe Thr Val Ser Arg Asp Ile Ala Lys Asn Thr Met Tyr Leu
65                  70                  75                  80
Gln Met Asn Asp Leu Lys Pro Glu His Thr Ala Lys Tyr Leu Cys Ser
                85                  90                  95
Ser Trp Arg Glu Gly Phe Tyr Glu Tyr Trp Gly Gln Gly Thr Gln Val
            100                 105                 110
Thr Val Ser Ser
        115

<210> SEQ ID NO 43
<211> LENGTH: 116
<212> TYPE: PRT
<213> ORGANISM: Artificial Sequence
<220> FEATURE:
<223> OTHER INFORMATION: Nanobody sequence

<400> SEQUENCE: 43

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Pro Asn
            20                  25                  30

Ser Ala Gly Trp Tyr Arg Gln Ala Pro Gly Lys Gln Arg Lys Phe Val
        35                  40                  45

Ala Arg Ile Arg Arg Gly Gly Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Ile Tyr Phe Cys Ser
                85                  90                  95

Ser Trp Arg Glu Gly Phe Asp Gly Tyr Trp Ala Gln Gly Thr Gln Val
            100                 105                 110

Thr Val Ser Ser
        115

<210> SEQ ID NO 44
<211> LENGTH: 116
<212> TYPE: PRT
<213> ORGANISM: Artificial Sequence
<220> FEATURE:
<223> OTHER INFORMATION: Nanobody sequence

<400> SEQUENCE: 44

Glu Val Gln Leu Val Glu Ser Gly Gly Gly Leu Val Gln Ala Gly Gly
1               5                   10                  15

Pro Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Leu Ala Phe Val
        35                  40                  45

Gly Arg Ile Gly Met Gly Gly Cys Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Met Asn Gly Leu Lys Pro Glu Asp Thr Ala Lys Tyr Phe Cys Ser
                85                  90                  95

Ser Trp Arg Glu Gly Phe Tyr Gly Tyr Trp Gly Gln Gly Thr Gln Val
            100                 105                 110

Thr Val Ser Ser
        115

<210> SEQ ID NO 45
<211> LENGTH: 116
<212> TYPE: PRT
<213> ORGANISM: Artificial Sequence
<220> FEATURE:
<223> OTHER INFORMATION: Nanobody sequence

<400> SEQUENCE: 45

Glu Val Gln Leu Val Glu Ser Gly Gly Gly Leu Val Gln Ala Ala Gly
1               5                   10                  15

Ser Leu Gly Leu Pro Cys Ser Ala Ser Gly Leu Leu Phe Ser Arg Met
            20                  25                  30

```
Ser Ala Arg Trp Tyr Arg Gln Ala Pro Gly Glu Gln Arg Glu Phe Val
        35                  40                  45

Ala Arg Ile Arg Met Gly Gly Ser Ile Asn Tyr Gly Asp Ser Val Lys
 50                  55                  60

Gly Arg Phe Thr Val Thr Arg Asp Ile Ala Lys Asn Thr Met Tyr Leu
 65                  70                  75                  80

Gln Met Asn Asp Leu Lys Pro Glu Asp Thr Ala Lys Tyr Phe Cys Ser
                85                  90                  95

Ser Trp Arg Glu Gly Phe Tyr Glu Tyr Trp Cys Gln Gly Thr Gln Val
                100                 105                 110

Thr Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Nanobody sequence

<400> SEQUENCE: 46

Glu Val Gln Leu Val Glu Ser Gly Glu Gly Leu Val Pro Ala Gly Gly
 1               5                  10                  15

Ser Leu Gly Pro Ser Cys Ser Ala Ser Gly Leu Leu Phe Ser Arg Tyr
                20                  25                  30

Ser Ala Gly Trp Tyr Arg Gln Ala Pro Gly Lys Gln Arg Glu Phe Val
        35                  40                  45

Ala Arg Ser Arg Met Gly Gly Ser Ile Asn Tyr Gly Asp Ser Val Lys
 50                  55                  60

Gly Arg Phe Thr Val Ser Arg Asp Ile Ala Lys Asn Thr Met Tyr Leu
 65                  70                  75                  80

Gln Met Asn Asp Leu Lys Pro Glu Asp Thr Ala Glu Tyr Phe Cys Ser
                85                  90                  95

Ser Trp Arg Glu Gly Phe Tyr Glu Tyr Trp Gly Ile Gly Thr Gln Val
                100                 105                 110

Thr Val Ser Ser
        115

<210> SEQ ID NO 47
<211> LENGTH: 116
<212> TYPE: PRT
<213> ORGANISM: Artificial Sequence
<220> FEATURE:
<223> OTHER INFORMATION: Nanobody sequence

<400> SEQUENCE: 47

Glu Val Gln Leu Val Glu Ser Gly Gly Ala Leu Val Gln Ala Gly Gly
 1               5                  10                  15

Pro Pro Gly Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Asp Gly Asp Ser Val Lys
 50                  55                  60

Gly Arg Phe Thr Val Ser Arg Asp Ile Asp Lys Asn Thr Met Tyr Leu
 65                  70                  75                  80

Gln Met Asn Asp Leu Lys Pro Glu Asn Thr Ala Lys Tyr Phe Cys Ser
                85                  90                  95
```

```
Ser Trp Arg Glu Gly Phe Tyr Lys Tyr Trp Gly Gln Gly Thr Gln Val
            100                 105                 110

Thr Val Ser Ser
        115

<210> SEQ ID NO 48
<211> LENGTH: 116
<212> TYPE: PRT
<213> ORGANISM: Artificial Sequence
<220> FEATURE:
<223> OTHER INFORMATION: Nanobody sequence

<400> SEQUENCE: 48

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Gln Lys Arg Glu Phe Val
        35                  40                  45

Ala Arg Ile Arg Thr Gly Gly Ser Thr Asn Tyr Ala Asp Ser Val Lys
    50                  55                  60

Gly Arg Phe Thr Val Ser Arg Gly Asn Ala Lys Asn Thr Val Tyr Leu
65                  70                  75                  80

Gln Met Asn Asn Leu Lys Pro Glu Asp Thr Ala Val Tyr Tyr Cys Ser
                85                  90                  95

Ser Trp Arg Thr Gly Ala Tyr Glu Tyr Trp Gly Gln Gly Thr Gln Val
            100                 105                 110

Thr Val Ser Ser
        115

<210> SEQ ID NO 49
<211> LENGTH: 116
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ile Ala Gly Trp Tyr Arg Pro Ala Pro Gly Lys Gln Arg Glu Phe Val
        35                  40                  45

Ala Arg Ile Arg Met Gly Gly Ser Ile Asn Tyr Gly Asp Ser Val Lys
    50                  55                  60

Gly Arg Phe Asn Gly Ser Arg Asp Ile Ala Lys Asn Thr Met Tyr Leu
65                  70                  75                  80

Gln Met Asp Asp Leu Lys Pro Glu Asp Thr Ala Ile Cys Phe Cys Ser
                85                  90                  95

Ser Gly Arg Glu Gly Phe Tyr Glu Tyr Trp Gly Gln Gly Thr Gln Val
            100                 105                 110

Thr Val Ser Ser
        115

<210> SEQ ID NO 50
<211> LENGTH: 116
<212> TYPE: PRT
```

```
<213> ORGANISM: Artificial Sequence
<220> FEATURE:
<223> OTHER INFORMATION: Nanobody sequence

<400> SEQUENCE: 50

Glu Val Gln Leu Val Glu Ser Ala Gly Gly Leu Val Gln Ala Gly
1               5                   10                  15

Pro Leu Gly Leu Ser Cys Ser Ser Gly Leu Leu Phe Ser Leu Asn
            20                  25                  30

Ser Ala Gly Cys Ser Arg Gln Pro Pro Gly Lys Gln Arg Glu Phe Val
        35                  40                  45

Ala Arg Ile Arg Met Gly Gly Ser Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Lys Tyr Phe Cys Ser
                85                  90                  95

Ser Trp Arg Glu Gly Phe Tyr Glu Tyr Trp Gly Gln Gly Thr Gln Val
                100                 105                 110

Thr Val Ser Ser
        115

<210> SEQ ID NO 51
<211> LENGTH: 116
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Val Glu Ser Gly Gly Ala Leu Met Gln Ala Gly Gly
1               5                   10                  15

Ser Leu Gly Pro Pro Cys Pro Ala Ser Gly Pro Leu Phe Arg Arg Thr
            20                  25                  30

Arg Ala Gly Trp Tyr Arg Gln Ala Pro Gly Lys Gln Arg Glu Phe Val
        35                  40                  45

Ala Arg Ile Arg Met Gly Gly Ser Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Met Asn Asp Leu Lys Pro Glu Asp Thr Ala Lys Tyr Phe Cys Ser
                85                  90                  95

Ser Trp Arg Glu Gly Phe Tyr Glu Tyr Trp Gly Gln Gly Thr Gln Val
                100                 105                 110

Thr Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Val Glu Ser Gly Gly Cys Leu Val Gln Ala Gly Gly
1               5                   10                  15

Ser Leu Gly Leu Ser Cys Ser Ala Pro Gly Leu Leu Phe Ser Pro Asn
            20                  25                  30
```

Ser Ala Gly Trp Tyr Arg Gln Ala Pro Gly Lys Gln Arg Glu Phe Val
        35                  40                  45

Ala Arg Ile Leu Met Gly Gly Ser Ile Asn Tyr Gly Asp Ser Val Lys
    50                  55                  60

Gly Arg Phe Thr Val Ser Arg Asp Ile Ala Lys Asn Thr Met Tyr Leu
65                  70                  75                  80

Gln Met Lys Asp Leu Lys Pro Glu Asp Thr Ala Lys Tyr Phe Cys Ser
                85                  90                  95

Arg Trp Arg Glu Gly Phe Tyr Glu Tyr Cys Gly Gln Gly Thr Gln Val
            100                 105                 110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: Nanobody sequence

<400> SEQUENCE: 53

Glu Val Gln Leu Val Glu Ser Gly Gly Gly Leu Val Gln Ala Gly Gly
1               5                   10                  15

Pro Leu Gly Leu Ser Cys Ser Ala Ser Gly Ile Pro Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Arg Asn Tyr Gly Asp Ser Val Lys
    50                  55                  60

Gly Arg Phe Thr Val Ser Gly Asp Ile Ala Lys Asn Thr Met Tyr Leu
65                  70                  75                  80

Gln Met Asn Asp Leu Lys Pro Glu Asp Thr Ala Lys Asp Phe Gly Ser
                85                  90                  95

Ser Trp Arg Glu Gly Phe Tyr Glu Tyr Trp Gly Gln Gly Thr Gln Val
            100                 105                 110

Thr Val Ser Ser
        115

<210> SEQ ID NO 54
<211> LENGTH: 116
<212> TYPE: PRT
<213> ORGANISM: Artificial Sequence
<220> FEATURE:
<223> OTHER INFORMATION: Nanobody sequence

<400> SEQUENCE: 54

Glu Val Gln Leu Val Glu Ser Gly Gly Gly Leu Val Gln Thr Gly Gly
1               5                   10                  15

Ser Leu Thr Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Arg Gly Gly Asp Thr Asn Tyr Ala Glu Ser Val Arg
    50                  55                  60

Gly Arg Phe Thr Val Ser Arg Asp Lys Ala Lys Asn Thr Met Tyr Leu
65                  70                  75                  80

Gln Met Asn Ser Leu Lys Pro Glu Asp Thr Ala Val Tyr Tyr Cys Ala

```
                    85                  90                  95
Ser Trp Arg Thr Gly Ser Tyr Glu Tyr Trp Gly Gln Gly Thr Gln Val
                100                 105                 110

Thr Val Ser Ser
        115

<210> SEQ ID NO 55
<211> LENGTH: 116
<212> TYPE: PRT
<213> ORGANISM: Artificial Sequence
<220> FEATURE:
<223> OTHER INFORMATION: Nanobody sequence

<400> SEQUENCE: 55

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Ile Phe Val
        35                  40                  45

Ala Arg Leu Arg Arg Gly Gly Asp Thr Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ala Trp Arg Ala Gly Thr Tyr Glu Tyr Trp Gly Gln Val Thr Gln Val
                100                 105                 110

Thr Val Ser Ser
        115

<210> SEQ ID NO 56
<211> LENGTH: 116
<212> TYPE: PRT
<213> ORGANISM: Artificial Sequence
<220> FEATURE:
<223> OTHER INFORMATION: Nanobody sequence

<400> SEQUENCE: 56

Glu Val Gln Leu Val Glu Ser Gly Gly Gly Ser Val His Pro Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Ile Phe Val
        35                  40                  45

Ala Arg Leu Arg Arg Gly Gly Asp Thr Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ala Trp Arg Ala Gly Thr Tyr Glu Tyr Trp Gly Gln Gly Thr Gln Val
                100                 105                 110

Thr Val Ser Ser
        115

<210> SEQ ID NO 57
<211> LENGTH: 116
```

```
<212> TYPE: PRT
<213> ORGANISM: Artificial Sequence
<220> FEATURE:
<223> OTHER INFORMATION: Nanobody sequence

<400> SEQUENCE: 57

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Val Gly Trp Tyr Arg Arg Ala Pro Gly Lys Gln Arg Glu Phe Val
        35                  40                  45

Ala Arg Leu Arg Thr Thr Gly Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Ser
                85                  90                  95

Ala Trp Arg Ile Glu Ala Tyr Glu Tyr Trp Gly Gln Gly Thr Gln Val
            100                 105                 110

Thr Val Ser Ser
        115

<210> SEQ ID NO 58
<211> LENGTH: 116
<212> TYPE: PRT
<213> ORGANISM: Artificial Sequence
<220> FEATURE:
<223> OTHER INFORMATION: Nanobody sequence

<400> SEQUENCE: 58

Glu Val Gln Leu Val Glu Ser Gly Gly Gly Leu Glu Gln Ala Gly Gly
1               5                   10                  15

Ser Leu Arg Leu Ser Cys Ser Ala Ser Gly Leu Leu Phe Ser Val Asn
            20                  25                  30

Ser Ala Gly Trp Tyr Arg Gln Ala Pro Gly Lys Gln Arg Asp Phe Val
        35                  40                  45

Ala Arg Ile Arg Ser Gly Gly Ser Thr Asn Tyr Ala Asp Ser Val Lys
    50                  55                  60

Gly Arg Ser Thr Val Ser Arg Asp Asn Ala Lys Asn Thr Leu Tyr Leu
65                  70                  75                  80

Gln Leu Tyr Ser Leu Lys Pro Glu Asp Thr Ala Val Tyr Tyr Cys Ser
                85                  90                  95

Ser Trp Arg Thr Gly Ala Tyr Glu Tyr Trp Gly Gln Trp Thr Gln Val
            100                 105                 110

Thr Val Ser Ser
        115

<210> SEQ ID NO 59
<211> LENGTH: 116
<212> TYPE: PRT
<213> ORGANISM: Artificial Sequence
<220> FEATURE:
<223> OTHER INFORMATION: Nanobody sequence

<400> SEQUENCE: 59

Glu Val Gln Leu Val Glu Ser Gly Gly Gly Leu Val Lys Ala Gly Gly
1               5                   10                  15

Ser Leu Arg Leu Ser Cys Ser Ala Ser Gly Leu Leu Phe Arg Val Asn
```

```
                    20                  25                  30
Ser Val Gly Trp Tyr Arg Gln Ala Pro Gly Lys Gln Arg Asp Phe Val
                35                  40                  45

Ala Arg Ile Arg Arg Gly Gly Ser Thr Asn Tyr Ala Asp Thr Val Lys
     50                  55                  60

Gly Arg Val Thr Ile Ser Arg Asp Asn Ala Lys Asn Thr Val Tyr Leu
 65                  70                  75                  80

Gln Met Asn Ser Leu Ser Pro Ala Asp Thr Gly Val Tyr Tyr Cys Ser
                85                  90                  95

Ser Trp Arg Glu Gly Ala Tyr Glu Tyr Trp Gly Gln Gly Thr Gln Val
                100                 105                 110

Thr Val Ser Ser
        115

<210> SEQ ID NO 60
<211> LENGTH: 116
<212> TYPE: PRT
<213> ORGANISM: Artificial Sequence
<220> FEATURE:
<223> OTHER INFORMATION: Nanobody sequence

<400> SEQUENCE: 60

Glu Val Gln Leu Val Glu Ser Gly Gly Gly Leu Val Gln Ala Gly Gly
 1               5                  10                  15

Ser Leu Arg Leu Ser Cys Ser Ala Ser Gly Leu Leu Phe Ser Val Asn
                20                  25                  30

Ser Ala Gly Trp Tyr Arg Arg Ala Pro Gly Lys Gln Arg Glu Phe Val
                35                  40                  45

Ala Arg Leu Arg Arg Gly Gly Glu Thr Asn Tyr Gly Asp Ser Val Lys
     50                  55                  60

Gly Arg Phe Thr Ile Ser Arg Asp Lys Ala Thr Asn Thr Leu Tyr Leu
 65                  70                  75                  80

Gln Met Asn Ser Leu Arg Thr Glu Asp Thr Ala Val Tyr Tyr Cys Ser
                85                  90                  95

Ser Trp Arg Thr Gly Ser Tyr Glu Tyr Trp Gly Gln Gly Thr Gln Val
                100                 105                 110

Thr Val Ser Ser
        115

<210> SEQ ID NO 61
<211> LENGTH: 116
<212> TYPE: PRT
<213> ORGANISM: Artificial Sequence
<220> FEATURE:
<223> OTHER INFORMATION: Nanobody sequence

<400> SEQUENCE: 61

Glu Val Gln Leu Val Glu Ser Gly Gly Gly Leu Val Gln Ala Gly Gly
 1               5                  10                  15

Ser Leu Arg Leu Ser Cys Ser Ala Ser Gly Leu Leu Phe Arg Val Asn
                20                  25                  30

Ser Ala Gly Trp Tyr Arg Gln Ala Gln Gly Lys Gln Arg Glu Phe Val
                35                  40                  45

Ala Arg Ile Arg Ser Gly Gly Ser Thr Asn Tyr Ala Asp Ser Val Lys
     50                  55                  60

Gly Arg Phe Ile Ile Ser Arg Asp Asn Ala Gln Asn Thr Leu Tyr Leu
 65                  70                  75                  80
```

Gln Met Asn Asn Leu Ser Pro Glu Asp Thr Ala Ala Tyr Tyr Cys Ser
            85                  90                  95

Ser Trp Arg Ile Asp Ala Tyr Glu Tyr Trp Gly Gln Gly Thr Gln Val
            100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: Nanobody sequence

<400> SEQUENCE: 62

Glu Val Gln Leu Val Glu Ser Ala Gly Gly Leu Val Pro Ala Gly Gly
1               5                   10                  15

Ser Leu Arg Leu Pro Cys Ser Ala Pro Gly Leu Leu Phe Ser Val Asp
            20                  25                  30

Ser Ala Gly Trp Tyr Arg Gln Ala Pro Gly Lys Gln Arg Asp Phe Val
            35                  40                  45

Ala Arg Ile Arg Ser Gly Gly Ser Thr Asn Asp Ala Asp Ser Val Lys
        50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Ala Tyr Glu Tyr Trp Gly Gln Gly Thr Gln Val
            100                 105                 110

Thr Val Ser Ser
        115

<210> SEQ ID NO 63
<211> LENGTH: 116
<212> TYPE: PRT
<213> ORGANISM: Artificial Sequence
<220> FEATURE:
<223> OTHER INFORMATION: Nanobody sequence

<400> SEQUENCE: 63

Glu Val Gln Leu Val Glu Ser Gly Gly Gly Phe Val Gln Ala Gly Gly
1               5                   10                  15

Ser Leu Arg Leu Ser Cys Ser Ala Ser Gly Leu Leu Phe Ser Val Asn
            20                  25                  30

Ser Thr Val Ser Tyr Arg Gln Ala Pro Gly Lys Gln Arg Asp Cys Val
            35                  40                  45

Ala Arg Ile Arg Ser Gly Gly Ser Thr Asn Tyr Ala Asp Ser Val Lys
        50                  55                  60

Gly Arg Phe Thr Val Ser Arg Asp Asn Ala Lys Asn Thr Val Tyr Leu
65                  70                  75                  80

Gln Met Asn Ser Leu Lys His Glu Asp Thr Ala Val Tyr Tyr Cys Ser
            85                  90                  95

Ser Trp Arg Thr Gly Ala Tyr Glu Tyr Trp Gly Gln Gly Thr Gln Val
            100                 105                 110

Thr Val Ser Ser
        115

<210> SEQ ID NO 64

```
<211> LENGTH: 116
<212> TYPE: PRT
<213> ORGANISM: Artificial Sequence
<220> FEATURE:
<223> OTHER INFORMATION: Nanobody sequence

<400> SEQUENCE: 64

Glu Val Gln Leu Val Glu Ser Gly Gly Gly Leu Val Lys Ala Gly Glu
1               5                   10                  15

Ser Leu Arg Leu Ser Cys Ser Ala Ser Gly Leu Phe Ser Val Asp
            20                  25                  30

Ser Thr Gly Trp Tyr Arg Gln Ala Pro Gly Lys Gln Arg Glu Phe Phe
        35                  40                  45

Ala Arg Ile Arg Ser Gly Gly Ser Ile Asn Tyr Gly Asp Ser Val Lys
    50                  55                  60

Gly Arg Phe Thr Ile Ser Arg Asp Lys Ala Thr Asn Thr Leu Tyr Leu
65                  70                  75                  80

Gln Met Ser Asn Leu Asn Pro Glu Asp Thr Ala Val Tyr Tyr Cys Ser
                85                  90                  95

Ser Trp Arg Ile Gly Ser Tyr Glu Tyr Trp Gly Gln Gly Thr Gln Val
            100                 105                 110

Thr Val Ser Ser
        115

<210> SEQ ID NO 65
<211> LENGTH: 127
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Val Glu Ser Gly Gly Gly Leu Val Gln Ala Gly Asp
1               5                   10                  15

Ser Leu Ser Leu Ser Cys Thr Ala Ser Arg Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly His Lys Tyr Tyr Ser Asp Ser Val
    50                  55                  60

Lys Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Leu Val Thr Val Ser Ser
        115                 120                 125

<210> SEQ ID NO 66
<211> LENGTH: 127
<212> TYPE: PRT
<213> ORGANISM: Artificial Sequence
<220> FEATURE:
<223> OTHER INFORMATION: Nanobody sequence

<400> SEQUENCE: 66

Glu Val Gln Leu Val Glu Ser Gly Gly Gly Leu Val Gln Ala Gly Asp
1               5                   10                  15
```

```
Ser Leu Ser Leu Ser Cys Thr Ala Ser Arg Gly Thr Phe Arg Asn Phe
            20                  25                  30

Gly Met Gly Trp Ser Arg Gln Ala Gln Gly Lys Glu Arg Glu Phe Val
            35                  40                  45

Ala Ala Ile Ser Arg Ser Gly Gly His Lys Tyr Tyr Ser Asp Ser Val
        50                  55                  60

Lys Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Leu Val Thr Val Ser Ser
            115                 120                 125

<210> SEQ ID NO 67
<211> LENGTH: 127
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Val Glu Ser Gly Gly Gly Leu Val Gln Ala Gly Asp
1               5                   10                  15

Ser Leu Ser Leu Ser Cys Thr Ala Ser Ala Gly Thr Phe Arg Asn Phe
            20                  25                  30

Gly Met Gly Trp Phe Arg Gln Ala Arg Gly Glu Glu Arg Glu Phe Val
            35                  40                  45

Ala Thr Ile Ser Arg Ser Ala Arg His Thr Tyr Tyr Ser Asp Ser Val
        50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125

<210> SEQ ID NO 68
<211> LENGTH: 127
<212> TYPE: PRT
<213> ORGANISM: Artificial Sequence
<220> FEATURE:
<223> OTHER INFORMATION: Nanobody sequence

<400> SEQUENCE: 68

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
            35                  40                  45

Ala Ala Ile Ser Arg Ser Ala Gly Arg Thr Tyr Tyr Ser Asp Ser Val
        50                  55                  60

Lys Gly Arg Phe Thr Ile Ser Lys Asn Asn Ala Lys Asn Ile Met Ser
65                  70                  75                  80
```

```
Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Leu Val Thr Val Ser Ser
            115                 120                 125
```

<210> SEQ ID NO 69
<211> LENGTH: 127
<212> TYPE: PRT
<213> ORGANISM: Artificial Sequence
<220> FEATURE:
<223> OTHER INFORMATION: Nanobody sequence

<400> SEQUENCE: 69

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
                20                  25                  30

Gly Met Gly Trp Phe Arg Gln Ala Gln Gly Lys Glu Arg Glu Phe Val
            35                  40                  45

Ala Ala Ile Ser Arg Ser Ala Ser Arg Thr Tyr Tyr Ser Asp Ser Val
        50                  55                  60

Lys Gly Arg Phe Thr Ile Ser Lys Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125
```

<210> SEQ ID NO 70
<211> LENGTH: 127
<212> TYPE: PRT
<213> ORGANISM: Artificial Sequence
<220> FEATURE:
<223> OTHER INFORMATION: Nanobody sequence

<400> SEQUENCE: 70

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
                20                  25                  30

Gly Met Gly Trp Phe Arg Gln Ala Gln Gly Lys Glu Arg Glu Phe Val
            35                  40                  45

Ala Ala Ile Ser Arg Ser Gly Gly His Ile Tyr Tyr Ser Asp Ser Val
        50                  55                  60

Lys Gly Arg Phe Thr Ile Ala Arg Ala Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125
```

```
<210> SEQ ID NO 71
<211> LENGTH: 127
<212> TYPE: PRT
<213> ORGANISM: Artificial Sequence
<220> FEATURE:
<223> OTHER INFORMATION: Nanobody sequence

<400> SEQUENCE: 71

Glu Val Gln Leu Val Glu Ser Gly Gly Gly Leu Val Gln Ala Gly Gly
1               5                   10                  15

Ser Leu Ser Leu Ser Cys Thr Val Ser Gly Gly Asn Phe Arg Asn Phe
            20                  25                  30

Gly Met Gly Trp Phe Arg Gln Ala His Gly Lys Glu Arg Glu Phe Val
        35                  40                  45

Ala Ala Ile Ser Arg Ser Gly Gly Arg Thr Tyr Tyr Ala Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Ser Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 72
<211> LENGTH: 127
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly Arg Thr Tyr Tyr Ser Asp Ser Val
    50                  55                  60

Lys Gly Arg Phe Thr Ile Ser Lys Asn Asn Ala Lys Asn Val Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Leu Val Thr Val Ser Ser
        115                 120                 125

<210> SEQ ID NO 73
<211> LENGTH: 127
<212> TYPE: PRT
<213> ORGANISM: Artificial Sequence
<220> FEATURE:
<223> OTHER INFORMATION: Nanobody sequence

<400> SEQUENCE: 73

Glu Val Gln Leu Val Glu Ser Gly Gly Gly Leu Val Arg Ala Gly Gly
1               5                   10                  15
```

```
Ser Leu Ser Leu Ser Cys Thr Ser Ser Gly Thr Phe Arg Asn Phe
            20                  25                  30

Ala Met Gly Trp Phe Arg Gln Ala Gln Gly Lys Glu Arg Glu Phe Val
        35                  40                  45

Ala Thr Ile Ser Arg Ser Gly His Thr Tyr Tyr Ser Asp Ser Val
    50                  55                  60

Lys Gly Arg Phe Thr Ile Ser Arg Asp Asn Ala Lys Asn Leu Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Thr Tyr Tyr Tyr Gln Arg Ala
            100                 105                 110

Phe Tyr Asp Phe Trp Gly Gln Gly Thr Leu Val Thr Val Ser Ser
        115                 120                 125
```

<210> SEQ ID NO 74
<211> LENGTH: 127
<212> TYPE: PRT
<213> ORGANISM: Artificial Sequence
<220> FEATURE:
<223> OTHER INFORMATION: Nanobody sequence

<400> SEQUENCE: 74

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly Arg Thr Tyr Tyr Ser Asp Ser Val
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125
```

<210> SEQ ID NO 75
<211> LENGTH: 127
<212> TYPE: PRT
<213> ORGANISM: Artificial Sequence
<220> FEATURE:
<223> OTHER INFORMATION: Nanobody sequence

<400> SEQUENCE: 75

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
            20                  25                  30

Gly Met Gly Trp Phe Arg Gln Asp Gln Gly Gln Glu Arg Glu Phe Val
        35                  40                  45

Ala Ala Ile Ser Arg Ser Gly Gly Arg Thr Tyr Phe Ser Asp Ser Val
    50                  55                  60

Lys Gly Arg Phe Thr Ile Ser Lys Asp Asn Ala Lys Asn Ile Leu Ser
```

```
                65                  70                  75                  80
Leu Gln Met Asn Ser Leu Lys Pro Glu Asp Thr Ala Val Tyr Tyr Cys
                    85                  90                  95

Ala Ala Arg Phe Arg Phe Asp Asp Gly Thr Tyr Tyr Tyr Gln Arg Ala
                100                 105                 110

Phe Tyr Asp Phe Trp Gly Gln Gly Thr Gln Val Thr Val Ser Ser
            115                 120                 125

<210> SEQ ID NO 76
<211> LENGTH: 127
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Val Glu Ser Gly Gly Gly Leu Val Gln Ala Gly Gly
1               5                   10                  15

Ser Leu Ser Leu Ser Cys Thr Ala Ser Arg Gly Thr Phe Arg Asn Phe
                20                  25                  30

Gly Met Gly Trp Phe Arg Gln Ala Gln Gly Lys Glu Arg Glu Phe Val
            35                  40                  45

Ala Ala Ile Ser Arg Ser Ala Gly His Thr Tyr Tyr Ser Asp Ser Val
        50                  55                  60

Lys Gly Arg Phe Thr Ile Ser Arg Asp Asn Ala Lys Asn Met Val Ser
65                  70                  75                  80

Leu Gln Met Asp Ser Leu Lys Pro Glu Asp Thr Ala Val Tyr Tyr Cys
                    85                  90                  95

Ala Ala Arg Phe Arg Phe Asp Asp Gly Thr Tyr Tyr Tyr Gln Arg Thr
                100                 105                 110

Phe Tyr Asp Phe Trp Gly Gln Gly Thr Gln Val Thr Val Ser Ser
            115                 120                 125

<210> SEQ ID NO 77
<211> LENGTH: 127
<212> TYPE: PRT
<213> ORGANISM: Artificial Sequence
<220> FEATURE:
<223> OTHER INFORMATION: Nanobody sequence

<400> SEQUENCE: 77

Glu Val Gln Leu Val Glu Ser Gly Gly Gly Leu Ala Gln Ala Gly Gly
1               5                   10                  15

Ser Leu Ser Leu Ser Cys Thr Ala Ser Gly Gly Asn Phe Arg Asn Phe
                20                  25                  30

Gly Met Gly Trp Phe Arg Gln Val Gln Gly Thr Glu Arg Glu Phe Val
            35                  40                  45

Ala Ala Ile Ser Arg Thr Gly Gly Arg Thr Tyr Phe Ser Asp Ser Val
        50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Ser Ala Val Tyr Tyr Cys
                    85                  90                  95

Ala Ala Arg Phe Arg Phe Gly Asp Gly Thr Tyr Tyr Tyr Gln Arg Asn
                100                 105                 110

Phe Tyr Asp Phe Trp Gly Gln Gly Thr Gln Val Thr Val Ser Ser
            115                 120                 125
```

<210> SEQ ID NO 78
<211> LENGTH: 127
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Val Glu Ser Gly Gly Gly Leu Val Gln Ala Gly Asp
1               5                   10                  15

Ser Leu Ser Leu Ser Cys Thr Ala Ser Arg Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly His Lys Tyr Tyr Ser Asp Ser Val
    50                  55                  60

Gln Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 79
<211> LENGTH: 127
<212> TYPE: PRT
<213> ORGANISM: Artificial Sequence
<220> FEATURE:
<223> OTHER INFORMATION: Nanobody sequence

<400> SEQUENCE: 79

Glu Val Gln Leu Val Glu Ser Gly Gly Gly Leu Val Gln Thr Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly Arg Thr Tyr Tyr Ser Asp Ser Val
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 80
<211> LENGTH: 127
<212> TYPE: PRT
<213> ORGANISM: Artificial Sequence
<220> FEATURE:
<223> OTHER INFORMATION: Nanobody sequence

<400> SEQUENCE: 80

Glu Val Gln Leu Val Glu Ser Gly Gly Gly Leu Val Gln Ala Gly Gly

```
  1               5                  10                 15
Ser Leu Ser Leu Ser Cys Thr Ala Ser Gly Gly Thr Phe Arg Asn Tyr
                20                  25                 30

Ala Met Gly Trp Phe Arg Gln Ala Gln Gly Lys Glu Arg Glu Phe Val
            35                  40                 45

Ala Thr Ile Ser Arg Ser Gly Gly Tyr Thr Tyr Tyr Ser Asp Ser Val
        50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Tyr Gln Arg Ala
                100                 105                110

Phe Tyr Asp Phe Trp Gly Gln Gly Thr Gln Val Thr Val Ser Ser
                115                 120                 125
```

<210> SEQ ID NO 81
<211> LENGTH: 127
<212> TYPE: PRT
<213> ORGANISM: Artificial Sequence
<220> FEATURE:
<223> OTHER INFORMATION: Nanobody sequence

<400> SEQUENCE: 81

```
Glu Val Gln Leu Val Glu Ser Gly Gly Gly Leu Val Gln Ala Gly Gly
1               5                  10                 15

Ser Leu Ser Leu Ser Cys Thr Ala Ser Gly Gly Thr Phe Arg Asn Phe
                20                  25                 30

Gly Met Gly Trp Phe Arg Gln Ala Gln Gly Lys Glu Arg Glu Phe Val
            35                  40                 45

Ala Ala Ile Ser Arg Ser Gly Gly Arg Thr Tyr Tyr Ser Asp Ser Val
        50                  55                  60

Lys Gly Arg Phe Thr Ile Ser Lys Asp Asn Ala Lys Asn Ile Met Ser
65                  70                  75                  80

Leu Gln Met Asn Ser Leu Arg Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
                100                 105                110

Phe Tyr Asp Phe Trp Gly Gln Gly Thr Gln Val Thr Val Ser Ser
                115                 120                 125
```

<210> SEQ ID NO 82
<211> LENGTH: 127
<212> TYPE: PRT
<213> ORGANISM: Artificial Sequence
<220> FEATURE:
<223> OTHER INFORMATION: Nanobody sequence

<400> SEQUENCE: 82

```
Glu Val Gln Leu Val Glu Ser Gly Gly Gly Ser Val Gln Ala Gly Gly
1               5                  10                 15

Ser Leu Ser Leu Ser Cys Thr Ala Ser Arg Gly Thr Phe Arg Asn Phe
                20                  25                 30

Gly Met Gly Trp Phe Arg Gln Ala Gln Gly Lys Glu Arg Glu Phe Val
            35                  40                 45

Ala Ala Ile Ser Arg Thr Gly Gly Arg Thr Tyr Tyr Ser Asp Ser Val
        50                  55                  60
```

```
Lys Gly Arg Phe Thr Ile Ser Arg Asp Asn Ala Lys Asn Met Val Ser
 65                  70                  75                  80

Leu Gln Met Asn Ser Leu Lys Pro Glu Asp Thr Ala Ile Tyr Tyr Cys
                 85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Leu Val Thr Val Ser Ser
            115                 120                 125
```

<210> SEQ ID NO 83
<211> LENGTH: 127
<212> TYPE: PRT
<213> ORGANISM: Artificial Sequence
<220> FEATURE:
<223> OTHER INFORMATION: Nanobody sequence

<400> SEQUENCE: 83

```
Glu Val Gln Leu Val Glu Ser Gly Gly Gly Leu Val Gln Ala Gly Asp
1                5                  10                  15

Ser Leu Ser Leu Ser Cys Thr Ala Ser Ala Gly Thr Phe Arg Asn Phe
             20                  25                  30

Gly Met Gly Trp Phe Arg Gln Ala Arg Gly Glu Arg Glu Phe Val
         35                  40                  45

Ala Thr Ile Ser Arg Ser Ala Arg His Thr Tyr Tyr Ser Asp Ser Val
     50                  55                  60

Lys Gly Arg Phe Thr Ile Ser Arg Asp Asn Ala Lys Asn Met Val Ser
 65                  70                  75                  80

Leu Gln Met Asn Ser Leu Lys Pro Glu Asp Thr Ala Val Tyr Tyr Cys
                 85                  90                  95

Ala Ala Arg Phe Arg Ser Asp Gly Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125
```

<210> SEQ ID NO 84
<211> LENGTH: 127
<212> TYPE: PRT
<213> ORGANISM: Artificial Sequence
<220> FEATURE:
<223> OTHER INFORMATION: Nanobody sequence

<400> SEQUENCE: 84

```
Glu Val Gln Leu Val Glu Ser Gly Gly Gly Leu Val Gln Ala Gly Gly
1                5                  10                  15

Ser Leu Ser Leu Ser Cys Thr Ala Ser Ala Gly Thr Phe Arg Asn Phe
             20                  25                  30

Gly Met Gly Trp Phe Arg Gln Ala Gln Gly Lys Glu Arg Glu Phe Val
         35                  40                  45

Ala Ala Ile Ser Arg Ser Gly Gly His Thr Tyr Tyr Ser Asp Ser Val
     50                  55                  60

Lys Gly Arg Phe Thr Ile Ser Lys Asp Asn Ala Lys Asn Met Val Ser
 65                  70                  75                  80

Leu Lys Met Asn Ser Leu Lys Pro Glu Asp Thr Ala Asp Tyr Tyr Cys
                 85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125
```

-continued

<210> SEQ ID NO 85
<211> LENGTH: 127
<212> TYPE: PRT
<213> ORGANISM: Artificial Sequence
<220> FEATURE:
<223> OTHER INFORMATION: Nanobody sequence

<400> SEQUENCE: 85

```
Glu Val Gln Leu Val Glu Ser Gly Gly Gly Leu Val Gln Ala Gly Gly
1               5                  10                  15

Ser Leu Ser Leu Ser Cys Thr Ala Ser Gly Gly Thr Phe Arg Asn Phe
            20                  25                  30

Gly Met Gly Trp Phe Arg Gln Val Gln Gly Lys Glu Arg Glu Phe Val
        35                  40                  45

Ala Ala Ile Ser Arg Ser Gly His Ile Phe Tyr Ser Asp Ser Val
    50                  55                  60

Lys Gly Arg Phe Thr Ile Ser Lys Asp Asn Ala Lys Asn Ile Leu Phe
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Gln Arg Ala
            100                 105                 110

Phe Tyr Asp Phe Trp Gly Gln Gly Thr Gln Val Thr Val Ser Ser
        115                 120                 125
```

<210> SEQ ID NO 86
<211> LENGTH: 127
<212> TYPE: PRT
<213> ORGANISM: Artificial Sequence
<220> FEATURE:
<223> OTHER INFORMATION: Nanobody sequence

<400> SEQUENCE: 86

```
Glu Val Gln Leu Val Glu Ser Gly Gly Gly Leu Val Gln Ala Gly Gly
1               5                  10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly Arg Thr Tyr Tyr Ser Asp Ser Ala
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Gln Arg Ala
            100                 105                 110

Phe Tyr Asp Phe Trp Gly Gln Gly Thr Leu Val Thr Val Ser Ser
        115                 120                 125
```

<210> SEQ ID NO 87
<211> LENGTH: 127
<212> TYPE: PRT
<213> ORGANISM: Artificial Sequence
<220> FEATURE:
<223> OTHER INFORMATION: Nanobody sequence

<400> SEQUENCE: 87

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Asn Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Tyr Gly Asp Gly Thr Tyr Tyr Tyr Gln Arg Ala
            100                 105                 110

Phe Tyr Asp Phe Trp Gly Gln Gly Thr Leu Val Thr Val Ser Ser
            115                 120                 125
```

<210> SEQ ID NO 88
<211> LENGTH: 127
<212> TYPE: PRT
<213> ORGANISM: Artificial Sequence
<220> FEATURE:
<223> OTHER INFORMATION: Nanobody sequence

<400> SEQUENCE: 88

```
Glu Val Gln Leu Val Glu Ser Gly Gly Gly Leu Val Gln Ala Gly Asp
1               5                   10                  15

Ser Leu Ser Leu Ser Cys Thr Ala Ser Arg Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly Arg Lys Tyr Tyr Ser Asp Ser Val
    50                  55                  60

Lys Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Leu Val Thr Val Ser Ser
            115                 120                 125
```

<210> SEQ ID NO 89
<211> LENGTH: 127
<212> TYPE: PRT
<213> ORGANISM: Artificial Sequence
<220> FEATURE:
<223> OTHER INFORMATION: Nanobody sequence

<400> SEQUENCE: 89

```
Glu Val Gln Leu Val Glu Ser Gly Gly Gly Leu Val Glu Ala Gly Gly
1               5                   10                  15

Ser Leu Ser Leu Ser Cys Thr Ala Ser Ala Gly Thr Phe Arg Asn Phe
            20                  25                  30

Gly Met Gly Trp Phe Arg Gln Ala Arg Gly Glu Glu Arg Glu Phe Val
        35                  40                  45

Ala Thr Ile Ser Arg Ser Ala Arg His Thr Tyr Tyr Ser Asp Ser Val
    50                  55                  60
```

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 90
<211> LENGTH: 127
<212> TYPE: PRT
<213> ORGANISM: Artificial Sequence
<220> FEATURE:
<223> OTHER INFORMATION: Nanobody sequence

<400> SEQUENCE: 90

Glu Val Gln Leu Val Glu Ser Gly Gly Gly Leu Val Gln Ala Gly Asp
1               5                   10                  15

Ser Leu Ser Leu Ser Cys Thr Ala Ser Ala Gly Thr Leu Arg Asn Phe
            20                  25                  30

Gly Met Gly Trp Phe Arg Gln Ala Arg Gly Glu Glu Arg Glu Phe Val
        35                  40                  45

Ala Thr Ile Ser Arg Ser Ala Arg His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Arg
            100                 105                 110

Phe Tyr Asp Phe Trp Gly Gln Gly Thr Gln Val Thr Val Ser Ser
        115                 120                 125

<210> SEQ ID NO 91
<211> LENGTH: 127
<212> TYPE: PRT
<213> ORGANISM: Artificial Sequence
<220> FEATURE:
<223> OTHER INFORMATION: Nanobody sequence

<400> SEQUENCE: 91

Glu Val Gln Leu Val Glu Ser Gly Gly Gly Leu Val Gln Ala Gly Asp
1               5                   10                  15

Ser Leu Ser Leu Ser Cys Thr Ala Ser Ala Gly Thr Leu Arg Asn Phe
            20                  25                  30

Gly Met Gly Trp Phe Arg Gln Ala Arg Gly Glu Glu Arg Glu Phe Val
        35                  40                  45

Ala Thr Ile Ser Arg Ser Ala Arg His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Gly Asp Gly Thr Tyr Tyr Tyr Gln Arg Ala
            100                 105                 110

Phe Tyr Asp Phe Trp Gly Gln Gly Thr Gln Val Thr Val Ser Ser

<210> SEQ ID NO 92
<211> LENGTH: 127
<212> TYPE: PRT
<213> ORGANISM: Artificial Sequence
<220> FEATURE:
<223> OTHER INFORMATION: Nanobody sequence

<400> SEQUENCE: 92

```
Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Thr Gly Gly His Thr Tyr Tyr Ser Asp Ser Val
    50                  55                  60

Lys Gly Arg Phe Thr Ile Ser Lys Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Tyr Gln Arg Ala
            100                 105                 110

Phe Tyr Asp Phe Trp Gly Gln Gly Thr Leu Val Thr Val Ser Ser
        115                 120                 125
```

<210> SEQ ID NO 93
<211> LENGTH: 127
<212> TYPE: PRT
<213> ORGANISM: Artificial Sequence
<220> FEATURE:
<223> OTHER INFORMATION: Nanobody sequence

<400> SEQUENCE: 93

```
Glu Val Gln Leu Val Glu Ser Gly Gly Gly Leu Val Gln Ala Gly Asp
1               5                   10                  15

Ser Leu Ser Leu Ser Cys Thr Ala Ser Ala Gly Thr Leu Arg Asn Phe
            20                  25                  30

Gly Met Gly Trp Phe Arg Gln Ala Arg Gly Glu Glu Arg Glu Phe Val
        35                  40                  45

Ala Thr Ile Ser Arg Ser Ala Arg His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125
```

<210> SEQ ID NO 94
<211> LENGTH: 127
<212> TYPE: PRT
<213> ORGANISM: Artificial Sequence
<220> FEATURE:
<223> OTHER INFORMATION: Nanobody sequence

<400> SEQUENCE: 94

-continued

Glu Val Gln Leu Val Glu Ser Gly Gly Gly Leu Val Gln Ala Gly Gly
1               5                   10                  15

Ser Leu Ser Leu Ser Cys Thr Ser Ser Lys Gly Thr Phe Arg Asn Phe
            20                  25                  30

Ala Met Gly Trp Phe Arg Gln Ala Gln Gly Lys Glu Arg Glu Phe Val
        35                  40                  45

Ala Thr Ile Ser Arg Ser Gly Gly His Thr Tyr Tyr Ser Asp Ser Val
    50                  55                  60

Lys Gly Arg Phe Ala Ile Ser Arg Asp Asn Ala Lys Asn Leu Val Ser
65                  70                  75                  80

Leu Gln Met Asn Ser Leu Asn Ala Glu Asp Thr Ala Val Tyr Tyr Cys
                85                  90                  95

Ala Ala Arg Phe Arg Ser Asp Asp Thr Tyr Tyr Tyr Gln Arg Ala
                100                 105                 110

Phe Tyr Asp Phe Trp Gly Gln Gly Thr Leu Val Thr Val Ser Ser
            115                 120                 125

<210> SEQ ID NO 95
<211> LENGTH: 127
<212> TYPE: PRT
<213> ORGANISM: Artificial Sequence
<220> FEATURE:
<223> OTHER INFORMATION: Nanobody sequence

<400> SEQUENCE: 95

Glu Val Gln Leu Val Glu Ser Gly Gly Gly Leu Val Gln Ala Gly Gly
1               5                   10                  15

Ser Leu Ser Leu Pro Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly Arg Thr Tyr Tyr Ser Asp Ser Val
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Gln Arg Ala
                100                 105                 110

Phe Tyr Asp Phe Trp Gly Gln Gly Thr Leu Val Thr Val Ser Ser
            115                 120                 125

<210> SEQ ID NO 96
<211> LENGTH: 127
<212> TYPE: PRT
<213> ORGANISM: Artificial Sequence
<220> FEATURE:
<223> OTHER INFORMATION: Nanobody sequence

<400> SEQUENCE: 96

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Asp Phe Val
        35                  40                  45

Ala Ala Ile Ser Arg Thr Asn Gly His Ile Tyr Tyr Ser Asp Ser Val

```
                50              55              60
Lys Gly Arg Phe Thr Ile Ser Lys Asp Asn Ala Lys Asn Ile Leu Ser
 65              70              75              80

Leu Gln Met Asn Ser Leu Lys Pro Glu Asp Thr Ala Val Tyr Tyr Cys
                 85              90              95

Ala Ala Arg Phe Arg Phe Gly Asp Gly Thr Tyr Tyr Gln Arg Thr
            100             105             110

Phe Tyr Asp Phe Trp Gly Gln Gly Thr Leu Val Thr Val Ser Ser
        115             120             125

<210> SEQ ID NO 97
<211> LENGTH: 127
<212> TYPE: PRT
<213> ORGANISM: Artificial Sequence
<220> FEATURE:
<223> OTHER INFORMATION: Nanobody sequence

<400> SEQUENCE: 97

Glu Val Gln Leu Val Glu Ser Gly Gly Leu Val Gln Ala Gly Gly
 1               5              10              15

Ser Leu Ser Leu Ser Cys Thr Ala Ser Gly Gly Thr Phe Arg Asn Phe
                20              25              30

Ala Met Gly Trp Phe Arg Gln Ala Gln Gly Lys Glu Arg Glu Phe Val
             35              40              45

Ala Thr Ile Ser Arg Ser Gly His Ile Tyr Tyr Ser Asp Ser Val
         50              55              60

Lys Gly Arg Phe Thr Ile Ser Arg Asp Asn Ala Lys Asn Met Val Ser
 65              70              75              80

Leu Gln Met Asn Ser Leu Lys Pro Glu Asp Thr Ala Val Tyr Tyr Cys
                 85              90              95

Ala Ala Arg Phe Arg Phe Asp Asp Gly Thr Ser Tyr Tyr Gln Arg Ala
            100             105             110

Phe Tyr Asp Phe Trp Gly Gln Gly Thr Leu Val Thr Val Ser Ser
        115             120             125

<210> SEQ ID NO 98
<211> LENGTH: 127
<212> TYPE: PRT
<213> ORGANISM: Artificial Sequence
<220> FEATURE:
<223> OTHER INFORMATION: Nanobody sequence

<400> SEQUENCE: 98

Glu Val Gln Leu Val Glu Ser Gly Gly Asp Leu Val Gln Pro Gly Gly
 1               5              10              15

Ser Leu Arg Leu Ser Cys Thr Ala Ser Gly Gly Thr Phe Arg Asn Tyr
                20              25              30

Gly Met Gly Trp Phe Arg Gln Ala Gln Gly Lys Glu Arg Glu Phe Val
             35              40              45

Ala Ala Ile Ser Arg Thr Gly Gly His Thr Tyr Tyr Ser Asp Ser Val
         50              55              60

Lys Gly Arg Phe Thr Ile Ser Lys Asp Asn Ala Lys Asn Ile Val Ser
 65              70              75              80

Leu Gln Met Asn Ser Leu Lys Pro Glu Asp Thr Ala Val Tyr Tyr Cys
                 85              90              95

Ala Ala Arg Phe Arg Phe Gly Asp Gly Thr Tyr Tyr Tyr Gln Arg Asn
            100             105             110
```

```
Phe Tyr Asp Phe Trp Gly Gln Gly Thr Gln Val Thr Val Ser Ser
        115                 120                 125
```

<210> SEQ ID NO 99
<211> LENGTH: 127
<212> TYPE: PRT
<213> ORGANISM: Artificial Sequence
<220> FEATURE:
<223> OTHER INFORMATION: Nanobody sequence

<400> SEQUENCE: 99

```
Glu Val Gln Leu Val Glu Ser Gly Gly Gly Leu Val Gln Ala Gly Gly
1               5                   10                  15

Pro Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly Arg Thr Tyr Tyr Ser Asp Ser Val
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Leu Val Thr Val Ser Ser
        115                 120                 125
```

<210> SEQ ID NO 100
<211> LENGTH: 127
<212> TYPE: PRT
<213> ORGANISM: Artificial Sequence
<220> FEATURE:
<223> OTHER INFORMATION: Nanobody sequence

<400> SEQUENCE: 100

```
Glu Val Gln Leu Val Glu Ser Gly Gly Gly Ser Val Gln Ala Gly Gly
1               5                   10                  15

Ser Leu Arg Leu Val Cys Ala Phe Ser Gly Gly Thr Phe Arg Asn Phe
            20                  25                  30

Ala Met Gly Trp Phe Arg Gln Ala Gln Gly Lys Glu Arg Glu Phe Val
        35                  40                  45

Ala Thr Ile Ser Arg Ser Gly Gly His Thr Tyr Tyr Ser Asp Ser Val
    50                  55                  60

Lys Gly Arg Phe Thr Ile Ser Lys Asp Asn Ala Lys Asn Met Val Tyr
65                  70                  75                  80

Leu Gln Met Tyr Ser Leu Lys Pro Glu Asp Thr Ala Val Tyr Tyr Cys
                85                  90                  95

Ala Gly Arg Phe Arg Phe Gly Asp Gly Ala Tyr Tyr Tyr Gln Arg Thr
            100                 105                 110

Phe Tyr Asp Phe Trp Gly Gln Gly Thr Leu Val Thr Val Ser Ser
        115                 120                 125
```

<210> SEQ ID NO 101
<211> LENGTH: 127
<212> TYPE: PRT
<213> ORGANISM: Artificial Sequence
<220> FEATURE:
<223> OTHER INFORMATION: Nanobody sequence -continued

```
<400> SEQUENCE: 101

Glu Val Gln Leu Val Glu Ser Gly Gly Gly Leu Val Gln Ala Gly Gly
1               5                   10                  15

Ser Leu Ser Leu Ser Cys Thr Ala Ser Arg Gly Thr Phe Arg Asn Phe
            20                  25                  30

Ala Met Gly Trp Phe Arg Gln Ala Gln Gly Lys Glu Arg Glu Phe Val
        35                  40                  45

Ala Thr Ile Ser Arg Ser Gly Gly His Ile Tyr Tyr Ser Asp Ser Val
    50                  55                  60

Lys Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 102
<211> LENGTH: 127
<212> TYPE: PRT
<213> ORGANISM: Artificial Sequence
<220> FEATURE:
<223> OTHER INFORMATION: Nanobody sequence

<400> SEQUENCE: 102

Glu Val Gln Leu Val Glu Ser Gly Gly Gly Leu Val Gln Ala Gly Gly
1               5                   10                  15

Ser Leu Ser Leu Ser Cys Thr Ala Ser Arg Gly Thr Phe Arg Asn Tyr
            20                  25                  30

Ala Met Gly Trp Phe Arg Gln Ala Gln Gly Lys Glu Arg Glu Phe Val
        35                  40                  45

Ala Thr Ile Ser Arg Ser Gly Gly His Ile Tyr Tyr Ser Asp Ser Val
    50                  55                  60

Lys Gly Arg Phe Ala Ile Ser Lys Asp Asn Ala Lys Asn Met Met Ser
65                  70                  75                  80

Leu Arg Met Asn Ser Leu Lys Pro Glu Asp Thr Ala Val Tyr Tyr Cys
                85                  90                  95

Ala Ala Arg Phe Arg Phe Asp Asp Gly Thr Tyr Phe Tyr Gln Arg Ala
            100                 105                 110

Phe Tyr Asp Phe Trp Gly Gln Gly Thr Gln Val Thr Val Ser Ser
        115                 120                 125

<210> SEQ ID NO 103
<211> LENGTH: 127
<212> TYPE: PRT
<213> ORGANISM: Artificial Sequence
<220> FEATURE:
<223> OTHER INFORMATION: Nanobody sequence

<400> SEQUENCE: 103

Lys Val Gln Leu Val Glu Ser Arg Gly Gly Leu Val Gln Ala Gly Gly
1               5                   10                  15

Ser Leu Arg Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45
```

```
Ala Ala Val Ser Arg Thr Gly Gly Arg Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Lys Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
                100                 105                 110

Phe Tyr Asp Phe Trp Gly Gln Gly Thr Gln Val Thr Val Ser Ser
                115                 120                 125

<210> SEQ ID NO 104
<211> LENGTH: 127
<212> TYPE: PRT
<213> ORGANISM: Artificial Sequence
<220> FEATURE:
<223> OTHER INFORMATION: Nanobody sequence

<400> SEQUENCE: 104

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Ser Tyr
                20                  25                  30

Gly Met Gly Trp Phe Arg Gln Ala Gln Gly Lys Glu Arg Glu Phe Val
                35                  40                  45

Ala Ala Ile Ser Arg Thr Gly Gly His Thr Tyr Tyr Ser Asp Ser Val
    50                  55                  60

Lys Gly Arg Phe Thr Ile Ser Lys Asn Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Tyr Gln Arg Ala
                100                 105                 110

Phe Tyr Asp Phe Trp Gly Gln Gly Thr Gln Val Thr Val Ser Ser
                115                 120                 125

<210> SEQ ID NO 105
<211> LENGTH: 127
<212> TYPE: PRT
<213> ORGANISM: Artificial Sequence
<220> FEATURE:
<223> OTHER INFORMATION: Nanobody sequence

<400> SEQUENCE: 105

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Asn Phe Arg Asn Phe
                20                  25                  30

Gly Met Gly Trp Phe Arg Gln Ala Gln Gly Thr Glu Arg Glu Phe Val
                35                  40                  45

Ala Ala Ile Ser Arg Thr Gly Gly Arg Thr Tyr Phe Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Asn
                100                 105                 110
```

Phe Tyr Asp Phe Trp Gly Gln Gly Ala Gln Val Thr Val Ser Ser
            115                 120                 125

<210> SEQ ID NO 106
<211> LENGTH: 127
<212> TYPE: PRT
<213> ORGANISM: Artificial Sequence
<220> FEATURE:
<223> OTHER INFORMATION: Nanobody sequence

<400> SEQUENCE: 106

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
            20                  25                  30

Ala Met Gly Trp Phe Arg Glu Ala Gln Gly Lys Glu Arg Glu Phe Val
            35                  40                  45

Ala Thr Ile Ser Arg Ser Gly Gly His Thr Tyr Tyr Ser Asp Ser Val
        50                  55                  60

Lys Gly Arg Phe Thr Ile Ser Arg Asp Asn Ala Lys Asn Met Val Ala
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asn Leu Trp Gly Gln Gly Thr Gln Val Thr Val Ser Ser
            115                 120                 125

<210> SEQ ID NO 107
<211> LENGTH: 127
<212> TYPE: PRT
<213> ORGANISM: Artificial Sequence
<220> FEATURE:
<223> OTHER INFORMATION: Nanobody sequence

<400> SEQUENCE: 107

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
            35                  40                  45

Ala Ala Ile Ser Arg Thr Gly Gly His Thr Tyr Tyr Ser Asp Ser Val
        50                  55                  60

Lys Gly Arg Phe Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Tyr Gln Arg Asn
            100                 105                 110

Phe Tyr Asp Phe Trp Gly Gln Gly Thr Gln Val Thr Val Ser Ser
            115                 120                 125

<210> SEQ ID NO 108
<211> LENGTH: 127
<212> TYPE: PRT
<213> ORGANISM: Artificial Sequence
<220> FEATURE:
<223> OTHER INFORMATION: Nanobody sequence

<400> SEQUENCE: 108

Glu Val Gln Leu Val Glu Ser Gly Gly Gly Leu Val Gln Ala Gly Gly
1               5                   10                  15

Ser Leu Ser Leu Ser Cys Thr Ala Ser Val Gly Asn Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 109
<211> LENGTH: 127
<212> TYPE: PRT
<213> ORGANISM: Artificial Sequence
<220> FEATURE:
<223> OTHER INFORMATION: Nanobody sequence

<400> SEQUENCE: 109

Glu Val Gln Leu Val Glu Ser Gly Gly Gly Leu Val Gln Ala Gly Gly
1               5                   10                  15

Ser Leu Ser Leu Ser Cys Thr Val Ser Gly Gly Asn Phe Arg Asn Phe
            20                  25                  30

Gly Met Gly Trp Phe Arg Gln Ala His Gly Lys Glu Arg Glu Phe Val
        35                  40                  45

Ala Ala Ile Ser Arg Ser Gly Gly Arg Thr Tyr Tyr Ala Asp Ser Val
    50                  55                  60

Lys Gly Arg Phe Thr Val Ser Arg Asp Asn Ala Lys Asn Met Val Ser
65                  70                  75                  80

Leu Gln Met Asn Ser Leu Lys Pro Glu Asp Thr Ala Val Tyr Ser Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 110
<211> LENGTH: 127
<212> TYPE: PRT
<213> ORGANISM: Artificial Sequence
<220> FEATURE:
<223> OTHER INFORMATION: Nanobody sequence

<400> SEQUENCE: 110

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
            20                  25                  30

Gly Met Gly Trp Phe Arg Gln Ala Gln Gly Lys Glu Arg Glu Phe Val
        35                  40                  45

```
Ala Ala Ile Ser Arg Thr Gly His Thr Tyr Tyr Gln Asp Ser Val
        50                  55                  60

Lys Gly Arg Phe Thr Ile Ser Lys Asp Asn Ala Lys Asn Ile Leu Ser
 65                  70                  75                  80

Leu Gln Met Asn Ser Leu Lys Pro Glu Asp Thr Ala Val Tyr Tyr Cys
                 85                  90                  95

Ala Ala Arg Phe Arg Phe Gly Asp Gly Thr Tyr Tyr Tyr Gln Arg Ala
                100                 105                 110

Phe Tyr Asp Phe Trp Gly Gln Gly Thr Gln Val Thr Val Ser Ser
                115                 120                 125

<210> SEQ ID NO 111
<211> LENGTH: 127
<212> TYPE: PRT
<213> ORGANISM: Artificial Sequence
<220> FEATURE:
<223> OTHER INFORMATION: Nanobody sequence

<400> SEQUENCE: 111

Glu Val Gln Leu Val Glu Ser Gly Gly Gly Leu Val Gln Ala Gly Gly
 1               5                  10                  15

Ser Leu Ser Leu Ser Cys Thr Ala Ser Gly Gly Thr Phe Arg Asn Phe
                 20                  25                  30

Ala Met Gly Trp Phe Arg Gln Ala Gln Gly Lys Glu Arg Glu Phe Val
                 35                  40                  45

Ala Thr Ile Ser Arg Ser Gly Gly His Ile Phe Tyr Ser Glu Ser Val
        50                  55                  60

Lys Gly Arg Phe Thr Ile Ser Arg Asp Asn Ala Lys Asn Met Val Ser
 65                  70                  75                  80

Leu Gln Met Asn Ser Leu Lys Pro Glu Asp Thr Ala Val Tyr Tyr Cys
                 85                  90                  95

Ala Ala Arg Phe Arg Ser Asp Asp Gly Thr Tyr Tyr Tyr Gln Arg Ile
                100                 105                 110

Phe Tyr Asp Phe Trp Gly Gln Gly Thr Gln Val Thr Val Ser Ser
                115                 120                 125

<210> SEQ ID NO 112
<211> LENGTH: 127
<212> TYPE: PRT
<213> ORGANISM: Artificial Sequence
<220> FEATURE:
<223> OTHER INFORMATION: Nanobody sequence

<400> SEQUENCE: 112

Glu Val Gln Leu Val Glu Ser Gly Gly Gly Leu Val Gln Pro Gly Gly
 1               5                  10                  15

Ser Leu Ser Leu Ser Cys Thr Ala Ser Ala Gly Thr Phe Arg Asn Phe
                 20                  25                  30

Gly Met Gly Trp Phe Arg Gln Ala Arg Gly Glu Glu Arg Glu Phe Val
                 35                  40                  45

Ala Thr Ile Ser Arg Ser Ala Arg His Thr Tyr Tyr Ser Asp Ser Val
        50                  55                  60

Lys Gly Arg Phe Thr Ile Ser Arg Asp Asn Ala Lys Asn Met Val Ser
 65                  70                  75                  80

Leu Gln Met Asn Ser Leu Lys Pro Glu Asp Thr Ala Val Tyr Tyr Cys
                 85                  90                  95

Ala Ala Arg Phe Arg Ser Asp Asp Gly Thr Tyr Tyr Tyr Gln Arg Ala
```

```
                    100                 105                 110

Phe Tyr Asp Phe Trp Gly Gln Gly Thr Gln Val Thr Val Ser Ser
        115                 120                 125

<210> SEQ ID NO 113
<211> LENGTH: 127
<212> TYPE: PRT
<213> ORGANISM: Artificial Sequence
<220> FEATURE:
<223> OTHER INFORMATION: Nanobody sequence

<400> SEQUENCE: 113

Glu Val Gln Leu Val Glu Ser Gly Gly Ser Val Gln Ala Gly Gly
1               5                   10                  15

Ser Leu Ser Leu Ser Cys Thr Ala Ser Arg Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Gly His Thr Tyr Tyr Ser Asp Ser Val
    50                  55                  60

Lys Gly Arg Phe Thr Ile Ser Lys Asp Asn Ala Lys Asn Ile Met Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Gln Arg Ala
                100                 105                 110

Phe Tyr Asp Phe Trp Gly Gln Gly Thr Gln Val Thr Val Ser Ser
        115                 120                 125

<210> SEQ ID NO 114
<211> LENGTH: 127
<212> TYPE: PRT
<213> ORGANISM: Artificial Sequence
<220> FEATURE:
<223> OTHER INFORMATION: Nanobody sequence

<400> SEQUENCE: 114

Glu Val Gln Leu Val Glu Ser Gly Gly Gly Leu Val Gln Ala Gly Gly
1               5                   10                  15

Ser Leu Ser Leu Ser Cys Thr Val Ser Gly Gly Asn Phe Arg Asn Phe
            20                  25                  30

Gly Val Gly Trp Phe Arg Gln Ala His Gly Lys Glu Arg Glu Phe Val
        35                  40                  45

Ala Ala Ile Ser Arg Ala Gly Gly Arg Thr Tyr Tyr Ala Asp Ser Val
    50                  55                  60

Lys Gly Arg Phe Ala Ile Ser Arg Asp Asn Ala Lys Asn Met Val Ser
65                  70                  75                  80

Leu Gln Met Asn Ser Leu Lys Pro Glu Asp Thr Ala Val Tyr Thr Cys
                85                  90                  95

Ala Ala Arg Phe Arg Ser Gly Asp Gly Thr Ser Tyr Tyr Glu Arg Ala
                100                 105                 110

Phe Tyr Asp Phe Trp Gly Gln Gly Thr Gln Val Thr Val Ser Ser
        115                 120                 125

<210> SEQ ID NO 115
<211> LENGTH: 127
<212> TYPE: PRT
<213> ORGANISM: Artificial Sequence
<220> FEATURE:
```

<223> OTHER INFORMATION: Nanobody sequence

<400> SEQUENCE: 115

Lys Val Gln Leu Val Glu Ser Gly Gly Gly Leu Val Gln Pro Gly Gly
1               5                   10                  15

Ser Leu Ser Leu Ser Cys Thr Ala Ser Ala Gly Thr Phe Arg Asn Phe
            20                  25                  30

Gly Met Gly Trp Phe Arg Gln Ala Gln Gly Thr Glu Arg Glu Phe Val
        35                  40                  45

Ala Ala Ile Ser Arg Ser Gly Gly Arg Thr Tyr Phe Ser Asp Ser Val
    50                  55                  60

Lys Gly Arg Phe Thr Ile Ser Lys Asp Asn Ala Lys Asn Met Leu Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Ala Gln Val Thr Val Ser Ser
            115                 120                 125

<210> SEQ ID NO 116
<211> LENGTH: 127
<212> TYPE: PRT
<213> ORGANISM: Artificial Sequence
<220> FEATURE:
<223> OTHER INFORMATION: Nanobody sequence

<400> SEQUENCE: 116

Glu Val Gln Leu Val Glu Ser Gly Gly Gly Leu Val Gln Ala Gly Gly
1               5                   10                  15

Ser Leu Ser Leu Ser Cys Thr Val Ser Gly Gly Thr Phe Arg Asn Tyr
            20                  25                  30

Gly Met Gly Trp Phe Arg Gln Phe Gln Gly Lys Glu Arg Glu Phe Val
        35                  40                  45

Ala Ala Ile Ser Arg Ser Gly Gly His Ile Phe Tyr Ser Glu Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Gly Asp Gly Thr Tyr Tyr Tyr Gln Arg Ala
            100                 105                 110

Phe Tyr Asp Phe Trp Gly Gln Gly Thr Gln Val Thr Val Ser Ser
            115                 120                 125

<210> SEQ ID NO 117
<211> LENGTH: 127
<212> TYPE: PRT
<213> ORGANISM: Artificial Sequence
<220> FEATURE:
<223> OTHER INFORMATION: Nanobody sequence

<400> SEQUENCE: 117

Glu Val Gln Leu Val Glu Ser Gly Gly Gly Leu Val Gln Ala Gly Gly
1               5                   10                  15

Ser Leu Ser Leu Ser Cys Thr Ala Ser Ala Gly Thr Phe Arg Asn Phe
            20                  25                  30

Gly Met Gly Trp Phe Arg Gln Ala Arg Gly Glu Ala Arg Glu Phe Val

```
            35                  40                  45
Ala Thr Ile Ser Arg Ser Gly Gly His Ile Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Gln Arg Ala
                100                 105                 110

Phe Tyr Asp Phe Trp Gly Gln Gly Thr Gln Val Thr Val Ser Ser
            115                 120                 125

<210> SEQ ID NO 118
<211> LENGTH: 127
<212> TYPE: PRT
<213> ORGANISM: Artificial Sequence
<220> FEATURE:
<223> OTHER INFORMATION: Nanobody sequence

<400> SEQUENCE: 118

Glu Val Gln Leu Val Glu Ser Gly Gly Gly Leu Val Arg Ala Gly Gly
1               5                   10                  15

Ser Leu Ser Leu Ser Cys Thr Ser Ser Gly Thr Phe Arg Asn Phe
                20                  25                  30

Ala Met Gly Trp Phe Arg Gln Ala Gln Gly Lys Glu Arg Glu Phe Val
            35                  40                  45

Ala Thr Ile Ser Arg Ser Gly Gly His Thr Tyr Tyr Ser Asp Ser Val
    50                  55                  60

Lys Gly Arg Phe Thr Ile Ser Arg Asp Asn Ala Lys Asn Leu Val Ser
65                  70                  75                  80

Leu Gln Met Ser Ser Leu Lys Pro Glu Asp Thr Ala Val Tyr Tyr Cys
                85                  90                  95

Ala Ala Arg Phe Arg Phe Asp Asp Thr Tyr Tyr Gln Arg Ala
                100                 105                 110

Phe Tyr Asp Phe Trp Gly Gln Gly Thr Gln Val Thr Val Ser Ser
            115                 120                 125

<210> SEQ ID NO 119
<211> LENGTH: 127
<212> TYPE: PRT
<213> ORGANISM: Artificial Sequence
<220> FEATURE:
<223> OTHER INFORMATION: Nanobody sequence

<400> SEQUENCE: 119

Glu Val Gln Leu Val Glu Ser Gly Gly Gly Ser Val Gln Ala Gly Asn
1               5                   10                  15

Ser Leu Ser Leu Ser Cys Thr Ala Ser Gly Gly Thr Phe Arg Asn Tyr
                20                  25                  30

Ala Met Gly Trp Phe Arg Gln Ala Gln Gly Lys Glu Arg Glu Phe Val
            35                  40                  45

Ala Thr Ile Ser Arg Ser Gly Gly His Ile Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Ala Tyr Tyr Cys
                85                  90                  95
```

-continued

Ala Ala Arg Phe Arg Phe Gly Asp Gly Thr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 120
<211> LENGTH: 127
<212> TYPE: PRT
<213> ORGANISM: Artificial Sequence
<220> FEATURE:
<223> OTHER INFORMATION: Nanobody sequence

<400> SEQUENCE: 120

Glu Val Gln Leu Val Glu Ser Gly Gly Gly Leu Val Gln Ala Gly Asp
1               5                   10                  15

Ser Leu Ser Leu Ser Cys Thr Ala Ser Arg Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Ser Gly Gly His Lys Tyr Tyr Ser Asp Ser Val
    50                  55                  60

Lys Gly Arg Ser Thr Ile Ser Lys Asp Asn Ala Lys Asn Met Val Ser
65                  70                  75                  80

Leu Gln Met Asn Ser Leu Lys Pro Glu Asp Thr Ala Val Tyr Tyr Cys
            85                  90                  95

Ala Ala Arg Phe Arg Phe Asp Asp Gly Thr Ser Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 121
<211> LENGTH: 127
<212> TYPE: PRT
<213> ORGANISM: Artificial Sequence
<220> FEATURE:
<223> OTHER INFORMATION: Nanobody sequence

<400> SEQUENCE: 121

Glu Val Gln Leu Val Glu Ser Gly Gly Gly Leu Ala Gln Ala Gly Gly
1               5                   10                  15

Ser Leu Ser Leu Ser Cys Thr Ala Ser Gly Gly Asn Phe Arg Asn Phe
            20                  25                  30

Gly Met Gly Trp Phe Arg Gln Val Gln Gly Thr Glu Arg Glu Phe Val
        35                  40                  45

Ala Ala Ile Ser Arg Thr Gly Gly Arg Thr Tyr Phe Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Ser Ala Val Tyr Tyr Cys
            85                  90                  95

Ala Ala Arg Phe Arg Phe Gly Asp Gly Thr Tyr Tyr Tyr Gln Arg Asn
            100                 105                 110

Phe Tyr Gly Phe Trp Gly Gln Gly Ala Gln Val Thr Val Ser Ser
        115                 120                 125

<210> SEQ ID NO 122
<211> LENGTH: 127
<212> TYPE: PRT
<213> ORGANISM: Artificial Sequence

```
<220> FEATURE:
<223> OTHER INFORMATION: Nanobody sequence

<400> SEQUENCE: 122

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Tyr
            20                  25                  30

Gly Met Gly Trp Phe Arg Gln Ala Gln Gly Lys Glu Arg Glu Phe Val
        35                  40                  45

Ala Ala Ile Ser Arg Ser Ala Gly His Ile Tyr Tyr Leu Asn Ser Val
    50                  55                  60

Lys Gly Arg Phe Thr Ile Ser Lys Asp Asn Ala Lys Asn Ile Leu Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 123
<211> LENGTH: 127
<212> TYPE: PRT
<213> ORGANISM: Artificial Sequence
<220> FEATURE:
<223> OTHER INFORMATION: Nanobody sequence

<400> SEQUENCE: 123

Glu Val Gln Leu Val Glu Ser Gly Gly Gly Leu Val Gln Ala Gly Asn
1               5                   10                  15

Ser Leu Ser Leu Ser Cys Thr Ala Ser Ala Gly Thr Leu Arg Asn Phe
            20                  25                  30

Gly Met Gly Trp Phe Arg Gln Ala Arg Gly Glu Glu Arg Glu Phe Val
        35                  40                  45

Ala Thr Ile Ser Arg Ser Ala Arg His Thr Tyr Tyr Ser Asp Ser Val
    50                  55                  60

Lys Gly Arg Phe Thr Ile Ser Arg Asp Asn Ala Lys Asn Met Val Ser
65                  70                  75                  80

Leu Gln Met Asn Ser Leu Lys Pro Glu Asp Thr Ala Val Tyr Tyr Cys
                85                  90                  95

Ala Ala Arg Phe Arg Ser Asp Asp Gly Thr Tyr Tyr Tyr Gln Arg Ala
            100                 105                 110

Phe Tyr Asp Phe Trp Gly Gln Gly Thr Gln Val Thr Val Ser Ser
        115                 120                 125

<210> SEQ ID NO 124
<211> LENGTH: 25
<212> TYPE: PRT
<213> ORGANISM: Artificial Sequence
<220> FEATURE:
<223> OTHER INFORMATION: framework 1 sequence

<400> SEQUENCE: 124

Glu Val Gln Leu Val Glu Ser Gly Gly Gly Leu Val Gln Ala Gly Gly
1               5                   10                  15

Ser Leu Arg Leu Ser Cys Ser Ala Ser
            20                  25
```

<210> SEQ ID NO 125
<211> LENGTH: 25
<212> TYPE: PRT
<213> ORGANISM: Artificial Sequence
<220> FEATURE:
<223> OTHER INFORMATION: framework 1 sequence

<400> SEQUENCE: 125

Glu Val Gln Leu Val Glu Ser Gly Gly Gly Leu Val Gln Ala Gly Gly
1               5                   10                  15

Ser Leu Gly Leu Ser Cys Ser Ala Ser
            20                  25

<210> SEQ ID NO 126
<211> LENGTH: 25
<212> TYPE: PRT
<213> ORGANISM: Artificial Sequence
<220> FEATURE:
<223> OTHER INFORMATION: framework 1 sequence

<400> SEQUENCE: 126

Glu Val Gln Leu Val Glu Ser Gly Gly Gly Leu Val Gln Ala Gly Gly
1               5                   10                  15

Ser Leu Glu Leu Ser Cys Ser Ala Ser
            20                  25

<210> SEQ ID NO 127
<211> LENGTH: 25
<212> TYPE: PRT
<213> ORGANISM: Artificial Sequence
<220> FEATURE:
<223> OTHER INFORMATION: framework 1 sequence

<400> SEQUENCE: 127

Glu Val Gln Leu Val Glu Ser Gly Gly Gly Leu Val Gln Pro Gly Gly
1               5                   10                  15

Ser Leu Gly Leu Ser Cys Ser Ala Ser
            20                  25

<210> SEQ ID NO 128
<211> LENGTH: 25
<212> TYPE: PRT
<213> ORGANISM: Artificial Sequence
<220> FEATURE:
<223> OTHER INFORMATION: framework 1 sequence

<400> SEQUENCE: 128

Glu Val Gln Leu Val Glu Ser Ala Gly Gly Leu Val Gln Ala Gly Gly
1               5                   10                  15

Ser Pro Gly Leu Ser Ser Ser Asp Ser
            20                  25

<210> SEQ ID NO 129
<211> LENGTH: 25
<212> TYPE: PRT
<213> ORGANISM: Artificial Sequence
<220> FEATURE:
<223> OTHER INFORMATION: framework 1 sequence

<400> SEQUENCE: 129

Glu Val Gln Leu Val Glu Ser Gly Gly Gly Leu Val Gln Ala Gly Gly
1               5                   10                  15

Ala Leu Gly Leu Pro Cys Ser Ala Ser
            20                  25

<210> SEQ ID NO 130
<211> LENGTH: 25
<212> TYPE: PRT
<213> ORGANISM: Artificial Sequence
<220> FEATURE:
<223> OTHER INFORMATION: framework 1 sequence

<400> SEQUENCE: 130

Glu Val Gln Leu Val Glu Ser Gly Gly Gly Leu Ala Gln Ala Gly Gly
1               5                   10                  15

Ser Leu Gly Leu Ser Cys Ser Ala Ser
            20                  25

<210> SEQ ID NO 131
<211> LENGTH: 25
<212> TYPE: PRT
<213> ORGANISM: Artificial Sequence
<220> FEATURE:
<223> OTHER INFORMATION: framework 1 sequence

<400> SEQUENCE: 131

Glu Val Gln Leu Val Glu Ser Gly Gly Gly Phe Val Gln Ala Gly Gly
1               5                   10                  15

Ser Leu Gly His Ser Cys Ser Ala Ser
            20                  25

<210> SEQ ID NO 132
<211> LENGTH: 25
<212> TYPE: PRT
<213> ORGANISM: Artificial Sequence
<220> FEATURE:
<223> OTHER INFORMATION: framework 1 sequence

<400> SEQUENCE: 132

Glu Val Gln Leu Val Glu Ser Gly Gly Gly Leu Val Gln Ala Gly Gly
1               5                   10                  15

Ser Leu Gly Ala Ser Arg Ser Ala Ser
            20                  25

<210> SEQ ID NO 133
<211> LENGTH: 25
<212> TYPE: PRT
<213> ORGANISM: Artificial Sequence
<220> FEATURE:
<223> OTHER INFORMATION: framework 1 sequence

<400> SEQUENCE: 133

Glu Val Gln Leu Val Glu Ser Gly Gly Gly Leu Val Gln Ala Gly Gly
1               5                   10                  15

Ser Leu Gly Leu Ser Cys Ser Ala Pro
            20                  25

<210> SEQ ID NO 134
<211> LENGTH: 25
<212> TYPE: PRT
<213> ORGANISM: Artificial Sequence
<220> FEATURE:
<223> OTHER INFORMATION: framework 1 sequence

<400> SEQUENCE: 134

Glu Val Gln Leu Val Glu Ser Gly Gly Cys Leu Val Gln Ala Gly Gly
1               5                   10                  15

Ser Leu Gly Leu Ser Cys Ser Ala Ser

<210> SEQ ID NO 135
<211> LENGTH: 25
<212> TYPE: PRT
<213> ORGANISM: Artificial Sequence
<220> FEATURE:
<223> OTHER INFORMATION: framework 1 sequence

<400> SEQUENCE: 135

Glu Val Gln Leu Val Glu Ser Gly Gly Gly Leu Val Gln Ala Gly Gly
1               5                   10                  15

Ser Leu Gly Leu Ala Cys Ser Ala Ser
            20                  25

<210> SEQ ID NO 136
<211> LENGTH: 25
<212> TYPE: PRT
<213> ORGANISM: Artificial Sequence
<220> FEATURE:
<223> OTHER INFORMATION: framework 1 sequence

<400> SEQUENCE: 136

Glu Val Gln Leu Val Glu Ser Gly Gly Gly Leu Val Gln Ala Gly Gly
1               5                   10                  15

Ala Leu Gly Leu Ser Cys Ser Ala Ser
            20                  25

<210> SEQ ID NO 137
<211> LENGTH: 25
<212> TYPE: PRT
<213> ORGANISM: Artificial Sequence
<220> FEATURE:
<223> OTHER INFORMATION: framework 1 sequence

<400> SEQUENCE: 137

Glu Val Gln Leu Val Glu Ser Gly Gly Gly Ser Ala Gln Pro Gly Glu
1               5                   10                  15

Ser Leu Arg Leu Ser Cys Ser Ala Ser
            20                  25

<210> SEQ ID NO 138
<211> LENGTH: 25
<212> TYPE: PRT
<213> ORGANISM: Artificial Sequence
<220> FEATURE:
<223> OTHER INFORMATION: framework 1 sequence

<400> SEQUENCE: 138

Glu Val Gln Leu Val Glu Ser Gly Gly Gly Leu Val Gln Ala Gly Gly
1               5                   10                  15

Ala Leu Gly Phe Thr Cys Ser Asp Ser
            20                  25

<210> SEQ ID NO 139
<211> LENGTH: 25
<212> TYPE: PRT
<213> ORGANISM: Artificial Sequence
<220> FEATURE:
<223> OTHER INFORMATION: framework 1 sequence

<400> SEQUENCE: 139

Glu Val Gln Leu Val Glu Ser Gly Gly Ala Leu Val Gln Ala Gly Gly
1               5                   10                  15

-continued

Ser Leu Gly Leu Pro Cys Ser Ala Pro
            20                  25

<210> SEQ ID NO 140
<211> LENGTH: 25
<212> TYPE: PRT
<213> ORGANISM: Artificial Sequence
<220> FEATURE:
<223> OTHER INFORMATION: framework 1 sequence

<400> SEQUENCE: 140

Glu Val Gln Leu Val Glu Ser Gly Gly Gly Phe Asp Gln Ala Gly Gly
1               5                   10                  15

Ser Leu Gly Leu Pro Cys Ser Ala Pro
            20                  25

<210> SEQ ID NO 141
<211> LENGTH: 25
<212> TYPE: PRT
<213> ORGANISM: Artificial Sequence
<220> FEATURE:
<223> OTHER INFORMATION: framework 1 sequence

<400> SEQUENCE: 141

Glu Val Gln Leu Val Glu Ser Gly Gly Asp Leu Val Gln Ala Gly Gly
1               5                   10                  15

Ala Leu Gly Leu Ser Cys Pro Ala Ser
            20                  25

<210> SEQ ID NO 142
<211> LENGTH: 25
<212> TYPE: PRT
<213> ORGANISM: Artificial Sequence
<220> FEATURE:
<223> OTHER INFORMATION: framework 1 sequence

<400> SEQUENCE: 142

Glu Val Gln Leu Val Glu Ser Gly Gly Gly Leu Val Lys Ala Gly Gly
1               5                   10                  15

Ser Leu Gly Leu Ser Cys Ser Ala Ser
            20                  25

<210> SEQ ID NO 143
<211> LENGTH: 25
<212> TYPE: PRT
<213> ORGANISM: Artificial Sequence
<220> FEATURE:
<223> OTHER INFORMATION: framework 1 sequence

<400> SEQUENCE: 143

Glu Val Gln Leu Val Glu Ser Ala Gly Gly Leu Val Gln Ala Gly Gly
1               5                   10                  15

Ser Leu Gly Leu Ser Cys Ser Ala Ser
            20                  25

<210> SEQ ID NO 144
<211> LENGTH: 25
<212> TYPE: PRT
<213> ORGANISM: Artificial Sequence
<220> FEATURE:
<223> OTHER INFORMATION: framework 1 sequence

<400> SEQUENCE: 144

Glu Val Gln Leu Val Glu Ser Gly Gly Gly Leu Leu Gln Ala Gly Gly
1               5                   10                  15

Ser Leu Gly Leu Ser Cys Ser Ala Ser
            20                  25

<210> SEQ ID NO 145
<211> LENGTH: 25
<212> TYPE: PRT
<213> ORGANISM: Artificial Sequence
<220> FEATURE:
<223> OTHER INFORMATION: framework 1 sequence

<400> SEQUENCE: 145

Glu Val Gln Leu Val Glu Ser Gly Gly Gly Leu Val Gln Ala Gly Gly
1               5                   10                  15

Arg Arg Gly Leu Ser Cys Ser Ala Ser
            20                  25

<210> SEQ ID NO 146
<211> LENGTH: 25
<212> TYPE: PRT
<213> ORGANISM: Artificial Sequence
<220> FEATURE:
<223> OTHER INFORMATION: framework 1 sequence

<400> SEQUENCE: 146

Glu Val Gln Leu Val Glu Ser Gly Gly Ala Leu Val Gln Ala Gly Gly
1               5                   10                  15

Ser Leu Gly Leu Ser Cys Ser Ala Ser
            20                  25

<210> SEQ ID NO 147
<211> LENGTH: 25
<212> TYPE: PRT
<213> ORGANISM: Artificial Sequence
<220> FEATURE:
<223> OTHER INFORMATION: framework 1 sequence

<400> SEQUENCE: 147

Glu Val Gln Leu Val Glu Ser Gly Gly Gly Leu Val Glu Ala Gly Gly
1               5                   10                  15

Ser Leu Gly Leu Ser Cys Ser Ala Ser
            20                  25

<210> SEQ ID NO 148
<211> LENGTH: 25
<212> TYPE: PRT
<213> ORGANISM: Artificial Sequence
<220> FEATURE:
<223> OTHER INFORMATION: framework 1 sequence

<400> SEQUENCE: 148

Glu Val Gln Leu Val Glu Ser Gly Glu Gly Leu Val Gln Ala Gly Gly
1               5                   10                  15

Ser Leu Gly Leu Ser Cys Ser Ala Ser
            20                  25

<210> SEQ ID NO 149
<211> LENGTH: 25
<212> TYPE: PRT
<213> ORGANISM: Artificial Sequence
<220> FEATURE:
<223> OTHER INFORMATION: framework 1 sequence

<400> SEQUENCE: 149

Glu Val Gln Leu Val Glu Ser Gly Gly Gly Leu Val Gln Ala Gly Gly

```
                1               5                   10                  15

Pro Leu Gly Leu Ser Cys Ser Ala Ser
            20                  25

<210> SEQ ID NO 150
<211> LENGTH: 25
<212> TYPE: PRT
<213> ORGANISM: Artificial Sequence
<220> FEATURE:
<223> OTHER INFORMATION: framework 1 sequence

<400> SEQUENCE: 150

Glu Val Gln Leu Val Glu Ser Gly Gly Gly Leu Val Gln Ala Ala Gly
1               5                   10                  15

Ser Leu Gly Leu Pro Cys Ser Ala Ser
            20                  25

<210> SEQ ID NO 151
<211> LENGTH: 25
<212> TYPE: PRT
<213> ORGANISM: Artificial Sequence
<220> FEATURE:
<223> OTHER INFORMATION: framework 1 sequence

<400> SEQUENCE: 151

Glu Val Gln Leu Val Glu Ser Gly Glu Gly Leu Val Pro Ala Gly Gly
1               5                   10                  15

Ser Leu Gly Pro Ser Cys Ser Ala Ser
            20                  25

<210> SEQ ID NO 152
<211> LENGTH: 25
<212> TYPE: PRT
<213> ORGANISM: Artificial Sequence
<220> FEATURE:
<223> OTHER INFORMATION: framework 1 sequence

<400> SEQUENCE: 152

Glu Val Gln Leu Val Glu Ser Gly Gly Ala Leu Val Gln Ala Gly Gly
1               5                   10                  15

Pro Pro Gly Leu Ser Cys Ser Ala Ser
            20                  25

<210> SEQ ID NO 153
<211> LENGTH: 25
<212> TYPE: PRT
<213> ORGANISM: Artificial Sequence
<220> FEATURE:
<223> OTHER INFORMATION: framework 1 sequence

<400> SEQUENCE: 153

Glu Val Gln Leu Val Glu Ser Ala Gly Gly Leu Val Gln Ala Gly Gly
1               5                   10                  15

Pro Leu Gly Leu Ser Cys Ser Ser Ser
            20                  25

<210> SEQ ID NO 154
<211> LENGTH: 25
<212> TYPE: PRT
<213> ORGANISM: Artificial Sequence
<220> FEATURE:
<223> OTHER INFORMATION: framework 1 sequence

<400> SEQUENCE: 154
```

```
Glu Val Gln Leu Val Glu Ser Gly Gly Ala Leu Met Gln Ala Gly Gly
1               5                   10                  15

Ser Leu Gly Pro Pro Cys Pro Ala Ser
            20                  25
```

<210> SEQ ID NO 155
<211> LENGTH: 25
<212> TYPE: PRT
<213> ORGANISM: Artificial Sequence
<220> FEATURE:
<223> OTHER INFORMATION: framework 1 sequence

<400> SEQUENCE: 155

```
Glu Val Gln Leu Val Glu Ser Gly Gly Cys Leu Val Gln Ala Gly Gly
1               5                   10                  15

Ser Leu Gly Leu Ser Cys Ser Ala Pro
            20                  25
```

<210> SEQ ID NO 156
<211> LENGTH: 25
<212> TYPE: PRT
<213> ORGANISM: Artificial Sequence
<220> FEATURE:
<223> OTHER INFORMATION: framework 1 sequence

<400> SEQUENCE: 156

```
Glu Val Gln Leu Val Glu Ser Gly Gly Gly Leu Val Gln Thr Gly Gly
1               5                   10                  15

Ser Leu Thr Leu Ser Cys Ser Ala Ser
            20                  25
```

<210> SEQ ID NO 157
<211> LENGTH: 25
<212> TYPE: PRT
<213> ORGANISM: Artificial Sequence
<220> FEATURE:
<223> OTHER INFORMATION: framework 1 sequence

<400> SEQUENCE: 157

```
Glu Val Gln Leu Val Glu Ser Gly Gly Gly Ser Val His Pro Gly Gly
1               5                   10                  15

Ser Leu Arg Leu Ser Cys Ser Ala Ser
            20                  25
```

<210> SEQ ID NO 158
<211> LENGTH: 25
<212> TYPE: PRT
<213> ORGANISM: Artificial Sequence
<220> FEATURE:
<223> OTHER INFORMATION: framework 1 sequence

<400> SEQUENCE: 158

```
Glu Val Gln Leu Val Glu Ser Gly Gly Gly Leu Glu Gln Ala Gly Gly
1               5                   10                  15

Ser Leu Arg Leu Ser Cys Ser Ala Ser
            20                  25
```

<210> SEQ ID NO 159
<211> LENGTH: 25
<212> TYPE: PRT
<213> ORGANISM: Artificial Sequence
<220> FEATURE:
<223> OTHER INFORMATION: framework 1 sequence

<400> SEQUENCE: 159

```
Glu Val Gln Leu Val Glu Ser Gly Gly Gly Leu Val Lys Ala Gly Gly
1               5                   10                  15

Ser Leu Arg Leu Ser Cys Ser Ala Ser
            20                  25

<210> SEQ ID NO 160
<211> LENGTH: 25
<212> TYPE: PRT
<213> ORGANISM: Artificial Sequence
<220> FEATURE:
<223> OTHER INFORMATION: framework 1 sequence

<400> SEQUENCE: 160

Glu Val Gln Leu Val Glu Ser Ala Gly Gly Leu Val Pro Ala Gly Gly
1               5                   10                  15

Ser Leu Arg Leu Pro Cys Ser Ala Pro
            20                  25

<210> SEQ ID NO 161
<211> LENGTH: 25
<212> TYPE: PRT
<213> ORGANISM: Artificial Sequence
<220> FEATURE:
<223> OTHER INFORMATION: framework 1 sequence

<400> SEQUENCE: 161

Glu Val Gln Leu Val Glu Ser Gly Gly Gly Phe Val Gln Ala Gly Gly
1               5                   10                  15

Ser Leu Arg Leu Ser Cys Ser Ala Ser
            20                  25

<210> SEQ ID NO 162
<211> LENGTH: 25
<212> TYPE: PRT
<213> ORGANISM: Artificial Sequence
<220> FEATURE:
<223> OTHER INFORMATION: framework 1 sequence

<400> SEQUENCE: 162

Glu Val Gln Leu Val Glu Ser Gly Glu Gly Leu Val Lys Ala Gly Glu
1               5                   10                  15

Ser Leu Arg Leu Ser Cys Ser Ala Ser
            20                  25

<210> SEQ ID NO 163
<211> LENGTH: 25
<212> TYPE: PRT
<213> ORGANISM: Artificial Sequence
<220> FEATURE:
<223> OTHER INFORMATION: framework 1 sequence

<400> SEQUENCE: 163

Glu Val Gln Leu Val Glu Ser Gly Gly Gly Leu Val Gln Ala Gly Asp
1               5                   10                  15

Ser Leu Ser Leu Ser Cys Thr Ala Ser
            20                  25

<210> SEQ ID NO 164
<211> LENGTH: 25
<212> TYPE: PRT
<213> ORGANISM: Artificial Sequence
<220> FEATURE:
<223> OTHER INFORMATION: framework 1 sequence
```

```
<400> SEQUENCE: 164

Glu Val Gln Leu Val Glu Ser Gly Gly Gly Leu Val Gln Ala Gly Gly
1               5                   10                  15

Ser Leu Ser Leu Ser Cys Thr Ala Ser
            20                  25

<210> SEQ ID NO 165
<211> LENGTH: 25
<212> TYPE: PRT
<213> ORGANISM: Artificial Sequence
<220> FEATURE:
<223> OTHER INFORMATION: framework 1 sequence

<400> SEQUENCE: 165

Glu Val Gln Leu Val Glu Ser Gly Gly Gly Leu Val Gln Ala Gly Gly
1               5                   10                  15

Ser Leu Ser Leu Ser Cys Thr Val Ser
            20                  25

<210> SEQ ID NO 166
<211> LENGTH: 25
<212> TYPE: PRT
<213> ORGANISM: Artificial Sequence
<220> FEATURE:
<223> OTHER INFORMATION: framework 1 sequence

<400> SEQUENCE: 166

Glu Val Gln Leu Val Glu Ser Gly Gly Gly Leu Val Arg Ala Gly Gly
1               5                   10                  15

Ser Leu Ser Leu Ser Cys Thr Ser Ser
            20                  25

<210> SEQ ID NO 167
<211> LENGTH: 25
<212> TYPE: PRT
<213> ORGANISM: Artificial Sequence
<220> FEATURE:
<223> OTHER INFORMATION: framework 1 sequence

<400> SEQUENCE: 167

Glu Val Gln Leu Val Glu Ser Gly Gly Gly Leu Ala Gln Ala Gly Gly
1               5                   10                  15

Ser Leu Ser Leu Ser Cys Thr Ala Ser
            20                  25

<210> SEQ ID NO 168
<211> LENGTH: 25
<212> TYPE: PRT
<213> ORGANISM: Artificial Sequence
<220> FEATURE:
<223> OTHER INFORMATION: framework 1 sequence

<400> SEQUENCE: 168

Glu Val Gln Leu Val Glu Ser Gly Gly Gly Leu Val Gln Thr Gly Gly
1               5                   10                  15

Ser Leu Ser Leu Ser Cys Thr Ala Ser
            20                  25

<210> SEQ ID NO 169
<211> LENGTH: 25
<212> TYPE: PRT
<213> ORGANISM: Artificial Sequence
<220> FEATURE:
<223> OTHER INFORMATION: framework 1 sequence
```

```
<400> SEQUENCE: 169

Glu Val Gln Leu Val Glu Ser Gly Gly Gly Ser Val Gln Ala Gly Gly
1               5                   10                  15

Ser Leu Ser Leu Ser Cys Thr Ala Ser
            20                  25

<210> SEQ ID NO 170
<211> LENGTH: 25
<212> TYPE: PRT
<213> ORGANISM: Artificial Sequence
<220> FEATURE:
<223> OTHER INFORMATION: framework 1 sequence

<400> SEQUENCE: 170

Glu Val Gln Leu Val Glu Ser Gly Gly Gly Leu Val Glu Ala Gly Gly
1               5                   10                  15

Ser Leu Ser Leu Ser Cys Thr Ala Ser
            20                  25

<210> SEQ ID NO 171
<211> LENGTH: 25
<212> TYPE: PRT
<213> ORGANISM: Artificial Sequence
<220> FEATURE:
<223> OTHER INFORMATION: framework 1 sequence

<400> SEQUENCE: 171

Glu Val Gln Leu Val Glu Ser Gly Gly Gly Leu Val Gln Ala Gly Gly
1               5                   10                  15

Ser Leu Ser Leu Ser Cys Thr Ser Ser
            20                  25

<210> SEQ ID NO 172
<211> LENGTH: 25
<212> TYPE: PRT
<213> ORGANISM: Artificial Sequence
<220> FEATURE:
<223> OTHER INFORMATION: framework 1 sequence

<400> SEQUENCE: 172

Glu Val Gln Leu Val Glu Ser Gly Gly Gly Leu Val Gln Ala Gly Gly
1               5                   10                  15

Ser Leu Ser Leu Pro Cys Thr Ala Ser
            20                  25

<210> SEQ ID NO 173
<211> LENGTH: 25
<212> TYPE: PRT
<213> ORGANISM: Artificial Sequence
<220> FEATURE:
<223> OTHER INFORMATION: framework 1 sequence

<400> SEQUENCE: 173

Glu Val Gln Leu Val Glu Ser Gly Gly Asp Leu Val Gln Pro Gly Gly
1               5                   10                  15

Ser Leu Arg Leu Ser Cys Thr Ala Ser
            20                  25

<210> SEQ ID NO 174
<211> LENGTH: 25
<212> TYPE: PRT
<213> ORGANISM: Artificial Sequence
<220> FEATURE:
```

<223> OTHER INFORMATION: framework 1 sequence

<400> SEQUENCE: 174

Glu Val Gln Leu Val Glu Ser Gly Gly Gly Leu Val Gln Ala Gly Gly
1               5                   10                  15

Pro Leu Ser Leu Ser Cys Thr Ala Ser
            20                  25

<210> SEQ ID NO 175
<211> LENGTH: 25
<212> TYPE: PRT
<213> ORGANISM: Artificial Sequence
<220> FEATURE:
<223> OTHER INFORMATION: framework 1 sequence

<400> SEQUENCE: 175

Glu Val Gln Leu Val Glu Ser Gly Gly Gly Ser Val Gln Ala Gly Gly
1               5                   10                  15

Ser Leu Arg Leu Val Cys Ala Phe Ser
            20                  25

<210> SEQ ID NO 176
<211> LENGTH: 25
<212> TYPE: PRT
<213> ORGANISM: Artificial Sequence
<220> FEATURE:
<223> OTHER INFORMATION: framework 1 sequence

<400> SEQUENCE: 176

Lys Val Gln Leu Val Glu Ser Arg Gly Gly Leu Val Gln Ala Gly Gly
1               5                   10                  15

Ser Leu Arg Leu Ser Cys Thr Ala Ser
            20                  25

<210> SEQ ID NO 177
<211> LENGTH: 25
<212> TYPE: PRT
<213> ORGANISM: Artificial Sequence
<220> FEATURE:
<223> OTHER INFORMATION: framework 1 sequence

<400> SEQUENCE: 177

Glu Val Gln Leu Val Glu Ser Gly Gly Gly Leu Val Gln Pro Gly Gly
1               5                   10                  15

Ser Leu Ser Leu Ser Cys Thr Ala Ser
            20                  25

<210> SEQ ID NO 178
<211> LENGTH: 25
<212> TYPE: PRT
<213> ORGANISM: Artificial Sequence
<220> FEATURE:
<223> OTHER INFORMATION: framework 1 sequence

<400> SEQUENCE: 178

Lys Val Gln Leu Val Glu Ser Gly Gly Gly Leu Val Gln Pro Gly Gly
1               5                   10                  15

Ser Leu Ser Leu Ser Cys Thr Ala Ser
            20                  25

<210> SEQ ID NO 179
<211> LENGTH: 25
<212> TYPE: PRT
<213> ORGANISM: Artificial Sequence

```
<220> FEATURE:
<223> OTHER INFORMATION: framework 1 sequence

<400> SEQUENCE: 179

Glu Val Gln Leu Val Glu Ser Gly Gly Gly Ser Val Gln Ala Gly Asn
1               5                   10                  15

Ser Leu Ser Leu Ser Cys Thr Ala Ser
            20                  25

<210> SEQ ID NO 180
<211> LENGTH: 25
<212> TYPE: PRT
<213> ORGANISM: Artificial Sequence
<220> FEATURE:
<223> OTHER INFORMATION: framework 1 sequence

<400> SEQUENCE: 180

Glu Val Gln Leu Val Glu Ser Gly Gly Gly Leu Val Gln Ala Gly Asn
1               5                   10                  15

Ser Leu Ser Leu Ser Cys Thr Ala Ser
            20                  25

<210> SEQ ID NO 181
<211> LENGTH: 10
<212> TYPE: PRT
<213> ORGANISM: Artificial Sequence
<220> FEATURE:
<223> OTHER INFORMATION: CDR1 sequence

<400> SEQUENCE: 181

Gly Leu Leu Phe Ser Val Asn Ser Ala Gly
1               5                   10

<210> SEQ ID NO 182
<211> LENGTH: 10
<212> TYPE: PRT
<213> ORGANISM: Artificial Sequence
<220> FEATURE:
<223> OTHER INFORMATION: CDR1 sequence

<400> SEQUENCE: 182

Gly Leu Leu Phe Ser Arg Asn Ser Ala Gly
1               5                   10

<210> SEQ ID NO 183
<211> LENGTH: 10
<212> TYPE: PRT
<213> ORGANISM: Artificial Sequence
<220> FEATURE:
<223> OTHER INFORMATION: CDR1 sequence

<400> SEQUENCE: 183

Gly Leu Leu Phe Ser Arg Asn Ser Val Gly
1               5                   10

<210> SEQ ID NO 184
<211> LENGTH: 10
<212> TYPE: PRT
<213> ORGANISM: Artificial Sequence
<220> FEATURE:
<223> OTHER INFORMATION: CDR1 sequence

<400> SEQUENCE: 184

Gly Leu Leu Phe Ser Ala Asn Ser Ala Gly
1               5                   10
```

<210> SEQ ID NO 185
<211> LENGTH: 10
<212> TYPE: PRT
<213> ORGANISM: Artificial Sequence
<220> FEATURE:
<223> OTHER INFORMATION: CDR1 sequence

<400> SEQUENCE: 185

Gly Leu Leu Phe Ser Val Asn Ser Val Gly
1               5                   10

<210> SEQ ID NO 186
<211> LENGTH: 10
<212> TYPE: PRT
<213> ORGANISM: Artificial Sequence
<220> FEATURE:
<223> OTHER INFORMATION: CDR1 sequence

<400> SEQUENCE: 186

Gly Leu Leu Phe Ser Arg His Ser Ala Gly
1               5                   10

<210> SEQ ID NO 187
<211> LENGTH: 10
<212> TYPE: PRT
<213> ORGANISM: Artificial Sequence
<220> FEATURE:
<223> OTHER INFORMATION: CDR1 sequence

<400> SEQUENCE: 187

Gly Leu Leu Phe Ile Arg Asn Ser Ala Ser
1               5                   10

<210> SEQ ID NO 188
<211> LENGTH: 11
<212> TYPE: PRT
<213> ORGANISM: Artificial Sequence
<220> FEATURE:
<223> OTHER INFORMATION: CDR1 sequence

<400> SEQUENCE: 188

Gly Leu Leu Phe Ser Arg Asn Ser Ala Gly Arg
1               5                   10

<210> SEQ ID NO 189
<211> LENGTH: 10
<212> TYPE: PRT
<213> ORGANISM: Artificial Sequence
<220> FEATURE:
<223> OTHER INFORMATION: CDR1 sequence

<400> SEQUENCE: 189

Gly Leu Leu Ser Ser Cys Asn Thr Ala Gly
1               5                   10

<210> SEQ ID NO 190
<211> LENGTH: 10
<212> TYPE: PRT
<213> ORGANISM: Artificial Sequence
<220> FEATURE:
<223> OTHER INFORMATION: CDR1 sequence

<400> SEQUENCE: 190

Gly Leu Pro Leu Ser Arg Asn Ser Ala Gly
1               5                   10

```
<210> SEQ ID NO 191
<211> LENGTH: 10
<212> TYPE: PRT
<213> ORGANISM: Artificial Sequence
<220> FEATURE:
<223> OTHER INFORMATION: CDR1 sequence

<400> SEQUENCE: 191

Leu Leu Phe Phe Ser Arg Asn Ser Ala Arg
1               5                   10

<210> SEQ ID NO 192
<211> LENGTH: 10
<212> TYPE: PRT
<213> ORGANISM: Artificial Sequence
<220> FEATURE:
<223> OTHER INFORMATION: CDR1 sequence

<400> SEQUENCE: 192

Gly Leu Leu Ile Ser Arg Asn Ser Ala Gly
1               5                   10

<210> SEQ ID NO 193
<211> LENGTH: 10
<212> TYPE: PRT
<213> ORGANISM: Artificial Sequence
<220> FEATURE:
<223> OTHER INFORMATION: CDR1 sequence

<400> SEQUENCE: 193

Arg Leu Leu Phe Ser Arg Asn Ser Ala Gly
1               5                   10

<210> SEQ ID NO 194
<211> LENGTH: 10
<212> TYPE: PRT
<213> ORGANISM: Artificial Sequence
<220> FEATURE:
<223> OTHER INFORMATION: CDR1 sequence

<400> SEQUENCE: 194

Gly Leu Leu Phe Ser Arg Asn Arg Val Gly
1               5                   10

<210> SEQ ID NO 195
<211> LENGTH: 10
<212> TYPE: PRT
<213> ORGANISM: Artificial Sequence
<220> FEATURE:
<223> OTHER INFORMATION: CDR1 sequence

<400> SEQUENCE: 195

Gly Leu Leu Leu Ser Arg Asn Arg Ala Arg
1               5                   10

<210> SEQ ID NO 196
<211> LENGTH: 10
<212> TYPE: PRT
<213> ORGANISM: Artificial Sequence
<220> FEATURE:
<223> OTHER INFORMATION: CDR1 sequence

<400> SEQUENCE: 196

Gly Phe Leu Phe Arg Arg Pro Ser Ala Gly
1               5                   10

<210> SEQ ID NO 197
```

-continued

```
<211> LENGTH: 11
<212> TYPE: PRT
<213> ORGANISM: Artificial Sequence
<220> FEATURE:
<223> OTHER INFORMATION: CDR1 sequence

<400> SEQUENCE: 197

Gly Leu Leu Phe Ile Arg Asn Ser Ala Gly Cys
1               5                   10

<210> SEQ ID NO 198
<211> LENGTH: 10
<212> TYPE: PRT
<213> ORGANISM: Artificial Sequence
<220> FEATURE:
<223> OTHER INFORMATION: CDR1 sequence

<400> SEQUENCE: 198

Gly Leu Leu Phe Ser Arg Ile Ser Ala Gly
1               5                   10

<210> SEQ ID NO 199
<211> LENGTH: 10
<212> TYPE: PRT
<213> ORGANISM: Artificial Sequence
<220> FEATURE:
<223> OTHER INFORMATION: CDR1 sequence

<400> SEQUENCE: 199

Gly Leu Leu Phe Ser Pro Asn Ser Ala Gly
1               5                   10

<210> SEQ ID NO 200
<211> LENGTH: 10
<212> TYPE: PRT
<213> ORGANISM: Artificial Sequence
<220> FEATURE:
<223> OTHER INFORMATION: CDR1 sequence

<400> SEQUENCE: 200

Gly Leu Leu Phe Ser Arg Met Ser Ala Arg
1               5                   10

<210> SEQ ID NO 201
<211> LENGTH: 10
<212> TYPE: PRT
<213> ORGANISM: Artificial Sequence
<220> FEATURE:
<223> OTHER INFORMATION: CDR1 sequence

<400> SEQUENCE: 201

Gly Leu Leu Phe Ser Arg Tyr Ser Ala Gly
1               5                   10

<210> SEQ ID NO 202
<211> LENGTH: 10
<212> TYPE: PRT
<213> ORGANISM: Artificial Sequence
<220> FEATURE:
<223> OTHER INFORMATION: CDR1 sequence

<400> SEQUENCE: 202

Gly Leu Leu Phe Ser Arg Asn Ile Ala Gly
1               5                   10

<210> SEQ ID NO 203
<211> LENGTH: 12
```

-continued

```
<212> TYPE: PRT
<213> ORGANISM: Artificial Sequence
<220> FEATURE:
<223> OTHER INFORMATION: CDR1 sequence

<400> SEQUENCE: 203

Gly Leu Leu Phe Ser Leu Asn Ser Ala Gly Cys Ser
1               5                   10

<210> SEQ ID NO 204
<211> LENGTH: 10
<212> TYPE: PRT
<213> ORGANISM: Artificial Sequence
<220> FEATURE:
<223> OTHER INFORMATION: CDR1 sequence

<400> SEQUENCE: 204

Gly Pro Leu Phe Arg Arg Thr Arg Ala Gly
1               5                   10

<210> SEQ ID NO 205
<211> LENGTH: 10
<212> TYPE: PRT
<213> ORGANISM: Artificial Sequence
<220> FEATURE:
<223> OTHER INFORMATION: CDR1 sequence

<400> SEQUENCE: 205

Gly Ile Pro Phe Ser Arg Asn Ser Ala Gly
1               5                   10

<210> SEQ ID NO 206
<211> LENGTH: 10
<212> TYPE: PRT
<213> ORGANISM: Artificial Sequence
<220> FEATURE:
<223> OTHER INFORMATION: CDR1 sequence

<400> SEQUENCE: 206

Gly Leu Leu Phe Arg Val Asn Ser Val Gly
1               5                   10

<210> SEQ ID NO 207
<211> LENGTH: 10
<212> TYPE: PRT
<213> ORGANISM: Artificial Sequence
<220> FEATURE:
<223> OTHER INFORMATION: CDR1 sequence

<400> SEQUENCE: 207

Gly Leu Leu Phe Arg Val Asn Ser Ala Gly
1               5                   10

<210> SEQ ID NO 208
<211> LENGTH: 10
<212> TYPE: PRT
<213> ORGANISM: Artificial Sequence
<220> FEATURE:
<223> OTHER INFORMATION: CDR1 sequence

<400> SEQUENCE: 208

Gly Leu Leu Phe Ser Val Asp Ser Ala Gly
1               5                   10

<210> SEQ ID NO 209
<211> LENGTH: 11
<212> TYPE: PRT
```

```
<213> ORGANISM: Artificial Sequence
<220> FEATURE:
<223> OTHER INFORMATION: CDR1 sequence

<400> SEQUENCE: 209

Gly Leu Leu Phe Ser Val Asn Ser Thr Val Ser
1               5                   10

<210> SEQ ID NO 210
<211> LENGTH: 10
<212> TYPE: PRT
<213> ORGANISM: Artificial Sequence
<220> FEATURE:
<223> OTHER INFORMATION: CDR1 sequence

<400> SEQUENCE: 210

Gly Leu Leu Phe Ser Val Asp Ser Thr Gly
1               5                   10

<210> SEQ ID NO 211
<211> LENGTH: 10
<212> TYPE: PRT
<213> ORGANISM: Artificial Sequence
<220> FEATURE:
<223> OTHER INFORMATION: CDR1 sequence

<400> SEQUENCE: 211

Arg Gly Thr Phe Arg Asn Phe Gly Met Gly
1               5                   10

<210> SEQ ID NO 212
<211> LENGTH: 10
<212> TYPE: PRT
<213> ORGANISM: Artificial Sequence
<220> FEATURE:
<223> OTHER INFORMATION: CDR1 sequence

<400> SEQUENCE: 212

Ala Gly Thr Phe Arg Asn Phe Gly Met Gly
1               5                   10

<210> SEQ ID NO 213
<211> LENGTH: 10
<212> TYPE: PRT
<213> ORGANISM: Artificial Sequence
<220> FEATURE:
<223> OTHER INFORMATION: CDR1 sequence

<400> SEQUENCE: 213

Gly Gly Thr Phe Arg Asn Tyr Gly Met Gly
1               5                   10

<210> SEQ ID NO 214
<211> LENGTH: 10
<212> TYPE: PRT
<213> ORGANISM: Artificial Sequence
<220> FEATURE:
<223> OTHER INFORMATION: CDR1 sequence

<400> SEQUENCE: 214

Gly Gly Thr Phe Arg Asn Phe Gly Met Gly
1               5                   10

<210> SEQ ID NO 215
<211> LENGTH: 10
<212> TYPE: PRT
<213> ORGANISM: Artificial Sequence
```

```
<220> FEATURE:
<223> OTHER INFORMATION: CDR1 sequence

<400> SEQUENCE: 215

Gly Gly Asn Phe Arg Asn Phe Gly Met Gly
1               5                   10

<210> SEQ ID NO 216
<211> LENGTH: 10
<212> TYPE: PRT
<213> ORGANISM: Artificial Sequence
<220> FEATURE:
<223> OTHER INFORMATION: CDR1 sequence

<400> SEQUENCE: 216

Ser Gly Thr Phe Arg Asn Phe Ala Met Gly
1               5                   10

<210> SEQ ID NO 217
<211> LENGTH: 10
<212> TYPE: PRT
<213> ORGANISM: Artificial Sequence
<220> FEATURE:
<223> OTHER INFORMATION: CDR1 sequence

<400> SEQUENCE: 217

Gly Gly Thr Phe Arg Asn Tyr Ala Met Gly
1               5                   10

<210> SEQ ID NO 218
<211> LENGTH: 10
<212> TYPE: PRT
<213> ORGANISM: Artificial Sequence
<220> FEATURE:
<223> OTHER INFORMATION: CDR1 sequence

<400> SEQUENCE: 218

Ala Gly Thr Leu Arg Asn Phe Gly Met Gly
1               5                   10

<210> SEQ ID NO 219
<211> LENGTH: 10
<212> TYPE: PRT
<213> ORGANISM: Artificial Sequence
<220> FEATURE:
<223> OTHER INFORMATION: CDR1 sequence

<400> SEQUENCE: 219

Lys Gly Thr Phe Arg Asn Phe Ala Met Gly
1               5                   10

<210> SEQ ID NO 220
<211> LENGTH: 10
<212> TYPE: PRT
<213> ORGANISM: Artificial Sequence
<220> FEATURE:
<223> OTHER INFORMATION: CDR1 sequence

<400> SEQUENCE: 220

Gly Gly Thr Phe Arg Asn Phe Ala Met Gly
1               5                   10

<210> SEQ ID NO 221
<211> LENGTH: 10
<212> TYPE: PRT
<213> ORGANISM: Artificial Sequence
<220> FEATURE:
```

<223> OTHER INFORMATION: CDR1 sequence

<400> SEQUENCE: 221

Arg Gly Thr Phe Arg Asn Phe Ala Met Gly
1               5                   10

<210> SEQ ID NO 222
<211> LENGTH: 10
<212> TYPE: PRT
<213> ORGANISM: Artificial Sequence
<220> FEATURE:
<223> OTHER INFORMATION: CDR1 sequence

<400> SEQUENCE: 222

Arg Gly Thr Phe Arg Asn Tyr Ala Met Gly
1               5                   10

<210> SEQ ID NO 223
<211> LENGTH: 10
<212> TYPE: PRT
<213> ORGANISM: Artificial Sequence
<220> FEATURE:
<223> OTHER INFORMATION: CDR1 sequence

<400> SEQUENCE: 223

Gly Gly Thr Phe Arg Ser Tyr Gly Met Gly
1               5                   10

<210> SEQ ID NO 224
<211> LENGTH: 10
<212> TYPE: PRT
<213> ORGANISM: Artificial Sequence
<220> FEATURE:
<223> OTHER INFORMATION: CDR1 sequence

<400> SEQUENCE: 224

Val Gly Asn Phe Arg Asn Phe Gly Met Gly
1               5                   10

<210> SEQ ID NO 225
<211> LENGTH: 10
<212> TYPE: PRT
<213> ORGANISM: Artificial Sequence
<220> FEATURE:
<223> OTHER INFORMATION: CDR1 sequence

<400> SEQUENCE: 225

Arg Gly Thr Phe Arg Asn Tyr Gly Met Gly
1               5                   10

<210> SEQ ID NO 226
<211> LENGTH: 10
<212> TYPE: PRT
<213> ORGANISM: Artificial Sequence
<220> FEATURE:
<223> OTHER INFORMATION: CDR1 sequence

<400> SEQUENCE: 226

Gly Gly Asn Phe Arg Asn Phe Gly Val Gly
1               5                   10

<210> SEQ ID NO 227
<211> LENGTH: 14
<212> TYPE: PRT
<213> ORGANISM: Artificial Sequence
<220> FEATURE:
<223> OTHER INFORMATION: framework 2 sequence

```
<400> SEQUENCE: 227

Trp Tyr Arg Gln Ala Pro Gly Lys Gln Arg Asp Phe Val Ala
1               5                   10

<210> SEQ ID NO 228
<211> LENGTH: 14
<212> TYPE: PRT
<213> ORGANISM: Artificial Sequence
<220> FEATURE:
<223> OTHER INFORMATION: framework 2 sequence

<400> SEQUENCE: 228

Trp Tyr Arg Gln Ala Pro Gly Lys Gln Arg Glu Phe Val Ala
1               5                   10

<210> SEQ ID NO 229
<211> LENGTH: 14
<212> TYPE: PRT
<213> ORGANISM: Artificial Sequence
<220> FEATURE:
<223> OTHER INFORMATION: framework 2 sequence

<400> SEQUENCE: 229

Trp Tyr Arg Gln Ala Pro Gly Lys Gln Arg Asp Leu Val Ala
1               5                   10

<210> SEQ ID NO 230
<211> LENGTH: 14
<212> TYPE: PRT
<213> ORGANISM: Artificial Sequence
<220> FEATURE:
<223> OTHER INFORMATION: framework 2 sequence

<400> SEQUENCE: 230

Trp Tyr Arg Gln Ala Pro Gly Lys Lys Arg Asp Phe Val Ala
1               5                   10

<210> SEQ ID NO 231
<211> LENGTH: 14
<212> TYPE: PRT
<213> ORGANISM: Artificial Sequence
<220> FEATURE:
<223> OTHER INFORMATION: framework 2 sequence

<400> SEQUENCE: 231

Trp Tyr Arg Gln Ala Pro Gly Lys Arg Arg Glu Phe Val Ala
1               5                   10

<210> SEQ ID NO 232
<211> LENGTH: 14
<212> TYPE: PRT
<213> ORGANISM: Artificial Sequence
<220> FEATURE:
<223> OTHER INFORMATION: framework 2 sequence

<400> SEQUENCE: 232

Trp Tyr Arg Arg Ala Pro Gly Lys Gln Arg Glu Phe Val Ala
1               5                   10

<210> SEQ ID NO 233
<211> LENGTH: 14
<212> TYPE: PRT
<213> ORGANISM: Artificial Sequence
<220> FEATURE:
<223> OTHER INFORMATION: framework 2 sequence
```

<400> SEQUENCE: 233

Trp Tyr Arg Pro Ala Pro Gly Lys Arg Glu Phe Val Ala
1               5                   10

<210> SEQ ID NO 234
<211> LENGTH: 14
<212> TYPE: PRT
<213> ORGANISM: Artificial Sequence
<220> FEATURE:
<223> OTHER INFORMATION: framework 2 sequence

<400> SEQUENCE: 234

Trp Tyr Arg Gln Ala Pro Gly Lys Arg Arg Glu Leu Val Ala
1               5                   10

<210> SEQ ID NO 235
<211> LENGTH: 13
<212> TYPE: PRT
<213> ORGANISM: Artificial Sequence
<220> FEATURE:
<223> OTHER INFORMATION: framework 2 sequence

<400> SEQUENCE: 235

Tyr Arg Gln Ala Pro Gly Lys Arg Pro Glu Phe Phe Ala
1               5                   10

<210> SEQ ID NO 236
<211> LENGTH: 14
<212> TYPE: PRT
<213> ORGANISM: Artificial Sequence
<220> FEATURE:
<223> OTHER INFORMATION: framework 2 sequence

<400> SEQUENCE: 236

Trp Tyr Arg Gln Gly Pro Gly Lys Arg Arg Glu Phe Val Ala
1               5                   10

<210> SEQ ID NO 237
<211> LENGTH: 14
<212> TYPE: PRT
<213> ORGANISM: Artificial Sequence
<220> FEATURE:
<223> OTHER INFORMATION: framework 2 sequence

<400> SEQUENCE: 237

Trp Cys Arg Gln Ala Pro Gly Lys Arg Arg Glu Phe Val Ala
1               5                   10

<210> SEQ ID NO 238
<211> LENGTH: 14
<212> TYPE: PRT
<213> ORGANISM: Artificial Sequence
<220> FEATURE:
<223> OTHER INFORMATION: framework 2 sequence

<400> SEQUENCE: 238

Trp Tyr Arg Gln Ala Pro Val Lys Arg Arg Glu Phe Val Gly
1               5                   10

<210> SEQ ID NO 239
<211> LENGTH: 14
<212> TYPE: PRT
<213> ORGANISM: Artificial Sequence
<220> FEATURE:
<223> OTHER INFORMATION: framework 2 sequence

<400> SEQUENCE: 239

Trp Tyr Arg His Ala Pro Gly Lys Gln Arg Ala Phe Val Ala
1               5                   10

<210> SEQ ID NO 240
<211> LENGTH: 14
<212> TYPE: PRT
<213> ORGANISM: Artificial Sequence
<220> FEATURE:
<223> OTHER INFORMATION: framework 2 sequence

<400> SEQUENCE: 240

Trp Tyr Arg Gln Ala Ala Gly Lys Gln Arg Glu Phe Val Ala
1               5                   10

<210> SEQ ID NO 241
<211> LENGTH: 14
<212> TYPE: PRT
<213> ORGANISM: Artificial Sequence
<220> FEATURE:
<223> OTHER INFORMATION: framework 2 sequence

<400> SEQUENCE: 241

Trp Tyr Arg Gln Ala Pro Gly Lys Gln Arg Glu Leu Val Ala
1               5                   10

<210> SEQ ID NO 242
<211> LENGTH: 14
<212> TYPE: PRT
<213> ORGANISM: Artificial Sequence
<220> FEATURE:
<223> OTHER INFORMATION: framework 2 sequence

<400> SEQUENCE: 242

Trp His Arg Gln Ala Pro Gly Lys Gln Arg Glu Phe Val Ala
1               5                   10

<210> SEQ ID NO 243
<211> LENGTH: 14
<212> TYPE: PRT
<213> ORGANISM: Artificial Sequence
<220> FEATURE:
<223> OTHER INFORMATION: framework 2 sequence

<400> SEQUENCE: 243

Trp Tyr Arg Pro Ala Pro Gly Lys Gln Arg Glu Phe Val Ala
1               5                   10

<210> SEQ ID NO 244
<211> LENGTH: 14
<212> TYPE: PRT
<213> ORGANISM: Artificial Sequence
<220> FEATURE:
<223> OTHER INFORMATION: framework 2 sequence

<400> SEQUENCE: 244

Trp Tyr Arg Gln Asp Pro Gly Lys Gln Arg Glu Phe Val Ala
1               5                   10

<210> SEQ ID NO 245
<211> LENGTH: 13
<212> TYPE: PRT
<213> ORGANISM: Artificial Sequence
<220> FEATURE:
<223> OTHER INFORMATION: framework 2 sequence

<400> SEQUENCE: 245

Tyr Arg Gln Ala Pro Gly Lys His Arg Glu Phe Val Ala
1               5                   10

<210> SEQ ID NO 246
<211> LENGTH: 14
<212> TYPE: PRT
<213> ORGANISM: Artificial Sequence
<220> FEATURE:
<223> OTHER INFORMATION: framework 2 sequence

<400> SEQUENCE: 246

Trp Tyr Arg Glu Ala Pro Gly Gln Gln Arg Glu Cys Val Ala
1               5                   10

<210> SEQ ID NO 247
<211> LENGTH: 14
<212> TYPE: PRT
<213> ORGANISM: Artificial Sequence
<220> FEATURE:
<223> OTHER INFORMATION: framework 2 sequence

<400> SEQUENCE: 247

Trp Tyr Arg Gln Ala Pro Gly Lys Gln Arg Lys Phe Val Ala
1               5                   10

<210> SEQ ID NO 248
<211> LENGTH: 14
<212> TYPE: PRT
<213> ORGANISM: Artificial Sequence
<220> FEATURE:
<223> OTHER INFORMATION: framework 2 sequence

<400> SEQUENCE: 248

Trp Tyr Arg Gln Ala Pro Gly Lys Gln Leu Ala Phe Val Gly
1               5                   10

<210> SEQ ID NO 249
<211> LENGTH: 14
<212> TYPE: PRT
<213> ORGANISM: Artificial Sequence
<220> FEATURE:
<223> OTHER INFORMATION: framework 2 sequence

<400> SEQUENCE: 249

Trp Tyr Arg Gln Ala Pro Gly Glu Gln Arg Glu Phe Val Ala
1               5                   10

<210> SEQ ID NO 250
<211> LENGTH: 14
<212> TYPE: PRT
<213> ORGANISM: Artificial Sequence
<220> FEATURE:
<223> OTHER INFORMATION: framework 2 sequence

<400> SEQUENCE: 250

Trp Tyr Arg Gln Ala Pro Gly Gln Lys Arg Glu Phe Val Ala
1               5                   10

<210> SEQ ID NO 251
<211> LENGTH: 12
<212> TYPE: PRT
<213> ORGANISM: Artificial Sequence
<220> FEATURE:
<223> OTHER INFORMATION: framework 2 sequence

<400> SEQUENCE: 251

Arg Gln Pro Pro Gly Lys Gln Arg Glu Phe Val Ala

-continued

```
1               5                   10

<210> SEQ ID NO 252
<211> LENGTH: 14
<212> TYPE: PRT
<213> ORGANISM: Artificial Sequence
<220> FEATURE:
<223> OTHER INFORMATION: framework 2 sequence

<400> SEQUENCE: 252

Trp Tyr Arg Gln Ala Pro Gly Lys Gln Arg Ile Phe Val Ala
1               5                   10

<210> SEQ ID NO 253
<211> LENGTH: 14
<212> TYPE: PRT
<213> ORGANISM: Artificial Sequence
<220> FEATURE:
<223> OTHER INFORMATION: framework 2 sequence

<400> SEQUENCE: 253

Trp Tyr Arg Gln Ala Gln Gly Lys Gln Arg Glu Phe Val Ala
1               5                   10

<210> SEQ ID NO 254
<211> LENGTH: 13
<212> TYPE: PRT
<213> ORGANISM: Artificial Sequence
<220> FEATURE:
<223> OTHER INFORMATION: framework 2 sequence

<400> SEQUENCE: 254

Tyr Arg Gln Ala Pro Gly Lys Gln Arg Asp Cys Val Ala
1               5                   10

<210> SEQ ID NO 255
<211> LENGTH: 14
<212> TYPE: PRT
<213> ORGANISM: Artificial Sequence
<220> FEATURE:
<223> OTHER INFORMATION: framework 2 sequence

<400> SEQUENCE: 255

Trp Tyr Arg Gln Ala Pro Gly Lys Gln Arg Glu Phe Phe Ala
1               5                   10

<210> SEQ ID NO 256
<211> LENGTH: 14
<212> TYPE: PRT
<213> ORGANISM: Artificial Sequence
<220> FEATURE:
<223> OTHER INFORMATION: framework 2 sequence

<400> SEQUENCE: 256

Trp Phe Arg Gln Ala Gln Gly Lys Glu Arg Glu Phe Val Ala
1               5                   10

<210> SEQ ID NO 257
<211> LENGTH: 14
<212> TYPE: PRT
<213> ORGANISM: Artificial Sequence
<220> FEATURE:
<223> OTHER INFORMATION: framework 2 sequence

<400> SEQUENCE: 257

Trp Ser Arg Gln Ala Gln Gly Lys Glu Arg Glu Phe Val Ala
1               5                   10
```

```
<210> SEQ ID NO 258
<211> LENGTH: 14
<212> TYPE: PRT
<213> ORGANISM: Artificial Sequence
<220> FEATURE:
<223> OTHER INFORMATION: framework 2 sequence

<400> SEQUENCE: 258

Trp Phe Arg Gln Ala Arg Gly Glu Glu Arg Glu Phe Val Ala
1               5                   10

<210> SEQ ID NO 259
<211> LENGTH: 14
<212> TYPE: PRT
<213> ORGANISM: Artificial Sequence
<220> FEATURE:
<223> OTHER INFORMATION: framework 2 sequence

<400> SEQUENCE: 259

Trp Phe Arg Gln Ala His Gly Lys Glu Arg Glu Phe Val Ala
1               5                   10

<210> SEQ ID NO 260
<211> LENGTH: 14
<212> TYPE: PRT
<213> ORGANISM: Artificial Sequence
<220> FEATURE:
<223> OTHER INFORMATION: framework 2 sequence

<400> SEQUENCE: 260

Trp Phe Arg Gln Asp Gln Gly Gln Glu Arg Glu Phe Val Ala
1               5                   10

<210> SEQ ID NO 261
<211> LENGTH: 14
<212> TYPE: PRT
<213> ORGANISM: Artificial Sequence
<220> FEATURE:
<223> OTHER INFORMATION: framework 2 sequence

<400> SEQUENCE: 261

Trp Phe Arg Gln Val Gln Gly Thr Glu Arg Glu Phe Val Ala
1               5                   10

<210> SEQ ID NO 262
<211> LENGTH: 14
<212> TYPE: PRT
<213> ORGANISM: Artificial Sequence
<220> FEATURE:
<223> OTHER INFORMATION: framework 2 sequence

<400> SEQUENCE: 262

Trp Phe Arg Gln Val Gln Gly Lys Glu Arg Glu Phe Val Ala
1               5                   10

<210> SEQ ID NO 263
<211> LENGTH: 14
<212> TYPE: PRT
<213> ORGANISM: Artificial Sequence
<220> FEATURE:
<223> OTHER INFORMATION: framework 2 sequence

<400> SEQUENCE: 263

Trp Phe Arg Gln Ala Gln Gly Lys Glu Arg Asp Phe Val Ala
1               5                   10
```

<210> SEQ ID NO 264
<211> LENGTH: 14
<212> TYPE: PRT
<213> ORGANISM: Artificial Sequence
<220> FEATURE:
<223> OTHER INFORMATION: framework 2 sequence

<400> SEQUENCE: 264

Trp Phe Arg Gln Ala Gln Gly Thr Glu Arg Glu Phe Val Ala
1               5                   10

<210> SEQ ID NO 265
<211> LENGTH: 14
<212> TYPE: PRT
<213> ORGANISM: Artificial Sequence
<220> FEATURE:
<223> OTHER INFORMATION: framework 2 sequence

<400> SEQUENCE: 265

Trp Phe Arg Glu Ala Gln Gly Lys Glu Arg Glu Phe Val Ala
1               5                   10

<210> SEQ ID NO 266
<211> LENGTH: 14
<212> TYPE: PRT
<213> ORGANISM: Artificial Sequence
<220> FEATURE:
<223> OTHER INFORMATION: framework 2 sequence

<400> SEQUENCE: 266

Trp Phe Arg Gln Phe Gln Gly Lys Glu Arg Glu Phe Val Ala
1               5                   10

<210> SEQ ID NO 267
<211> LENGTH: 14
<212> TYPE: PRT
<213> ORGANISM: Artificial Sequence
<220> FEATURE:
<223> OTHER INFORMATION: framework 2 sequence

<400> SEQUENCE: 267

Trp Phe Arg Gln Ala Arg Gly Glu Ala Arg Glu Phe Val Ala
1               5                   10

<210> SEQ ID NO 268
<211> LENGTH: 9
<212> TYPE: PRT
<213> ORGANISM: Artificial Sequence
<220> FEATURE:
<223> OTHER INFORMATION: CDR2 sequence

<400> SEQUENCE: 268

Arg Ile Arg Ser Gly Gly Ser Thr Asn
1               5

<210> SEQ ID NO 269
<211> LENGTH: 9
<212> TYPE: PRT
<213> ORGANISM: Artificial Sequence
<220> FEATURE:
<223> OTHER INFORMATION: CDR2 sequence

<400> SEQUENCE: 269

Arg Ile Arg Met Gly Gly Ser Ile Asn
1               5

```
<210> SEQ ID NO 270
<211> LENGTH: 9
<212> TYPE: PRT
<213> ORGANISM: Artificial Sequence
<220> FEATURE:
<223> OTHER INFORMATION: CDR2 sequence

<400> SEQUENCE: 270

Arg Ile Arg Ser Ser Gly Ser Thr Asn
1               5

<210> SEQ ID NO 271
<211> LENGTH: 9
<212> TYPE: PRT
<213> ORGANISM: Artificial Sequence
<220> FEATURE:
<223> OTHER INFORMATION: CDR2 sequence

<400> SEQUENCE: 271

Arg Leu Arg Thr Thr Gly Ser Thr Asn
1               5

<210> SEQ ID NO 272
<211> LENGTH: 9
<212> TYPE: PRT
<213> ORGANISM: Artificial Sequence
<220> FEATURE:
<223> OTHER INFORMATION: CDR2 sequence

<400> SEQUENCE: 272

Arg Val Arg Met Gly Gly Ser Ile Asn
1               5

<210> SEQ ID NO 273
<211> LENGTH: 9
<212> TYPE: PRT
<213> ORGANISM: Artificial Sequence
<220> FEATURE:
<223> OTHER INFORMATION: CDR2 sequence

<400> SEQUENCE: 273

Arg Ile Arg Met Val Gly Ser Ile Asn
1               5

<210> SEQ ID NO 274
<211> LENGTH: 9
<212> TYPE: PRT
<213> ORGANISM: Artificial Sequence
<220> FEATURE:
<223> OTHER INFORMATION: CDR2 sequence

<400> SEQUENCE: 274

Arg Thr Arg Met Gly Gly Ser Ile Asn
1               5

<210> SEQ ID NO 275
<211> LENGTH: 9
<212> TYPE: PRT
<213> ORGANISM: Artificial Sequence
<220> FEATURE:
<223> OTHER INFORMATION: CDR2 sequence

<400> SEQUENCE: 275

Gly Val Arg Met Gly Gly Ser Ile Asn
1               5

<210> SEQ ID NO 276
```

```
<211> LENGTH: 9
<212> TYPE: PRT
<213> ORGANISM: Artificial Sequence
<220> FEATURE:
<223> OTHER INFORMATION: CDR2 sequence

<400> SEQUENCE: 276

Arg Ile Arg Met Gly Gly Ser Thr Asn
1               5

<210> SEQ ID NO 277
<211> LENGTH: 9
<212> TYPE: PRT
<213> ORGANISM: Artificial Sequence
<220> FEATURE:
<223> OTHER INFORMATION: CDR2 sequence

<400> SEQUENCE: 277

Cys Ile Arg Met Gly Gly Ser Ile Asn
1               5

<210> SEQ ID NO 278
<211> LENGTH: 9
<212> TYPE: PRT
<213> ORGANISM: Artificial Sequence
<220> FEATURE:
<223> OTHER INFORMATION: CDR2 sequence

<400> SEQUENCE: 278

Arg Ile Arg Met Gly Gly Ser Met Asn
1               5

<210> SEQ ID NO 279
<211> LENGTH: 9
<212> TYPE: PRT
<213> ORGANISM: Artificial Sequence
<220> FEATURE:
<223> OTHER INFORMATION: CDR2 sequence

<400> SEQUENCE: 279

Arg Ile Arg Arg Gly Gly Gly Ile Asn
1               5

<210> SEQ ID NO 280
<211> LENGTH: 9
<212> TYPE: PRT
<213> ORGANISM: Artificial Sequence
<220> FEATURE:
<223> OTHER INFORMATION: CDR2 sequence

<400> SEQUENCE: 280

Arg Ile Gly Met Gly Gly Cys Ile Asn
1               5

<210> SEQ ID NO 281
<211> LENGTH: 9
<212> TYPE: PRT
<213> ORGANISM: Artificial Sequence
<220> FEATURE:
<223> OTHER INFORMATION: CDR2 sequence

<400> SEQUENCE: 281

Arg Ser Arg Met Gly Gly Ser Ile Asn
1               5

<210> SEQ ID NO 282
<211> LENGTH: 9
```

```
<212> TYPE: PRT
<213> ORGANISM: Artificial Sequence
<220> FEATURE:
<223> OTHER INFORMATION: CDR2 sequence

<400> SEQUENCE: 282

Arg Ile Arg Thr Gly Gly Ser Thr Asn
1               5

<210> SEQ ID NO 283
<211> LENGTH: 9
<212> TYPE: PRT
<213> ORGANISM: Artificial Sequence
<220> FEATURE:
<223> OTHER INFORMATION: CDR2 sequence

<400> SEQUENCE: 283

Arg Ile Leu Met Gly Gly Ser Ile Asn
1               5

<210> SEQ ID NO 284
<211> LENGTH: 9
<212> TYPE: PRT
<213> ORGANISM: Artificial Sequence
<220> FEATURE:
<223> OTHER INFORMATION: CDR2 sequence

<400> SEQUENCE: 284

Arg Ile Arg Met Gly Gly Ser Arg Asn
1               5

<210> SEQ ID NO 285
<211> LENGTH: 9
<212> TYPE: PRT
<213> ORGANISM: Artificial Sequence
<220> FEATURE:
<223> OTHER INFORMATION: CDR2 sequence

<400> SEQUENCE: 285

Arg Ile Arg Arg Gly Gly Asp Thr Asn
1               5

<210> SEQ ID NO 286
<211> LENGTH: 9
<212> TYPE: PRT
<213> ORGANISM: Artificial Sequence
<220> FEATURE:
<223> OTHER INFORMATION: CDR2 sequence

<400> SEQUENCE: 286

Arg Leu Arg Arg Gly Gly Asp Thr Asn
1               5

<210> SEQ ID NO 287
<211> LENGTH: 9
<212> TYPE: PRT
<213> ORGANISM: Artificial Sequence
<220> FEATURE:
<223> OTHER INFORMATION: CDR2 sequence

<400> SEQUENCE: 287

Arg Ile Arg Arg Gly Gly Ser Thr Asn
1               5

<210> SEQ ID NO 288
<211> LENGTH: 9
<212> TYPE: PRT
```

```
<213> ORGANISM: Artificial Sequence
<220> FEATURE:
<223> OTHER INFORMATION: CDR2 sequence

<400> SEQUENCE: 288

Arg Leu Arg Arg Gly Gly Glu Thr Asn
1               5

<210> SEQ ID NO 289
<211> LENGTH: 9
<212> TYPE: PRT
<213> ORGANISM: Artificial Sequence
<220> FEATURE:
<223> OTHER INFORMATION: CDR2 sequence

<400> SEQUENCE: 289

Arg Ile Arg Ser Gly Gly Ser Ile Asn
1               5

<210> SEQ ID NO 290
<211> LENGTH: 10
<212> TYPE: PRT
<213> ORGANISM: Artificial Sequence
<220> FEATURE:
<223> OTHER INFORMATION: CDR2 sequence

<400> SEQUENCE: 290

Ala Ile Ser Arg Ser Gly Gly His Lys Tyr
1               5                   10

<210> SEQ ID NO 291
<211> LENGTH: 10
<212> TYPE: PRT
<213> ORGANISM: Artificial Sequence
<220> FEATURE:
<223> OTHER INFORMATION: CDR2 sequence

<400> SEQUENCE: 291

Thr Ile Ser Arg Ser Ala Arg His Thr Tyr
1               5                   10

<210> SEQ ID NO 292
<211> LENGTH: 10
<212> TYPE: PRT
<213> ORGANISM: Artificial Sequence
<220> FEATURE:
<223> OTHER INFORMATION: CDR2 sequence

<400> SEQUENCE: 292

Ala Ile Ser Arg Ser Ala Gly Arg Thr Tyr
1               5                   10

<210> SEQ ID NO 293
<211> LENGTH: 10
<212> TYPE: PRT
<213> ORGANISM: Artificial Sequence
<220> FEATURE:
<223> OTHER INFORMATION: CDR2 sequence

<400> SEQUENCE: 293

Ala Ile Ser Arg Ser Ala Ser Arg Thr Tyr
1               5                   10

<210> SEQ ID NO 294
<211> LENGTH: 10
<212> TYPE: PRT
<213> ORGANISM: Artificial Sequence
```

```
<220> FEATURE:
<223> OTHER INFORMATION: CDR2 sequence

<400> SEQUENCE: 294

Ala Ile Ser Arg Ser Gly Gly His Ile Tyr
1               5                   10

<210> SEQ ID NO 295
<211> LENGTH: 10
<212> TYPE: PRT
<213> ORGANISM: Artificial Sequence
<220> FEATURE:
<223> OTHER INFORMATION: CDR2 sequence

<400> SEQUENCE: 295

Ala Ile Ser Arg Ser Gly Gly Arg Thr Tyr
1               5                   10

<210> SEQ ID NO 296
<211> LENGTH: 10
<212> TYPE: PRT
<213> ORGANISM: Artificial Sequence
<220> FEATURE:
<223> OTHER INFORMATION: CDR2 sequence

<400> SEQUENCE: 296

Thr Ile Ser Arg Ser Gly Gly His Thr Tyr
1               5                   10

<210> SEQ ID NO 297
<211> LENGTH: 10
<212> TYPE: PRT
<213> ORGANISM: Artificial Sequence
<220> FEATURE:
<223> OTHER INFORMATION: CDR2 sequence

<400> SEQUENCE: 297

Ala Ile Ser Arg Ser Ala Gly His Thr Tyr
1               5                   10

<210> SEQ ID NO 298
<211> LENGTH: 10
<212> TYPE: PRT
<213> ORGANISM: Artificial Sequence
<220> FEATURE:
<223> OTHER INFORMATION: CDR2 sequence

<400> SEQUENCE: 298

Ala Ile Ser Arg Thr Gly Gly Arg Thr Tyr
1               5                   10

<210> SEQ ID NO 299
<211> LENGTH: 10
<212> TYPE: PRT
<213> ORGANISM: Artificial Sequence
<220> FEATURE:
<223> OTHER INFORMATION: CDR2 sequence

<400> SEQUENCE: 299

Thr Ile Ser Arg Ser Gly Gly Tyr Thr Tyr
1               5                   10

<210> SEQ ID NO 300
<211> LENGTH: 10
<212> TYPE: PRT
<213> ORGANISM: Artificial Sequence
<220> FEATURE:
```

<223> OTHER INFORMATION: CDR2 sequence

<400> SEQUENCE: 300

Ala Ile Ser Arg Ser Gly Gly His Thr Tyr
1               5                   10

<210> SEQ ID NO 301
<211> LENGTH: 10
<212> TYPE: PRT
<213> ORGANISM: Artificial Sequence
<220> FEATURE:
<223> OTHER INFORMATION: CDR2 sequence

<400> SEQUENCE: 301

Ala Ile Ser Arg Ser Gly Gly His Ile Phe
1               5                   10

<210> SEQ ID NO 302
<211> LENGTH: 10
<212> TYPE: PRT
<213> ORGANISM: Artificial Sequence
<220> FEATURE:
<223> OTHER INFORMATION: CDR2 sequence

<400> SEQUENCE: 302

Ala Ile Ser Arg Ser Gly Gly Arg Lys Tyr
1               5                   10

<210> SEQ ID NO 303
<211> LENGTH: 10
<212> TYPE: PRT
<213> ORGANISM: Artificial Sequence
<220> FEATURE:
<223> OTHER INFORMATION: CDR2 sequence

<400> SEQUENCE: 303

Ala Ile Ser Arg Thr Gly Gly His Thr Tyr
1               5                   10

<210> SEQ ID NO 304
<211> LENGTH: 10
<212> TYPE: PRT
<213> ORGANISM: Artificial Sequence
<220> FEATURE:
<223> OTHER INFORMATION: CDR2 sequence

<400> SEQUENCE: 304

Ala Ile Ser Arg Thr Asn Gly His Ile Tyr
1               5                   10

<210> SEQ ID NO 305
<211> LENGTH: 10
<212> TYPE: PRT
<213> ORGANISM: Artificial Sequence
<220> FEATURE:
<223> OTHER INFORMATION: CDR2 sequence

<400> SEQUENCE: 305

Thr Ile Ser Arg Ser Gly Gly His Ile Tyr
1               5                   10

<210> SEQ ID NO 306
<211> LENGTH: 10
<212> TYPE: PRT
<213> ORGANISM: Artificial Sequence
<220> FEATURE:
<223> OTHER INFORMATION: CDR2 sequence

<400> SEQUENCE: 306

Ala Val Ser Arg Thr Gly Gly Arg Thr Tyr
1               5                   10

<210> SEQ ID NO 307
<211> LENGTH: 10
<212> TYPE: PRT
<213> ORGANISM: Artificial Sequence
<220> FEATURE:
<223> OTHER INFORMATION: CDR2 sequence

<400> SEQUENCE: 307

Thr Ile Ser Arg Ser Gly Gly His Ile Phe
1               5                   10

<210> SEQ ID NO 308
<211> LENGTH: 10
<212> TYPE: PRT
<213> ORGANISM: Artificial Sequence
<220> FEATURE:
<223> OTHER INFORMATION: CDR2 sequence

<400> SEQUENCE: 308

Ala Ile Ser Arg Ala Gly Gly Arg Thr Tyr
1               5                   10

<210> SEQ ID NO 309
<211> LENGTH: 10
<212> TYPE: PRT
<213> ORGANISM: Artificial Sequence
<220> FEATURE:
<223> OTHER INFORMATION: CDR2 sequence

<400> SEQUENCE: 309

Ala Ile Ser Arg Ser Ala Gly His Ile Tyr
1               5                   10

<210> SEQ ID NO 310
<211> LENGTH: 39
<212> TYPE: PRT
<213> ORGANISM: Artificial Sequence
<220> FEATURE:
<223> OTHER INFORMATION: framework 3 sequence

<400> SEQUENCE: 310

Tyr Ala Asp Ser Val Lys Gly Arg Phe Thr Ile Ser Arg Asp Lys Ala
1               5                   10                  15

Thr Asn Thr Val Tyr Leu Gln Met Asn Ser Leu Lys Pro Glu Asp Thr
            20                  25                  30

Ala Val Tyr Tyr Cys Ser Ser
        35

<210> SEQ ID NO 311
<211> LENGTH: 39
<212> TYPE: PRT
<213> ORGANISM: Artificial Sequence
<220> FEATURE:
<223> OTHER INFORMATION: framework 3 sequence

<400> SEQUENCE: 311

Tyr Ala Asp Thr Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

```
Ala Val Tyr Tyr Cys Ser Ser
        35

<210> SEQ ID NO 312
<211> LENGTH: 39
<212> TYPE: PRT
<213> ORGANISM: Artificial Sequence
<220> FEATURE:
<223> OTHER INFORMATION: framework 3 sequence

<400> SEQUENCE: 312

Tyr Ala Asp Ser Val Lys Gly Arg Phe Thr Ile Ser Arg Asp Lys Ala
1               5                   10                  15

Thr Asn Thr Val His Leu Gln Met Asn Ser Leu Lys Pro Glu Asp Thr
            20                  25                  30

Ala Val Tyr Tyr Cys Gly Ser
        35

<210> SEQ ID NO 313
<211> LENGTH: 39
<212> TYPE: PRT
<213> ORGANISM: Artificial Sequence
<220> FEATURE:
<223> OTHER INFORMATION: framework 3 sequence

<400> SEQUENCE: 313

Tyr Ala Asp Ser Val Lys Gly Arg Phe Thr Ile Ser Arg Asp Lys Ala
1               5                   10                  15

Thr Asn Thr Leu Tyr Leu Gln Met Asn Asn Leu Lys Pro Glu Asp Thr
            20                  25                  30

Ala Val Tyr Tyr Cys Ser Ser
        35

<210> SEQ ID NO 314
<211> LENGTH: 39
<212> TYPE: PRT
<213> ORGANISM: Artificial Sequence
<220> FEATURE:
<223> OTHER INFORMATION: framework 3 sequence

<400> SEQUENCE: 314

Tyr Ala Asp Ser Val Lys Gly Arg Phe Thr Ile Ser Arg Asp Lys Ala
1               5                   10                  15

Thr Asn Thr Leu Tyr Leu Gln Val Asn Asn Leu Lys Pro Glu Asp Thr
            20                  25                  30

Ala Val Tyr Tyr Cys Ser Ser
        35

<210> SEQ ID NO 315
<211> LENGTH: 39
<212> TYPE: PRT
<213> ORGANISM: Artificial Sequence
<220> FEATURE:
<223> OTHER INFORMATION: framework 3 sequence

<400> SEQUENCE: 315

Tyr Ala Asp Ser Val Lys Gly Arg Phe Ile Ile Ser Arg Asp Asn Ala
1               5                   10                  15

Lys Asn Thr Leu Tyr Leu Gln Met Asn Ala Leu Lys Pro Glu Asp Thr
            20                  25                  30

Gly Val Tyr Tyr Cys Ser Ser
        35
```

<210> SEQ ID NO 316
<211> LENGTH: 39
<212> TYPE: PRT
<213> ORGANISM: Artificial Sequence
<220> FEATURE:
<223> OTHER INFORMATION: framework 3 sequence

<400> SEQUENCE: 316

Tyr Ala Asp Ser Val Lys Gly Arg Phe Thr Val Ser Arg Asp Asn Ala
1               5                   10                  15

Lys Asn Thr Met Tyr Leu Gln Met Asn Gly Leu Lys Pro Glu Asp Thr
            20                  25                  30

Ala Val Tyr Tyr Cys Ser Ser
        35

<210> SEQ ID NO 317
<211> LENGTH: 39
<212> TYPE: PRT
<213> ORGANISM: Artificial Sequence
<220> FEATURE:
<223> OTHER INFORMATION: framework 3 sequence

<400> SEQUENCE: 317

Tyr Ala Asp Ser Val Lys Gly Arg Phe Thr Val Ser Arg Asp Asn Ala
1               5                   10                  15

Lys Asn Met Met Tyr Leu Gln Met Asn Asp Leu Lys Pro Glu Asp Thr
            20                  25                  30

Ala Val Tyr Phe Cys Ser Gly
        35

<210> SEQ ID NO 318
<211> LENGTH: 39
<212> TYPE: PRT
<213> ORGANISM: Artificial Sequence
<220> FEATURE:
<223> OTHER INFORMATION: framework 3 sequence

<400> SEQUENCE: 318

Tyr Ala Asp Ser Val Lys Gly Arg Phe Thr Thr Ser Arg Asp Asn Ala
1               5                   10                  15

Lys Asn Thr Ile Tyr Leu Gln Met Asn Ser Leu Lys Pro Glu Asp Thr
            20                  25                  30

Ala Val Tyr Tyr Cys Ser Ser
        35

<210> SEQ ID NO 319
<211> LENGTH: 39
<212> TYPE: PRT
<213> ORGANISM: Artificial Sequence
<220> FEATURE:
<223> OTHER INFORMATION: framework 3 sequence

<400> SEQUENCE: 319

Tyr Ala Gln Ser Val Lys Gly Arg Phe Thr Ile Ser Arg Asp Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Ser Ala
        35

<210> SEQ ID NO 320

```
<211> LENGTH: 39
<212> TYPE: PRT
<213> ORGANISM: Artificial Sequence
<220> FEATURE:
<223> OTHER INFORMATION: framework 3 sequence

<400> SEQUENCE: 320

Tyr Gly Asp Ser Val Lys Gly Arg Phe Thr Val Ser Arg Asp Ile Ala
1               5                   10                  15

Lys Asn Thr Met Tyr Leu Gln Met Asn Asp Leu Lys Pro Glu Asp Thr
            20                  25                  30

Ala Lys Tyr Phe Cys Ser Ser
        35

<210> SEQ ID NO 321
<211> LENGTH: 39
<212> TYPE: PRT
<213> ORGANISM: Artificial Sequence
<220> FEATURE:
<223> OTHER INFORMATION: framework 3 sequence

<400> SEQUENCE: 321

Tyr Ala Asp Ser Val Lys Gly Arg Phe Thr Val Ser Arg Asp Asn Ala
1               5                   10                  15

Lys Asn Met Met Tyr Leu Leu Met Asn Asp Leu Asn Arg Glu Tyr Thr
            20                  25                  30

Ala Val Tyr Phe Cys Ser Gly
        35

<210> SEQ ID NO 322
<211> LENGTH: 39
<212> TYPE: PRT
<213> ORGANISM: Artificial Sequence
<220> FEATURE:
<223> OTHER INFORMATION: framework 3 sequence

<400> SEQUENCE: 322

Tyr Ala Asp Ser Val Lys Gly Arg Phe Thr Val Ser Arg Asp Asn Ala
1               5                   10                  15

Lys Asn Met Met Tyr Leu Gln Met Ile Asp Leu Lys Pro Glu Asp Thr
            20                  25                  30

Thr Val Tyr Cys Cys Ser Gly
        35

<210> SEQ ID NO 323
<211> LENGTH: 39
<212> TYPE: PRT
<213> ORGANISM: Artificial Sequence
<220> FEATURE:
<223> OTHER INFORMATION: framework 3 sequence

<400> SEQUENCE: 323

Tyr Ala Asp Ser Val Lys Gly Arg Phe Thr Val Ser Gly Asp Asn Ala
1               5                   10                  15

Lys Asn Met Met Tyr Leu Gln Met Asn Asp Leu Lys Pro Glu Asp Thr
            20                  25                  30

Ala Gly Tyr Phe Cys Ser Gly
        35

<210> SEQ ID NO 324
<211> LENGTH: 39
<212> TYPE: PRT
<213> ORGANISM: Artificial Sequence
```

<220> FEATURE:
<223> OTHER INFORMATION: framework 3 sequence

<400> SEQUENCE: 324

Tyr Ala Asp Ser Val Lys Gly Arg Phe Thr Val Ser Arg Asp Asn Ala
1               5                   10                  15

Lys Asn Met Met Tyr Leu Gln Met Asn Gly Leu Lys Pro Glu Asp Thr
            20                  25                  30

Ala Val Cys Leu Cys Ser Gly
        35

<210> SEQ ID NO 325
<211> LENGTH: 39
<212> TYPE: PRT
<213> ORGANISM: Artificial Sequence
<220> FEATURE:
<223> OTHER INFORMATION: framework 3 sequence

<400> SEQUENCE: 325

Tyr Ala Asp Ser Gly Lys Gly Arg Phe Thr Val Ser Arg Asp Asn Ala
1               5                   10                  15

Lys Asn Met Met Tyr Leu Gln Met Asn Asp Leu Lys Pro Glu Asp Thr
            20                  25                  30

Ala Val Tyr Phe Cys Ser Gly
        35

<210> SEQ ID NO 326
<211> LENGTH: 39
<212> TYPE: PRT
<213> ORGANISM: Artificial Sequence
<220> FEATURE:
<223> OTHER INFORMATION: framework 3 sequence

<400> SEQUENCE: 326

Tyr Gly Asp Ala Val Lys Gly Arg Phe Thr Ala Ser Arg Asp Ile Ala
1               5                   10                  15

Lys Asn Thr Met Tyr Leu Gln Met Asn Asp Leu Lys Pro Glu Asp Thr
            20                  25                  30

Ala Ile Tyr Phe Cys Ser Ser
        35

<210> SEQ ID NO 327
<211> LENGTH: 39
<212> TYPE: PRT
<213> ORGANISM: Artificial Sequence
<220> FEATURE:
<223> OTHER INFORMATION: framework 3 sequence

<400> SEQUENCE: 327

Tyr Gly Val Ser Val Lys Gly Arg Phe Thr Val Ser Arg Asp Ile Ala
1               5                   10                  15

Lys Asn Thr Met Tyr Pro Gln Met Asn Asp Leu Lys Pro Glu Asp Ala
            20                  25                  30

Ala Lys Tyr Phe Cys Ser Ser
        35

<210> SEQ ID NO 328
<211> LENGTH: 39
<212> TYPE: PRT
<213> ORGANISM: Artificial Sequence
<220> FEATURE:
<223> OTHER INFORMATION: framework 3 sequence

```
<400> SEQUENCE: 328

Tyr Gly Asp Ser Val Lys Gly Arg Phe Thr Val Ser Arg Asp Ile Ala
1               5                   10                  15

Lys Asn Thr Met Tyr Leu Arg Met Asn Asp Leu Lys Pro Glu Asp Thr
            20                  25                  30

Ala Ile Tyr Phe Cys Ser Ser
        35

<210> SEQ ID NO 329
<211> LENGTH: 39
<212> TYPE: PRT
<213> ORGANISM: Artificial Sequence
<220> FEATURE:
<223> OTHER INFORMATION: framework 3 sequence

<400> SEQUENCE: 329

Tyr Gly Gly Ser Val Lys Gly Arg Phe Thr Val Ser Arg Asp Ile Ala
1               5                   10                  15

Lys Asn Thr Met Tyr Leu Gln Met Asn Asp Leu Lys Pro Glu Asp Thr
            20                  25                  30

Ala Val Tyr Phe Cys Ser Ser
        35

<210> SEQ ID NO 330
<211> LENGTH: 39
<212> TYPE: PRT
<213> ORGANISM: Artificial Sequence
<220> FEATURE:
<223> OTHER INFORMATION: framework 3 sequence

<400> SEQUENCE: 330

Tyr Ala Asp Ser Val Lys Gly Arg Phe Thr Ile Ser Arg Asp Asn Ala
1               5                   10                  15

Lys Asn Met Val Tyr Leu Gln Met Asn Ser Leu Lys Pro Glu Asp Thr
            20                  25                  30

Ala Val Tyr Tyr Cys Ser Ser
        35

<210> SEQ ID NO 331
<211> LENGTH: 39
<212> TYPE: PRT
<213> ORGANISM: Artificial Sequence
<220> FEATURE:
<223> OTHER INFORMATION: framework 3 sequence

<400> SEQUENCE: 331

Tyr Gly Asp Ser Val Lys Gly Arg Phe Thr Val Ser Arg Asp Ile Ala
1               5                   10                  15

Lys Asn Thr Met Tyr Leu Gln Val Asp Asp Leu Lys Pro Glu Asp Thr
            20                  25                  30

Ala Ile Tyr Phe Cys Ser Ser
        35

<210> SEQ ID NO 332
<211> LENGTH: 39
<212> TYPE: PRT
<213> ORGANISM: Artificial Sequence
<220> FEATURE:
<223> OTHER INFORMATION: framework 3 sequence

<400> SEQUENCE: 332

Tyr Gly Gly Ser Val Lys Gly Arg Phe Thr Val Ser Arg Asp Ile Ala
```

```
1               5                   10                  15
Lys Asn Thr Met Tyr Leu Gln Met Asn Asp Leu Lys Pro Glu Glu Thr
                20                  25                  30

Ala Trp Tyr Phe Cys Ser Ser
            35
```

<210> SEQ ID NO 333
<211> LENGTH: 39
<212> TYPE: PRT
<213> ORGANISM: Artificial Sequence
<220> FEATURE:
<223> OTHER INFORMATION: framework 3 sequence

<400> SEQUENCE: 333

```
Tyr Gly Asp Ser Val Lys Gly Arg Phe Thr Val Ser Arg Asp Ile Ala
1               5                   10                  15

Lys Asp Thr Arg Tyr Met Gln Ile Asn Asp Leu Lys Pro Glu Asp Thr
                20                  25                  30

Ala Lys Tyr Phe Cys Arg Ser
            35
```

<210> SEQ ID NO 334
<211> LENGTH: 39
<212> TYPE: PRT
<213> ORGANISM: Artificial Sequence
<220> FEATURE:
<223> OTHER INFORMATION: framework 3 sequence

<400> SEQUENCE: 334

```
Asp Gly Asp Ser Val Lys Gly Arg Phe Thr Val Ser Arg Asp Ile Ala
1               5                   10                  15

Lys Asn Thr Met Tyr Leu Gln Met Asn Asp Leu Lys Pro Glu Asp Thr
                20                  25                  30

Ala Ile Tyr Phe Cys Arg Ser
            35
```

<210> SEQ ID NO 335
<211> LENGTH: 39
<212> TYPE: PRT
<213> ORGANISM: Artificial Sequence
<220> FEATURE:
<223> OTHER INFORMATION: framework 3 sequence

<400> SEQUENCE: 335

```
Tyr Gly Asp Ser Val Lys Gly Arg Phe Thr Val Ser Arg Asp Ile Ala
1               5                   10                  15

Lys Asn Thr Met Tyr Leu Gln Met Asn Glu Leu Lys Pro Glu Asp Thr
                20                  25                  30

Ala Lys Tyr Leu Cys Arg Ser
            35
```

<210> SEQ ID NO 336
<211> LENGTH: 39
<212> TYPE: PRT
<213> ORGANISM: Artificial Sequence
<220> FEATURE:
<223> OTHER INFORMATION: framework 3 sequence

<400> SEQUENCE: 336

```
Tyr Gly Asp Ser Val Lys Gly Arg Phe Thr Val Ala Arg Asp Ile Ala
1               5                   10                  15

Lys Asn Thr Met Tyr Leu Gln Met Asn Asp Leu Lys Pro Glu Glu Thr
```

```
                    20                  25                  30

Ala Ile Tyr Phe Cys Ser Ser
            35

<210> SEQ ID NO 337
<211> LENGTH: 39
<212> TYPE: PRT
<213> ORGANISM: Artificial Sequence
<220> FEATURE:
<223> OTHER INFORMATION: framework 3 sequence

<400> SEQUENCE: 337

Tyr Gly Asp Ser Val Lys Gly Arg Phe Thr Val Ser Arg Asp Ile Ala
1               5                   10                  15

Lys Asn Thr Met Tyr Leu Gln Met Asn Asp Val Lys Pro Glu Asp Thr
                20                  25                  30

Ala Lys Tyr Phe Cys Ser Ser
            35

<210> SEQ ID NO 338
<211> LENGTH: 39
<212> TYPE: PRT
<213> ORGANISM: Artificial Sequence
<220> FEATURE:
<223> OTHER INFORMATION: framework 3 sequence

<400> SEQUENCE: 338

Tyr Gly Asp Ser Val Lys Gly Arg Phe Thr Val Ser Arg Asp Ile Ala
1               5                   10                  15

Lys Asn Thr Val Tyr Leu Gln Met Asn Asp Leu Lys Pro Glu Tyr Thr
                20                  25                  30

Ala Ile Tyr Phe Cys Ser Ser
            35

<210> SEQ ID NO 339
<211> LENGTH: 39
<212> TYPE: PRT
<213> ORGANISM: Artificial Sequence
<220> FEATURE:
<223> OTHER INFORMATION: framework 3 sequence

<400> SEQUENCE: 339

Tyr Gly Asp Ser Val Lys Gly Arg Phe Thr Val Ser Arg Asp Ile Ala
1               5                   10                  15

Lys Asn Thr Met Tyr Leu Gln Met Asn Asp Leu Lys Pro Glu His Thr
                20                  25                  30

Ala Lys Tyr Leu Cys Ser Ser
            35

<210> SEQ ID NO 340
<211> LENGTH: 39
<212> TYPE: PRT
<213> ORGANISM: Artificial Sequence
<220> FEATURE:
<223> OTHER INFORMATION: framework 3 sequence

<400> SEQUENCE: 340

Tyr Gly Asp Ser Val Lys Gly Arg Phe Thr Val Ser Arg Asp Ile Ala
1               5                   10                  15

Lys Asn Thr Met Tyr Leu Gln Met Asn Asp Leu Lys Pro Glu Asp Thr
                20                  25                  30

Ala Ile Tyr Phe Cys Ser Ser
```

35

<210> SEQ ID NO 341
<211> LENGTH: 39
<212> TYPE: PRT
<213> ORGANISM: Artificial Sequence
<220> FEATURE:
<223> OTHER INFORMATION: framework 3 sequence

<400> SEQUENCE: 341

Tyr Gly Asp Ser Val Lys Gly Arg Phe Thr Val Ser Arg Asp Ile Ala
1               5                   10                  15

Lys Asn Thr Met Tyr Leu Gln Met Asn Gly Leu Lys Pro Glu Asp Thr
            20                  25                  30

Ala Lys Tyr Phe Cys Ser Ser
        35

<210> SEQ ID NO 342
<211> LENGTH: 39
<212> TYPE: PRT
<213> ORGANISM: Artificial Sequence
<220> FEATURE:
<223> OTHER INFORMATION: framework 3 sequence

<400> SEQUENCE: 342

Tyr Gly Asp Ser Val Lys Gly Arg Phe Thr Val Thr Arg Asp Ile Ala
1               5                   10                  15

Lys Asn Thr Met Tyr Leu Gln Met Asn Asp Leu Lys Pro Glu Asp Thr
            20                  25                  30

Ala Lys Tyr Phe Cys Ser Ser
        35

<210> SEQ ID NO 343
<211> LENGTH: 39
<212> TYPE: PRT
<213> ORGANISM: Artificial Sequence
<220> FEATURE:
<223> OTHER INFORMATION: framework 3 sequence

<400> SEQUENCE: 343

Tyr Gly Asp Ser Val Lys Gly Arg Phe Thr Val Ser Arg Asp Ile Ala
1               5                   10                  15

Lys Asn Thr Met Tyr Leu Gln Met Asn Asp Leu Lys Pro Glu Asp Thr
            20                  25                  30

Ala Glu Tyr Phe Cys Ser Ser
        35

<210> SEQ ID NO 344
<211> LENGTH: 39
<212> TYPE: PRT
<213> ORGANISM: Artificial Sequence
<220> FEATURE:
<223> OTHER INFORMATION: framework 3 sequence

<400> SEQUENCE: 344

Asp Gly Asp Ser Val Lys Gly Arg Phe Thr Val Ser Arg Asp Ile Asp
1               5                   10                  15

Lys Asn Thr Met Tyr Leu Gln Met Asn Asp Leu Lys Pro Glu Asn Thr
            20                  25                  30

Ala Lys Tyr Phe Cys Ser Ser
        35

```
<210> SEQ ID NO 345
<211> LENGTH: 39
<212> TYPE: PRT
<213> ORGANISM: Artificial Sequence
<220> FEATURE:
<223> OTHER INFORMATION: framework 3 sequence

<400> SEQUENCE: 345

Tyr Ala Asp Ser Val Lys Gly Arg Phe Thr Val Ser Arg Gly Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Ser Ser
        35

<210> SEQ ID NO 346
<211> LENGTH: 39
<212> TYPE: PRT
<213> ORGANISM: Artificial Sequence
<220> FEATURE:
<223> OTHER INFORMATION: framework 3 sequence

<400> SEQUENCE: 346

Tyr Gly Asp Ser Val Lys Gly Arg Phe Asn Gly Ser Arg Asp Ile Ala
1               5                   10                  15

Lys Asn Thr Met Tyr Leu Gln Met Asp Asp Leu Lys Pro Glu Asp Thr
            20                  25                  30

Ala Ile Cys Phe Cys Ser Ser
        35

<210> SEQ ID NO 347
<211> LENGTH: 39
<212> TYPE: PRT
<213> ORGANISM: Artificial Sequence
<220> FEATURE:
<223> OTHER INFORMATION: framework 3 sequence

<400> SEQUENCE: 347

Tyr Gly Asp Ser Val Lys Gly Arg Phe Thr Val Ser Arg Asp Ile Ala
1               5                   10                  15

Lys Asn Thr Met Tyr Leu Gln Met Lys Asp Leu Lys Pro Glu Asp Thr
            20                  25                  30

Ala Lys Tyr Phe Cys Ser Arg
        35

<210> SEQ ID NO 348
<211> LENGTH: 34
<212> TYPE: PRT
<213> ORGANISM: Artificial Sequence
<220> FEATURE:
<223> OTHER INFORMATION: framework 3 sequence

<400> SEQUENCE: 348

Tyr Gly Asp Ser Val Lys Gly Arg Phe Thr Val Ser Gly Asp Ile Ala
1               5                   10                  15

Lys Asn Thr Met Tyr Leu Gln Met Asn Asp Leu Lys Pro Glu Asp Thr
            20                  25                  30

Ala Lys

<210> SEQ ID NO 349
<211> LENGTH: 39
<212> TYPE: PRT
<213> ORGANISM: Artificial Sequence
```

```
<220> FEATURE:
<223> OTHER INFORMATION: framework 3 sequence

<400> SEQUENCE: 349

Tyr Ala Glu Ser Val Arg Gly Arg Phe Thr Val Ser Arg Asp Lys Ala
1               5                   10                  15

Lys Asn Thr Met Tyr Leu Gln Met Asn Ser Leu Lys Pro Glu Asp Thr
            20                  25                  30

Ala Val Tyr Tyr Cys Ala Ser
            35

<210> SEQ ID NO 350
<211> LENGTH: 39
<212> TYPE: PRT
<213> ORGANISM: Artificial Sequence
<220> FEATURE:
<223> OTHER INFORMATION: framework 3 sequence

<400> SEQUENCE: 350

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ser Ala
            35

<210> SEQ ID NO 351
<211> LENGTH: 39
<212> TYPE: PRT
<213> ORGANISM: Artificial Sequence
<220> FEATURE:
<223> OTHER INFORMATION: framework 3 sequence

<400> SEQUENCE: 351

Tyr Ala Glu Ser Val Lys Gly Arg Phe Thr Ile Ser Arg Asp Asn Ala
1               5                   10                  15

Lys Asn Thr Val Tyr Leu Gln Met Asn Asn Leu Lys Pro Glu Asp Thr
            20                  25                  30

Ala Val Tyr Tyr Cys Ser Ala
            35

<210> SEQ ID NO 352
<211> LENGTH: 39
<212> TYPE: PRT
<213> ORGANISM: Artificial Sequence
<220> FEATURE:
<223> OTHER INFORMATION: framework 3 sequence

<400> SEQUENCE: 352

Tyr Ala Asp Ser Val Lys Gly Arg Ser Thr Val Ser Arg Asp Asn Ala
1               5                   10                  15

Lys Asn Thr Leu Tyr Leu Gln Leu Tyr Ser Leu Lys Pro Glu Asp Thr
            20                  25                  30

Ala Val Tyr Tyr Cys Ser Ser
            35

<210> SEQ ID NO 353
<211> LENGTH: 39
<212> TYPE: PRT
<213> ORGANISM: Artificial Sequence
<220> FEATURE:
<223> OTHER INFORMATION: framework 3 sequence
```

<400> SEQUENCE: 353

Tyr Ala Asp Thr Val Lys Gly Arg Val Thr Ile Ser Arg Asp Asn Ala
1               5                   10                  15

Lys Asn Thr Val Tyr Leu Gln Met Asn Ser Leu Ser Pro Ala Asp Thr
            20                  25                  30

Gly Val Tyr Tyr Cys Ser Ser
        35

<210> SEQ ID NO 354
<211> LENGTH: 39
<212> TYPE: PRT
<213> ORGANISM: Artificial Sequence
<220> FEATURE:
<223> OTHER INFORMATION: framework 3 sequence

<400> SEQUENCE: 354

Tyr Gly Asp Ser Val Lys Gly Arg Phe Thr Ile Ser Arg Asp Lys Ala
1               5                   10                  15

Thr Asn Thr Leu Tyr Leu Gln Met Asn Ser Leu Arg Thr Glu Asp Thr
            20                  25                  30

Ala Val Tyr Tyr Cys Ser Ser
        35

<210> SEQ ID NO 355
<211> LENGTH: 39
<212> TYPE: PRT
<213> ORGANISM: Artificial Sequence
<220> FEATURE:
<223> OTHER INFORMATION: framework 3 sequence

<400> SEQUENCE: 355

Tyr Ala Asp Ser Val Lys Gly Arg Phe Ile Ile Ser Arg Asp Asn Ala
1               5                   10                  15

Gln Asn Thr Leu Tyr Leu Gln Met Asn Asn Leu Ser Pro Glu Asp Thr
            20                  25                  30

Ala Ala Tyr Tyr Cys Ser Ser
        35

<210> SEQ ID NO 356
<211> LENGTH: 39
<212> TYPE: PRT
<213> ORGANISM: Artificial Sequence
<220> FEATURE:
<223> OTHER INFORMATION: framework 3 sequence

<400> SEQUENCE: 356

Asp Ala Asp Ser Val Lys Gly Arg Phe Thr Val Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ser Ser
        35

<210> SEQ ID NO 357
<211> LENGTH: 39
<212> TYPE: PRT
<213> ORGANISM: Artificial Sequence
<220> FEATURE:
<223> OTHER INFORMATION: framework 3 sequence

<400> SEQUENCE: 357

Tyr Ala Asp Ser Val Lys Gly Arg Phe Thr Val Ser Arg Asp Asn Ala

-continued

```
                1               5                  10                  15
Lys Asn Thr Val Tyr Leu Gln Met Asn Ser Leu Lys His Glu Asp Thr
                20                  25                  30

Ala Val Tyr Tyr Cys Ser Ser
            35

<210> SEQ ID NO 358
<211> LENGTH: 39
<212> TYPE: PRT
<213> ORGANISM: Artificial Sequence
<220> FEATURE:
<223> OTHER INFORMATION: framework 3 sequence

<400> SEQUENCE: 358

Tyr Gly Asp Ser Val Lys Gly Arg Phe Thr Ile Ser Arg Asp Lys Ala
1               5                   10                  15

Thr Asn Thr Leu Tyr Leu Gln Met Ser Asn Leu Asn Pro Glu Asp Thr
                20                  25                  30

Ala Val Tyr Tyr Cys Ser Ser
            35

<210> SEQ ID NO 359
<211> LENGTH: 39
<212> TYPE: PRT
<213> ORGANISM: Artificial Sequence
<220> FEATURE:
<223> OTHER INFORMATION: framework 3 sequence

<400> SEQUENCE: 359

Tyr Ser Asp Ser Val Lys Gly Arg Phe Thr Ile Ser Lys Asp Asn Ala
1               5                   10                  15

Lys Asn Met Val Ser Leu Gln Met Asn Ser Leu Lys Pro Glu Asp Thr
                20                  25                  30

Ala Val Tyr Tyr Cys Ala Ala
            35

<210> SEQ ID NO 360
<211> LENGTH: 39
<212> TYPE: PRT
<213> ORGANISM: Artificial Sequence
<220> FEATURE:
<223> OTHER INFORMATION: framework 3 sequence

<400> SEQUENCE: 360

Tyr Ser Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
                20                  25                  30

Ala Val Tyr Tyr Cys Ala Ala
            35

<210> SEQ ID NO 361
<211> LENGTH: 39
<212> TYPE: PRT
<213> ORGANISM: Artificial Sequence
<220> FEATURE:
<223> OTHER INFORMATION: framework 3 sequence

<400> SEQUENCE: 361

Tyr Ser Asp Ser Val Lys Gly Arg Phe Thr Ile Ser Lys Asn Asn Ala
1               5                   10                  15

Lys Asn Ile Met Ser Leu Gln Met Asn Ser Leu Lys Pro Glu Asp Thr
```

-continued

```
                20                  25                  30

Ala Val Tyr Tyr Cys Ala Ala
        35

<210> SEQ ID NO 362
<211> LENGTH: 39
<212> TYPE: PRT
<213> ORGANISM: Artificial Sequence
<220> FEATURE:
<223> OTHER INFORMATION: framework 3 sequence

<400> SEQUENCE: 362

Tyr Ser Asp Ser Val Lys Gly Arg Phe Thr Ile Ala Arg Ala Asn Ala
1               5                   10                  15

Lys Asn Met Val Ser Leu Gln Met Asn Ser Leu Lys Pro Glu Asp Thr
            20                  25                  30

Ala Val Tyr Tyr Cys Ala Ala
        35

<210> SEQ ID NO 363
<211> LENGTH: 39
<212> TYPE: PRT
<213> ORGANISM: Artificial Sequence
<220> FEATURE:
<223> OTHER INFORMATION: framework 3 sequence

<400> SEQUENCE: 363

Tyr Ala Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
            20                  25                  30

Ala Val Tyr Ser Cys Ala Ala
        35

<210> SEQ ID NO 364
<211> LENGTH: 39
<212> TYPE: PRT
<213> ORGANISM: Artificial Sequence
<220> FEATURE:
<223> OTHER INFORMATION: framework 3 sequence

<400> SEQUENCE: 364

Tyr Ser Asp Ser Val Lys Gly Arg Phe Thr Ile Ser Lys Asn Asn Ala
1               5                   10                  15

Lys Asn Val Met Ser Leu Gln Met Asn Ser Leu Lys Pro Glu Asp Thr
            20                  25                  30

Ala Val Tyr Tyr Cys Ala Ala
        35

<210> SEQ ID NO 365
<211> LENGTH: 39
<212> TYPE: PRT
<213> ORGANISM: Artificial Sequence
<220> FEATURE:
<223> OTHER INFORMATION: framework 3 sequence

<400> SEQUENCE: 365

Tyr Ser Asp Ser Val Lys Gly Arg Phe Thr Ile Ser Arg Asp Asn Ala
1               5                   10                  15

Lys Asn Leu Val Ser Leu Gln Met Asn Ser Leu Lys Pro Glu Asp Thr
            20                  25                  30

Ala Val Tyr Tyr Cys Ala Ala
```

```
<210> SEQ ID NO 366
<211> LENGTH: 39
<212> TYPE: PRT
<213> ORGANISM: Artificial Sequence
<220> FEATURE:
<223> OTHER INFORMATION: framework 3 sequence

<400> SEQUENCE: 366

Phe Ser Asp Ser Val Lys Gly Arg Phe Thr Ile Ser Lys Asp Asn Ala
1               5                   10                  15

Lys Asn Ile Leu Ser Leu Gln Met Asn Ser Leu Lys Pro Glu Asp Thr
            20                  25                  30

Ala Val Tyr Tyr Cys Ala Ala
        35

<210> SEQ ID NO 367
<211> LENGTH: 39
<212> TYPE: PRT
<213> ORGANISM: Artificial Sequence
<220> FEATURE:
<223> OTHER INFORMATION: framework 3 sequence

<400> SEQUENCE: 367

Tyr Ser Asp Ser Val Lys Gly Arg Phe Thr Ile Ser Arg Asp Asn Ala
1               5                   10                  15

Lys Asn Met Val Ser Leu Gln Met Asp Ser Leu Lys Pro Glu Asp Thr
            20                  25                  30

Ala Val Tyr Tyr Cys Ala Ala
        35

<210> SEQ ID NO 368
<211> LENGTH: 39
<212> TYPE: PRT
<213> ORGANISM: Artificial Sequence
<220> FEATURE:
<223> OTHER INFORMATION: framework 3 sequence

<400> SEQUENCE: 368

Phe Ser Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Ser
            20                  25                  30

Ala Val Tyr Tyr Cys Ala Ala
        35

<210> SEQ ID NO 369
<211> LENGTH: 39
<212> TYPE: PRT
<213> ORGANISM: Artificial Sequence
<220> FEATURE:
<223> OTHER INFORMATION: framework 3 sequence

<400> SEQUENCE: 369

Tyr Ser Asp Ser Val Gln Gly Arg Phe Thr Ile Ser Lys Asp Asn Ala
1               5                   10                  15

Lys Asn Met Val Ser Leu Gln Met Asn Ser Leu Lys Pro Glu Asp Thr
            20                  25                  30

Ala Val Tyr Tyr Cys Ala Ala
        35
```

-continued

<210> SEQ ID NO 370
<211> LENGTH: 39
<212> TYPE: PRT
<213> ORGANISM: Artificial Sequence
<220> FEATURE:
<223> OTHER INFORMATION: framework 3 sequence

<400> SEQUENCE: 370

Tyr Ser Asp Ser Val Lys Gly Arg Phe Thr Ile Ser Lys Asp Asn Ala
1               5                   10                  15

Lys Asn Ile Met Ser Leu Gln Met Asn Ser Leu Arg Pro Glu Asp Thr
            20                  25                  30

Ala Val Tyr Tyr Cys Ala Ala
        35

<210> SEQ ID NO 371
<211> LENGTH: 39
<212> TYPE: PRT
<213> ORGANISM: Artificial Sequence
<220> FEATURE:
<223> OTHER INFORMATION: framework 3 sequence

<400> SEQUENCE: 371

Tyr Ser Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
            20                  25                  30

Ala Ile Tyr Tyr Cys Ala Ala
        35

<210> SEQ ID NO 372
<211> LENGTH: 39
<212> TYPE: PRT
<213> ORGANISM: Artificial Sequence
<220> FEATURE:
<223> OTHER INFORMATION: framework 3 sequence

<400> SEQUENCE: 372

Tyr Ser Asp Ser Val Lys Gly Arg Phe Thr Ile Ser Lys Asp Asn Ala
1               5                   10                  15

Lys Asn Met Val Ser Leu Lys Met Asn Ser Leu Lys Pro Glu Asp Thr
            20                  25                  30

Ala Asp Tyr Tyr Cys Ala Ala
        35

<210> SEQ ID NO 373
<211> LENGTH: 39
<212> TYPE: PRT
<213> ORGANISM: Artificial Sequence
<220> FEATURE:
<223> OTHER INFORMATION: framework 3 sequence

<400> SEQUENCE: 373

Tyr Ser Asp Ser Val Lys Gly Arg Phe Thr Ile Ser Lys Asp Asn Ala
1               5                   10                  15

Lys Asn Ile Leu Phe Leu Gln Met Asn Ser Leu Lys Pro Glu Asp Thr
            20                  25                  30

Ala Val Tyr Tyr Cys Ala Ala
        35

<210> SEQ ID NO 374
<211> LENGTH: 39
<212> TYPE: PRT

-continued

<213> ORGANISM: Artificial Sequence
<220> FEATURE:
<223> OTHER INFORMATION: framework 3 sequence

<400> SEQUENCE: 374

Tyr Ser Asp Ser Ala Lys Gly Arg Phe Thr Ile Ser Lys Asn Asn Ala
1               5                   10                  15
Lys Asn Ile Met Ser Leu Gln Met Asn Ser Leu Lys Pro Glu Asp Thr
            20                  25                  30
Ala Val Tyr Tyr Cys Ala Ala
        35

<210> SEQ ID NO 375
<211> LENGTH: 39
<212> TYPE: PRT
<213> ORGANISM: Artificial Sequence
<220> FEATURE:
<223> OTHER INFORMATION: framework 3 sequence

<400> SEQUENCE: 375

Tyr Ser Asp Ser Val Lys Gly Arg Phe Ala Ile Ser Arg Asp Asn Ala
1               5                   10                  15
Lys Asn Leu Val Ser Leu Gln Met Asn Ser Leu Asn Ala Glu Asp Thr
            20                  25                  30
Ala Val Tyr Tyr Cys Ala Ala
        35

<210> SEQ ID NO 376
<211> LENGTH: 39
<212> TYPE: PRT
<213> ORGANISM: Artificial Sequence
<220> FEATURE:
<223> OTHER INFORMATION: framework 3 sequence

<400> SEQUENCE: 376

Tyr Ser Asp Ser Val Lys Gly Arg Phe Thr Ile Ser Lys Asp Asn Ala
1               5                   10                  15
Lys Asn Ile Leu Ser Leu Gln Met Asn Ser Leu Lys Pro Glu Asp Thr
            20                  25                  30
Ala Val Tyr Tyr Cys Ala Ala
        35

<210> SEQ ID NO 377
<211> LENGTH: 39
<212> TYPE: PRT
<213> ORGANISM: Artificial Sequence
<220> FEATURE:
<223> OTHER INFORMATION: framework 3 sequence

<400> SEQUENCE: 377

Tyr Ser Asp Ser Val Lys Gly Arg Phe Thr Ile Ser Lys Asp Asn Ala
1               5                   10                  15
Lys Asn Ile Val Ser Leu Gln Met Asn Ser Leu Lys Pro Glu Asp Thr
            20                  25                  30
Ala Val Tyr Tyr Cys Ala Ala
        35

<210> SEQ ID NO 378
<211> LENGTH: 39
<212> TYPE: PRT
<213> ORGANISM: Artificial Sequence
<220> FEATURE:
<223> OTHER INFORMATION: framework 3 sequence

<400> SEQUENCE: 378

Tyr Ser Asp Ser Val Lys Gly Arg Phe Thr Ile Ser Lys Asp Asn Ala
1               5                   10                  15

Lys Asn Met Val Tyr Leu Gln Met Tyr Ser Leu Lys Pro Glu Asp Thr
            20                  25                  30

Ala Val Tyr Tyr Cys Ala Gly
            35

<210> SEQ ID NO 379
<211> LENGTH: 39
<212> TYPE: PRT
<213> ORGANISM: Artificial Sequence
<220> FEATURE:
<223> OTHER INFORMATION: framework 3 sequence

<400> SEQUENCE: 379

Tyr Ser Asp Ser Val Lys Gly Arg Phe Ala Ile Ser Lys Asp Asn Ala
1               5                   10                  15

Lys Asn Met Met Ser Leu Arg Met Asn Ser Leu Lys Pro Glu Asp Thr
            20                  25                  30

Ala Val Tyr Tyr Cys Ala Ala
            35

<210> SEQ ID NO 380
<211> LENGTH: 39
<212> TYPE: PRT
<213> ORGANISM: Artificial Sequence
<220> FEATURE:
<223> OTHER INFORMATION: framework 3 sequence

<400> SEQUENCE: 380

Tyr Ser Asp Ser Val Lys Gly Arg Phe Thr Ile Ser Arg Asp Asn Ala
1               5                   10                  15

Lys Asn Met Val Ser Leu Gln Met Asn Lys Leu Lys Pro Glu Asp Thr
            20                  25                  30

Ala Val Tyr Tyr Cys Ala Ala
            35

<210> SEQ ID NO 381
<211> LENGTH: 39
<212> TYPE: PRT
<213> ORGANISM: Artificial Sequence
<220> FEATURE:
<223> OTHER INFORMATION: framework 3 sequence

<400> SEQUENCE: 381

Phe Ser Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
            20                  25                  30

Ala Val Tyr Tyr Cys Ala Ala
            35

<210> SEQ ID NO 382
<211> LENGTH: 39
<212> TYPE: PRT
<213> ORGANISM: Artificial Sequence
<220> FEATURE:
<223> OTHER INFORMATION: framework 3 sequence

<400> SEQUENCE: 382

Tyr Ser Asp Ser Val Lys Gly Arg Phe Thr Ile Ser Arg Asp Asn Ala
1               5                   10                  15

Lys Asn Met Val Ala Leu Gln Met Asn Ser Leu Lys Pro Glu Asp Thr
            20                  25                  30

Ala Val Tyr Tyr Cys Ala Ala
            35

<210> SEQ ID NO 383
<211> LENGTH: 39
<212> TYPE: PRT
<213> ORGANISM: Artificial Sequence
<220> FEATURE:
<223> OTHER INFORMATION: framework 3 sequence

<400> SEQUENCE: 383

Tyr Ala Asp Ser Val Lys Gly Arg Phe Thr Val Ser Arg Asp Asn Ala
1               5                   10                  15

Lys Asn Met Val Ser Leu Gln Met Asn Ser Leu Lys Pro Glu Asp Thr
            20                  25                  30

Ala Val Tyr Ser Cys Ala Ala
            35

<210> SEQ ID NO 384
<211> LENGTH: 39
<212> TYPE: PRT
<213> ORGANISM: Artificial Sequence
<220> FEATURE:
<223> OTHER INFORMATION: framework 3 sequence

<400> SEQUENCE: 384

Tyr Gln Asp Ser Val Lys Gly Arg Phe Thr Ile Ser Lys Asp Asn Ala
1               5                   10                  15

Lys Asn Ile Leu Ser Leu Gln Met Asn Ser Leu Lys Pro Glu Asp Thr
            20                  25                  30

Ala Val Tyr Tyr Cys Ala Ala
            35

<210> SEQ ID NO 385
<211> LENGTH: 39
<212> TYPE: PRT
<213> ORGANISM: Artificial Sequence
<220> FEATURE:
<223> OTHER INFORMATION: framework 3 sequence

<400> SEQUENCE: 385

Tyr Ser Glu Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
            20                  25                  30

Ala Val Tyr Tyr Cys Ala Ala
            35

<210> SEQ ID NO 386
<211> LENGTH: 39
<212> TYPE: PRT
<213> ORGANISM: Artificial Sequence
<220> FEATURE:
<223> OTHER INFORMATION: framework 3 sequence

<400> SEQUENCE: 386

Tyr Ser Asp Ser Val Lys Gly Arg Phe Thr Ile Ser Lys Asp Asn Ala
1               5                   10                  15

Lys Asn Ile Met Ser Leu Gln Met Asn Ser Leu Lys Pro Glu Asp Thr
            20                  25                  30

Ala Val Tyr Tyr Cys Ala Ala
        35

<210> SEQ ID NO 387
<211> LENGTH: 39
<212> TYPE: PRT
<213> ORGANISM: Artificial Sequence
<220> FEATURE:
<223> OTHER INFORMATION: framework 3 sequence

<400> SEQUENCE: 387

Tyr Ala Asp Ser Val Lys Gly Arg Phe Ala Ile Ser Arg Asp Asn Ala
1               5                   10                  15

Lys Asn Met Val Ser Leu Gln Met Asn Ser Leu Lys Pro Glu Asp Thr
            20                  25                  30

Ala Val Tyr Thr Cys Ala Ala
        35

<210> SEQ ID NO 388
<211> LENGTH: 39
<212> TYPE: PRT
<213> ORGANISM: Artificial Sequence
<220> FEATURE:
<223> OTHER INFORMATION: framework 3 sequence

<400> SEQUENCE: 388

Phe Ser Asp Ser Val Lys Gly Arg Phe Thr Ile Ser Lys Asp Asn Ala
1               5                   10                  15

Lys Asn Met Leu Ser Leu Gln Met Asn Ser Leu Lys Pro Glu Asp Thr
            20                  25                  30

Ala Val Tyr Tyr Cys Ala Ala
        35

<210> SEQ ID NO 389
<211> LENGTH: 39
<212> TYPE: PRT
<213> ORGANISM: Artificial Sequence
<220> FEATURE:
<223> OTHER INFORMATION: framework 3 sequence

<400> SEQUENCE: 389

Tyr Ser Asp Ser Val Lys Gly Arg Phe Thr Ile Ser Arg Asp Asn Ala
1               5                   10                  15

Lys Asn Leu Val Ser Leu Gln Met Ser Ser Leu Lys Pro Glu Asp Thr
            20                  25                  30

Ala Val Tyr Tyr Cys Ala Ala
        35

<210> SEQ ID NO 390
<211> LENGTH: 39
<212> TYPE: PRT
<213> ORGANISM: Artificial Sequence
<220> FEATURE:
<223> OTHER INFORMATION: framework 3 sequence

<400> SEQUENCE: 390

Tyr Ser Asp Ser Val Lys Gly Arg Phe Thr Ile Ser Arg Asp Asn Ala
1               5                   10                  15

Lys Asn Met Val Ser Leu Gln Met Asn Ser Leu Lys Pro Glu Asp Thr
            20                  25                  30

```
Ala Ala Tyr Tyr Cys Ala Ala
        35

<210> SEQ ID NO 391
<211> LENGTH: 39
<212> TYPE: PRT
<213> ORGANISM: Artificial Sequence
<220> FEATURE:
<223> OTHER INFORMATION: framework 3 sequence

<400> SEQUENCE: 391

Tyr Ser Asp Ser Val Lys Gly Arg Ser Thr Ile Ser Lys Asp Asn Ala
1               5                   10                  15

Lys Asn Met Val Ser Leu Gln Met Asn Ser Leu Lys Pro Glu Asp Thr
            20                  25                  30

Ala Val Tyr Tyr Cys Ala Ala
        35

<210> SEQ ID NO 392
<211> LENGTH: 39
<212> TYPE: PRT
<213> ORGANISM: Artificial Sequence
<220> FEATURE:
<223> OTHER INFORMATION: framework 3 sequence

<400> SEQUENCE: 392

Tyr Leu Asn Ser Val Lys Gly Arg Phe Thr Ile Ser Lys Asp Asn Ala
1               5                   10                  15

Lys Asn Ile Leu Ser Leu Gln Met Asn Ser Leu Lys Pro Glu Asp Thr
            20                  25                  30

Ala Val Tyr Tyr Cys Ala Ala
        35

<210> SEQ ID NO 393
<211> LENGTH: 8
<212> TYPE: PRT
<213> ORGANISM: Artificial Sequence
<220> FEATURE:
<223> OTHER INFORMATION: CDR3 sequence

<400> SEQUENCE: 393

Trp Arg Thr Gly Ala Tyr Glu Tyr
1               5

<210> SEQ ID NO 394
<211> LENGTH: 8
<212> TYPE: PRT
<213> ORGANISM: Artificial Sequence
<220> FEATURE:
<223> OTHER INFORMATION: CDR3 sequence

<400> SEQUENCE: 394

Trp Arg Thr Gly Phe Tyr Glu Tyr
1               5

<210> SEQ ID NO 395
<211> LENGTH: 8
<212> TYPE: PRT
<213> ORGANISM: Artificial Sequence
<220> FEATURE:
<223> OTHER INFORMATION: CDR3 sequence

<400> SEQUENCE: 395

Trp Arg Thr Glu Ala Tyr Glu Tyr
1               5
```

<210> SEQ ID NO 396
<211> LENGTH: 8
<212> TYPE: PRT
<213> ORGANISM: Artificial Sequence
<220> FEATURE:
<223> OTHER INFORMATION: CDR3 sequence

<400> SEQUENCE: 396

Trp Arg Thr Gly Ala Tyr Glu His
1               5

<210> SEQ ID NO 397
<211> LENGTH: 8
<212> TYPE: PRT
<213> ORGANISM: Artificial Sequence
<220> FEATURE:
<223> OTHER INFORMATION: CDR3 sequence

<400> SEQUENCE: 397

Trp Arg Glu Gly Phe Tyr Glu Tyr
1               5

<210> SEQ ID NO 398
<211> LENGTH: 8
<212> TYPE: PRT
<213> ORGANISM: Artificial Sequence
<220> FEATURE:
<223> OTHER INFORMATION: CDR3 sequence

<400> SEQUENCE: 398

Trp Arg Ile Glu Ala Tyr Glu Tyr
1               5

<210> SEQ ID NO 399
<211> LENGTH: 8
<212> TYPE: PRT
<213> ORGANISM: Artificial Sequence
<220> FEATURE:
<223> OTHER INFORMATION: CDR3 sequence

<400> SEQUENCE: 399

Trp Arg Glu Gly Phe Phe Glu Tyr
1               5

<210> SEQ ID NO 400
<211> LENGTH: 8
<212> TYPE: PRT
<213> ORGANISM: Artificial Sequence
<220> FEATURE:
<223> OTHER INFORMATION: CDR3 sequence

<400> SEQUENCE: 400

Trp Arg Glu Gly Phe Tyr Gly Tyr
1               5

<210> SEQ ID NO 401
<211> LENGTH: 8
<212> TYPE: PRT
<213> ORGANISM: Artificial Sequence
<220> FEATURE:
<223> OTHER INFORMATION: CDR3 sequence

<400> SEQUENCE: 401

Trp Arg Lys Gly Phe Tyr Glu Tyr
1               5

<210> SEQ ID NO 402
<211> LENGTH: 8
<212> TYPE: PRT
<213> ORGANISM: Artificial Sequence
<220> FEATURE:
<223> OTHER INFORMATION: CDR3 sequence

<400> SEQUENCE: 402

Trp Arg Gly Gly Phe Tyr Glu Tyr
1               5

<210> SEQ ID NO 403
<211> LENGTH: 8
<212> TYPE: PRT
<213> ORGANISM: Artificial Sequence
<220> FEATURE:
<223> OTHER INFORMATION: CDR3 sequence

<400> SEQUENCE: 403

Trp Arg Glu Gly Leu Tyr Glu Tyr
1               5

<210> SEQ ID NO 404
<211> LENGTH: 8
<212> TYPE: PRT
<213> ORGANISM: Artificial Sequence
<220> FEATURE:
<223> OTHER INFORMATION: CDR3 sequence

<400> SEQUENCE: 404

Trp Arg Glu Gly Phe Tyr Glu Ser
1               5

<210> SEQ ID NO 405
<211> LENGTH: 8
<212> TYPE: PRT
<213> ORGANISM: Artificial Sequence
<220> FEATURE:
<223> OTHER INFORMATION: CDR3 sequence

<400> SEQUENCE: 405

Trp Arg Glu Gly Val Tyr Lys Tyr
1               5

<210> SEQ ID NO 406
<211> LENGTH: 8
<212> TYPE: PRT
<213> ORGANISM: Artificial Sequence
<220> FEATURE:
<223> OTHER INFORMATION: CDR3 sequence

<400> SEQUENCE: 406

Trp Arg Glu Gly Tyr Tyr Glu Tyr
1               5

<210> SEQ ID NO 407
<211> LENGTH: 8
<212> TYPE: PRT
<213> ORGANISM: Artificial Sequence
<220> FEATURE:
<223> OTHER INFORMATION: CDR3 sequence

<400> SEQUENCE: 407

Trp Arg Glu Gly Phe Asp Glu Tyr
1               5

```
<210> SEQ ID NO 408
<211> LENGTH: 8
<212> TYPE: PRT
<213> ORGANISM: Artificial Sequence
<220> FEATURE:
<223> OTHER INFORMATION: CDR3 sequence

<400> SEQUENCE: 408

Trp Arg Glu Gly Phe Tyr Lys Tyr
1               5

<210> SEQ ID NO 409
<211> LENGTH: 8
<212> TYPE: PRT
<213> ORGANISM: Artificial Sequence
<220> FEATURE:
<223> OTHER INFORMATION: CDR3 sequence

<400> SEQUENCE: 409

Gly Arg Glu Gly Phe Tyr Glu Tyr
1               5

<210> SEQ ID NO 410
<211> LENGTH: 13
<212> TYPE: PRT
<213> ORGANISM: Artificial Sequence
<220> FEATURE:
<223> OTHER INFORMATION: CDR3 sequence

<400> SEQUENCE: 410

Asp Phe Gly Ser Ser Trp Arg Glu Gly Phe Tyr Glu Tyr
1               5                   10

<210> SEQ ID NO 411
<211> LENGTH: 8
<212> TYPE: PRT
<213> ORGANISM: Artificial Sequence
<220> FEATURE:
<223> OTHER INFORMATION: CDR3 sequence

<400> SEQUENCE: 411

Trp Arg Thr Gly Ser Tyr Glu Tyr
1               5

<210> SEQ ID NO 412
<211> LENGTH: 8
<212> TYPE: PRT
<213> ORGANISM: Artificial Sequence
<220> FEATURE:
<223> OTHER INFORMATION: CDR3 sequence

<400> SEQUENCE: 412

Trp Arg Ala Gly Thr Tyr Glu Tyr
1               5

<210> SEQ ID NO 413
<211> LENGTH: 8
<212> TYPE: PRT
<213> ORGANISM: Artificial Sequence
<220> FEATURE:
<223> OTHER INFORMATION: CDR3 sequence

<400> SEQUENCE: 413

Trp Arg Glu Gly Ala Tyr Glu Tyr
1               5

<210> SEQ ID NO 414
```

```
<211> LENGTH: 8
<212> TYPE: PRT
<213> ORGANISM: Artificial Sequence
<220> FEATURE:
<223> OTHER INFORMATION: CDR3 sequence

<400> SEQUENCE: 414

Trp Arg Ile Asp Ala Tyr Glu Tyr
1               5

<210> SEQ ID NO 415
<211> LENGTH: 8
<212> TYPE: PRT
<213> ORGANISM: Artificial Sequence
<220> FEATURE:
<223> OTHER INFORMATION: CDR3 sequence

<400> SEQUENCE: 415

Trp Arg Ile Gly Ser Tyr Glu Tyr
1               5

<210> SEQ ID NO 416
<211> LENGTH: 18
<212> TYPE: PRT
<213> ORGANISM: Artificial Sequence
<220> FEATURE:
<223> OTHER INFORMATION: CDR3 sequence

<400> SEQUENCE: 416

Arg Phe Arg Phe Asp Asp Gly Thr Ser Tyr Tyr Gln Arg Ala Phe Tyr
1               5                   10                  15

Asp Phe

<210> SEQ ID NO 417
<211> LENGTH: 18
<212> TYPE: PRT
<213> ORGANISM: Artificial Sequence
<220> FEATURE:
<223> OTHER INFORMATION: CDR3 sequence

<400> SEQUENCE: 417

Arg Phe Arg Ser Asp Asp Gly Thr Tyr Tyr Tyr Gln Arg Ala Phe Tyr
1               5                   10                  15

Asp Phe

<210> SEQ ID NO 418
<211> LENGTH: 18
<212> TYPE: PRT
<213> ORGANISM: Artificial Sequence
<220> FEATURE:
<223> OTHER INFORMATION: CDR3 sequence

<400> SEQUENCE: 418

Arg Phe Arg Phe Asp Asp Gly Thr Tyr Tyr Tyr Gln Arg Ala Phe Tyr
1               5                   10                  15

Asp Phe

<210> SEQ ID NO 419
<211> LENGTH: 18
<212> TYPE: PRT
<213> ORGANISM: Artificial Sequence
<220> FEATURE:
<223> OTHER INFORMATION: CDR3 sequence

<400> SEQUENCE: 419
```

-continued

Arg Phe Arg Phe Asp Asp Asp Thr Tyr Tyr Tyr Gln Arg Ala Phe Tyr
1               5                   10                  15

Asp Phe

<210> SEQ ID NO 420
<211> LENGTH: 18
<212> TYPE: PRT
<213> ORGANISM: Artificial Sequence
<220> FEATURE:
<223> OTHER INFORMATION: CDR3 sequence

<400> SEQUENCE: 420

Arg Phe Arg Phe Asp Asp Gly Thr Tyr Tyr Tyr Gln Arg Thr Phe Tyr
1               5                   10                  15

Asp Phe

<210> SEQ ID NO 421
<211> LENGTH: 18
<212> TYPE: PRT
<213> ORGANISM: Artificial Sequence
<220> FEATURE:
<223> OTHER INFORMATION: CDR3 sequence

<400> SEQUENCE: 421

Arg Phe Arg Phe Gly Asp Gly Thr Tyr Tyr Tyr Gln Arg Asn Phe Tyr
1               5                   10                  15

Asp Phe

<210> SEQ ID NO 422
<211> LENGTH: 18
<212> TYPE: PRT
<213> ORGANISM: Artificial Sequence
<220> FEATURE:
<223> OTHER INFORMATION: CDR3 sequence

<400> SEQUENCE: 422

Arg Phe Arg Phe Gly Asp Gly Thr Tyr Tyr Tyr Gln Arg Ala Phe Tyr
1               5                   10                  15

Asp Phe

<210> SEQ ID NO 423
<211> LENGTH: 18
<212> TYPE: PRT
<213> ORGANISM: Artificial Sequence
<220> FEATURE:
<223> OTHER INFORMATION: CDR3 sequence

<400> SEQUENCE: 423

Arg Phe Arg Ser Asp Gly Gly Thr Tyr Tyr Tyr Gln Arg Ala Phe Tyr
1               5                   10                  15

Asp Phe

<210> SEQ ID NO 424
<211> LENGTH: 18
<212> TYPE: PRT
<213> ORGANISM: Artificial Sequence
<220> FEATURE:
<223> OTHER INFORMATION: CDR3 sequence

<400> SEQUENCE: 424

Arg Phe Arg Tyr Gly Asp Gly Thr Tyr Tyr Tyr Gln Arg Ala Phe Tyr
1               5                   10                  15

Asp Phe

<210> SEQ ID NO 425
<211> LENGTH: 18
<212> TYPE: PRT
<213> ORGANISM: Artificial Sequence
<220> FEATURE:
<223> OTHER INFORMATION: CDR3 sequence

<400> SEQUENCE: 425

Arg Phe Arg Ser Asp Asp Gly Thr Tyr Tyr Tyr Gln Arg Arg Phe Tyr
1               5                   10                  15

Asp Phe

<210> SEQ ID NO 426
<211> LENGTH: 18
<212> TYPE: PRT
<213> ORGANISM: Artificial Sequence
<220> FEATURE:
<223> OTHER INFORMATION: CDR3 sequence

<400> SEQUENCE: 426

Arg Phe Arg Ser Gly Asp Gly Thr Tyr Tyr Tyr Gln Arg Ala Phe Tyr
1               5                   10                  15

Asp Phe

<210> SEQ ID NO 427
<211> LENGTH: 18
<212> TYPE: PRT
<213> ORGANISM: Artificial Sequence
<220> FEATURE:
<223> OTHER INFORMATION: CDR3 sequence

<400> SEQUENCE: 427

Arg Phe Arg Ser Asp Asp Asp Thr Tyr Tyr Tyr Gln Arg Ala Phe Tyr
1               5                   10                  15

Asp Phe

<210> SEQ ID NO 428
<211> LENGTH: 18
<212> TYPE: PRT
<213> ORGANISM: Artificial Sequence
<220> FEATURE:
<223> OTHER INFORMATION: CDR3 sequence

<400> SEQUENCE: 428

Arg Phe Arg Phe Gly Asp Gly Thr Tyr Tyr Tyr Gln Arg Thr Phe Tyr
1               5                   10                  15

Asp Phe

<210> SEQ ID NO 429
<211> LENGTH: 18
<212> TYPE: PRT
<213> ORGANISM: Artificial Sequence
<220> FEATURE:
<223> OTHER INFORMATION: CDR3 sequence

<400> SEQUENCE: 429

Arg Phe Arg Phe Gly Asp Gly Ala Tyr Tyr Tyr Gln Arg Thr Phe Tyr
1               5                   10                  15

Asp Phe

<210> SEQ ID NO 430
<211> LENGTH: 18

```
<212> TYPE: PRT
<213> ORGANISM: Artificial Sequence
<220> FEATURE:
<223> OTHER INFORMATION: CDR3 sequence

<400> SEQUENCE: 430

Arg Phe Arg Phe Asp Asp Gly Thr Tyr Phe Tyr Gln Arg Ala Phe Tyr
1               5                   10                  15

Asp Phe

<210> SEQ ID NO 431
<211> LENGTH: 18
<212> TYPE: PRT
<213> ORGANISM: Artificial Sequence
<220> FEATURE:
<223> OTHER INFORMATION: CDR3 sequence

<400> SEQUENCE: 431

Arg Phe Arg Phe Asp Asp Gly Thr Tyr Tyr Tyr Gln Arg Asn Phe Tyr
1               5                   10                  15

Asp Phe

<210> SEQ ID NO 432
<211> LENGTH: 18
<212> TYPE: PRT
<213> ORGANISM: Artificial Sequence
<220> FEATURE:
<223> OTHER INFORMATION: CDR3 sequence

<400> SEQUENCE: 432

Arg Phe Arg Phe Asp Asp Gly Thr Tyr Tyr Tyr Gln Arg Ala Phe Tyr
1               5                   10                  15

Asn Leu

<210> SEQ ID NO 433
<211> LENGTH: 18
<212> TYPE: PRT
<213> ORGANISM: Artificial Sequence
<220> FEATURE:
<223> OTHER INFORMATION: CDR3 sequence

<400> SEQUENCE: 433

Arg Phe Arg Ser Asp Asp Gly Thr Tyr Tyr Tyr Gln Arg Ile Phe Tyr
1               5                   10                  15

Asp Phe

<210> SEQ ID NO 434
<211> LENGTH: 18
<212> TYPE: PRT
<213> ORGANISM: Artificial Sequence
<220> FEATURE:
<223> OTHER INFORMATION: CDR3 sequence

<400> SEQUENCE: 434

Arg Phe Arg Ser Gly Asp Gly Thr Ser Tyr Tyr Glu Arg Ala Phe Tyr
1               5                   10                  15

Asp Phe

<210> SEQ ID NO 435
<211> LENGTH: 18
<212> TYPE: PRT
<213> ORGANISM: Artificial Sequence
<220> FEATURE:
<223> OTHER INFORMATION: CDR3 sequence
```

<400> SEQUENCE: 435

Arg Phe Arg Phe Gly Asp Gly Thr Tyr Tyr Gln Arg Asn Phe Tyr
1               5                   10                  15

Gly Phe

<210> SEQ ID NO 436
<211> LENGTH: 11
<212> TYPE: PRT
<213> ORGANISM: Artificial Sequence
<220> FEATURE:
<223> OTHER INFORMATION: framework 4 sequence

<400> SEQUENCE: 436

Trp Gly Gln Gly Thr Leu Val Thr Val Ser Ser
1               5                   10

<210> SEQ ID NO 437
<211> LENGTH: 11
<212> TYPE: PRT
<213> ORGANISM: Artificial Sequence
<220> FEATURE:
<223> OTHER INFORMATION: framework 4 sequence

<400> SEQUENCE: 437

Trp Gly Gln Gly Thr Gln Val Thr Val Ser Ser
1               5                   10

<210> SEQ ID NO 438
<211> LENGTH: 11
<212> TYPE: PRT
<213> ORGANISM: Artificial Sequence
<220> FEATURE:
<223> OTHER INFORMATION: framework 4 sequence

<400> SEQUENCE: 438

Trp Gly Arg Gly Thr Leu Val Thr Val Ser Ser
1               5                   10

<210> SEQ ID NO 439
<211> LENGTH: 11
<212> TYPE: PRT
<213> ORGANISM: Artificial Sequence
<220> FEATURE:
<223> OTHER INFORMATION: framework 4 sequence

<400> SEQUENCE: 439

Trp Gly Gln Gly Ala Gln Val Thr Val Ser Ser
1               5                   10

<210> SEQ ID NO 440
<211> LENGTH: 11
<212> TYPE: PRT
<213> ORGANISM: Artificial Sequence
<220> FEATURE:
<223> OTHER INFORMATION: framework 4 sequence

<400> SEQUENCE: 440

Trp Gly Arg Gly Thr Gln Val Thr Val Ser Ser
1               5                   10

<210> SEQ ID NO 441
<211> LENGTH: 11
<212> TYPE: PRT
<213> ORGANISM: Artificial Sequence
<220> FEATURE:

<223> OTHER INFORMATION: framework 4 sequence

<400> SEQUENCE: 441

Trp Gly Gln Val Thr Gln Val Thr Val Ser Ser
1               5                   10

<210> SEQ ID NO 442
<211> LENGTH: 11
<212> TYPE: PRT
<213> ORGANISM: Artificial Sequence
<220> FEATURE:
<223> OTHER INFORMATION: framework 4 sequence

<400> SEQUENCE: 442

Ser Gly Gln Gly Thr Gln Val Thr Val Ser Ser
1               5                   10

<210> SEQ ID NO 443
<211> LENGTH: 11
<212> TYPE: PRT
<213> ORGANISM: Artificial Sequence
<220> FEATURE:
<223> OTHER INFORMATION: framework 4 sequence

<400> SEQUENCE: 443

Trp Arg Gln Gly Thr Gln Val Thr Val Ser Ser
1               5                   10

<210> SEQ ID NO 444
<211> LENGTH: 11
<212> TYPE: PRT
<213> ORGANISM: Artificial Sequence
<220> FEATURE:
<223> OTHER INFORMATION: framework 4 sequence

<400> SEQUENCE: 444

Trp Ser Gln Arg Thr Gln Val Thr Val Ser Ser
1               5                   10

<210> SEQ ID NO 445
<211> LENGTH: 11
<212> TYPE: PRT
<213> ORGANISM: Artificial Sequence
<220> FEATURE:
<223> OTHER INFORMATION: framework 4 sequence

<400> SEQUENCE: 445

Gly Gly Lys Gly Thr Gln Val Thr Val Ser Ser
1               5                   10

<210> SEQ ID NO 446
<211> LENGTH: 11
<212> TYPE: PRT
<213> ORGANISM: Artificial Sequence
<220> FEATURE:
<223> OTHER INFORMATION: framework 4 sequence

<400> SEQUENCE: 446

Trp Ala Gln Gly Thr Gln Val Thr Val Ser Ser
1               5                   10

<210> SEQ ID NO 447
<211> LENGTH: 11
<212> TYPE: PRT
<213> ORGANISM: Artificial Sequence
<220> FEATURE:
<223> OTHER INFORMATION: framework 4 sequence

<400> SEQUENCE: 447

Trp Cys Gln Gly Thr Gln Val Thr Val Ser Ser
1               5                   10

<210> SEQ ID NO 448
<211> LENGTH: 11
<212> TYPE: PRT
<213> ORGANISM: Artificial Sequence
<220> FEATURE:
<223> OTHER INFORMATION: framework 4 sequence

<400> SEQUENCE: 448

Trp Gly Ile Gly Thr Gln Val Thr Val Ser Ser
1               5                   10

<210> SEQ ID NO 449
<211> LENGTH: 11
<212> TYPE: PRT
<213> ORGANISM: Artificial Sequence
<220> FEATURE:
<223> OTHER INFORMATION: framework 4 sequence

<400> SEQUENCE: 449

Cys Gly Gln Gly Thr Gln Val Thr Val Ser Ser
1               5                   10

<210> SEQ ID NO 450
<211> LENGTH: 11
<212> TYPE: PRT
<213> ORGANISM: Artificial Sequence
<220> FEATURE:
<223> OTHER INFORMATION: framework 4 sequence

<400> SEQUENCE: 450

Trp Gly Gln Trp Thr Gln Val Thr Val Ser Ser
1               5                   10

<210> SEQ ID NO 451
<211> LENGTH: 294
<212> TYPE: PRT
<213> ORGANISM: Artificial Sequence
<220> FEATURE:
<223> OTHER INFORMATION: Nanobody sequence

<400> SEQUENCE: 451

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Thr Gly Gly His Thr Tyr Tyr Gln Asp Ser Val
    50                  55                  60

Lys Gly Arg Phe Thr Ile Ser Lys Asp Asn Lys Asn Ile Leu Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Gln Arg Ala
            100                 105                 110

Phe Tyr Asp Phe Trp Gly Gln Gly Thr Gln Val Thr Val Ser Ser Gly
        115                 120                 125

```
Gly Gly Gly Ser Gly Gly Gly Ser Gly Gly Gly Ser Gly Gly
    130                 135                 140

Gly Gly Ser Gly Gly Gly Ser Gly Gly Gly Ser Gly Gly Gly
145                 150                 155                 160

Gly Ser Gly Gly Gly Ser Glu Val Gln Leu Val Glu Ser Gly Gly
            165                 170                 175

Gly Leu Val Gln Ala Gly Gly Ser Leu Ser Leu Ser Cys Thr Ala Ser
            180                 185                 190

Gly Gly Thr Phe Arg Asn Phe Gly Met Gly Trp Phe Arg Gln Ala Gln
        195                 200                 205

Gly Lys Glu Arg Glu Phe Val Ala Ala Ile Ser Arg Thr Gly His
    210                 215                 220

Thr Tyr Tyr Gln Asp Ser Val Lys Gly Arg Phe Thr Ile Ser Lys Asp
225                 230                 235                 240

Asn Ala Lys Asn Ile Leu Ser Leu Gln Met Asn Ser Leu Lys Pro Glu
            245                 250                 255

Asp Thr Ala Val Tyr Tyr Cys Ala Ala Arg Phe Arg Phe Gly Asp Gly
            260                 265                 270

Thr Tyr Tyr Tyr Gln Arg Ala Phe Tyr Asp Phe Trp Gly Gln Gly Thr
        275                 280                 285

Gln Val Thr Val Ser Ser
    290
```

```
<210> SEQ ID NO 452
<211> LENGTH: 267
<212> TYPE: PRT
<213> ORGANISM: Artificial Sequence
<220> FEATURE:
<223> OTHER INFORMATION: Nanobody sequence

<400> SEQUENCE: 452

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Phe Tyr Val Tyr Trp Gly Gln Gly Thr Leu Val
        100                 105                 110

Thr Val Ser Ser Gly Gly Gly Gly Ser Gly Gly Gly Gly Ser Gly Gly
    115                 120                 125

Gly Gly Ser Gly Gly Gly Ser Gly Gly Gly Ser Gly Gly Gly
    130                 135                 140

Gly Ser Gly Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
            165                 170                 175

Gly Leu Leu Phe Ser Arg Asn Ser Ala Gly Trp Tyr Arg Gln Ala Pro
        180                 185                 190
```

Gly Lys Gln Arg Glu Phe Val Ala Arg Ile Arg Met Gly Gly Ser Ile
            195                 200                 205

Asn Tyr Ala Asp Thr Val Lys Gly Arg Phe Thr Ile Ser Arg Asp Asn
210                 215                 220

Ala Lys Asn Thr Val Tyr Leu Gln Met Asn Ser Leu Lys Pro Glu Asp
225                 230                 235                 240

Thr Ala Val Tyr Tyr Cys Ser Ser Trp Arg Thr Gly Phe Tyr Glu Tyr
                245                 250                 255

Trp Gly Gln Gly Thr Leu Val Thr Val Ser Ser
            260                 265

<210> SEQ ID NO 453
<211> LENGTH: 278
<212> TYPE: PRT
<213> ORGANISM: Artificial Sequence
<220> FEATURE:
<223> OTHER INFORMATION: Nanobody sequence

<400> SEQUENCE: 453

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Ser Gly Gly Gly Ser Gly Gly Gly Gly
        115                 120                 125

Gly Gly Ser Gly Gly Gly Ser Gly Gly Gly Ser Gly Gly Gly Gly Gly
    130                 135                 140

Gly Ser Gly Gly Gly Ser Glu Val Gln Leu Val Glu Ser Gly Gly Gly
145                 150                 155                 160

Gly Leu Val Gln Ala Gly Gly Ser Leu Ser Leu Ser Cys Thr Ala Ser
                165                 170                 175

Gly Gly Thr Phe Arg Asn Phe Gly Met Gly Trp Phe Arg Gln Ala Gln
            180                 185                 190

Gly Lys Glu Arg Glu Phe Val Ala Ala Ile Ser Arg Thr Gly Gly His
        195                 200                 205

Thr Tyr Tyr Gln Asp Ser Val Lys Gly Arg Phe Thr Ile Ser Lys Asp
    210                 215                 220

Asn Ala Lys Asn Ile Leu Ser Leu Gln Met Asn Ser Leu Lys Pro Glu
225                 230                 235                 240

Asp Thr Ala Val Tyr Tyr Cys Ala Ala Arg Phe Arg Phe Gly Asp Gly
                245                 250                 255

Thr Tyr Tyr Tyr Gln Arg Ala Phe Tyr Asp Phe Trp Gly Gln Gly Thr
            260                 265                 270

Leu Val Thr Val Ser Ser
        275

-continued

```
<210> SEQ ID NO 454
<211> LENGTH: 278
<212> TYPE: PRT
<213> ORGANISM: Artificial Sequence
<220> FEATURE:
<223> OTHER INFORMATION: Nanobody sequence

<400> SEQUENCE: 454

Glu Val Gln Leu Val Glu Ser Gly Gly Gly Leu Val Gln Ala Gly Gly
1               5                   10                  15

Ser Leu Ser Leu Ser Cys Thr Ala Ser Gly Gly Thr Phe Arg Asn Phe
            20                  25                  30

Gly Met Gly Trp Phe Arg Gln Ala Gln Gly Lys Glu Arg Glu Phe Val
        35                  40                  45

Ala Ala Ile Ser Arg Thr Gly Gly His Thr Tyr Tyr Gln Asp Ser Val
    50                  55                  60

Lys Gly Arg Phe Thr Ile Ser Lys Asp Asn Ala Lys Asn Ile Leu Ser
65                  70                  75                  80

Leu Gln Met Asn Ser Leu Lys Pro Glu Asp Thr Ala Val Tyr Tyr Cys
                85                  90                  95

Ala Ala Arg Phe Arg Phe Gly Asp Gly Thr Tyr Tyr Tyr Gln Arg Ala
            100                 105                 110

Phe Tyr Asp Phe Trp Gly Gln Gly Thr Leu Val Thr Val Ser Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Gly Gly Gly Ser Gly Gly Gly
145                 150                 155                 160

Gly Ser Glu Val Gln Leu Val Glu Ser Gly Gly Gly Leu Val Gln Ala
                165                 170                 175

Gly Gly Ser Leu Gly Leu Ser Cys Ser Ala Ser Gly Leu Leu Phe Ser
            180                 185                 190

Arg Asn Ser Ala Gly Trp Tyr Arg Gln Ala Pro Gly Lys Gln Arg Glu
        195                 200                 205

Phe Val Ala Arg Ile Arg Met Gly Gly Ser Ile Asn Tyr Ala Asp Thr
    210                 215                 220

Val Lys Gly Arg Phe Thr Ile Ser Arg Asp Asn Ala Lys Asn Thr Val
225                 230                 235                 240

Tyr Leu Gln Met Asn Ser Leu Lys Pro Glu Asp Thr Ala Val Tyr Tyr
                245                 250                 255

Cys Ser Ser Trp Arg Thr Gly Phe Tyr Glu Tyr Trp Gly Gln Gly Thr
            260                 265                 270

Leu Val Thr Val Ser Ser
        275

<210> SEQ ID NO 455
<211> LENGTH: 278
<212> TYPE: PRT
<213> ORGANISM: Artificial Sequence
<220> FEATURE:
<223> OTHER INFORMATION: Nanobody sequence

<400> SEQUENCE: 455

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30
```

Ser Ala Gly Trp Tyr Arg Gln Ala Pro Gly Lys Gln Arg Glu Phe Val
         35                  40                  45

Ala Arg Ile Arg Met Gly Gly Ser Ile Asn Tyr Ala Asp Thr Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ser
                 85                  90                  95

Ser Trp Arg Thr Gly Phe Tyr Glu Tyr Trp Gly Gln Gly Thr Leu Val
            100                 105                 110

Thr Val Ser Ser Gly Gly Gly Ser Gly Gly Gly Ser Gly Gly Gly Gly
        115                 120                 125

Gly Gly Ser Gly Gly Gly Ser Gly Gly Gly Ser Gly Gly Gly
        130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Ser Leu Ser Cys Thr Ala Ser
                165                 170                 175

Gly Gly Thr Phe Arg Asn Phe Gly Met Gly Trp Phe Arg Gln Ala Gln
            180                 185                 190

Gly Lys Glu Arg Glu Phe Val Ala Ala Ile Ser Arg Thr Gly Gly His
        195                 200                 205

Thr Tyr Tyr Gln Asp Ser Val Lys Gly Arg Phe Thr Ile Ser Lys Asp
    210                 215                 220

Asn Ala Lys Asn Ile Leu Ser Leu Gln Met Asn Ser Leu Lys Pro Glu
225                 230                 235                 240

Asp Thr Ala Val Tyr Tyr Cys Ala Ala Arg Phe Arg Phe Gly Asp Gly
                245                 250                 255

Thr Tyr Tyr Tyr Gln Arg Ala Phe Tyr Asp Phe Trp Gly Gln Gly Thr
            260                 265                 270

Leu Val Thr Val Ser Ser
        275

<210> SEQ ID NO 456
<211> LENGTH: 267
<212> TYPE: PRT
<213> ORGANISM: Artificial Sequence
<220> FEATURE:
<223> OTHER INFORMATION: Nanobody sequence

<400> SEQUENCE: 456

Glu Val Gln Leu Val Glu Ser Gly Gly Gly Leu Val Gln Ala Gly Gly
1               5                  10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
         35                  40                  45

Ala Arg Ile Arg Met Gly Gly Ser Ile Asn Tyr Ala Asp Thr Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ser
                 85                  90                  95

Ser Trp Arg Thr Gly Phe Tyr Glu Tyr Trp Gly Gln Gly Thr Leu Val
            100                 105                 110

```
Thr Val Ser Ser Gly Gly Gly Ser Gly Gly Gly Ser Gly Gly
            115                 120                 125
Gly Gly Ser Gly Gly Gly Ser Gly Gly Gly Ser Gly Gly Gly
        130                 135                 140
Gly Ser Gly Gly Gly Ser Glu Val Gln Leu Val Glu Ser Gly
145                 150                 155                 160
Gly Leu Val Gln Ala Gly Gly Ser Leu Gly Leu Ser Cys Ser Ala Ser
                165                 170                 175
Gly Leu Leu Phe Ser Arg Asn Ser Ala Gly Trp Tyr Arg Gln Ala Pro
                180                 185                 190
Gly Lys Gln Arg Glu Phe Val Ala Arg Ile Arg Met Gly Gly Ser Ile
                195                 200                 205
Asn Tyr Ala Asp Thr Val Lys Gly Arg Phe Thr Ile Ser Arg Asp Asn
                210                 215                 220
Ala Lys Asn Thr Val Tyr Leu Gln Met Asn Ser Leu Lys Pro Glu Asp
225                 230                 235                 240
Thr Ala Val Tyr Tyr Cys Ser Ser Trp Arg Thr Gly Phe Tyr Glu Tyr
                245                 250                 255
Trp Gly Gln Gly Thr Leu Val Thr Val Ser Ser
                260                 265
```

<210> SEQ ID NO 457
<211> LENGTH: 278
<212> TYPE: PRT
<213> ORGANISM: Artificial Sequence
<220> FEATURE:
<223> OTHER INFORMATION: Nanobody sequence

<400> SEQUENCE: 457

```
Glu Val Gln Leu Val Glu Ser Gly Gly Gly Leu Val Gln Ala Gly Gly
1               5                   10                  15
Ser Leu Ser Leu Ser Cys Thr Ala Ser Gly Gly Thr Phe Arg Asn Phe
                20                  25                  30
Gly Met Gly Trp Phe Arg Gln Ala Gln Gly Lys Glu Arg Glu Phe Val
            35                  40                  45
Ala Ala Ile Ser Arg Thr Gly Gly His Thr Tyr Tyr Gln Asp Ser Val
        50                  55                  60
Lys Gly Arg Phe Thr Ile Ser Lys Asp Asn Ala Lys Asn Ile Leu Ser
65                  70                  75                  80
Leu Gln Met Asn Ser Leu Lys Pro Glu Asp Thr Ala Val Tyr Tyr Cys
                85                  90                  95
Ala Ala Arg Phe Arg Phe Gly Asp Gly Thr Tyr Tyr Gln Arg Ala
                100                 105                 110
Phe Tyr Asp Phe Trp Gly Gln Gly Thr Leu Val Thr Val Ser Ser Gly
            115                 120                 125
Gly Gly Ser Gly Gly Gly Gly Ser Gly Gly Gly Gly Ser Gly Gly Gly
        130                 135                 140
Gly Gly Ser Gly Gly Gly Ser Gly Gly Gly Ser Gly Gly Gly
145                 150                 155                 160
Gly Ser Glu Val Gln Leu Val Glu Ser Gly Gly Leu Val Gln Ala
                165                 170                 175
Gly Gly Ser Leu Gly Leu Ser Cys Ser Ala Ser Gly Leu Leu Phe Ser
                180                 185                 190
Arg Asn Ser Ala Gly Trp Tyr Arg Gln Ala Pro Gly Lys Gln Arg Glu
                195                 200                 205
```

Phe Val Ala Arg Ile Arg Met Gly Gly Ser Ile Asn Tyr Ala Asp Thr
    210                 215                 220

Val Lys Gly Arg Phe Thr Ile Ser Arg Asp Asn Ala Lys Asn Thr Val
225                 230                 235                 240

Tyr Leu Gln Met Asn Ser Leu Lys Pro Glu Asp Thr Ala Val Tyr Tyr
            245                 250                 255

Cys Ser Ser Trp Arg Thr Gly Phe Tyr Glu Tyr Trp Gly Gln Gly Thr
            260                 265                 270

Leu Val Thr Val Ser Ser
        275

<210> SEQ ID NO 458
<211> LENGTH: 418
<212> TYPE: PRT
<213> ORGANISM: Artificial Sequence
<220> FEATURE:
<223> OTHER INFORMATION: Nanobody sequence

<400> SEQUENCE: 458

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
            165                 170                 175

Gly Leu Leu Phe Ser Arg Asn Ser Ala Gly Trp Tyr Arg Gln Ala Pro
        180                 185                 190

Gly Lys Gln Arg Glu Phe Val Ala Arg Ile Arg Met Gly Gly Ser Ile
    195                 200                 205

Asn Tyr Ala Asp Thr Val Lys Gly Arg Phe Thr Ile Ser Arg Asp Asn
    210                 215                 220

Ala Lys Asn Thr Val Tyr Leu Gln Met Asn Ser Leu Lys Pro Glu Asp
225                 230                 235                 240

Thr Ala Val Tyr Tyr Cys Ser Ser Trp Arg Thr Gly Phe Tyr Glu Tyr
            245                 250                 255

Trp Gly Gln Gly Thr Leu Val Thr Val Ser Ser Gly Gly Gly Gly Ser
        260                 265                 270

Gly Gly Gly Gly Ser Gly Gly Gly Gly Ser Gly Gly Gly Gly Ser Gly
    275                 280                 285

```
Gly Gly Gly Ser Gly Gly Gly Ser Gly Gly Gly Ser Glu Val
    290                 295                 300

Gln Leu Val Glu Ser Gly Gly Leu Val Gln Ala Gly Gly Ser Leu
305                 310                 315                 320

Gly Leu Ser Cys Ser Ala Ser Gly Leu Leu Phe Ser Arg Asn Ser Ala
                325                 330                 335

Gly Trp Tyr Arg Gln Ala Pro Gly Lys Gln Arg Glu Phe Val Ala Arg
                340                 345                 350

Ile Arg Met Gly Gly Ser Ile Asn Tyr Ala Asp Thr Val Lys Gly Arg
            355                 360                 365

Phe Thr Ile Ser Arg Asp Asn Ala Lys Asn Thr Val Tyr Leu Gln Met
            370                 375                 380

Asn Ser Leu Lys Pro Glu Asp Thr Ala Val Tyr Tyr Cys Ser Ser Trp
385                 390                 395                 400

Arg Thr Gly Phe Tyr Glu Tyr Trp Gly Gln Gly Thr Leu Val Thr Val
                405                 410                 415

Ser Ser

<210> SEQ ID NO 459
<211> LENGTH: 569
<212> TYPE: PRT
<213> ORGANISM: Artificial Sequence
<220> FEATURE:
<223> OTHER INFORMATION: Nanobody sequence

<400> SEQUENCE: 459

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Met Gly Gly Ser Ile
        195                 200                 205

Asn Tyr Ala Asp Thr Val Lys Gly Arg Phe Thr Ile Ser Arg Asp Asn
    210                 215                 220
```

```
Ala Lys Asn Thr Val Tyr Leu Gln Met Asn Ser Leu Lys Pro Glu Asp
225                 230                 235                 240

Thr Ala Val Tyr Tyr Cys Ser Ser Trp Arg Thr Gly Phe Tyr Glu Tyr
            245                 250                 255

Trp Gly Gln Gly Thr Leu Val Thr Val Ser Ser Gly Gly Gly Gly Ser
        260                 265                 270

Gly Gly Gly Gly Ser Gly Gly Gly Ser Gly Gly Gly Gly Ser Gly
    275                 280                 285

Gly Gly Gly Ser Gly Gly Gly Ser Gly Gly Gly Ser Glu Val
    290                 295                 300

Gln Leu Val Glu Ser Gly Gly Leu Val Gln Ala Gly Gly Ser Leu
305                 310                 315                 320

Gly Leu Ser Cys Ser Ala Ser Gly Leu Leu Phe Ser Arg Asn Ser Ala
            325                 330                 335

Gly Trp Tyr Arg Gln Ala Pro Gly Lys Gln Arg Glu Phe Val Ala Arg
        340                 345                 350

Ile Arg Met Gly Gly Ser Ile Asn Tyr Ala Asp Thr Val Lys Gly Arg
        355                 360                 365

Phe Thr Ile Ser Arg Asp Asn Ala Lys Asn Thr Val Tyr Leu Gln Met
370                 375                 380

Asn Ser Leu Lys Pro Glu Asp Thr Ala Val Tyr Tyr Cys Ser Ser Trp
385                 390                 395                 400

Arg Thr Gly Phe Tyr Glu Tyr Trp Gly Gln Gly Thr Leu Val Thr Val
            405                 410                 415

Ser Ser Gly Gly Gly Gly Ser Gly Gly Gly Gly Ser Gly Gly Gly Gly
        420                 425                 430

Ser Gly Gly Gly Gly Ser Gly Gly Gly Gly Ser Gly Gly Gly Gly Ser
        435                 440                 445

Gly Gly Gly Ser Glu Val Gln Leu Val Glu Ser Gly Gly Gly Leu
    450                 455                 460

Val Gln Ala Gly Gly Ser Leu Leu Ser Cys Ser Ala Ser Gly Leu
465                 470                 475                 480

Leu Phe Ser Arg Asn Ser Ala Gly Trp Tyr Arg Gln Ala Pro Gly Lys
            485                 490                 495

Gln Arg Glu Phe Val Ala Arg Ile Arg Met Gly Gly Ser Ile Asn Tyr
        500                 505                 510

Ala Asp Thr Val Lys Gly Arg Phe Thr Ile Ser Arg Asp Asn Ala Lys
        515                 520                 525

Asn Thr Val Tyr Leu Gln Met Asn Ser Leu Lys Pro Glu Asp Thr Ala
        530                 535                 540

Val Tyr Tyr Cys Ser Ser Trp Arg Thr Gly Phe Tyr Glu Tyr Trp Gly
545                 550                 555                 560

Gln Gly Thr Leu Val Thr Val Ser Ser
            565
```

<210> SEQ ID NO 460
<211> LENGTH: 267
<212> TYPE: PRT
<213> ORGANISM: Artificial Sequence
<220> FEATURE:
<223> OTHER INFORMATION: Nanobody sequence

<400> SEQUENCE: 460

```
Asp Val Gln Leu Val Glu Ser Gly Gly Gly Leu Val Gln Ala Gly Gly
1               5                   10                  15
```

Ser Leu Gly Leu Ser Cys Ser Ala Ser Gly Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
50                      55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gly Gly Gly Ser Gly Gly Gly Ser Gly Gly Gly
        130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
            165                 170                 175

Gly Leu Leu Phe Ser Arg Asn Ser Ala Gly Trp Tyr Arg Gln Ala Pro
            180                 185                 190

Gly Lys Arg Arg Glu Phe Val Ala Arg Ile Arg Met Gly Gly Ser Ile
            195                 200                 205

Asn Tyr Ala Asp Ser Val Lys Gly Arg Phe Thr Val Ser Arg Asp Asn
210                 215                 220

Ala Lys Asn Met Met Tyr Leu Gln Met Asn Asp Leu Lys Pro Glu Asp
225                 230                 235                 240

Thr Ala Val Tyr Phe Cys Ser Gly Trp Arg Glu Gly Phe Tyr Glu Tyr
                245                 250                 255

Trp Gly Gln Gly Thr Leu Val Thr Val Ser Ser
            260                 265

<210> SEQ ID NO 461
<211> LENGTH: 417
<212> TYPE: PRT
<213> ORGANISM: Artificial Sequence
<220> FEATURE:
<223> OTHER INFORMATION: Nanobody sequence

<400> SEQUENCE: 461

Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Val Gly Trp Tyr Arg Arg Ala Pro Gly Lys Gln Arg Glu Phe Val
        35                  40                  45

Ala Arg Leu Arg Thr Thr Gly Ser Thr Asn Tyr Ala Gln Ser Val Lys
50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Ser
                85                  90                  95

Ala Trp Arg Ile Glu Ala Tyr Glu Tyr Trp Gly Gln Gly Thr Leu Val
            100                 105                 110

-continued

```
Thr Val Ser Ser Gly Gly Gly Ser Gly Gly Gly Ser Gly Gly
            115                 120                 125
Gly Gly Ser Gly Gly Gly Ser Gly Gly Gly Ser Gly Gly Gly
    130                 135                 140
Gly Ser Gly Gly Gly Ser Glu Val Gln Leu Val Glu Ser Gly Gly
145                 150                 155                 160
Gly Leu Val Gln Ala Gly Gly Ser Leu Arg Leu Ser Cys Ser Ala Ser
                165                 170                 175
Gly Leu Leu Phe Ser Val Asn Ser Val Gly Trp Tyr Arg Arg Ala Pro
                180                 185                 190
Gly Lys Gln Arg Glu Phe Val Ala Arg Leu Arg Thr Thr Gly Ser Thr
                195                 200                 205
Asn Tyr Ala Gln Ser Val Lys Gly Arg Phe Thr Ile Ser Arg Asp Asn
                210                 215                 220
Ala Lys Asn Thr Val Tyr Leu Gln Met Asn Asn Leu Lys Pro Glu Asp
225                 230                 235                 240
Thr Ala Val Tyr Tyr Cys Ser Ala Trp Arg Ile Glu Ala Tyr Glu Tyr
                245                 250                 255
Trp Gly Gln Gly Thr Leu Val Thr Val Ser Ser Gly Gly Gly Gly Ser
                260                 265                 270
Gly Gly Gly Gly Ser Gly Gly Gly Ser Gly Gly Gly Ser Gly
    275                 280                 285
Gly Gly Gly Ser Gly Gly Gly Ser Gly Gly Gly Ser Glu Val
    290                 295                 300
Gln Leu Val Glu Ser Gly Gly Leu Val Gln Pro Gly Asn Ser Leu
305                 310                 315                 320
Arg Leu Ser Cys Ala Ala Ser Gly Phe Thr Phe Ser Ser Phe Gly Met
                325                 330                 335
Ser Trp Val Arg Gln Ala Pro Gly Lys Gly Leu Glu Trp Val Ser Ser
                340                 345                 350
Ile Ser Gly Ser Gly Ser Asp Thr Leu Tyr Ala Asp Ser Val Lys Gly
                355                 360                 365
Arg Phe Thr Ile Ser Arg Asp Asn Ala Lys Thr Thr Leu Tyr Leu Gln
                370                 375                 380
Met Asn Ser Leu Arg Pro Glu Asp Thr Ala Val Tyr Tyr Cys Thr Ile
385                 390                 395                 400
Gly Gly Ser Leu Ser Arg Ser Ser Gln Gly Thr Leu Val Thr Val Ser
                405                 410                 415
Ser
```

<210> SEQ ID NO 462
<211> LENGTH: 417
<212> TYPE: PRT
<213> ORGANISM: Artificial Sequence
<220> FEATURE:
<223> OTHER INFORMATION: Nanobody sequence

<400> SEQUENCE: 462

```
Glu Val Gln Leu Val Glu Ser Gly Gly Gly Leu Val Gln Ala Gly Gly
1               5                   10                  15
Ser Leu Gly Leu Ser Cys Ser Ala Ser Gly Leu Leu Phe Ser Arg Asn
                20                  25                  30
Ser Ala Gly Trp Tyr Arg Gln Ala Pro Gly Lys Arg Arg Glu Phe Val
                35                  40                  45
Ala Arg Ile Arg Met Gly Gly Ser Ile Asn Tyr Ala Asp Ser Val Lys
```

```
                  50                  55                  60

Gly Arg Phe Thr Val Ser Arg Asp Asn Ala Lys Asn Met Met Tyr Leu
 65                  70                  75                  80

Gln Met Asn Asp Leu Lys Pro Glu Asp Thr Ala Val Tyr Phe Cys Ser
                     85                  90                  95

Gly Trp Arg Glu Gly Phe Tyr Glu Tyr Trp Gly Gln Gly Thr Leu Val
                    100                 105                 110

Thr Val Ser Ser Gly Gly Gly Ser Gly Gly Gly Ser Gly Gly
                115                 120                 125

Gly Gly Ser Gly Gly Gly Ser Gly Gly Gly Ser Gly Gly Gly
            130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
                    165                 170                 175

Gly Leu Leu Phe Ser Arg Asn Ser Ala Gly Trp Tyr Arg Gln Ala Pro
                    180                 185                 190

Gly Lys Arg Arg Glu Phe Val Ala Arg Ile Arg Met Gly Gly Ser Ile
                    195                 200                 205

Asn Tyr Ala Asp Ser Val Lys Gly Arg Phe Thr Val Ser Arg Asp Asn
210                 215                 220

Ala Lys Asn Met Met Tyr Leu Gln Met Asn Asp Leu Lys Pro Glu Asp
225                 230                 235                 240

Thr Ala Val Tyr Phe Cys Ser Gly Trp Arg Glu Gly Phe Tyr Glu Tyr
                    245                 250                 255

Trp Gly Gln Gly Thr Leu Val Thr Val Ser Ser Gly Gly Gly Gly Ser
                    260                 265                 270

Gly Gly Gly Gly Ser Gly Gly Gly Ser Gly Gly Gly Ser Gly
            275                 280                 285

Gly Gly Gly Ser Gly Gly Gly Ser Gly Gly Gly Ser Glu Val
            290                 295                 300

Gln Leu Val Glu Ser Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                    325                 330                 335

Ser Trp Val Arg Gln Ala Pro Gly Lys Gly Leu Glu Trp Val Ser Ser
                    340                 345                 350

Ile Ser Gly Ser Gly Ser Asp Thr Leu Tyr Ala Asp Ser Val Lys Gly
                    355                 360                 365

Arg Phe Thr Ile Ser Arg Asp Asn Ala Lys Thr Thr Leu Tyr Leu Gln
                    370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                    405                 410                 415

Ser

<210> SEQ ID NO 463
<211> LENGTH: 365
<212> TYPE: PRT
<213> ORGANISM: Artificial Sequence
<220> FEATURE:
<223> OTHER INFORMATION: Nanobody sequence

<400> SEQUENCE: 463
```

```
Glu Val Gln Leu Val Glu Ser Gly Gly Gly Leu Val Gln Ala Gly Gly
1               5                   10                  15

Ser Leu Arg Leu Ser Cys Ser Ala Ser Gly Leu Leu Phe Ser Val Asn
            20                  25                  30

Ser Val Gly Trp Tyr Arg Arg Ala Pro Gly Lys Gln Arg Glu Phe Val
        35                  40                  45

Ala Arg Leu Arg Thr Thr Gly Ser Thr Asn Tyr Ala Gln Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Ser
                85                  90                  95

Ala Trp Arg Ile Glu Ala Tyr Glu Tyr Trp Gly Gln Gly Thr Leu Val
            100                 105                 110

Thr Val Ser Ser Gly Gly Gly Ser Gly Gly Gly Ser Glu Val Gln
        115                 120                 125

Leu Val Glu Ser Gly Gly Gly Leu Val Gln Pro Gly Asn Ser Leu Arg
    130                 135                 140

Leu Ser Cys Ala Ala Ser Gly Phe Thr Phe Ser Ser Phe Gly Met Ser
145                 150                 155                 160

Trp Val Arg Gln Ala Pro Gly Lys Gly Leu Glu Trp Val Ser Ser Ile
            165                 170                 175

Ser Gly Ser Gly Ser Asp Thr Leu Tyr Ala Asp Ser Val Lys Gly Arg
        180                 185                 190

Phe Thr Ile Ser Arg Asp Asn Ala Lys Thr Thr Leu Tyr Leu Gln Met
        195                 200                 205

Asn Ser Leu Arg Pro Glu Asp Thr Ala Val Tyr Tyr Cys Thr Ile Gly
    210                 215                 220

Gly Ser Leu Ser Arg Ser Ser Gln Gly Thr Leu Val Thr Val Ser Ser
225                 230                 235                 240

Gly Gly Gly Gly Ser Gly Gly Ser Glu Val Gln Leu Val Glu Ser
                245                 250                 255

Gly Gly Gly Leu Val Gln Ala Gly Gly Ser Leu Arg Leu Ser Cys Ser
            260                 265                 270

Ala Ser Gly Leu Leu Phe Ser Val Asn Ser Val Gly Trp Tyr Arg Arg
        275                 280                 285

Ala Pro Gly Lys Gln Arg Glu Phe Val Ala Arg Leu Arg Thr Thr Gly
    290                 295                 300

Ser Thr Asn Tyr Ala Gln Ser Val Lys Gly Arg Phe Thr Ile Ser Arg
305                 310                 315                 320

Asp Asn Ala Lys Asn Thr Val Tyr Leu Gln Met Asn Asn Leu Lys Pro
                325                 330                 335

Glu Asp Thr Ala Val Tyr Tyr Cys Ser Ala Trp Arg Ile Glu Ala Tyr
            340                 345                 350

Glu Tyr Trp Gly Gln Gly Thr Leu Val Thr Val Ser Ser
            355                 360                 365

<210> SEQ ID NO 464
<211> LENGTH: 365
<212> TYPE: PRT
<213> ORGANISM: Artificial Sequence
<220> FEATURE:
<223> OTHER INFORMATION: Nanobody sequence

<400> SEQUENCE: 464
```

-continued

```
Glu Val Gln Leu Val Glu Ser Gly Gly Gly Leu Val Gln Ala Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Ser Gly Gly Gly Ser Glu Val Gln
        115                 120                 125

Leu Val Glu Ser Gly Gly Gly Leu Val Gln Pro Gly Asn Ser Leu Arg
    130                 135                 140

Leu Ser Cys Ala Ala Ser Gly Phe Thr Phe Ser Ser Phe Gly Met Ser
145                 150                 155                 160

Trp Val Arg Gln Ala Pro Gly Lys Gly Leu Glu Trp Val Ser Ser Ile
                165                 170                 175

Ser Gly Ser Gly Ser Asp Thr Leu Tyr Ala Asp Ser Val Lys Gly Arg
            180                 185                 190

Phe Thr Ile Ser Arg Asp Asn Ala Lys Thr Thr Leu Tyr Leu Gln Met
        195                 200                 205

Asn Ser Leu Arg Pro Glu Asp Thr Ala Val Tyr Tyr Cys Thr Ile Gly
    210                 215                 220

Gly Ser Leu Ser Arg Ser Ser Gln Gly Thr Leu Val Thr Val Ser Ser
225                 230                 235                 240

Gly Gly Gly Gly Ser Gly Gly Ser Glu Val Gln Leu Val Glu Ser
                245                 250                 255

Gly Gly Gly Leu Val Gln Ala Gly Gly Ser Leu Gly Leu Ser Cys Ser
            260                 265                 270

Ala Ser Gly Leu Leu Phe Ser Arg Asn Ser Ala Gly Trp Tyr Arg Gln
        275                 280                 285

Ala Pro Gly Lys Gln Arg Glu Phe Val Ala Arg Ile Arg Met Gly Gly
    290                 295                 300

Ser Ile Asn Tyr Ala Asp Thr Val Lys Gly Arg Phe Thr Ile Ser Arg
305                 310                 315                 320

Asp Asn Ala Lys Asn Thr Val Tyr Leu Gln Met Asn Ser Leu Lys Pro
                325                 330                 335

Glu Asp Thr Ala Val Tyr Tyr Cys Ser Ser Trp Arg Thr Gly Phe Tyr
            340                 345                 350

Glu Tyr Trp Gly Gln Gly Thr Leu Val Thr Val Ser Ser
        355                 360                 365

<210> SEQ ID NO 465
<211> LENGTH: 417
<212> TYPE: PRT
<213> ORGANISM: Artificial Sequence
<220> FEATURE:
<223> OTHER INFORMATION: Nanobody sequence

<400> SEQUENCE: 465
```

```
Glu Val Gln Leu Val Glu Ser Gly Gly Gly Leu Val Gln Ala Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Gly Gly Gly Ser Gly Gly Gly Ser Gly Gly
    130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
            165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Met Gly Gly Ser Ile
        195                 200                 205

Asn Tyr Ala Asp Thr Val Lys Gly Arg Phe Thr Ile Ser Arg Asp Asn
210                 215                 220

Ala Lys Asn Thr Val Tyr Leu Gln Met Asn Ser Leu Lys Pro Glu Asp
225                 230                 235                 240

Thr Ala Val Tyr Tyr Cys Ser Ser Trp Arg Thr Gly Phe Tyr Glu Tyr
            245                 250                 255

Trp Gly Gln Gly Thr Leu Val Thr Val Ser Ser Gly Gly Gly Ser
        260                 265                 270

Gly Gly Gly Gly Ser Gly Gly Gly Ser Gly Gly Gly Ser Gly
    275                 280                 285

Gly Gly Ser Gly Gly Gly Ser Gly Gly Gly Ser Glu Val
    290                 295                 300

Gln Leu Val Glu Ser Gly Gly Leu Val Gln Pro Gly Asn Ser Leu
305                 310                 315                 320

Arg Leu Ser Cys Ala Ala Ser Gly Phe Thr Phe Ser Ser Phe Gly Met
            325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
            405                 410                 415
```

Ser

<210> SEQ ID NO 466
<211> LENGTH: 365
<212> TYPE: PRT
<213> ORGANISM: Artificial Sequence
<220> FEATURE:
<223> OTHER INFORMATION: Nanobody sequence

<400> SEQUENCE: 466

```
Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Ser Gly Gly Gly Ser Glu Val Gln
        115                 120                 125

Leu Val Glu Ser Gly Gly Gly Leu Val Gln Pro Gly Asn Ser Leu Arg
130                 135                 140

Leu Ser Cys Ala Ala Ser Gly Phe Thr Phe Ser Ser Phe Gly Met Ser
145                 150                 155                 160

Trp Val Arg Gln Ala Pro Gly Lys Gly Leu Glu Trp Val Ser Ser Ile
                165                 170                 175

Ser Gly Ser Gly Ser Asp Thr Leu Tyr Ala Asp Ser Val Lys Gly Arg
            180                 185                 190

Phe Thr Ile Ser Arg Asp Asn Ala Lys Thr Thr Leu Tyr Leu Gln Met
        195                 200                 205

Asn Ser Leu Arg Pro Glu Asp Thr Ala Val Tyr Tyr Cys Thr Ile Gly
    210                 215                 220

Gly Ser Leu Ser Arg Ser Ser Gln Gly Thr Leu Val Thr Val Ser Ser
225                 230                 235                 240

Gly Gly Gly Gly Ser Gly Gly Gly Ser Glu Val Gln Leu Val Glu Ser
                245                 250                 255

Gly Gly Gly Leu Val Gln Ala Gly Gly Ser Leu Gly Leu Ser Cys Ser
            260                 265                 270

Ala Ser Gly Leu Leu Phe Ser Arg Asn Ser Ala Gly Trp Tyr Arg Gln
        275                 280                 285

Ala Pro Gly Lys Arg Arg Glu Phe Val Ala Arg Ile Arg Met Gly Gly
    290                 295                 300

Ser Ile Asn Tyr Ala Asp Ser Val Lys Gly Arg Phe Thr Val Ser Arg
305                 310                 315                 320

Asp Asn Ala Lys Asn Met Met Tyr Leu Gln Met Asn Asp Leu Lys Pro
                325                 330                 335

Glu Asp Thr Ala Val Tyr Phe Cys Ser Gly Trp Arg Glu Gly Phe Tyr
            340                 345                 350

Glu Tyr Trp Gly Gln Gly Thr Leu Val Thr Val Ser Ser
        355                 360                 365
```

355                 360                 365

<210> SEQ ID NO 467
<211> LENGTH: 417
<212> TYPE: PRT
<213> ORGANISM: Artificial Sequence
<220> FEATURE:
<223> OTHER INFORMATION: nanobody sequence

<400> SEQUENCE: 467

Asp Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Arg Arg Glu Phe Val Ala Arg Ile Arg Met Gly Gly Ser Ile
        195                 200                 205

Asn Tyr Ala Asp Ser Val Lys Gly Arg Phe Thr Val Ser Arg Asp Asn
    210                 215                 220

Ala Lys Asn Met Met Tyr Leu Gln Met Asn Asp Leu Lys Pro Glu Asp
225                 230                 235                 240

Thr Ala Val Tyr Phe Cys Ser Gly Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Gly Gly Gly Gly Ser Gly
        275                 280                 285

Gly Gly Gly Ser Gly Gly Gly Gly Ser Gly Gly Gly Gly Ser Glu Val
    290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly

```
                    355                 360                 365
Arg Phe Thr Ile Ser Arg Asp Asn Ala Lys Thr Thr Leu Tyr Leu Gln
370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Gln Gly Thr Leu Val Thr Val Ser
                405                 410                 415

Ser

<210> SEQ ID NO 468
<211> LENGTH: 391
<212> TYPE: PRT
<213> ORGANISM: Artificial Sequence
<220> FEATURE:
<223> OTHER INFORMATION: Nanobody sequence

<400> SEQUENCE: 468

Glu Val Gln Leu Val Glu Ser Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Arg Arg Glu Phe Val
                35                  40                  45

Ala Arg Ile Arg Met Gly Gly Ser Ile Asn Tyr Ala Asp Ser Val Lys
50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
                100                 105                 110

Thr Val Ser Ser Gly Gly Gly Gly Ser Gly Gly Gly Ser Glu Val Gln
                115                 120                 125

Leu Val Glu Ser Gly Gly Gly Leu Val Gln Ala Gly Gly Ser Leu Gly
130                 135                 140

Leu Ser Cys Ser Ala Ser Gly Leu Leu Phe Ser Arg Asn Ser Ala Gly
145                 150                 155                 160

Trp Tyr Arg Gln Ala Pro Gly Lys Arg Arg Glu Phe Val Ala Arg Ile
                165                 170                 175

Arg Met Gly Gly Ser Ile Asn Tyr Ala Asp Ser Val Lys Gly Arg Phe
                180                 185                 190

Thr Val Ser Arg Asp Asn Ala Lys Asn Met Met Tyr Leu Gln Met Asn
                195                 200                 205

Asp Leu Lys Pro Glu Asp Thr Ala Val Tyr Phe Cys Ser Gly Trp Arg
                210                 215                 220

Glu Gly Phe Tyr Glu Tyr Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Ser Gly Gly Gly Gly Ser Gly
                260                 265                 270

Gly Gly Gly Ser Glu Val Gln Leu Val Glu Ser Gly Gly Gly Leu Val
                275                 280                 285

Gln Pro Gly Asn Ser Leu Arg Leu Ser Cys Ala Ala Ser Gly Phe Thr
                290                 295                 300
```

```
Phe Ser Ser Phe Gly Met Ser Trp Val Arg Gln Ala Pro Gly Lys Gly
305                 310                 315                 320

Leu Glu Trp Val Ser Ser Ile Ser Gly Ser Gly Ser Asp Thr Leu Tyr
                325                 330                 335

Ala Asp Ser Val Lys Gly Arg Phe Thr Ile Ser Arg Asp Asn Ala Lys
            340                 345                 350

Thr Thr Leu Tyr Leu Gln Met Asn Ser Leu Arg Pro Glu Asp Thr Ala
        355                 360                 365

Val Tyr Tyr Cys Thr Ile Gly Gly Ser Leu Ser Arg Ser Ser Gln Gly
    370                 375                 380

Thr Leu Val Thr Val Ser Ser
385                 390

<210> SEQ ID NO 469
<211> LENGTH: 397
<212> TYPE: PRT
<213> ORGANISM: Artificial Sequence
<220> FEATURE:
<223> OTHER INFORMATION: Nanobody sequence

<400> SEQUENCE: 469

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Ala Gly Gly Ser Leu Gly Leu Ser Cys Ser Ala Ser Gly Leu Leu Phe
145                 150                 155                 160

Ser Arg Asn Ser Ala Gly Trp Tyr Arg Gln Ala Pro Gly Lys Arg Arg
                165                 170                 175

Glu Phe Val Ala Arg Ile Arg Met Gly Gly Ser Ile Asn Tyr Ala Asp
            180                 185                 190

Ser Val Lys Gly Arg Phe Thr Val Ser Arg Asp Asn Ala Lys Asn Met
        195                 200                 205

Met Tyr Leu Gln Met Asn Asp Leu Lys Pro Glu Asp Thr Ala Val Tyr
    210                 215                 220

Phe Cys Ser Gly Trp Arg Glu Gly Phe Tyr Glu Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Gly Gly Gly Gly Ser Gly Gly Gly Gly Ser
            260                 265                 270
```

```
Gly Gly Gly Gly Ser Gly Gly Gly Ser Glu Val Gln Leu Val Glu
            275                 280                 285

Ser Gly Gly Gly Leu Val Gln Pro Gly Asn Ser Leu Arg Leu Ser Cys
290                 295                 300

Ala Ala Ser Gly Phe Thr Phe Ser Ser Phe Gly Met Ser Trp Val Arg
305                 310                 315                 320

Gln Ala Pro Gly Lys Gly Leu Glu Trp Val Ser Ser Ile Ser Gly Ser
                325                 330                 335

Gly Ser Asp Thr Leu Tyr Ala Asp Ser Val Lys Gly Arg Phe Thr Ile
            340                 345                 350

Ser Arg Asp Asn Ala Lys Thr Thr Leu Tyr Leu Gln Met Asn Ser Leu
355                 360                 365

Arg Pro Glu Asp Thr Ala Val Tyr Tyr Cys Thr Ile Gly Gly Ser Leu
370                 375                 380

Ser Arg Ser Ser Gln Gly Thr Leu Val Thr Val Ser Ser
385                 390                 395

<210> SEQ ID NO 470
<211> LENGTH: 402
<212> TYPE: PRT
<213> ORGANISM: Artificial Sequence
<220> FEATURE:
<223> OTHER INFORMATION: Nanobody sequence

<400> SEQUENCE: 470

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Arg Arg Glu Phe Val
            35                  40                  45

Ala Arg Ile Arg Met Gly Gly Ser Ile Asn Tyr Ala Asp Ser Val Lys
50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Ser Gly Gly Gly Gly Ser Gly Gly
            115                 120                 125

Gly Gly Ser Gly Gly Gly Ser Glu Val Gln Leu Val Glu Ser Gly
        130                 135                 140

Gly Gly Leu Val Gln Ala Gly Gly Ser Leu Leu Ser Cys Ser Ala
145                 150                 155                 160

Ser Gly Leu Leu Phe Ser Arg Asn Ser Ala Gly Trp Tyr Arg Gln Ala
                165                 170                 175

Pro Gly Lys Arg Arg Glu Phe Val Ala Arg Ile Arg Met Gly Gly Ser
            180                 185                 190

Ile Asn Tyr Ala Asp Ser Val Lys Gly Arg Phe Thr Val Ser Arg Asp
            195                 200                 205

Asn Ala Lys Asn Met Met Tyr Leu Gln Met Asn Asp Leu Lys Pro Glu
210                 215                 220

Asp Thr Ala Val Tyr Phe Cys Ser Gly Trp Arg Glu Gly Phe Tyr Glu
225                 230                 235                 240
```

```
Tyr Trp Gly Gln Gly Thr Leu Val Thr Val Ser Ser Gly Gly Gly
                245                 250                 255
Ser Gly Gly Gly Gly Ser Gly Gly Gly Gly Ser Gly Gly Gly Ser
                260                 265                 270
Gly Gly Gly Gly Ser Gly Gly Gly Ser Gly Gly Gly Ser Glu
            275                 280                 285
Val Gln Leu Val Glu Ser Gly Gly Leu Val Gln Pro Gly Asn Ser
        290                 295                 300
Leu Arg Leu Ser Cys Ala Ala Ser Gly Phe Thr Phe Ser Ser Phe Gly
305                 310                 315                 320
Met Ser Trp Val Arg Gln Ala Pro Gly Lys Gly Leu Glu Trp Val Ser
                325                 330                 335
Ser Ile Ser Gly Ser Gly Ser Asp Thr Leu Tyr Ala Asp Ser Val Lys
                340                 345                 350
Gly Arg Phe Thr Ile Ser Arg Asp Asn Ala Lys Thr Thr Leu Tyr Leu
                355                 360                 365
Gln Met Asn Ser Leu Arg Pro Glu Asp Thr Ala Val Tyr Tyr Cys Thr
        370                 375                 380
Ile Gly Gly Ser Leu Ser Arg Ser Ser Gln Gly Thr Leu Val Thr Val
385                 390                 395                 400

Ser Ser

<210> SEQ ID NO 471
<211> LENGTH: 407
<212> TYPE: PRT
<213> ORGANISM: Artificial Sequence
<220> FEATURE:
<223> OTHER INFORMATION: Nanobody sequence

<400> SEQUENCE: 471

Glu Val Gln Leu Val Glu Ser Gly Gly Gly Leu Val Gln Ala Gly Gly
1               5                   10                  15
Ser Leu Gly Leu Ser Cys Ser Ala Ser Gly Leu Leu Phe Ser Arg Asn
                20                  25                  30
Ser Ala Gly Trp Tyr Arg Gln Ala Pro Gly Lys Arg Arg Glu Phe Val
            35                  40                  45
Ala Arg Ile Arg Met Gly Gly Ser Ile Asn Tyr Ala Asp Ser Val Lys
50                  55                  60
Gly Arg Phe Thr Val Ser Arg Asp Asn Ala Lys Asn Met Met Tyr Leu
65                  70                  75                  80
Gln Met Asn Asp Leu Lys Pro Glu Asp Thr Ala Val Tyr Phe Cys Ser
                85                  90                  95
Gly Trp Arg Glu Gly Phe Tyr Gly Tyr Trp Gly Gln Gly Thr Leu Val
            100                 105                 110
Thr Val Ser Ser Gly Gly Gly Gly Ser Gly Gly Gly Gly Ser Gly Gly
        115                 120                 125
Gly Gly Ser Gly Gly Gly Gly Ser Gly Gly Gly Gly Ser Glu Val Gln
    130                 135                 140
Leu Val Glu Ser Gly Gly Gly Leu Val Gln Ala Gly Gly Ser Leu Gly
145                 150                 155                 160
Leu Ser Cys Ser Ala Ser Gly Leu Leu Phe Ser Arg Asn Ser Ala Gly
                165                 170                 175
Trp Tyr Arg Gln Ala Pro Gly Lys Arg Arg Glu Phe Val Ala Arg Ile
            180                 185                 190
```

```
Arg Met Gly Gly Ser Ile Asn Tyr Ala Asp Ser Val Lys Gly Arg Phe
            195                 200                 205
Thr Val Ser Arg Asp Asn Ala Lys Asn Met Met Tyr Leu Gln Met Asn
210                 215                 220
Asp Leu Lys Pro Glu Asp Thr Ala Val Tyr Phe Cys Ser Gly Trp Arg
225                 230                 235                 240
Glu Gly Phe Tyr Glu Tyr Trp Gly Gln Gly Thr Leu Val Thr Val Ser
            245                 250                 255
Ser Gly Gly Gly Ser Gly Gly Gly Ser Gly Gly Gly Ser
            260                 265                 270
Gly Gly Gly Gly Ser Gly Gly Gly Ser Gly Gly Gly Ser Gly
        275                 280                 285
Gly Gly Gly Ser Glu Val Gln Leu Val Glu Ser Gly Gly Gly Leu Val
        290                 295                 300
Gln Pro Gly Asn Ser Leu Arg Leu Ser Cys Ala Ala Ser Gly Phe Thr
305                 310                 315                 320
Phe Ser Ser Phe Gly Met Ser Trp Val Arg Gln Ala Pro Gly Lys Gly
            325                 330                 335
Leu Glu Trp Val Ser Ser Ile Ser Gly Ser Gly Ser Asp Thr Leu Tyr
            340                 345                 350
Ala Asp Ser Val Lys Gly Arg Phe Thr Ile Ser Arg Asp Asn Ala Lys
            355                 360                 365
Thr Thr Leu Tyr Leu Gln Met Asn Ser Leu Arg Pro Glu Asp Thr Ala
        370                 375                 380
Val Tyr Tyr Cys Thr Ile Gly Gly Ser Leu Ser Arg Ser Ser Gln Gly
385                 390                 395                 400
Thr Leu Val Thr Val Ser Ser
            405

<210> SEQ ID NO 472
<211> LENGTH: 422
<212> TYPE: PRT
<213> ORGANISM: Artificial Sequence
<220> FEATURE:
<223> OTHER INFORMATION: Nanobody sequence

<400> SEQUENCE: 472

Glu Val Gln Leu Val Glu Ser Gly Gly Gly Leu Val Gln Ala Gly Gly
1               5                   10                  15
Ser Leu Gly Leu Ser Cys Ser Ala Ser Gly Leu Leu Phe Ser Arg Asn
            20                  25                  30
Ser Ala Gly Trp Tyr Arg Gln Ala Pro Gly Lys Arg Arg Glu Phe Val
        35                  40                  45
Ala Arg Ile Arg Met Gly Gly Ser Ile Asn Tyr Ala Asp Ser Val Lys
    50                  55                  60
Gly Arg Phe Thr Val Ser Arg Asp Asn Ala Lys Asn Met Met Tyr Leu
65                  70                  75                  80
Gln Met Asn Asp Leu Lys Pro Glu Asp Thr Ala Val Tyr Phe Cys Ser
            85                  90                  95
Gly Trp Arg Glu Gly Phe Tyr Glu Tyr Trp Gly Gln Gly Thr Leu Val
            100                 105                 110
Thr Val Ser Ser Gly Gly Gly Ser Gly Gly Gly Ser Gly Gly
        115                 120                 125
Gly Gly Ser Gly Gly Gly Ser Gly Gly Gly Ser Gly Gly Gly
    130                 135                 140
```

Gly Ser Gly Gly Gly Ser Gly Gly Gly Ser Glu Val Gln Leu
145              150              155              160

Val Glu Ser Gly Gly Leu Val Gln Ala Gly Gly Ser Leu Gly Leu
         165              170              175

Ser Cys Ser Ala Ser Gly Leu Leu Phe Ser Arg Asn Ser Ala Gly Trp
             180              185              190

Tyr Arg Gln Ala Pro Gly Lys Arg Arg Glu Phe Val Ala Arg Ile Arg
             195              200              205

Met Gly Gly Ser Ile Asn Tyr Ala Asp Ser Val Lys Gly Arg Phe Thr
         210              215              220

Val Ser Arg Asp Asn Ala Lys Asn Met Met Tyr Leu Gln Met Asn Asp
225              230              235              240

Leu Lys Pro Glu Asp Thr Ala Val Tyr Phe Cys Ser Gly Trp Arg Glu
             245              250              255

Gly Phe Tyr Glu Tyr Trp Gly Gln Gly Thr Leu Val Thr Val Ser Ser
             260              265              270

Gly Gly Gly Gly Ser Gly Gly Gly Ser Gly Gly Gly Gly Ser Gly
         275              280              285

Gly Gly Ser Gly Gly Gly Ser Gly Gly Gly Ser Gly Gly
290              295              300

Gly Gly Ser Glu Val Gln Leu Val Glu Ser Gly Gly Leu Val Gln
305              310              315              320

Pro Gly Asn Ser Leu Arg Leu Ser Cys Ala Ala Ser Gly Phe Thr Phe
             325              330              335

Ser Ser Phe Gly Met Ser Trp Val Arg Gln Ala Pro Gly Lys Gly Leu
             340              345              350

Glu Trp Val Ser Ser Ile Ser Gly Ser Gly Ser Asp Thr Leu Tyr Ala
             355              360              365

Asp Ser Val Lys Gly Arg Phe Thr Ile Ser Arg Asp Asn Ala Lys Thr
             370              375              380

Thr Leu Tyr Leu Gln Met Asn Ser Leu Arg Pro Glu Asp Thr Ala Val
385              390              395              400

Tyr Tyr Cys Thr Ile Gly Gly Ser Leu Ser Arg Ser Ser Gln Gly Thr
             405              410              415

Leu Val Thr Val Ser Ser
             420

<210> SEQ ID NO 473
<211> LENGTH: 417
<212> TYPE: PRT
<213> ORGANISM: Artificial Sequence
<220> FEATURE:
<223> OTHER INFORMATION: Nanobody sequence

<400> SEQUENCE: 473

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
             20                  25                  30

Ser Ala Gly Trp Tyr Arg Gln Ala Pro Gly Lys Arg Arg Glu Phe Val
         35                  40                  45

Ala Arg Ile Arg Met Gly Gly Ser Ile Asn Tyr Ala Asp Ser Val Lys
     50                  55                  60

Gly Arg Phe Thr Val Ser Arg Asp Asn Ala Lys Asn Met Met Tyr Leu
65                  70                  75                  80

```
Gln Met Asn Asp Leu Lys Pro Glu Asp Thr Ala Val Tyr Phe Cys Ser
             85                  90                  95

Gly Trp Arg Glu Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
        130                 135                 140

Gly Ser Gly Gly Gly Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Ser Phe Gly Met Ser Trp Val Arg Gln Ala Pro
            180                 185                 190

Gly Lys Gly Leu Glu Trp Val Ser Ser Ile Ser Gly Ser Gly Ser Asp
            195                 200                 205

Thr Leu Tyr Ala Asp Ser Val Lys Gly Arg Phe Thr Ile Ser Arg Asp
        210                 215                 220

Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Arg Ser
                245                 250                 255

Ser Gln Gly Thr Leu Val Thr Val Ser Ser Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Gly Gly Gly Gly Ser Gly Gly Gly Gly Ser Glu Val Gln
        290                 295                 300

Leu Val Glu Ser Gly Gly Gly Leu Val Gln Ala Gly Gly Ser Leu Gly
305                 310                 315                 320

Leu Ser Cys Ser Ala Ser Gly Leu Leu Phe Ser Arg Asn Ser Ala Gly
                325                 330                 335

Trp Tyr Arg Gln Ala Pro Gly Lys Arg Arg Glu Phe Val Ala Arg Ile
            340                 345                 350

Arg Met Gly Gly Ser Ile Asn Tyr Ala Asp Ser Val Lys Gly Arg Phe
            355                 360                 365

Thr Val Ser Arg Asp Asn Ala Lys Asn Met Met Tyr Leu Gln Met Asn
        370                 375                 380

Asp Leu Lys Pro Glu Asp Thr Ala Val Tyr Phe Cys Ser Gly Trp Arg
385                 390                 395                 400

Glu Gly Phe Tyr Glu Tyr Trp Gly Gln Gly Thr Leu Val Thr Val Ser
                405                 410                 415

Ser

<210> SEQ ID NO 474
<211> LENGTH: 575
<212> TYPE: PRT
<213> ORGANISM: Homo sapiens

<400> SEQUENCE: 474

Met Asp Glu Arg Leu Ser Leu Leu Arg Ser Pro Pro Pro Pro Ser Ala
1               5                   10                  15

Arg His Arg Ala His Pro Pro Gln Arg Pro Ala Ser Ser Gly Gly Ala
            20                  25                  30
```

-continued

His Thr Leu Val Asn His Gly Tyr Ala Glu Pro Ala Ala Gly Arg Glu
            35                  40                  45

Leu Pro Pro Asp Met Thr Val Val Pro Gly Asp His Leu Leu Glu Pro
 50                  55                  60

Glu Val Ala Asp Gly Gly Ala Pro Pro Gln Gly Gly Cys Gly Gly
 65                  70                  75                  80

Gly Gly Cys Asp Arg Tyr Glu Pro Leu Pro Pro Ser Leu Pro Ala Ala
                 85                  90                  95

Gly Glu Gln Asp Cys Cys Gly Glu Arg Val Val Ile Asn Ile Ser Gly
                100                 105                 110

Leu Arg Phe Glu Thr Gln Leu Lys Thr Leu Cys Gln Phe Pro Glu Thr
        115                 120                 125

Leu Leu Gly Asp Pro Lys Arg Arg Met Arg Tyr Phe Asp Pro Leu Arg
130                 135                 140

Asn Glu Tyr Phe Phe Asp Arg Asn Arg Pro Ser Phe Asp Ala Ile Leu
145                 150                 155                 160

Tyr Tyr Tyr Gln Ser Gly Gly Arg Ile Arg Arg Pro Val Asn Val Pro
                165                 170                 175

Ile Asp Ile Phe Ser Glu Glu Ile Arg Phe Tyr Gln Leu Gly Glu Glu
            180                 185                 190

Ala Met Glu Lys Phe Arg Glu Asp Glu Gly Phe Leu Arg Glu Glu Glu
        195                 200                 205

Arg Pro Leu Pro Arg Arg Asp Phe Gln Arg Gln Val Trp Leu Leu Phe
    210                 215                 220

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
                245                 250                 255

Pro Glu Phe Arg Asp Glu Lys Asp Tyr Pro Ala Ser Thr Ser Gln Asp
            260                 265                 270

Ser Phe Glu Ala Ala Gly Asn Ser Thr Ser Gly Ser Arg Ala Gly Ala
        275                 280                 285

Ser Ser Phe Ser Asp Pro Phe Phe Val Val Glu Thr Leu Cys Ile Ile
    290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
                325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
        355                 360                 365

Val Arg Val Phe Arg Ile Phe Lys Leu Ser Arg His Ser Lys Gly Leu
    370                 375                 380

Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
                405                 410                 415

Tyr Phe Ala Glu Ala Asp Asp Pro Thr Ser Gly Phe Ser Ser Ile Pro
            420                 425                 430

Asp Ala Phe Trp Trp Ala Val Val Thr Met Thr Thr Val Gly Tyr Gly
        435                 440                 445

Asp Met His Pro Val Thr Ile Gly Gly Lys Ile Val Gly Ser Leu Cys

```
                450             455             460
Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Glu Gln
                485                 490                 495

Ser Gln Tyr Met His Val Gly Ser Cys Gln His Leu Ser Ser Ser Ala
            500                 505                 510

Glu Glu Leu Arg Lys Ala Arg Ser Asn Ser Thr Leu Ser Lys Ser Glu
            515                 520                 525

Tyr Met Val Ile Glu Glu Gly Gly Met Asn His Ser Ala Phe Pro Gln
            530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val
                565                 570                 575

<210> SEQ ID NO 475
<211> LENGTH: 525
<212> TYPE: PRT
<213> ORGANISM: Rattus norvegicus

<400> SEQUENCE: 475

Met Thr Val Val Pro Gly Asp His Leu Leu Glu Pro Glu Ala Ala Gly
1               5                   10                  15

Gly Gly Gly Gly Asp Pro Pro Gln Gly Gly Cys Val Ser Gly Gly Gly
                20                  25                  30

Cys Asp Arg Tyr Glu Pro Leu Pro Pro Ala Leu Pro Ala Ala Gly Glu
            35                  40                  45

Gln Asp Cys Cys Gly Glu Arg Val Val Ile Asn Ile Ser Gly Leu Arg
50                  55                  60

Phe Glu Thr Gln Leu Lys Thr Leu Cys Gln Phe Pro Glu Thr Leu Leu
65                  70                  75                  80

Gly Asp Pro Lys Arg Arg Met Arg Tyr Phe Asp Pro Leu Arg Asn Glu
                85                  90                  95

Tyr Phe Phe Asp Arg Asn Arg Pro Ser Phe Asp Ala Ile Leu Tyr Tyr
            100                 105                 110

Tyr Gln Ser Gly Gly Arg Ile Arg Arg Pro Val Asn Val Pro Ile Asp
            115                 120                 125

Ile Phe Ser Glu Glu Ile Arg Phe Tyr Gln Leu Gly Glu Glu Ala Met
130                 135                 140

Glu Lys Phe Arg Glu Asp Glu Gly Phe Leu Arg Glu Glu Glu Arg Pro
145                 150                 155                 160

Leu Pro Arg Arg Asp Phe Gln Arg Gln Val Trp Leu Leu Phe Glu Tyr
                165                 170                 175

Pro Glu Ser Ser Gly Pro Ala Arg Gly Ile Ala Ile Val Ser Val Leu
            180                 185                 190

Val Ile Leu Ile Ser Ile Val Ile Phe Cys Leu Glu Thr Leu Pro Glu
            195                 200                 205

Phe Arg Asp Glu Lys Asp Tyr Pro Ala Ser Pro Ser Gln Asp Val Phe
            210                 215                 220

Glu Ala Ala Asn Asn Ser Thr Ser Gly Ala Ser Ser Gly Ala Ser Ser
225                 230                 235                 240

Phe Ser Asp Pro Phe Phe Val Val Glu Thr Leu Cys Ile Ile Trp Phe
                245                 250                 255
```

```
Ser Phe Glu Leu Leu Val Arg Phe Phe Ala Cys Pro Ser Lys Ala Thr
                260                 265                 270

Phe Ser Arg Asn Ile Met Asn Leu Ile Asp Ile Val Ala Ile Ile Pro
            275                 280                 285

Tyr Phe Ile Thr Leu Gly Thr Glu Leu Ala Glu Arg Gln Gly Asn Gly
        290                 295                 300

Gln Gln Ala Met Ser Leu Ala Ile Leu Arg Val Ile Arg Leu Val Arg
305                 310                 315                 320

Val Phe Arg Ile Phe Lys Leu Ser Arg His Ser Lys Gly Leu Gln Ile
                325                 330                 335

Leu Gly Gln Thr Leu Lys Ala Ser Met Arg Glu Leu Gly Leu Leu Ile
            340                 345                 350

Phe Phe Leu Phe Ile Gly Val Ile Leu Phe Ser Ser Ala Val Tyr Phe
        355                 360                 365

Ala Glu Ala Asp Asp Pro Ser Ser Gly Phe Asn Ser Ile Pro Asp Ala
370                 375                 380

Phe Trp Trp Ala Val Val Thr Met Thr Thr Val Gly Tyr Gly Asp Met
385                 390                 395                 400

His Pro Val Thr Ile Gly Gly Lys Ile Val Gly Ser Leu Cys Ala Ile
                405                 410                 415

Ala Gly Val Leu Thr Ile Ala Leu Pro Val Pro Val Ile Val Ser Asn
            420                 425                 430

Phe Asn Tyr Phe Tyr His Arg Glu Thr Glu Gly Glu Glu Gln Ala Gln
        435                 440                 445

Tyr Met His Val Gly Ser Cys Gln His Leu Ser Ser Ser Ala Glu Glu
450                 455                 460

Leu Arg Lys Ala Arg Ser Asn Ser Thr Leu Ser Lys Ser Glu Tyr Met
465                 470                 475                 480

Val Ile Glu Glu Gly Gly Met Asn His Ser Ala Phe Pro Gln Thr Pro
                485                 490                 495

Phe Lys Thr Gly Asn Ser Thr Ala Thr Cys Thr Thr Asn Asn Asn Pro
            500                 505                 510

Asn Ser Cys Val Asn Ile Lys Lys Ile Phe Thr Asp Val
        515                 520                 525

<210> SEQ ID NO 476
<211> LENGTH: 528
<212> TYPE: PRT
<213> ORGANISM: Mus musculus

<400> SEQUENCE: 476

Met Thr Val Val Pro Gly Asp His Leu Leu Glu Pro Glu Ala Ala Gly
1               5                   10                  15

Gly Gly Gly Gly Asp Pro Gln Gly Gly Cys Gly Ser Gly Gly Gly
            20                  25                  30

Gly Gly Gly Cys Asp Arg Tyr Glu Pro Leu Pro Pro Ala Leu Pro Ala
        35                  40                  45

Ala Gly Glu Gln Asp Cys Cys Gly Glu Arg Val Val Ile Asn Ile Ser
50                  55                  60

Gly Leu Arg Phe Glu Thr Gln Leu Lys Thr Leu Cys Gln Phe Pro Glu
65                  70                  75                  80

Thr Leu Leu Gly Asp Pro Lys Arg Arg Met Arg Tyr Phe Asp Pro Leu
                85                  90                  95

Arg Asn Glu Tyr Phe Phe Asp Arg Asn Arg Pro Ser Phe Asp Ala Ile
            100                 105                 110
```

```
Leu Tyr Tyr Tyr Gln Ser Gly Gly Arg Ile Arg Pro Val Asn Val
        115                 120                 125

Pro Ile Asp Ile Phe Ser Glu Glu Ile Arg Phe Tyr Gln Leu Gly Glu
130                 135                 140

Glu Ala Met Glu Lys Phe Arg Glu Asp Glu Gly Phe Leu Arg Glu Glu
145                 150                 155                 160

Glu Arg Pro Leu Pro Arg Arg Asp Phe Gln Arg Gln Val Trp Leu Leu
                165                 170                 175

Phe Glu Tyr Pro Glu Ser Ser Gly Pro Ala Arg Gly Ile Ala Ile Val
                180                 185                 190

Ser Val Leu Val Ile Leu Ile Ser Ile Val Ile Phe Cys Leu Glu Thr
            195                 200                 205

Leu Pro Glu Phe Arg Asp Glu Lys Asp Tyr Pro Ala Ser Pro Ser Gln
        210                 215                 220

Asp Val Phe Glu Ala Ala Asn Asn Ser Thr Ser Gly Ala Pro Ser Gly
225                 230                 235                 240

Ala Ser Ser Phe Ser Asp Pro Phe Phe Val Glu Thr Leu Cys Ile
                245                 250                 255

Ile Trp Phe Ser Phe Glu Leu Leu Val Arg Phe Phe Ala Cys Pro Ser
            260                 265                 270

Lys Ala Thr Phe Ser Arg Asn Ile Met Asn Leu Ile Asp Ile Val Ala
        275                 280                 285

Ile Ile Pro Tyr Phe Ile Thr Leu Gly Thr Glu Leu Ala Glu Arg Gln
        290                 295                 300

Gly Asn Gly Gln Gln Ala Met Ser Leu Ala Ile Leu Arg Val Ile Arg
305                 310                 315                 320

Leu Val Arg Val Phe Arg Ile Phe Lys Leu Ser Arg His Ser Lys Gly
                325                 330                 335

Leu Gln Ile Leu Gly Gln Thr Leu Lys Ala Ser Met Arg Glu Leu Gly
                340                 345                 350

Leu Leu Ile Phe Phe Leu Phe Ile Gly Val Ile Leu Phe Ser Ser Ala
            355                 360                 365

Val Tyr Phe Ala Glu Ala Asp Asp Pro Ser Ser Gly Phe Asn Ser Ile
        370                 375                 380

Pro Asp Ala Phe Trp Trp Ala Val Val Thr Met Thr Thr Val Gly Tyr
385                 390                 395                 400

Gly Asp Met His Pro Val Thr Ile Gly Gly Lys Ile Val Gly Ser Leu
                405                 410                 415

Cys Ala Ile Ala Gly Val Leu Thr Ile Ala Leu Pro Val Pro Val Ile
                420                 425                 430

Val Ser Asn Phe Asn Tyr Phe Tyr His Arg Glu Thr Glu Gly Glu Glu
            435                 440                 445

Gln Ala Gln Tyr Met His Val Gly Ser Cys Gln His Leu Ser Ser Ser
        450                 455                 460

Ala Glu Glu Leu Arg Lys Ala Arg Ser Asn Ser Thr Leu Ser Lys Ser
465                 470                 475                 480

Glu Tyr Met Val Ile Glu Glu Gly Gly Met Asn His Ser Ala Phe Pro
                485                 490                 495

Gln Thr Pro Phe Lys Thr Gly Asn Ser Thr Ala Thr Cys Thr Thr Asn
                500                 505                 510

Asn Asn Pro Asn Ser Cys Val Asn Ile Lys Lys Ile Phe Thr Asp Val
            515                 520                 525
```

<210> SEQ ID NO 477
<211> LENGTH: 575
<212> TYPE: PRT
<213> ORGANISM: Macaca fascicularis

<400> SEQUENCE: 477

Met Asp Glu His Leu Ser Leu Leu Arg Ser Pro Pro Pro Ser Ala
1               5                   10                  15

Arg His Arg Ala His Pro Ala Gln Arg Pro Ala Ser Ser Gly Gly Ala
            20                  25                  30

His Thr Leu Val Asn Pro Gly Tyr Ala Glu Pro Ala Ala Gly Pro Glu
        35                  40                  45

Leu Pro Pro Asp Met Thr Val Val Pro Gly Asp His Leu Leu Glu Pro
    50                  55                  60

Glu Val Ala Asp Gly Gly Ala Pro Pro Gln Gly Gly Cys Gly Gly
65                  70                  75                  80

Gly Gly Cys Asp Arg Tyr Glu Pro Leu Pro Ser Leu Pro Ala Ala
                85                  90                  95

Gly Glu Gln Asp Cys Cys Gly Glu Arg Val Val Ile Asn Ile Ser Gly
            100                 105                 110

Leu Arg Phe Glu Thr Gln Leu Lys Thr Leu Cys Gln Phe Pro Glu Thr
        115                 120                 125

Leu Leu Gly Asp Pro Lys Arg Arg Met Arg Tyr Phe Asp Pro Leu Arg
    130                 135                 140

Asn Glu Tyr Phe Phe Asp Arg Asn Arg Pro Ser Phe Asp Ala Ile Leu
145                 150                 155                 160

Tyr Tyr Tyr Gln Ser Gly Gly Arg Ile Arg Arg Pro Val Asn Val Pro
                165                 170                 175

Ile Asp Ile Phe Ser Glu Glu Ile Arg Phe Tyr Gln Leu Gly Glu Glu
            180                 185                 190

Ala Met Glu Lys Phe Arg Glu Asp Glu Gly Phe Leu Arg Glu Glu Glu
        195                 200                 205

Arg Pro Leu Pro Arg Arg Asp Phe Gln Arg Gln Val Trp Leu Leu Phe
    210                 215                 220

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
                245                 250                 255

Pro Glu Phe Arg Asp Glu Lys Asp Tyr Pro Ala Ser Pro Ser Gln Asp
            260                 265                 270

Ser Phe Asp Ala Ala Gly Asn Ser Thr Ser Gly Ala Ala Ala Gly Ala
        275                 280                 285

Ser Ser Phe Ser Asp Pro Phe Phe Val Val Glu Thr Leu Cys Ile Ile
    290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
                325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
        355                 360                 365

Val Arg Val Phe Arg Ile Phe Lys Leu Ser Arg His Ser Lys Gly Leu
    370                 375                 380

```
Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
            405                 410                 415

Tyr Phe Ala Glu Ala Asp Asp Pro Thr Ser Gly Phe Ser Ile Pro
        420                 425                 430

Asp Ala Phe Trp Trp Ala Val Val Thr Met Thr Thr Val Gly Tyr Gly
            435                 440                 445

Asp Met His Pro Val Thr Ile Gly Lys Ile Val Gly Ser Leu Cys
        450                 455                 460

Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Gln
            485                 490                 495

Ala Gln Tyr Met His Val Gly Ser Cys Gln His Leu Ser Ser Ser Ala
        500                 505                 510

Glu Glu Leu Arg Lys Ala Arg Ser Asn Ser Thr Leu Ser Lys Ser Glu
            515                 520                 525

Tyr Met Val Ile Glu Gly Gly Met Asn His Ser Ala Phe Pro Gln
        530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val
            565                 570                 575

<210> SEQ ID NO 478
<211> LENGTH: 115
<212> TYPE: PRT
<213> ORGANISM: Artificial Sequence
<220> FEATURE:
<223> OTHER INFORMATION: Nanobody sequence

<400> SEQUENCE: 478

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 479
<211> LENGTH: 5
<212> TYPE: PRT
<213> ORGANISM: Artificial Sequence
<220> FEATURE:
<223> OTHER INFORMATION: linker sequence
```

```
<400> SEQUENCE: 479

Gly Gly Gly Gly Ser
1               5

<210> SEQ ID NO 480
<211> LENGTH: 7
<212> TYPE: PRT
<213> ORGANISM: Artificial Sequence
<220> FEATURE:
<223> OTHER INFORMATION: linker sequence

<400> SEQUENCE: 480

Ser Gly Gly Ser Gly Gly Ser
1               5

<210> SEQ ID NO 481
<211> LENGTH: 9
<212> TYPE: PRT
<213> ORGANISM: Artificial Sequence
<220> FEATURE:
<223> OTHER INFORMATION: linker sequence

<400> SEQUENCE: 481

Gly Gly Gly Gly Cys Gly Gly Gly Ser
1               5

<210> SEQ ID NO 482
<211> LENGTH: 9
<212> TYPE: PRT
<213> ORGANISM: Artificial Sequence
<220> FEATURE:
<223> OTHER INFORMATION: linker sequence

<400> SEQUENCE: 482

Gly Gly Gly Gly Ser Gly Gly Gly Ser
1               5

<210> SEQ ID NO 483
<211> LENGTH: 10
<212> TYPE: PRT
<213> ORGANISM: Artificial Sequence
<220> FEATURE:
<223> OTHER INFORMATION: linker sequence

<400> SEQUENCE: 483

Gly Gly Gly Gly Ser Gly Gly Gly Gly Ser
1               5                   10

<210> SEQ ID NO 484
<211> LENGTH: 15
<212> TYPE: PRT
<213> ORGANISM: Artificial Sequence
<220> FEATURE:
<223> OTHER INFORMATION: linker sequence

<400> SEQUENCE: 484

Gly Gly Gly Gly Ser Gly Gly Gly Gly Ser Gly Gly Gly Gly Ser
1               5                   10                  15

<210> SEQ ID NO 485
<211> LENGTH: 18
<212> TYPE: PRT
<213> ORGANISM: Artificial Sequence
<220> FEATURE:
<223> OTHER INFORMATION: linker sequence

<400> SEQUENCE: 485
```

Gly Gly Gly Gly Ser Gly Gly Gly Gly Gly
1               5                   10                  15

Gly Ser

<210> SEQ ID NO 486
<211> LENGTH: 20
<212> TYPE: PRT
<213> ORGANISM: Artificial Sequence
<220> FEATURE:
<223> OTHER INFORMATION: linker sequence

<400> SEQUENCE: 486

Gly Gly Gly Gly Ser Gly Gly Gly Gly Ser Gly Gly Gly Ser Gly
1               5                   10                  15

Gly Gly Gly Ser
            20

<210> SEQ ID NO 487
<211> LENGTH: 25
<212> TYPE: PRT
<213> ORGANISM: Artificial Sequence
<220> FEATURE:
<223> OTHER INFORMATION: linker sequence

<400> SEQUENCE: 487

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 488
<211> LENGTH: 30
<212> TYPE: PRT
<213> ORGANISM: Artificial Sequence
<220> FEATURE:
<223> OTHER INFORMATION: linker sequence

<400> SEQUENCE: 488

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 489
<211> LENGTH: 35
<212> TYPE: PRT
<213> ORGANISM: Artificial Sequence
<220> FEATURE:
<223> OTHER INFORMATION: linker sequence

<400> SEQUENCE: 489

Gly Gly Gly Gly Ser Gly Gly Gly Gly Ser Gly Gly Gly Ser Gly
1               5                   10                  15

Gly Gly Ser Gly Gly Gly Gly Ser Gly Gly Gly Ser Gly Gly
            20                  25                  30

Gly Gly Ser
        35

<210> SEQ ID NO 490
<211> LENGTH: 40
<212> TYPE: PRT
<213> ORGANISM: Artificial Sequence
<220> FEATURE:

<223> OTHER INFORMATION: linker sequence

<400> SEQUENCE: 490

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 491
<211> LENGTH: 15
<212> TYPE: PRT
<213> ORGANISM: Artificial Sequence
<220> FEATURE:
<223> OTHER INFORMATION: linker sequence

<400> SEQUENCE: 491

Glu Pro Lys Ser Cys Asp Lys Thr His Thr Cys Pro Pro Cys Pro
1               5                   10                  15

<210> SEQ ID NO 492
<211> LENGTH: 24
<212> TYPE: PRT
<213> ORGANISM: Artificial Sequence
<220> FEATURE:
<223> OTHER INFORMATION: linker sequence

<400> SEQUENCE: 492

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 493
<211> LENGTH: 12
<212> TYPE: PRT
<213> ORGANISM: Artificial Sequence
<220> FEATURE:
<223> OTHER INFORMATION: linker sequence

<400> SEQUENCE: 493

Glu Pro Lys Thr Pro Lys Pro Gln Pro Ala Ala Ala
1               5                   10

<210> SEQ ID NO 494
<211> LENGTH: 62
<212> TYPE: PRT
<213> ORGANISM: Artificial Sequence
<220> FEATURE:
<223> OTHER INFORMATION: linker sequence

<400> SEQUENCE: 494

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60

<210> SEQ ID NO 495

```
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 495

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Met Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 496
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 496

Asp Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Arg Arg Glu Phe Val
        35                  40                  45

Ala Arg Ile Arg Met Gly Gly Ser Ile Asn Tyr Ala Asp Ser Val Lys
    50                  55                  60

Gly Arg Phe Thr Val Ser Arg Asp Asn Ala Lys Asn Met Met Tyr Leu
65                  70                  75                  80

Gln Met Asn Asp Leu Lys Pro Glu Asp Thr Ala Val Tyr Phe Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Arg Leu Ser Cys Ala Ser
                165                 170                 175

Gly Leu Leu Phe Ser Arg Asn Ser Ala Gly Trp Tyr Arg Gln Ala Pro
            180                 185                 190

Gly Lys Arg Arg Glu Phe Val Ala Arg Ile Arg Met Gly Gly Ser Ile
```

```
                195                 200                 205
Asn Tyr Ala Asp Ser Val Lys Gly Arg Phe Thr Val Ser Arg Asp Asn
210                 215                 220

Ala Lys Asn Met Met Tyr Leu Gln Met Asn Asp Leu Lys Pro Glu Asp
225                 230                 235                 240

Thr Ala Val Tyr Phe Cys Ser Gly Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Gly Ser Gly
        275                 280                 285

Gly Gly Gly Ser Gly Gly Gly Ser Gly Gly Gly Ser Glu Val
    290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 497
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 497

Asp Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Met Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140
```

```
Gly Ser Gly Gly Gly Ser Glu Val Gln Leu Val Glu Ser Gly Gly
145                 150                 155                 160

Gly Leu Val Gln Ala Gly Gly Ser Leu Gly Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Met Gly Gly Ser Ile
        195                 200                 205

Asn Tyr Ala Asp Thr Val Lys Gly Arg Phe Thr Ile Ser Arg Asp Asn
210                 215                 220

Ala Lys Asn Thr Val Tyr Leu Gln Met Asn Ser Leu Lys Pro Glu Asp
225                 230                 235                 240

Thr Ala Val Tyr Tyr Cys Ser Ser Trp Arg Thr Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Gly Ser Gly
        275                 280                 285

Gly Gly Gly Ser Gly Gly Gly Ser Gly Gly Gly Gly Ser Glu Val
        290                 295                 300

Gln Leu Val Glu Ser Gly Gly Gly Leu Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
        370                 375                 380

Met Asn Ser Leu Arg Pro Glu Asp Thr Ala Val Tyr Tyr Cys Thr Ile
385                 390                 395                 400

Gly Gly Ser Leu Ser Arg Ser Gln Gly Thr Leu Val Thr Val Ser
                405                 410                 415

Ser Ala

<210> SEQ ID NO 498
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 498

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Ala Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80
```

Gln Met Asn Ser Leu Lys Pro Glu Asp Thr Ala Val Tyr Tyr Cys Ser
            85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 499
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 499

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Glu Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 500
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 500

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Phe Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
            85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 501

```
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 501

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gly Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 502
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 502

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg His Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 503
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 503

Glu Val Gln Leu Val Glu Ser Gly Gly Gly Leu Val Gln Ala Gly Gly
1               5                   10                  15
```

```
Ser Leu Gly Leu Ser Cys Ser Ala Ser Gly Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Lys Gly Gly Ser Ile Asn Tyr Ala Asp Thr Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Glu Tyr Trp Gly Gln Gly Thr Leu Val
                100                 105                 110

Thr Val Ser Ser
        115

<210> SEQ ID NO 504
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 504

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Leu Gly Gly Ser Ile Asn Tyr Ala Asp Thr Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
                100                 105                 110

Thr Val Ser Ser
        115

<210> SEQ ID NO 505
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 505

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Pro Gly Gly Ser Ile Asn Tyr Ala Asp Thr Val Lys
50                  55                  60

Gly Arg Phe Thr Ile Ser Arg Asp Asn Ala Lys Asn Thr Val Tyr Leu
65                  70                  75                  80
```

```
Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 506
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 506

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Gln Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 507
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 507

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Arg Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115
```

-continued

```
<210> SEQ ID NO 508
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 508

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ser Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 509
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 509

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Thr Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 510
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 510

Glu Val Gln Leu Val Glu Ser Gly Gly Gly Leu Val Gln Ala Gly Gly
1               5                   10                  15
```

```
Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Val Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 511
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 511

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Trp Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 512
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 512

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
            35                  40                  45

Ala Arg Ile Arg Tyr Gly Gly Ser Ile Asn Tyr Ala Asp Thr Val Lys
        50                  55                  60

Gly Arg Phe Thr Ile Ser Arg Asp Asn Ala Lys Asn Thr Val Tyr Leu
```

```
                65                  70                  75                  80
Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 513
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 513

Glu Val Gln Leu Val Glu Ser Gly Gly Gly Leu Val Gln Ala Gly Gly
1               5                   10                  15

Ser Leu Gly Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ile Gly Gly Ser Ile Asn Tyr Ala Asp Thr Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Ser Trp Arg Thr Gly Phe Tyr Glu Tyr Trp Gly Gln Gly Thr Leu Val
            100                 105                 110

Thr Val Ser Ser
        115

<210> SEQ ID NO 514
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 514

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125
```

Gly Gly Ser Gly Gly Gly Ser Gly Gly Gly Ser Gly Gly
        130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
                180                 185                 190

Gly Lys Gln Arg Glu Phe Val Ala Arg Ile Arg Gln Gly Gly Ser Ile
                195                 200                 205

Asn Tyr Ala Asp Ser Val Lys Gly Arg Phe Thr Ile Ser Arg Asp Asn
                210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Thr Gly Phe Tyr Glu Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Ser Gly Gly Gly Ser Gly
                275                 280                 285

Gly Gly Ser Gly Gly Gly Ser Gly Gly Gly Ser Glu Val
                290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 515
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 515

Asp Val Gln Leu Val Glu Ser Gly Gly Val Val Gln Pro Gly Gly
1                   5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
                35                  40                  45

Ala Arg Ile Arg Gln Gly Gly Ser Ile Asn Tyr Ala Asp Ser Val Lys
                50                  55                  60

Gly Arg Phe Thr Ile Ser Arg Asp Asn Ser Lys Asn Thr Val Tyr Leu

```
            65                  70                  75                  80
Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gly Gly Gly Ser Gly Gly Gly Ser Gly Gly Gly
130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Gln Gly Gly Ser Ile
            195                 200                 205

Asn Tyr Ala Asp Ser Val Lys Gly Arg Phe Thr Ile Ser Arg Asp Asn
210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Ser Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Gly Ser Gly
            275                 280                 285

Gly Gly Gly Ser Gly Gly Gly Ser Gly Gly Gly Gly Ser Glu Val
            290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
            355                 360                 365

Arg Phe Thr Ile Ser Arg Asp Asn Ala Lys Thr Thr Leu Tyr Leu Gln
            370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 516
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 516

Asp Val Gln Leu Val Glu Ser Gly Gly Gly Val Val Gln Pro Gly Gly
1               5                   10                  15
```

```
Ser Leu Arg Leu Ser Cys Ser Ala Ser Gly Leu Phe Ser Arg Asn
             20                  25                  30

Ser Ala Gly Trp Tyr Arg Gln Ala Pro Gly Lys Gln Arg Glu Phe Val
         35                  40                  45

Ala Arg Ile Arg Ala Gly Gly Ser Ile Asn Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Leu Tyr Tyr Cys Ser
                 85                  90                  95

Gly Trp Arg Thr Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gly Gly Gly Gly Ser Gly Gly Gly Gly Ser Gly Gly Gly
        130                 135                 140

Gly Ser Gly Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Ala Gly Gly Ser Ile
        195                 200                 205

Asn Tyr Ala Asp Ser Val Lys Gly Arg Phe Thr Ile Ser Arg Asp Asn
    210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Thr Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Gly Gly Gly Gly Ser Gly
        275                 280                 285

Gly Gly Gly Ser Gly Gly Gly Gly Ser Gly Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala
```

<210> SEQ ID NO 517
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 517

```
Asp Val Gln Leu Val Glu Ser Gly Gly Gly Val Val Gln Pro Gly Gly
1               5                   10                  15

Ser Leu Arg Leu Ser Cys Ser Ala Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Ala Gly Gly Ser Ile
        195                 200                 205

Asn Tyr Ala Asp Ser Val Lys Gly Arg Phe Thr Ile Ser Arg Asp Asn
    210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Ser Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Gly Gly Gly Gly Ser Gly
        275                 280                 285

Gly Gly Ser Gly Gly Gly Gly Ser Gly Gly Gly Gly Ser Glu Val
    290                 295                 300

Gln Leu Val Glu Ser Gly Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
```

```
                370                 375                 380
Met Asn Ser Leu Arg Pro Glu Asp Thr Ala Leu Tyr Tyr Cys Thr Ile
385                 390                 395                 400

Gly Gly Ser Leu Ser Arg Ser Gln Gly Thr Leu Val Thr Val Ser
                405                 410                 415

Ser Ala

<210> SEQ ID NO 518
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 518

Asp Val Gln Leu Val Glu Ser Gly Gly Gly Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Ala Gly Gly Ser Ile Asn Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Glu Tyr Trp Gly Gln Gly Thr Leu Val
            100                 105                 110

Thr Val Ser Ser Gly Gly Gly Gly Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Ala Gly Gly Ser Ile
        195                 200                 205

Asn Tyr Ala Asp Ser Val Lys Gly Arg Phe Thr Ile Ser Arg Asp Asn
    210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Ser Gly
        275                 280                 285

Gly Gly Ser Gly Gly Gly Ser Gly Gly Gly Ser Glu Val
    290                 295                 300

Gln Leu Val Glu Ser Gly Gly Gly Val Val Gln Pro Gly Asn Ser Leu
305                 310                 315                 320
```

```
Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 519
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 519

Asp Val Gln Leu Val Glu Ser Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Tyr Gly Gly Ser Ile Asn Tyr Ala Asp Ser Val Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Ser Gly Gly Gly Ser Gly Gly Gly
        130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Tyr Gly Gly Ser Ile
        195                 200                 205

Asn Tyr Ala Asp Ser Val Lys Gly Arg Phe Thr Ile Ser Arg Asp Asn
210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Thr Gly Phe Tyr Glu Tyr
                245                 250                 255
```

-continued

Trp Gly Gln Gly Thr Leu Val Thr Val Ser Ser Gly Gly Gly Ser
                260                 265                 270

Gly Gly Gly Gly Ser Gly Gly Gly Ser Gly Gly Gly Ser Gly
        275                 280                 285

Gly Gly Gly Ser Gly Gly Gly Ser Gly Gly Gly Ser Glu Val
        290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 520
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 520

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Tyr Gly Gly Ser Ile Asn Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
                100                 105                 110

Thr Val Ser Ser Gly Gly Gly Ser Gly Gly Gly Ser Gly Gly
            115                 120                 125

Gly Gly Ser Gly Gly Gly Ser Gly Gly Gly Ser Gly Gly Gly
        130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
                180                 185                 190

Gly Lys Gln Arg Glu Phe Val Ala Arg Ile Arg Tyr Gly Gly Ser Ile

```
                195                 200                 205
Asn Tyr Ala Asp Ser Val Lys Gly Arg Phe Thr Ile Ser Arg Asp Asn
210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Ser Trp Arg Glu Gly Phe Tyr Glu Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Ser Gly Gly Gly Gly Ser Gly
                275                 280                 285

Gly Gly Gly Ser Gly Gly Gly Ser Gly Gly Gly Ser Glu Val
                290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
                340                 345                 350

Ile Ser Gly Ser Gly Ser Asp Thr Leu Tyr Ala Asp Ser Val Lys Gly
                355                 360                 365

Arg Phe Thr Ile Ser Arg Asp Asn Ala Lys Thr Thr Leu Tyr Leu Gln
                370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
                405                 410                 415

Ser Ala

<210> SEQ ID NO 521
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 521

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
                35                  40                  45

Ala Arg Ile Arg Tyr Gly Gly Ser Ile Asn Tyr Ala Asp Ser Val Lys
                50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Gly Tyr Trp Gly Gln Gly Thr Leu Val
                100                 105                 110

Thr Val Ser Ser Gly Gly Gly Gly Ser Gly Gly Gly Ser Gly Gly
                115                 120                 125

Gly Gly Ser Gly Gly Gly Gly Ser Gly Gly Gly Ser Gly Gly Gly
                130                 135                 140
```

```
Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
                165                 170                 175

Gly Leu Leu Phe Ser Arg Asn Ser Ala Gly Trp Tyr Arg Gln Ala Pro
            180                 185                 190

Gly Lys Gln Arg Glu Phe Val Ala Arg Ile Arg Tyr Gly Gly Ser Ile
        195                 200                 205

Asn Tyr Ala Asp Ser Val Lys Gly Arg Phe Thr Ile Ser Arg Asp Asn
    210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Glu Gly Phe Tyr Glu Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Gly Ser Gly
        275                 280                 285

Gly Gly Gly Ser Gly Gly Gly Ser Gly Gly Gly Gly Ser Glu Val
    290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
                325                 330                 335

Ser Trp Val Arg Gln Ala Pro Gly Lys Gly Leu Glu Trp Val Ser Ser
            340                 345                 350

Ile Ser Gly Ser Gly Ser Asp Thr Leu Tyr Ala Asp Ser Val Lys Gly
        355                 360                 365

Arg Phe Thr Ile Ser Arg Asp Asn Ala Lys Thr Thr Leu Tyr Leu Gln
    370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Gln Gly Thr Leu Val Thr Val Ser
                405                 410                 415

Ser Ala

<210> SEQ ID NO 522
<211> LENGTH: 418
<212> TYPE: PRT
<213> ORGANISM: Artificial Sequence
<220> FEATURE:
<223> OTHER INFORMATION: Nanobody Sequency

<400> SEQUENCE: 522

Asp Val Gln Leu Val Glu Ser Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
            35                  40                  45

Ala Arg Ile Arg Gln Gly Gly Ser Ile Asn Tyr Ala Asp Ser Val Lys
        50                  55                  60

Gly Arg Phe Thr Ile Ser Arg Asp Asn Ser Lys Asn Thr Val Tyr Leu
65                  70                  75                  80
```

```
Gln Met Asn Ser Leu Arg Pro Glu Asp Thr Ala Leu Tyr Tyr Cys Ser
            85                  90                  95

Gly Trp Arg Glu Gly Phe Tyr Glu Tyr Trp Gly Gln Gly Thr Leu Val
       100                 105                 110

Thr Val Ser Ser Gly Gly Gly Gly Ser Gly Gly Gly Gly Ser Gly Gly
           115                 120                 125

Gly Gly Ser Gly Gly Gly Ser Gly Gly Gly Ser Gly Gly
       130                 135                 140

Gly Ser Gly Gly Gly Ser Glu Val Gln Leu Val Glu Ser Gly Gly
145                 150                 155                 160

Gly Val Val Gln Pro Gly Gly Ser Leu Arg Leu Ser Cys Ser Ala Ser
               165                 170                 175

Gly Leu Leu Phe Ser Arg Asn Ser Ala Gly Trp Tyr Arg Gln Ala Pro
               180                 185                 190

Gly Lys Gln Arg Glu Phe Val Ala Arg Ile Arg Gln Gly Gly Ser Ile
               195                 200                 205

Asn Tyr Ala Asp Ser Val Lys Gly Arg Phe Thr Ile Ser Arg Asp Asn
       210                 215                 220

Ser Lys Asn Thr Val Tyr Leu Gln Met Asn Ser Leu Arg Pro Glu Asp
225                 230                 235                 240

Thr Ala Leu Tyr Tyr Cys Ser Gly Trp Arg Glu Gly Phe Tyr Glu Tyr
               245                 250                 255

Trp Gly Gln Gly Thr Leu Val Thr Val Ser Ser Gly Gly Gly Gly Ser
           260                 265                 270

Gly Gly Gly Gly Ser Gly Gly Gly Ser Gly Gly Gly Gly Ser Gly
       275                 280                 285

Gly Gly Gly Ser Gly Gly Gly Ser Gly Gly Gly Ser Glu Val
       290                 295                 300

Gln Leu Val Glu Ser Gly Gly Val Val Gln Pro Gly Asn Ser Leu
305                 310                 315                 320

Arg Leu Ser Cys Ala Ala Ser Gly Phe Thr Phe Ser Ser Phe Gly Met
               325                 330                 335

Ser Trp Val Arg Gln Ala Pro Gly Lys Gly Leu Glu Trp Val Ser Ser
               340                 345                 350

Ile Ser Gly Ser Gly Ser Asp Thr Leu Tyr Ala Asp Ser Val Lys Gly
           355                 360                 365

Arg Phe Thr Ile Ser Arg Asp Asn Ala Lys Thr Thr Leu Tyr Leu Gln
       370                 375                 380

Met Asn Ser Leu Arg Pro Glu Asp Thr Ala Leu Tyr Tyr Cys Thr Ile
385                 390                 395                 400

Gly Gly Ser Leu Ser Arg Ser Ser Gln Gly Thr Leu Val Thr Val Ser
               405                 410                 415

Ser Ala

<210> SEQ ID NO 523
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 523

Asp Val Gln Leu Val Glu Ser Gly Gly Val Val Gln Pro Gly Gly
1               5                   10                  15

Ser Leu Arg Leu Ser Cys Ser Ala Ser Gly Leu Leu Phe Ser Arg Asn
```

```
                    20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 524
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 524

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115

<210> SEQ ID NO 525
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 525

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80
```

```
Gln Met Asn Ser Leu Arg Pro Glu Asp Thr Ala Leu Tyr Tyr Cys Ser
                85                  90                  95

Gly Trp Arg Glu Gly Phe Tyr Gly Tyr Trp Gly Gln Gly Thr Leu Val
            100                 105                 110

Thr Val Ser Ser
        115

<210> SEQ ID NO 526
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 526

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 527
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 527

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115

<210> SEQ ID NO 528
```

```
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 528

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Glu Tyr Trp Gly Gln Gly Thr Leu Val
            100                 105                 110

Thr Val Ser Ser
        115

<210> SEQ ID NO 529
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 529

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Tyr Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 530
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 530

Asp Val Gln Leu Val Glu Ser Gly Gly Gly Val Val Gln Pro Gly Gly
1               5                   10                  15
```

-continued

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Tyr Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115

<210> SEQ ID NO 531
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 531

Asp Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Tyr Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Glu Tyr Trp Gly Gln Gly Thr Leu Val
            100                 105                 110

Thr Val Ser Ser
        115

<210> SEQ ID NO 532
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 532

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

```
Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 533
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 533

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115

<210> SEQ ID NO 534
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 534

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Ala Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Glu Tyr Trp Gly Gln Gly Thr Leu Val
            100                 105                 110

Thr Val Ser Ser
        115
```

-continued

<210> SEQ ID NO 535
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 535

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 536
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 536

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                85                  90                  95

Ser Trp Arg Glu Gly Phe Tyr Glu Tyr Trp Gly Gln Gly Thr Leu Val
            100                 105                 110

Thr Val Ser Ser
        115

<210> SEQ ID NO 537
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 537

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Gln Gly Gly Ser Ile Asn Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Leu Tyr Tyr Cys Ser
                85                  90                  95

Gly Trp Arg Glu Gly Phe Tyr Glu Tyr Trp Gly Gln Gly Thr Leu Val
            100                 105                 110

Thr Val Ser Ser
        115

<210> SEQ ID NO 538
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 538

Glu Val Gln Leu Val Glu Ser Gly Gly Gly Val Val Gln Pro Gly Gly
 1               5                  10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Tyr Gly Gly Ser Ile Asn Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Leu Tyr Tyr Cys Ser
                85                  90                  95

Gly Trp Arg Thr Gly Phe Tyr Glu Tyr Trp Gly Gln Gly Thr Leu Val
            100                 105                 110

Thr Val Ser Ser
        115

<210> SEQ ID NO 539
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 539

Glu Val Gln Leu Val Glu Ser Gly Gly Gly Val Val Gln Pro Gly Gly
 1               5                  10                  15

Ser Leu Arg Leu Ser Cys Ser Ala Ser Gly Leu Leu Phe Ser Arg Asn
            20                  25                  30

Ser Ala Gly Trp Tyr Arg Gln Ala Pro Gly Lys Gln Arg Glu Phe Val
        35                  40                  45

Ala Arg Ile Arg Tyr Gly Gly Ser Ile Asn Tyr Ala Asp Ser Val Lys
 50                  55                  60

Gly Arg Phe Thr Ile Ser Arg Asp Asn Ser Lys Asn Thr Val Tyr Leu

```
                65                  70                  75                  80
Gln Met Asn Ser Leu Arg Pro Glu Asp Thr Ala Leu Tyr Tyr Cys Ser
                    85                  90                  95

Ser Trp Arg Glu Gly Phe Tyr Glu Tyr Trp Gly Gln Gly Thr Leu Val
                100                 105                 110

Thr Val Ser Ser
        115

<210> SEQ ID NO 540
<211> LENGTH: 116
<212> TYPE: PRT
<213> ORGANISM: Artificial Sequence
<220> FEATURE:
<223> OTHER INFORMATION: Nanobody Sequency

<400> SEQUENCE: 540

Glu Val Gln Leu Val Glu Ser Gly Gly Gly Val Val Gln Pro Gly Gly
1               5                   10                  15

Ser Leu Arg Leu Ser Cys Ser Ala Ser Gly Leu Leu Phe Ser Arg Asn
                20                  25                  30

Ser Ala Gly Trp Tyr Arg Gln Ala Pro Gly Lys Gln Arg Glu Phe Val
                35                  40                  45

Ala Arg Ile Arg Tyr Gly Gly Ser Ile Asn Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Ser
                    85                  90                  95

Gly Trp Arg Glu Gly Phe Tyr Glu Tyr Trp Gly Gln Gly Thr Leu Val
                100                 105                 110

Thr Val Ser Ser
        115

<210> SEQ ID NO 541
<211> LENGTH: 9
<212> TYPE: PRT
<213> ORGANISM: Artificial Sequence
<220> FEATURE:
<223> OTHER INFORMATION: CDR2 sequence

<400> SEQUENCE: 541

Arg Ile Arg Ala Gly Gly Ser Ile Asn
1               5

<210> SEQ ID NO 542
<211> LENGTH: 9
<212> TYPE: PRT
<213> ORGANISM: Artificial Sequence
<220> FEATURE:
<223> OTHER INFORMATION: CDR2 sequence

<400> SEQUENCE: 542

Arg Ile Arg Glu Gly Gly Ser Ile Asn
1               5

<210> SEQ ID NO 543
<211> LENGTH: 9
<212> TYPE: PRT
<213> ORGANISM: Artificial Sequence
<220> FEATURE:
<223> OTHER INFORMATION: CDR2 sequence
```

<400> SEQUENCE: 543

Arg Ile Arg Phe Gly Gly Ser Ile Asn
1               5

<210> SEQ ID NO 544
<211> LENGTH: 9
<212> TYPE: PRT
<213> ORGANISM: Artificial Sequence
<220> FEATURE:
<223> OTHER INFORMATION: CDR2 sequence

<400> SEQUENCE: 544

Arg Ile Arg Gly Gly Gly Ser Ile Asn
1               5

<210> SEQ ID NO 545
<211> LENGTH: 9
<212> TYPE: PRT
<213> ORGANISM: Artificial Sequence
<220> FEATURE:
<223> OTHER INFORMATION: CDR2 sequence

<400> SEQUENCE: 545

Arg Ile Arg His Gly Gly Ser Ile Asn
1               5

<210> SEQ ID NO 546
<211> LENGTH: 9
<212> TYPE: PRT
<213> ORGANISM: Artificial Sequence
<220> FEATURE:
<223> OTHER INFORMATION: CDR2 sequence

<400> SEQUENCE: 546

Arg Ile Arg Lys Gly Gly Ser Ile Asn
1               5

<210> SEQ ID NO 547
<211> LENGTH: 9
<212> TYPE: PRT
<213> ORGANISM: Artificial Sequence
<220> FEATURE:
<223> OTHER INFORMATION: CDR2 sequence

<400> SEQUENCE: 547

Arg Ile Arg Leu Gly Gly Ser Ile Asn
1               5

<210> SEQ ID NO 548
<211> LENGTH: 9
<212> TYPE: PRT
<213> ORGANISM: Artificial Sequence
<220> FEATURE:
<223> OTHER INFORMATION: CDR2 sequence

<400> SEQUENCE: 548

Arg Ile Arg Pro Gly Gly Ser Ile Asn
1               5

<210> SEQ ID NO 549
<211> LENGTH: 9
<212> TYPE: PRT
<213> ORGANISM: Artificial Sequence
<220> FEATURE:
<223> OTHER INFORMATION: CDR2 sequence

<400> SEQUENCE: 549

Arg Ile Arg Gln Gly Gly Ser Ile Asn
1               5

<210> SEQ ID NO 550
<211> LENGTH: 9
<212> TYPE: PRT
<213> ORGANISM: Artificial Sequence
<220> FEATURE:
<223> OTHER INFORMATION: CDR2 sequence

<400> SEQUENCE: 550

Arg Ile Arg Arg Gly Gly Ser Ile Asn
1               5

<210> SEQ ID NO 551
<211> LENGTH: 9
<212> TYPE: PRT
<213> ORGANISM: Artificial Sequence
<220> FEATURE:
<223> OTHER INFORMATION: CDR2 sequence

<400> SEQUENCE: 551

Arg Ile Arg Thr Gly Gly Ser Ile Asn
1               5

<210> SEQ ID NO 552
<211> LENGTH: 9
<212> TYPE: PRT
<213> ORGANISM: Artificial Sequence
<220> FEATURE:
<223> OTHER INFORMATION: CDR2 sequence

<400> SEQUENCE: 552

Arg Ile Arg Val Gly Gly Ser Ile Asn
1               5

<210> SEQ ID NO 553
<211> LENGTH: 9
<212> TYPE: PRT
<213> ORGANISM: Artificial Sequence
<220> FEATURE:
<223> OTHER INFORMATION: CDR2 sequence

<400> SEQUENCE: 553

Arg Ile Arg Trp Gly Gly Ser Ile Asn
1               5

<210> SEQ ID NO 554
<211> LENGTH: 9
<212> TYPE: PRT
<213> ORGANISM: Artificial Sequence
<220> FEATURE:
<223> OTHER INFORMATION: CDR2 sequence

<400> SEQUENCE: 554

Arg Ile Arg Tyr Gly Gly Ser Ile Asn
1               5

<210> SEQ ID NO 555
<211> LENGTH: 9
<212> TYPE: PRT
<213> ORGANISM: Artificial Sequence
<220> FEATURE:
<223> OTHER INFORMATION: CDR2 sequence

<400> SEQUENCE: 555

```
Arg Ile Arg Ile Gly Gly Ser Ile Asn
1               5

<210> SEQ ID NO 556
<211> LENGTH: 25
<212> TYPE: PRT
<213> ORGANISM: Artificial Sequence
<220> FEATURE:
<223> OTHER INFORMATION: framework 1 sequence

<400> SEQUENCE: 556

Glu Val Gln Leu Val Glu Ser Gly Gly Gly Val Val Gln Pro Gly Gly
1               5                   10                  15

Ser Leu Arg Leu Ser Cys Ser Ala Ser
            20                  25

<210> SEQ ID NO 557
<211> LENGTH: 39
<212> TYPE: PRT
<213> ORGANISM: Artificial Sequence
<220> FEATURE:
<223> OTHER INFORMATION: framework 3 sequence

<400> SEQUENCE: 557

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ser Gly
        35

<210> SEQ ID NO 558
<211> LENGTH: 39
<212> TYPE: PRT
<213> ORGANISM: Artificial Sequence
<220> FEATURE:
<223> OTHER INFORMATION: framework 3 sequence

<400> SEQUENCE: 558

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ser Ser
        35

<210> SEQ ID NO 559
<211> LENGTH: 25
<212> TYPE: PRT
<213> ORGANISM: Artificial Sequence
<220> FEATURE:
<223> OTHER INFORMATION: framework 1 sequence

<400> SEQUENCE: 559

Asp Val Gln Leu Val Glu Ser Gly Gly Gly Val Val Gln Pro Gly Gly
1               5                   10                  15

Ser Leu Arg Leu Ser Cys Ser Ala Ser
            20                  25
```

KV1.3 BINDING IMMUNOGLOBULINS

RELATED APPLICATIONS

This application is a national stage filing under 35 U.S.C. § 371 of International Application No. PCT/EP2015/063748, filed Jun. 18, 2015, and entitled "KV1.3 BINDING IMMUNOGLOBULINS," which claims the benefit under 35 U.S.C. § 119(e) of U.S. provisional application Ser. No. 62/014,023, filed Jun. 18, 2014 and U.S. provisional application Ser. No. 62/133,624, filed Mar. 16, 2015, the disclosures of which are hereby incorporated by reference in their entireties.

FIELD OF THE INVENTION

The present invention relates to immunoglobulins that bind Kv1.3 and more in particular to polypeptides, that comprise or essentially consist of one or more such immunoglobulins (also referred to herein as "immunoglobulin(s) of the invention", and "polypeptides of the invention", respectively).

The invention also relates to nucleic acids encoding such polypeptides (also referred to herein as "nucleic acid(s) of the invention"; to methods for preparing such polypeptides; to host cells expressing or capable of expressing such polypeptides; to compositions, and in particular to pharmaceutical compositions, that comprise such polypeptides, nucleic acids and/or host cells; and to uses of polypeptides, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND ART

Ion channels are complex pore-forming membrane proteins that control the selective flux of ions across the membrane, thereby allowing the rapid movement of ions during electrical signaling processes. They are present in the membranes of all living cells and are key to establish a resting membrane potential, shape action potentials and other electrical signals by gating the flow of ions across the cell membrane.

Many channels are gated (i.e. opening and closing of the ion channel pore) such that ionic flow is only triggered in response to a specific stimulus e.g. ligand association, mechanical stress, pH or membrane voltage. As a consequence ion channels have been classified accordingly. A large group of ion channels (e.g., K, Na, Ca, HCN and TRP channels) that respond to potential differences across the cellular membrane for channel gating, share several structural similarities. These channels are thought to have evolved from a common ancestor and have been classified together as the "voltage-gated-like (VGL) ion channel chanome" (Yu et al., Pharmacol Rev 57(4): 387-95, 2005). Other ion channels, such as Cl channels, aquaporins and connexins have evolved quite separately and exhibit completely different structural properties to the VGL channels.

The Kv1.3 channel is a potassium selective voltage gated ion channel with an overall topology representative for these voltage gated like ion channels. Structurally, Kv1.3 exists in a homotetrameric configuration where each monomer consists of six transmembrane segments (S1 to S6) with the S5-S6 region forming the pore. The six transmembrane domains are interconnected by three extracellular loops, termed EL1-EL3, which are accessible from the external side. Both the N-terminal and the C-terminal end of the channel are located on the intracellular side of a cell and can associate with auxiliary subunits (FIG. 1). The first extracellular loop EL1 connects the first and second transmembrane segment (S1-S2). The top of the voltage sensor formed by the connecting loop between the third and fourth transmembrane segment (S3-S4), constitutes the second extracellular accessible region EL2. As the voltage sensor moves substantially during the gating process, the conformation of this potential epitope is likely to be altered by the gating process of the channel. The last extracellular region EL3 is the pore region, delineated by the fifth and sixth transmembrane segments (S5-S6) of the four constituting subunits with the pore helix lining the top of the channel pore. The amino acid position of each transmembrane protein S1 to S6 is provided by the UniProtKB/Swiss-Prot database. The amino acid sequence of extracellular loop EL1 starts after the transmembrane region S1 and ends at S2. The amino acid sequence of extracellular loop EL2 starts after the transmembrane region S3 and ends at S4. The amino acid sequences of extracellular loop EL3 starts after the transmembrane region S5 and ends at S6. The mechanism by which potassium ions are transported through this ion channel and the molecular mechanisms for its selectivity towards potassium ions are described in Yellen et al. (Q Rev Biophys 31(3):239-95, 1998), Morais-Cabral et al. (Nature 414 (6859):37, 2001), Kurata and Fedida (Prog Biophys Mol Biol 92(2):185, 2006), and Hoshi and Armstrong (J Gen Physiol 141(2):151, 2013).

Physiologically, this channel was originally identified in human islet cells and T lymphocytes, where, along with the calcium-activated potassium channel, it supports the activation of specific subsets of T cells. In particular, up-regulation and activation of Kv1.3 in activated effector memory T cell populations (TEM) allow sustained calcium influx into the cell through calciumrelease-activated channels, leading to the initiation of signaling cascades and gene regulation.

Blockade of the channel causes membrane depolarization, which attenuates intracellular Ca2+ levels required for lymphocyte activation upon T-cell stimulation, and inhibits immune responses in vivo. To date, the relevance of Kv1.3 to disease has been demonstrated by several animal and human studies, and its potential as a target to treat disease associated T cells in autoimmune settings such as MS, type 1 diabetes or rheumatoid arthritis has been widely investigated (Ther Adv Neurol Disord 6(5): 322-36, 2013).

Modulators of Kv1.3 ion channel function typically include small molecules and peptide toxins derived from plants and venoms. Several natural toxin fragments have been identified and characterized to bind to the third extracellular (EL3) region of Kv1.3 i.e. the pore region (Zhu et al., Mol Cell Proteomics 10(2): M110.002832, 2011; Bergeron and Bingham, Toxins 4(11): 1082-1119, 2012). This region of Kv1.3 is considered of particular interest, since perturbation through EL3-binding is likely to affect conductance. Binding of the toxin peptides physically occludes the pore thereby eliminating the flow of K+ ions. However, as the pore region is relatively conserved among family members of Kv1.3, these natural toxins tend to lack high specificity towards one family member. Given the ubiquitous distribution of Kv1.3 ion channels in living organisms, this lack of specificity for Kv1.3 is a major impediment for the use of natural toxins as a therapeutic agent. Researchers in the pharmaceutical industry and academia have invested considerable engineering efforts to improve this specificity drawback with variable success (Chi et al., Toxicon 59(4): 529-46, 2012; Berkut et al., J Biol Chem 289: 14331-14340, 2014; Takacs et al., PNAS 106 (52): 22211-22216, 2009). Furthermore, such detailed engineering would be required for each individual toxin peptide, which is a time consuming and costly process. Dalazatide, formerly ShK-186, is an example of a toxin peptide derived from a sea anemone for which recently positive phase 1b clinical results in patients with active plaque psoriasis were reported (http://www.kinetabio.com/autoimmunediseases.html).

Next to natural toxin peptides, also antibodies have been generated against ion channels in an attempt to block the channel in its function. Whilst antibodies are clearly desirable, due to their exquisite specificity, it has not been straightforward to generate functionally blocking antibodies. The lack of FDA approved antibody derived therapeutics against ion channels is exemplary in this regard.

So far, at least eleven ion channels have been targeted by the generation of antibodies binding to the third extracellular loop (Naylor and Beech, Methods Mol Biol 998:245-56, 2013). Unfortunately, often these tool antibodies were polyclonal and attempts to isolate the functional monoclonal antibody within the pool has resulted in loss of all activity. Furthermore, limited efficacy in prohibiting ionic flow has been noted. As the pore region forms a cavity towards the selectivity filter, it might be difficult for a full sized mAb to dock into this region such that it would directly block the ionic flow. One described antibody seemed to block the function of the channel but functioned more through the modulation of channel protein turn over (Yang et al., PlosOne 7(4): e36379, 2012).

There clearly remains a widely recognized need for improved potent and selective Kv1.3 inhibitors for use as therapeutic immunosuppressive agents. Moreover, there clearly remains a need for improved potent and selective Kv1.3 inhibitors which, in addition, do not compromise the protective immune response.

SUMMARY OF THE INVENTION

The present invention provides immunoglobulins with improved prophylactic, therapeutic and/or pharmacological properties, in addition to other advantageous properties (such as, for example, improved ease of preparation, good stability, and/or reduced costs of goods), compared to the prior art amino acid sequences and antibodies.

Based on extensive screening, characterization and combinatory strategies, the present inventors surprisingly observed that immunoglobulins recognizing particular epitopes on the first extracellular loop EL1 of Kv1.3 exhibited different modulating activities, highly improved interspecies cross-reactivity and exquisite selectivity properties. More specifically, the present inventors surprisingly observed that immunoglobulins that bind to the first extracellular loop (EL1) of Kv1.3 could modulate and/or partially or fully block the activity of this ion channel, as was e.g. demonstrated by electrophysiology (IonFlux™, Molecular Devices), by their blocking of $^{125}$I-margatoxin binding to Kv1.3 and by their capacity to inhibit T-cell activation and/or proliferation.

As described above, the pore channel of Kv1.3 is made up by the extracellular region EL3 of Kv1.3. Therefore, the finding of immunoglobulins that bind EL1 and still modulate, inhibit and/or block Kv1.3 activity was unexpected. The immunoglobulins of the present invention indeed cannot physically block the Kv1.3 pore channel, but would rather exert an indirect effect on the activity of the Kv1.3 pore, also referred to herein as allosteric modulation (as further defined herein).

Accordingly, the present invention relates to immunoglobulins that are directed against/and or that can specifically bind (as defined herein) to the EL1 extracellular loop of potassium channel 3 (Kv1.3), wherein the binding of said immunoglobulin to said EL1 extracellular loop modulates the activity of Kv1.3 (in particular human Kv1.3). More particularly, the present invention provides immunoglobulins wherein the immunoglobulin modulates the activity of Kv1.3 by partially or fully blocking of Kv1.3 activity.

As described above, the Kv1.3 channel is a potassium selective voltage gated ion channel. The partially or fully blocking of Kv1.3 activity will result in a reduction or even totally inhibit the efflux of potassium ions from cells that have Kv1.3 channels. Accordingly, the present invention also relates to immunoglobulins that specifically bind to the EL1 extracellular loop Kv1.3, wherein the binding of said immunoglobulin to said EL1 extracellular loop modulates the activity of Kv1.3 by reducing or even totally inhibiting the efflux of potassium ions from T-cells.

In a particular aspect the efflux of potassium ions from T-cells was inhibited with an IC50 value of $10^{-7}$ M or lower, preferably of $10^{-8}$ M or lower, more preferably of $10^{-9}$ M or lower, or even of $10^{-10}$ M or lower, as determined in Patch Clamp assay.

Furthermore, contrary to what is observed with natural toxins (which tend to lack high specificity towards one family member) the immunoglobulins of the present invention were shown highly specific for Kv1.3, with a more than 1000 fold selectivity over other related Kv ion family members. Accordingly, the present invention also relates to immunoglobulins that specifically bind to the EL1 extracellular loop Kv1.3, wherein the immunoglobulin has a more than 10 fold, more than 100 fold, preferably more than 1000 fold, and even up to 10000 fold or more selectivity over other related Kv ion channel family members for modulating and/or inhibiting the activity of Kv1.3.

In one aspect, the immunoglobulins of the invention have the same number of amino acids within their sequence compared to any one of SEQ ID NOs: 1-64, 495, 498-513 and 523-540 and have an amino acid sequence between position 8 and position 106 (according to Kabat numbering) with 89% or more sequence identity compared to any one of SEQ ID NOs: 1-64, 495, 498-513 and 523-540.

In another aspect, the immunoglobulins of the invention have the same number of amino acids within their sequence compared to any one of SEQ ID NOs: 65-123 and have an amino acid sequence between position 8 and position 106 (according to Kabat numbering) with 89% or more sequence identity compared to any one of SEQ ID NOs: 65-123.

In a preferred aspect, the immunoglobulins of the invention have the structure FR1-CDR1-FR2-CDR2-FR3-CDR3-FR4, in which CDR1, CDR2 and CDR3 are as defined herein, and FR1, FR2, FR3 and FR4 are framework sequences. Accordingly, the present invention relates to immunoglobulins that (essentially) consist of 4 framework regions (FR1 to FR4, respectively) and 3 complementarity determining regions (CDR1 to CDR3, respectively), in which:

i) CDR1 is chosen from the group consisting of:
 a) SEQ ID NOs: 181-210; or
 b) amino acid sequences that have 4, 3, 2, or 1 amino acid(s) difference with the amino acid sequence of SEQ ID NO: 182;

and/or
ii) CDR2 is chosen from the group consisting of:
c) SEQ ID NOs: 268-289 and SEQ ID NOs: 541-555; or
d) amino acid sequences that have 3, 2, or 1 amino acid(s) difference with the amino acid sequence of SEQ ID NO: 269;
and/or
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397.

Preferred immunoglobulins of the invention (essentially) consist of 4 framework regions (FR1 to FR4, respectively) and 3 complementarity determining regions (CDR1 to CDR3, respectively), in which:
i) CDR1 is chosen from the group consisting of:
a) SEQ ID NOs: 181-210; or
b) amino acid sequences that have 4, 3, 2, or 1 amino acid(s) difference with the amino acid sequence of SEQ ID NO: 182, wherein
at position 1 the G has been changed into L, or R;
at position 2 the L has been changed into F, P, or I;
at position 3 the L has been changed into P, or F;
at position 4 the F has been changed into S, L, or I;
at position 5 the S has been changed into I, or R;
at position 6 the R has been changed into C, A, P, V, or L;
at position 7 the N has been changed into H, P, I, M, Y, T or D:
at position 8 the S has been changed into T, R, or I;
at position 9 the A has been changed into V or T; and/or
at position 10 the G has been changed into S, R, or V;
and/or
ii) CDR2 is chosen from the group consisting of:
c) SEQ ID NOs: 268-289 and SEQ ID NOs: 541-555; or
d) amino acid sequences that have 4, 3, 2, or 1 amino acid(s) difference with the amino acid sequence of SEQ ID NO: 269, wherein
at position 1 the R has been changed into G, or C;
at position 2 the I has been changed into V, T, S or L;
at position 3 the R has been changed into G, or L;
at position 4 the M has been changed into S, R, A, E, F, G, H, K, L, P, Q, V, W, Y, I, or T;
at position 5 the G has been changed into V, S, or T;
at position 7 the S has been changed into G, C, D, or E; and/or
at position 8 the I has been changed into T, M, or R;
and/or
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397, wherein
at position 1 the W has been changed into G;
at position 3 the E has been changed into T, K, G, A, or I;
at position 4 the G has been changed into E, or D;
at position 5 the F has been changed into A, L, V, Y, T, or 5;
at position 6 the Y has been changed into F, or D:
at position 7 the E has been changed into G, or K;
at position 8 the Y has been changed into S or H; and/or
at position 9 the W has been changed into S, G or C.

In particular, the immunoglobulins of the invention (essentially) consist of 4 framework regions (FR1 to FR4, respectively) and 3 complementarity determining regions (CDR1 to CDR3, respectively), in which:
i) CDR1 is chosen from the group consisting of:
a) SEQ ID NOs: 181-185; or
b) amino acid sequences that have 2, or 1 amino acid(s) difference with the amino acid sequence of SEQ ID NO: 182, wherein
at position 6 the R has been changed into A, or V; and/or
at position 9 the A has been changed into V;
and/or
ii) CDR2 is chosen from the group consisting of:
c) SEQ ID NOs: 268-271, 541 and 549; or
d) amino acid sequences that have 4, 3, 2, or 1 amino acid(s) difference with the amino acid sequence of SEQ ID NO: 269, wherein
at position 2 the I has been changed into L;
at position 4 the M has been changed into S, Q, A or T;
at position 5 the G has been changed into S or T; and/or
at position 8 the I has been changed into T;
and/or
iii) CDR3 is chosen from the group consisting of:
e) SEQ ID NOs: 393-398; or
f) amino acid sequences that have 4, 3, 2, or 1 amino acid(s) difference with the amino acid sequence of SEQ ID NO: 397, wherein
at position 3 the E has been changed into T or I;
at position 4 the G has been changed into E;
at position 5 the F has been changed into A; and/or
at position 8 the Y has been changed into H.

In another aspect, the present invention relates to immunoglobulins that (essentially) consist of 4 framework regions (FR1 to FR4, respectively) and 3 complementarity determining regions (CDR1 to CDR3, respectively), in which:
i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214;
and/or
ii) CDR2 is chosen from the group consisting of:
c) SEQ ID NOs: 290-309; or
d) amino acid sequences that have 4, 3, 2, or 1 amino acid(s) difference with the amino acid sequence of SEQ ID NO: 303;
and/or
iii) CDR3 is chosen from the group consisting of:
e) SEQ ID NOs: 416-435; or
f) amino acid sequences that have 4, 3, 2, or 1 amino acid(s) difference with the amino acid sequence of SEQ ID NO: 422.

Preferred immunoglobulins (essentially) consist of 4 framework regions (FR1 to FR4, respectively) and 3 complementarity determining regions (CDR1 to CDR3, respectively), in which:
i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214, wherein
at position 1 the G has been changed into R, A, V, S, or K;
at position 3 the T has been changed into N;
at position 4 the F has been changed into L;
at position 6 the N has been changed into 5;
at position 7 the F has been changed into Y:
at position 8 the G has been changed into A; and/or
at position 9 the M has been changed into V;

and/or ii) CDR2 is chosen from the group consisting of:
c) SEQ ID NOs: 290-309; or
d) amino acid sequences that have 4, 3, 2, or 1 amino acid(s) difference with the amino acid sequence of SEQ ID NO: 303, wherein
at position 1 the A has been changed into T;
at position 2 the I has been changed into V;
at position 5 the T has been changed into S, or A;
at position 6 the G has been changed into N, or A;
at position 7 the G has been changed into S, or R;
at position 8 the H has been changed into R, or Y;
at position 9 the T has been changed into I, or K; and/or
at position 10 the Y has been changed into F;
and/or
iii) CDR3 is chosen from the group consisting of:
e) SEQ ID NOs: 416-435; or
f) amino acid sequences that have 4, 3, 2, or 1 amino acid(s) difference with the amino acid sequence of SEQ ID NO: 422, wherein
at position 4 the F has been changed into Y, or S;
at position 5 the G has been changed into D;
at position 6 the D has been changed into G;
at position 7 the G has been changed into D;
at position 8 the T has been changed into A:
at position 9 the Y has been changed into 5;
at position 10 the Y has been changed into F;
at position 12 the Q has been changed into E;
at position 14 the A has been changed into N, T, I, or R;
at position 17 the D has been changed into N, or G; and/or
at position 18 the F has been changed into L.

In a preferred aspect, the immunoglobulin of the invention is chosen from the group of polypeptides, wherein:
CDR1 is SEQ ID NO: 182, CDR2 is SEQ ID NO: 269, and CDR3 is SEQ ID NO: 397;
CDR1 is SEQ ID NO: 182, CDR2 is SEQ ID NO: 269, and CDR3 is SEQ ID NO: 394;
CDR1 is SEQ ID NO: 181, CDR2 is SEQ ID NO: 268, and CDR3 is SEQ ID NO: 393;
CDR1 is SEQ ID NO: 181, CDR2 is SEQ ID NO: 268, and CDR3 is SEQ ID NO: 395;
CDR1 is SEQ ID NO: 181, CDR2 is SEQ ID NO: 268, and CDR3 is SEQ ID NO: 396;
CDR1 is SEQ ID NO: 181, CDR2 is SEQ ID NO: 270, and CDR3 is SEQ ID NO: 393;
CDR1 is SEQ ID NO: 183, CDR2 is SEQ ID NO: 268, and CDR3 is SEQ ID NO: 393;
CDR1 is SEQ ID NO: 184, CDR2 is SEQ ID NO: 268, and CDR3 is SEQ ID NO: 393;
CDR1 is SEQ ID NO: 185, CDR2 is SEQ ID NO: 271, and CDR3 is SEQ ID NO: 398;
CDR1 is SEQ ID NO: 182, CDR2 is SEQ ID NO: 541, and CDR3 is SEQ ID NO: 394;
CDR1 is SEQ ID NO: 182, CDR2 is SEQ ID NO: 541, and CDR3 is SEQ ID NO: 397;
CDR1 is SEQ ID NO: 182, CDR2 is SEQ ID NO: 549, and CDR3 is SEQ ID NO: 394;
CDR1 is SEQ ID NO: 182, CDR2 is SEQ ID NO: 549, and CDR3 is SEQ ID NO: 397;
CDR1 is SEQ ID NO: 214, CDR2 is SEQ ID NO: 303, and CDR3 is SEQ ID NO: 422;
CDR1 is SEQ ID NO: 211, CDR2 is SEQ ID NO: 290, and CDR3 is SEQ ID NO: 416;
CDR1 is SEQ ID NO: 212, CDR2 is SEQ ID NO: 291, and CDR3 is SEQ ID NO: 417;
CDR1 is SEQ ID NO: 213, CDR2 is SEQ ID NO: 292, and CDR3 is SEQ ID NO: 418;
CDR1 is SEQ ID NO: 213, CDR2 is SEQ ID NO: 293, and CDR3 is SEQ ID NO: 418;
CDR1 is SEQ ID NO: 214, CDR2 is SEQ ID NO: 294, and CDR3 is SEQ ID NO: 418;
CDR1 is SEQ ID NO: 215, CDR2 is SEQ ID NO: 295, and CDR3 is SEQ ID NO: 417;
CDR1 is SEQ ID NO: 216, CDR2 is SEQ ID NO: 296, and CDR3 is SEQ ID NO: 419;
CDR1 is SEQ ID NO: 213, CDR2 is SEQ ID NO: 295, and CDR3 is SEQ ID NO: 418;
CDR1 is SEQ ID NO: 214, CDR2 is SEQ ID NO: 295, and CDR3 is SEQ ID NO: 418;
CDR1 is SEQ ID NO: 211, CDR2 is SEQ ID NO: 297, and CDR3 is SEQ ID NO: 420;
CDR1 is SEQ ID NO: 215, CDR2 is SEQ ID NO: 298, and CDR3 is SEQ ID NO: 421;
CDR1 is SEQ ID NO: 217, CDR2 is SEQ ID NO: 299, and CDR3 is SEQ ID NO: 422;
CDR1 is SEQ ID NO: 211, CDR2 is SEQ ID NO: 298, and CDR3 is SEQ ID NO: 418;
CDR1 is SEQ ID NO: 212, CDR2 is SEQ ID NO: 291, and CDR3 is SEQ ID NO: 423;
CDR1 is SEQ ID NO: 212, CDR2 is SEQ ID NO: 300, and CDR3 is SEQ ID NO: 418;
CDR1 is SEQ ID NO: 214, CDR2 is SEQ ID NO: 301, and CDR3 is SEQ ID NO: 418;
CDR1 is SEQ ID NO: 215, CDR2 is SEQ ID NO: 300, and CDR3 is SEQ ID NO: 424;
CDR1 is SEQ ID NO: 211, CDR2 is SEQ ID NO: 302, and CDR3 is SEQ ID NO: 416;
CDR1 is SEQ ID NO: 218, CDR2 is SEQ ID NO: 291, and CDR3 is SEQ ID NO: 425;
CDR1 is SEQ ID NO: 218, CDR2 is SEQ ID NO: 291, and CDR3 is SEQ ID NO: 426;
CDR1 is SEQ ID NO: 213, CDR2 is SEQ ID NO: 303, and CDR3 is SEQ ID NO: 422;
CDR1 is SEQ ID NO: 218, CDR2 is SEQ ID NO: 291, and CDR3 is SEQ ID NO: 417;
CDR1 is SEQ ID NO: 219, CDR2 is SEQ ID NO: 296, and CDR3 is SEQ ID NO: 427;
CDR1 is SEQ ID NO: 213, CDR2 is SEQ ID NO: 304, and CDR3 is SEQ ID NO: 428;
CDR1 is SEQ ID NO: 220, CDR2 is SEQ ID NO: 305, and CDR3 is SEQ ID NO: 416;
CDR1 is SEQ ID NO: 213, CDR2 is SEQ ID NO: 303, and CDR3 is SEQ ID NO: 421;
CDR1 is SEQ ID NO: 220, CDR2 is SEQ ID NO: 296, and CDR3 is SEQ ID NO: 429;
CDR1 is SEQ ID NO: 221, CDR2 is SEQ ID NO: 305, and CDR3 is SEQ ID NO: 416;
CDR1 is SEQ ID NO: 222, CDR2 is SEQ ID NO: 305, and CDR3 is SEQ ID NO: 430;
CDR1 is SEQ ID NO: 213, CDR2 is SEQ ID NO: 306, and CDR3 is SEQ ID NO: 418;
CDR1 is SEQ ID NO: 223, CDR2 is SEQ ID NO: 303, and CDR3 is SEQ ID NO: 422;
CDR1 is SEQ ID NO: 215, CDR2 is SEQ ID NO: 298 and CDR3 is SEQ ID NO: 431;
CDR1 is SEQ ID NO: 220, CDR2 is SEQ ID NO: 296, and CDR3 is SEQ ID NO: 432;
CDR1 is SEQ ID NO: 224, CDR2 is SEQ ID NO: 300, and CDR3 is SEQ ID NO: 418;

CDR1 is SEQ ID NO: 220, CDR2 is SEQ ID NO: 307, and CDR3 is SEQ ID NO: 433;
CDR1 is SEQ ID NO: 225, CDR2 is SEQ ID NO: 300, and CDR3 is SEQ ID NO: 418;
CDR1 is SEQ ID NO: 226, CDR2 is SEQ ID NO: 308, and CDR3 is SEQ ID NO: 434;
CDR1 is SEQ ID NO: 212, CDR2 is SEQ ID NO: 295, and CDR3 is SEQ ID NO: 417;
CDR1 is SEQ ID NO: 213, CDR2 is SEQ ID NO: 301, and CDR3 is SEQ ID NO: 426;
CDR1 is SEQ ID NO: 212, CDR2 is SEQ ID NO: 305, and CDR3 is SEQ ID NO: 417;
CDR1 is SEQ ID NO: 217, CDR2 is SEQ ID NO: 305, and CDR3 is SEQ ID NO: 422;
CDR1 is SEQ ID NO: 215, CDR2 is SEQ ID NO: 298, and CDR3 is SEQ ID NO: 435; and
CDR1 is SEQ ID NO: 213, CDR2 is SEQ ID NO: 309, and CDR3 is SEQ ID NO: 418.

The immunoglobulins of the invention may (essentially) consist of an immunoglobulin single variable domain selected from a light chain variable domain sequence (e.g., a $V_L$-sequence) and from a heavy chain variable domain sequence (e.g., a $V_H$-sequence). The immunoglobulins of the invention may (essentially) consist of an immunoglobulin single variable domain selected from a heavy chain variable domain sequence that is derived from a conventional four-chain antibody and from a heavy chain variable domain sequence that is derived from heavy chain antibody. The immunoglobulins of the invention may (essentially) consist of an immunoglobulin single variable domain selected from a domain antibody (or an amino acid that is suitable for use as a domain antibody), a single domain antibody (or an amino acid that is suitable for use as a single domain antibody), a "dAb" (or an amino acid that is suitable for use as a dAb), a Nanobody, a VHH sequence, a camelized VH sequence, or a VHH sequence that has been obtained by affinity maturation. In a preferred aspect, the immunoglobulin of the invention (essentially) consists of a partially or fully humanized Nanobody, such as a partially or fully humanized VHH.

Preferred immunoglobulins of the invention are selected from any of SEQ ID NOs: 1-123, 495, 498-513 and 523-540 or immunoglobulins that have a sequence identity of more than 80%, preferably more than 90%, more preferably more than 95%, such as 99% or more sequence identity (as defined herein) with any of SEQ ID NOs: 1-123, 495, 498-513 and 523-540.

The invention also relates to immunoglobulins directed against Kv1.3 that cross-block the binding to Kv1.3 of at least one of the immunoglobulin single variable domains with SEQ ID NOs: 1-123, 495, 498-513 and 523-540 and/or that are cross-blocked from binding to Kv1.3 by at least one of the immunoglobulin single variable domains with SEQ ID NOs: 1-123, 495, 498-513 and 523-540.

The immunoglobulins provided by the invention are preferably in essentially isolated form (as defined herein), or form part of a polypeptide (also referred to as "polypeptide of the invention"), which may comprise, or (essentially) consist of one or more immunoglobulins of the invention and which may optionally further comprise one or more further immunoglobulins (all optionally linked via one or more suitable linkers).

More particularly, the present invention provides multivalent polypeptide comprising, or (essentially) consisting of at least two immunoglobulins of the invention, wherein said at least two immunoglobulins can be the same or different and wherein said at least two immunoglobulins are directly linked to each other or linked to each other via a linker. Without being limiting, suitable linkers may be selected from the group of linkers with SEQ ID NOs: 479-494.

In a preferred aspect, the invention relates to a multivalent polypeptide as defined above, which is selected from any of SEQ ID NOs: 451-473, 496-497 and 514-522 or polypeptides that have a sequence identity of more than 80% with any of SEQ ID NOs: 451-473, 496-497 and 514-522 (see Table A-3).

In another aspect, the invention relates to a compound or construct (also referred to herein as a "compound of the invention" or "construct of the invention", respectively) that comprises or (essentially) consists of one or more immunoglobulins or polypeptides of the invention (or suitable fragments thereof), and optionally further comprises one or more other groups, residues, moieties or binding units, optionally linked via one or more peptidic linkers. As will become clear to the skilled person from the further disclosure herein, such further groups, residues, moieties or binding units may or may not provide further functionality to the immunoglobulins of the invention (and/or to the compound, construct or polypeptide in which it is present) and may or may not modify the properties of the immunoglobulin of the invention.

In one specific aspect of the invention, a compound of the invention or a construct of the invention may have an increased half-life, compared to the corresponding immunoglobulin or polypeptide of the invention. Some preferred, but non-limiting examples of such compounds or constructs will become clear to the skilled person based on the further disclosure herein, and for example comprise immunoglobulins or polypeptides of the invention that have been chemically modified to increase the half-life thereof (for example, by means of pegylation); immunoglobulins or polypeptides of the invention that comprise at least one additional binding site for binding to a serum protein (such as serum albumin); or immunoglobulins or polypeptides of the invention that comprise at least one immunoglobulin or polypeptide of the invention that is linked to at least one moiety that increases the half-life of the immunoglobulin or polypeptide of the invention.

Examples of immunoglobulins or polypeptides of the invention that comprise such half-life extending moieties will become clear to the skilled person based on the further disclosure herein; and for example include, without limitation, polypeptides in which the one or more immunoglobulins or polypeptides of the invention are suitable linked to one or more serum proteins or fragments thereof (such as (human) serum albumin or suitable fragments thereof) or to one or more binding units that can bind to serum proteins (such as, for example, domain antibodies, amino acids that are suitable for use as a domain antibody, single domain antibodies, amino acids that are suitable for use as a single domain antibody, "dAb"'s, amino acids that are suitable for use as a dAb, Nanobodies, VHH sequences, humanized VHH sequences, or camelized VH sequences that can bind to serum albumin (such as human serum albumin) or a serum immunoglobulin (such as IgG); reference is made to the further description and references mentioned herein); polypeptides in which an immunoglobulin or polypeptide of the invention is linked to an Fc portion (such as a human Fc) or a suitable part or fragment thereof; or polypeptides in which the one or more immunoglobulins or polypeptides of the invention are suitable linked to one or more small proteins or peptides that can bind to serum proteins (such as, without limitation, the proteins and peptides described in WO 91/01743, WO 01/45746, WO 02/076489).

Generally, the compounds or constructs of the invention with increased half-life preferably have a half-life that is at least 1.5 times, preferably at least 2 times, such as at least 5 times, for example at least 10 times or more than 20 times, greater than the half-life of the corresponding immunoglobulin or polypeptide of the invention per se.

In a preferred, but non-limiting aspect, such compounds or constructs of the invention have a serum half-life that is increased with more than 1 hour, preferably more than 2 hours, more preferably more than 6 hours, such as more than 12 hours, or even more than 24, 48 or 72 hours, compared to the corresponding immunoglobulin or polypeptide of the invention per se.

In another preferred, but non-limiting aspect, such compounds or constructs of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a preferred aspect, the invention relates to a compound or construct as defined above, which is selected from any of SEQ ID NOs: 461-473, 496-497 and 514-522 or compounds or constructs that have a sequence identity of more than 80% with any of SEQ ID NOs: 461-473, 496-497 and 514-522 (see Table A-3).

The invention also relates to nucleic acids or nucleotide sequences that encode an immunoglobulin, a polypeptide, a compound and/or construct of the invention. Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

Nucleic acids encoding an immunoglobulin, a polypeptide, a compound and/or construct of the invention can be linked to obtain a nucleic acid encoding a multivalent polypeptide of the invention. Accordingly, the present invention also relates to the use of a nucleic acid or nucleotide sequence that encodes an immunoglobulin, a polypeptide, a compound and/or construct of the invention for the preparation of a genetic construct that encodes a multivalent polypeptide of the invention.

The invention further relates to a host or host cell that expresses (or that under suitable circumstances is capable of expressing) an immunoglobulin, a polypeptide, a compound and/or construct of the invention; and/or that contains a nucleic acid of the invention. Some preferred but non-limiting examples of such hosts or host cells will become clear from the further description herein.

The invention further relates to a composition containing or comprising at least one immunoglobulin, polypeptide, compound and/or construct of the invention and/or at least one nucleic acid of the invention, and optionally one or more further components of such compositions known per se, i.e. depending on the intended use of the composition. Such a composition may for example be a pharmaceutical composition (as described herein) or a veterinary composition. Some preferred but non-limiting examples of such compositions will become clear from the further description herein.

The invention further relates to methods for preparing the immunoglobulins, polypeptides, compounds and/or constructs, nucleic acids, host cells, and composition described herein. The method for producing an immunoglobulin, polypeptide, compound and/or construct, nucleic acid, host cell, and composition of the invention may comprise the following steps:
  a) expressing, in a suitable host cell or host organism or in another suitable expression system, a nucleic acid or nucleotide sequence of the invention, or a genetic construct of the invention; optionally followed by:
  b) isolating and/or purifying the immunoglobulin, polypeptide, compound and/or construct of the invention thus obtained.

The invention further relates to applications and uses of the immunoglobulins, polypeptides, compound and/or constructs, nucleic acids, host cells, and compositions described herein, as well as to methods for the prevention and/or treatment of Kv1.3 associated diseases, disorders or conditions. Some preferred but non-limiting applications and uses will become clear from the further description herein.

The immunoglobulins, polypeptides, compounds and/or constructs and compositions of the present invention can be used for reducing and/or inhibiting the efflux of potassium ions from T-cells.

The immunoglobulins, polypeptides, compounds and/or constructs and compositions of the present invention can be used for inhibiting and/or blocking T-cell activation and/or proliferation.

The immunoglobulins, polypeptides, compounds and/or constructs and compositions of the present invention can be used for inhibiting and/or blocking of activated T-cells.

The immunoglobulins, polypeptides, compounds and/or constructs and compositions of the present invention can be used for prevention and/or treatment of T cell mediated diseases.

The immunoglobulins, polypeptides, compounds and/or constructs and compositions of the present invention can be used for prevention and/or treatment of autoimmune diseases.

As such, the immunoglobulins, polypeptides, compounds and/or constructs and compositions of the present invention can be used for the prevention and/or treatment of Kv1.3 associated diseases, disorders or conditions. Patient groups susceptible to Kv1.3 associated diseases, disorders or conditions will be clear to the skilled person and for example include (without being limiting) multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity.

Accordingly, the present invention also relates to a method for the prevention and/or treatment of a Kv1.3 associated disease, disorder or condition in at least one of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity, said method comprising administering, to a subject in need thereof, a pharmaceutically active amount of at least one immunoglobulin, polypeptide, compound and/or construct of the invention or composition of the invention.

The invention also relates to the use of an immunoglobulin, polypeptide, compound and/or construct of the invention or composition of the invention in the preparation of a pharmaceutical composition for the prevention and/or treatment of Kv1.3 associated diseases, disorders or conditions in least one of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity; and/or for use in one or more of the methods described herein.

The invention also relates to an immunoglobulin, polypeptide, compound and/or construct of the invention or a composition of the invention for prevention and/or treatment of Kv1.3 associated diseases, disorders or conditions in least one of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

FIGURE LEGENDS

FIG. 1: Planar membrane topology of a single potassium channel subunit of the Kv1.3 protein. Structurally, Kv1.3 channels exist as tetramers of four identical subunits. Each subunit is composed of six transmembrane domains S1-S6 with the S5-S6 region forming the K$^+$pore. These six transmembrane domains are interconnected by three extracellular loops, termed EL1-EL3. Both the N- and C-termini are on the cytoplasmic side of the cell membrane.

Figure 2:
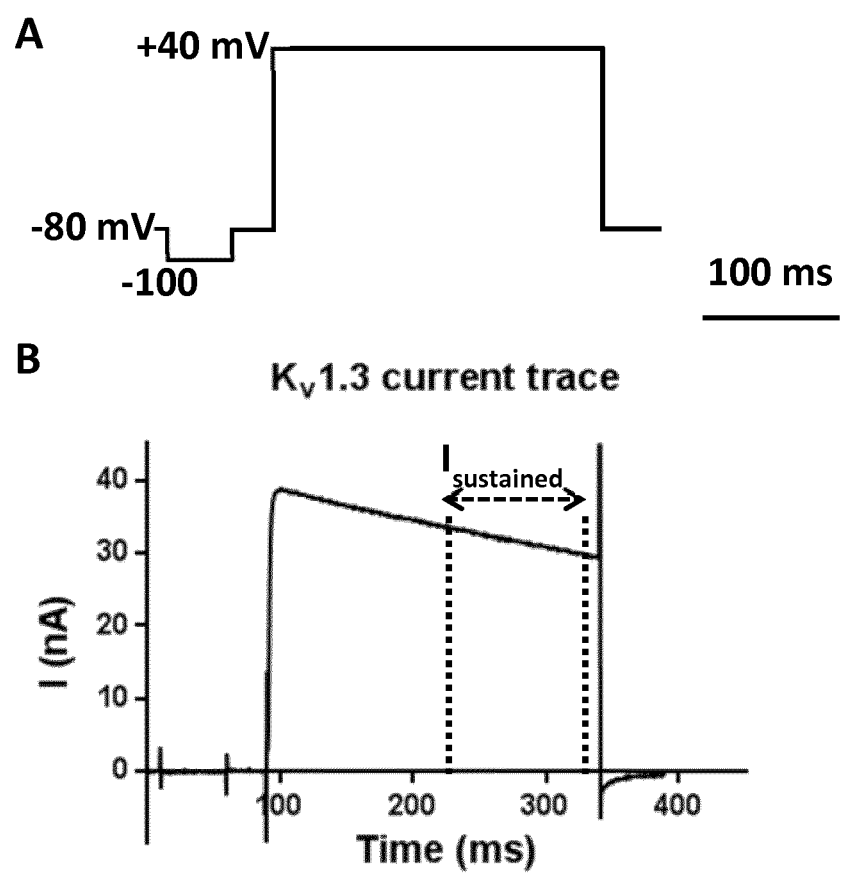
Figure 3:
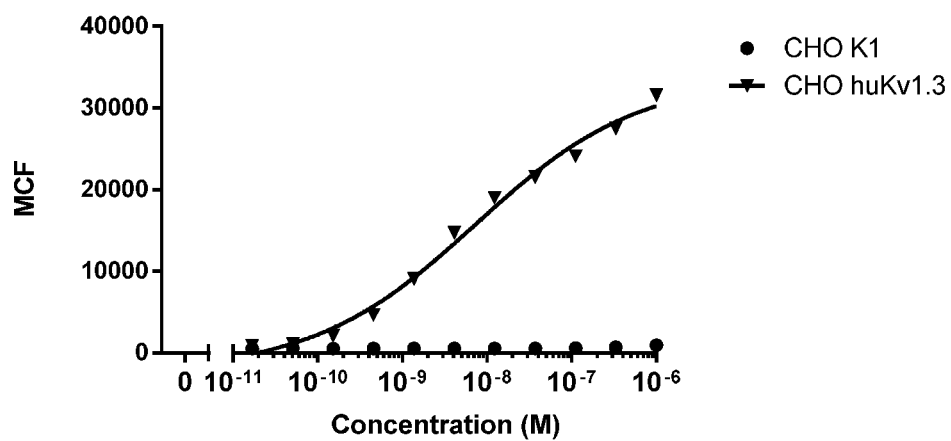
Figure 3:
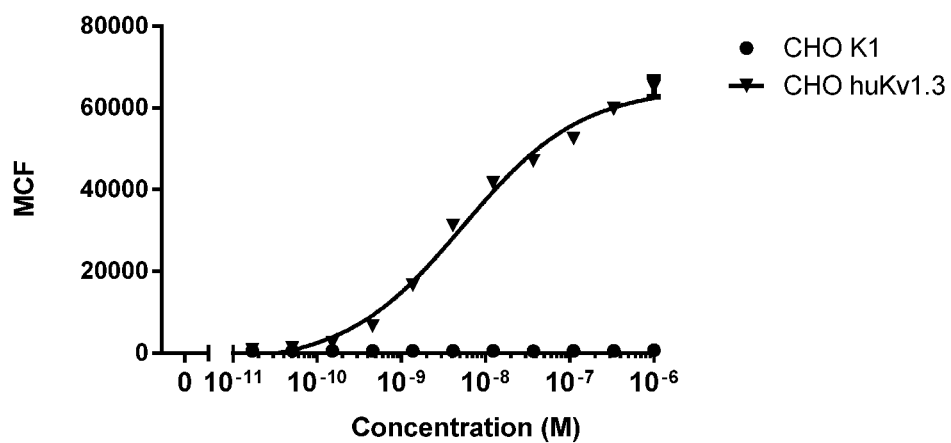
Figure 3:
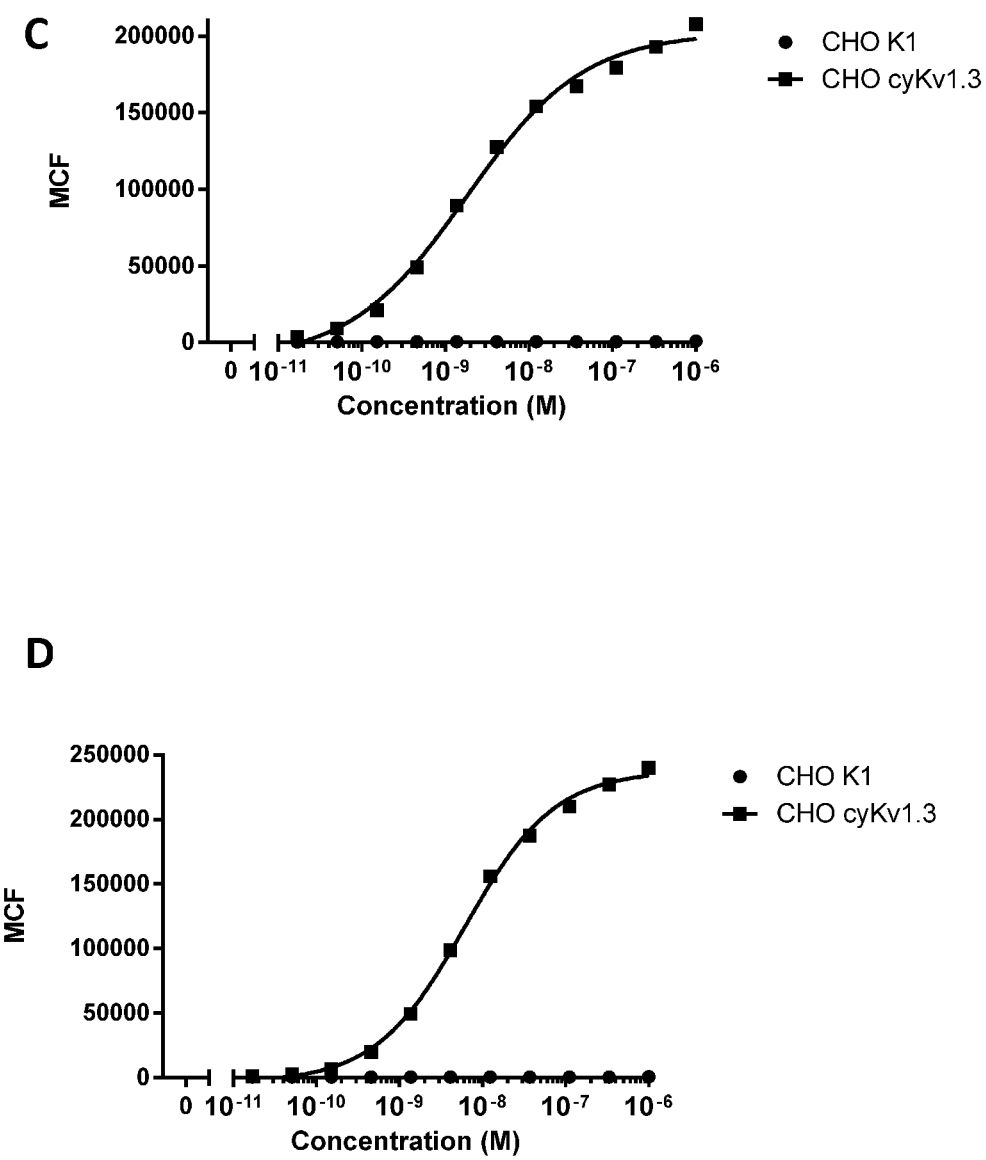
Figure 3:
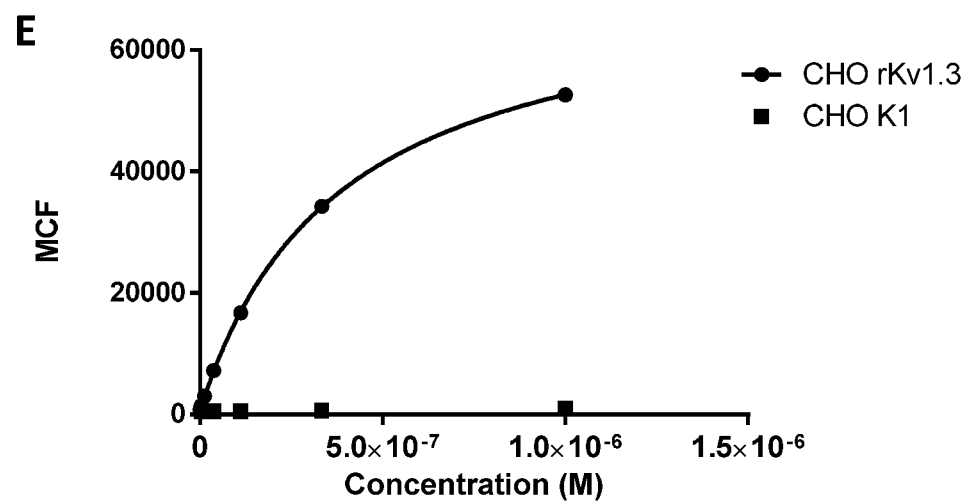
Figure 3:
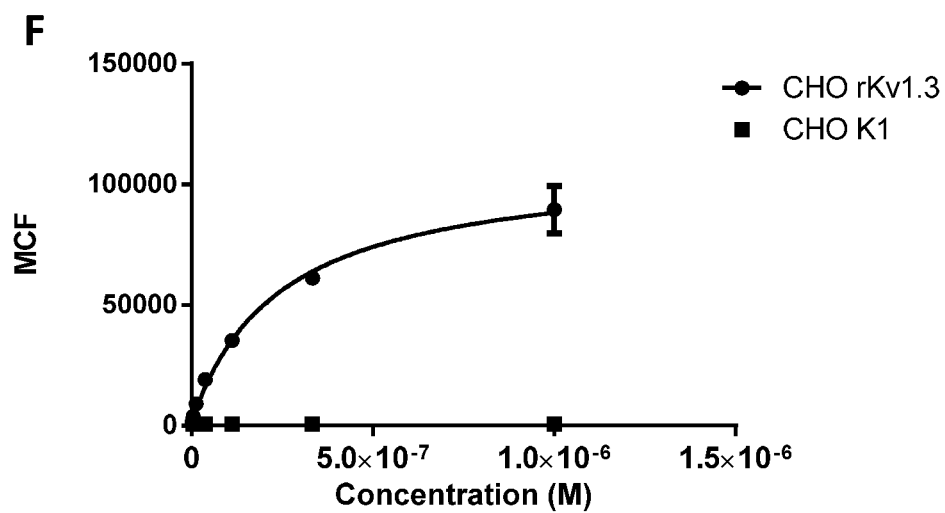

FIGS. 2A-2B: Schematic representation of the voltage protocol applied on the automated patch clamp IonFlux™ system, in either population or single cell mode. Kv1.3 potassium currents were elicited by a depolarization pulse to +40 mV from $V_H$ of −80 mV every 30 s (A). The data points used in analysis represent normalized mean sustained current amplitudes ($I_{sustained}$) obtained from the area between the designated cursors (B).

FIGS. 3A-3F: Titration of monovalent anti-Kv1.3 Nanobodies (A: A019400003; B: A0194009G09) on human Kv1.3 expressed on CHO cells (closed triangles) and on parental CHO cells (closed circles). Cross species binding of a dilution series of anti Kv1.3 Nanobodies (C and E: A019400003; D and F: A0194009G09) to cyno Kv1.3 (C & D; parental CHO cells are depicted as closed circles; cyno Kv1.3 CHO cells are shown as closed squares) and rat Kv1.3 (E and F; parental CHO cells are depicted as closed squares; cyno Kv1.3 CHO cells are shown as closed circles). The MCF value (mean channel fluorescence) is plotted against the concentration of the Nanobody.

FIGS. 4A-4C: Effect of monovalent anti-Kv1.3 Nanobodies (A: A019400003; B: an irrelevant Nanobody (squares) and A0194009G09 (closed circles)) or the peptide toxin ShK (C) on binding of radiolabeled margatoxin to cyno Kv1.3 that is expressed on CHO cells. The counts per minute (cpm) value is plotted against the concentration of the Nanobody. Both anti-Kv1.3 Nanobodies completely block binding of 150 pM I125 margatoxin to cyno Kv1.3. The background (BG) is the control condition where no I125 margatoxin was added.

FIGS. 5A-5B: Dose-dependent effect of monovalent Nanobody A0194009G09 on human Kv1.3 channels stably expressed in HEK293H. Kv1.3 currents were recorded by automated population patch clamp using a depolarizing voltage protocol with a time interval of 30 s (as shown in FIG. 2A) using the IonFlux™ system. A0194009G09 was sequentially applied to the same cell population by continuous perfusion of each concentration for 120 s. Representative Kv1.3 current traces (A) show a clear dose-dependent inhibitory effect and the correlated concentration-response curves for the inhibition of human Kv1.3 channels, measured as normalized mean $I_{sustained}$ are presented in (B).

FIGS. 6A-6B: Dose-dependent effect of monovalent Nanobody A01940020A06 on human Kv1.3 channels stably expressed in HEK293H. Kv1.3 currents were recorded by automated population patch clamp using a depolarizing voltage protocol with a time interval of 30 s (as shown in FIG. 2A) using the IonFlux™ system. A01940020A06 was sequentially applied to the same cell population by continuous perfusion of each concentration for 120 s. Representative Kv1.3 current traces (A) show a clear dose-dependent inhibitory effect and the correlated concentration-response curves for the inhibition of human Kv1.3 channels, measured as normalized mean $I_{sustained}$ are presented in (B).

FIGS. 7A-7B: Current recovery during washout of the selected monovalent Nanobodies. HEK293H cells stably expressing Kv1.3 were perfused with a single high dose of Nanobody (300 nM) for 120 s to achieve steady state inhibition and subsequently superfused for at least 5 min with extracellular buffer. Kv1.3 currents were recorded by automated population patch clamp using a depolarizing voltage protocol with a time interval of 30 s, using the IonFlux™ system. The Kv1.3 currents recorded after washing the cell were superimposed on control Kv1.3. An almost full recovery from inhibition could be observed (A). For stability reasons and comparison, Kv1.3 currents were also recorded by automated single cell patch clamp. As expected, the inhibitory effect could be reversed for monovalent Nanobody A0194009G09 (B).

Figure 8:
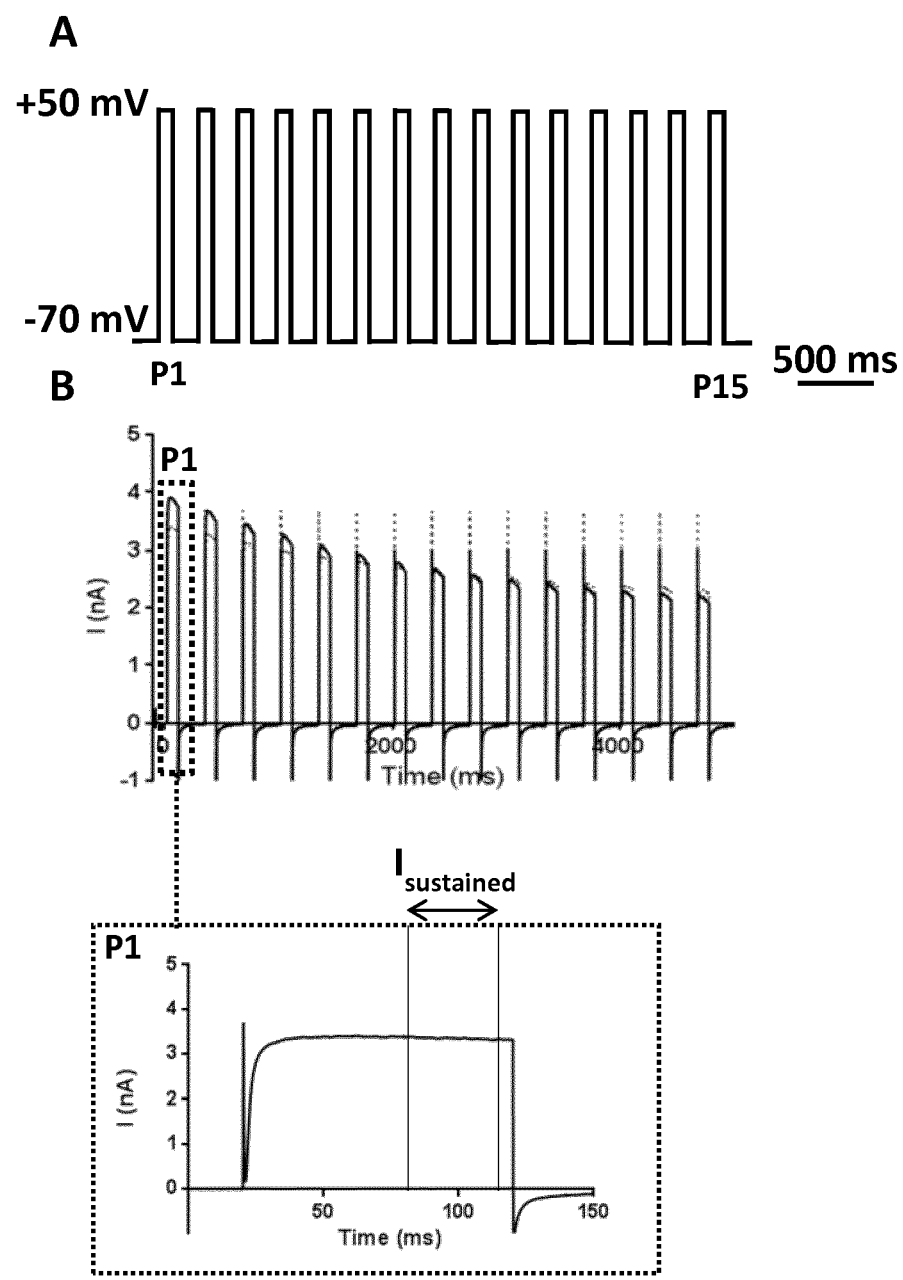

FIGS. 8A-8B: Schematic representation of the voltage protocol applied to each well before and after the application of test compound on the automated patch clamp IonWorks system. Kv1.3 potassium currents were elicited by a repeated gating voltage command protocol. K+ currents were evoked by a train of 100 ms depolarizing steps to +50 mV from a holding potential of −80 mV, applied 15 times (P1 to P15) at 3 Hz (A). The data points used in analysis represent normalized mean sustained current amplitudes ($I_{sustained}$) obtained from the area between the designated cursors in P1 (B).

Figure 9:
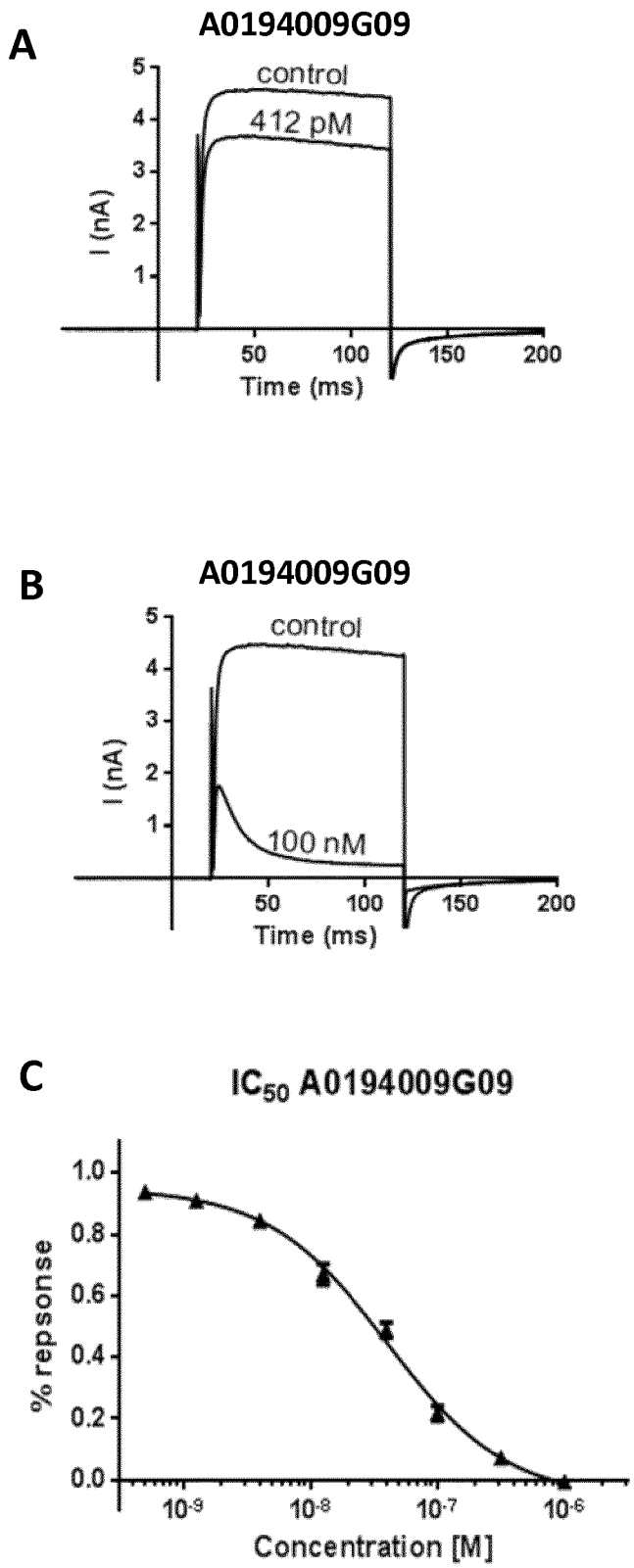

FIGS. 9A-9C: Dose-dependent effect of A0194009G09 on human Kv1.3 channels stably expressed in CHL cells at exemplified concentrations of 412 pM (A) and 100 nM (B). Kv1.3 currents were recorded by automated population patch clamp using the repeated gating voltage command protocol on the IonWorks system, as described in Example 4 Recordings were done in control conditions (prior to compound addition). A0194009G09 was then incubated for 6 to 7 min prior to the second measurement using the identical pulse train. The correlated concentration-response curve for the inhibition of human Kv1.3 channels, measured as normalized mean $I_{sustained}$ is presented in (C).

Figure 10:
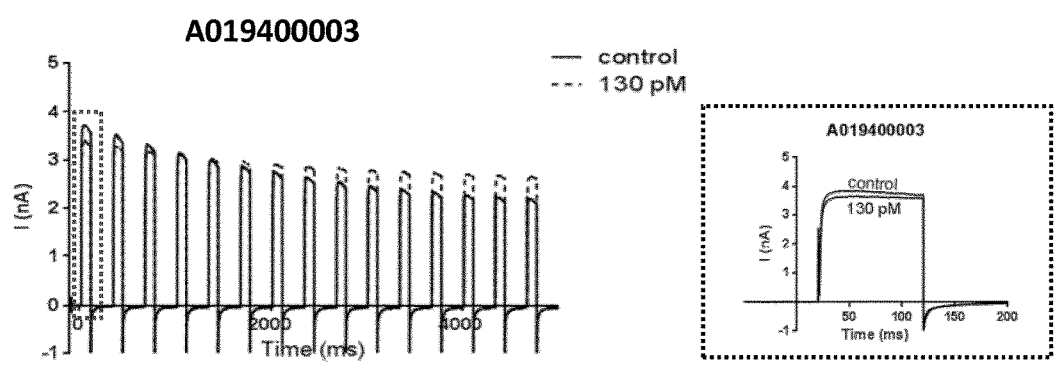
Figure 10:
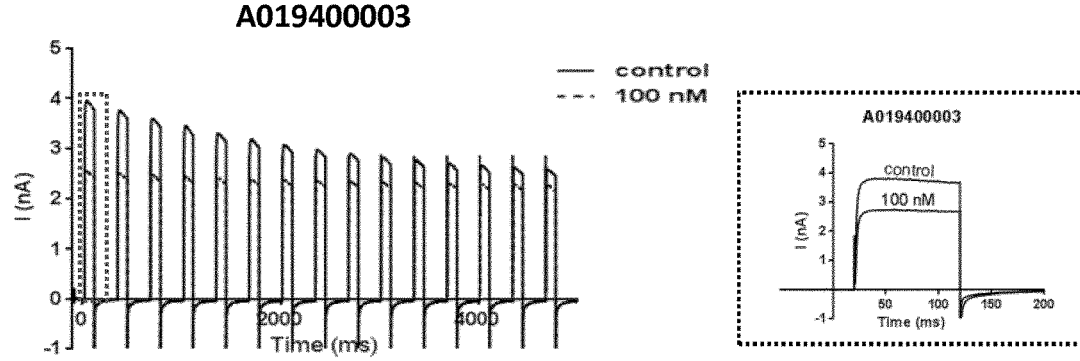
Figure 10:
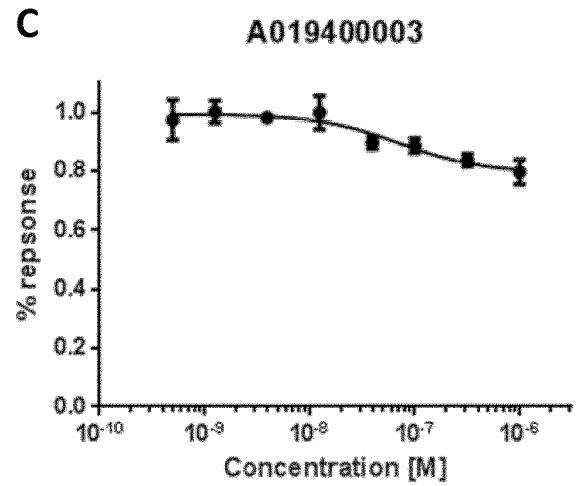

FIGS. 10A-10C: Kv1.3 current traces of A019400003 at low concentration (A) and high (B) concentration. The correlated concentration-response curve for the inhibition of human Kv1.3 channels, measured as normalized mean $I_{sustained}$ is presented in (C).

FIGS. 11A-11D: Inhibition by monovalent anti-Kv1.3 Nanobodies and ShK [A: A019400003 (open circles) and A0194009G09 (closed circles); B: A019400020A06 (closed circles); C: A0194009G09 (closed circles) and ShK (open squares); D: A0194020A06 (closed circles)] of IFNγ production (A and B) and CD25 expression (C and D) by CCR7−CD45RA− T-cells after stimulation with OKT3. For the IFNγ readout, the IFNγ concentration (pg/ml) is plotted against the concentration of the Nanobody. For the measurement of CD25 expression, the MCF value (mean channel fluorescence) is plotted against the concentration of the Nanobody. The control condition where cells are not stimulated is indicated by 'no stim'.

FIGS. 12A-12D: Binding of a dilution series of multivalent Nanobodies to human, cyno and rat Kv1.3 expressed on CHO cells. A: A019400004; B: A019400013; C: A019400014; D: A019400015; closed circles: binding to parental CHO cells; closed squares: binding to cyno Kv1.3 CHO cells; closed up righted triangle: binding to rat Kv1.3 and closed down righted triangle: binding to human Kv1.3 CHO cells. The MCF value (mean channel fluorescence) is plotted against the concentration of the Nanobody.

FIGS. 13A-13E: Effect of multivalent anti-Kv1.3 Nanobodies on binding of radiolabeled margatoxin to CHO expressed cyno Kv1.3. A: A019400013 (closed triangles) and unlabeled margatoxin (closed squares); B: A019400004 (closed squares); C: A019400012 (closed squares) and A019400014 (closed triangles); D: A019400015 (closed circles) and unlabeled margatoxin (closed squares); E: A019400032 (closed squares). The counts per minute (cpm) value is plotted against the concentration of the Nanobody.

FIGS. 14A-14C: Dose-dependent effect of bivalent A019400009 on human Kv1.3 channels stably expressed in HEK293H. Kv1.3 currents were recorded by automated population patch clamp using a depolarizing voltage protocol with a time interval of 30 s on the IonFlux™ system, as described in FIG. 2A. A019400009 was sequentially applied to the same cell population by continuous perfusion of each concentration for 120 s. Kv1.3 current traces of A019400009 are depicted in (A). The correlated concentration-response curve for the inhibition of human Kv1.3 channels, measured as normalized mean $I_{sustained}$ is presented in (B). The current recovery during washout of A019400009 is shown in (C)

FIGS. 15A-15C: Dose-dependent effect of biparatopic A019400012 on human Kv1.3 channels stably expressed in HEK293H. Kv1.3 currents were recorded by automated population patch clamp using a depolarizing voltage protocol with a time interval of 30 s on the IonFlux™ system, as described in FIG. 2A. A019400012 was sequentially applied to the same cell population by continuous perfusion of each concentration for 120 s. Kv1.3 current traces of A019400012 are depicted in (A). The correlated concentration-response curve for the inhibition of human Kv1.3 channels, measured as normalized mean $I_{sustained}$ is presented in (B). The current recovery during washout of A019400010 (=A019400012) is shown in (C).

FIGS. 16A-16C: Dose-dependent effect of biparatopic A019400014 on human Kv1.3 channels stably expressed in HEK293H. Kv1.3 currents were recorded by automated population patch clamp using a depolarizing voltage protocol with a time interval of 30 s on the IonFlux™ system, as described in FIG. 2A. A019400014 was sequentially applied to the same cell population by continuous perfusion of each concentration for 120 s. Kv1.3 current traces of A019400014 are depicted in (A). The correlated concentration-response curve for the inhibition of human Kv1.3 channels, measured as normalized mean $I_{sustained}$ is presented in (B). The current recovery during washout of A019400014 is shown in (C).

FIGS. 17A-17C to FIG. 22A-22C: Dose-dependent effect of multivalent Nanobodies on human Kv1.3 channels stably expressed in CHL cells. Kv1.3 currents were recorded by automated population patch clamp using the repeated gating voltage command protocol on the IonWorks system, as described in FIG. 8. Recordings were done in control conditions (prior to compound addition). The Nanobodies were then incubated for 6 to 7 min prior to the second measurement using the identical pulse train. Representative Kv1.3 current traces of the multivalent Nanobodies A019400004, A019400009, A019400012, A019400014, A019400015 and A019400032 are depicted in FIGS. 17A-17B to 22A-22B, respectively. The correlated concentration-response curves for the inhibition of human Kv1.3 channels, measured as normalized mean $I_{sustained}$ are presented in FIGS. 17C to 22C, respectively.

FIGS. 23A to 23F: Inhibition by multivalent anti-Kv1.3 Nanobodies and Shk (A and D: A019400013 (open circles) and ShK (closed squares); B and E: A019400012 (open circles) and A019400014 (closed squares); C and F: A019400015 (closed squares)) of IFNγ production (A, B and C) and CD25 expression (D, E and F) by CCR7−CD45RA− T-cells after stimulation with anti-CD3. For the IFNγ readout, the IFNγ concentration (pg/ml) is plotted against the concentration of the Nanobody. For the measurement of CD25 expression, the MCF value (mean channel fluorescence) is plotted against the concentration of the Nanobody. The control condition where cells are not stimulated is indicated by 'no stim'.

Figure 24:
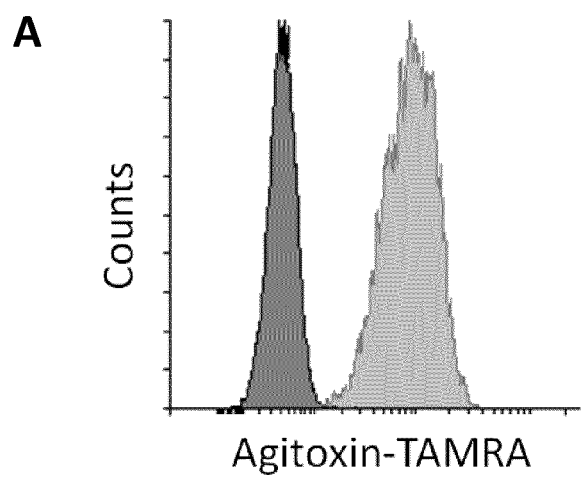
Figure 24:
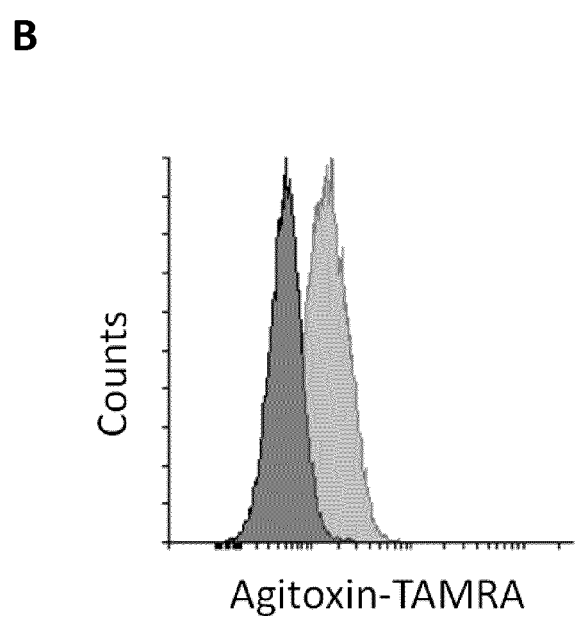

FIGS. 24A-24B: Histograms evaluating the binding of agitoxin-TAMRA to WT Kv1.3 (B) and a Kv1.3 EL1 mutant (A) expressed on HEK293H cells. The counts obtained in a FACS binding experiment are plotted against the fluorescence intensity of agitoxin-TAMRA. The histograms show that both constructs are bound by agitoxin indicating their functionality.

Figure 25:
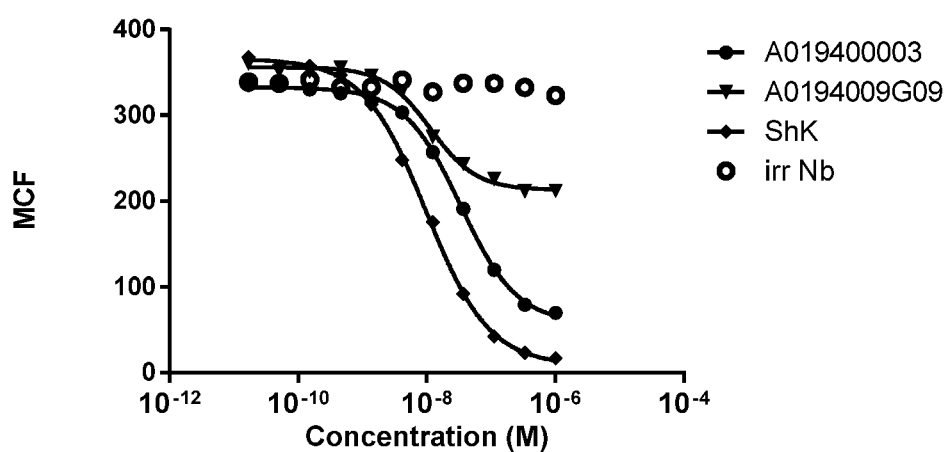

FIG. 25: Dilutions series of monovalent Nanobodies (A019400003 (closed circles); A0194009G09 (closed triangles), irrelevant Nanobody (open circles)) and the ShK compound (closed checks) competing with a saturating concentration of FAM-labeled ShK for binding to human Kv1.3 expressed on HEK293H cells. The MCF value (mean channel fluorescence) is plotted against the concentration of the Nanobody.

FIGS. 26A to 26D: Binding to cyno Kv1.3 expressed on CHO cells by half-life extended bivalent constructs with the albumin binding Nanobody (Alb11) at different positions. Both A019400028 (A and C; Alb11 in the middle) and A019400024 (B and D; Alb11 at the C-terminus) bind similarly to cyno Kv1.3 expressed on CHO cells in absence of human serum albumin (HSA) (A and B); in presence of HSA (C and D), the potency is slightly decreased. The MCF value (mean channel fluorescence) is plotted against the concentration of the Nanobody.

Figure 27:
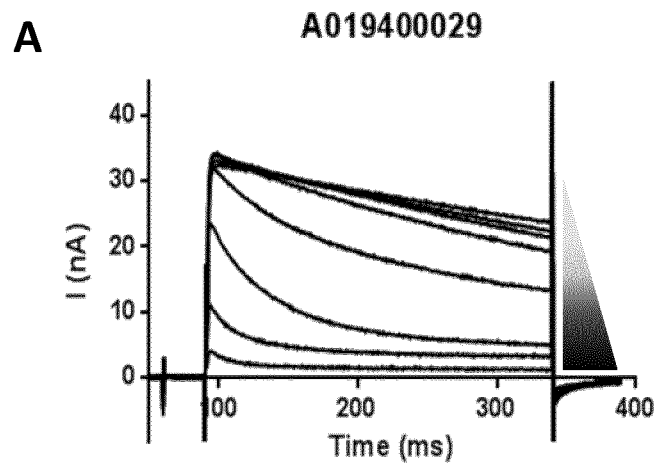
Figure 27:
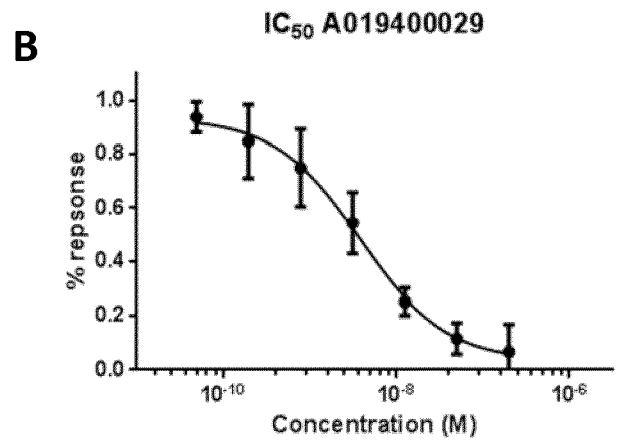
Figure 27:
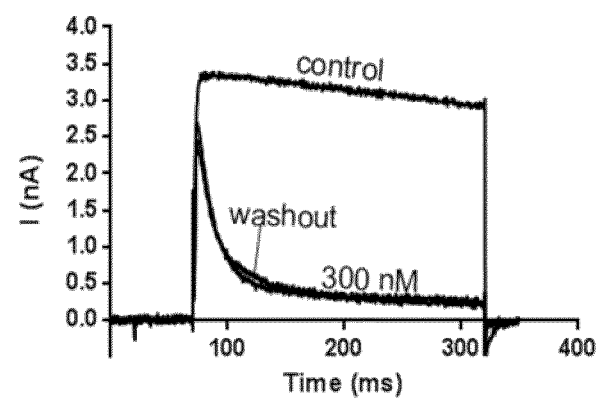

FIGS. 27A-27C: Dose-dependent effect of trivalent A019400029 on human Kv1.3 channels stably expressed in HEK293H. Kv1.3 currents were recorded by automated population patch clamp using a depolarizing voltage protocol with a time interval of 30 s on the IonFlux™ system, as described in FIG. 2A. A019400029 was sequentially applied to the same cell population by continuous perfusion of each concentration for 120 s. Kv1.3 current traces of A019400029 are depicted in (A). The correlated concentration-response curve for the inhibition of human Kv1.3 channels, measured as normalized mean $I_{sustained}$ is presented in (B). The current recovery during washout of A019400029 is shown in (C).

Figure 28:
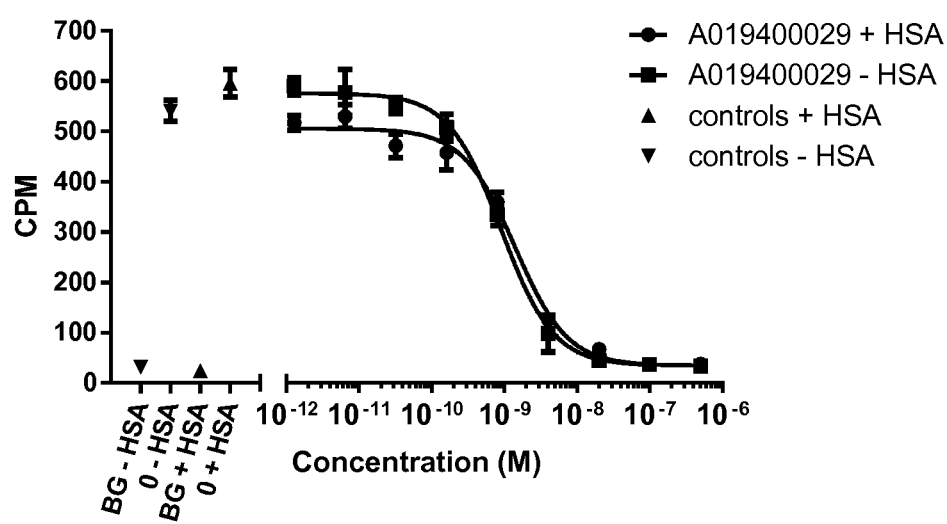

FIG. 28: Competition of the half-life extended bivalent A019400029 Nanobody construct with I125 margatoxin in absence (closed squares) and presence (closed circles) of HSA. Cyno Kv1.3 was expressed on CHO cells. The counts per minute (cpm) value is plotted against the concentration of the Nanobody. The background (BG) is the control condition where no I125 margatoxin was added and was evaluated in presence (up righted closed triangles) and absence of HSA (down righted closed triangles).

Figure 29:
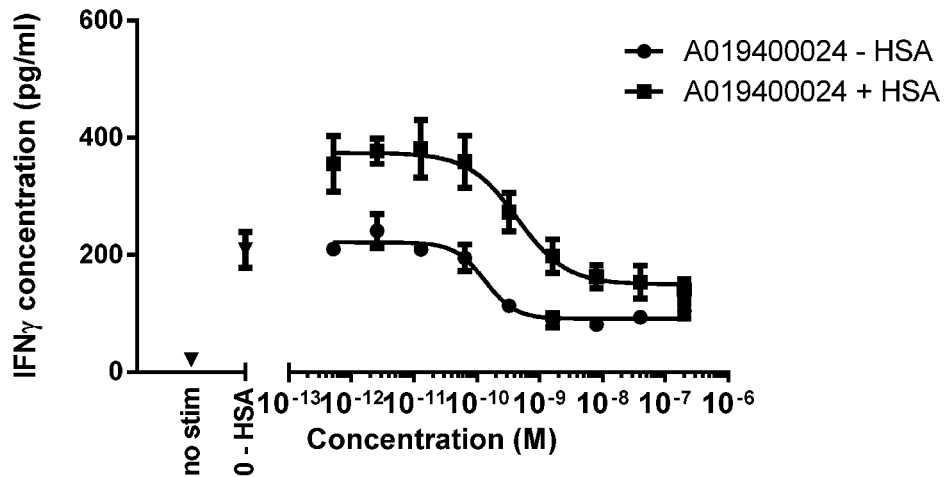
Figure 29:
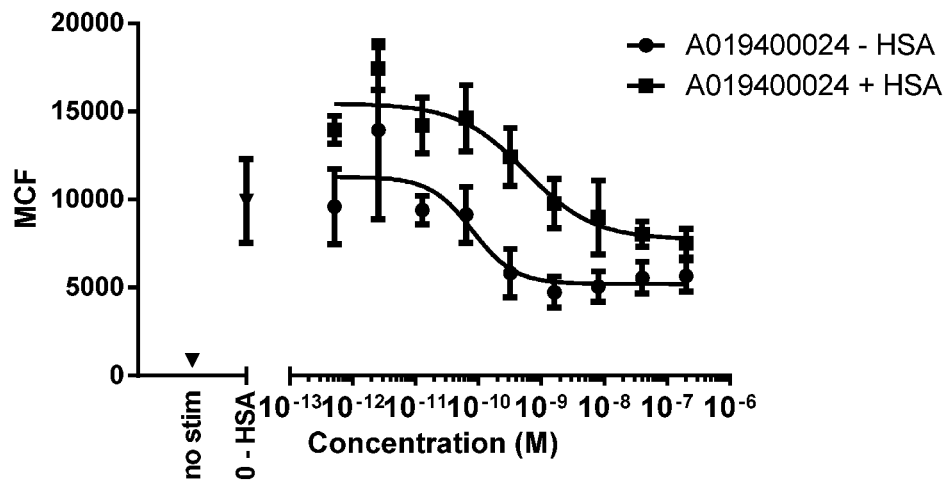

FIGS. 29A-29B: IFNγ production (A) and CD25 expression (B) by CCR⁻CD45RA⁻ T-cells after stimulation with anti-CD3 (OKT3) in presence of a dilution series of the A019400024 Nanobody construct in absence (closed circles) and presence (closed squares) of HSA. For the IFNγ readout, the IFNγ concentration (pg/ml) is plotted against the concentration of the Nanobody. For the measurement of CD25 expression, the MCF value (mean channel fluorescence) is plotted against the concentration of the Nanobody. The control condition where cells are not stimulated is indicated by 'no stim'.

FIGS. 30A-30B: Inhibition of IFNγ production in anti-CD3 stimulated human PBMCs by a dilution series of the A019400029 Nanobody construct (closed circles) and ShK toxin (closed squares) (A). Same Nanobody and toxin do not inhibit IFNγ production in human PBMCs co-stimulated with anti-CD3 and anti-CD28 (B). The IFNγ concentration (pg/ml) is plotted against the concentration of the Nanobody or toxin. The control condition where cells are not stimulated is indicated by 'no stim'.

FIGS. 31A-31D: Effect of A019400029 on the voltage-dependence of activation on human Kv1.3 channels stably expressed in CHL cells. Kv1.3 currents were recorded by conventional planar patch clamp. Superimposed current traces were elicited by a 500 ms depolarizing pulse to +50 mV in 10 mV steps from a holding potential of −80 mV at 30 s intervals in the absence (B) and presence (C) of 10 nM A019400029. A schematic of the voltage protocols is given in FIG. 31A. The data points used in analysis represent peak current amplitudes ($I_{peak}$) 1 as indicated in B (arrow). The conductances were calculated as described in Example 10, normalized with their respective maximum conductance (Gmax) and plotted against the applied depolarization voltages (D). The Boltzmann equation was used to fit the curve (as described in Example 10).

Figure 32:
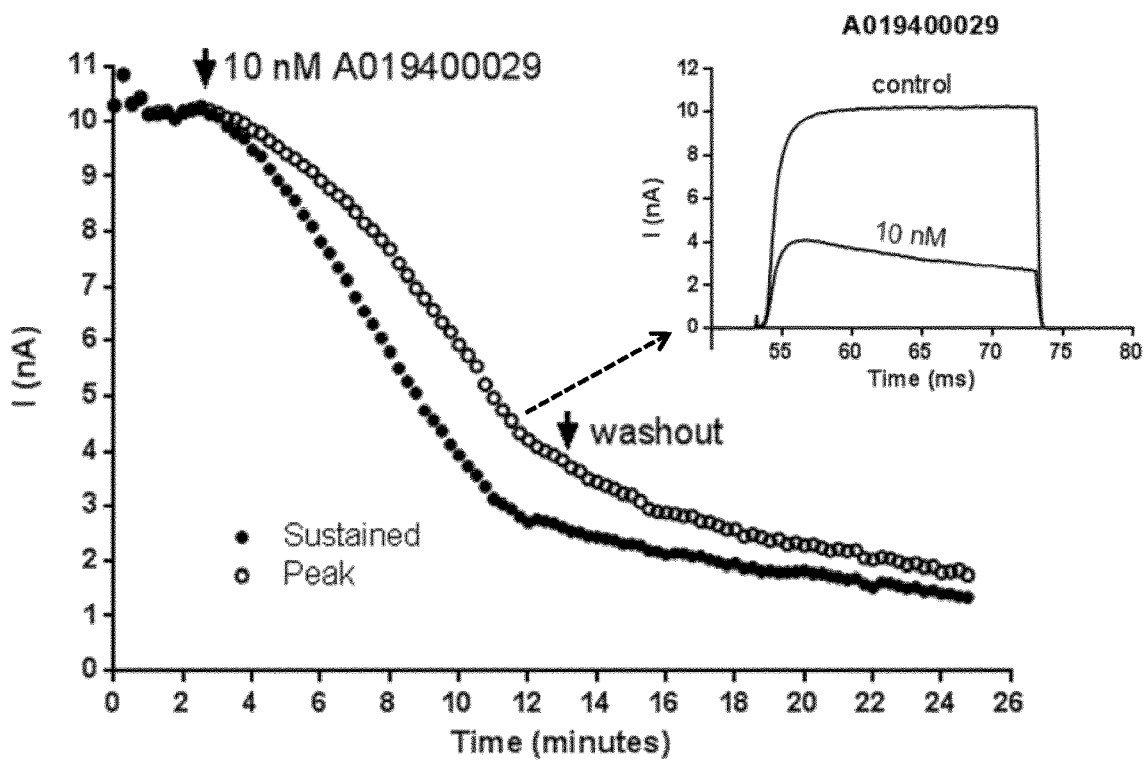
Figure 32:
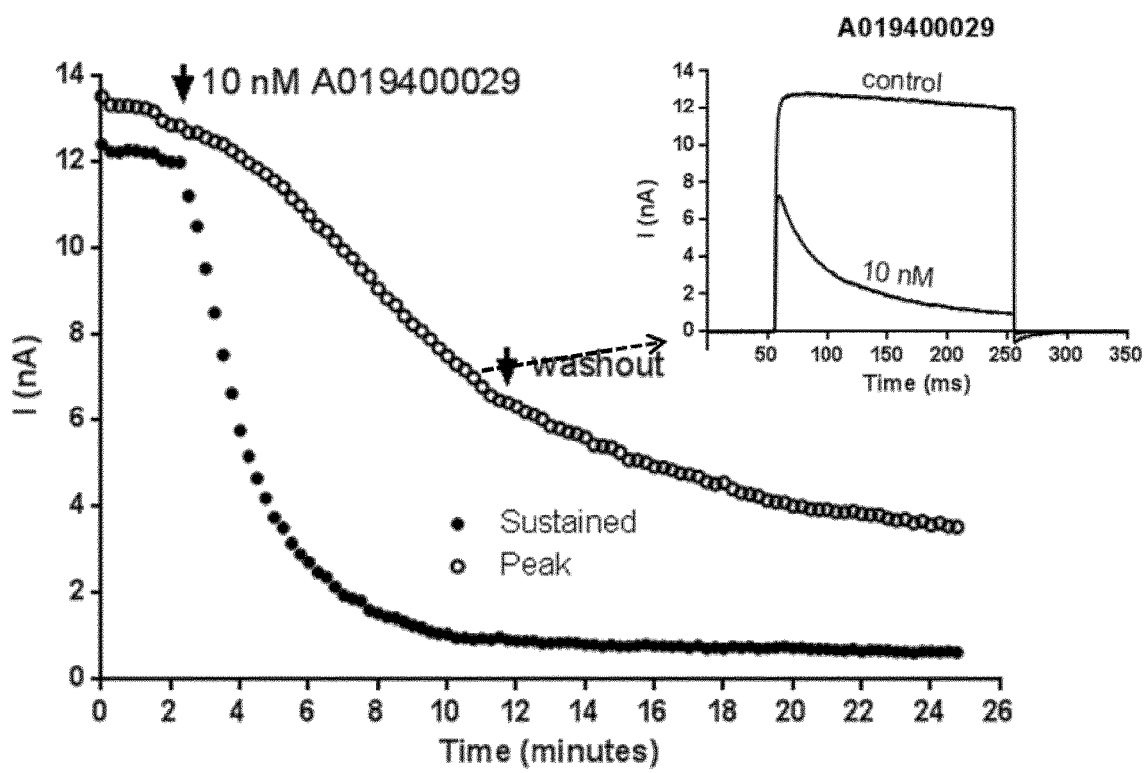

FIGS. 32A-32B: Effect of A019400029 on association and washout of Kv1.3 currents on human Kv1.3 channels stably expressed in CHL cells. Kv1.3 currents were recorded by conventional planar patch clamp using a repeated gating voltage command protocol. Currents were provoked by a test pulse from −80 mV to +40 mV every 15 s. The test pulse duration was either 20 ms (A) or 200 ms (B). Recordings were done in control conditions (prior to compound addition) and during a 3 to 5 min incubation of 10 nM A019400029, followed by compound washout. Peak and sustained current amplitudes were then plotted against the different time points.

FIGS. 33A-33B: Effect of A019400029 on association and washout of Kv1.3 currents on human Kv1.3 channels stably expressed in CHL cells. Kv1.3 currents were recorded by conventional planar patch clamp using a repeated gating voltage command protocol. Currents were provoked by a 200 ms test pulse from −80 mV to +40 mV every 15 s. Recordings were done in control conditions (prior to compound addition) and during a 3 to 5 min incubation of 10 nM A019400029, followed by compound washout. During this period of Nanobody incubation, the cells were held at a holding potential of either −80 mV (A) or −40 mV (B). Peak and sustained current amplitudes were then plotted against the different time points.

FIGS. 34A-34C: Effect of A019400029 on recovery from inactivation of Kv1.3 currents on human Kv1.3 channels stably expressed in CHL cells. Kv1.3 currents were recorded by conventional planar patch clamp. The recovery of inactivation from two inter-pulse potentials (−80 mV and −50 mv; C) was measured using a standard variable interval gapped pulse protocol (as shown in A). An initial 1 s pulse from −80 mV to +40 mV (P1) was followed by a second pulse from −80 mV to +40 mV for 150 ms (P2) after an interval of between 0.5 to 30 s. Representative traces in the absence and presence of 10 nM A019400029 are given in B. The percentage of recovery was calculated (see below) and plotted against pulse interval to show the recovery of inactivation (C).

$$\% \text{ recovery} = \frac{(P2_{peak} - P1_{sustained})}{(P1_{peak} - P1_{sustained})} * 100$$

FIGS. 35A-35D: Schematic representation of the voltage protocols applied to each well before and after the application of test compound on the automated patch clamp Ion-Works system. Kv1.5 and Kv1.6 potassium currents were elicited by a repeated gating voltage command protocol. K⁺ currents were evoked by a train of 100 ms depolarizing steps to +50 mV from a holding potential of −80 mV, applied 15 times (P1 to P15) at 3 Hz (A). The data points used in analysis represent normalized mean sustained current amplitudes ($I_{sustained}$) obtained from the area between the designated cursors in P1 (B). The hERG currents were elicited by a pulse train of five pulses to +40 mV from $V_H$ of −70 mV for 1 sec, then to −30 mV for 1 s, and back to the $V_H$ of −70 mV, at 03 Hz (C). The data points used in analysis represent normalized mean peak current amplitudes ($I_{peak}$) obtained from the area between the designated cursors in the tail step from pulse P5 (D).

FIGS. 36A-36D: Comparative pharmacology of the selected Nanobodies on human Kv1.3, Kv1.5, Kv1.6 and hERG K⁺ channels. The Kv1.3 and Kv1.5 currents were recorded by automated population patch clamp (PPC) and the Kv1.6 and hERG K⁺ current were recorded in single patch clamp mode (HT), using the repeated gating voltage command protocols on the IonWorks system, as described in FIG. 35. Recordings were done in control conditions (prior to compound addition). The Nanobodies were then incubated for 6 to 7 min prior to the second measurement using identical pulse protocols. The obtained concentration-response relationships are shown in A, B, C and D for Kv1.5, Kv1.6, hERG and Kv1.3 respectively. All selected Nanobodies display profound (i.e. greater than 1.000 fold) selectivity for Kv1.3 over the other K⁺ channels tested. The maximal inhibition at the highest concentration tested (i.e. 1 µM) was <50% in all other channels.

Figure 37:
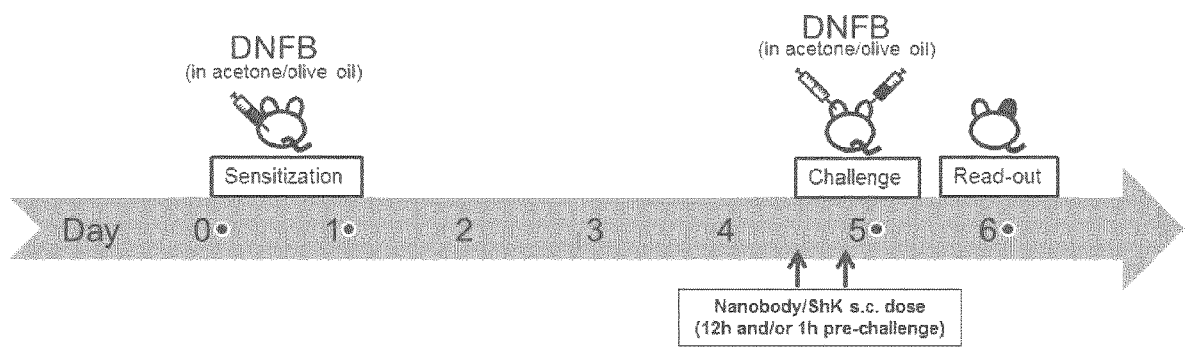

FIG. 37: Study design for testing the efficacy of anti-Kv1.3 Nanobodies in a rat model of 2, 4-dinitrofluorobenzene (DNFB)-induced delayed-type hypersensitivity (DTH).

Figure 38:
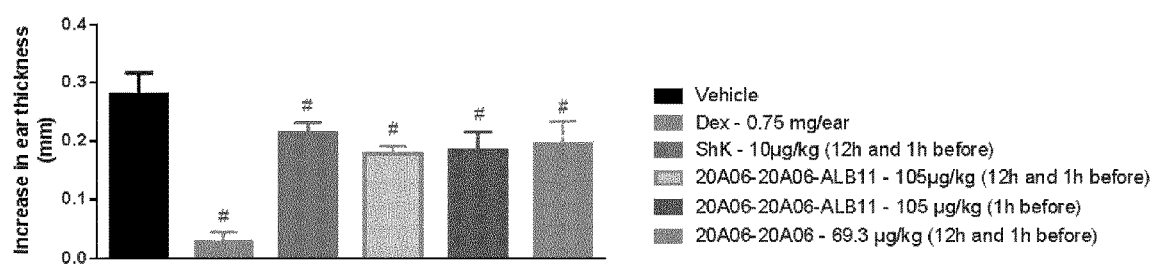

FIG. 38: Ear swelling responses of the different treatment groups (n=10 rats/group) in a rat model of 2, 4-dinitrofluorobenzene (DNFB)-induced delayed-type hypersensitivity. Animals received two subcutaneous injections of either vehicle, the reference compound ShK (10 µg/kg), the half-life extended anti-Kv1.3 Nanobody A019400029 (105 µg/kg) or the non-half-life extended anti-Kv1.3 Nanobody A019400032 (69.3 µg/kg) at 12 hours and 1 hour preceding the challenge, or one s.c. injection of A019400029 (105 µg/kg) at 1 hour before the challenge. Dexamethasone (Dex) was administered topically at 1 hour and 6 hours post-challenge (0.75 mg/ear) as positive control group. Data are represented as mean±standard deviation. #$p<0.05$ vs. vehicle group.

Figure 39:
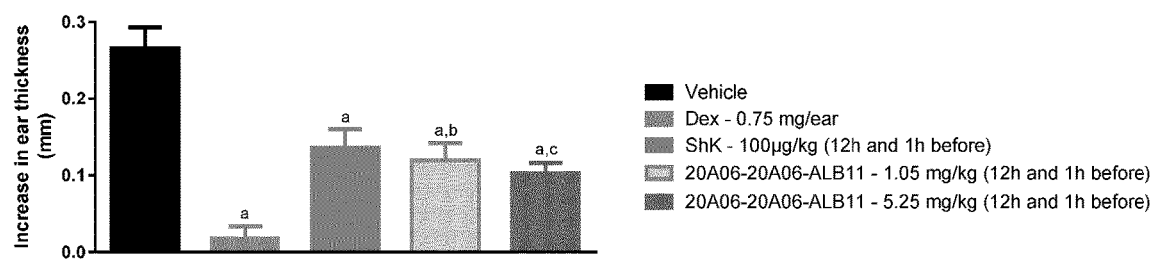

FIG. 39: Ear swelling responses of the different treatment groups (n=10 rats/group) in a rat model of 2, 4-dinitrofluorobenzene (DNFB)-induced delayed-type hypersensitivity. Animals received two subcutaneous injections of either vehicle, the reference compound ShK (100 µg/kg), or the half-life extended anti-Kv1.3 Nanobody A019400029 (1.05 mg/kg or 5.25 mg/kg) at 12 hours and 1 hour preceding the challenge. Dexamethasone (Dex) was administered topically at 1 hour and 6 hours post-challenge (0.75 mg/ear) as positive control group. Data are represented as mean±standard deviation. a: $p<0.05$ vs. vehicle group; b: non-inferior compared to ShK group; c: superior compared to ShK group.

Figure 40:
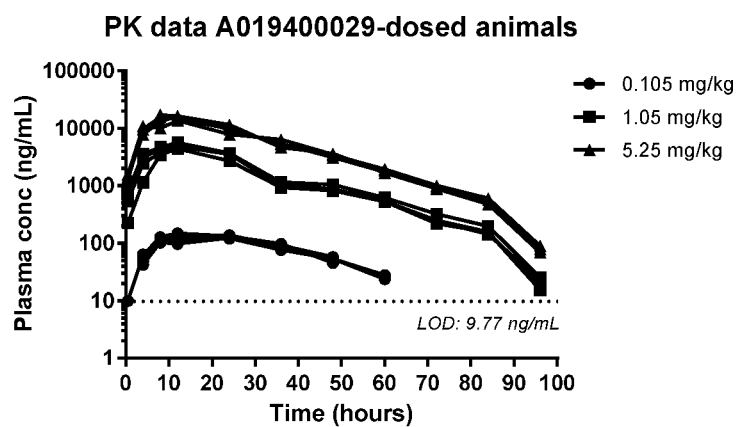

FIG. 40: Plasma pharmacokinetic profiles of A019400029 in individual animals at different time points after challenge with DNFB.

Figure 41:
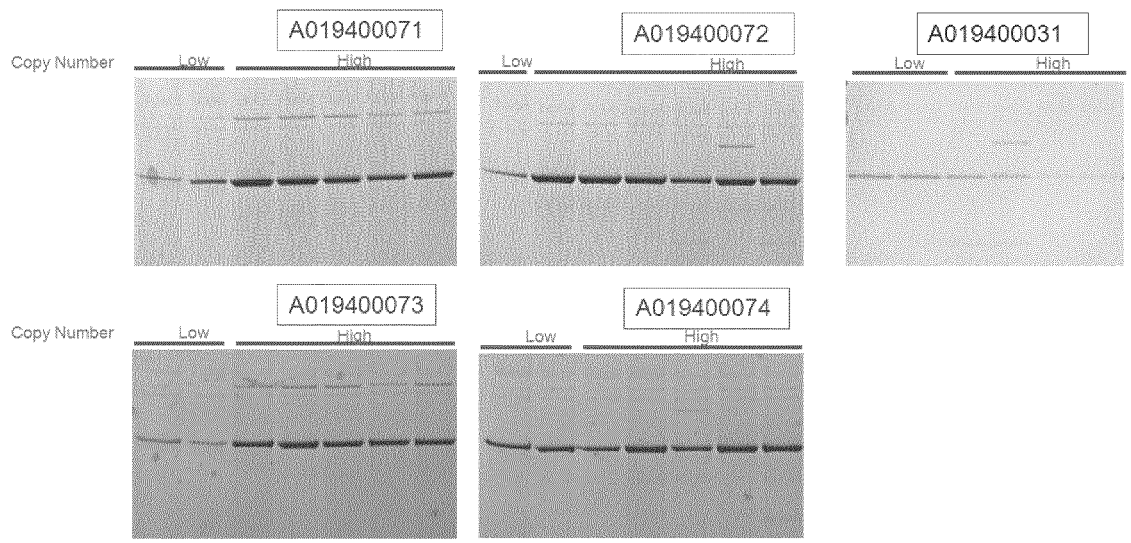

FIG. 41: SDS-PAGE analysis of A019400071, A019400072, A019400073, A019400074 and A019400031 for yield estimation. *Pichia* clones were generated containing 1 copy of the Nanobody expression cassette in the genome (Low) or with more than 1 copy number (High). Equal volumes of supernatant were compared from the different clones on 12% SDS-PAGE gel using Instant blue staining.

DETAILED DESCRIPTION

Definitions

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd. Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes I I, John Wiley & Sons, New York, N.Y., 1985), Old et al. (Principles of Gene Manipulation: An Introduction to Genetic Engineering (2nd edition) University of California Press, Berkeley, Calif., 1981); Roitt et al. (Immunology (6th. Ed.) Mosby/Elsevier, Edinburgh, 2001), Roitt et al. (Roitt's Essential Immunology (10$^{th}$ Ed.) Blackwell Publishing, U K, 2001), and Janeway et al. (Immunobiology (6th Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein).

By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two, three or maximal four such amino acid differences compared to the CDR sequence of respectively a), c) or e).

The "amino acid difference" can be any one, two, three or maximal four substitutions, deletions or insertions, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind Kv1.3 with the same, about the same, or a higher affinity compared to the polypeptide comprising the one or more CDR sequences without the one, two, three or maximal four substitutions, deletions or insertions, said affinity as measured by surface plasmon resonance (SPR).

In this respect, the amino acid sequence according to b), d) and/or f) may be an amino acid sequence that is derived from an amino acid sequence according to a), c) and/or e) respectively by means of affinity maturation using one or more techniques of affinity maturation known per se.

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

A "Nanobody family", "VHH family" or "family" as used in the present specification refers to a group of Nanobodies and/or VHH sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-Kv1.3).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) liters/mol is generally considered to indicate non-specific binding. Preferably, a monovalent polypeptide of the invention will bind to the desired antigen with an affinity less than 500 nM, preferably less than 200 nM, more preferably less than 10 nM, such as e.g., between 10 and 5 nM or less. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less, such as 10000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays. Particularly suitable quantitative cross-blocking assays are described in the Examples and include e.g. a fluorescence-activated cell sorting (FACS) binding assay with Kv1.3 expressed on cells. The extent of (cross)-blocking can be measured by the (reduced) channel fluorescence.

The following generally describes a suitable FACS assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The FACS instrument (e.g. FACS Canto; Becton Dickinson) is operated in line with the manufacturer's recommendations.

To evaluate the "(cross)-blocking" or "(cross)-competition" between two binding agents (such as e.g. two immunoglobulin single variable domains and/or Nanobodies) for binding Kv1.3, a FACS competition experiment can be performed using cells (such as e.g. CHO cells or HEK293H cells) overexpressing human Kv1.3 and the parental cells as background cell line. Different detection reagents can be used including e.g. monoclonal ANT-FLAG® M2 antibody (Sigma-Aldrich, cat #F1804), monoclonal anti-C-myc antibody (Sigma-Aldrich, cat #WH0004609M2), monoclonal ANTI-HIS TAG antibody (Sigma-Aldrich, cat #SAB1305538), each labeled differently. A wide range of fluorophores can be used as labels in flow cytometry (such as e.g PE (R-Phycoerythrin), 7-aminoactinomycin D (7-AAD), Acridine Orange, various forms of Alexa Fluor, Allophycocyanin (APC), AmCyan, Aminocoumarin, APC Cy5, APC Cy7, APC-H7, APC/Alexa Fluor 750, AsRed2, Azami-Green, Azurite, B ODIPY FL C5-ceramide, BCECF-AM, Bis-oxonol DiBAC2(3), BODIPY-FL, Calcein, Calcein AM, Caroxy-H2DCFDA, Cascade Blue, Cascade Yellow, Cell Tracker Green, Cerulean, CFSE, Chromomycin A3, CM-H2DCFDA, Cy2, Cy3, Cy3.5, Cy3B, Cy5, Cy5.5, Cy7, CyPet, DAF-FM DAF-FM diacetate, DAPI, DCFH (2'7'Dichorodihydrofluorescein), DHR, Dihydrocalcein AM, Dihydrorhoadamine, Dihydrothidium, DiLC1(5), DiOC6(3), DiOC7(3), dKeima-Red, DRAQ5, Dronpa-Green, various forms of DsRed dTomato, various forms of DyLight, E. coli BioParticles AF488, E2-Crimson, E2-Orange, EBFP2, ECFP, various forms of eFluor, EGFP, EGFP*, Emerald, eqFP650, eqFP670, ER-Tracker Blue-White DPX, Ethidium Bromide, Express2, EYFP, Fc OxyBurst Green, Fc OxyBurst Green 123, FITC, Fluo-3, Fluo-4, Fluorescein, Fura-2, Fura-Red, GFPuv, H2DCFDA, HcRed1, Hoechst Blue (33258), Hoechst Red (33342), Hydroxycoumarin, HyPer, Indo-1, Indo-1 Blue (Low Ca2+), Indo-1 Violet (High Ca2+), iRFP, J-Red, JC-1, JC-9, Katushka (TurboFP635), Katushka2 Kusabira-Orange, LDS 751, Lissamine Rhodamine B, various forms of Live/Dead, Lucifer yellow, Lucifer Yellow CH, Lyso Tracker Blue, Lyso Tracker Green, Lyso Tracker Red, mAmertrine, Marina Blue, mBanana, mCFP, mCherry, mCitrine, Methoxycoumarin, mHoneyDew, Midoriishi-Cyan, Mithramycin, Mito Tracker Deep Red, Mito Tracker Green, Mito Tracker Orange, Mito Tracker Red, MitoFluor Green, mKate (TagFP635), mKate2, mKeima, mKeima-Red, mKO, mKOk, mNeptune, Monochlorobimane, mOrange, mOrange2, mRaspberry, mPlum, mRFP1, mStrawberry, mTangerine, mTarquoise, mTFP1, mTFP1 (Teal), NBD, OxyBurst Green H2DCFDA, OxyBurst Green H2HFF BSA, Pacific Blue, PE (R-Phycoerythrin), PE Cy5, PE Cy5.5, PE Cy7, PE Texas Red, PE-Cy5 conjugates, PE-Cy7 conjugates, PerCP (Peridinin chlorphyll protein), PerCP Cy5.5, PhiYFP, PhiYFP-m, Propidium Iodide (PI), various forms of Qdot, Red 613, RFP Tomato, Rhod-2, S65A, S65C, S65L, S65T, Singlet Oxygen Sensor Green, Sirius, SNARF, Superfolder GFP, SYTOX Blue, SYTOX Green, SYTOX Orange, T-Sapphire, TagBFP, TagCFP, TagGFP, TagRFP, TagRFP657, TagYFP, tdTomato, Texas Red, Thiazole Orange, TMRE, TMRM, Topaz, TOTO-1, TO-PRO-1, TRITC, TRITC TruRed, TurboFP602, TurboFP635, TurboGFP, TurboRFP, TurboYFP, Venus, Vybrant CycleDye Violet, Wild Type GFP, X-Rhodamin, Y66F, Y66H, Y66W, YOYO-1, YPet, ZsGreenl, ZsYellowl, Zymosan A BioParticles AF488 (see more at: http://www.thefcn.org/flow-fluorochromes). Fluorophores, or simply "fluors", are typically attached to the antibody (e.g. the immunoglobulin single variable domains and/or Nanobodies) that recognizes Kv1.3 or to the antibody that is used as detection reagent. Various conjugated antibodies are available, such as (without being limiting) for example antibodies conjugated to Alexa Fluor®, DyLight®, Rhodamine, PE, FITC, and Cy3. Each fluorophore has a characteristic peak excitation and emission wavelength. The combination of labels which can be used will depend on the wavelength of the lamp(s) or laser(s) used to excite the fluorophore and on the detectors available.

To evaluate the competition between two test binding agents (termed A and B) for binding to Kv1.3, a dilution series of cold (without any label) binding agent A is added to (e.g. 200 000) cells together with the labeled binding agent B*. The concentration of binding agent B* in the test mix should be high enough to readily saturate the binding sites on Kv1.3 expressed on the cells. The concentration of binding agent B* that saturates the binding sites for that binding agent on Kv1.3 expressed on the cells can be determined with a titration series of binding agent B* on the Kv1.3 cells and determination of the $EC_{50}$ value for binding. In order to work at saturating concentration, binding agent B* can be used at 100× the $EC_{50}$ concentration.

After incubation of the cells with the mixture of binding agent A and binding agent B* and cells wash, read out can be performed on a FACS. First a gate is set on the intact cells as determined from the scatter profile and the total amount of channel fluorescence is recorded.

A separate solution of binding agent B* is also prepared. Binding agent B* in this solutions should be in the same buffer and at the same concentration as in the test mix (with binding agent A and B*). This separate solution is also added to the cells. After incubation and cells wash, read out can be performed on a FACS. First a gate is set on the intact cells as determined from the scatter profile and the total amount of channel fluorescence is recorded.

A reduction of fluorescence for the cells incubated with the mixture of binding agent A and B* compared to the fluorescence for the cells incubated with the separate solution of binding agent B* indicates that binding agent A (cross)-blocks binding by binding agent B* for binding to Kv1.3 expressed on the cells.

A cross-blocking immunoglobulin, antibody, immunoglobulin single variable domain, polypeptide or other binding agent according to the invention is one which will bind to the Kv1.3 in the above FACS cross-blocking assay such that during the assay and in the presence of a second immunoglobulin, antibody, immunoglobulin single variable domain, polypeptide or other binding agent the recorded fluorescence is between 80% and 0.1% (e.g. 80% to 4%) of the maximum fluorescence (measured for the separate labelled immunoglobulin, antibody, immunoglobulin single variable domain, polypeptide or other binding agent), specifically between 75% and 0.1% (e.g. 75% to 4%) of the maximum fluorescence, and more specifically between 70% and 0.1% (e.g. 70% to 4%) of maximum fluorescence (as just defined above).

The competition between two test binding agents (termed A* and B*) for binding to Kv1.3 can also be evaluated by adding both binding agents, each labeled with a different fluorophore, to the Kv1.3 expressing cells. After incubation and cells wash, read out can be performed on a FACS. A gate is set for each fluorophore and the total amount of channel fluorescence is recorded. Reduction and/or absence of fluorescence of one of the fluorophore indicate (cross)-blocking by the binding agents for binding to Kv1.3 expressed on the cells.

Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al (Journal of Immunological Methods 288: 91-98, 2004), Miller et al. (Journal of Immunological Methods 365: 118-125, 2011) and/or the methods described herein (see e.g. Example 7).

An amino acid sequence is said to be "cross-reactive" for two different antigens or antigenic determinants (such as e.g., serum albumin from two different species of mammal, such as e.g., human serum albumin and cyno serum albumin, such as e.g., Kv1.3 from different species of mammal, such as e.g., human Kv1.3, cyno Kv1.3 and rat Kv1.3) if it is specific for (as defined herein) these different antigens or antigenic determinants.

In the context of the present invention, "modulating" or "to modulate" generally means reducing or inhibiting the activity of Kv1.3, as measured using a suitable in vitro, cellular or in vivo assay (such as those mentioned herein). In particular, "modulating" or "to modulate" may mean either reducing or inhibiting the activity of, or alternatively increasing the activity of Kv1.3, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of Kv1.3 in the same assay under the same conditions but without the presence of the immunoglobulin or polypeptide of the invention.

"Modulating" may also mean effecting a change with respect to one or more biological or physiological mechanisms, effects, responses, functions, pathways or activities in which Kv1.3 (or in which its substrate(s), ligand(s) or pathway(s) are involved, such as its signalling pathway or metabolic pathway and their associated biological or physiological effects) is involved. Again, as will be clear to the skilled person, such an action may be determined in any suitable manner and/or using any suitable (in vitro and usually cellular or in vivo assay) assay known per se, such as the assays described herein or in the prior art cited herein. In particular, an action may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the immunoglobulin or polypeptide of the invention.

Modulating may for example involve reducing and/or inhibiting the efflux of potassium ions from T-cells. Modulation may involve the reduction and/or inhibition of T-cell activation and/or proliferation. Modulation may involve the reduction, inhibition and/or suppression of (unwanted) immune responses.

The term "allosteric modulation", "allosteric modulating", "allosteric modulator" as used in the present invention refers to the indirect modulation of the activity of Kv1.3. Allosteric modulators do not physically block the Kv1.3 channel, but rather bind at a site in Kv1.3 that is not directly involved in the activity of Kv1.3. Usually an allosteric modulator induces a conformational change within the protein structure of Kv1.3, which may ultimately also impose a structural stress on the pore channel. This may in its turn result in the blocking of the pore, the ion channel to adopt a non-functional state (resting or inactivated state) and/or maintain the ion channel in a non-functional state.

The term "potency" of a polypeptide of the invention, as used herein, is a function of the amount of polypeptide of the invention required for its specific effect to occur. It is measured simply as the inverse of the $IC_{50}$ for that polypeptide. It refers to the capacity of said polypeptide of the invention to modulate and/or partially or fully inhibit the function of Kv1.3. More particularly, it may refer to the capacity of said polypeptide to reduce or even totally inhibit the efflux of potassium ions from T-cells. As such, it may refer to the capacity of said polypeptide to inhibit proliferation of T-cells and/or suppress activation of T-cells resulting in the inhibition of certain immune responses in vivo.

The potency may be measured by any suitable assay known in the art or described herein. Without being limiting, various ion channel screening technologies are described e.g. by Dabrowski et al. (CNS & Neurological Disorders Drug Targets 7: 122, 2008), Lü and An (Comb. Chem. High Throughput Screen. 11:185-94, 2008), and Zheng et al. (Assay Drug Dev. Technol. 2: 543-52, 2004). Potency assays include (without being limiting) ion flux assays (Hanson et al. Br. J. Pharmacol. 126: 1707-16, 1999; Wang et al. Assay Drug Dev. Technol. 2: 525-34, 2004; Weaver et al. J. Biomol. Screen. 9: 671-7, 2004), radioligand binding studies (Felix et al. Biochemistry 38: 4922-30, 1999; Knaus et al. Biochemistry 34: 13627-13634, 1995; Helms et al. Biochemistry. 36: 3737-44, 1997), fluorescent dye assays, electrophysiology, such as voltage clamp (Huxley, Trends Neurosci. 25: 553-8, 2002), and in particular, the patch-clamp (Hamill et al. Pflügers Archiv European Journal of Physiology 391: 85-100, 1981) or high throughput versions thereof (Southan and Clark, Methods Mol. Biol. 565: 187-208, 2009), including PatchXpress (Molecular Devices; Ghetti et al. Methods Mol. Biol. 403: 59-69, 2007), Qpatch and Qpatch HTX (Sophion; Mathes et al. Comb. Chem. High Throughput Screen. 12: 78-95, 2009; Korsgaard et al. Comb. Chem. High Throughput Screen. 12: 51-63, 2009), PatchLiner (Nanion; Farre et al. Comb. Chem. High Throughput Screen 12: 24-37, 2009), IonWorks® HT, IonWorks® Quattro and IonFlux™ Systems (Molecular Devices; Jow et al. J Biomol. Screen. 12: 1059-67, 2007; Dale et al. Mol. Biosyst. 3: 714-22, 2007), T-cell activation assays (Nguyten et al. Molecular Pharmacology 50: 1672-1679, 1996; Hanson et al. Br. J. Pharmacol. 126: 1707-1716, 1999) and/or in vivo assays, such as Diabetes-prone Biobreeding Worchester rats (Beeton et al. Proc Natl Acad Sci USA. 103: 17414-9, 2006), a rat model for allergic contact dermatitis (Azam et al. J. Invest. Dermatol. 127: 1419-29, 2007), and the animal model for T cell-mediated skin graft rejection (Ren et al. PLoS One 3:e4009, 2008).

In contrast, the "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth et al (Chemical Stability of Pharmaceuticals: A Handbook for Pharmacists, John Wiley & Sons Inc, 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t½-beta, either with or without an increase in the t½-alpha and/or the AUC or both.

Unless indicated otherwise, the terms "immunoglobulin" and "immunoglobulin sequence"-whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e., against the same or another epitope on Kv1.3 and/or against one or more other antigens, proteins or targets than Kv1.3).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., Kv1.3) and at least one binding unit is directed against a second antigen (i.e., different from Kv1.3) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., Kv1.3) and at least one further immunoglobulin single variable domain directed against a second antigen (i.e., different from Kv1.3), whereas a "trispecific" polypeptide of the invention is a polypeptide that comprises at least one immunoglobulin single variable domain directed against a first antigen (i.e., Kv1.3), at least one further immunoglobulin single variable domain directed against a second antigen (i.e., different from Kv1.3) and at least one further immunoglobulin single variable domain directed against a third antigen (i.e., different from both Kv1.3 and the second antigen); etc.

"Multiparatopic polypeptides", such as e.g., "biparatopic polypeptides" or "triparatopic polypeptides", comprise or essentially consist of two or more binding units that each have a different paratope (as will be further described herein; see chapter on multivalent polypeptides of the invention).
Immunoglobulins that Bind Extracellular Loop EL1 of Voltage Gated Kv1.3 Potassium Channel The present invention provides immunoglobulins (also referred to herein as "immunoglobulins of the invention") and/or polypeptides (also referred to herein as "polypeptides of the invention") that have specificity for and/or that bind Kv1.3, preferably human Kv1.3. Kv1.3 also known as KCNA3, MK3, HGK5, HLK3, PCN3, HPCN3 or HUKIII, is a protein that, in humans, is encoded by the KCNA3 gene (Accession No. P22001, human KCNA3), which is located at chromosome 1p13.3. Thus, the immunoglobulins and/or polypeptides of the invention preferably bind to human Kv1.3 (SEQ ID NO: 474).

In one aspect of the invention, the immunoglobulins and/or polypeptides of the present invention bind to the first extracellular loop EL1 of Kv1.3. The amino acid sequence of extracellular loop EL1 starts after the transmembrane region S1 and ends at S2. More specifically, the extracellular loop EL1 of Kv1.3 spans position 254 to position 294 of SEQ ID NO: 474.

The present inventors surprisingly observed that the immunoglobulins and/or polypeptides of the invention that bind this part of Kv1.3 exhibited different modulating activities on Kv1.3, such as partial or full blocking of Kv1.3, inhibition of T-cell activation and/or proliferation and/or suppression of (unwanted) immune reaction in vivo. In addition, these immunoglobulins showed highly improved interspecies cross-reactivity and exquisite selectivity properties.

Accordingly, the present invention relates to an immunoglobulin and/or polypeptide that specifically binds to the EL1 extracellular loop of potassium channel 3 (Kv1.3), and wherein the binding of said immunoglobulin to said EL1 extracellular loop modulates and/or inhibits the activity of Kv1.3. As the pore channel of Kv1.3 is made up by the extracellular region EL3 of Kv1.3, the finding of immunoglobulins that bind EL1 and still modulate, inhibit and/or block Kv1.3 activity (i.e. without physical interaction with and/or blocking of EL3) was unexpected.

Preferred immunoglobulins and/or polypeptides of the invention include immunoglobulins (such as heavy chain antibodies, conventional 4-chain antibodies (such as IgG, IgM, IgA, IgD or IgE molecules), Fab fragments, F(ab')2 fragments, Fv fragments such as disulphide linked Fv or scFv fragments, or diabodies derived from such conventional 4-chain antibody, the individual chains thereof, as well as all parts, domains or fragments thereof (including but not limited to antigen-binding domains or fragments such as immunoglobulin single variable domains), monovalent polypeptides of the invention, or other binding agents).

Binding of the immunoglobulins and/or polypeptides of the invention to Kv1.3 can be measured in binding assays that preserve that conformation of the Kv1.3 target. Typical assays include (without being limiting) assays in which Kv1.3 is exposed on a cell surface (such as e.g. CHO cells (e.g. CHO-K1), HEK cells, HeLa cells, Chinese Hamster Lung (CHL) cells, Caki cells etc.). A preferred assay for measuring binding of the immunoglobulins and/or polypeptides of the invention to Kv1.3 is a FACS assay, such as e.g. the FACS assay as described in the examples, wherein binding of the immunoglobulins and/or polypeptides of the invention to Kv1.3 expressed on CHO-K1 cells and/or HEK293H cells is determined. Some preferred EC50 values for binding of the immunoglobulins and/or polypeptides of the invention to Kv1.3 will become clear from the further description and examples herein.

In such FACS binding assay, the immunoglobulins and/or polypeptides of the present invention may have EC50 values in binding human Kv1.3 of $10^{-8}$ M or lower, more preferably of $10^{-9}$ M or lower, or even of $10^{-10}$ M or lower. For example, in such FACS binding assay, the immunoglobulins and/or polypeptides of the present invention may have EC50 values in binding human Kv1.3 between $10^{-10}$ M and $10^{-8}$ M, such as between $10^{-9}$ M and $10^{-8}$ M or between $10^{-10}$ M and $10^{-9}$ M.

In such FACS binding assay, the immunoglobulins and/or polypeptides of the present invention may have EC50 values in binding cyno Kv1.3 of $10^{-7}$ M or lower, preferably of $10^{-8}$ M or lower, more preferably of $10^{-9}$ M or lower, or even of $10^{-10}$ M or lower. For example, in such FACS binding assay, the polypeptides of the present invention may have EC50 values in binding cyno Kv1.3 between $10^{-10}$ M and $10^{-7}$ M, such as between $10^{-10}$ M and $10^{-8}$ M, between $10^{-10}$ M and $10^{-9}$ M.

In such FACS binding assay, the immunoglobulins and/or polypeptides of the present invention may have EC50 values in binding rat Kv1.3 of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such FACS binding assay, the polypeptides of the present invention may have EC50 values in binding rat Kv1.3 between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

The immunoglobulins and/or polypeptides of the invention bind EL1 of Kv1.3 and modulate and/or (partially or fully) inhibit the function of Kv1.3. More particularly, the immunoglobulins and/or polypeptides of the present invention may depolarize the T cell membrane and/or reduce or even totally inhibit the efflux of potassium ions from T-cells. As such, the immunoglobulins and/or polypeptides of the invention may partially or fully inhibit proliferation of T-cells and/or suppress activation of T-cells resulting of the inhibition of certain immune responses in vivo.

More particularly, the immunoglobulins and/or polypeptides of the invention may indirectly modulate the function of Kv1.3, i.e. as an allosteric modulator (as defined herein). For example, the immunoglobulins and/or polypeptides of the invention may induce a conformational change within the structure of the Kv1.3 pore channel.

Accordingly, in one aspect, the present invention relates to an immunoglobulin and/or polypeptide that specifically binds to the EL1 extracellular loop of Kv1.3, and wherein the binding of said immunoglobulin and/or polypeptide to said EL1 extracellular loop modulates and/or (partially or fully) inhibits the activity of Kv1.3 by allosteric modulation of the activity of Kv1.3. More particularly, the immunoglobulins and/or polypeptides of the present invention may allosterically depolarize the T cell membrane and/or reduce or even totally inhibit the efflux of potassium ions from T-cells. As such, the immunoglobulins and/or polypeptides of the invention may inhibit proliferation of T-cells and/or suppress activation of T-cells resulting of the inhibition of certain immune responses in vivo.

Modulation and/or inhibition of the efflux of potassium ions can be determined by a variety of ion channel screening technologies including (without being limiting) ion flux assays, radioligand binding studies, fluorescent dye assays, and electrophysiology, such as voltage clamp, and in particular, the patch-clamp. An overview of different ion channel technologies is provided by e.g. Dabrowski et al. (CNS & Neurological Disorders Drug Targets 7: 122, 2008), Lü and An (Comb. Chem. High Throughput Screen. 11:185-94, 2008), and Zheng et al. (Assay Drug Dev. Technol. 2: 543-52, 2004).

Voltage clamp (Huxley, Trends Neurosci. 25: 553-8, 2002) is used to measure the ion currents through the membrane of excitable cells. The patch-clamp variant of this technique (Hamill et al. Pflügers Archiv European Journal of Physiology 391: 85-100, 1981) allows the study of single or multiple ion channels in cells.

Higher throughput electrophysiological platforms have been developed ranging from medium throughput systems to higher throughput platforms (see e.g. Southan and Clark, Methods Mol. Biol. 565: 187-208, 2009), including PatchXpress (Molecular Devices; Ghetti et al. Methods Mol. Biol. 403: 59-69, 2007), Qpatch and Qpatch HTX (Sophion; Mathes et al. Comb. Chem. High Throughput Screen. 12: 78-95, 2009; Korsgaard et al. Comb. Chem. High Throughput Screen. 12: 51-63, 2009), PatchLiner (Nanion; Farre et al. Comb. Chem. High Throughput Screen 12: 24-37, 2009), IonWorks® HT, IonWorks® Quattro and IonFlux™ Systems (Molecular Devices; Jow et al. J Biomol. Screen. 12: 1059-67, 2007; Dale et al. Mol. Biosyst. 3: 714-22, 2007). Some preferred IC50 values for the polypeptides of the invention in these assays will become clear from the further description and examples herein.

On the IonFlux™ (Molecular Devices) using Kv1.3-expressing HEK293H cells, for example, the immunoglobulins and/or polypeptides of the invention have IC50 values of $10^{-7}$ M or lower, preferably of $10^{-8}$ M or lower, more preferably of $10^{-9}$ M or lower, or even of $10^{-10}$ M or lower. For example, in this automated Patch Clamp assay, the polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-9}$ M and $10^{-7}$ M, between $10^{-9}$ M and $10^{-8}$ M, between $10^{-8}$ M and $10^{-7}$ M or between $10^{-10}$ M and $10^{-9}$ M.

Accordingly, the present invention relates to an immunoglobulin and/or polypeptide that specifically binds to the EL1 extracellular loop of Kv1.3, and that modulates and/or inhibits the activity of Kv1.3 by (allosteric) modulation of the efflux of potassium ions, with a potency of $10^{-7}$ M or lower, preferably of $10^{-8}$ M or lower, more preferably of $10^{-9}$ M or lower, or even of $10^{-10}$ M or lower, as measured on IonFlux™ (Molecular Devices).

On the IonWorks® Quattro (Molecular Devices) using Kv1.3-expressing Chinese Hamster Lung (CHL) cells, for example, the immunoglobulins and/or polypeptides of the invention have IC50 values of $10^{-7}$ M or lower, preferably of $10^{-8}$ M or lower, more preferably of $10^{-9}$ M or lower, or even of $10^{-10}$ M or lower. For example, on this high-throughput planar perforated patch clamp, the polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-8}$ M and $10^{-7}$ M, between $10^{-9}$ M and $10^{-7}$ M or between $10^{-10}$ M and $10^{-9}$ M.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular loop inhibits the activity of Kv1.3 by (allosteric) modulation of the efflux of potassium ions, with a potency of $10^{-7}$ M or lower, preferably of $10^{-8}$ M or lower, more preferably of $10^{-9}$ M or lower, or even of $10^{-10}$ M or lower, as measured on IonWorks® Quattro (Molecular Devices).

Modulation and/or inhibition of Kv1.3 by the polypeptides of the invention can also be assessed in radioligand binding studies. Binding studies with tritiated correolide (e.g. C20-29-[3H]dihydrocorreolide (diTC)) to a single class of sites in membranes prepared from CHO/Kv1.3 cells has been described by Felix et al. (Biochemistry 38: 4922-30, 1999). Knaus et al. (Biochemistry 34: 13627-13634, 1995) describes, for example, the binding of monoiodotyrosinyl margatoxin (125I-margatoxin) to heterotetrameric Kv channels in rat brain synaptic plasma membranes. Binding studies of 125I-margatoxin to plasma membranes prepared from either Jurkat cells, a human leukemic T cell line, or CHO cells stably transfected with the Shaker-type voltage-gated K+ channel, K(V)1.3 have been described by Helms et al. (Biochemistry. 36: 3737-44, 1997). Some preferred IC50 values for blocking 125I-margatoxin binding to Kv1.3 by the polypeptides of the invention will become clear from the further description and examples herein.

The immunoglobulins and/or polypeptides of the present invention may block binding of 125I-margatoxin to cynomolgus Kv1.3 overexpressing CHO cells with IC50 values of $10^{-8}$ M or lower, more preferably of $10^{-9}$ M or lower, or even of $10^{-10}$ M or lower. For example, in such 125I-margatoxin blocking assay, the immunoglobulins and/or polypeptides of the present invention may have IC50 values between $10^{-10}$ M and $10^{-8}$ M, between $10^{-10}$ M and $10^{-9}$ M, such as e.g. between $10^{-9}$ M and $10^{-8}$ M or between $10^{-10}$ M and $10^{-9}$ M.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular loop blocks binding of 125I-margatoxin to cynomolgus Kv1.3 overexpressing CHO cells with a potency of $10^{-8}$ M or lower, more preferably of $10^{-9}$ M or lower, or even of $10^{-10}$ M or lower.

Other flux assays for measuring modulation and/or inhibition of Kv1.3 by the polypeptides of the invention include (without being limiting) the high-throughput efflux assay with radiolabelled[86] Rubidium described by Hanson et al. (Br. J. Pharmacol. 126: 1707-16, 1999), the nonradioactive rubidium (Rb(+)) efflux assay described by Wang et al. (Assay Drug Dev. Technol. 2: 525-34, 2004) and a fluorescence-based thallium flux assay (Weaver et al. J. Biomol. Screen. 9: 671-7, 2004).

Inhibition of T-cell activation and/or proliferation by the polypeptides of the present invention can be measured in T-cell activation assays. Without being limiting, T-cell activation assays have been described by Nguyten et al. (Molecular Pharmacology 50: 1672-1679, 1996) and Hanson et al. (Br. J. Pharmacol. 126: 1707-1716, 1999). Some preferred IC50 values for inhibition of T-cell activation and/or proliferation by the monovalent polypeptides of the invention will become clear from the further description and examples herein.

In a T-cell activation assay with CCR7⁻CD45RA⁻ T cells stimulated with anti-CD3 antibody OKT3 (as described in the Examples 4.4 and 5.5), the immunoglobulins and/or polypeptides of the invention have IC50 values for inhibiting IFNgamma production of $10^{-7}$ M or lower, preferably of $10^{-8}$ M or lower, more preferably of $10^{-9}$ M or lower, $10^{-10}$ M or lower, or even of $10^{-11}$ M or lower. For example, in this T-cell activation assay, the immunoglobulins and/or polypeptides of the present invention inhibit IFNgamma production with IC50 values between $10^{-11}$ M and $10^{-7}$ M, between $10^{-11}$ M and $10^{-8}$ M, between $10^{-11}$ M and $10^{-9}$ M, such as e.g. between $10^{-8}$ M and $10^{-7}$ M, between $10^{-11}$ M and $10^{-9}$ M, between $10^{-10}$ M and $10^{-9}$ M, or between $10^{-11}$ M and $10^{-10}$ M.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular loop inhibits IFNgamma production in T cells with a potency of $10^{-7}$ M or lower, preferably of $10^{-8}$ M or lower, more preferably of $10^{-9}$ M or lower, or even of $10^{-10}$ M or lower, or even of $10^{-11}$ M or lower, as measured in a T-cell activation assay with CCR7⁻CD45RA⁻ T cells stimulated with anti-CD3 antibody OKT3 (as described in the Examples 4.4 and 5.5).

In this T-cell activation assay with CCR7⁻CD45RA⁻ T cells stimulated with anti-CD3 antibody OKT3 (as described in the Examples 4.4 and 5.5), the immunoglobulins and/or polypeptides of the invention have IC50 values for inhibiting CD25 upregulation of $10^{-7}$ M or lower, preferably of $10^{-8}$ M or lower, more preferably of $10^{-9}$ M or lower, $10^{-10}$ M or lower, or even of $10^{-11}$ M or lower. For example, in this T-cell activation assay, the immunoglobulins and/or polypeptides of the present invention inhibit CD25 upregulation with IC50 values between $10^{-11}$ M and $10^{-7}$ M, between $10^{-11}$ M and $10^{-8}$ M, between $10^{-11}$ M and $10^{-9}$ M, such as e.g. between $10^{-8}$ M and $10^{-7}$ M, between $10^{-11}$ M and $10^{-9}$ M, between $10^{-10}$ M and $10^{-9}$ M or between $10^{-11}$ M and $10^{-10}$ M.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular loop inhibits CD25 upregulation in T cells with a potency of $10^{-7}$ M or lower, preferably of $10^{-8}$ M or lower, more preferably of $10^{-9}$ M or lower, or even of $10^{-10}$ M or lower, or even of $10^{-11}$ M or lower, as measured in a T-cell activation assay with CCR7⁻CD45RA⁻ T cells stimulated with anti-CD3 antibody OKT3 (as described in the Examples 4.4 and 5.5).

In a cell activation assay with peripheral blood mononucleated cells (PBMCs) stimulated with anti-CD3 antibody OKT3 and anti-CD28 (as described in the Example 9), the polypeptides of the invention do not block IFNgamma production.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular does not block INFgamma production in a cell activation assay with peripheral blood mononucleated cells (PBMCs) stimulated with anti-CD3 antibody OKT3 and anti-CD28 antibody (as described in the Example 9).

Immunosuppressive effects of the polypeptides of the invention can further be evaluated in in vivo models, such as e.g. in rats, pigs and/or primates. Diabetes-prone Biobreeding Worchester rats have been used as a model for autoimmune diabetes (Beeton et al. Proc Natl Acad Sci USA. 103: 17414-9, 2006). A rat model for allergic contact dermatitis, an animal model for psoriasis, has been described by Azam et al. (J. Invest. Dermatol. 127: 1419-29, 2007). Immunodeficient mice reconstituted with human T cells have been used as animal model for T cell-mediated skin graft rejection (Ren et al. PLoS One 3:e4009, 2008). For example, in the rat model for allergic contact dermatitis as described in Example 12 and 13, the polypeptides of the invention (significantly) reduce the increase in ear thickness with at least about 0.085-0.102 mm and at least about 0.147-0.164 mm versus vehicle, respectively.

Accordingly, the present invention relates to an immunoglobulin and/or polypeptide that specifically binds to the EL1 extracellular loop of Kv1.3, and wherein the binding of said immunoglobulin and/or polypeptide to said EL1 extracellular loop reduces the increase in ear thickness with at least about 0.085-0.102 mm and at least about 0.147-0.164 mm versus vehicle in a rat model for allergic contact dermatitis as described in Example 12 and Example 13, respectively.

The immunoglobulins and/or polypeptides that specifically bind to the EL1 extracellular loop of Kv1.3 show more than 1000 fold, and even up to 10000 fold selectivity for modulating and/or inhibiting the activity of Kv1.3 over other related Kv ion channel family members. The selective inhibition by the immunoglobulin and/or polypeptide of the present invention can be determined e.g. by comparing the concentration of immunoglobulin and/or polypeptide needed for inhibiting the respective channel with the concentration of immunoglobulin and/or polypeptide needed for inhibiting Kv1.3. Ion channel family members include hERG, KCa3.1 (SK4), Kv4.3/KChIP2.2, Kv1.2, Kv1.4, Cav1.3/b3/a2d1, Kir2.1, KCa2.2, KCa2.3, Kv7.2/Kv7.3, Kv1.1, Kv1.5, Kv3.4, Nav1.1, Nav1.2 and Nav1.6.

More in particular the immunoglobulins and/or polypeptides show a more than 1000 fold, and even up to 10000 fold selectivity over Kv1.5, Kv1.6, and hERG.

Monovalent Polypeptides of the Invention

The present invention provides stretches of amino acid residues (SEQ ID NOs: 181-210, SEQ ID NOs: 268-289, SEQ ID NOs: 541-555, SEQ ID NOs: 393-415 and SEQ ID NOs: 211-226, SEQ ID NOs: 290-309, SEQ ID NOs: 416-435; Table A-2) that are particularly suited for binding to the EL1 extracellular loop of Kv1.3. In particular, the invention provides stretches of amino acid residues which bind to the EL1 extracellular loop of human Kv1.3 and wherein the binding of said stretches to said EL1 extracellular loop inhibits the activity of Kv1.3 (as described above). These stretches of amino acid residues may be present in, and/or may be incorporated into, a polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against Kv1.3. These stretches of amino acid residues are also referred to herein as "CDR sequence(s) of the invention" (i.e., as "CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in a polypeptide of the invention, as long as these stretches of amino acid residues allow the polypeptide of the invention to bind to Kv1.3 with a certain affinity and potency (as defined herein). Thus, generally, the invention in its broadest sense provides monovalent polypeptides (also referred to herein as "monovalent polypeptide(s) of the invention") that are capable of binding to Kv1.3 with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to Kv1.3. It should however also be noted that the presence of only one such CDR sequence in a monovalent polypeptide of the invention may by itself already be sufficient to provide the monovalent polypeptide of the invention the capacity of binding to Kv1.3; reference is for example again made to the so-called "Expedite fragments" described in WO 03/050531.

In a specific, but non-limiting aspect, the monovalent polypeptide of the invention, may comprise at least one stretch of amino acid residues that is chosen from the group consisting of:
  i) CDR1 sequences:
  a) SEQ ID NOs: 181-210; or
  b) amino acid sequences that have 4, 3, 2, or 1 amino acid(s) difference with the amino acid sequence of SEQ ID NO: 182;
  and/or
  ii) CDR2 sequences:
  c) SEQ ID NOs: 268-289 and SEQ ID NOs: 541-555; or
  d) amino acid sequences that have 4, 3, 2, or 1 amino acid(s) difference with the amino acid sequence of SEQ ID NO: 269;
  and/or
  iii) CDR3 sequences:
  e) SEQ ID NOs: 393-415; or
  f) amino acid sequences that have 3, 2, or 1 amino acid(s) difference with the amino acid sequence of SEQ ID NO: 397.

In a further aspect, the monovalent polypeptide of the invention, may comprise at least one stretch of amino acid residues that is chosen from the group consisting of:
  i) CDR1 sequences:
  a) SEQ ID NOs: 181-210; or
  b) amino acid sequences that have 4, 3, 2, or 1 amino acid(s) difference with the amino acid sequence of SEQ ID NO: 182, wherein
    at position 1 the G has been changed into L, or R;
    at position 2 the L has been changed into F, P, or I;
    at position 3 the L has been changed into P, or F;
    at position 4 the F has been changed into S, L, or I;
    at position 5 the S has been changed into I, or R;
    at position 6 the R has been changed into C, A, P, V, or L;
    at position 7 the N has been changed into H, P, I, M, Y, T or D:
    at position 8 the S has been changed into T, R, or I;
    at position 9 the A has been changed into V or T; and/or
    at position 10 the G has been changed into S, R, or V;
  and/or
  ii) CDR2 sequences:
  c) SEQ ID NOs: 268-289 and SEQ ID NOs: 541-555; or
  d) amino acid sequences that have 4, 3, 2, or 1 amino acid(s) difference with the amino acid sequence of SEQ ID NO: 269, wherein
    at position 1 the R has been changed into G, or C;
    at position 2 the I has been changed into V, T, S or L;
    at position 3 the R has been changed into G, or L;
    at position 4 the M has been changed into S, R, A, E, F, G, H, K, L, P, Q, V, W, Y, I, or T;
    at position 5 the G has been changed into V, S, or T;
    at position 7 the S has been changed into G, C, D, or E; and/or
    at position 8 the I has been changed into T, M, or R;
  and/or
  iii) CDR3 sequences:
  e) SEQ ID NOs: 393-415; or
  f) amino acid sequences that have 3, 2, or 1 amino acid(s) difference with the amino acid sequence of SEQ ID NO: 397, wherein
    at position 1 the W has been changed into G;
    at position 3 the E has been changed into T, K, G, A, or I;
    at position 4 the G has been changed into E, or D;
    at position 5 the F has been changed into A, L, V, Y, T, or 5;
    at position 6 the Y has been changed into F, or D:
    at position 7 the E has been changed into G, or K;
    at position 8 the Y has been changed into S or H; and/or
    at position 9 the W has been changed into S, G or C.

In a further aspect, the monovalent polypeptide of the invention, may comprise at least one stretch of amino acid residues that is chosen from the group consisting of:
  i) CDR1 sequences:
  a) SEQ ID NOs: 181-185; or
  b) amino acid sequences that have 2, or 1 amino acid(s) difference with the amino acid sequence of SEQ ID NO: 182, wherein
    at position 6 the R has been changed into A, or V; and/or
    at position 9 the A has been changed into V;
  and/or
  ii) CDR2 sequences:
  c) SEQ ID NOs: 268-271, 541 and 549; or
  d) amino acid sequences that have 4, 3, 2, or 1 amino acid(s) difference with the amino acid sequence of SEQ ID NO: 269, wherein
    at position 2 the I has been changed into L;
    at position 4 the M has been changed into S, Q, A or T;
    at position 5 the G has been changed into S or T; and/or
    at position 8 the I has been changed into T;
  and/or
  iii) CDR3 sequences:
  e) SEQ ID NOs: 393-398; or
  f) amino acid sequences that have 3, 2, or 1 amino acid(s) difference with the amino acid sequence of SEQ ID NO: 397, wherein
    at position 3 the E has been changed into T or I;
    at position 4 the G has been changed into E;
    at position 5 the F has been changed into A; and/or
    at position 8 the Y has been changed into H.

In a further aspect, the monovalent polypeptide of the invention, may comprise at least one stretch of amino acid residues that is chosen from the group consisting of:
  i) CDR1 sequences:
  a) SEQ ID NOs: 211-226; or
  b) amino acid sequences that have 3, 2, or 1 amino acid(s) difference with the amino acid sequence of SEQ ID NO: 214;

and/or ii) CDR2 sequences:
c) SEQ ID NOs: 290-309; or
d) amino acid sequences that have 4, 3, 2, or 1 amino acid(s) difference with the amino acid sequence of SEQ ID NO: 303;

and/or iii) CDR3 sequences:
e) SEQ ID NOs: 416-435; or
f) amino acid sequences that have 3, 2, or 1 amino acid(s) difference with the amino acid sequence of SEQ ID NO: 422.

In a further aspect, the monovalent polypeptide of the invention, may comprise at least one stretch of amino acid residues that is chosen from the group consisting of:

i) CDR1 sequences:
a) SEQ ID NOs: 211-226; or
b) amino acid sequences that have 3, 2, or 1 amino acid(s) difference with the amino acid sequence of SEQ ID NO: 214, wherein
  at position 1 the G has been changed into R, A, V, S, or K;
  at position 3 the T has been changed into N;
  at position 4 the F has been changed into L;
  at position 6 the N has been changed into S;
  at position 7 the F has been changed into Y;
  at position 8 the G has been changed into A; and/or
  at position 9 the M has been changed into V;

and/or ii) CDR2 sequences:
c) SEQ ID NOs: 290-309; or
d) amino acid sequences that have 4, 3, 2, or 1 amino acid(s) difference with the amino acid sequence of SEQ ID NO: 303, wherein
  at position 1 the A has been changed into T;
  at position 2 the I has been changed into V;
  at position 5 the T has been changed into S, or A;
  at position 6 the G has been changed into N, or A;
  at position 7 the G has been changed into S, or R;
  at position 8 the H has been changed into R, or Y;
  at position 9 the T has been changed into I, or K; and/or
  at position 10 the Y has been changed into F;

and/or iii) CDR3 sequences:
e) SEQ ID NOs: 416-435; or
f) amino acid sequences that have 3, 2, or 1 amino acid(s) difference with the amino acid sequence of SEQ ID NO: 422, wherein
  at position 4 the F has been changed into Y, or 5;
  at position 5 the G has been changed into D;
  at position 6 the D has been changed into G;
  at position 7 the G has been changed into D;
  at position 8 the T has been changed into A;
  at position 9 the Y has been changed into 5;
  at position 10 the Y has been changed into F;
  at position 12 the Q has been changed into E;
  at position 14 the A has been changed into N, T, I, or R;
  at position 17 the D has been changed into N, or G; and/or
  at position 18 the F has been changed into L.

In particular, a monovalent polypeptide of the invention may be a monovalent polypeptide that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the monovalent polypeptide of the invention comprises more than one, such as two or more stretches of amino acid residues chosen from the group consisting of the CDR1 sequences of the invention, the CDR2 sequences of the invention and/or the CDR3 sequences of the invention. Preferably, the monovalent polypeptide of the invention comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the monovalent polypeptides of the invention are listed in Table A-2.

It should be further noted that the invention is not limited as to the origin of the monovalent polypeptide of the invention (or of the nucleic acid of the invention used to express it), nor as to the way that the monovalent polypeptide or nucleic acid of the invention is (or has been) generated or obtained. Thus, the monovalent polypeptides of the invention may be naturally occurring monovalent polypeptides (from any suitable species) or synthetic or semi-synthetic monovalent polypeptides.

Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In said monovalent polypeptides of the invention, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's.

According to a preferred, but non-limiting embodiment, the monovalent polypeptides of the invention comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. In such a monovalent polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-210; or
b) amino acid sequences that have 4, 3, 2, or 1 amino acid(s) difference with the amino acid sequence of SEQ ID NO: 182;
and/or
ii) CDR2 is chosen from the group consisting of:
c) SEQ ID NOs: 268-289 and SEQ ID NOs: 541-555; or
d) amino acid sequences that have 4, 3, 2, or 1 amino acid(s) difference with the amino acid sequence of SEQ ID NO: 269;
and/or
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397.

In particular, according to this preferred but non-limiting aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-210; or
b) amino acid sequences that have 4, 3, 2, or 1 amino acid(s) difference with the amino acid sequence of SEQ ID NO: 182;
and
ii) CDR2 is chosen from the group consisting of:
c) SEQ ID NOs: 268-289 and SEQ ID NOs: 541-555; or
d) amino acid sequences that have 4, 3, 2, or 1 amino acid(s) difference with the amino acid sequence of SEQ ID NO: 269;
and
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397.

In a further aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-210; or
b) amino acid sequences that have 4, 3, 2, or 1 amino acid(s) difference with the amino acid sequence of SEQ ID NO: 182, wherein
at position 1 the G has been changed into L, or R;
at position 2 the L has been changed into F, P, or I;
at position 3 the L has been changed into P, or F;
at position 4 the F has been changed into S, L, or I;
at position 5 the S has been changed into I, or R;
at position 6 the R has been changed into C, A, P, V, or L;
at position 7 the N has been changed into H, P, I, M, Y, T or D:
at position 8 the S has been changed into T, R, or I;
at position 9 the A has been changed into V or T; and/or
at position 10 the G has been changed into S, R, or V;
and/or
ii) CDR2 is chosen from the group consisting of:
c) SEQ ID NOs: 268-289 and SEQ ID NOs: 541-555; or
d) amino acid sequences that have 4, 3, 2, or 1 amino acid(s) difference with the amino acid sequence of SEQ ID NO: 269, wherein
at position 1 the R has been changed into G, or C;
at position 2 the I has been changed into V, T, S or L;
at position 3 the R has been changed into G, or L;
at position 4 the M has been changed into S, R, A, E, F, G, H, K, L, P, Q, V, W, Y, I, or T;
at position 5 the G has been changed into V, S, or T;
at position 7 the S has been changed into G, C, D, or E; and/or
at position 8 the I has been changed into T, M, or R;
and/or
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397, wherein
at position 1 the W has been changed into G;
at position 3 the E has been changed into T, K, G, A, or I;
at position 4 the G has been changed into E, or D;
at position 5 the F has been changed into A, L, V, Y, T, or 5;
at position 6 the Y has been changed into F, or D:
at position 7 the E has been changed into G, or K;
at position 8 the Y has been changed into S or H; and/or
at position 9 the W has been changed into S, G or C.

In particular, according to this preferred but non-limiting aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-210; or
b) amino acid sequences that have 4, 3, 2, or 1 amino acid(s) difference with the amino acid sequence of SEQ ID NO: 182, wherein
at position 1 the G has been changed into L, or R;
at position 2 the L has been changed into F, P, or I;
at position 3 the L has been changed into P, or F;
at position 4 the F has been changed into S, L, or I;
at position 5 the S has been changed into I, or R;
at position 6 the R has been changed into C, A, P, V, or L;
at position 7 the N has been changed into H, P, I, M, Y, T or D:
at position 8 the S has been changed into T, R, or I;
at position 9 the A has been changed into V or T; and/or
at position 10 the G has been changed into S, R, or V;

and
ii) CDR2 is chosen from the group consisting of:
c) SEQ ID NOs: 268-289 and SEQ ID NOs: 541-555; or
d) amino acid sequences that have 4, 3, 2, or 1 amino acid(s) difference with the amino acid sequence of SEQ ID NO: 269, wherein
at position 1 the R has been changed into G, or C;
at position 2 the I has been changed into V, T, S or L;
at position 3 the R has been changed into G, or L;
at position 4 the M has been changed into S, R, A, E, F, G, H, K, L, P, Q, V, W, Y, I, or T;
at position 5 the G has been changed into V, S, or T;
at position 7 the S has been changed into G, C, D, or E; and/or
at position 8 the I has been changed into T, M, or R;
and
iii) CDR3 is chosen from the group consisting of:
e) SEQ ID NOs: 393-415; or
f) amino acid sequences that have 3, 2, or 1 amino acid(s) difference with the amino acid sequence of SEQ ID NO: 397, wherein
at position 1 the W has been changed into G;
at position 3 the E has been changed into T, K, G, A, or I;
at position 4 the G has been changed into E, or D;
at position 5 the F has been changed into A, L, V, Y, T, or 5;
at position 6 the Y has been changed into F, or D:
at position 7 the E has been changed into G, or K;
at position 8 the Y has been changed into S or H; and/or
at position 9 the W has been changed into S, G or C.

In a further aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-185; or
b) amino acid sequences that have 2, or 1 amino acid(s) difference with the amino acid sequence of SEQ ID NO: 182, wherein
at position 6 the R has been changed into A, or V; and/or
at position 9 the A has been changed into V;
and/or
ii) CDR2 is chosen from the group consisting of:
c) SEQ ID NOs: 268-271, 541 and 549; or
d) amino acid sequences that have 4, 3, 2, or 1 amino acid(s) difference with the amino acid sequence of SEQ ID NO: 269, wherein
at position 2 the I has been changed into L;
at position 4 the M has been changed into S, Q, A or T;
at position 5 the G has been changed into S or T; and/or
at position 8 the I has been changed into T;
and/or
iii) CDR3 is chosen from the group consisting of:
e) SEQ ID NOs: 393-398; or
f) amino acid sequences that have 3, 2, or 1 amino acid(s) difference with the amino acid sequence of SEQ ID NO: 397, wherein
at position 3 the E has been changed into T or I;
at position 4 the G has been changed into E;
at position 5 the F has been changed into A; and/or
at position 8 the Y has been changed into H.

In particular, according to this preferred but non-limiting aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 181-185; or
b) amino acid sequences that have 2, or 1 amino acid(s) difference with the amino acid sequence of SEQ ID NO: 182, wherein
at position 6 the R has been changed into A, or V; and/or
at position 9 the A has been changed into V;
and
ii) CDR2 is chosen from the group consisting of:
c) SEQ ID NOs: 268-271, 541 and 549; or
d) amino acid sequences that have 4, 3, 2, or 1 amino acid(s) difference with the amino acid sequence of SEQ ID NO: 269, wherein
at position 2 the I has been changed into L;
at position 4 the M has been changed into S, Q, A or T;
at position 5 the G has been changed into S or T; and/or
at position 8 the I has been changed into T;
and
iii) CDR3 is chosen from the group consisting of:
e) SEQ ID NOs: 393-398; or
f) amino acid sequences that have 3, 2, or 1 amino acid(s) difference with the amino acid sequence of SEQ ID NO: 397, wherein
at position 3 the E has been changed into T or I;
at position 4 the G has been changed into E;
at position 5 the F has been changed into A; and/or
at position 8 the Y has been changed into H.

In a further aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214;
and/or
ii) CDR2 is chosen from the group consisting of:
c) SEQ ID NOs: 290-309; or
d) amino acid sequences that have 4, 3, 2, or 1 amino acid(s) difference with the amino acid sequence of SEQ ID NO: 303;
and/or
iii) CDR3 is chosen from the group consisting of:
e) SEQ ID NOs: 416-435; or
f) amino acid sequences that have 3, 2, or 1 amino acid(s) difference with the amino acid sequence of SEQ ID NO: 422.

In particular, according to this preferred but non-limiting aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214;
and
ii) CDR2 is chosen from the group consisting of:
c) SEQ ID NOs: 290-309; or d) amino acid sequences that have 4, 3, 2, or 1 amino acid(s) difference with the amino acid sequence of SEQ ID NO: 303;
and
iii) CDR3 is chosen from the group consisting of:
e) SEQ ID NOs: 416-435; or
f) amino acid sequences that have 3, 2, or 1 amino acid(s) difference with the amino acid sequence of SEQ ID NO: 422.

In a further aspect, a monovalent polypeptide of the present invention essentially consists of 4 framework regions (FR1 to FR4, respectively) and 3 complementarity determining regions (CDR1 to CDR3, respectively), in which:
i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214, wherein
at position 1 the G has been changed into R, A, V, S, or K;
at position 3 the T has been changed into N;
at position 4 the F has been changed into L;
at position 6 the N has been changed into 5;
at position 7 the F has been changed into Y:
at position 8 the G has been changed into A; and/or
at position 9 the M has been changed into V;
and/or
ii) CDR2 is chosen from the group consisting of:
c) SEQ ID NOs: 290-309; or
d) amino acid sequences that have 4, 3, 2, or 1 amino acid(s) difference with the amino acid sequence of SEQ ID NO: 303, wherein
at position 1 the A has been changed into T;
at position 2 the I has been changed into V;
at position 5 the T has been changed into S, or A;
at position 6 the G has been changed into N, or A;
at position 7 the G has been changed into S, or R;
at position 8 the H has been changed into R, or Y;
at position 9 the T has been changed into I, or K; and/or
at position 10 the Y has been changed into F;
and/or
iii) CDR3 is chosen from the group consisting of:
e) SEQ ID NOs: 416-435; or
f) amino acid sequences that have 3, 2, or 1 amino acid(s) difference with the amino acid sequence of SEQ ID NO: 422, wherein
at position 4 the F has been changed into Y, or S;
at position 5 the G has been changed into D;
at position 6 the D has been changed into G;
at position 7 the G has been changed into D;
at position 8 the T has been changed into A:
at position 9 the Y has been changed into 5;
at position 10 the Y has been changed into F;
at position 12 the Q has been changed into E;
at position 14 the A has been changed into N, T, I, or R;
at position 17 the D has been changed into N, or G; and/or
at position 18 the F has been changed into L.

In particular, according to this preferred but non-limiting aspect, a monovalent polypeptide of the present invention essentially consists of 4 framework regions (FR1 to FR4, respectively) and 3 complementarity determining regions (CDR1 to CDR3, respectively), in which:

i) CDR1 is chosen from the group consisting of:
a) SEQ ID NOs: 211-226; or
b) amino acid sequences that have 3, 2, or 1 amino acid(s) difference with the amino acid sequence of SEQ ID NO: 214, wherein
at position 1 the G has been changed into R, A, V, S, or K;
at position 3 the T has been changed into N;
at position 4 the F has been changed into L;
at position 6 the N has been changed into 5;
at position 7 the F has been changed into Y:
at position 8 the G has been changed into A; and/or
at position 9 the M has been changed into V;
and
ii) CDR2 is chosen from the group consisting of:
c) SEQ ID NOs: 290-309; or
d) amino acid sequences that have 4, 3, 2, or 1 amino acid(s) difference with the amino acid sequence of SEQ ID NO: 303, wherein
at position 1 the A has been changed into T;
at position 2 the I has been changed into V;
at position 5 the T has been changed into S, or A;
at position 6 the G has been changed into N, or A;
at position 7 the G has been changed into S, or R;
at position 8 the H has been changed into R, or Y;
at position 9 the T has been changed into I, or K; and/or
at position 10 the Y has been changed into F;
and
iii) CDR3 is chosen from the group consisting of:
e) SEQ ID NOs: 416-435; or
f) amino acid sequences that have 3, 2, or 1 amino acid(s) difference with the amino acid sequence of SEQ ID NO: 422, wherein
at position 4 the F has been changed into Y, or 5;
at position 5 the G has been changed into D;
at position 6 the D has been changed into G;
at position 7 the G has been changed into D;
at position 8 the T has been changed into A:
at position 9 the Y has been changed into 5;
at position 10 the Y has been changed into F;
at position 12 the Q has been changed into E;
at position 14 the A has been changed into N, T, I, or R;
at position 17 the D has been changed into N, or G; and/or
at position 18 the F has been changed into L.

In one specific aspect, the monovalent polypeptide of the invention is chosen from the group of amino acid sequences, wherein:
CDR1 is SEQ ID NO: 182, CDR2 is SEQ ID NO: 269, and CDR3 is SEQ ID NO: 397;
CDR1 is SEQ ID NO: 182, CDR2 is SEQ ID NO: 269, and CDR3 is SEQ ID NO: 394;
CDR1 is SEQ ID NO: 181, CDR2 is SEQ ID NO: 268, and CDR3 is SEQ ID NO: 393;
CDR1 is SEQ ID NO: 181, CDR2 is SEQ ID NO: 268, and CDR3 is SEQ ID NO: 395;
CDR1 is SEQ ID NO: 181, CDR2 is SEQ ID NO: 268, and CDR3 is SEQ ID NO: 396;
CDR1 is SEQ ID NO: 181, CDR2 is SEQ ID NO: 270, and CDR3 is SEQ ID NO: 393;
CDR1 is SEQ ID NO: 183, CDR2 is SEQ ID NO: 268, and CDR3 is SEQ ID NO: 393;
CDR1 is SEQ ID NO: 184, CDR2 is SEQ ID NO: 268, and CDR3 is SEQ ID NO: 393;
CDR1 is SEQ ID NO: 185, CDR2 is SEQ ID NO: 271, and CDR3 is SEQ ID NO: 398;
CDR1 is SEQ ID NO: 182, CDR2 is SEQ ID NO: 541, and CDR3 is SEQ ID NO: 394;

CDR1 is SEQ ID NO: 182, CDR2 is SEQ ID NO: 541, and CDR3 is SEQ ID NO: 397;
CDR1 is SEQ ID NO: 182, CDR2 is SEQ ID NO: 549, and CDR3 is SEQ ID NO: 394; and
CDR1 is SEQ ID NO: 182, CDR2 is SEQ ID NO: 549, and CDR3 is SEQ ID NO: 397.

In a further aspect, the monovalent polypeptide of the invention is chosen from the group of amino acid sequences, wherein:
CDR1 is SEQ ID NO: 214, CDR2 is SEQ ID NO: 303, and CDR3 is SEQ ID NO: 422;
CDR1 is SEQ ID NO: 211, CDR2 is SEQ ID NO: 290, and CDR3 is SEQ ID NO: 416;
CDR1 is SEQ ID NO: 212, CDR2 is SEQ ID NO: 291, and CDR3 is SEQ ID NO: 417;
CDR1 is SEQ ID NO: 213, CDR2 is SEQ ID NO: 292, and CDR3 is SEQ ID NO: 418;
CDR1 is SEQ ID NO: 213, CDR2 is SEQ ID NO: 293, and CDR3 is SEQ ID NO: 418;
CDR1 is SEQ ID NO: 214, CDR2 is SEQ ID NO: 294, and CDR3 is SEQ ID NO: 418;
CDR1 is SEQ ID NO: 215, CDR2 is SEQ ID NO: 295, and CDR3 is SEQ ID NO: 417;
CDR1 is SEQ ID NO: 216, CDR2 is SEQ ID NO: 296, and CDR3 is SEQ ID NO: 419;
CDR1 is SEQ ID NO: 213, CDR2 is SEQ ID NO: 295, and CDR3 is SEQ ID NO: 418;
CDR1 is SEQ ID NO: 214, CDR2 is SEQ ID NO: 295, and CDR3 is SEQ ID NO: 418;
CDR1 is SEQ ID NO: 211, CDR2 is SEQ ID NO: 297, and CDR3 is SEQ ID NO: 420;
CDR1 is SEQ ID NO: 215, CDR2 is SEQ ID NO: 298, and CDR3 is SEQ ID NO: 421;
CDR1 is SEQ ID NO: 217, CDR2 is SEQ ID NO: 299, and CDR3 is SEQ ID NO: 422;
CDR1 is SEQ ID NO: 211, CDR2 is SEQ ID NO: 298, and CDR3 is SEQ ID NO: 418;
CDR1 is SEQ ID NO: 212, CDR2 is SEQ ID NO: 291, and CDR3 is SEQ ID NO: 423;
CDR1 is SEQ ID NO: 212, CDR2 is SEQ ID NO: 300, and CDR3 is SEQ ID NO: 418;
CDR1 is SEQ ID NO: 214, CDR2 is SEQ ID NO: 301, and CDR3 is SEQ ID NO: 418;
CDR1 is SEQ ID NO: 215, CDR2 is SEQ ID NO: 300, and CDR3 is SEQ ID NO: 424;
CDR1 is SEQ ID NO: 211, CDR2 is SEQ ID NO: 302, and CDR3 is SEQ ID NO: 416;
CDR1 is SEQ ID NO: 218, CDR2 is SEQ ID NO: 291, and CDR3 is SEQ ID NO: 425;
CDR1 is SEQ ID NO: 218, CDR2 is SEQ ID NO: 291, and CDR3 is SEQ ID NO: 426;
CDR1 is SEQ ID NO: 213, CDR2 is SEQ ID NO: 303, and CDR3 is SEQ ID NO: 422;
CDR1 is SEQ ID NO: 218, CDR2 is SEQ ID NO: 291, and CDR3 is SEQ ID NO: 417;
CDR1 is SEQ ID NO: 219, CDR2 is SEQ ID NO: 296, and CDR3 is SEQ ID NO: 427;
CDR1 is SEQ ID NO: 213, CDR2 is SEQ ID NO: 304, and CDR3 is SEQ ID NO: 428;
CDR1 is SEQ ID NO: 220, CDR2 is SEQ ID NO: 305, and CDR3 is SEQ ID NO: 416;
CDR1 is SEQ ID NO: 213, CDR2 is SEQ ID NO: 303, and CDR3 is SEQ ID NO: 421;
CDR1 is SEQ ID NO: 220, CDR2 is SEQ ID NO: 296, and CDR3 is SEQ ID NO: 429;
CDR1 is SEQ ID NO: 221, CDR2 is SEQ ID NO: 305, and CDR3 is SEQ ID NO: 416;
CDR1 is SEQ ID NO: 222, CDR2 is SEQ ID NO: 305, and CDR3 is SEQ ID NO: 430;
CDR1 is SEQ ID NO: 213, CDR2 is SEQ ID NO: 306, and CDR3 is SEQ ID NO: 418;
CDR1 is SEQ ID NO: 223, CDR2 is SEQ ID NO: 303, and CDR3 is SEQ ID NO: 422;
CDR1 is SEQ ID NO: 215, CDR2 is SEQ ID NO: 298 and CDR3 is SEQ ID NO: 431;
CDR1 is SEQ ID NO: 220, CDR2 is SEQ ID NO: 296, and CDR3 is SEQ ID NO: 432;
CDR1 is SEQ ID NO: 224, CDR2 is SEQ ID NO: 300, and CDR3 is SEQ ID NO: 418;
CDR1 is SEQ ID NO: 220, CDR2 is SEQ ID NO: 307, and CDR3 is SEQ ID NO: 433;
CDR1 is SEQ ID NO: 225, CDR2 is SEQ ID NO: 300, and CDR3 is SEQ ID NO: 418;
CDR1 is SEQ ID NO: 226, CDR2 is SEQ ID NO: 308, and CDR3 is SEQ ID NO: 434;
CDR1 is SEQ ID NO: 212, CDR2 is SEQ ID NO: 295, and CDR3 is SEQ ID NO: 417;
CDR1 is SEQ ID NO: 213, CDR2 is SEQ ID NO: 301, and CDR3 is SEQ ID NO: 426;
CDR1 is SEQ ID NO: 212, CDR2 is SEQ ID NO: 305, and CDR3 is SEQ ID NO: 417;
CDR1 is SEQ ID NO: 217, CDR2 is SEQ ID NO: 305, and CDR3 is SEQ ID NO: 422;
CDR1 is SEQ ID NO: 215, CDR2 is SEQ ID NO: 298, and CDR3 is SEQ ID NO: 435; and
CDR1 is SEQ ID NO: 213, CDR2 is SEQ ID NO: 309, and CDR3 is SEQ ID NO: 418.

Representative polypeptides of the present invention having the CDRs described above are shown in Table A-2.

In one aspect, the monovalent polypeptide has the same number of amino acids within its sequence compared to any one of SEQ ID NOs: 1-64, 495, 498-513 and 523-540. In another aspect, the monovalent polypeptide has an amino acid sequence between position 8 and position 106 (according to Kabat numbering) that has 89% or more sequence identity compared to any one of SEQ ID NOs: 1-64, 495, 498-513 and 523-540. Preferably, the monovalent polypeptide has the same number of amino acids within its sequence compared to any one of SEQ ID NOs: 1-64, 495, 498-513 and 523-540 and the monovalent polypeptide has an amino acid sequence between position 8 and position 106 (according to Kabat numbering) that has 89% or more sequence identity compared to any one of SEQ ID NOs: 1-64, 495, 498-513 and 523-540. In another preferred aspect, the monovalent polypeptide belongs to family 12, such as e.g. a monovalent polypeptide selected from any one of SEQ ID NOs: 1-64, 495, 498-513 and 523-540.

In one aspect, the monovalent polypeptide has the same number of amino acids within its sequence compared to any one of SEQ ID NOs: 65-123. In another aspect, the monovalent polypeptide has an amino acid sequence between position 8 and position 106 (according to Kabat numbering) that has 89% or more sequence identity compared to any one of SEQ ID NOs: 65-123. Preferably, the monovalent polypeptide has the same number of amino acids within its sequence compared to any one of SEQ ID NOs: 65-123 and the monovalent polypeptide has an amino acid sequence between position 8 and position 106 (according to Kabat numbering) that has 89% or more sequence identity compared to any one of SEQ ID NOs: 65-123. In another preferred aspect, the monovalent polypeptide belongs to family 1, such as e.g. a monovalent polypeptide selected from any one of SEQ ID NOs: 65-123. Monovalent polypeptides comprising one or more of the above specified stretches of amino acid residues may modulate and/or partially or fully inhibit the function of Kv1.3. More particularly, these polypeptides of the present invention may depolarize the T cell membrane and/or reduce or even totally inhibit the efflux of potassium ions from T-cells. As such, these polypeptides of the invention may inhibit proliferation of T-cells and/or suppress activation of T-cells resulting of the inhibition of certain immune responses in vivo.

In one particular aspect, the polypeptides of the invention indirectly modulate the function of Kv1.3, i.e. as an allosteric modulator (as defined herein). More specifically, the polypeptides of the invention may induce a conformational change within the structure of the Kv1.3 pore.

Binding of the polypeptides of the invention to Kv1.3 can be measured in binding assays that preserve the conformation of the Kv1.3 target. Typical assays include (without being limiting) assays in which Kv1.3 is exposed on a cell surface (such as e.g. CHO cells, HEK cells, HeLa cells, Chinese Hamster Lung (CHL) cells, Caki cells, etc.). A preferred assay for measuring binding of the polypeptides of the invention to Kv1.3 is a FACS assay, such as e.g. the FACS assay as described in the examples, wherein binding of the polypeptides of the invention to Kv1.3 expressed on CHO-K1 cells and/or HEK293H cells is determined. Some preferred EC50 values for binding of the polypeptides of the invention to Kv1.3 will become clear from the further description and examples herein.

In such FACS binding assay, the monovalent polypeptides of the present invention may have EC50 values in binding human Kv1.3 of $10^{-8}$ M or lower, more preferably of $10^{-9}$ M or lower, or even of $10^{-10}$ M or lower. For example, in such FACS binding assay, the monovalent polypeptides of the present invention may have EC50 values in binding human Kv1.3 between $10^{-9}$ M and $10^{-8}$ M.

In such FACS binding assay, the monovalent polypeptides of the present invention may have EC50 values in binding cyno Kv1.3 of $10^{-7}$ M or lower, preferably of $10^{-8}$ M or lower, more preferably of $10^{-9}$ M or lower, or even of $10^{-10}$ M or lower. For example, in such FACS binding assay, the monovalent polypeptides of the present invention may have EC50 values in binding cyno Kv1.3 between $10^{-10}$ M and $10^{-7}$ M, such as between $10^{-9}$ M and $10^{-8}$ M.

In such FACS binding assay, the monovalent polypeptides of the present invention may have EC50 values in binding rat Kv1.3 of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such FACS binding assay, the monovalent polypeptides of the present invention may have EC50 values in binding rat Kv1.3 between $10^{-10}$ M and $10^{-6}$ M, such as between $10^{-7}$ M and $10^{-6}$ M.

Modulation and/or inhibition of the efflux of potassium ions can be determined by a variety of ion channel screening technologies including (without being limiting) ion flux assays, radioligand binding studies, fluorescent dye assays, and electrophysiology, such as voltage clamp, and in particular, the patch-clamp. An overview of different ion channel technologies is provided by e.g. Dabrowski et al. (CNS & Neurological Disorders Drug Targets 7: 122, 2008), Lü and An (Comb. Chem. High Throughput Screen. 11:185-94, 2008), and Zheng et al. (Assay Drug Dev. Technol. 2: 543-52, 2004).

Voltage clamp (Huxley, Trends Neurosci. 25: 553-8, 2002) is used to measure the ion currents through the membrane of excitable cells. The patch-clamp variant of this technique (Hamill et al. Pflügers Archiv European Journal of Physiology 391: 85-100, 1981) allows the study of single or multiple ion channels in cells.

Higher throughput electrophysiological platforms have been developed ranging from medium throughput systems to higher throughput platforms (see e.g. Southan and Clark, Methods Mol. Biol. 565: 187-208, 2009), including PatchXpress (Molecular Devices; Ghetti et al. Methods Mol. Biol. 403: 59-69, 2007), Qpatch and Qpatch HTX (Sophion; Mathes et al. Comb. Chem. High Throughput Screen. 12: 78-95, 2009; Korsgaard et al. Comb. Chem. High Throughput Screen. 12: 51-63, 2009), PatchLiner (Nanion; Farre et al. Comb. Chem. High Throughput Screen 12: 24-37, 2009), IonWorks® HT, IonWorks® Quattro and IonFlux™ Systems (Molecular Devices; Jow et al. J Biomol. Screen. 12: 1059-67, 2007; Dale et al. Mol. Biosyst. 3: 714-22, 2007). Some preferred IC50 values for the polypeptides of the invention in these assays will become clear from the further description and examples herein.

On the IonFlux™ (Molecular Devices) using Kv1.3-expressing HEK293H cells, for example, the monovalent polypeptides of the invention have IC50 values of $10^{-7}$ M or lower, preferably of $10^{-8}$ M or lower, more preferably of $10^{-9}$ M or lower, or even of $10^{-10}$ M or lower. For example, in this automated Patch Clamp assay, the monovalent polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-9}$ M and $10^{-7}$ M.

On the IonWorks® Quattro (Molecular Devices) using Kv1.3-expressing Chinese Hamster Lung (CHL) cells, for example, the monovalent polypeptides of the invention have IC50 values of $10^{-7}$ M or lower, preferably of $10^{-8}$ M or lower, more preferably of $10^{-9}$ M or lower, or even of $10^{-10}$ M or lower. For example, on this high-throughput planar perforated patch clamp, the monovalent polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-8}$ M and $10^{-7}$ M. More in particular, the monovalent polypeptides that belong to family 12 may have an IC50 value on the IonWorks® Quattro (Molecular Devices) between $10^{-8}$ M and $10^{-7}$ M.

Modulation and/or inhibition of Kv1.3 by the polypeptides of the invention can also be assessed in radioligand binding studies. Binding studies with tritiated correolide (e.g. C20-29-[3H]dihydrocorreolide (diTC)) to a single class of sites in membranes prepared from CHO/Kv1.3 cells has been described by Felix et al. (Biochemistry 38: 4922-30, 1999). Knaus et al. (Biochemistry 34: 13627-13634, 1995) describes, for example, the binding of monoiodotyrosinyl margatoxin (125I-margatoxin) to heterotetrameric Kv channels in rat brain synaptic plasma membranes. Binding studies of 125I-margatoxin to plasma membranes prepared from either Jurkat cells, a human leukemic T cell line, or CHO cells stably transfected with the Shaker-type voltage-gated K+ channel, K(V)1.3 have been described by Helms et al. (Biochemistry. 36: 3737-44, 1997). Some preferred IC50 values for blocking 125I-margatoxin binding to Kv1.3 by the polypeptides of the invention will become clear from the further description and examples herein.

The monovalent polypeptides of the present invention may block binding of 125I-margatoxin to cynomolgus Kv1.3 overexpressing CHO cells with IC50 values of $10^{-8}$ M or lower, more preferably of $10^{-9}$ M or lower, or even of $10^{-10}$ M or lower. For example, in such 125I-margatoxin blocking assay, the monovalent polypeptides of the present invention may have IC50 values between $10^{-10}$ M and $10^{-8}$ M, such as e.g. between $10^{-9}$ M and $10^{-8}$ M.

Other flux assays for measuring modulation and/or inhibition of Kv1.3 by the polypeptides of the invention include (without being limiting) the high-throughput efflux assay with radiolabelled[86] Rubidium described by Hanson et al. (Br. J. Pharmacol. 126: 1707-16, 1999), the nonradioactive rubidium (Rb(+)) efflux assay described by Wang et al. (Assay Drug Dev. Technol. 2: 525-34, 2004) and a fluorescence-based thallium flux assay (Weaver et al. J. Biomol. Screen. 9: 671-7, 2004).

Inhibition of T-cell activation and/or proliferation by the polypeptides of the present invention can be measured in T-cell activation assays. Without being limiting, T-cell activation assays have been described by Nguyten et al. (Molecular Pharmacology 50: 1672-1679, 1996) and Hanson et al. (Br. J. Pharmacol. 126: 1707-1716, 1999). Some preferred IC50 values for inhibition of T-cell activation and/or proliferation by the monovalent polypeptides of the invention will become clear from the further description and examples herein.

In a T-cell activation assay with CCR7⁻CD45RA⁻ T cells stimulated with anti-CD3 antibody OKT3 (as described in the Examples 4.4 and 5.5), the monovalent polypeptides of the invention have IC50 values for inhibiting IFNgamma production of $10^{-7}$ M or lower, preferably of $10^{-8}$ M or lower, more preferably of $10^{-9}$ M or lower, $10^{-10}$ M or lower, or even of $10^{-11}$ M or lower. For example, in this T-cell activation assay, the monovalent polypeptides of the present invention inhibit IFNgamma production with IC50 values between $10^{-11}$ M and $10^{-7}$ M, between $10^{-11}$ M and $10^{-8}$ M, between $10^{-11}$ M and $10^{-9}$ M, such as e.g. between $10^{-8}$ M and $10^{-7}$ M. More in particular, the monovalent polypeptides that belong to family 12 may inhibit IFNgamma production with IC50 values between $10^{-8}$ M and $10^{-7}$ M.

In this T-cell activation assay with CCR7⁻CD45RA⁻ T cells stimulated with anti-CD3 antibody OKT3 (as described in the Examples 4.4 and 5.5), the monovalent polypeptides of the invention have IC50 values for inhibiting CD25 upregulation of $10^{-7}$ M or lower, preferably of $10^{-8}$ M or lower, more preferably of $10^{-9}$ M or lower, $10^{-10}$ M or lower, or even of $10^{-11}$ M or lower. For example, in this T-cell activation assay, the monovalent polypeptides of the present invention inhibit CD25 upregulation with IC50 values between $10^{-11}$ M and $10^{-7}$ M, between $10^{-11}$ M and $10^{-8}$ M, between $10^{-11}$ M and $10^{-9}$ M, such as e.g. between $10^{-8}$ M and $10^{-7}$ M. More in particular, the monovalent polypeptides that belong to family 12 may inhibit CD25 upregulation with IC50 values between $10^{-8}$ M and $10^{-7}$ M.

The invention also relates to a monovalent polypeptide which has at least 80% amino acid identity (or sequence identity as defined herein), preferably at least 85% amino acid identity, more preferably at least 90% amino acid identity, such as 95% amino acid identity or more or even (essentially) 100% amino acid identity with at least one of the amino acid sequences of SEQ ID NOs: 1-123, 495, 498-513 and 523-540.

In one specific, but non-limiting aspect, the monovalent polypeptide of the invention may be a monovalent polypeptide that comprises an immunoglobulin fold or a monovalent polypeptide that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding Kv1.3. Accordingly, in a preferred aspect the monovalent polypeptide of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the monovalent polypeptide of the invention is an immunoglobulin single variable domain such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

In particular, the framework sequences present in the monovalent polypeptides of the invention may contain one or more of Hallmark residues (as defined in WO 08/020079 (Tables A-3 to A-8)), such that the monovalent polypeptide of the invention is a Nanobody. Some preferred, but non-limiting examples of (suitable combinations of) such framework sequences will become clear from the further disclosure herein (see e.g., Table A-2). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, a Nanobody can be an immunoglobulin and/or polypeptide with the (general) structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and which:

i) have at least 80% amino acid identity with at least one of the amino acid sequences of SEQ ID NOs: 1-123 or 495 (see Table A-1), in which for the purposes of determining the degree of amino acid identity, the amino acid residues that form the CDR sequences are disregarded. In this respect, reference is also made to Table A-2, which lists the framework 1 sequences (SEQ ID NOs: 124-180), framework 2 sequences (SEQ ID NOs: 227-267), framework 3 sequences (SEQ ID NOs: 310-392) and framework 4 sequences (SEQ ID NOs: 436-450) of the immunoglobulin single variable domains of SEQ ID NOs: 1-123 or 495 (see Table A-1); or ii) combinations of framework sequences as depicted in Table A-2;

and in which:

iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The present invention also provides a number of sequence optimized immunoglobulin single variable domains.

In particular, sequence optimized immunoglobulin single variable domains may be amino acid sequences that are as generally defined for immunoglobulin single variable domains in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domains may be partially humanized or fully humanized.

The present invention also provides a number of sequence optimized immunoglobulin single variable domains that may show improved expression and/or increased stability upon storage during stability studies. The amino acid sequences of the present invention may show reduced pyroglutamate post-translational modification of the N-terminus and hence have increased product stability. In addition, the amino acid sequences of the present invention may show other improved properties such as e.g. less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for Kv1.3, improved affinity and/or improved avidity for Kv1.3 and/or improved efficacy and/or potency for blocking Kv1.3, compared to their corresponding parental amino acid sequences.

Some particularly preferred sequence optimized immunoglobulin single variable domains of the invention are sequence optimized variants of the immunoglobulin single variable domains of SEQ ID NOs: 1-123 or 495, of which the amino acid sequences of SEQ ID NOs: 498-513 or 523-540 are some especially preferred examples.

Thus, some other preferred immunoglobulin single variable domains of the invention are Nanobodies which can bind (as further defined herein) to Kv1.3 and which:

i) are a sequence optimized variant of one of the immunoglobulin single variable domains of SEQ ID NOs: 1-123 or 495; and/or ii) have at least 80% amino acid identity with at least one of the immunoglobulin single variable domains of SEQ ID NOs: 1-123 or 495 and/or at least one of the immunoglobulin single variable domains of SEQ ID NOs: 498-513 or 523-540 (see Table A-9), in which for the purposes of determining the degree of amino acid identity, the amino acid residues that form the CDR sequences are disregarded; In this respect, reference is also made to Table A-2, which lists the framework 1 sequences (SEQ ID NOs: 124-180 and SEQ ID NOs: 556 and 559), framework 2 sequences (SEQ ID NOs: 227-267), framework 3 sequences (SEQ ID NOs: 310-392 and SEQ ID NOs: 557-558) and framework 4 sequences (SEQ ID NOs: 436-450) of the immunoglobulin single variable domains of SEQ ID NOs: 1-123, 495, 498-513 or 523-540 (see Table A-1 and Table A-9); and/or iii) have combinations of framework sequences as depicted in Table A-2;

and in which:

iv) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The immunoglobulins (and in particular immunoglobulin single variable domains) of the invention may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the immunoglobulins (and in particular immunoglobulin single variable domains) of the invention may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the immunoglobulins of the invention contain the mutations according to one of (i) to (v) above (or a suitable combination thereof):

the amino acid residue at position 11 is preferably chosen from L, V or K (and is most preferably V); and the amino acid residue at position 14 is preferably suitably chosen from A or P; and the amino acid residue at position 41 is preferably suitably chosen from A or P; and the amino acid residue at position 89 is preferably suitably chosen from T, V or L; and the amino acid residue at position 108 is preferably suitably chosen from Q or L; and the amino acid residue at position 110 is preferably suitably chosen from T, K or Q; and the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the immunoglobulins of the invention may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I), for which reference is again made to said US provisional applications as well as to WO 12/175741. In particular, an immunoglobulin of the invention may contain such a C-terminal extension when it forms the C-terminal end of a protein, polypeptide or other compound or construct comprising the same (again, as further described in said US provisional applications as well as WO 12/175741).

Some specifically preferred, but non-limiting examples of immunoglobulins of the invention that contain such mutations and/or such a C-terminal extension are given in SEQ ID NOs: 496-497 and 514-540.

In a preferred aspect, the present invention provides an immunoglobulin or monovalent polypeptide that is selected from any of SEQ ID NOs: 1-123, 495, 498-513 and 523-540.

The present invention also relates to monovalent polypeptides and/or immunoglobulin single variable domains directed against Kv1.3, that cross-blocks the binding to Kv1.3 of at least one of the immunoglobulins with SEQ ID NOs: 1-123, 495, 498-513 and 523-540 and/or that are cross-blocked from binding to Kv1.3 by at least one of the immunoglobulins with SEQ ID NOs: 1-123, 495, 498-513 and 523-540.

The invention further relates to monovalent polypeptides and/or immunoglobulin single variable domains directed against Kv1.3 that bind the same epitope as is bound by the monovalent polypeptides of the present invention, more particularly by the monovalent polypeptides with SEQ ID NOs: 1-123, 495, 498-513 and 523-540.

In a particular aspect, the invention relates to monovalent polypeptides and/or immunoglobulin single variable domains directed against Kv1.3 that bind the same epitope as is bound by the monovalent polypeptides of the present invention that belong to family 12, more particularly by the monovalent polypeptides with SEQ ID NO: 1-64, 495, 498-513 and 523-540.

In another particular aspect, the invention relates to monovalent polypeptides and/or immunoglobulin single variable domains directed against Kv1.3 that bind the same epitope as is bound by the monovalent polypeptides of the present invention that belong to family 1, more particularly by the monovalent polypeptides with SEQ ID NO: 65-123.

Again, such monovalent polypeptides may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

These monovalent polypeptides of the invention, and in particular the immunoglobulins comprising the CDR sequences of the invention are particularly suited for use as building block or binding unit for the preparation of multivalent polypeptides.

Accordingly, the monovalent polypeptides of the invention that bind Kv1.3 can be in essentially isolated form (as defined herein), or they may form part of a protein or polypeptide, which may comprise or essentially consist of one or more monovalent polypeptides that bind Kv1.3 and which may optionally further comprise one or more further amino acid sequences (all optionally linked via one or more suitable linkers). The present invention also relates to a protein or polypeptide that comprises or essentially consists of one or more monovalent polypeptides of the invention (or suitable fragments thereof).

The one or more monovalent polypeptides of the invention are thus used as a binding unit or building block in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of one monovalent polypeptide of the invention. The present invention thus also relates to a polypeptide which is a multivalent polypeptide, such as e.g., a bivalent or trivalent polypeptide comprising or essentially consisting of two or more monovalent polypeptides of the invention (for multivalent and multispecific polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998).

Multivalent Polypeptides of the Invention

The invention further relates to a multivalent polypeptide (also referred to herein as a "multivalent polypeptide(s) of the invention") that comprises or (essentially) consists of at least one immunoglobulin single variable domain (or suitable fragments thereof) directed against Kv1.3, preferably human Kv1.3, and one additional immunoglobulin single variable domain.

In a preferred aspect, the multivalent polypeptide of the invention comprises or essentially consists of two or more immunoglobulin single variable domains directed against Kv1.3. The two or more immunoglobulin single variable domains may optionally be linked via one or more peptidic linkers.

In the multivalent polypeptide of the invention, the two or more immunoglobulin single variable domains or Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical immunoglobulin single variable domains or Nanobodies; (b) a first immunoglobulin single variable domain or Nanobody directed against a first antigenic determinant of a protein or antigen and a second immunoglobulin single variable domain or Nanobody directed against the same antigenic determinant of said protein or antigen which is different from the first immunoglobulin single variable domain or Nanobody; (c) a first immunoglobulin single variable domain or Nanobody directed against a first antigenic determinant of a protein or antigen and a second immunoglobulin single variable domain or Nanobody directed against another antigenic determinant of said protein or antigen; or (d) a first immunoglobulin single variable domain or Nanobody directed against a first protein or antigen and a second immunoglobulin single variable domain or Nanobody directed against a second protein or antigen (i.e. different from said first antigen). Similarly, a trivalent polypeptide of the invention may, for example and without being limited thereto, comprise (a) three identical immunoglobulin single variable domains or Nanobodies; (b) two identical immunoglobulin single variable domains or Nanobodies against a first antigenic determinant of an antigen and a third immunoglobulin single variable domain or Nanobody directed against a different antigenic determinant of the same antigen; (c) two identical immunoglobulin single variable domains or Nanobodies against a first antigenic determinant of an antigen and a third immunoglobulin single variable domain or Nanobody directed against a second antigen different from said first antigen; (d) a first immunoglobulin single variable domain or Nanobody directed against a first antigenic determinant of a first antigen, a second immunoglobulin single variable domain or Nanobody directed against a second antigenic determinant of said first antigen and a third immunoglobulin single variable domain or Nanobody directed against a second antigen different from said first antigen; or (e) a first immunoglobulin single variable domain or Nanobody directed against a first antigen, a second immunoglobulin single variable domain or Nanobody directed against a second antigen different from said first antigen, and a third immunoglobulin single variable domain or Nanobody directed against a third antigen different from said first and second antigen.

Polypeptides of the invention that contain at least two immunoglobulin single variable domains and/or Nanobodies, in which at least one immunoglobulin single variable domain or Nanobody is directed against a first antigen (i.e. against Kv1.3) and at least one immunoglobulin single variable domain or Nanobody is directed against a second antigen (i.e. different from Kv1.3), will also be referred to as "multispecific" polypeptides of the invention, and the immunoglobulin single variable domains or Nanobodies present in such polypeptides will also be referred to herein as being in a "multispecific format". Thus, for example, a "bispecific" polypeptide of the invention is a polypeptide that comprises at least one immunoglobulin single variable domain or Nanobody directed against a first antigen (i.e. Kv1.3) and at least one further immunoglobulin single variable domain or Nanobody directed against a second antigen (i.e. different from Kv1.3), whereas a "trispecific" polypeptide of the invention is a polypeptide that comprises at least one immunoglobulin single variable domain or Nanobody directed against a first antigen (i.e. Kv1.3), at least one further immunoglobulin single variable domain or Nanobody directed against a second antigen (i.e. different from Kv1.3) and at least one further immunoglobulin single variable domain or Nanobody directed against a third antigen (i.e. different from both Kv1.3, and the second antigen); etc.

Accordingly, in one aspect, in its simplest form, the multivalent polypeptide of the invention is a bivalent polypeptide of the invention comprising a first immunoglobulin single variable domain or Nanobody directed against Kv1.3, and an identical second immunoglobulin single variable domain or Nanobody directed against Kv1.3, wherein said first and second immunoglobulin single variable domain or Nanobody may optionally be linked via a linker sequence (as defined herein); in its simplest form a multivalent polypeptide of the invention may be a trivalent polypeptide of the invention, comprising a first immunoglobulin single variable domain or Nanobody directed against Kv1.3, an identical second immunoglobulin single variable domain or Nanobody directed against Kv1.3 and an identical third immunoglobulin single variable domain or Nanobody directed against Kv1.3, in which said first, second and third immunoglobulin single variable domain or Nanobody may optionally be linked via one or more, and in particular two, linker sequences.

In another aspect, the multivalent polypeptide of the invention may be a bispecific polypeptide of the invention, comprising a first immunoglobulin single variable domain or Nanobody directed against Kv1.3, and a second immunoglobulin single variable domain or Nanobody directed against a second antigen, in which said first and second immunoglobulin single variable domain or Nanobody may optionally be linked via a linker sequence (as defined herein); whereas a multivalent polypeptide of the invention may also be a trispecific polypeptide of the invention, comprising a first immunoglobulin single variable domain or Nanobody directed against Kv1.3, a second immunoglobulin single variable domain or Nanobody directed against a second antigen and a third immunoglobulin single variable domain or Nanobody directed against a third antigen, in which said first, second and third immunoglobulin single variable domain or Nanobody may optionally be linked via one or more, and in particular two, linker sequences.

In a preferred aspect, the polypeptide of the invention is a trivalent, bispecific polypeptide. A trivalent, bispecific polypeptide of the invention in its simplest form may be a trivalent polypeptide of the invention (as defined herein), comprising two identical immunoglobulin single variable domains or Nanobodies against Kv1.3 and a third immunoglobulin single variable domain or Nanobody directed against another antigen (e.g. serum albumin), in which said first, second and third immunoglobulin single variable domain or Nanobody may optionally be linked via one or more, and in particular two, linker sequences. Particularly preferred trivalent, bispecific polypeptides in accordance with the invention are those shown in the Examples described herein and in Table A-3.

In another aspect, the polypeptide of the invention is a bispecific polypeptide. A bispecific polypeptide of the invention in its simplest form may be a bivalent polypeptide of the invention (as defined herein), comprising a immunoglobulin single variable domain or Nanobody against Kv1.3 and a second immunoglobulin single variable domain or Nanobody directed against another antigen, in which said first and second immunoglobulin single variable domain or Nanobody may optionally be linked via a linker sequence.

In a further aspect, the polypeptide of the invention is a multiparatopic polypeptide (also referred to herein as "multiparatopic polypeptide(s) of the invention"), such as e.g., (a) "biparatopic polypeptide(s) of the invention" or "triparatopic polypeptide(s) of the invention". The term "multiparatopic" (antigen-) binding molecule or "multiparatopic" polypeptide as used herein shall mean a polypeptide comprising at least two (i.e. two or more) immunoglobulin single variable domains, wherein a "first" immunoglobulin single variable domain is directed against Kv1.3 and a "second" immunoglobulin single variable domain is directed against Kv1.3, and wherein these "first" and "second" immunoglobulin single variable domains have a different paratope. Accordingly, the multiparatopic polypeptide comprises or consists of two or more immunoglobulin single variable domains that are directed against Kv1.3, wherein at least one "first" immunoglobulin single variable domain is directed against a first epitope on Kv1.3 and at least one "second" immunoglobulin single variable domain is directed against a second epitope on Kv1.3 different from the first epitope on Kv1.3.

In a preferred aspect, the polypeptide of the invention is a biparatopic polypeptide. The term "biparatopic" (antigen-)binding molecule or "biparatopic" polypeptide as used herein shall mean a polypeptide comprising a "first" immunoglobulin single variable domain directed against Kv1.3 and a "second" immunoglobulin single variable domain directed against Kv1.3, wherein these "first" and "second" immunoglobulin single variable domains have a different paratope. Accordingly, the biparatopic polypeptide comprises or consists of two or more immunoglobulin single variable domains that are directed against Kv1.3, wherein a "first" immunoglobulin single variable domain is directed against a first epitope on Kv1.3 and a "second" immunoglobulin single variable domain is directed against a second epitope on Kv1.3 different from the first epitope on Kv1.3.

In another further aspect, the polypeptide of the invention is a triparatopic polypeptide. The term "triparatopic" (antigen-)binding molecule or "triparatopic" polypeptide as used herein shall mean a polypeptide comprising a "first" immunoglobulin single variable domain directed against Kv1.3, a "second" immunoglobulin single variable domain directed against Kv1.3 and a "third" immunoglobulin single variable domain directed against Kv1.3, wherein these "first", "second" and "third" immunoglobulin single variable domains have a different paratope. Accordingly, the triparatopic polypeptide comprises or consists of three or more immunoglobulin single variable domains that are directed against Kv1.3, wherein a "first" immunoglobulin single variable domain is directed against a first epitope on Kv1.3, a "second" immunoglobulin single variable domain is directed against a second epitope on Kv1.3 different from the first epitope on Kv1.3, and a "third" immunoglobulin single variable domain is directed against a third epitope on Kv1.3 different from the first and second epitope on Kv1.3.

The two or more immunoglobulin single variable domains present in the multivalent polypeptide of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody or a partially or fully humanized VHH. In a preferred aspect of the invention, the immunoglobulin single variable domains encompassed in the multivalent polypeptide of the invention are one or more monovalent polypeptides of the invention, as defined herein.

In a preferred aspect of the invention, the first immunoglobulin single variable domain and the second immunoglobulin single variable domain present in the multiparatopic (preferably biparatopic or triparatopic) polypeptide of the invention do not (cross-)compete with each other for binding to Kv1.3 and, as such, belong to different families. Accordingly, the present invention relates to a multiparatopic (preferably biparatopic) polypeptide comprising two or more immunoglobulin single variable domains wherein each immunoglobulin single variable domain belongs to a different family. In one aspect, the first immunoglobulin single variable domain of this preferred multiparatopic (preferably biparatopic) polypeptide of the invention does not cross-block the binding to Kv1.3 of the second immunoglobulin single variable domain of this preferred multiparatopic (preferably biparatopic) polypeptide of the invention and/or the first immunoglobulin single variable is not cross-blocked from binding to Kv1.3 by the second immunoglobulin single variable domain. In another aspect, the first immunoglobulin single variable domain of this preferred multiparatopic (preferably biparatopic) polypeptide of the invention cross-blocks the binding to Kv1.3 of the second immunoglobulin single variable domain of this preferred multiparatopic (preferably biparatopic) polypeptide of the invention and/or the first immunoglobulin single variable is cross-blocked from binding to Kv1.3 by the second immunoglobulin single variable domain.

Preferred combination of immunoglobulin single variable domains present in a multiparatopic (such as biparatopic or triparatopic) polypeptide of the invention may encompass any of the following:

the first immunoglobulin single variable domain cross-blocks the binding to Kv1.3 of at least one of the immunoglobulin single variable domains with SEQ ID NOs: 1-64, 495, 498-513 and 523-540 [family 12] and/or is cross-blocked from binding to Kv1.3 by at least one of the immunoglobulin single variable domains with SEQ ID NOs: 1-64, 495, 498-513 and 523-540 [family 12]; and the second immunoglobulin single variable domain cross-blocks the binding to Kv1.3 of at least one of the immunoglobulin single variable domains with SEQ ID NOs: 65-123 [family 1] and/or is cross-blocked from binding to Kv1.3 by at least one of immunoglobulin single variable domains with SEQ ID NOs: 65-123 [family 1];

the first immunoglobulin single variable domain cross-blocks the binding to Kv1.3 of at least one of the immunoglobulin single variable domains with SEQ ID NOs: 65-123 [family 1] and/or is cross-blocked from binding to Kv1.3 by at least one of the immunoglobulin single variable domains with SEQ ID NOs: 65-123 [family 1]; and the second immunoglobulin single variable domain cross-blocks the binding to Kv1.3 of at least one of the immunoglobulin single variable domains with SEQ ID NOs: 1-64, 495, 498-513 and 523-540 [family 12] and/or is cross-blocked from binding to Kv1.3 by at least one of the immunoglobulin single variable domains with SEQ ID NOs: 1-64, 495, 498-513 and 523-540 [family 12];

the first immunoglobulin single variable domain cross-blocks the binding to Kv1.3 of at least one of the immunoglobulin single variable domains with SEQ ID NOs: 1-64, 495, 498-513 and 523-540 [family 12] and/or is cross-blocked from binding to Kv1.3 by at least one of the immunoglobulin single variable domains with SEQ ID NOs: 1-64, 495, 498-513 and 523-540 [family 12]; and the second immunoglobulin single variable domain cross-blocks the binding to Kv1.3 of at least one of the immunoglobulin single variable domains with SEQ ID NOs: 1-64, 495, 498-

513 and 523-540 [family 12] and/or is cross-blocked from binding to Kv1.3 by at least one of the immunoglobulin single variable domains with SEQ ID NOs: 1-64, 495, 498-513 and 523-540 [family 12];

the first immunoglobulin single variable domain cross-blocks the binding to Kv1.3 of at least one of the immunoglobulin single variable domains with SEQ ID NOs: 65-123 [family 1] and/or is cross-blocked from binding to Kv1.3 by at least one of the immunoglobulin single variable domains with SEQ ID NOs: 65-123 [family 1]; and the second immunoglobulin single variable domain cross-blocks the binding to Kv1.3 of at least one of the immunoglobulin single variable domains with SEQ ID NOs: 65-123 [family 1] and/or is cross-blocked from binding to Kv1.3 by at least one of the immunoglobulin single variable domains with SEQ ID NOs: 65-123 [family 1];

the first immunoglobulin single variable domain binds the same epitope as is bound by SEQ ID NOs: 1-64, 495, 498-513 and 523-540 [family 12] and the second immunoglobulin single variable domain binds the same epitope as is bound by SEQ ID NOs: 65-123 [family 1];

the first immunoglobulin single variable domain binds the same epitope as is bound by SEQ ID NOs: 65-123 [family 1] and the second immunoglobulin single variable domain binds the same epitope as is bound by SEQ ID NOs: 1-64, 495, 498-513 and 523-540 [family 12];

the first immunoglobulin single variable domain binds the same epitope as is bound by SEQ ID NOs: 1-64, 495, 498-513 and 523-540 [family 12] and the second immunoglobulin single variable domain binds the same epitope as is bound by SEQ ID NOs: 1-64, 495, 498-513 and 523-540 [family 12]; or the first immunoglobulin single variable domain binds the same epitope as is bound by SEQ ID NOs: 65-123 [family 1] and the second immunoglobulin single variable domain binds the same epitope as is bound by SEQ ID NOs: 65-123 [family 1].

In a further aspect, the invention relates to a multiparatopic (preferably biparatopic) polypeptide comprising two or more immunoglobulin single variable domains directed against Kv1.3 that bind the same epitope as is bound by any one of SEQ ID NOs: 1-123, 495, 498-513 and 523-540.

Different families (1 and 12) exhibiting different functional profiles have been identified amongst the monovalent polypeptides of the invention (see Tables A-4 and A-5). Accordingly, the present invention relates to a multiparatopic polypeptide comprising two or more immunoglobulin single variable domains wherein each immunoglobulin single variable domain belongs to a different family as defined herein.

Preferred immunoglobulin single variable domains for use in these multiparatopic (preferably biparatopic) polypeptides of the invention are the monovalent polypeptides of the invention (see Table A-1 and Table A-9), belonging to families 1 and 12. Particularly preferred biparatopic polypeptides in accordance with the invention are those shown in the Examples described herein and in Table A-3.

Accordingly, preferred combination of immunoglobulin single variable domains that belong to families 1 and 12 present in a multiparatopic (such as biparatopic or triparatopic) polypeptide of the invention may encompass any of the following:

the first immunoglobulin single variable domain belongs to family 12; and the second immunoglobulin single variable belongs to family 1;

the first immunoglobulin single variable domain belongs to family 1; and the second immunoglobulin single variable belongs to family 12;

the first immunoglobulin single variable domain belongs to family 1; and the second immunoglobulin single variable belongs to family 1;

the first immunoglobulin single variable domain belongs to family 12; and the second immunoglobulin single variable belongs to family 12;

the first immunoglobulin single variable domain has the same number of amino acids within its sequence compared to any one of SEQ ID NOs: 1-64, 495, 498-513 and 523-540 and has an amino acid sequence between position 8 and position 106 (according to Kabat numbering) with 89% or more sequence identity compared to any one of SEQ ID NOs: 1-64, 495, 498-513 and 523-540; and the second immunoglobulin single variable domain has the same number of amino acids within its sequence compared to any one of SEQ ID NOs: 65-123 and has an amino acid sequence between position 8 and position 106 (according to Kabat numbering) with 89% or more sequence identity compared to any one of SEQ ID NOs: 65-123;

the first immunoglobulin single variable domain has the same number of amino acids within its sequence compared to any one of SEQ ID NOs: 65-123 and has an amino acid sequence between position 8 and position 106 (according to Kabat numbering) with 89% or more sequence identity compared to any one of SEQ ID NOs: 65-123; and the second immunoglobulin single variable domain has the same number of amino acids within its sequence compared to any one of SEQ ID NOs: 1-64, 495, 498-513 and 523-540 and has an amino acid sequence between position 8 and position 106 (according to Kabat numbering) with 89% or more sequence identity compared to any one of SEQ ID NOs: 1-64, 495, 498-513 and 523-540;

the first immunoglobulin single variable domain has the same number of amino acids within its sequence compared to any one of SEQ ID NOs: 65-123 and has an amino acid sequence between position 8 and position 106 (according to Kabat numbering) with 89% or more sequence identity compared to any one of SEQ ID NOs: 65-123; and the second immunoglobulin single variable domain has the same number of amino acids within its sequence compared to any one of SEQ ID NOs: 65-123 and has an amino acid sequence between position 8 and position 106 (according to Kabat numbering) with 89% or more sequence identity compared to any one of SEQ ID NOs: 65-123; or the first immunoglobulin single variable domain has the same number of amino acids within its sequence compared to any one of SEQ ID NOs: 1-64, 495, 498-513 and 523-540 and has an amino acid sequence between position 8 and position 106 (according to Kabat numbering) with 89% or more sequence identity compared to any one of SEQ ID NOs: 1-64, 495, 498-513 and 523-540; and the second immunoglobulin single variable domain has the same number of amino acids within its sequence compared to any one of SEQ ID NOs: 65-123 and has an amino acid sequence between position 8 and position 106 (according to Kabat numbering) with 89% or more sequence identity compared to any one of SEQ ID NOs: 1-64, 495, 498-513 and 523-540.

The multivalent polypeptides of the invention may modulate and/or partially or fully inhibit the function of Kv1.3.

More particularly, the multivalent polypeptides of the present invention may depolarize the T cell membrane and/or reduce or even totally inhibit the efflux of potassium ions from T-cells. As such, the multivalent polypeptides of the invention may inhibit proliferation of T-cells and/or suppress activation of T-cells resulting of the inhibition of certain immune responses in vivo.

In one particular aspect, the multivalent polypeptides of the invention indirectly modulate the function of Kv1.3, i.e. as an allosteric modulator (as defined herein). More specifically, the multivalent polypeptides of the invention may induce a conformational change within the structure of the Kv1.3 pore.

Binding of the multivalent polypeptides of the invention to Kv1.3 can be measured in binding assays that preserve the conformation of the Kv1.3 target. Typical assays include (without being limiting) assays in which Kv1.3 is exposed on a cell surface (such as e.g. CHO cells, HEK cells, HeLa cells, Chinese Hamster Lung (CHL) cells, etc.). A preferred assay for measuring binding of the multivalent polypeptides of the invention to Kv1.3 is a FACS assay, such as e.g. the FACS assay as described in the examples, wherein binding of the multivalent polypeptides of the invention to Kv1.3 expressed on CHO-K1 cells and/or HEK293H cells is determined. Some preferred EC50 values for binding of the multivalent polypeptides of the invention to Kv1.3 will become clear from the further description and examples herein.

In such FACS binding assay, the multivalent polypeptides of the present invention may have EC50 values in binding human Kv1.3 of $10^{-8}$ M or lower, more preferably of $10^{-9}$ M or lower, or even of $10^{-10}$ M or lower. For example, in such FACS binding assay, the immunoglobulins and/or polypeptides of the present invention may have EC50 values in binding human Kv1.3 between $10^{-10}$ M and $10^{-8}$ M, such as between $10^{-9}$ M and $10^{-8}$ M or between $10^{-10}$ M and $10^{-9}$ M. More particularly, multivalent polypeptides of the present invention that comprise 2 or more monovalent polypeptides belonging to family 12 may have EC50 values in binding human Kv1.3 between $10^{-10}$ M and $10^{-8}$ M, such as between $10^{-10}$ M and $10^{-9}$ M. Biparatopic polypeptides of the present invention that comprise 2 monovalent polypeptides belonging to different families (e.g. one monovalent polypeptide belonging to family 1 and one monovalent polypeptide belonging to family 12) may have EC50 values in binding human Kv1.3 between $10^{-10}$ M and $10^{-8}$ M, such as between $10^{-10}$ M and $10^{-9}$ M. Multivalent polypeptides of the present invention that comprise 2 or more monovalent polypeptides belonging to family 1 may have EC50 values in binding human Kv1.3 between $10^{-10}$ M and $10^{-8}$ M, such as between $10^{-9}$ M and $10^{-8}$ M.

In such FACS binding assay, the multivalent polypeptides of the present invention may have EC50 values in binding cyno Kv1.3 of $10^{-7}$ M or lower, preferably of $10^{-8}$ M or lower, more preferably of $10^{-9}$ M or lower, or even of $10^{-10}$ M or lower. For example, in such FACS binding assay, the multivalent polypeptides of the present invention may have EC50 values in binding cyno Kv1.3 between $10^{-10}$ M and $10^{-7}$ M, such as between $10^{-10}$ M and $10^{-9}$ M.

In such FACS binding assay, the multivalent polypeptides of the present invention may have EC50 values in binding rat Kv1.3 of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such FACS binding assay, the multivalent polypeptides of the present invention may have EC50 values in binding rat Kv1.3 between $10^{-10}$ M and $10^{-8}$ M, such as between $10^{-10}$ M and $10^{-9}$ M, or between $10^{-9}$ M and $10^{-8}$ M. More particularly, multivalent polypeptides of the present invention that comprise 2 or more monovalent polypeptides belonging to family 12 may have EC50 values in binding rat Kv1.3 between $10^{-10}$ M and $10^{-8}$ M, such as between $10^{-10}$ M and $10^{-9}$ M. Biparatopic polypeptides of the present invention that comprise 2 monovalent polypeptides belonging to different families (e.g. one monovalent polypeptide belonging to family 1 and one monovalent polypeptide belonging to family 12) may have EC50 values in binding rat Kv1.3 between $10^{-10}$ M and $10^{-8}$ M, such as between $10^{-10}$ M and $10^{-9}$ M. Multivalent polypeptides of the present invention that comprise 2 or more monovalent polypeptides belonging to family 1 may have EC50 values in binding rat Kv1.3 between $10^{-10}$ M and $10^{-8}$ M, such as between $10^{-9}$ M and $10^{-8}$ M.

Modulation and/or inhibition of the efflux of potassium ions can be determined by a variety of ion channel screening technologies including (without being limiting) ion flux assays, radioligand binding studies, fluorescent dye assays, and electrophysiology, such as voltage clamp, and in particular, the patch-clamp. An overview of different ion channel technologies is provided by e.g. Dabrowski et al. (CNS & Neurological Disorders Drug Targets 7: 122, 2008), Lü and An (Comb. Chem. High Throughput Screen. 11:185-94, 2008), and Zheng et al. (Assay Drug Dev. Technol. 2: 543-52, 2004).

Voltage clamp (Huxley, Trends Neurosci. 25: 553-8, 2002) is used to measure the ion currents through the membrane of excitable cells. The patch-clamp variant of this technique (Hamill et al. Pflügers Archiv European Journal of Physiology 391: 85-100, 1981) allows the study of single or multiple ion channels in cells.

Higher throughput electrophysiological platforms have been developed ranging from medium throughput systems to higher throughput platforms (see e.g. Southan and Clark, Methods Mol. Biol. 565: 187-208, 2009), including PatchXpress (Molecular Devices; Ghetti et al. Methods Mol. Biol. 403: 59-69, 2007), Qpatch and Qpatch HTX (Sophion; Mathes et al. Comb. Chem. High Throughput Screen. 12: 78-95, 2009; Korsgaard et al. Comb. Chem. High Throughput Screen. 12: 51-63, 2009), PatchLiner (Nanion; Farre et al. Comb. Chem. High Throughput Screen 12: 24-37, 2009), IonWorks® HT, IonWorks® Quattro and IonFlux™ Systems (Molecular Devices; Jow et al. J Biomol. Screen. 12: 1059-67, 2007; Dale et al. Mol. Biosyst. 3: 714-22, 2007). Some preferred IC50 values for the polypeptides of the invention in these assays will become clear from the further description and examples herein.

On the IonFlux™ (Molecular Devices) using Kv1.3-expressing HEK293H cells, for example, the multivalent polypeptides of the invention have IC50 values of $10^{-7}$ M or lower, preferably of $10^{-8}$ M or lower, more preferably of $10^{-9}$ M or lower, or even of $10^{-10}$ M or lower. For example, in this automated Patch Clamp assay, the multivalent polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-9}$ M and $10^{-8}$ M, between $10^{-8}$ M and $10^{-7}$ M or between $10^{-10}$ M and $10^{-9}$ M. More particularly, multivalent polypeptides of the present invention that comprise 2 or more monovalent polypeptides belonging to family 12 may have IC50 values on the IonFlux™ (Molecular Devices) between $10^{-10}$ M and $10^{-7}$ M, such as between $10^{-10}$ M and $10^{-9}$ M. Biparatopic polypeptides of the present invention that comprise 2 monovalent polypeptides belonging to different families (e.g. one monovalent polypeptide belonging to family 1 and one monovalent polypeptide belonging to family 12) may have IC50 values on the IonFlux™ (Molecular Devices) between $10^{-10}$ M and $10^{-7}$ M, such as between $10^{-9}$ M and $10^{-7}$ M.

On the IonWorks® Quattro (Molecular Devices) using Kv1.3-expressing Chinese Hamster Lung (CHL) cells, for example, the multivalent polypeptides of the invention have IC50 values of $10^{-7}$ M or lower, preferably of $10^{-8}$ M or lower, more preferably of $10^{-9}$ M or lower, or even of $10^{-10}$ M or lower. For example, on this high-throughput planar perforated patch clamp, the multivalent polypeptides of the present invention may have IC50 values between $10^{-10}$ M and $10^{-7}$ M, between $10^{-10}$ M and $10^{-8}$ M, between $10^{-10}$ M and $10^{-9}$ M, such as e.g. between $10^{-9}$ M and $10^{-8}$ M, between $10^{-8}$ M and $10^{-7}$ M or between $10^{-10}$ M and $10^{-9}$ M. More particularly, multivalent polypeptides of the present invention that comprise 2 or more monovalent polypeptides belonging to family 12 may have IC50 values on the IonWorks® Quattro (Molecular Devices) between $10^{-10}$ M and $10^{-7}$ M, such as between $10^{-10}$ M and $10^{-9}$ M. Biparatopic polypeptides of the present invention that comprise 2 monovalent polypeptides belonging to different families (e.g. one monovalent polypeptide belonging to family 1 and one monovalent polypeptide belonging to family 12) may have IC50 values on IonWorks® Quattro (Molecular Devices) between $10^{-10}$ M and $10^{-7}$ M, such as between $10^{-9}$ M and $10^{-7}$ M.

Modulation and/or inhibition of Kv1.3 by the multivalent polypeptides of the invention can also be assessed in radioligand binding studies. Binding studies with tritiated correolide (e.g. C20-29-[3H]dihydrocorreolide (diTC)) to a single class of sites in membranes prepared from CHO/Kv1.3 cells has been described by Felix et al. (Biochemistry 38: 4922-30, 1999). Knaus et al. (Biochemistry 34: 13627-13634, 1995) describes, for example, the binding of monoiodotyrosinyl margatoxin (125I-margatoxin) to heterotetrameric Kv channels in rat brain synaptic plasma membranes. Binding studies of 125I-margatoxin to plasma membranes prepared from either Jurkat cells, a human leukemic T cell line, or CHO cells stably transfected with the Shaker-type voltage-gated K+ channel, K(V)1.3 have been described by Helms et al. (Biochemistry. 36: 3737-44, 1997). Some preferred IC50 values for blocking 125I-margatoxin binding to Kv1.3 by the multivalent polypeptides of the invention will become clear from the further description and examples herein.

The multivalent polypeptides of the present invention may block binding of 125I-margatoxin to cynomolgus Kv1.3 overexpressing CHO cells with IC50 values of $10^{-8}$ M or lower, more preferably of $10^{-9}$ M or lower, or even of $10^{-10}$ M or lower. For example, in such 125I-margatoxin blocking assay, the multivalent polypeptides of the present invention may have IC50 values between $10^{-10}$ M and $10^{-8}$ M, such as e.g. between $10^{-10}$ M and $10^{-9}$ M.

Other flux assays for measuring modulation and/or inhibition of Kv1.3 by the multivalent polypeptides of the invention include (without being limiting) the high-throughput efflux assay with radiolabelled[86] Rubidium described by Hanson et al. (Br. J. Pharmacol. 126: 1707-16, 1999), the nonradioactive rubidium (Rb(+)) efflux assay described by Wang et al. (Assay Drug Dev. Technol. 2: 525-34, 2004) and a fluorescence-based thallium flux assay (Weaver et al. J. Biomol. Screen. 9: 671-7, 2004).

Inhibition of T-cell activation and/or proliferation by the multivalent polypeptides of the present invention can be measured in T-cell activation assays. Without being limiting, T-cell activation assays have been described by Nguyten et al. (Molecular Pharmacology 50: 1672-1679, 1996) and Hanson et al. (Br. J. Pharmacol. 126: 1707-1716, 1999). Some preferred IC50 values for inhibition of T-cell activation and/or proliferation by the multivalent polypeptides of the invention will become clear from the further description and examples herein.

In a T-cell activation assay with CCR7⁻CD45RA⁻ T cells stimulated with anti-CD3 antibody OKT3 (as described in the Examples 4.4 and 5.5), the polypeptides of the invention have IC50 values for inhibiting IFNgamma production of $10^{-7}$ M or lower, preferably of $10^{-8}$ M or lower, more preferably of $10^{-8}$ M or lower, $10^{-10}$ M or lower, or even of $10^{-11}$ M or lower. For example, in this T-cell activation assay, the polypeptides of the present invention inhibit IFNgamma production with IC50 values between $10^{-11}$ M and $10^{-7}$ M, between $10^{-11}$ M and $10^{-8}$ M, between $10^{-11}$ M and $10^{-8}$ M, such as e.g. between $10^{-11}$ M and $10^{-8}$ M, between $10^{-10}$ M and $10^{-8}$ M, or between $10^{-11}$ M and $10^{-10}$ M. More particularly, multivalent polypeptides of the present invention that comprise 2 or more monovalent polypeptides belonging to family 12 may inhibit IFNgamma production with IC50 values between $10^{-10}$ M and $10^{-8}$ M, such as between $10^{-11}$ M and $10^{-10}$ M. Biparatopic polypeptides of the present invention that comprise 2 monovalent polypeptides belonging to different families (e.g. one monovalent polypeptide belonging to family 1 and one monovalent polypeptide belonging to family 12) may inhibit IFNgamma production with IC50 values between $10^{-11}$ M and $10^{-8}$ M, such as between $10^{-10}$ M and $10^{-9}$ M.

In this T-cell activation assay with CCR7⁻CD45RA⁻ T cells stimulated with anti-CD3 antibody OKT3 (as described in the Examples 4.4 and 5.5), the multivalent polypeptides of the invention have IC50 values for inhibiting CD25 upregulation of $10^{-7}$ M or lower, preferably of $10^{-8}$ M or lower, more preferably of $10^{-9}$ M or lower, $10^{-10}$ M or lower, or even of $10^{-11}$ M or lower. For example, in this T-cell activation assay, the multivalent polypeptides of the present invention inhibit CD25 upregulation with IC50 values between $10^{-11}$ M and $10^{-7}$ M, between $10^{-11}$ M and $10^{-8}$ M, between $10^{-11}$ M and $10^{-8}$ M, such as e.g. between $10^{-11}$ M and $10^{-8}$ M, between $10^{-10}$ M and $10^{-8}$ M or between $10^{-11}$ M and $10^{-10}$ M.

In a cell activation assay with peripheral blood mononucleated cells (PBMCs) stimulated with anti-CD3 antibody OKT3 and anti-CD28 (as described in Example 9), the multivalent polypeptides of the invention do not block IFNgamma production.

Immunosuppressive effects of the multivalent polypeptides of the invention can further be evaluated in in vivo models, such as e.g. in rats, pigs and/or primates. Diabetes-prone Biobreeding Worchester rats have been used as a model for autoimmune diabetes (Beeton et al. Proc Natl Acad Sci USA. 103: 17414-9, 2006). A rat model for allergic contact dermatitis, an animal model for psoriasis, has been described by Azam et al. (J. Invest. Dermatol. 127: 1419-29, 2007). Immunodeficient mice reconstituted with human T cells have been used as animal model for T cell-mediated skin graft rejection (Ren et al. PLoS One 3:e4009, 2008). For example, in the rat model for allergic contact dermatitis as described in Example 12 and 13, the polypeptides of the invention (significantly) reduce the increase in ear thickness with at least about 0.085-0.102 mm and at least about 0.147-0.164 mm versus vehicle, respectively.

Furthermore, the multivalent polypeptides of the invention demonstrated a dramatically improved interspecies cross-reactivity and potency. The multivalent polypeptide of the invention have a more than 1000 fold, and even up to 10000 fold selectivity (as defined herein) over the closest related ion channels (such as e.g. hERG, KCa3.1 (SK4), Kv4.3/KChIP2.2, Kv1.2, Kv1.4, Cav1.3/b3/a2d1, Kir2.1, KCa2.2, KCa2.3, Kv7.2/Kv7.3, Kv1.1, Kv1.5, Kv3.4, Nav1.1, Nav1.2 and Nav1.6). More specifically, the multivalent polypeptides show more than 1000 fold, and even up to 10000 fold selectivity for modulating and/or inhibiting the activity of Kv1.3 over other related Kv ion channel family members. The selective inhibition by the multivalent polypeptides of the present invention can be determined e.g. by comparing the concentration of polypeptide needed for inhibiting the respective channel with the concentration of polypeptide needed for inhibiting Kv1.3. More in particular the multivalent polypeptides show a more than 1000 fold, and even up to 10000 fold selectivity over Kv1.5, Kv1.6, and hERG.

Compounds, Constructs and/or Polypeptides of the Invention

The monovalent polypeptide of the invention and the multivalent polypeptide of the invention, may or may not further comprise one or more other groups, residues, moieties or binding units (these monovalent polypeptides as well as multivalent polypeptides (with or without additional groups, residues, moieties or binding units) are all referred to as "compound(s) of the invention", "construct(s) of the invention" and/or "polypeptide(s) of the invention"). If present, such further groups, residues, moieties or binding units may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are immunoglobulin single variable domains chosen from the group consisting of Domain antibodies, amino acids that are suitable for use as a domain antibody, single domain antibodies, amino acids that are suitable for use as a single domain antibody, "dAb"'s, amino acids that are suitable for use as a dAb, Nanobodies (such as e.g. VHH, humanized VHH or camelized VH sequences).

As described above, additional binding units, such as immunoglobulin single variable domains having different antigen specificity can be linked to form multispecific polypeptides. By combining immunoglobulin single variable domains of two or more specificities, bispecific, trispecific etc. constructs can be formed. For example, a polypeptide according to the invention may comprise one, two or more immunoglobulin single variable domains directed against Kv1.3 and one immunoglobulin single variable domain against another target. Such constructs and modifications thereof, which the skilled person can readily envisage, are all encompassed by the term "compound of the invention, construct of the invention and/or polypeptide of the invention" as used herein.

In the compounds, constructs and/or polypeptides described above, the one, two or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Examples of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compound, construct and/or polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In one specific aspect of the invention, a polypeptide is prepared that has an increased half-life, compared to the corresponding polypeptide of the invention. Examples of polypeptides of the invention that comprise such half-life extending moieties for example include, without limitation, polypeptides in which the immunoglobulin single variable domains are suitable linked to one or more serum proteins or fragments thereof (such as (human) serum albumin or suitable fragments thereof) or to one or more binding units that can bind to serum proteins (such as, for example, Domain antibodies, amino acids that are suitable for use as a domain antibody, single domain antibodies, amino acids that are suitable for use as a single domain antibody, "dAb"'s, amino acids that are suitable for use as a dAb, Nanobodies, VHH sequences, humanized VHH sequences or camelized VH sequences) that can bind to serum proteins (such as serum albumin (such as human serum albumin)), serum immunoglobulins (such as IgG), transferrin or one of the other serum proteins listed in WO 04/003019; polypeptides in which the immunoglobulin single variable domain is linked to an Fc portion (such as a human Fc) or a suitable part or fragment thereof; or polypeptides in which the one or more immunoglobulin single variable domains are suitably linked to one or more small proteins or peptides that can bind to serum proteins (such as, without limitation, the proteins and peptides described in WO 91/01743, WO 01/45746 or WO 02/076489). Reference is also made to the dAb's described in WO 03/002609 and WO 04/003019 and to Harmsen et al. (Vaccine 23: 4926-42, 2005); to EP 0368684, as well as to WO 08/028977, WO 08/043821, WO 08/043822 by Ablynx N.V. and WO 08/068280.

According to a specific, but non-limiting aspect of the invention, the polypeptides of the invention may contain, besides the one or more immunoglobulin single variable domains and/or monovalent polypeptides of the invention against Kv1.3, at least one immunoglobulin single variable domain against human serum albumin. These immunoglobulin single variable domains against human serum albumin may be as generally described in the applications by Ablynx N.V. cited above (see for example WO 04/062551). Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred, as well as the Nanobodies disclosed in WO 2012/175400 (SEQ ID NOs: 1-11 of WO 2012/175400) and the Nanobody with SEQ ID NO: 109 disclosed in the U.S. provisional application No. 62/047,560 entitled "Improved immunoglobulin single variable domains" (date of filing: Sep. 8, 2014; assignee: Ablynx N.V.).

The polypeptide of the invention may, for example, be a trivalent, bispecific polypeptide, comprising two immunoglobulin single variable domains, preferably monovalent polypeptides of the invention against Kv1.3 and a third immunoglobulin single variable domain directed against (human) serum albumin, in which said first, second and third immunoglobulin single variable domain may optionally be linked via one or more, and in particular two, linker sequences.

According to one specific aspect, one or more polypeptides of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068628. Coupling of a polypeptide of the invention to an Fc portion may also lead to an increased half-life, compared to the corresponding polypeptide of the invention. For some applications, the use of an Fc portion and/or of constant domains (i.e., $C_H2$ and/or $C_H3$ domains) that confer increased half-life without any biologically significant effector function may also be suitable or even preferred. Other suitable constructs comprising one or more polypeptides of the invention and one or more constant domains with increased half-life in vivo will be clear to the skilled person, and may for example comprise polypeptides linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, the polypeptides of the invention may be linked (optionally via a suitable linker or hinge region) to naturally occurring, synthetic or semi-synthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al. (J. Biol. Chem. 271: 7494, 1996), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

Generally, the polypeptides of the invention with increased half-life preferably have a half-life that is increased with more than 1 hour, preferably more than 2 hours, more preferably more than 6 hours, such as more than 12 hours, or even more than 24, 48 or 72 hours, compared to the half-life of the corresponding immunoglobulin single variable domain or polypeptide of the invention per se.

In another preferred, but non-limiting aspect, such polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.
b) may form a signal sequence or leader sequence that directs secretion of the polypeptide from a host cell upon synthesis (for example to provide a pre-, pro- or preproform of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 206);

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

The multivalent polypeptides of the invention can generally be prepared by a method which comprises at least the step of suitably linking the immunoglobulin single variable domain and/or monovalent polypeptide of the invention to one or more further immunoglobulin single variable domains and/or monovalent polypeptides of the invention, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more immunoglobulin single variable domains and/or monovalent polypeptides of the invention and for example one or more linkers together in a suitable manner. The immunoglobulin single variable domains and/or monovalent polypeptides of the invention (and linkers) can be coupled by any method known in the art and as further described herein. Preferred techniques include the linking of the nucleic acid sequences that encode the immunoglobulin single variable domains and/or monovalent polypeptides of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an immunoglobulin single variable domain and/or monovalent polypeptide of the invention in preparing a multivalent polypeptide of the invention. The method for the preparation of a multivalent polypeptide will comprise the linking of an immunoglobulin single variable domain and/or monovalent polypeptide of the invention to at least one further immunoglobulin single variable domain and/or monovalent polypeptide of the invention, optionally via one or more linkers. The immunoglobulin single variable domain and/or monovalent polypeptide of the invention is then used as a binding domain or binding unit in providing and/or preparing the multivalent polypeptide comprising two (e.g., in a bivalent polypeptide), three (e.g., in a trivalent polypeptide), four (e.g., in a tetravalent) or more (e.g., in a multivalent polypeptide) binding units. In this respect, the immunoglobulin singe variable domain and/or the monovalent polypeptide of the invention may be used as a binding domain or binding unit in providing and/or preparing a multivalent, such as bivalent, trivalent or tetravalent polypeptide of the invention comprising two, three, four or more binding units.

Accordingly, the present invention also relates to the use of an immunoglobulin single variable domain and/or particularly, a monovalent polypeptide of the invention (as described herein) in preparing a multivalent polypeptide. The method for the preparation of the multivalent polypeptide will comprise the linking of the immunoglobulin single variable domain and/or monovalent polypeptide of the invention to at least one further immunoglobulin single variable domain and/or monovalent polypeptide of the invention, optionally via one or more linkers.

Suitable spacers or linkers for use in multivalent polypeptides of the invention will be clear to the skilled person, and may generally be any linker or spacer used in the art to link amino acid sequences. Preferably, said linker or spacer is suitable for use in constructing polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, hinge-like regions such as the hinge regions of naturally occurring heavy chain antibodies or similar sequences (such as described in WO 94/04678).

Some other particularly preferred linkers are mentioned in Table A-8, of which GS35 (SEQ ID NO: 489) is particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for Kv1.3, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g., as described herein for the derivatives of the polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three of more amino acid sequences or Nanobodies, it is possible to link them by use of a linker with three or more "arms", which each "arm" being linked to an amino acid sequence or Nanobody, so as to provide a "star-shaped" construct. It is also possible, although usually less preferred, to use circular constructs.

Also encompassed in the present invention are compounds, constructs and/or polypeptides that comprise an immunoglobulin or polypeptide of the invention and further comprising tags or other functional moieties, e.g., toxins, labels, radiochemicals, etc.

Alternatively, the additional groups, residues, moieties or binding units may for example be chemical groups, residues, moieties, which may or may not by themselves be biologically and/or pharmacologically active. For example, and without limitation, such groups may be linked to the one or more immunoglobulin single variable domains or monovalent polypeptides of the invention so as to provide a "derivative" of the polypeptide of the invention.

Accordingly, the invention in its broadest sense also comprises compounds, constructs and/or polypeptides that are derivatives of the polypeptides of the invention. Such derivatives can generally be obtained by modification, and in particular by chemical and/or biological (e.g., enzymatical) modification, of the polypeptides of the invention and/or of one or more of the amino acid residues that form polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more functional groups, residues or moieties into or onto the polypeptide of the invention, and in particular of one or more functional groups, residues or moieties that confer one or more desired properties or functionalities to the polypeptide of the invention. Examples of such functional groups will be clear to the skilled person.

For example, such modification may comprise the introduction (e.g., by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, Pa., 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above.

Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example are the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the compounds, constructs, polypeptides and/or derivatives are such that they bind to Kv1.3, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention). Such derivatives will usually also have a Kv1.3 blocking efficacy and/or potency as defined herein.

Such compounds, constructs and/or polypeptides of the invention and derivatives thereof may also be in essentially isolated form (as defined herein).

The invention further relates to methods for preparing the compounds, constructs, polypeptides, nucleic acids, host cells, and compositions described herein.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:
the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:
isolating and/or purifying the polypeptide of the invention thus obtained.

In particular, such a method may comprise the steps of:
cultivating and/or maintaining a host of the invention under conditions that are such that said host of the invention expresses and/or produces at least one polypeptide of the invention;
optionally followed by:
isolating and/or purifying the polypeptide of the invention thus obtained.

Accordingly, the present invention also relates to a nucleic acid or nucleotide sequence that encodes a polypeptide of the invention (also referred to as "nucleic acid of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding an immunoglobulin single variable domain or a monovalent polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g., a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e., under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g., in a specific part or organelle of a cell and/or in (a) specific cell(s), tissue(s), organ(s) or part(s) of a multicellular organism. Such reporter genes may also be expressed as a protein fusion with the amino acid sequence or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. Nos. 7,207,410, 5,693,492 and EP 1085089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism, for example:

- a bacterial strain, including but not limited to gram-negative strains such as strains of *Escherichia* COM of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
- an amphibian cell or cell line, such as *Xenopus oocytes*;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells (for example CHO-K1 cells), BHK-cells and human cells or cell lines such as HeLa, COS, Caki and HEK293H cells;

as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein.

The polypeptides of the invention may also be expressed as so-called "intrabodies", as for example described in WO 94/02610, WO 95/22618 and U.S. Pat. No. 7,004,940; WO 03/014960; in Cattaneo and Biocca ("Intracellular Antibodies: Development and Applications" Landes and Springer-Verlag, 1997); and in Kontermann (Methods 34: 163-170, 2004).

The polypeptides of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing polypeptide therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of an immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the kind, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting embodiment of the invention, the polypeptide of the invention is glycosylated. According to another non-limiting embodiment of the invention, the polypeptide of the invention is non-glycosylated.

According to one preferred, but non-limiting embodiment of the invention, the polypeptide of the invention is produced in a bacterial cell, in particular a bacterial cell suitable for large scale pharmaceutical production, such as cells of the strains mentioned above.

According to another preferred, but non-limiting embodiment of the invention, the polypeptide of the invention is produced in a yeast cell, in particular a yeast cell suitable for large scale pharmaceutical production, such as cells of the species mentioned above.

According to yet another preferred, but non-limiting embodiment of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the polypeptides of the invention, the polypeptides of the invention can be produced either intracellularly (e.g., in the cytosol, in the periplasma or in inclusion bodies) and then isolated from the host cells and optionally further purified; or can be produced extracellularly (e.g., in the medium in which the host cells are cultured) and then isolated from the culture medium and optionally further purified. When eukaryotic host cells are used, extracellular production is usually preferred since this considerably facilitates the further isolation and downstream processing of the polypeptides obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a polypeptide of the invention, can be used.

Thus, according to one non-limiting embodiment of the invention, the polypeptide of the invention is a polypeptide that has been produced intracellularly and that has been isolated from the host cell, and in particular from a bacterial cell or from an inclusion body in a bacterial cell. According to another non-limiting embodiment of the invention, the polypeptide of the invention is a polypeptide that has been produced extracellularly, and that has been isolated from the medium in which the host cell is cultivated.

Some preferred, but non-limiting promoters for use with these host cells include:

for expression in *E. coli*: lac promoter (and derivatives thereof such as the lacUV5 promoter); arabinose promoter; left—(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in *Pichia pastoris*: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:
vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;
vectors for expression in bacterial cells: pET vectors (Novagen) and pQE vectors (Qiagen);
vectors for expression in yeast or other fungal cells: pYES2 (Invitrogen) and *Pichia* expression vectors (Invitrogen);
vectors for expression in insect cells: pBlueBacll (Invitrogen) and other baculovirus vectors
vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:
for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal;
for use in yeast: α-mating factor prepro-sequence, phosphatase (pho1), invertase (Suc), etc.;
for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g., using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g., when the nucleotide sequences of the invention are under the control of an inducible promoter); all of which may be selected by the skilled person. Again, under such conditions, the polypeptides of the invention may be expressed in a constitutive manner, in a transient manner, or only when suitably induced.

It will also be clear to the skilled person that the polypeptide of the invention may (first) be generated in an immature form (as mentioned above), which may then be subjected to post-translational modification, depending on the host cell/host organism used. Also, the polypeptide of the invention may be glycosylated, again depending on the host cell/host organism used.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

Compositions of the Invention

Generally, for pharmaceutical use, the immunoglobulins, polypeptides, compounds, and/or constructs of the invention may be formulated as a pharmaceutical preparation or composition comprising at least one immunoglobulins, polypeptides, compound, and/or construct of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one immunoglobulin of the invention, at least one polypeptide of the invention, at least one compound of the invention, at least one construct of the invention or at least one nucleic acid of the invention and at least one suitable carrier, diluent or excipient (i.e., suitable for pharmaceutical use), and optionally one or more further active substances. In a particular aspect, the invention relates to a pharmaceutical composition that contains at least one of SEQ ID NOs: 1-123, 451-473, and 495-540 and at least one suitable carrier, diluent or excipient (i.e., suitable for pharmaceutical use), and optionally one or more further active substances.

Generally, the immunoglobulins, polypeptides, compounds and/or constructs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The immunoglobulins, polypeptides, compounds and/or constructs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The immunoglobulins, polypeptides, compounds and/or constructs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding an immunoglobulin, polypeptide, compound and/or construct of the invention can additionally be transfected with tissue specific promoters to target specific organs, tissue, grafts, tumors, or cells and can additionally be transfected with signal and stabilization sequences for sub-cellularly localized expression.

Thus, the immunoglobulins, polypeptides, compounds and/or constructs of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the immunoglobulins, polypeptides, compounds and/or constructs of the invention may be combined with one or more excipients and used in the form of ingestible tablets, buccal tablets, troches, capsules, elixirs, suspensions, syrups, wafers, and the like. Such compositions and preparations should contain at least 0.1% of the immunoglobulin, polypeptide, compound and/or construct of the invention. Their percentage in the compositions and preparations may, of course, be varied and may conveniently be between about 2 to about 60% of the weight of a given unit dosage form. The amount of the immunoglobulin, polypeptide, compound and/or construct of the invention in such therapeutically useful compositions is such that an effective dosage level will be obtained.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the immunoglobulins, polypeptides, compounds and/or constructs of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the immunoglobulins, polypeptides, compounds and/or constructs of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The immunoglobulins, polypeptides, compounds and/or constructs of the invention may also be administered intravenously or intraperitoneally by infusion or injection. Particular examples are as further described on pages 144 and 145 of WO 08/020079 or in PCT/EP2010/062975 (entire document).

For topical administration, the immunoglobulins, polypeptides, compounds and/or constructs of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Useful dosages of the immunoglobulins, polypeptides, compounds and/or constructs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the immunoglobulins, polypeptides, compounds and/or constructs of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the immunoglobulins, polypeptides, compounds and/or constructs of the invention required for use in treatment will vary not only with the particular immunoglobulin, polypeptide, compound and/or construct selected but also with the route of administration, the nature of the condition being treated and the age and condition of the patient and will be ultimately at the discretion of the attendant physician or clinician. Also the dosage of the immunoglobulins, polypeptides, compounds and/or constructs of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

Uses of the Immunoglobulins, Polypeptides, Compounds and/or Constructs of the Invention The invention further relates to applications and uses of the immunoglobulins, polypeptides, compounds and/or constructs, nucleic acids, host cells and compositions described herein, as well as to methods for the prevention and/or treatment of Kv1.3 associated diseases, disorders or conditions. Some preferred but non-limiting applications and uses will become clear from the further description herein.

The immunoglobulin, polypeptide, compound and/or construct of the invention can generally be used to modulate the activity of Kv1.3; such as partially or fully inhibit or partially or fully block the activity of Kv1.3. In particular, the immunoglobulin, polypeptide, compound and/or construct of the invention can modulate the activity of Kv1.3 such that it decreases the activity by at least 1%, preferably at least 5%, such as at least 10%, or at least 25%, preferably, at least 50%, at least 60%, at least 70%, at least 80%, or at least 90% or more, such as 100% compared to the activity of Kv1.3 in the absence of the immunoglobulin, polypeptide, compound and/or construct of the invention as determined by a suitable assay, such as those described herein.

In one aspect, the immunoglobulin, polypeptide, compound and/or construct of the invention can reduce the flow of ions through Kv1.3 by at least 1%, preferably at least 5%, such as at least 10%, or at least 25%, preferably, at least 50%, at least 60%, at least 70%, at least 80%, or at least 90% or more, such as 100% compared to the flow of ions through the Kv1.3 pore channel in the absence of the immunoglobulin, polypeptide, compound and/or construct of the invention, as determined by a suitable assay, such as those described herein.

In another aspect, the invention relates to a method for the prevention and/or treatment of at least one Kv1.3 associated disease, disorder or condition, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases, disorders and conditions mentioned herein.

The invention relates to a method for the prevention and/or treatment of at least one disease, disorder or condition that is associated with Kv1.3, with its biological or pharmacological activity, and/or with the biological pathways or signaling in which Kv1.3 is involved, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same. In particular, the invention relates to a method for the prevention and/or treatment of at least one disease, disorder or condition that can be prevented and/or treated by modulating Kv1.3, its biological or pharmacological activity, and/or the biological pathways or signaling in which Kv1.3 is involved, said method comprising administering, to a subject in need thereof, a pharmaceutically active amount of an immunoglobulin of the invention, of a polypeptide of the invention, of a compound of the invention, of a construct of the invention, and/or of a pharmaceutical composition comprising the same.

In particular, said pharmaceutically effective amount may be an amount that is sufficient to modulate Kv1.3, its biological or pharmacological activity, and/or the biological pathways or signaling in which Kv1.3 is involved; and/or an amount that provides a level of the immunoglobulin of the invention, of the polypeptide of the invention, of the compound of the invention, and/or of the construct of the invention in the circulation that is sufficient to modulate Kv1.3, its biological or pharmacological activity, and/or the biological pathways or signaling in which Kv1.3 is involved.

The invention also relates to a method for the prevention and/or treatment of at least one disease, disorder and/or condition that can be prevented and/or treated by administering of an immunoglobulin of the invention, of a polypeptide of the invention, of a compound of the invention and/or of a construct of the invention to a patient, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

More in particular, the invention relates to a method for the prevention and/or treatment of at least one disease, disorder and/or condition chosen from the group consisting of the diseases, disorders and conditions listed herein, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

The invention also relates to a method for reducing and/or inhibiting the efflux of potassium ions from T-cells.

The invention also relates to a method for inhibiting and/or blocking T-cell activation and/or proliferation.

The invention also relates to a method for inhibiting and/or blocking of activated T-cells.

The invention also relates to a method for prevention and/or treatment of T cell mediated diseases.

The invention also relates to a method for prevention and/or treatment of autoimmune diseases.

More in particular, the invention also relates to a method for reducing and/or inhibiting the efflux of potassium ions from T-cells, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

The invention also relates to a method for inhibiting and/or blocking T-cell activation and/or proliferation, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

The invention also relates to a method for inhibiting and/or blocking of activated T-cells, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

The invention also relates to a method for prevention and/or treatment of T cell mediated diseases, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

The invention also relates to a method for prevention and/or treatment of autoimmune diseases, said method comprising administering, to a subject in need thereof, a pharmaceutically active amount of an immunoglobulin of the invention, of a polypeptide of the invention, of a compound of the invention, of a construct of the invention and/or of a pharmaceutical composition comprising the same.

More in particular, the invention also relates to a method for reducing and/or inhibiting the efflux of potassium ions from T-cells, said method comprising administering a pharmaceutically active amount of at least one of SEQ ID NOs: 1-123, 451-473, and 495-540, and/or of a pharmaceutical composition comprising the same.

The invention also relates to a method for inhibiting and/or blocking T-cell activation and/or proliferation, said method comprising administering a pharmaceutically active amount of at least one of SEQ ID NOs: 1-123, 451-473, and 495-540, and/or of a pharmaceutical composition comprising the same.

The invention also relates to a method for inhibiting and/or blocking of activated T-cells, said method comprising administering a pharmaceutically active amount of at least one of SEQ ID NOs: 1-123, 451-473, and 495-540, and/or of a pharmaceutical composition comprising the same.

The invention also relates to a method for prevention and/or treatment of T cell mediated diseases, said method comprising administering a pharmaceutically active amount of at least one of SEQ ID NOs: 1-123, 451-473, and 495-540, and/or of a pharmaceutical composition comprising the same.

The invention also relates to a method for prevention and/or treatment of autoimmune diseases, said method comprising administering a pharmaceutically active amount of at least one of SEQ ID NOs: 1-123, 451-473, and 495-540, and/or of a pharmaceutical composition comprising the same.

In particular, the present invention relates to a method for the prevention and/or treatment of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity.

In another particular aspect, the present invention relates to a method for the prevention and/or treatment of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity, said method comprising administering a pharmaceutically active amount of at least one of SEQ ID NOs: 1-123, 451-473, and 495-540, and/or of a pharmaceutical composition comprising the same.

In a further aspect, the invention relates to a method for immunotherapy, and in particular for passive immunotherapy, which method comprises administering, to a subject suffering from or at risk of the diseases and disorders mentioned herein, a pharmaceutically active amount of an immunoglobulin of the invention, of a polypeptide of the invention, of a compound of the invention, of a construct of the invention and/or of a pharmaceutical composition comprising the same.

In the above methods, the immunoglobulins, polypeptides, compounds and/or constructs of the invention and/or the compositions comprising the same can be administered in any suitable manner, depending on the specific pharmaceutical formulation or composition to be used. Thus, the immunoglobulins, polypeptides, compounds and/or constructs of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease, disorder or condition to be prevented or treated and other factors well known to the clinician.

The immunoglobulins, polypeptides, compounds and/or constructs of the invention and/or the compositions comprising the same are administered according to a regime of treatment that is suitable for preventing and/or treating the disease, disorder or condition to be prevented or treated. The clinician will generally be able to determine a suitable treatment regimen, depending on factors such as the disease, disorder or condition to be prevented or treated, the severity of the disease to be treated and/or the severity of the symptoms thereof, the specific immunoglobulins, polypeptides, compounds and/or constructs of the invention to be used, the specific route of administration and pharmaceutical formulation or composition to be used, the age, gender, weight, diet, general condition of the patient, and similar factors well known to the clinician.

Generally, the treatment regimen will comprise the administration of one or more immunoglobulins, polypeptides, compounds and/or constructs of the invention, or of one or more compositions comprising the same, in one or more pharmaceutically effective amounts or doses. The specific amount(s) or doses to be administered can be determined by the clinician, again based on the factors cited above.

Generally, depending on the specific disease, disorder or condition to be treated, the potency of the specific immunoglobulin, polypeptide, compound and/or construct of the invention to be used, the specific route of administration and the specific pharmaceutical formulation or composition used, the clinician will be able to determine a suitable daily dose.

Usually, in the above method, an immunoglobulin, polypeptide, compound and/or construct of the invention will be used. It is however within the scope of the invention to use two or more immunoglobulins, polypeptides, compounds and/or constructs of the invention in combination.

The immunoglobulins, polypeptides, compounds and/or constructs of the invention may be used in combination with one or more further pharmaceutically active compounds or principles, i.e., as a combined treatment regimen, which may or may not lead to a synergistic effect.

Again, the clinician will be able to select such further compounds or principles, as well as a suitable combined treatment regimen, based on the factors cited above and his expert judgment.

In particular, the immunoglobulins, polypeptides, compounds and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an immunoglobulin, polypeptide, compound and/or construct of the invention in the preparation of a pharmaceutical composition for prevention and/or treatment of at least one disease, disorder and condition associated with Kv1.3; and/or for use in one or more of the methods of treatment mentioned herein.

The invention also relates to the use of an immunoglobulin, polypeptide, compound and/or construct of the invention, in the preparation of a pharmaceutical composition for prevention and/or treatment of at least one of the diseases, disorders and conditions associated with Kv1.3 and/or with the signaling pathways and/or the biological functions and responses in which Kv1.3 are involved; and/or for use in one or more of the methods described herein.

The invention also relates to the use of an immunoglobulin, polypeptide, compound and/or construct of the invention in the preparation of a pharmaceutical composition for the prevention and/or treatment of at least one disease or disorder that can be prevented and/or treated by modulating Kv1.3, its biological or pharmacological activity, and/or the biological pathways or signaling in which Kv1.3 is involved.

The invention also relates to the use of an immunoglobulin, polypeptide, compound and/or construct of the invention in the preparation of a pharmaceutical composition for the prevention and/or treatment of at least one disease, disorder or condition that can be prevented and/or treated by administering an immunoglobulin, polypeptide, compound and/or construct of the invention to a patient.

More in particular, the invention relates to the use of an immunoglobulin, polypeptide, compound and/or construct of the invention in the preparation of a pharmaceutical composition for reducing and/or inhibiting the efflux of potassium ions from T-cells.

The invention also relates to the use of an immunoglobulin, polypeptide, compound and/or construct of the invention in the preparation of a pharmaceutical composition for inhibiting and/or blocking T-cell activation and/or proliferation.

The invention also relates to the use of an immunoglobulin, polypeptide, compound and/or construct of the invention in the preparation of a pharmaceutical composition for inhibiting and/or blocking of activated T-cells.

The invention also relates to the use of an immunoglobulin, polypeptide, compound and/or construct of the invention in the preparation of a pharmaceutical composition for prevention and/or treatment of T cell mediated diseases.

The invention also relates to the use of an immunoglobulin, polypeptide, compound and/or construct of the invention in the preparation of a pharmaceutical composition for prevention and/or treatment of autoimmune diseases.

More in particular, the invention relates to the use of an immunoglobulin, polypeptide, compound and/or construct of the invention in the preparation of a pharmaceutical composition for the prevention and/or treatment of Kv1.3 related disorders, and in particular for the prevention and treatment of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity.

The invention further relates to an immunoglobulin, polypeptide, compound and/or construct of the invention or a pharmaceutical composition comprising the same for use in the prevention and/or treatment of at least one Kv1.3 related disease, disorder and/or condition.

The invention further relates to an immunoglobulin, polypeptide, compound and/or construct of the invention or a pharmaceutical composition comprising the same for use in the prevention and/or treatment of at least one disease, disorder and/or condition associated with Kv1.3, with its biological or pharmacological activity, and/or with the biological pathways or signaling in which Kv1.3 involved.

The invention further relates to an immunoglobulin, polypeptide, compound and/or construct of the invention or a pharmaceutical composition comprising the same for use in the prevention and/or treatment of at least one disease, disorder and/or condition that can be prevented and/or treated by modulating Kv1.3, its biological or pharmacological activity, and/or the biological pathways or signaling in which Kv1.3 is involved.

The invention also relates to an immunoglobulin, polypeptide, compound and/or construct of the invention or a pharmaceutical composition comprising the same for use in the prevention and/or treatment of at least one disease, disorder and/or condition that can be prevented and/or treated by administering of an immunoglobulin, polypeptide, compound and/or construct of the invention to a patient. More in particular, the invention also relates to an immunoglobulin, polypeptide, compound and/or construct of the invention or a pharmaceutical compositions comprising the same for use in reducing and/or inhibiting the efflux of potassium ions from T-cells.

The invention also relates to an immunoglobulin, polypeptide, compound and/or construct of the invention or a pharmaceutical composition comprising the same for use in inhibiting and/or blocking T-cell activation and/or proliferation.

The invention also relates to an immunoglobulin, polypeptide, compound and/or construct of the invention or a pharmaceutical composition comprising the same for use in inhibiting and/or blocking of activated T-cells.

The invention also relates to an immunoglobulin, polypeptide, compound and/or construct of the invention or a pharmaceutical composition comprising the same for use in prevention and/or treatment of T cell mediated diseases.

The invention also relates to an immunoglobulin, polypeptide, compound and/or construct of the invention or a pharmaceutical composition comprising the same for use in prevention and/or treatment of autoimmune diseases.

The invention further relates to immunoglobulin, polypeptide, compound and/or construct of the invention or a pharmaceutical composition comprising the same for use in the prevention and/or treatment of multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, anti-neutrophil cytoplasmic antibody (ANCA)-associated vasculitis (AAV), uveitis and delayed type hypersensitivity.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein.

Again, in such a pharmaceutical composition, the one or more immunoglobulins, polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention).

The immunoglobulins, polypeptides, compounds and/or constructs of the present invention ameliorate the effects of inflammation in a relevant delayed-type hypersensitivity (DTH) rat model. Based on their mode of action, the immunoglobulins, polypeptides, compounds and/or constructs of the present invention may be useful in the treatment of other Kv1.3 associated diseases, including but not limited to multiple sclerosis, rheumatoid arthritis, type-1 diabetes mellitus, type-2 diabetes mellitus, psoriasis, inflammatory bowel disease, contact-mediated dermatitis, psoriatic arthritis, asthma, allergy, restenosis, systemic sclerosis, fibrosis, scleroderma, glomerulonephritis, chronic obstructive pulmonary disease (COPD), Sjogren's syndrome, Alzheimer's disease, inflammatory bone resorption, systemic lupus erythematosus, ulcerative colitis, obesity, graft-versus host disease, transplant rejection, vasculitis, antineutrophil cytoplasmic antibody (ANCA)-associated vasculitis (AAV), uveitis and delayed type hypersensitivity.

It is to be understood that reference to treatment includes both treatment of established symptoms and prophylactic treatment, unless explicitly stated otherwise.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

Examples

Example 1: Immunization of Llamas with Kv1.3, Cloning of the Heavy Chain-Only Antibody Fragment Repertoires and Preparation of Phage 1.1 Immunizations After approval of the Ethical Committee (University Antwerp, Belgium), 3 llamas (llama *glama*) were immunized with a pVAX1-human Kv1.3 plasmid vector (Invitrogen, Carlsbad, Calif., USA) (2×150 µg/dose) according to standard protocols by ⅝ bilateral, intradermal in vivo electroporation at biweekly intervals. After the 6th (5th for 1 llama) injection, the llamas received 1 subcutaneous injection of HEK293H (DSMZ, ACC 635) or Caki cells (Nguyen et al., Adv Immunol 79: 261-296, 2001) overexpressing human Kv1.3 (2E07 cells/dose). Cells were re-suspended in D-PBS and kept on ice prior to injection. 1 animal received also human Kv1.3 expressing VLP's (Molecular Integral, INT-793A) after the cell boost.

1.2 Cloning of Heavy Chain-Only Antibody Fragment Repertoires and Preparation of Phage Following the final injection of each subset, immune tissues as the source of B-cells that produce the heavy-chain antibodies were collected from the immunized llamas. Blood samples, collected few days after the last injection of each subset, were collected per animal. From the blood samples, peripheral blood lymphocytes (PBLs) were prepared using Ficoll-Hypaque according to the manufacturer's instructions (Amersham Biosciences, Piscataway, N.J., USA). From the PBLs and the lymph node biopsy (LN), total RNA was extracted, which was used as starting material for RT-PCR to amplify the VHH encoding DNA segments. For each immunized llama, libraries were constructed by pooling the total RNA isolated from samples originating from a certain subset of the immunization schedule i.e. after one type of immunization antigen.

In short, the PCR-amplified VHH repertoire was cloned via specific restriction sites into a vector designed to facilitate phage display of the VHH library. The vector was derived from pUC119 which contains a resistance gene for ampicillin or carbenicillin and the lac promoter followed by the coding sequence of the pIII protein signal peptide in frame with a downstream Nanobody cloning site (pAX212). In frame with the VHH coding sequence, the vector encodes a C-terminal 3×FLAG and His6 tag and a coliphage pIII protein. Phage were prepared according to standard protocols (see for example WO 04/041865, WO 04/041863, WO 04/062551, WO 05/044858 and other prior art and applications filed by Ablynx N.V. cited herein) and stored after filter sterilization at 4° C. or at −80° C. in 20% glycerol for further use.

Example 2: Selection of Kv1.3 Specific VHHs Via Phage Display

VHH repertoires obtained from all llamas and cloned as phage library were used in different selection strategies, applying a multiplicity of selection conditions. Variables included i) the presentation form of the Kv1.3 (on different cell backgrounds or on liposomes/VLPs), ii) the antigen presentation method (in solution when using cells or coated onto plates when using VLPs), iii) the antigen concentration, iv) the orthologue used (human or cynomolgus), and v) the number of selection rounds. All solid coated phase selections were done in Maxisorp 96-well plates (Nunc, Wiesbaden, Germany).

Selections were performed as follows: Kv1.3 antigen preparations for solid and solution phase selection formats were presented as described above at multiple concentrations. After 2 h incubation with the phage libraries followed by extensive washing, bound phages were eluted with trypsin (1 mg/mL) for 15 minutes. When trypsin was used for phage elution, the protease activity was immediately neutralized by applying 0.8 mM protease inhibitor ABSF. As control, selections without antigen were performed in parallel.

Phage outputs were used to infect *E. coli* which were then in turn used to prepare phage for the next selection round (phage rescue). The phage outputs were also used to infect *E. coli* which were then plated on agar plates (LB+carb+glucose[2%]) for analysis of individual VHH clones. In order to screen a selection output for specific binders, single colonies were picked from the agar plates and grown in 1 mL 96-deep-well plates. LacZ-controlled VHH expression was induced by adding IPTG (1 mM final) in the absence of glucose. Periplasmic extracts (in a volume of ~80 uL) were prepared according to standard protocols (see for example WO 03/035694, WO 04/041865, WO 04/041863, WO 04/062551 and other prior art and applications filed by Ablynx N.V. cited herein).

Example 3: Screening of Periplasmic Extracts 3.1 Screening for Kv1.3 Binding Nanobodies in a Flow Cytometry Assay Periplasmic extracts were screened for cell expressed Kv1.3 binding in a FACS assay using in house made Kv1.3-expressing CHO-K1 and/or HEK293H cells. 2×10⁵ cells were incubated in 1:5 diluted periplasmic extracts for 30 min at 4° C., and then thoroughly washed. Next, cells were incubated with 1 µg/ml monoclonal ANT-FLAG® M2 antibody (Sigma-Aldrich, cat #F1804) for 30 min at 4° C., washed again, and incubated for 30 min at 4° C. with goat anti-mouse PE labelled antibody (1:1000). Samples were washed, resuspended in FACS Buffer (D-PBS from Gibco, with 10% FBS from Sigma and 0.05% sodium azide from Merck) supplemented with 5 nM TOPRO3 (Molecular Probes cat #T3605). Cell suspensions were then analyzed on a FACS Array. Gating was set on live, intact cells using forward/side scatter and TOPRO3 channel fluorescence parameters. Live cell PE channel mean channel fluorescence values higher than those obtained for control experiments including an irrelevant specificity binding Nanobody, indicated that a clone bound the cell line. In addition, absence of binding to the parental cell line was checked.

3.2 Screening for Kv1.3 Inhibitory Nanobodies in Electrophysiology

Periplasmic extracts were electrophysiologically screened for inhibitory effects on the voltage-gated potassium channel Kv1.3 on the IonFlux™ automated Patch Clamp using Kv1.3-expressing HEK293H cells. The complete procedure for evaluating the modulatory effect of periplasmic extracts on human Kv1.3 via electrophysiological recordings is given below.

IonFlux™ 16

The IonFlux™ (Molecular Devices) is an automated patch clamp system with integrated Well Plate Microfluidic™ Technology, temperature control and continuous perfusion and voltage clamp. The IonFlux™ 16 has sixteen parallel amplifiers and uses 96-well IonFlux plates conform to the Society for Biomolecular Sciences. This system allows both population and single cell patch clamp.

Solutions and Nanobodies Handling

Extracellular solution contained (in mM): 132 NaCl, 5.4 KCl, 1.8 CaCl2, 0.8 MgCl2, 10 HEPES, 5 glucose (pH 7.2 with NaOH, and 285-290 mOsmolar). Intracellular solution contained (in mM): 40 KF, 100 KCl, 2 MgCl2, 10 HEPES, 5 EGTA (pH 7.45 with CsOH, and 300-315 mOsmolar). These solutions were freshly made, stocked for no longer than a month at 4° C. and filtered prior to use. Periplasmic extract were 1:5 diluted in extracellular solution and transferred to a V-bottom deep well square well plate (Westburg, #AB0932).

Cell Preparation

HEK293H cells stably expressing the human Kv1.3 channel were generated in house. Cells were cultured in T-175 cell culture flasks (Greinerbio-one, #660160) using standard culture medium DMEM Glutamax™ (GIBCO, #31966) containing 10% FBS (Sigma-Aldrich, #F7524), 1% penicillin+streptomycin (GIBCO, #15140-122), 1 mg/ml G418 (GIBCO, #10131-027). Cells were seeded at a density of 25.000 cells/cm$^2$ or 12.000 cells/cm$^2$ for 2 or 3 days respectively before being used on the IonFlux™ 16 (Fluxion, Molecular Devices). Optimal Cell confluence prior to harvesting never exceeded 80%. The cells were washed twice with d-PBS without Ca2+ and Mg2+ (Invitrogen, #14190) and detached with 3 ml Trypsin/EDTA 0.25% (Invitrogen, Cat 25200-056) for 5 to 10 min at 37° C. DMEM Glutamax™ containing 10% FBS was added to inactivate the enzymatic reaction triggered by the trypsin. Subsequently, the cell pellet was re-suspended in 20 ml d-PBS+10% FBS and centrifuged at 200×g during 10 min at RT in 50 ml conical CELLSTAR® tube (Greinerbio-one, #227-261). Cells were counted (Casy T T, Roche), suspended at 1 million cells/ml, transferred to a new 50 ml conical CELL-STAR® tube and gently shaken at RT for approximately 20 min. One million cells were centrifuged for 2 min at 200×g. The pellet was gently resuspended in 5 ml extracellular buffer and centrifuged a second time for 2 min at 200×g. Finally, the pellet was resuspended in 2000 µl extracellular buffer and immediately tested on the IonFlux™.

IonFlux™ 16 Procedure and the Human Kv1.3 Assay

250 µl of sterile cell culture grade water was dispensed into every well of the IonFlux 96-well plate except the outlet wells, using an 8 channel multi-pipette. Before rinsing the plate, excess water present on the rim of the plate was wiped off. The designated plate was inserted into the IonFlux system and subsequently rinsed 4 times according to a standard Water Rinse protocol. After rinsing, the plate was emptied. The inlet wells were then manually filled with extracellular buffer, trap wells with intracellular buffer and the diluted Nanobodies or selective peptides were distributed into the compounds wells (250 µl/well). Subsequently, the plate was primed before the actual experiment according to the plate specific protocols. For population plates (Molecular Devices, #910-0098): 1) traps and compounds at 5 psi for t=0-160 s and 2 psi for t=160-175 s, 2) traps but not compounds at 2 psi for t=175-180 s, and 3) main channel at 1 psi for t=0-160 s and 0.3 psi for t=162-180 s. For single cell plates (Molecular Devices, #910-0100): 1) traps but not compounds at 11 psi for t=0-350 s and 1.5 psi for t=625-630 2) traps and compounds at 5 psi for t=350-600 s and 1.5 psi for t=600-625 s, and 3) main channel at 0.5 psi for t=0-350 s and 1 psi for t=350-600 s, and 0.3 psi for t=600-627 s. After priming, the out- and inlet wells were emptied and 250 µl of the prepared cell suspension (i.e. approximately 1 million cells) was distributed into the inlet wells of the designated plate. After introduction of the cells, the plate was reprimed: 1) traps and compounds at 5 psi for t=0-20 s and 2 psi for t=25-50 s, 2) traps not with compounds at 2 psi for t=50-55 s, and 3) main channel at 1 for t=0-30 s and 0.4 psi for t=30-55 s. Then, cells were introduced to the main channel and trapped at lateral trapping sites with the trapping protocol: 1) trapping vacuum of 8 mmHg for t=0 to 76 s, 2) main channel pressure of 0.2 psi for t=0-2 s, followed by 13 repeated square pulses of 0-0.2 psi with baseline duration of 4.5 s and pulse duration of 0.8 s, followed by 0.2 psi for 2 s. Whole cell access was achieved by rupturing the patch of the membrane over the hole using the following break protocol: 1) breaking vacuum of 8 mmHg for t=0-15 s, followed by a pulse square pulse of 8-16 mmHg with a pulse duration of 10 s, and followed by 5 mmHg for 10 s, and 2) main channel pressure at 0.15 psi for t=0-35 s. After whole cell configuration, the vacuum pressure was held at 5 mmHg and the main channel pressure at 0.1 psi until the end of the experiment. Cells were first allowed to dialyze for 240 s, before compounds were tested. A time course protocol was applied to assess the effect of the compounds on potassium currents elicited by a depolarizing pulse protocol. In order to be able to perform an off-line linear leak subtraction, cells were clamped at −80 mV for 10 ms then hyperpolarized to −100 mV for 50 ms, and repolarized to −80 mV for 30 ms. Subsequently, potassium currents were provoked by a depolarizing step from −80 mV to +40 mV for 250 ms at 30 s interval (as shown in FIG. 2A). After the stabilizing period, extracellular buffer was continuously perfused during 120 s as a negative control, followed by sequential perfusion of periplasmic extracts, different concentrations of Nanobodies or selective peptides. The interval between several compound additions was 120 s. The inhibitory responses were recorded at room temperature (21° C.-24° C.) with a minimum of n=2 at each compound.

IonFlux Data Inclusion Criteria and Data Analysis

Data points were accepted if:

A) Automated Population Patch
1) Individual membrane resistance quality and stability was >50 MΩ during data acquisition
2) Current amplitude quality and stability was >5 nA at +40 mV after negative control
3) Run-up/run-down<10% during data acquisition
4) Standard IC$_{50}$ value within anticipated range B) Automated Single Cell Patch
1) Individual membrane resistance quality and stability was >500 MΩ during data acquisition
2) Current amplitude quality and stability was >200 pA at +40 mV after negative control 3) Run-up/run-down<10% during data acquisition
4) Standard IC$_{50}$ value within anticipated range Currents were measured using IonFlux software (Fluxion Biosciences), monitored continuously during the exposure to the compounds, and outliers were excluded to filter out recordings that were lost. Measured currents were normalized by the mean sustained current corrected amplitude prior to compound addition (FIG. 2B). Current inhibition was estimated by the residual response after 120 s of each compound application. IonFlux software (Fluxion Biosciences), Microsoft Excel (Microsoft) and Prism 6 (GraphPad Software) were used for current analysis.

3.3 Screening for Nanobodies Blocking 125I-Margatoxin Binding to Kv1.3 Expressing Cells Periplasmic extracts were screened in a radioligand 125I-margatoxin competition assay to assess the blocking capacity of the expressed Nanobodies. Cynomolgous Kv1.3 was presented on CHO cells overexpressing Kv1.3.

In order to detect binding of margatoxin to cell expressed Kv1.3, a radiolabeled toxin was used (125I-margatoxin; MgTX; Perkin Elmer, NEX083). To setup the assay, first a titration series of the radiolabeled 125I-margatoxin was performed on the CHO-cyKv1.3 and parental CHO K1 cells. To have maximum sensitivity of the screening, the $EC_{30}$ concentration (150 pM) was chosen for competition during screening and later on, also characterization.

In brief, 35 µl of periplasmic extract was added to 150 pM labeled margatoxin (50 µl) and 40000 CHO-cyKv1.3 cells that were seeded the day before in a poly-D-lysine coated 96-well plate (BD Biocoat, Cat354620) in a total of 200 µl. After two hours incubation at RT, cells were washed two times before read out was performed with 100 µl/well MicroScint-20 (Perkin Elmer) on a TopCount device (Perkin Elmer).

As reference compounds, a dilution series of ShK-1aJ (Smartox, #08SHK001) and unlabeled margatoxin (Alamone labs, Cat RTM-325) were included. As controls, conditions were taken along where there was no Nanobody present in the peri extract or a known irrelevant Nanbody and samples were included where excess cold margatoxin was included. For each sample the percentage block was determined using the control samples to determine the assay window.

3.4 Conclusion

Nanobodies which scored positive in the flow cytometric screening, the ephys assay or 125I-Margatoxin competition assay were sequenced. Corresponding amino acid sequences are shown in Table A-1. Clones were clustered into sequence families based on their overall sequence. 2 distinct families (Family 1 and 12) belonging to 2 different B-cell lineages of Kv1.3 binders were identified. Corresponding alignments are provided in Table A-4 and Table A-5, respectively.

Example 4: Characterization of Purified Nanobodies

Binding/inhibitory anti-Kv1.3 Nanobodies selected from the screening described in Example 3 supra were further purified and characterized. Selected Nanobodies were expressed in *E. coli* TG1 as triple Flag, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and Nanobodies were purified via IMAC and size exclusion chromatography (SEC) resulting in 95% purity as assessed via SDS-PAGE.

4.1 Binding of Anti-Kv1.3 Nanobodies to Human, Cyno and Rat Kv1.3 Expressed on CHO Cells Binding of 2 exemplified monovalent Nanobodies of family 1 and 12 to human, cyno and rat Kv1.3 expressed on CHO cells was evaluated on FACS as outlined in Example 3.1. Dilution series of anti-Kv1.3 Nanobodies starting from 1 µM down to 10 pM were applied to the cells. As a control, the parental CHO cell line was included (see FIG. 3 A-F). Both Nanobodies clearly bound to human, cyno and rat Kv1.3 although with slightly lower potency to the latter. The $EC_{50}$ values obtained from the dose response curve are depicted in Table B-1.

TABLE B-1

$EC_{50}$ (M) of anti-Kv1.3 monovalent Nanobodies in binding to cyno, rat, and human Kv1.3 expressed on CHO cells as determined in FACS.

| VHH ID | CHO cyKv1.3 | CHO ratKv1.3 | CHO huKv1.3 |
| --- | --- | --- | --- |
| A019400003 | 2.5E−09 | 3.8E−07 | 6.2E−09 |
| A0194009G09 | 1.1E−08 | 2.4E−07 | 7.9E−09 |

Figure 4:
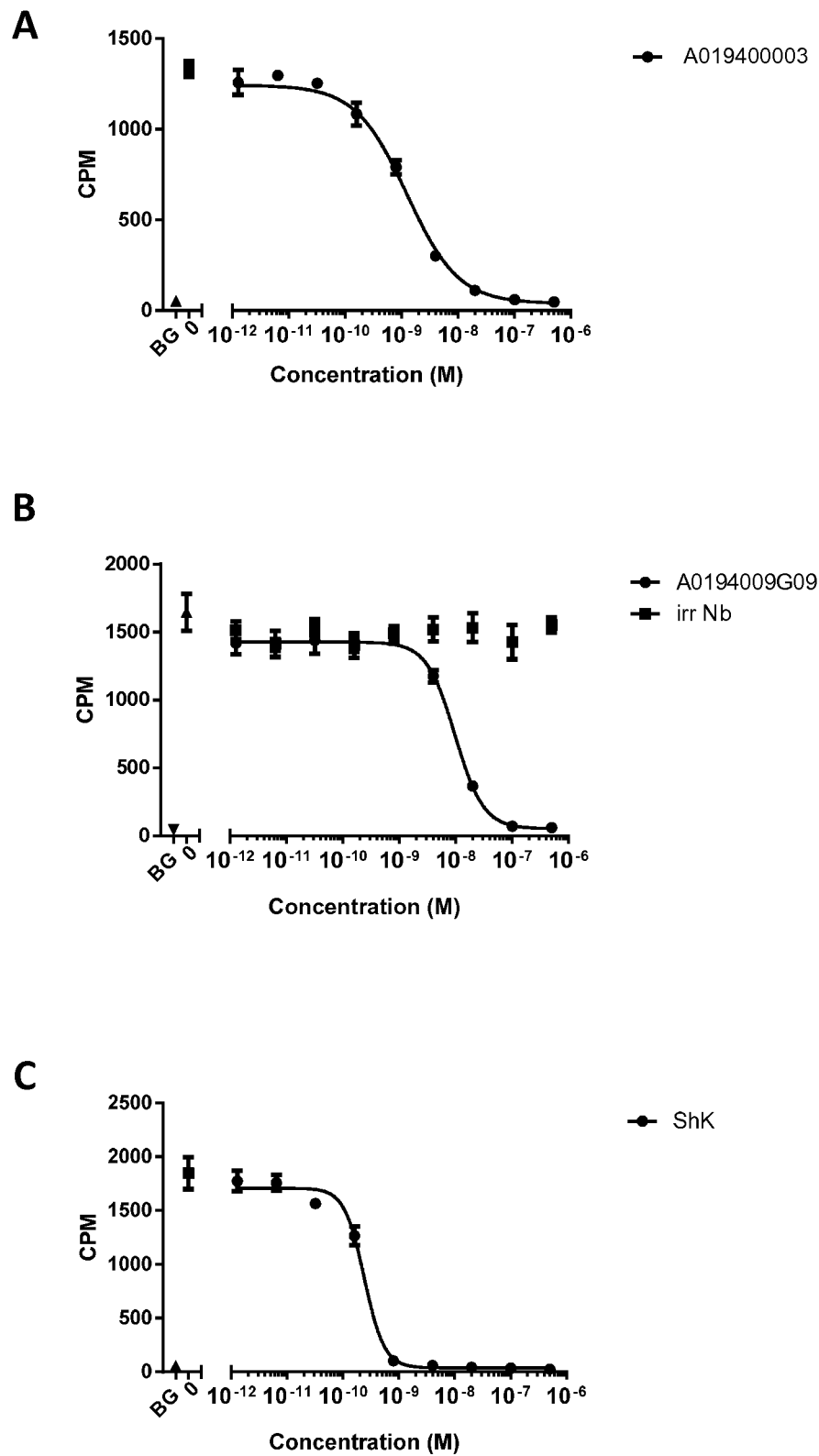

4.2 Inhibition by Monovalent Anti-Kv1.3 Nanobodies of 125I Margatoxin Binding to Cyno Kv1.3 Expressed on CHO Cells The blocking capacity towards radiolabeled margatoxin by the Nanobodies was evaluated in a human 125I-MgTX competition assay as outlined in Example 3.3, with the difference that here a dilution series of the purified Nanobodies/toxins was applied (FIG. 4 A-C). The $IC_{50}$ values for the Nano bodies/toxin (Shk, Smartox, #08SHK001) in blocking the interaction of MgTX to human Kv1.3 are depicted in Table B-2.

TABLE B-2

$IC_{50}$ (M) of anti-Kv1.3 monovalent Nanobodies and ShK or MgTX compound for Inhibition of radiolabeled 125I-MgTX binding to cyKv1.3 expressed on CHO cells by binding.

| VHH ID/compound | $IC_{50}$ (in M) |
| --- | --- |
| A019400003 | 1.3E−09 |
| A0194009G09 | 9.8E−09 |
| ShK | 2.4E−10 |
| MgTX | 2.4E−10 |

4.3 Electrophysiological Characterization of Monovalent Kv1.3 Inhibitory Nanobodies on Human Kv1.3 Expressing HEK293H IonFlux™

Selected Nanobodies were electrophysiologically characterized on human Kv1.3 on the IonFlux™ automated Patch Clamp using Kv1.3-expressing HEK293H cells. The procedure for evaluating the modulatory effect of the purified Nanobodies on human Kv1.3 via electrophysiological recordings is given in Example 3.2 supra. A time course protocol was applied to assess the Nanobody potencies ($IC_{50}$) on potassium currents elicited by a depolarizing pulse protocol (FIG. 2A). After the stabilizing period, extracellular buffer was continuously perfused during 120 s as a negative control, followed by sequential perfusion of different concentrations of Nanobodies or the selective hKv1.3 channel blocker *Stichodactyla helianthus* (ShK-1aj Smartox, #08SHK001). The interval between several additions of compound concentrations was 120 s. The half maximal inhibitory concentrations ($IC_{50}$) were calculated at room temperature from seven-point (unless stated otherwise) concentration-response curves with a minimum of n=2 at each concentration.

In a "wash-off" experiment, a single high dose (300 nM) was applied during 120 s, followed by a continuous perfusion of extracellular buffer for at least 5 min, in order to assess the rate of current recovery during washout. In these experiments both population and single cell automated patch clamp were used to record current amplitudes.

Measured currents were normalized by the mean sustained current corrected amplitude prior to Nanobody addition (as shown in FIG. 2B). Current inhibition was estimated by the residual response after 120 s of each Nanobody concentration application. The $IC_{50}$ and hill slope for compound concentration were then fit to the following formula:

$$Y = Bottom + (Top - Bottom)/(1 + 10^{((Log\ IC50 - X)*Hill\ Slope)})$$

IonFlux software (Fluxion Biosciences), Microsoft Excel (Microsoft) and Prism 6 (GraphPad Software) were used to analyze and present $IC_{50}$ values and currents.

Figure 5:
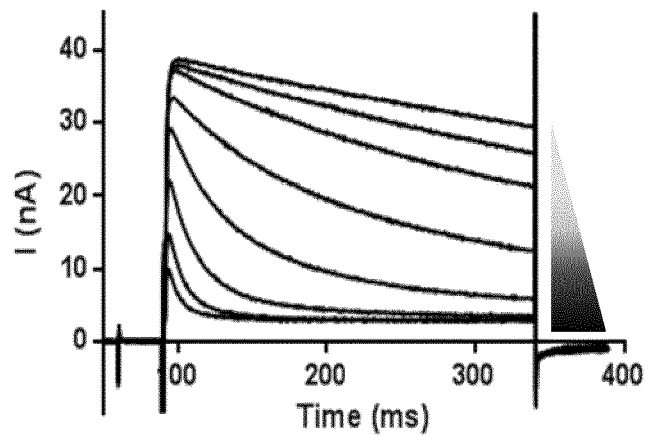
Figure 5:
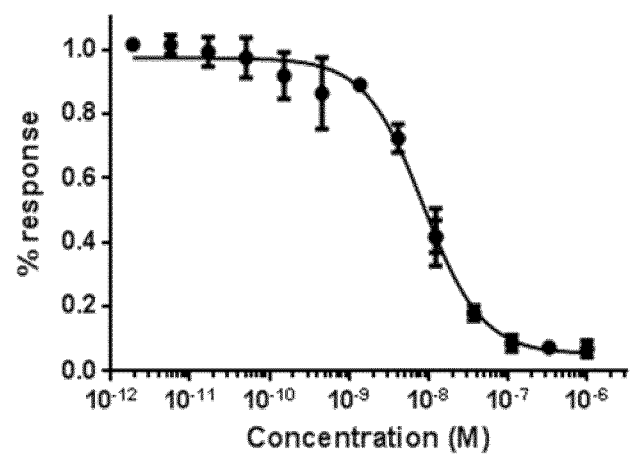
Figure 6:
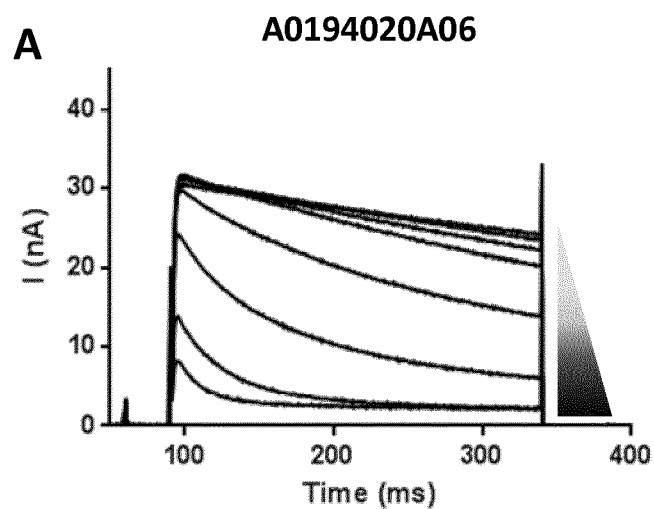
Figure 6:
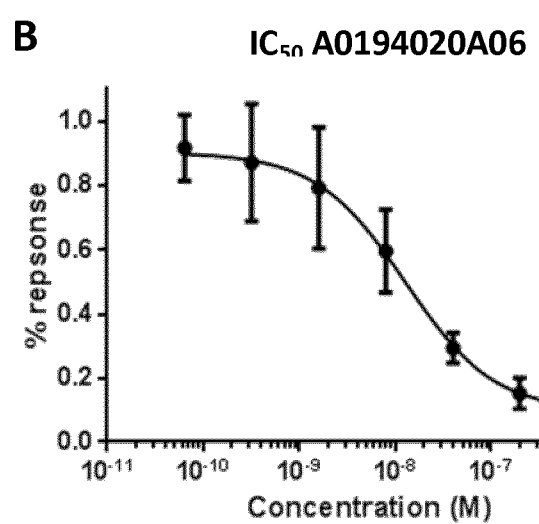
Figure 7:
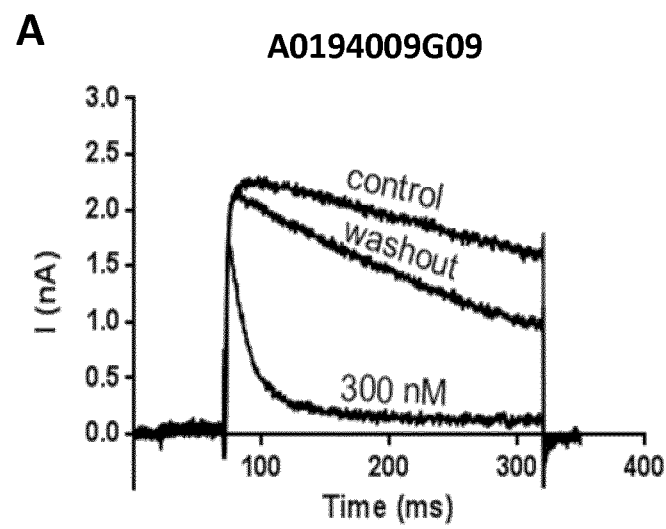
Figure 7:
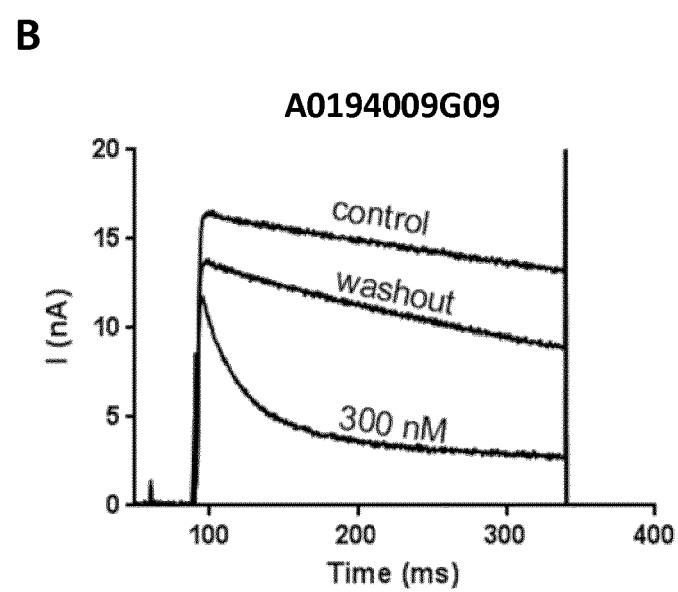

The results show a dose-dependent inhibition of the selected Nanobodies with almost complete current recovery. Data are given below in Table B-3, and the typical experiments are shown in FIGS. 5 to 7.

TABLE B-3

Characterization of monovalent human Kv1.3 channel inhibitory Nanobodies on Ionflux ™

| Nanobody ID | Average $IC_{50}$* (M) |
|---|---|
| A0194009G09 | 8.2E−09 |
| A01940016B04 | 8.4E−08 |
| A01940020A06 | 1.34E−08 |
| Reference compound | Average $IC_{50}$ (M) |
| ShK-1aJ (Smartox, #08SHK001) | 7.6E−11 |

*$IC_{50}$ values generated on the IonFlux ™ system (compound concentration at which Kv1.3 Ion channel current is 50% of the current in absence of the compound)

IonWorks

Selected Nanobodies were electrophysiologically characterized on human Kv1.3 on the IonWorks automated perforated-Patch Clamp using Kv1.3-expressing Chinese Hamster Lung (CHL) cells. The procedure for evaluating the modulatory effect of the purified Nanobodies on human Kv1.3 via electrophysiological recordings is given below.

IonWorks Quattro

IonWorks Quattro (Molecular Devices) is a second-generation screening instrument that provides membrane voltage control and provides a direct electrophysiological assay for screening and characterization of compounds. It is an automated, high-throughput planar perforated patch clamp that uses a 384-well PatchPlate™ substrate.

Solutions and Nanobody handling

Extracellular solution contained (in mM): 138 NaCl, 2.7 KCl, 0.9 CaCl2, 0.5 MgCl2, 8 $Na_2HPO_4$, and 1.5 $KH_2PO_4$ (pH 7.3 with NaOH, and 285-290 mOsmolar). The intracellular solution contained (in mM): 100 K-gluconate, 40 KCl, 3.2 EGTA, 5 HEPES and 3.2 MgCl2 (pH 7.3 with KOH, and 300-315 mOsmolar). These solutions were freshly made, stocked for no longer than a month at 4° C. and filtered prior to use. The selected Nanobodies were directly diluted in extracellular solution to obtain a 3 µM sample solution. A 96 well master plate was prepared by transferring 300 µL of 3 µM sample solution and an up plate dilution was carried out (1:3). For the Kv1.3 assay, 50 µl of each sample was transferred to columns of a 384-well plate (Costar polypropylene, #3657). Quinidine standard curves were included, along with vehicle (low) and quinidine (high: 300 µM final assay concentration) controls.

Cell Preparation Chinese Hamster Lung (CHL; Essen Bioscience) cell lines stably expressing the full length human Kv1.3 channel were cultured in T-175 cell culture flasks (Greinerbio-one, #660160) using standard culture medium DMEM (Invitrogen, #41965) containing 10% FBS (HyClone, #SH3007103), 1% non-essential amino acids (Invitrogen, #11140), 1% sodium-pyruvate (Invitrogen, #C11360), 1% penicillin+streptomycin (Invitrogen, #C10378), 200 µg/ml G418 (Invitrogen, #10131), 20 mM HEPES (Invitrogen, #15630-114), and 29 mM KCl (Sigma, #P5405). Cells were seeded at a density of 25.000 cells/$cm^2$ or 12.000 cells/$cm^2$ for 2 or 3 days respectively before being used on the IonWorks (Essen Bioscience). Optimal Cell confluence prior to harvesting was 50-80%. The cells were washed with 20 ml PBS without $Ca^{2+}$ and $Mg^{2+}$ (GibCo, #14190-094) and detached with 2 ml Trypsin/EDTA 0.25% (GibCo, #25200-056) for 6 min at 37° C. The cells were diluted with 10 ml of external buffer (GibCo, #14040). The suspension was transferred to a 15 ml centrifuge tube and centrifuged for 2 minutes at 200×g. The supernatant was removed and the pellet re-suspended in 4.5 ml of extracellular buffer. Following approximately 3 titrations with a 5 ml Corning Costar® stripette (Sigma-Aldrich, #CLS4487), a further 70 titrations were conducted with a 200 µl pipette. The cell suspension (at a density of 3-5M cells per ml) was added to the cell boat within the IonWorks and the experiment instigated.

IonWorks Procedure and Assay

The basic principles of IonWorks automated patch clamp electrophysiology are described by Schroeder et al. (J Biomol Screen 8(1):50-64, 2003). The experiments summarized therein used the population patch clamp (PPC) configuration described by Finkel et al. (J Biomol Screen 11(5):488-96, 2006). Either single cell single cell mode (HT) or population (PPC) mode was used in the assays, depending on the K, ion channel. In PPC mode, an ensemble average of the current from up to 64 cells per well was recorded.

Electrical access was achieved using 100 µg/ml amphotericin (Sigma, #A4888) in the internal solution to obtain the perforated-patch clamp configuration. Cells were initially held for a period of 30 s at −80 mV. A pulse train of fifteen depolarizing steps (P1 to P15) from −80 mV to +50 mV for 100 ms at 3 Hz pulse intervals was performed in control conditions (prior to compound addition). The Nanobodies were then incubated for 6 to 7 min prior to the second measurement using the identical pulse train (as shown in FIG. 8A).

IonWorks Data Inclusion Criteria and Data Analysis

Data points were accepted if the following well and plate Quality Control criteria were met:
 1) Individual seal resistances>20 MΩ on pre- and post-compound reads
 2) Individual peak Kv1.x current amplitude>500 pA
 3) Plate Z' value>0.4 (where determined)
 4) Plate average seal resistance>30 MΩ
 5) Plate average mean current amplitude>0.5 nA
 6) Standard $IC_{50}$ value within anticipated range Currents were measured using IonWorks software v.2.0.4.4. (Fluxion Biosciences). Kv1.3 currents were measured as sustained currents in the gating step pulse P1 (FIG. 8B). The effects of the compounds were quantified by dividing the current in the presence of the compound by the pre-compound current. The selective hKv1.3 channel blocker ShK-1aJ was used as reference standard in the hKv1.3 assay, while for the Kv1.5, Kv1.6 and hERG assay quinidine was used. This percentage of inhibition value was then normalized by using the following equation:

$$\text{Norm \% } I = \frac{100 - \left[\left(\frac{\text{post}}{\text{pre}}\right) \times 100\right]}{\text{Average}\left[\left(\frac{DMSOpost}{DMSOpre}\right) \times 100\right]}$$

Subsequently, the Kv1.3 data were further normalized to the maximal block control to remove the impact of the small (~10%) residual outward currents unblocked by quinidine. IonWorks software (Molecular devices), Microsoft Excel (Microsoft) and Prism 6 (GraphPad Software) were used to analyze and present $IC_{50}$ values and currents.

Representative Kv1.3 current traces of Nanobody A0194009G09 reveal a potent concentration-dependent inhibition with nearly full block at highest tested dose (FIGS. 9A and 9B). The correlated concentration-response curve for the inhibition of human Kv1.3 channels, measured as normalized mean $I_{sustained}$ is presented in FIG. 9C.

Representative Kv1.3 current traces of Nanobody A0194000003 demonstrate a biphasic modulatory effect on Kv1.3 ion channels with at low concentrations (e.g. 130 pM) an attenuated cumulative pulse to pulse interaction (FIG. 10A), and at higher concentrations (e.g. 100 nM) an inhibitory effect (FIG. 10B). The correlated concentration-response curve for the inhibition of human Kv1.3 channels, measured as normalized mean $I_{sustained}$ is presented in FIG. 10C. Corresponding $IC_{50}$ values are given in Table B-4.

TABLE B-4

Characterization of monovalent human Kv1.3 inhibitory Nanobodies on IonWorks

| Nanobody ID | Average $IC_{50}$* (M) |
| --- | --- |
| A0194009G09 | 3.7E−08 |
| A0194016B04 | 3.4E−08 |
| A019400003 | >1 µM |
| Reference compound | Average $IC_{50}$ (M) |
| ShK-1aJ (Smartox, #08SHK001) | 4E−10 |

*$IC_{50}$ values generated on the IonWorks (compound concentration at which Kv1.3 Ion channel current is 50% of the current in absence of the compound)

4.4 Inhibition by Monovalent Anti-Kv1.3 Nanobodies of IFNγ Production and CD25 Expression of CCR7⁻CD45RA⁻ T Cells after Stimulation with Anti-CD3

The purified anti-Kv1.3 Nanobodies were characterized in a T Cell-activation assay. Human T Cells were first collected from Buffy Coat blood (from healthy volunteers, Bloodbank Gent) using RosetteSep (StemCell Technologies, #15061) followed by an enrichment on Ficoll-Paque™ PLUS (GE Healthcare #17-1440-03). CCR7–CD45RA– T cells were isolated through negative selection using biotinylated antibodies against CD45RA (BD Bioscience #624008) and CCR7 (BD Bioscence #624009) in addition to the Dynabeads Biotin Binder (Invitrogen #110.47). The purity of the population was afterwards checked with anti-CD3 (eBioscience #12-0037-73); anti-CD8 (BD Bioscience #345775); anti-CD4 (BD Bioscience #345771); anti-CD45RO (BD Bioscience #555493); anti-CD45RA (BD Bioscience #550855); anti-rat IgG (Jackson ImmunoResearch Laboratories #112-116-143); anti-CD19 (BD Bioscience #555413) and anti-Human CCR7 (R&D Systems #MAB197) labeled antibodies in flow cytometric assay.

Isolated CCR7⁻CD45RA⁻ T Cells were then stimulated on anti-CD3 (eBioscience 16-0037-85; 540 ng/ml) coated 96-well plates at a concentration of 200 000 cells/well in absence or presence of dilution series of anti-Kv1.3 antibodies and ShK positive control (Smartox, #08SHK001). After 72 h, IFN-gamma production was measured with anti-human IFNγ antibody capture in ELISA (BD Bioscence #551221) combined with biotinylated anti-human IFNγ (BD Bioscience, #554550) and streptavidin-HRP (Dakocytomation #P0397) as detection (FIG. 11A-11B).

Figure 11:
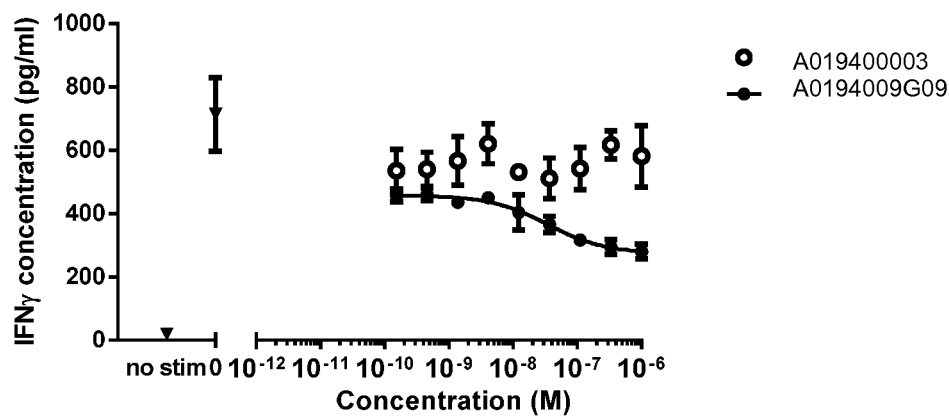
Figure 11:
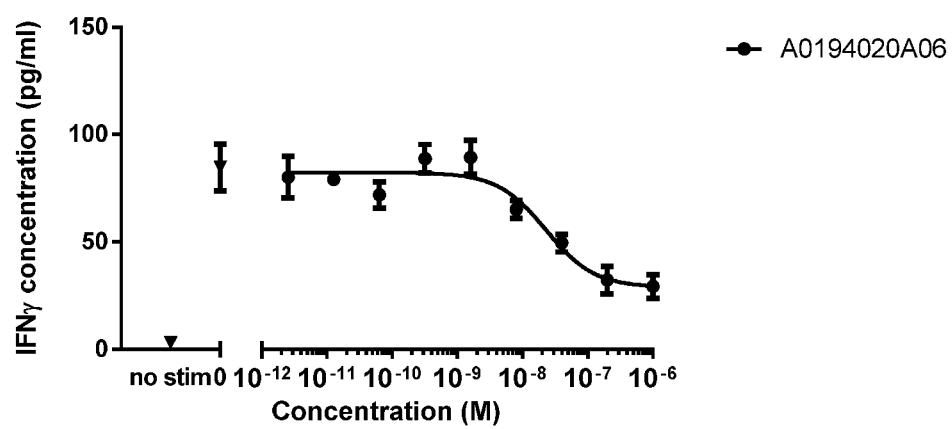
Figure 11:
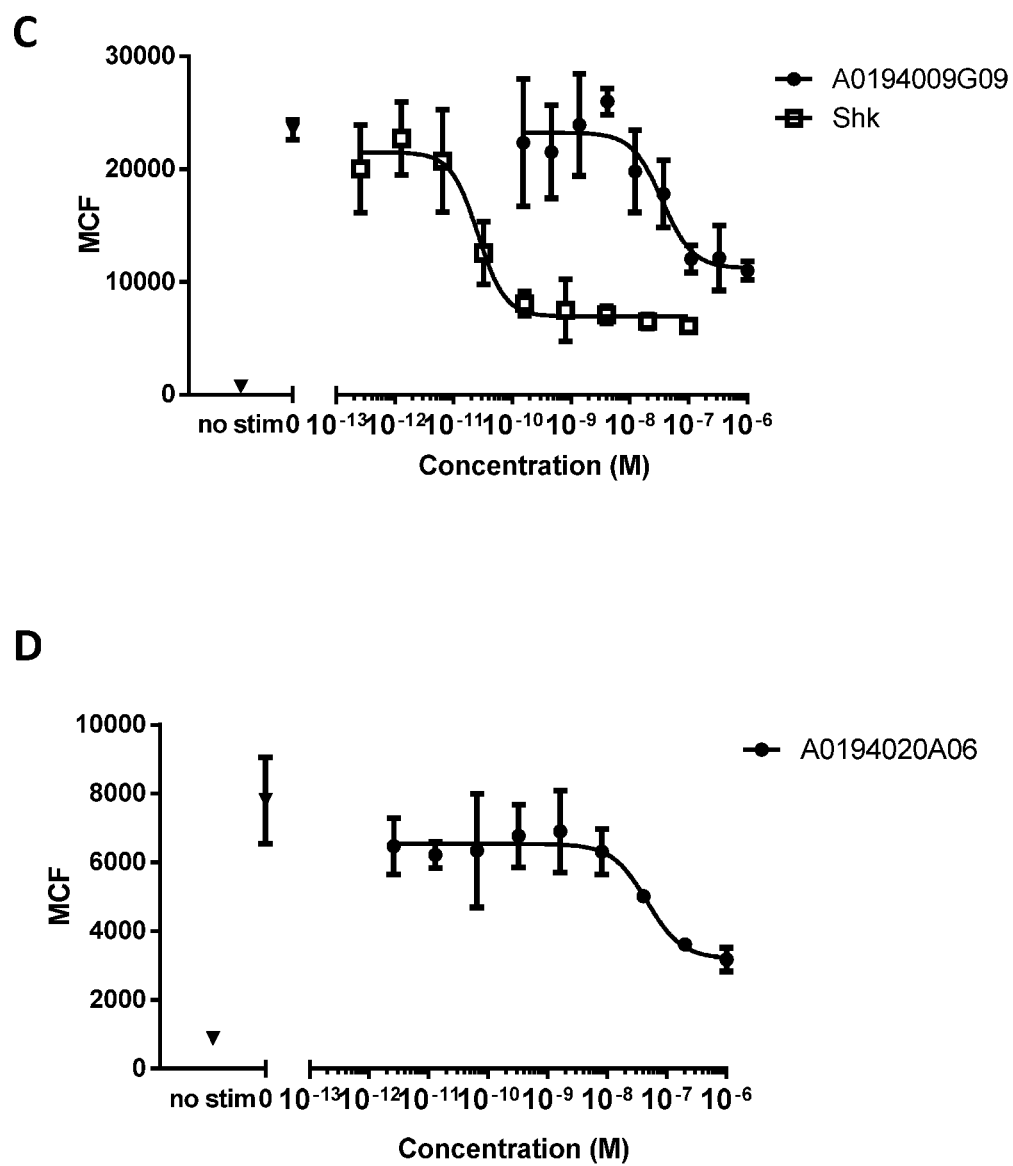
Figure 12:
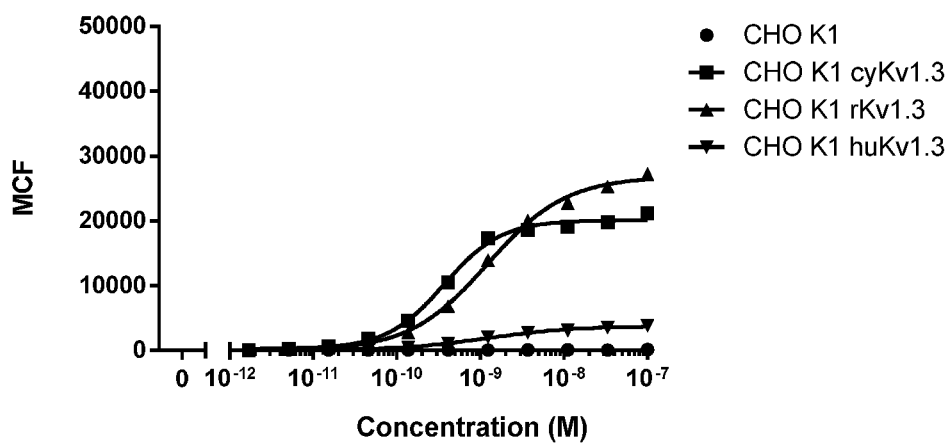
Figure 12:
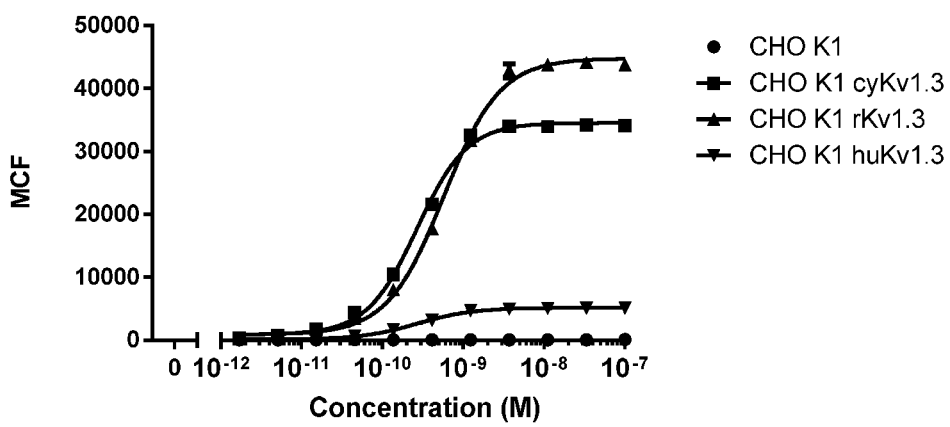
Figure 12:
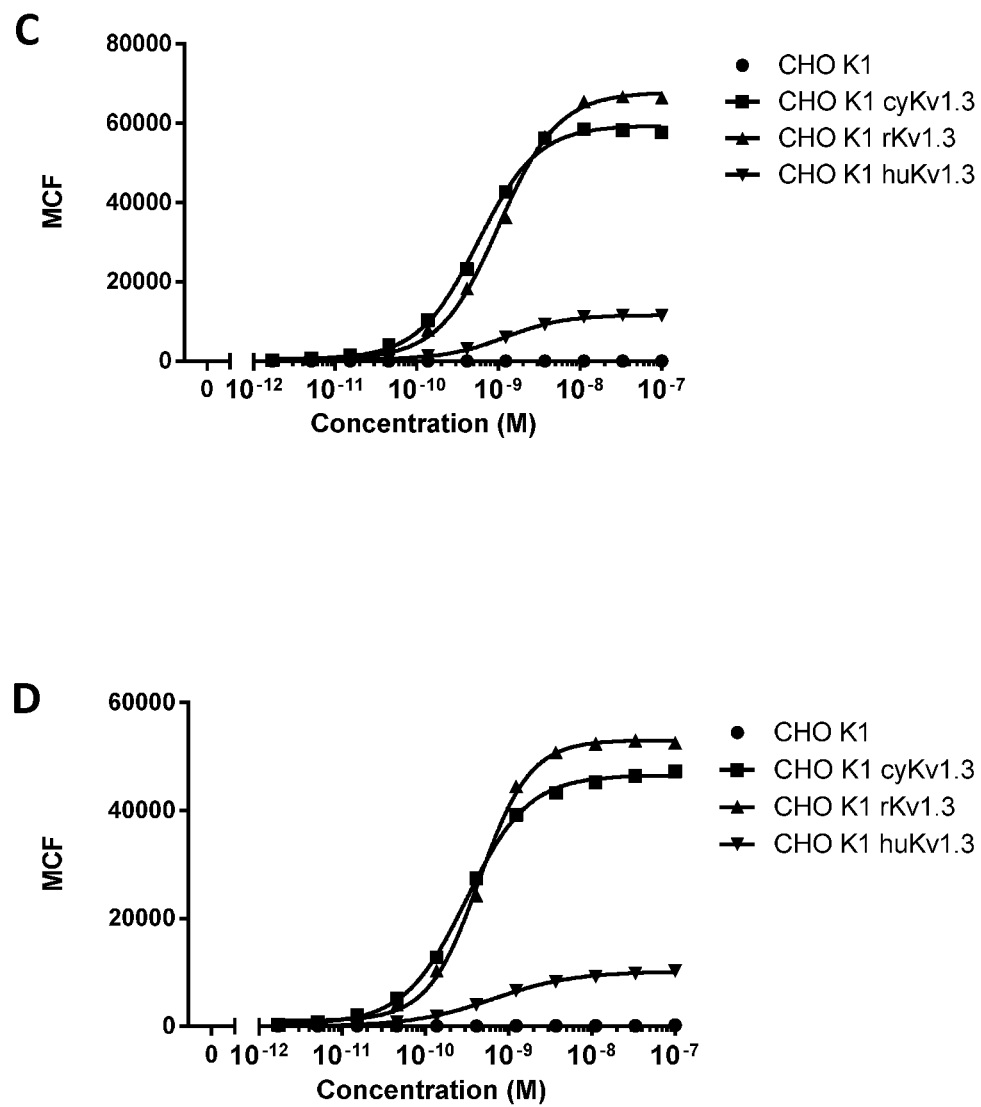
Figure 13:
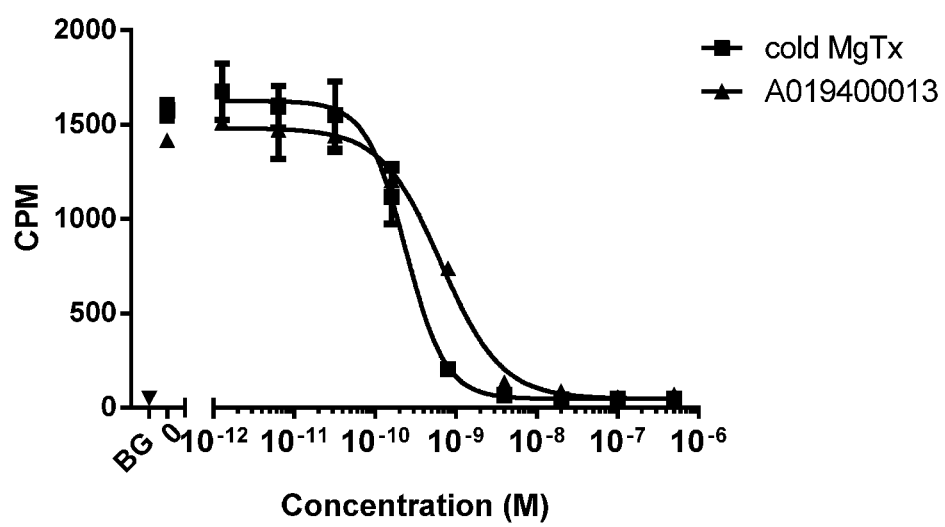
Figure 13:
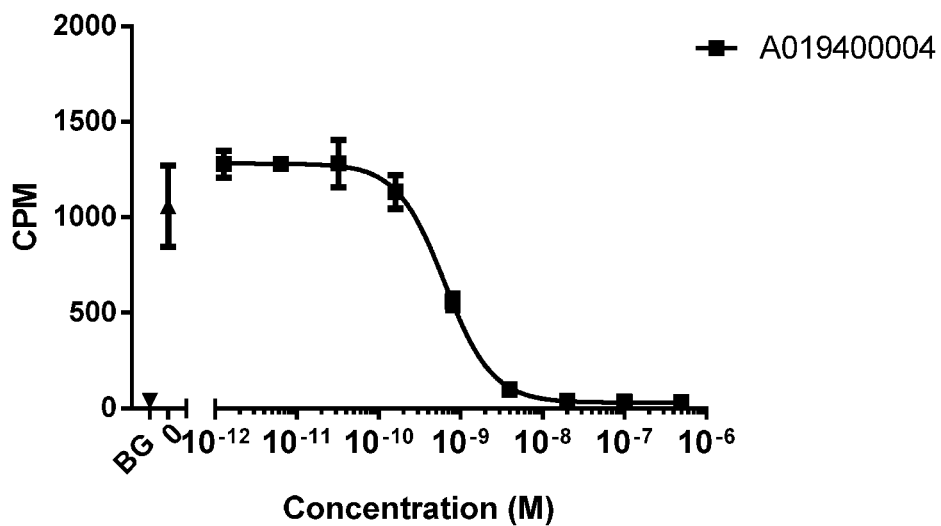
Figure 13:
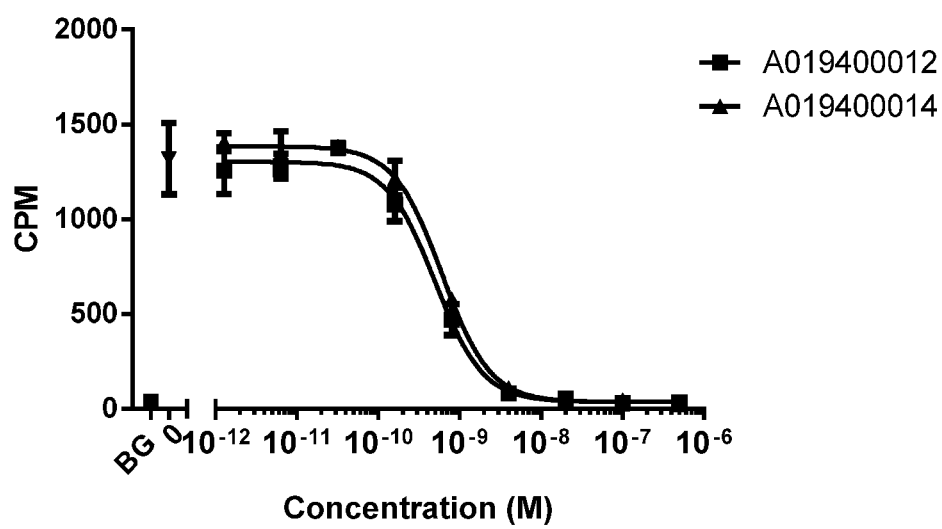
Figure 13:
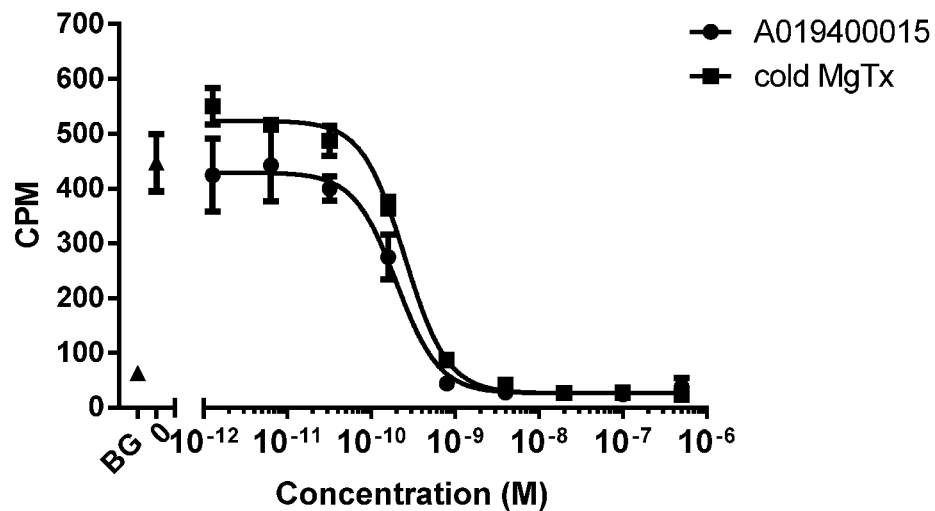
Figure 13:
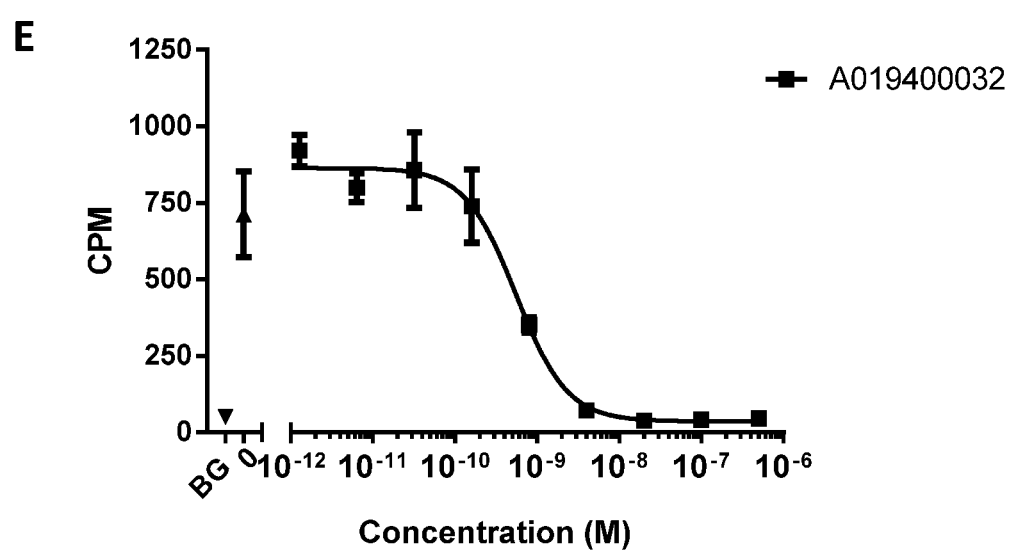

In addition, also CD25 expression was measured in flow cytometry, using an anti-CD25 antibody (BD Pharmingen, cat 557138) (FIG. 11C-11D). The A019400003 Nanobody did not block the stimulation of T-cells, whereas A0194009G09 and A0194020A06 clearly inhibited the responses, however with lower potency compared to ShK. The average inhibitory $IC_{50}$ values of the anti-Kv1.3 monovalent Nanobodies are depicted in Table B-5.

TABLE B-5

Inhibition by monovalent anti-Kv1.3 Nanobodies of IFNγ secretion and CD25 expression by CCR7⁻CD45RA⁻ T cells after stimulation with plate bound anti-CD3

| VHH ID/compound | $IC_{50}$ (in M) IFNγ read out | $IC_{50}$ (in M) CD25 read out |
| --- | --- | --- |
| irrelevant Nb | no effect | no effect |
| MgTX | 9.4E−11 | no fit |
| ShK | 7.6E−11 | 2.7E−10 |
| A0194009G09 | 4.7E−08 | 6.2E−08 |
| A019400003 | no effect | no effect |
| A01940020A06 | 3.0E−08 | 3.6E−08 |

Example 5: Generation and Screening of Multivalent Kv1.3 Blocking Nanobodies 5.1 Construction of Bivalent and Trivalent, Mono- and Bispecific Formats In order to increase potency and/or efficacy, bi- and trivalent molecules were constructed by genetic engineering. Two or three Nanobodies were genetically linked together with a 35GS linker in between the building blocks and subsequently expressed in *Pichia* according to standard conditions. Different multivalent constructs were made as listed in Table A-6.

5.2 Binding of Multivalent Anti-Kv1.3 Nanobodies to Human, Cyno and Rat Kv1.3 Expressed on CHO Cells Binding of the bi- and trivalent constructs to human, cyno and rat Kv1.3 was performed as outlined in Example 4.1 and is presented in FIG. 12A-12D. The data indicate an improved binding of the formatted variants on all targets compared to their monovalent counterparts (see FIG. 3). The $EC_{50}$ values obtained from the dose response curve are depicted in Table B-6.

TABLE B-6

$EC_{50}$ (M) of anti-Kv1.3 multivalent Nanobodies for binding on cyno, rat, and human Kv1.3 expressed on CHO cells as determined in FACS

| VHH ID | CHO cyKv1.3 | CHO ratKv1.3 | CHO huKv1.3 |
| --- | --- | --- | --- |
| A019400004 | 4.4E−10 | 1.1E−09 | 2.2E−09 |
| A019400013 | 2.4E−10 | 4.9E−10 | 3.2E−10 |

TABLE B-6-continued

EC$_{50}$ (M) of anti-Kv1.3 multivalent Nanobodies
for binding on cyno, rat, and human Kv1.3 expressed
on CHO cells as determined in FACS

| VHH ID | CHO cyKv1.3 | CHO ratKv1.3 | CHO huKv1.3 |
|---|---|---|---|
| A019400014 | 4.1E−10 | 7.4E−10 | 1.1E−09 |
| A019400015 | 3.1E−10 | 4.4E−10 | 6.6E−10 |

5.3 Inhibition by Multivalent Anti-Kv1.3 Nanobodies of 125I Margatoxin Binding to Cyno Kv1.3 Expressed on CHO Cell The inhibition of margatoxin binding to cyno Kv1.3 was investigated for the different formats as described in Example 3.3 and Example 4.2 (FIG. 13A-13E). Anti-Kv1.3 Nanobodies completely block binding of 150 pM I125 margatoxin to cyno Kv1.3. The background (BG) is the control condition where no I125 margatoxin was added. A clearly improved potency was observed compared to its monovalent counterparts (FIG. 4). An overview of the obtained IC$_{50}$ values is shown in Table B-7.

TABLE B-7

Inhibition of radiolabeled 125I-MgTX binding to cyno Kv1.3
expressed on CHO cells by anti-Kv1.3 multivalent Nanobodies

| VHH ID/compound | IC$_{50}$ (in M) |
|---|---|
| A019400013 | 6.6E−10 |
| A019400004 | 6.4E−10 |
| A019400012 | 5.0E−10 |
| A019400014 | 6.1E−10 |
| A019400015 | 2.0E−10 |
| A019400032 | 5.6E−10 |
| ShK-1aJ (Smartox, #08SHK001) | 2.4E−10 |

5.4 Electrophysiological Characterization of Multivalent Kv1.3 Inhibitory Nanobodies on Human Kv1.3 Expressing HEK293H and Kv1.3 Expressing CHL Cells IonFlux™

Selected Nanobodies were electrophysiologically characterized on human Kv1.3 on the IonFlux™ automated Patch Clamp using Kv1.3-expressing HEK293H cells. The complete procedure for evaluating the modulatory effect of the purified Nanobodies on human Kv1.3 via electrophysiological recordings is given in Examples 3.2 and 4.3. A time course protocol was applied to assess the Nanobody potencies (IC$_{50}$) on potassium currents elicited by a depolarizing pulse protocol (FIG. 2A). In a "wash-off" experiment, a single high dose of Nanobody (300 nM) was applied during 120 s, followed by a continuous perfusion of extracellular buffer for at least 5 min, in order to assess the rate of current recovery during washout. In these experiments both population and single cell automated patch clamp were used to record current amplitudes.

Figure 14:
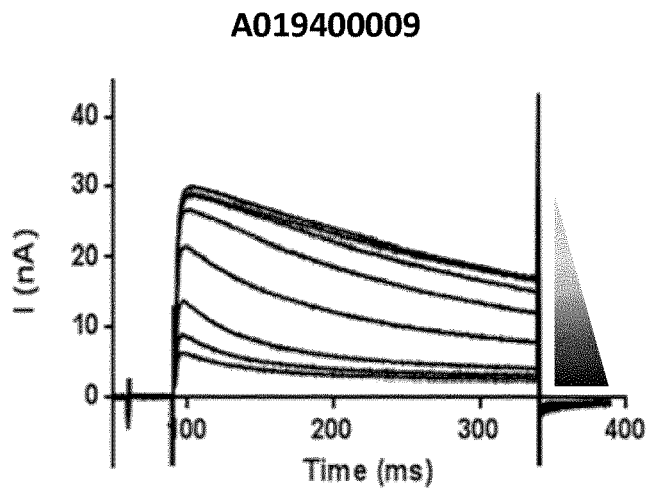
Figure 14:
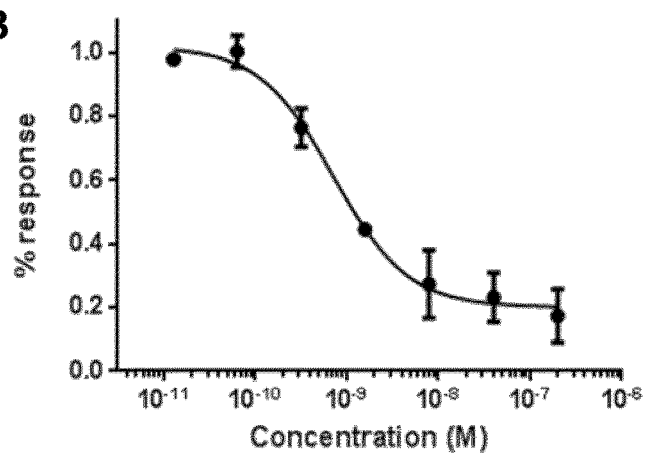
Figure 14:
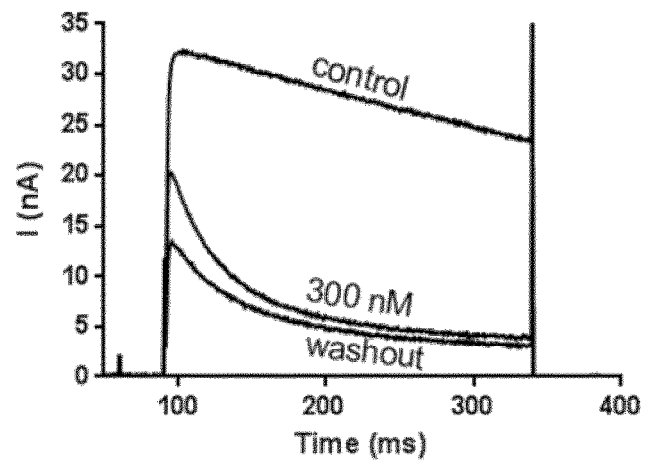
Figure 15:
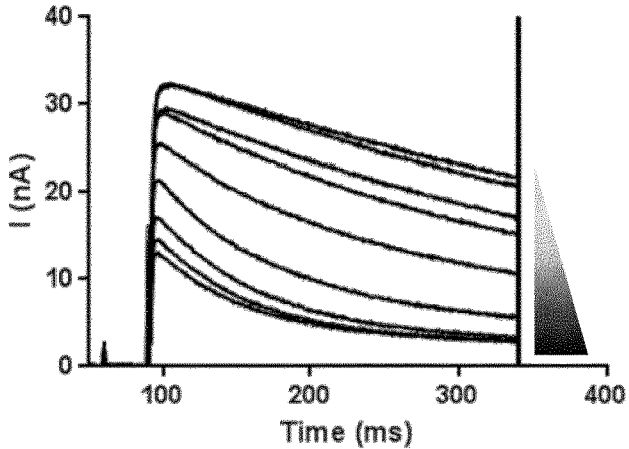
Figure 15:
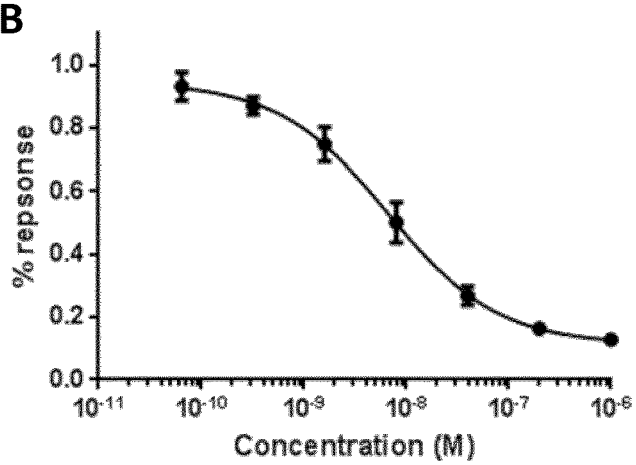
Figure 15:
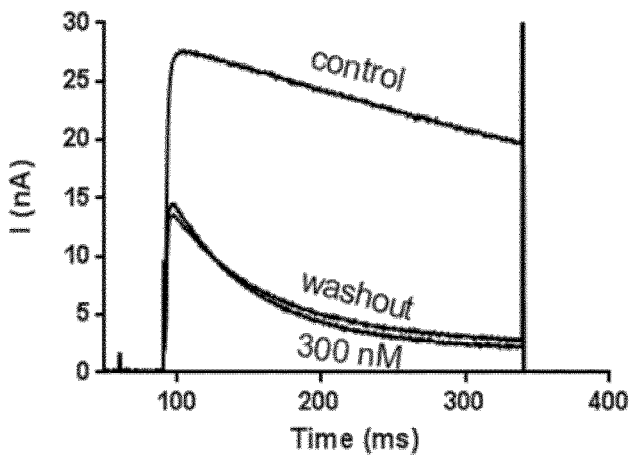
Figure 16:
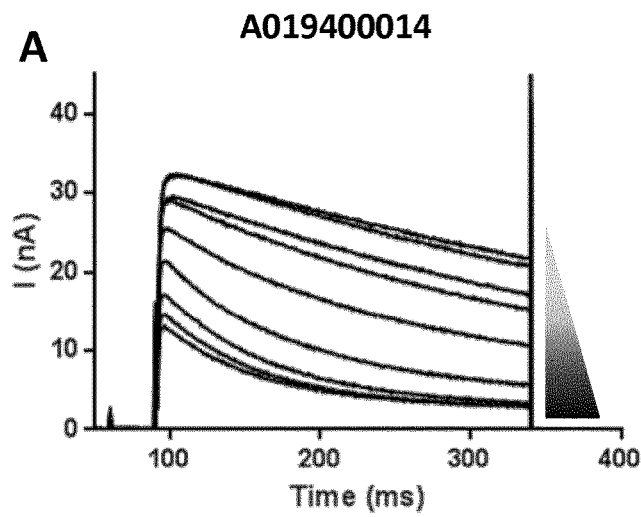
Figure 16:
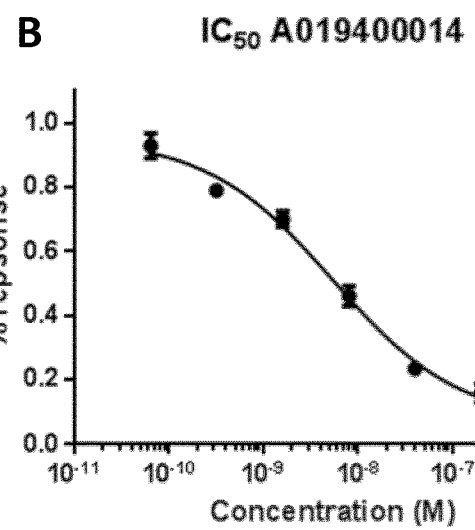
Figure 16:
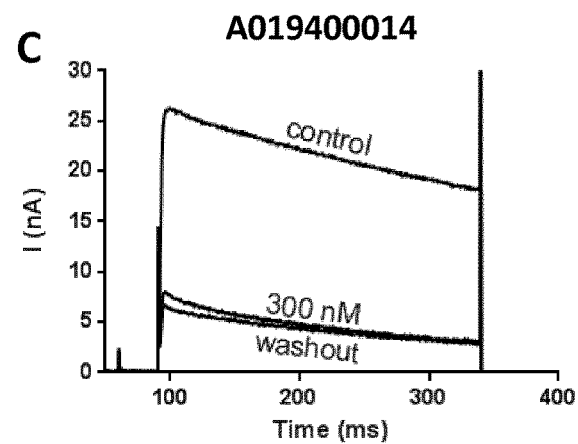
Figure 17:
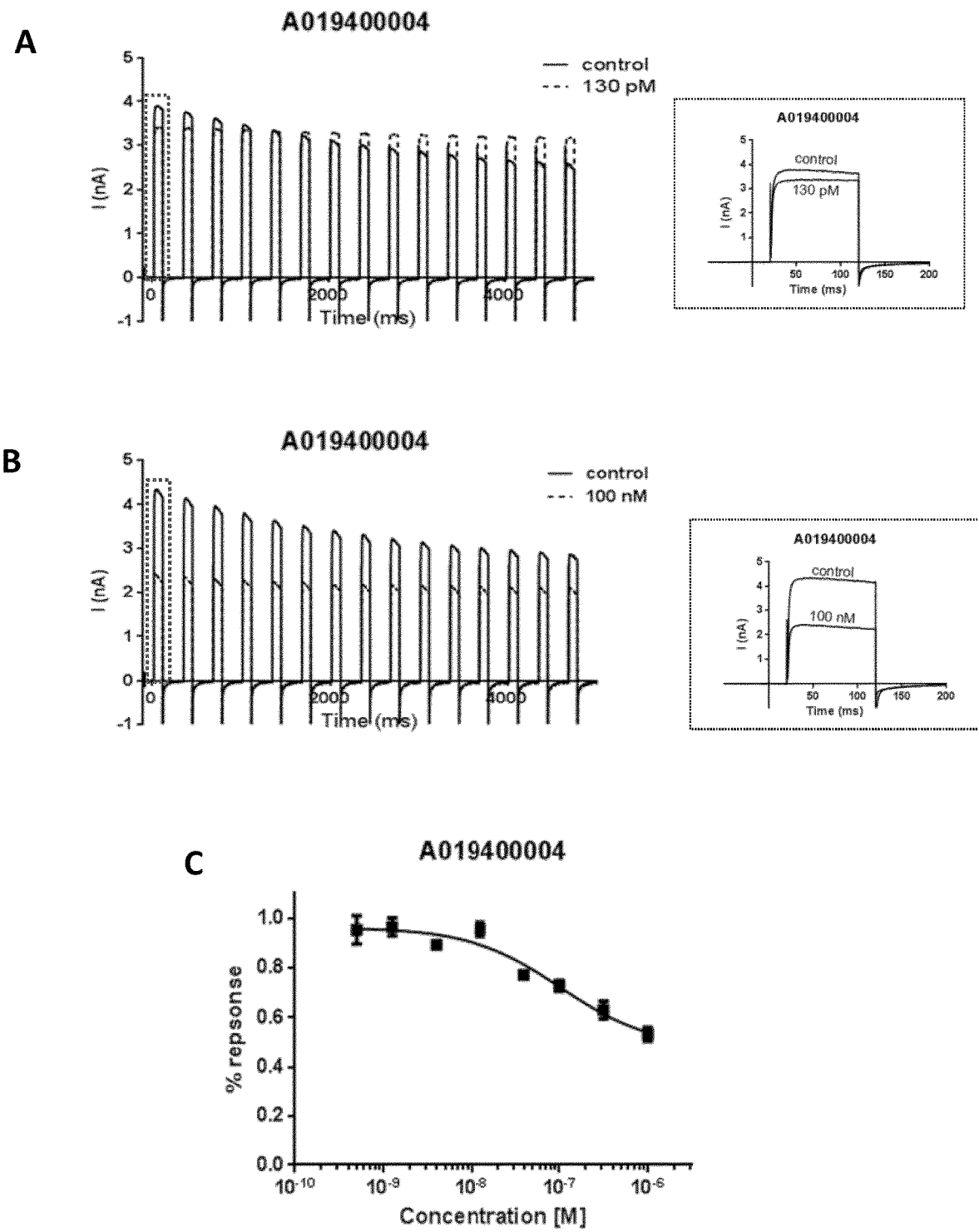
Figure 18:
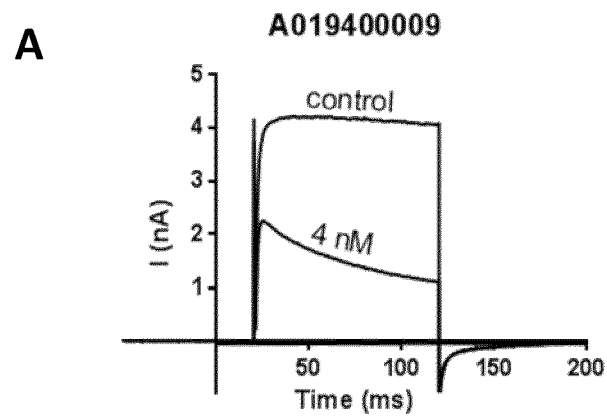
Figure 18:
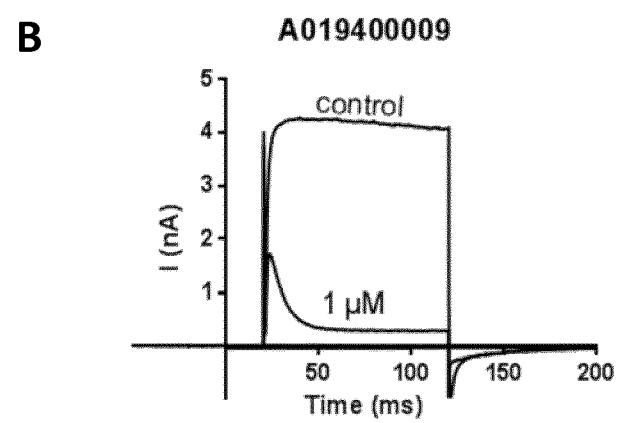
Figure 18:
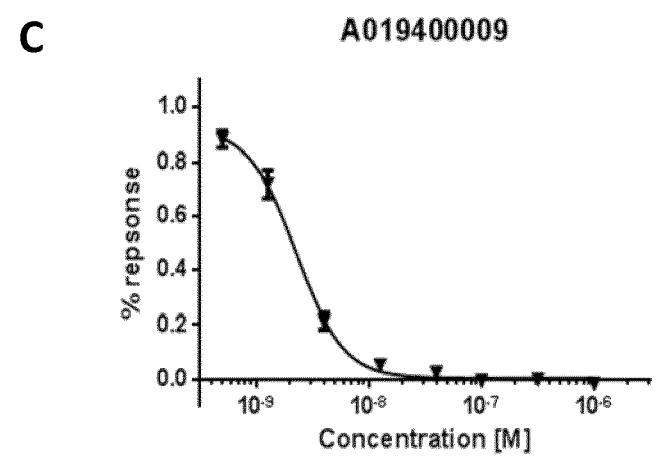
Figure 19:
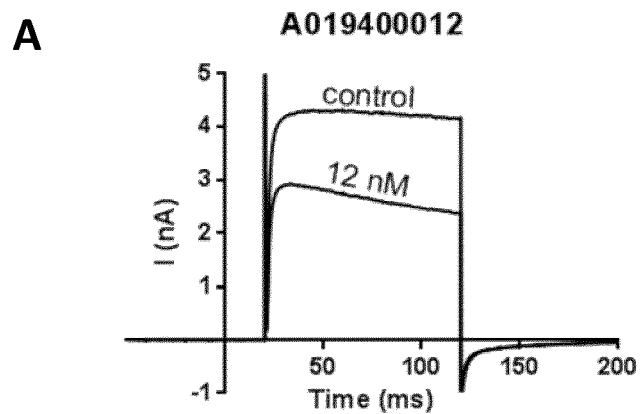
Figure 19:
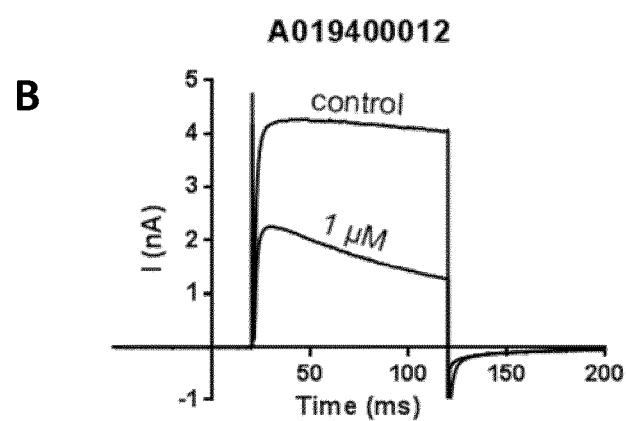
Figure 19:
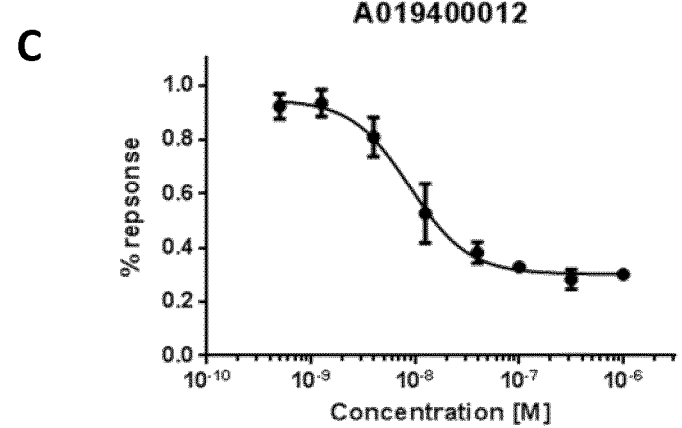
Figure 20:
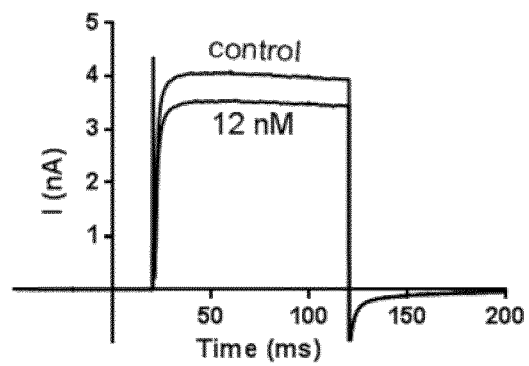
Figure 20:
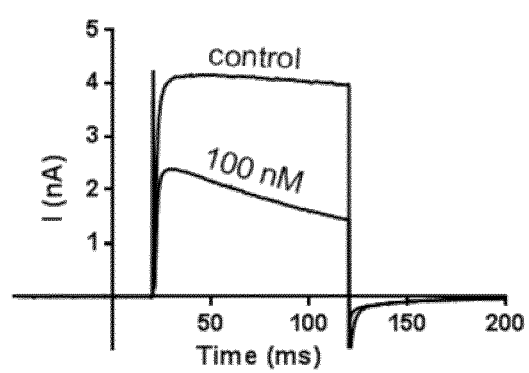
Figure 20:
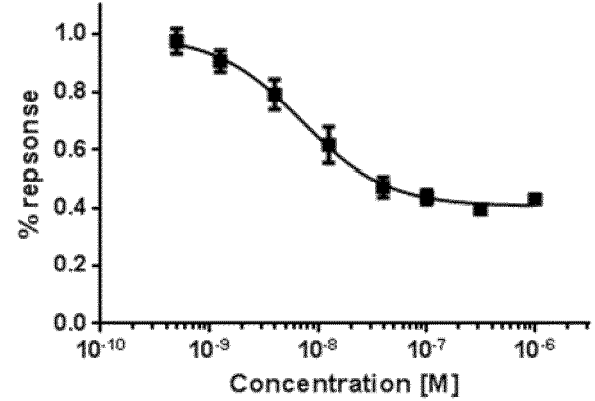
Figure 21:
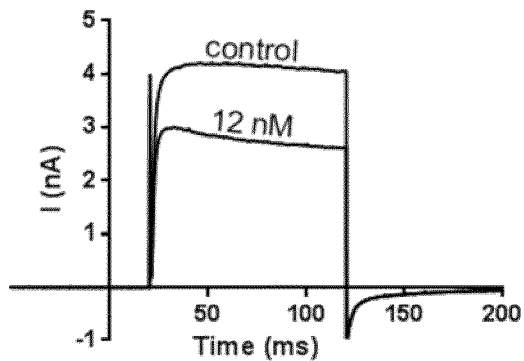
Figure 21:
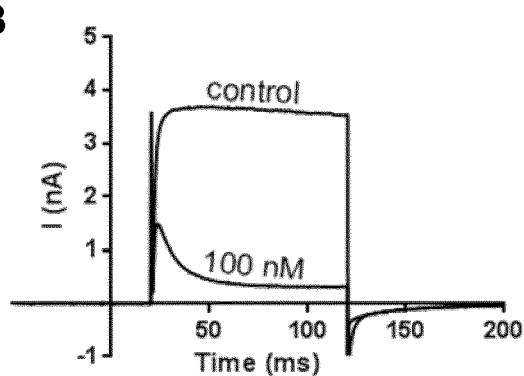
Figure 21:
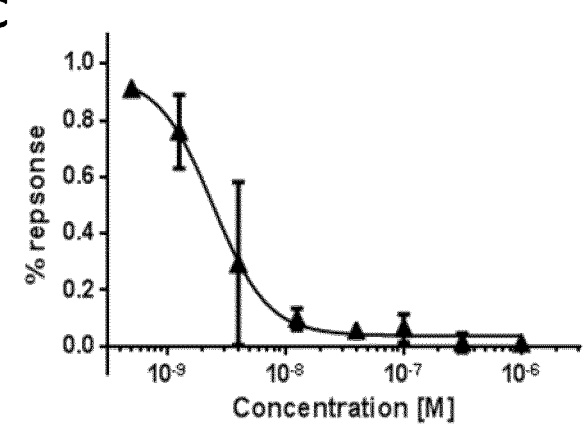
Figure 22:
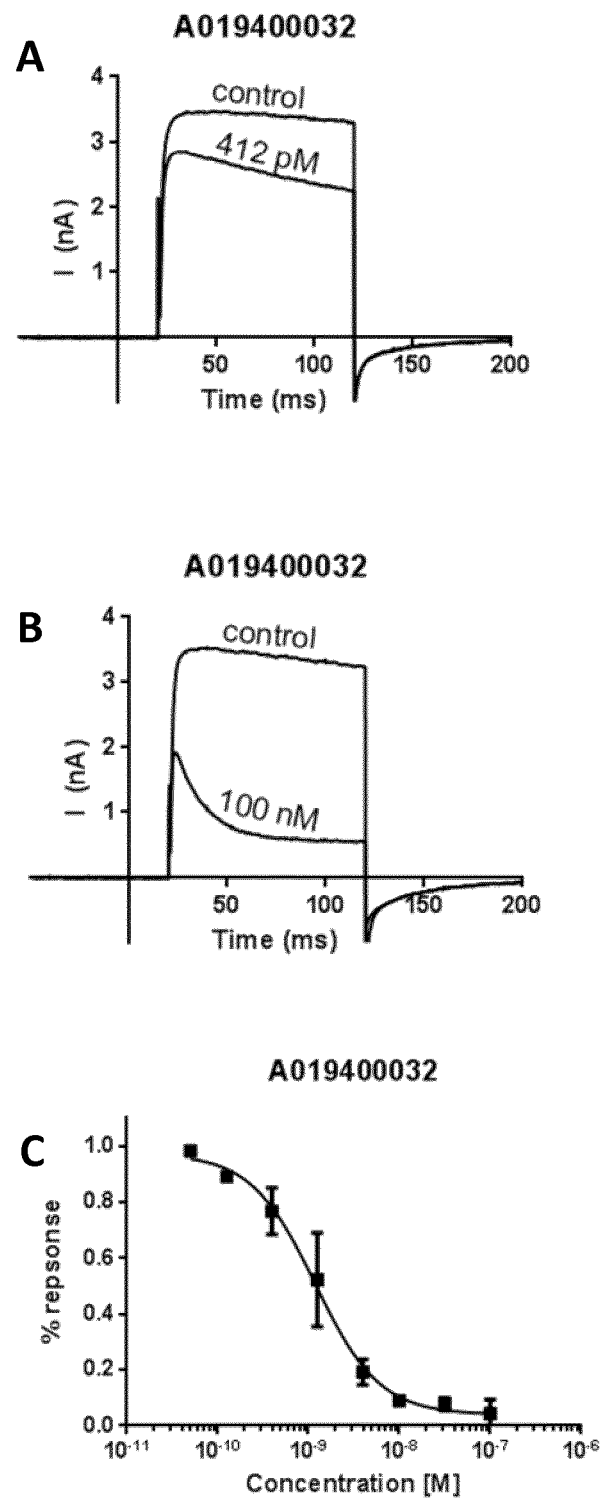
Figure 23:
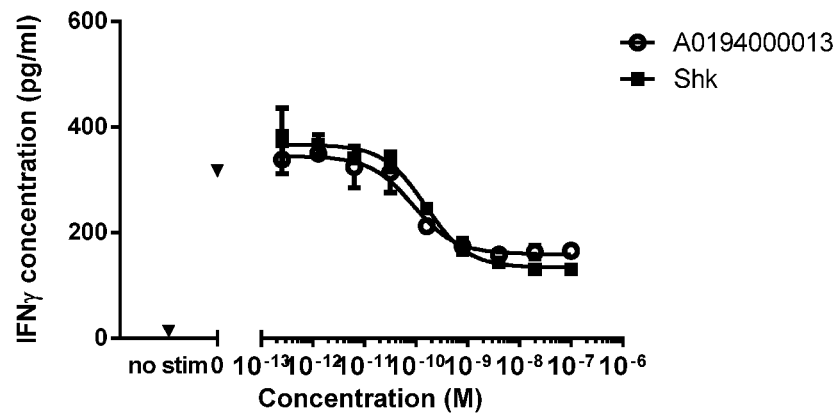
Figure 23:
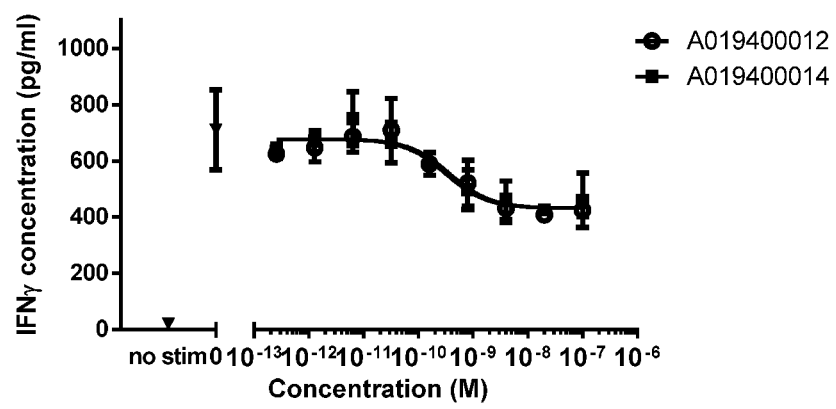
Figure 23:
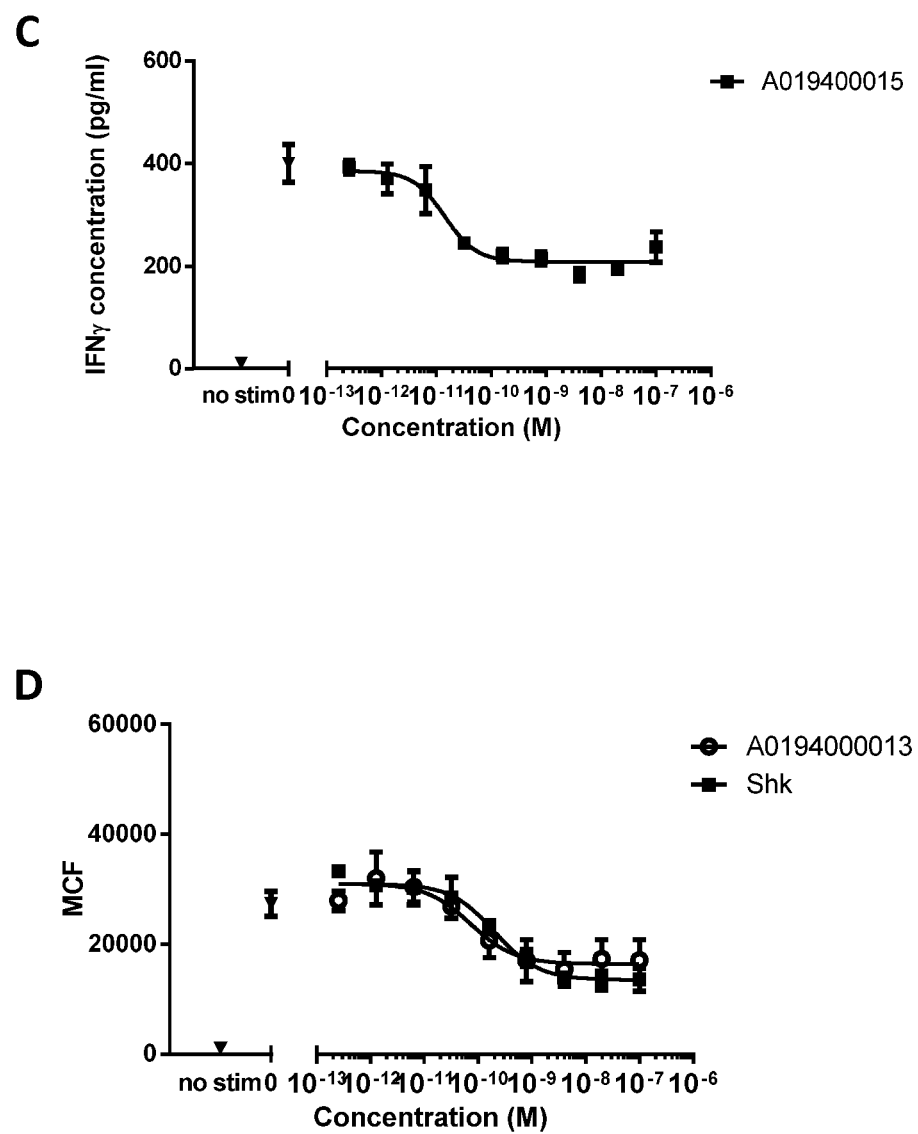
Figure 23:
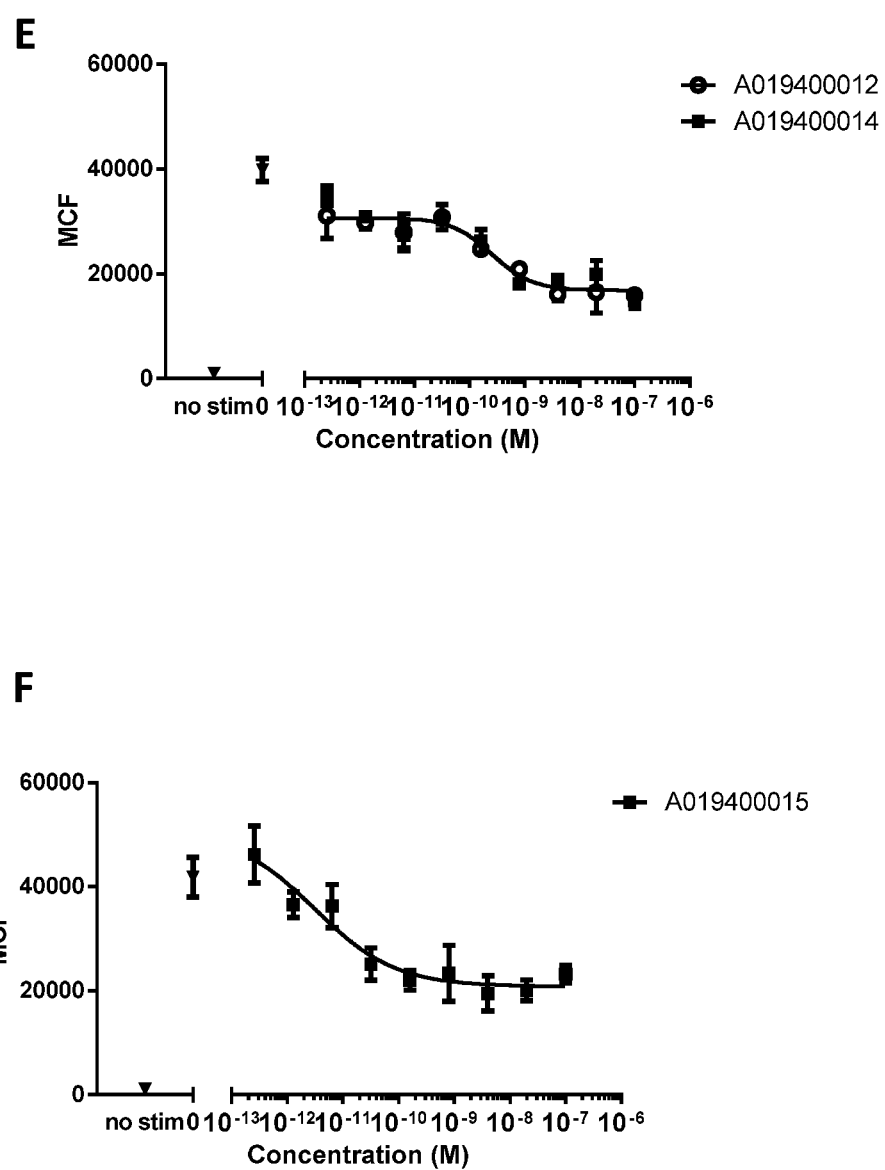

The selected Nanobodies A019400009, A019400012 and A019400014 produced a concentration-dependent inhibition with partial to full block at highest dose, and no current recovery could be observed after at least 5 min washout with extracellular buffer (FIGS. 14-16). Corresponding IC$_{50}$ values are given in Table B-8.

TABLE B-8

Characterization of multivalent human Kv1.3 channel inhibitors

| Nanobody ID | Nanobody format | Average IC$_{50}$ *(M) |
|---|---|---|
| A019400009 | Bivalent | 7.3E−10 |
| A019400012 | Biparatopic | 4.2E−09 |
| A019400014 | Biparatopic | 1.4E−08 |

| Reference compound | | Average IC$_{50}$ (M) |
|---|---|---|
| ShK-1aJ (Smartox, #08SHK001) | | 7.6E−11 |

* IC$_{50}$ values generated on the IonFlux ™ system (compound concentration at which Kv1.3 Ion channel current is 50% of the current in absence of the compound)

IonWorks

Selected Nanobodies were electrophysiologically characterized on human Kv1.3 on the IonWorks automated perforated Patch Clamp using Kv1.3-expressing Chinese Hamster Lung (CHL) cells. The procedure for evaluating the modulatory effect of the purified Nanobodies on human Kv1.3 via electrophysiological recordings is given in Example 4.3. Repeated gating voltage-command protocols were employed to determine Nanobody potencies (IC$_{50}$). Kv1.3 currents were measured as sustained currents in the first gating step pulse P1 (see FIG. 8).

The half maximal inhibitory concentrations (IC$_{50}$) were calculated at room temperature from eight-point concentration-response curves with an n=4 at each concentration. The effects of the compounds were quantified by dividing the current in the presence of the compound by the pre-compound current. The selective hKv1.3 channel blocker ShK-1aJ (Smartox, #08SHK001) was used as reference standard in the hKv1.3 assay. This percentage of inhibition value was then normalized as described in Example 4.3. The Kv1.3 data was then further normalized to the maximal block control to remove the impact of the small (~10%) residual outward currents unblocked by ShK-1aJ. IonWorks software v.2.0.4.4. (Molecular devices), Microsoft Excel (Microsoft) and Prism 6 (GraphPad Software) were used to analyze and present IC$_{50}$ values and currents.

Results are presented in FIGS. 17 to 22. Kv1.3 current traces of Nanobody A019400004 demonstrate a biphasic modulatory effect on Kv1.3 ion channels with, at low concentrations (e.g. 130 pM), an attenuated cumulative pulse to pulse interaction (FIG. 17A), and at higher concentrations (e.g. 100 nM), an inhibitory effect (FIG. 17B). The correlated concentration-response curve for the inhibition of human Kv1.3 channels, measured as normalized mean I$_{sustained}$ is presented in FIG. 17C.

Representative Kv1.3 current traces of the multivalent Nanobodies A019400009, A019400012, A019400014, A019400015 and A019400032 reveal a concentration-dependent inhibition with partial to full block at highest tested dose (FIGS. 18A-18B to 22A-22B, respectively) and the correlated concentration-response curves for the inhibition of human K$_v$1.3 channels, measured as normalized mean I$_{sustained}$ are presented in FIGS. 18C to 22C, respectively. The IC$_{50}$ values are given in Table B-9.

TABLE B-9

Characterization of the human Kv1.3 channel inhibitors

| Nanobody ID | Nanobody format | Average IC$_{50}$* (M) |
|---|---|---|
| A019400004 | Bivalent | >1 µM |
| A019400009 | Bivalent | 8.1E−10 |
| A019400012 | Biparatopic | 4.2E−09 |
| A019400014 | Biparatopic | 1.4E−08 |

TABLE B-9-continued

Characterization of the human Kv1.3 channel inhibitors

| A019400015 | Trivalent | 8E−10 |
|---|---|---|
| A019400032 | bivalent | 1.2E−09 |
| Reference compound | | Average IC$_{50}$ (M) |
| ShK-1aJ (Smartox, #08SHK001) | | 4E−10 |

*IC$_{50}$ values generated on the IonWorks (compound concentration at which Kv1.3 Ion channel current is 50% of the current in absence of the compound)

5.5 Inhibition by Multivalent Anti-Kv1.3 Nanobodies of IFNγ Production and CD25 Expression by CCR7⁻CD45RA⁻ T Cells after Stimulation with Anti-CD3

The inhibition of CCR7⁻CD45RA⁻ T cell activation after stimulation with anti-CD3 was evaluated for the bi- and trivalent constructs. An identical assay setup was used as described above (see Example 4.4). Obtained results are summarized in Table B-10 and FIGS. 23A-23F. The formatted bivalent (A019400013) and trivalent (A019400015) Nanobodies inhibited IFNγ secretion and CD25 expression with a similar potency compared to ShK. The biparatopic Nanobodies (A019400012 and A019400014) were slightly less potent.

TABLE B-10

Inhibition by multivalent anti-Kv1.3 Nanobodies of IFNγ secretion and CD25 expression by CCR7⁻CD45RA⁻ T cells after stimulation with plate bound anti-CD3.

| VHH ID/compound | IC$_{50}$ (in M) IFNγ read out | IC$_{50}$ (in M) CD25 read out |
|---|---|---|
| A019400004 | no effect | no effect |
| A019400013 | 8.3E−11 | 1.2E−10 |
| A019400015 | 3.2E−11 | 5.9E−11 |
| A019400012 | 3.1E−10 | 3.1E−10 |
| A019400014 | 3.2E−10 | 1.1E−10 |
| A019400032 | 6.9E−11 | 1.2E−10 |
| ShK-1aJ (Smartox, #08SHK001) | 6.5E−11 | 2.2E−10 |

Example 6: Mapping of the Binding Epitope of the Anti-Kv1.3 Nanobodies

In order to determine the binding epitope of the Nanobodies belonging to different B-cell lineages; binding of anti-Kv1.3 Nanobodies to mutant Kv1.3 constructs expressed on HEK293H cells was checked in flow cytometry. In these mutants the first extracellular loop (EL1) was replaced by an irrelevant amino acid stretch. Expression of these constructs was evaluated with fluorescently labeled agitoxin (rAgitoxin-2-Cys-TAMRA (Alomone Labs #RTA-420-T)) in flow cytometry (see FIG. 24). The experiment was performed as outlined in Example 4.1 with the difference that cells were used with expression of Kv1.3 EL1 mutants instead of WT human Kv1.3. None of the evaluated samples showed detectable binding to the Kv1.3 EL1 mutants (data not shown).

Example 7: Allosteric Binding

To evaluate the competition between the toxin ShK and the Nanobodies for binding to Kv1.3, a FACS competition experiment was performed using HEK293H cells overexpressing human Kv1.3 and the parental HEK293H cells as background cell line. As detection reagent, FAM-labeled ShK was used (6-FAM-AEEAc-*Stichodactyla helianthus* Neurotoxin (ShK) (Bachem, H-6088, 1046522, PRT00000366/01/01)). To setup the assay, first a titration series of the labeled Shk-FAM was performed on the HEK293H Kv1.3 cells in order to determine the EC$_{50}$ value for binding. In order to determine allosteric competition, so working at saturating concentration, the labeled ShK-FAM was used at 100× the EC$_{50}$ concentration in the competition experiment (70 nM).

In brief, a dilution series of ShK or Nanobody were added together with the labeled toxin to 200 000 cells in a 96-well plate. After 90 minutes incubation at 4° C., cells were washed three times before read out was performed on a FACS Canto (Becton Dickinson). First a gate was set on the intact cells as determined from the scatter profile. Next, dead cells were gated out by their fluorescence profile from the TOPRO stain (5 nM, Molecular probes, T3605). Results are provided in FIG. 25. The monovalent A019400003 and A0194009G09 only partially blocked binding of FAM labeled ShK to Kv1.3 whereas the unlabeled ShK completely blocked binding indicating that the monovalent Nanobodies allosteric compete with the ShK toxin. The percentage of inhibition for Nanobodies blocking the interaction of ShK to human Kv1.3 is depicted in Table B-11.

TABLE B-11

FACS competition assay: competition between high concentration of ShK-Fam (70 nM) and anti-Kv1.3 Nanobodies for binding to HEK 293H hu Kv1.3 cells

| | % inhibition |
|---|---|
| A019400003 | 87.13 |
| A0194009G09 | 40.79 |
| ShK (non labeled) | 102.27 |

Example 8: Exploration of Half-Life Extension

Alb11, a Nanobody binding to human serum albumin was linked to the multivalent Kv1.3 Nanobodies to increase the in vivo half-life of the formatted molecules (WO 06/122787). Different formats were made including different positioning of the different composing Nanobodies. An overview of the explored formats is shown in Table A-3.

As the binding of human serum albumin (HSA) to the Alb11 Nanobody might have an impact on the potency of the (multivalent) Nanobody, the half-life extended Nanobodies were characterized in several assays in the presence of HSA (see Examples 8.3, 8.4 and 8.5 infra).

8.1 Evaluation of positioning of the Alb11 Nanobody in FACS

Figure 26:
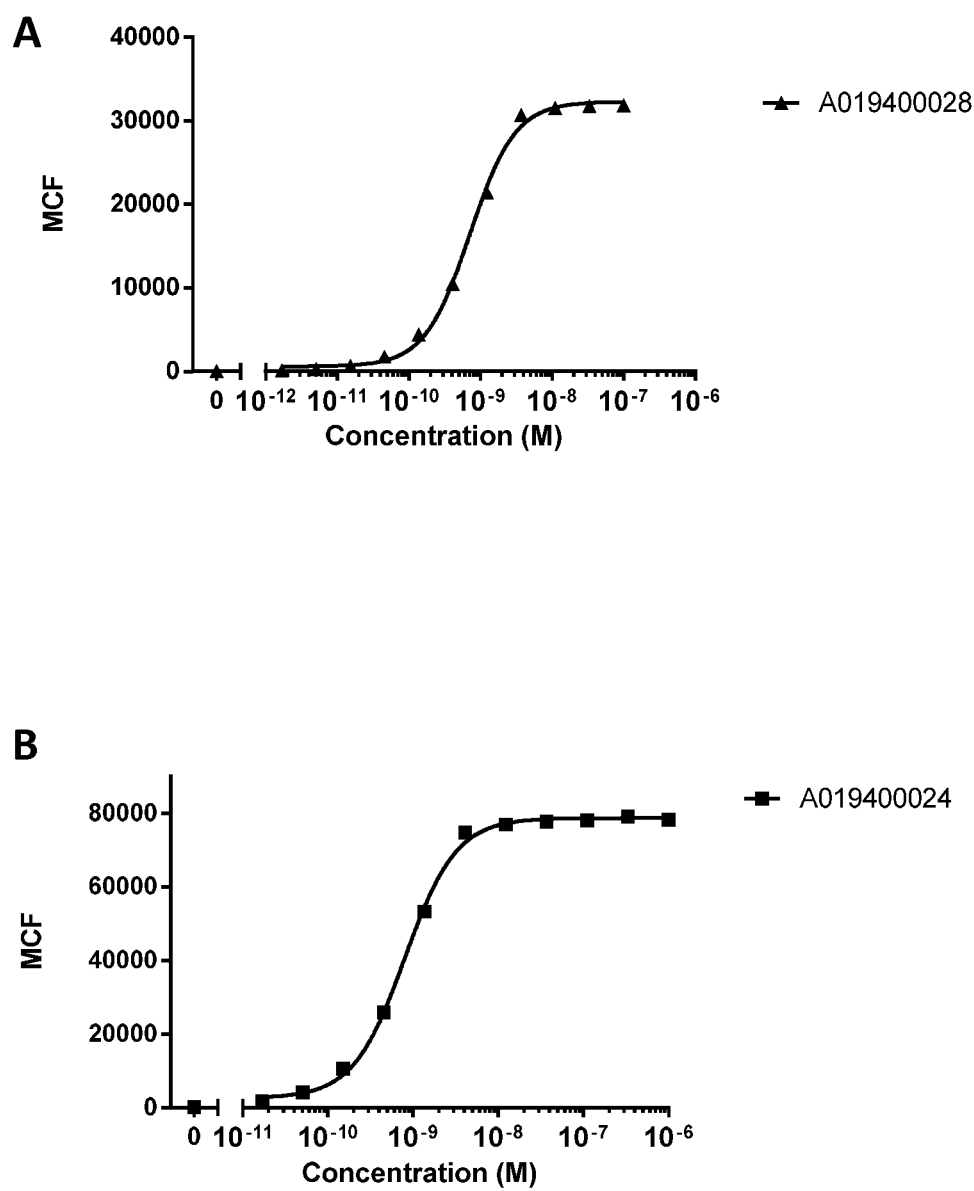
Figure 26:
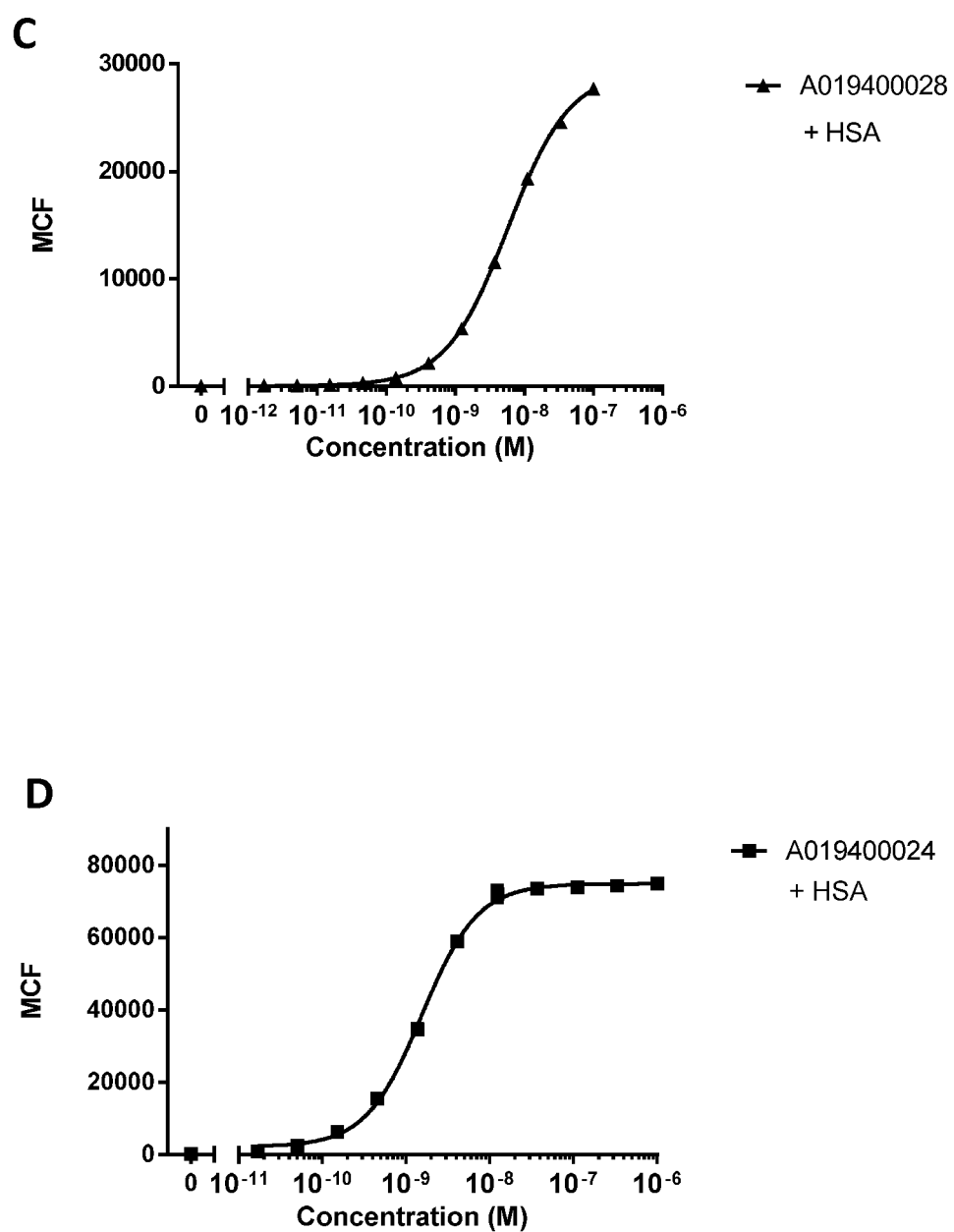

Analogous as Described in Example 4.1, Binding of Half-Life Extended Anti-Kv1.3 Nanobodies to cyno and rat Kv1.3 expressed on CHO cells was explored in a flow cytometric assay (FIGS. 26A-26B). The EC$_{50}$ values obtained in this assay are listed in Table B-12.

8.2 Evaluation of Positioning of the Alb11 Nanobody Using Automated Patch Clamp Electrophysiology The half-life (HLE) extended Nanobody was electrophysiologically characterized on the human Kv1.3 on the IonFlux™ automated Patch Clamp using Kv1.3-expressing HEK293H cells. The complete procedure for evaluating the modulatory effect of the purified Nanobodies on human Kv1.3 via electrophysiological recordings is given in Examples 4.3 and 5.4. A time course protocol was applied to assess the Nanobody potency (IC$_{50}$) on potassium currents elicited by a depolarizing pulse protocol (as shown in FIG.

2A). In a "wash-off" experiment, a single high dose was applied during 120 s, followed by a continuous perfusion of extracellular buffer for at least 5 min; this in order to assess the rate of current recovery during washout. In this experiment the single cell automated patch clamp was used to record current amplitudes.

The selected Nanobody produced a concentration-dependent inhibition with full block at highest dose (FIGS. 27A-27B), and no current recovery could be observed after at least 5 min washout with extracellular buffer (FIG. 27C). The $IC_{50}$ value for the trivalent Nanobody A019400029 was 3.8E-09 M.

8.3 Impact of Human Serum Albumin on the Potency in Binding FACS

The half-life extended Nanobodies were evaluated for binding to cyno and rat Kv1.3 expressed on CHO cells in a flow cytometric assay as outlined in Example 4.1. In addition, HSA (50 µM; Sigma, Cat A8763) was added to all reagents and buffers that were used during the assay to allow binding of HSA to Alb11 (FIG. 26C-26D). The $EC_{50}$ values are shown in Table B-12.

TABLE B-12

$EC_{50}$ (M) values of half-life extended Nanobodies for binding Kv1.3 (cyno and rat) in FACS assay in absence and presence of HSA

| Construct ID | $EC_{50}$ on cyno Kv1.3 | $EC_{50}$ on rat Kv1.3 |
| --- | --- | --- |
| A019400013 | 3.3E-10 | 7.04E-10 |
| A019400013 + HSA | 4.5E-10 | 8.5E-10 |
| A019400023 | 9.4E-10 | 1.2E-09 |
| A019400023 + HSA | 2.1E-09 | 3.7E-09 |
| A019400024 | 8.1E-10 | 1.3E-09 |
| A019400024 + HSA | 1.6E-09 | 3.2E-09 |
| A019400027 | 4.6E-10 | 8.3E-10 |
| A019400027 + HSA | 8.1E-10 | 2.0E-09 |
| A019400025 | 7.8E-10 | 1.1E-09 |
| A019400025 + HSA | 7.6E-09 | 2.3E-08 |
| A019400026 | 4.4E-10 | 7.2E-10 |
| A019400026 + HSA | 2.1E-09 | 7.3E-09 |
| A019400028 | 7.2E-10 | 1.2E-09 |
| A019400028 + HSA | 5.8E-09 | 2.0E-08 |

8.4 Impact of Human Serum Albumin on the Potency in 125I Margatoxin Competition

The half-life extended Nanobodies were also evaluated for competition with binding of 125I margatoxin to cyno Kv1.3 expressed on CHO cells in presence of HSA, as previously described in Examples 4.2 and 5.3. First, the influence of 25 µM HSA (Sigma, Cat A8763) was evaluated on the binding of radiolabeleld I125 margatoxin, to confirm that HSA did not affect the dose response curve of I125 MgTX (data not shown). Next, the competition was performed in the absence and presence of 25 µM HSA for comparison (Sigma, Cat A8763). The data presented in FIG. 28 show that HSA does not influence the potency of the construct. The $IC_{50}$ values are shown in Table B-13.

TABLE B-13

$IC_{50}$ values of half-life extended Nanobodies in 125I MgTX competition assay in presence and absence of HSA

| Construct ID | $IC_{50}$ on cyno Kv1.3 |
| --- | --- |
| A019400029 | 9.0E-10 |
| A019400029 + HSA | 1.4E-09 |

8.5 Impact of Human Serum Albumin on the Potency of the Half-Life Extended Nanobodies in T Cell Assay The half-life extended Nanobodies were also tested in the T cell assay as outlined in Example 5.5. The Nanobodies were tested both in absence and presence of 10 µM HSA (Sigma, Cat A8763) (see FIG. 29). The obtained $IC_{50}$ values in both IFNγ and CD25 read out are shown in Table B-14.

TABLE B-14

$IC_{50}$ values of half-life extended Nanobodies for IFNγ production and CD25 expression in T cell activation assay in the presence and absence of HSA

| VHH ID/compound | $IC_{50}$ (in M) IFNγ read out | $IC_{50}$ (in M) CD25 read out |
| --- | --- | --- |
| A019400013 | 8.3E-11 | 1.2E-10 |
| A019400013 + HSA | 3.1E-11 | 3.7E-11 |
| A019400032 | 6.9E-11 | 1.2E-10 |
| A019400032 + HSA | 8.6E-11 | 3.3E-10 |
| A019400024 | 1.9E-10 | 1.4E-10 |
| A019400024 + HSA | 6.6E-10 | 5.5E-10 |
| A019400028 | 1.0E-10 | 1.4E-10 |
| A019400028 + HSA | 2.7E-09 | 5.1E-09 |
| A019400027 | 3.8E-10 | 6.4E-10 |
| A019400027 + HSA | 9.8E-10 | 3.4E-09 |
| A019400026 | 3.6E-10 | 1.1E-10 |
| A019400026 + HSA | 1.8E-09 | 3.2E-10 |
| A019400029 | 1.9E-10 | 1.2E-10 |
| A019400029 + HSA | 6.2E-10 | 2.7E-10 |
| ShK | 1.4E-10 | 7.3E-10 |
| ShK + HSA | 2.7E-11 | 3.8E-11 |

8.6 Human and Rat HSA Binding in Surface Plasmon Resonance (SPR)

Binding of the half-life extended format to human and rat serum albumin (SA) was evaluated in SPR (surface plasmon resonance) on a BIAcore TWO instrument. For comparison, also the monovalent Alb11 Nanobody was tested for binding to human and rat SA.

Briefly, human and rat HSA (Sigma; #8763 and #A6272) were immobilized directly on a CM5 chip at respectively 320 and 2978 RU. The Nanobodies were then injected at different concentrations (between 1.6 nM and 1000 nM) for 120 s and allowed to dissociate for 900 s. Evelution of the binding curves was done using BIAcore T100 Evaluation software V2.0.3. Kinetic analysis was performed by fitting a 1:1 interaction model (Langmuir binding) ($R_{max}$=global; $R_I$=constant, offset=0). Obtained $K_D$ values can be found in Table B-15.

TABLE B-15

| Binding of HLE Nanobody to Human and Rat serum albumin | | | | | | |
|---|---|---|---|---|---|---|
| human SA | | | rat SA | | | $K_D$ on rat/ |
| $k_a$ (1/Ms) | $k_d$ (1/s) | $K_D$ (M) | $k_a$ (1/Ms) | $k_d$ (1/s) | $K_D$ (M) | $K_D$ on human |
| A019400029 4.0E+05 | 6.3E−03 | 1.6E−08 | 1.1E+05 | 4.9E−01 | 4.5E−06 | 281 |
| ALB00011 6.0E+05 | 1.6E−03 | 2.8E−09 | 2.8E+05 | 2.3E−01 | 8.3E−07 | 296 |

Figure 30:
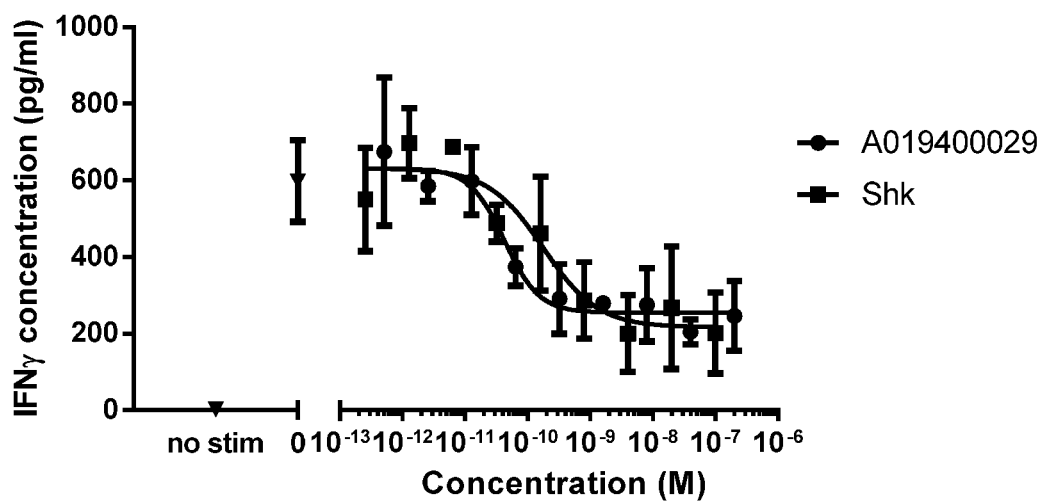
Figure 30:
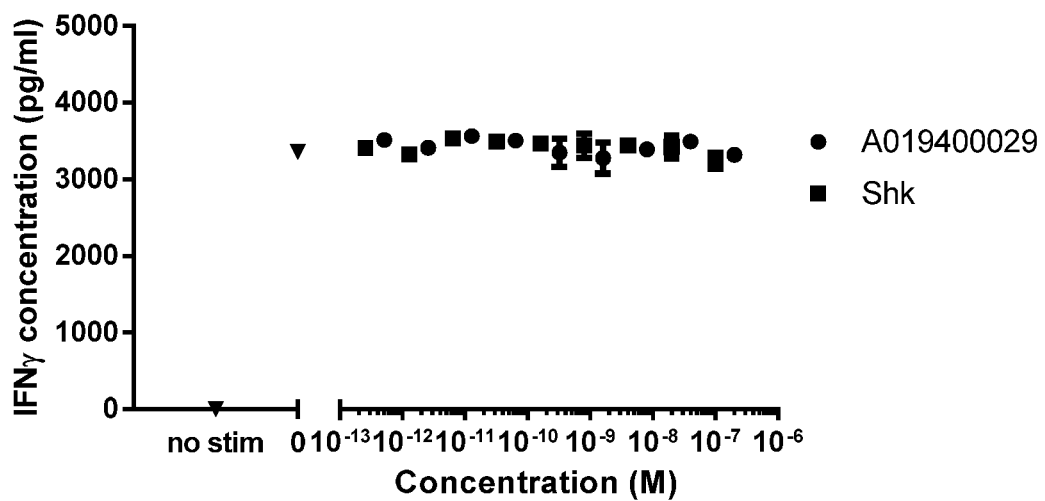

Example 9: Effect of Anti-Kv1.3 Nanobodies on IFNγ Production by Human PBMC's after Anti-CD28 and Anti-CD3 Stimulation The anti-Kv1.3 inhibitory Nanobodies were evaluated for their effect on cytokine secretion by plate-bound anti-CD3/CD28 stimulated PBMCs. ShK was included as reference compound (FIG. 30). This co-stimulation of T-cells with anti-CD3 and anti-CD28 reflects strong immune stimulation as encountered during an acute infection. Single stimulation with anti-CD3 imitates rather the moderate immune stimulation resembling the situation during e.g. an autoimmune disease.

Briefly, PBMCs were first collected from Buffy Coat blood (from healthy volunteers, Bloodbank Gent) using RosetteSep (StemCell Technologies, #15061) followed by an enrichment on Ficoll-Paque™ PLUS (GE Healthcare #17-1440-03). The purity of the population was afterwards checked with anti-CD3 (eBioscience #12-0037-73); anti-CD8 (BD Bioscience #345775); anti-CD4 (BD Bioscience #345771); anti-CD45RO (BD Bioscience #555493); anti-CD45RA (BD Bioscience #550855) and anti-CD19 (BD Bioscience #555413) fluorescently labeled antibodies in a flow cytometric assay. The isolated PBMCs were then stimulated on anti-CD3 (eBioscience 16-0037-85; 540 ng/ml) coated 96-well plates at a concentration of 200 000 cells/well in absence or presence of anti-CD28 (1 µg/ml, Sanguin, M1650) and a dilution series of anti-Kv1.3 Nanobodies or ShK reference compound. After 72 h, IFN-gamma production was measured with anti-human IFNγ antibody capture in ELISA (BD Bioscence #551221) combined with biotinylated anti-human IFNγ (BD Bioscience, #554550) and streptavidin-HRP (Dakocytomation #P0397) as detection.

As shown in FIG. 30, the anti-Kv1.3 Nanobodies did not block IFNγ production of human PBMC's after anti-CD28 and anti-CD3 stimulation but show inhibition of the single anti-CD3 stimulation of these primary cells.

Example 10: Effect of Kv1.3 Inhibitory Nanobodies on the Electrophysiological Properties (Mode-of-Action) of the Kv1.3 Ion Channel Measured by Conventional Planar Patch Clamp Electrophysiology The effects of HLE Nanobody A019400029 on the electrophysiological properties of the Kv1.3 K$^+$ channel were evaluated. Current recordings were performed by conventional planar patch clamp electrophysiology using overexpressing Kv1.3 CHL cells. This procedure, together with the detailed voltage command protocols are given below.

Solutions and Nanobodies Handling

Extracellular solution contained (in mM): 140 NaCl, 5 KCl, 2 CaCl2, 1 MgCl2, 10 HEPES, 10 glucose (pH 7.4 with NaOH, and 310-330 mOsmolar). Intracellular solution contained (in mM): 140 KCl, 1 MgCl2, 20 HEPES, 1 EGTA (pH 7.3 with KOH, and 295-310 mOsmolar). These solutions were filtered and stored for no longer than 6 weeks at 4° C. On each day of recording, an aliquot of the selected Nanobody was diluted with extracellular solution containing 0.1% BSA (Sigma, #A4503) to give a final concentration of 10 nM.

Cell Preparation

Chinese Hamster Lung (CHL; Essen Bioscience) cell lines stably expressing the full length human Kv1.3 channel were cultured in T-175 cell culture flasks (Greinerbio-one, #660160) using standard culture medium DMEM (Invitrogen, #41965) containing 10% FBS (HyClone, #SH3007103), 1% non-essential amino acids (Invitrogen, #11140), 1% sodium-pyruvate (Invitrogen, #C11360), 1% penicillin+streptomycin (Invitrogen, #C10378), 200 µg/ml G418 (Invitrogen, #10131), 20 mM HEPES (Invitrogen, #15630-114), and 29 mM KCl (Sigma, #P5405). Optimal Cell confluence prior to harvesting was 50-80%. The cells were washed with 20 ml PBS without Ca2+ and Mg2+ (GibCo, #14190-094) and detached with 2 ml Trypsin/EDTA 0.25% (GibCo, #25200-056) for 6 min at 37° C. The cells were diluted with 10 ml of standard cell culture medium containing 10% FBS, 1% non-essential amino acids, 1% sodium-pyruvate, 1% penicillin+streptomycin, 200 µg/ml G418, 20 mM HEPES, and 29 mM KCl. The suspension was transferred to a 15 ml centrifuge tube and centrifuged for 2 minutes at 200×g. The supernatant was removed and the pellet was re-suspended in the same medium as described above. Cells were seeded at a density of 25.000 cells/cm$^2$ or 12.000 cells/cm$^2$ on poly-D-lysine coated glass coverslips 1 or 2 days prior to recordings.

Conventional Planar Patch Clamp Electrophysiology

Kv1.3 expressing CHL cells grown on poly-D-lysine coated glass coverslips were placed in the recording chamber perfused with extracellular solution and visualized on a Nikon Eclipse inverted microscope. Currents were recorded using standard whole-cell voltage-clamp techniques (Hamill et al., Pflugers Arch 391:85-100, 1981), at room temperature using an Axopatch 200B amplifier, converted to a digital signal using a digidata 1440A analogue-to-digital converter (Molecular Devices) and low pass Bessel filtered at 5 kHz and digitized at 10 kHz. Recording electrodes were pulled from borosilicate glass pipettes on a Sutter P-97 horizontal pipette puller yielding resistances of 2-6 MΩ when filled with intracellular solution. After formation of a tight seal (>1GΩ) by manual suction in the voltage clamp mode, the command voltage set to −80 mV and pipette capacitance was compensated. The cell membrane was ruptured and compensation circuitry employed to minimize capacitance transients and 80-85% of series resistance errors (mean whole cell capacitance of 15±3 pF and series resistance of 6.0±2.3 MΩ; n=36). Leak currents were subtracted using the P/4 protocol supplied with the pClamp10 software. Membrane potentials were not corrected for junction potentials (4.1 mV as determined by Clampex 10 software). Descriptions of the voltage protocols to elucidate the Nanobody mechanism of action are provided in the figure legends. Samples were applied using a micro-injection needle coupled to a pressurized solenoid controller (ALA Scientific Instruments, ALA-VM8/BPS-8 valve control system) positioned close to the recording cell (~200 μm). Correct positioning was confirmed by observing small movement of the cells upon switching.

Data Analysis

The activation-conductance plot was fitted using a Boltzmann function: $g_K/g_K$ max=$1/[1+\exp(V_{1/2}-V/k)]$, where $g_K$ is the conductance which is normalized relative to the maximum conductance (gK max), $V_{1/2}$ is the membrane potential at which half the channels are activated and k is the slope of the curve. To allow the construction of inactivation curves the current was normalized (I) to that produced by a depolarization from −80 mV to +40 mV ($I_{max}$) and plotted against the conditioning pulse potential. The inactivation curves were fitted according to the Boltzmann function: I/Imax=$1/[1+\exp(V_{1/2}-V/k)]$, where V is the conditioning pulse potential, $V_{1/2}$ is the membrane potential at which half the channels are inactivated and k is the slope. Current amplitudes were determined as either peak outward current during the depolarizing pulse or the sustained current taken as the mean amplitude during the final 5 ms of the voltage step. The effects of the Nanobody or vehicle control were quantified by first dividing the KV1.3 current amplitude in the presence of treatment at the end of the incubation period by the amplitude of the KV1.3 current at the end of the pre-addition control period, multiplied by 100 yielding a % control current value. The % inhibition was determined by subtracting the % control current from 100. All data analyses were performed using Axon pClamp10, Microsoft Excel v7.0 and GraphPad Prism v5.0. The recovery from inactivation and/or inhibition studies used normalized currents employing the equation: % recovery=$(P2_{peak}-P1_{sustained})/(P1_{peak}-P1_{sustained})\times 100$, where $P2_{peak}$ is the maximal current from the test pulse, $P1_{sustained}$ is the current amplitude at the end of the conditioning pulse and $P1_{peak}$ is the maximal current from the conditioning pulse (see FIG. 34).

Voltage Protocols and Results

Figure 31:
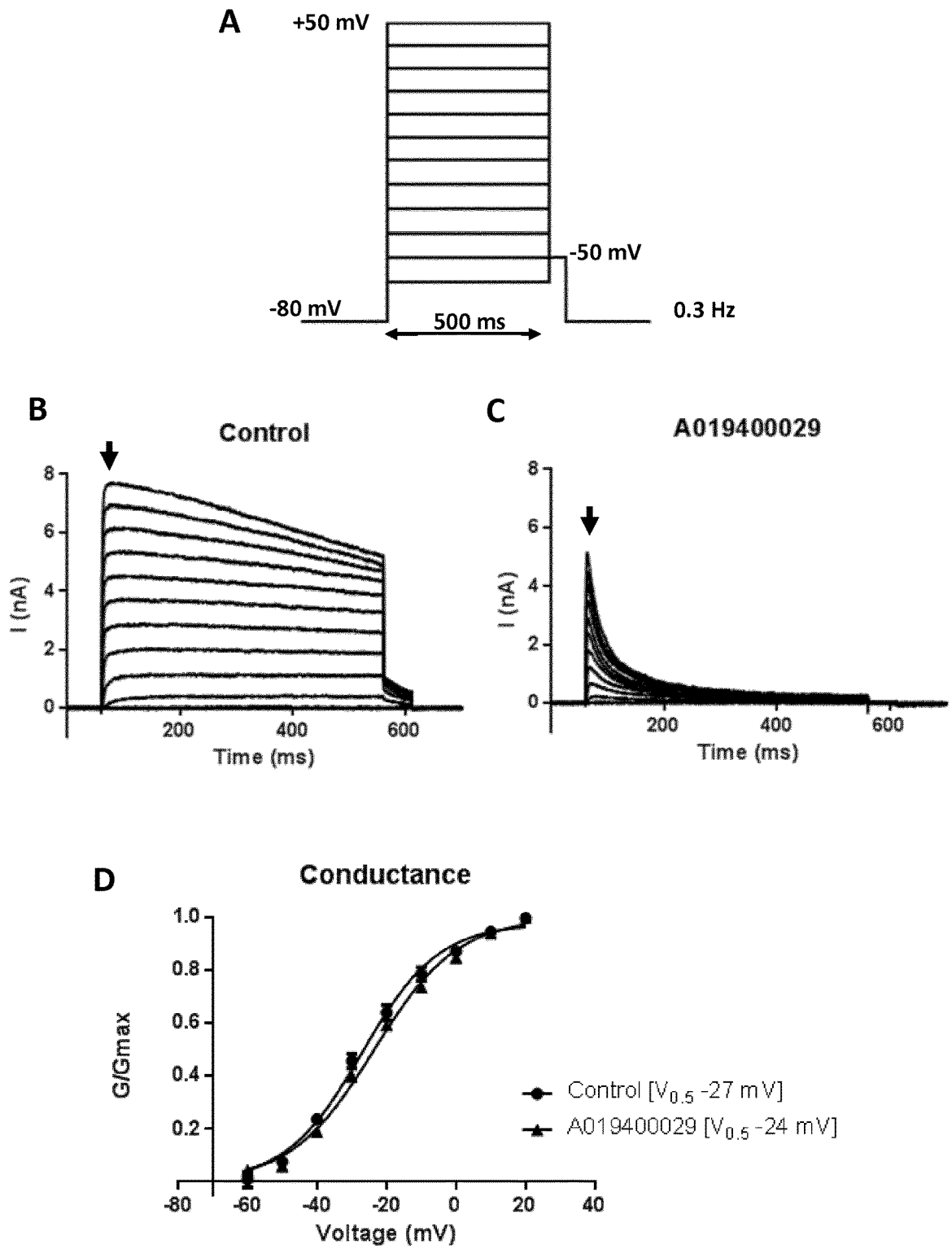

Effects on voltage-dependence of activation were evaluated by determining the current voltage-relationship prior Nanobody application and after 5 minutes incubation of A019400029. Kv currents were provoked by a 500 ms depolarizing pulse to +50 mV in 10 mV steps from a holding potential of −80 mV at 30 s intervals in the absence (FIG. 31B) and presence (FIG. 31C) of 10 nM A019400029. A schematic of the voltage protocols is given in FIG. 31A. The data points used in analysis represent peak current amplitudes as indicated in FIG. 31B (arrow). In order to determine voltage dependence of block, an I-V plot and calculation of fractional block at each test potential was performed (data not shown). A Boltzmann analysis (G/V) was done to measure effects on activation gating.

In order to evaluate the effect of A019400029 on the association and washout of Kv1.3 currents on human Kv1.3 channels stably expressed in CHL cells, Kv1.3 currents were provoked by a test pulse from −80 mV to +40 mV every 15 s. The test pulse duration was either 20 ms or 200 ms to determine whether kinetics of block were dependent on period of activation/inactivation (FIG. 32A-B). Recordings were done in control conditions (prior to compound addition) and during a 3 to 5 min incubation of 10 nM A019400029, followed by compound washout. Peak and sustained current amplitudes were then plotted against the different time points. In addition, to investigate the effect of A019400029 on voltage-dependence of inactivation, the cells were held at either −80 mV or −50 mV during the 3 to 5 minutes incubation with A019400029. Currents were provoked by a 200 ms test pulse from −80 mV to +40 mV every 15 s (FIG. 33A-B). Peak and Sustained current amplitudes were then plotted against the different time points.

Figure 33:
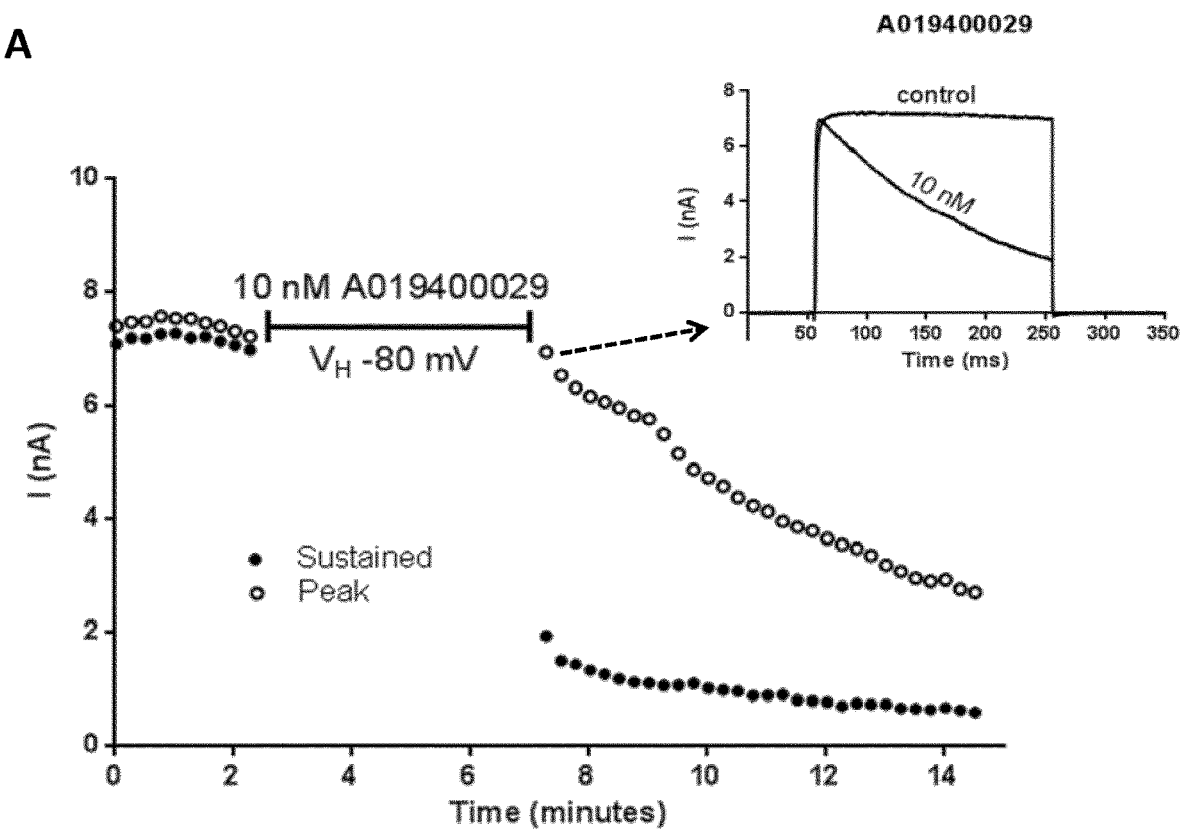
Figure 33:
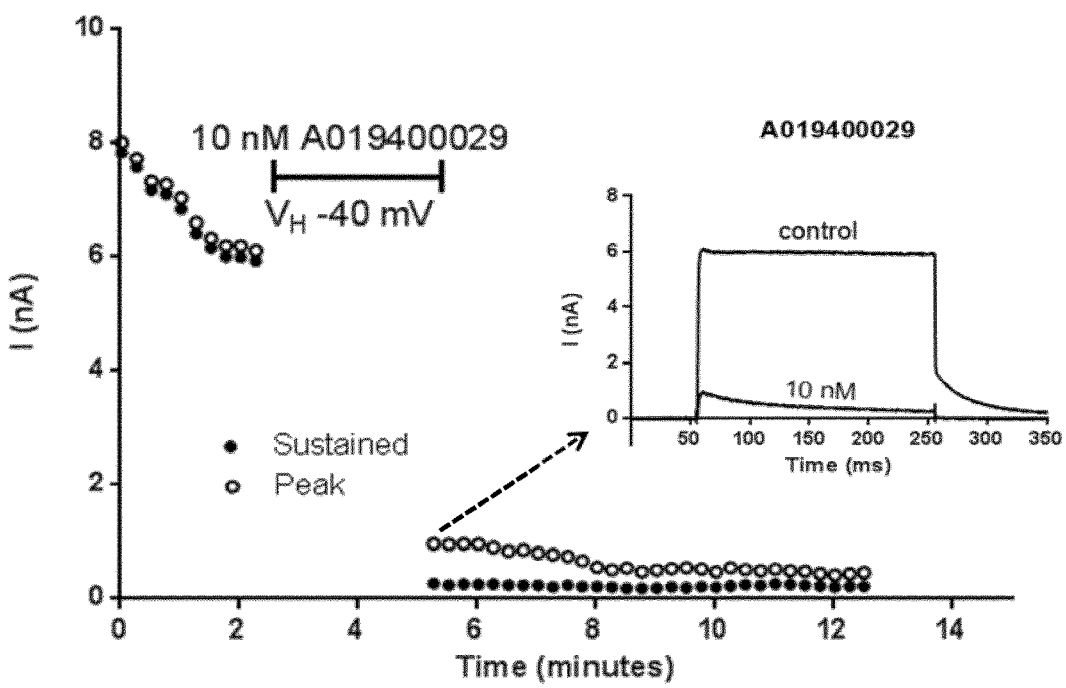

Application of 10 nM A019400029 markedly increased current decay following channel activation, but did not alter the voltage dependency of activation (FIG. 31C). The inhibitory Nanobody A019400029 produced cumulative block of Kv1.3 currents when channels were repeatedly gated. Within each pulse, inhibition of both the early peak and sustained current was observed, however the effect on the sustained current was more rapid and pronounced. The rate of onset of the Nanobody blocking effect was slower when shorter pulses were employed. No current recovery could be observed after washout with extracellular buffer. Inhibition did not require channel inactivation (FIG. 32) and using different pulse durations and holding potentials during Nanobody incubation showed that the inhibition induced by A019400029 appeared to be dependent on channel gating (FIG. 33).

Figure 34:
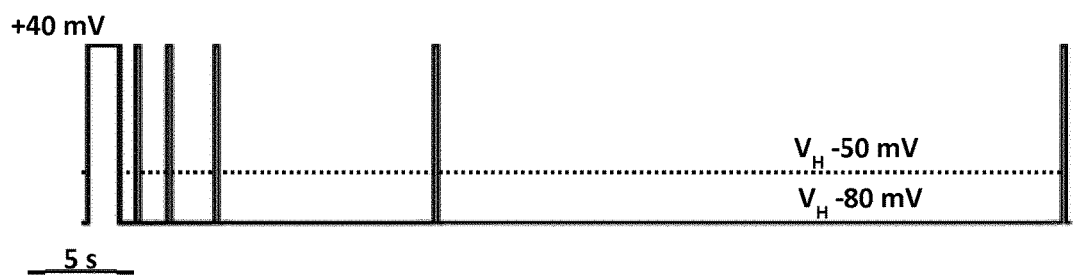
Figure 34:
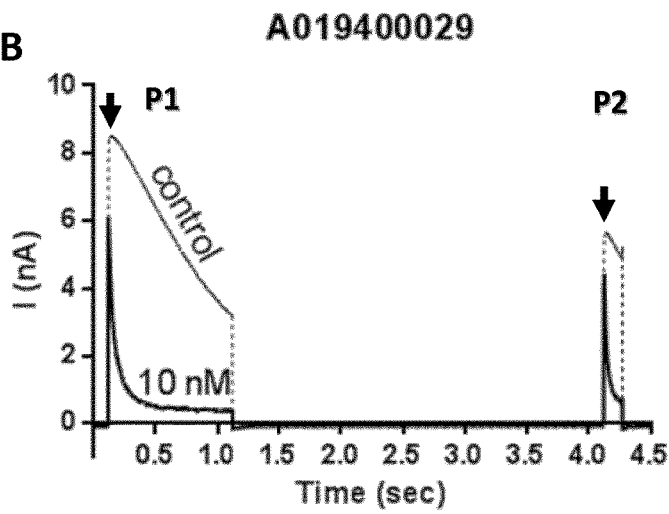
Figure 34:
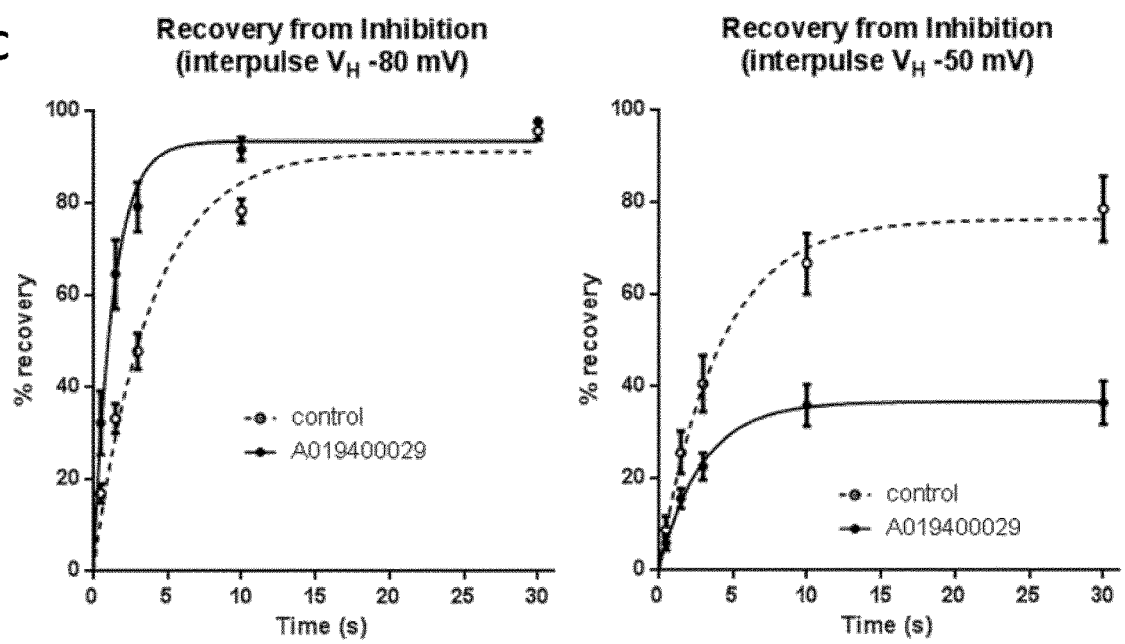

The recovery of inactivation from two inter-pulse potentials (−80 mV and −50 my; FIG. 34C) was measured using a standard variable interval gapped pulse protocol (as shown in FIG. 34A). An initial 1 s pulse from −80 mV to +40 mV (P1) was followed by a second pulse from −80 mV to +40 mV for 150 ms (P2) after an interval of between 0.5 to 30 s. Representative traces in the absence and presence of 10 nM A019400029 are given in FIG. 34B. The percentage of recovery was calculated (as described above) and plotted against pulse interval to show the recovery of inactivation (FIG. 34C). In the presence of A019400029 both recovery from inactivation and inhibition could be observed when an inter-pulse potential of −80 mV has been employed, whereas on application of an inter-pulse potential of −50 mV, an attenuation of recovery could be detected. Thus it appears that the relief of inhibition by 10 nM of A019400029 is voltage-dependent (FIG. 34).

Example 11: Comparative Pharmacology of Kv1.3 Inhibitory Nanobodies on Kv1.3, Kv1.5, Kv1.6 and Kv11.1 $K^+$ (hERG) Channels Measured by Automated Patch Clamp Electrophysiology Electrophysiological recordings were made from Chinese Hamster Lung (CHL) cell lines expressing the full length Kv1.3, Kv1.5 and hERG $K^+$ channels or Chinese Hamster Ovary (CHO) cells transiently transfected with Kv1.6 cDNA (ChanTest EZcells™ TT, #CT7220). Either single cell (HT) for hERG and Kv1.6 or population (PPC) patch clamp for Kv1.3 and Kv1.5 were made in the perforated patch clamp configuration using the IonWorks Quattro instrument. The more detailed procedure is explained in Example 4, together with cell culture conditions, cell preparations, the composition of the intracellular and extracellular solution used in these experiments. However, frozen Human Kv1.6-CHO EZcells™ TT were thawed very rapidly in a 37° C. water bath and transferred to a 50 ml conical tube. Ten ml growth media Ham's/F12 (GibCo, #31765-027) containing 10% FBS (HyClone, #SH3007103), and 1% penicillin+streptomycin (Invitrogen, #C10378) and cells were centrifuged at 250×g for 5 min. Pellet was resuspended in fresh 20 ml fresh medium and titrated to disperse cell clumps. The cell suspension (at a density of 3-5M cells per ml) was added to the cell boat within the IonWorks and the experiment was then initiated.

Additional note: for the hERG recordings the intracellular solution contained (mM): 140 KCl, 1 MgCl2, 1 EGTA, 20 HEPES (pH 7.3 with CsOH, and 300-315 mOsmolar). Kv1.3, Kv1.5 and Kv1.6 currents were elicited by a pulse train of fifteen depolarizing steps from −80 mV to +50 mV for 100 ms at 3 Hz pulse intervals in control conditions (prior to compound addition). The hERG currents were elicited by a pulse train of five pulses to +40 mV from $V_H$ of −70 mV for 1 sec, then to −30 mV for 1 s, and then to −70 mV, every 3 s. The schematics of the voltage protocols are given in FIG. 35. The Nanobodies were then incubated for 6 to 7 min prior to the second measurement using the identical pulse train. The selected Nanobodies were tested at 8 concentrations in up to 4 wells per concentration with repeated gating voltage-command.

Data points were accepted if the following well and plate Quality Control criteria were met.

Figure 35:
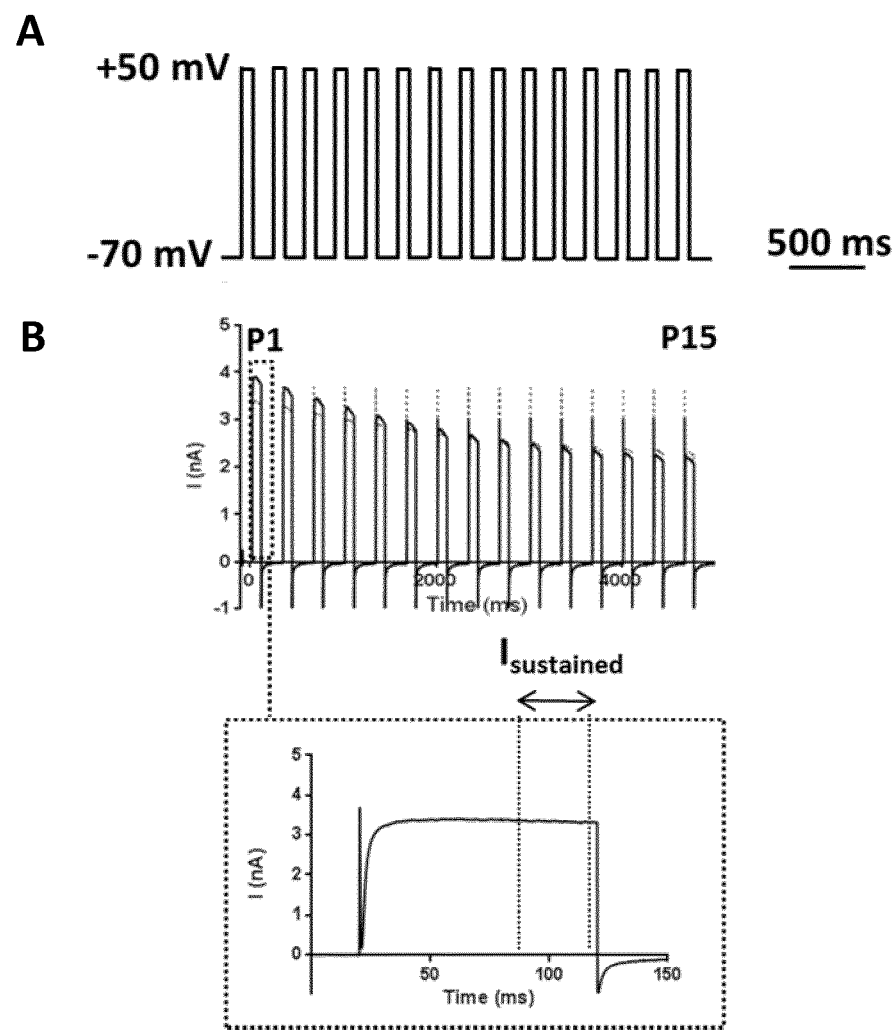
Figure 35:
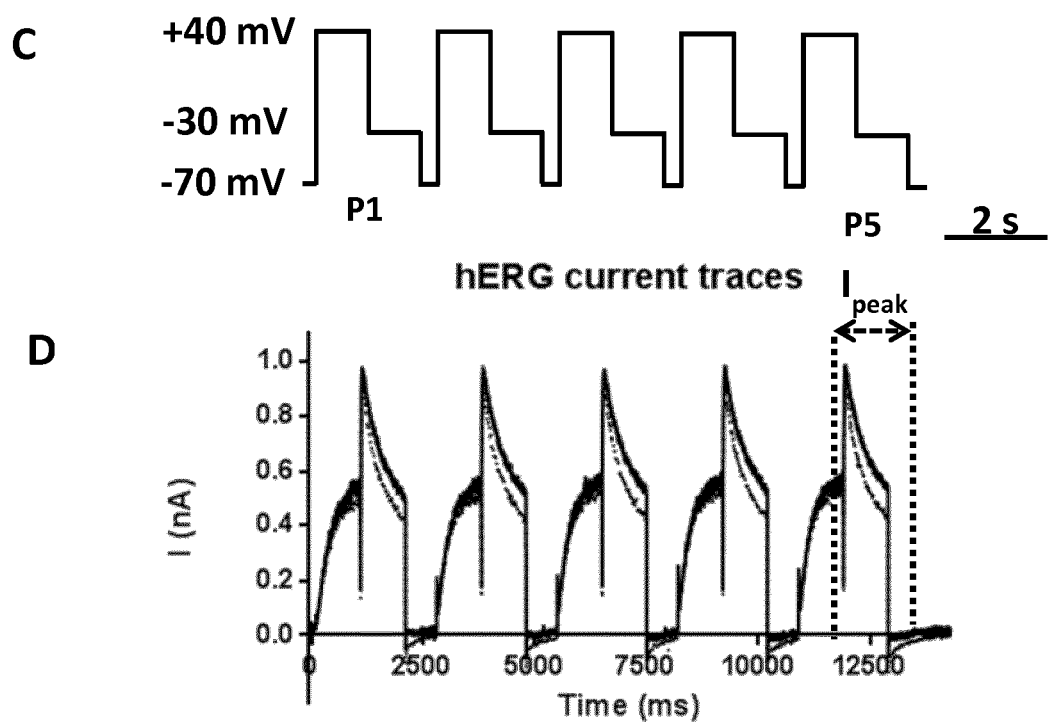

A) Kv1.3 and Kv1.5
  7) Individual seal resistances>20 MΩ on pre- and post-compound reads
  8) Individual peak Kv1.x current amplitude>500 pA
  9) Plate Z' value>0.4 (where determined)
  10) Plate average seal resistance>30 MΩ
  11) Plate average mean current amplitude>0.5 nA
  12) Standard $IC_{50}$ value within anticipated range B) hERG and Kv1.6
  1) Individual seal resistance>50 MΩ on pre- and post-compound reads
  2) Individual peak hERG tail current amplitude>150 pA or peak Kv1.6 outward current amplitude>400 pA
  3) Plate average seal resistance>100 MΩ
  4) Plate average mean current amplitude>0.3 nA Currents were first measured under control conditions and after an incubation period of 6 to 7 min with the Nanobody using an identical protocol. Kv1.3, Kv1.5 and Kv1.6 currents were measured as peak and sustained currents in the first gating step pulse P1 and pulse 15. The hERG currents were measured at the peak in the tail step from pulse P5 (as shown in FIG. 35). The effects of the compounds were quantified by dividing the current in the presence of the compound by the pre-compound current. This percentage of inhibition value was then normalized as described in Example 4. The Kv1.3 and Kv1.5 data was then further normalized to the maximal block control to remove the impact of the small (~10%) residual outward currents unblocked by quinidine. For Kv1.6 the small (mean current 0.24 nA) non-specific outward current was subtracted from all currents prior analysis.

Figure 36:
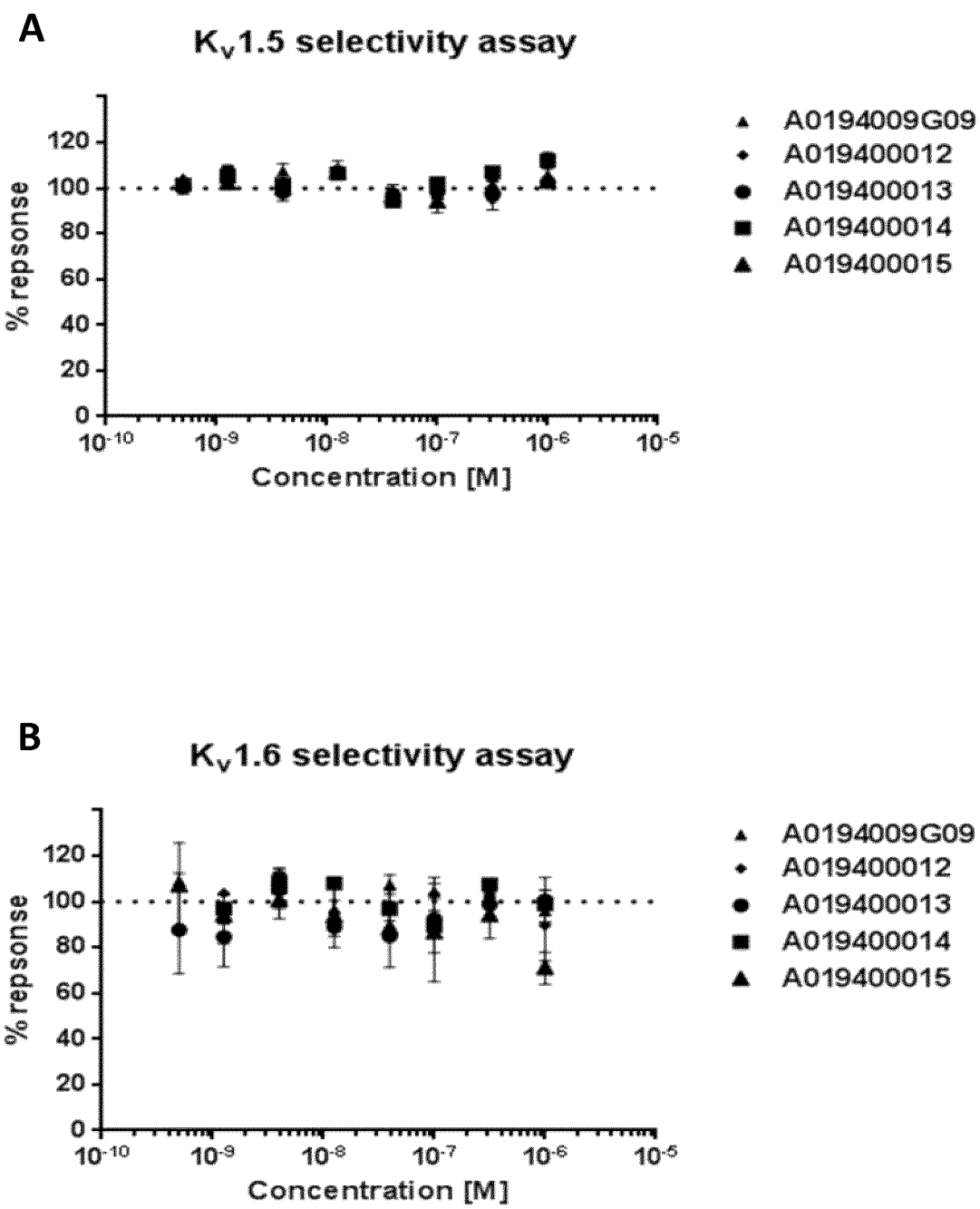
Figure 36:
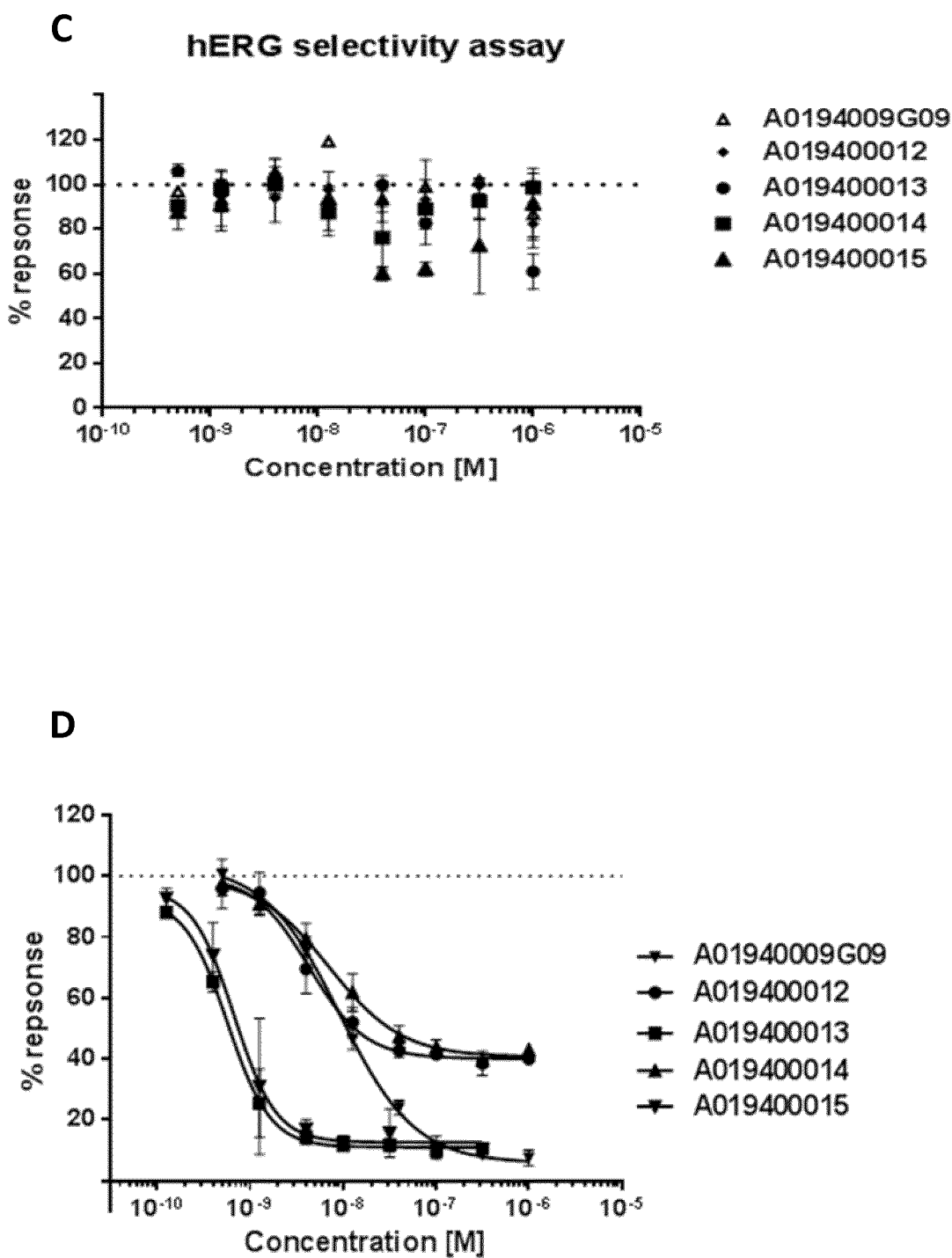

Based on the comparison of the Nanobody concentration needed for inhibiting the channel, all selected Nanobodies displayed profound selectivity (i.e. greater than 1.000 fold) for Kv1.3 with no evidence for off target effects against Kv1.5, Kv1.6 and hERG K$^+$ channels. The maximal block at highest concentration tested (i.e. 1 μM) was less than 50% in all other channels (FIG. 36).

Example 12: Evaluation of the Anti-Kv1.3 Nanobodies in a Delayed-Type Hypersensitivity (DTH) Rat Model A delayed-type hypersensitivity (DTH) reaction is an expression of T cell-mediated immunity in response to cutaneous sensitization and challenge with reactive haptens like 2, 4-dinitrofluorobenzene (DNFB), largely mediated by skin-homing effector memory T cells (Azam P et al., J Invest Dermatol 127(6):1419-29, 2007; Matheu M P et al., Immunity 29(4):602-14, 2008). The voltage-gated potassium channel Kv1.3 is expressed in T cells, and is important in maintaining T cell activation (predominantly effector memory T cells).

For the purpose of in vivo proof-of-concept, the efficacy of anti-Kv1.3 Nanobodies on DNFB-induced delayed type hypersensitivity in Wistar rats was evaluated. The DTH response in the rats was elicited as follows (see FIG. 37): on day 0 (start of the in-life) and day 1, 100 μl of 1% (wt/vol) DNFB prepared in 4:1 acetone/olive oil was applied to the shaved dorsum for sensitization. On day 5, animals were challenged on both sides of the right ear pinnae of the animals with 50 μl of 0.5% (wt/vol) DNFB prepared in 4:1 acetone: olive oil. Animals (n=10 rats/group) received one or two subcutaneous (s.c.) injection(s) of either vehicle, the reference compound ShK or an anti-Kv1.3 Nanobody (A019400029) at 12 hours and/or 1 hour preceding the challenge. As positive control, animals were treated with dexamethasone (topical, 0.75 mg at 1 hour and 6 hours post-challenge). On day 5 before DNFB challenge, the baseline right ear pinna thickness was measured, and the net ear swelling response was determined 24 hours after challenge with a spring-loaded micrometer.

The results of the experiments are shown in FIG. 38. The vehicle-treated control animals showed a mean increase in right ear thickness of 0.280±0.037 mm. Rats from the positive control group, treated with dexamethasone 1 h and 6 h post-challenge (topical), showed a clear reduction in the ear swelling response (mean increase in ear thickness of 0.027±0.017 mm). Rats treated with two s.c. injections of 10 μg/kg of the reference compound ShK showed a statistical significant reduction of the ear swelling response versus vehicle (mean increase in ear thickness of 0.213±0.019 mm). Also the three Nanobody-treated groups showed a comparable and significant reduction in ear swelling versus the vehicle-treated animals: (i) animals treated with two injections (12 h and 1 h pre-challenge) of an equimolar dose of 105 μg/kg of the half-life extended anti-Kv1.3 Nanobody A019400029 showed a mean increase in ear thickness of 0.178±0.013 mm; (ii) animals treated with only one administration of A019400029 (105 μg/kg, 1 h before challenge) showed a similar ear swelling response (mean increase in ear thickness of 0.184±0.033 mm); (iii) animals treated with two injections (12 h and 1 h pre-challenge) of an equimolar dose of 69.3 μg/kg of the non-half-life extended anti-Kv1.3 Nanobody A019400032 showed a mean increase in ear thickness of 0.195±0.038 mm. There were no statistical significant differences between any of the three Nanobody-treated groups, or between the ShK-treated group and any of the Nanobody-treated groups.

In conclusion, treatment with anti-Kv1.3 Nanobodies resulted in a significant reduction of the DTH response in rats versus the vehicle group, at equimolar doses compared to the reference compound ShK. These results highlight the immunosuppressant potential of the anti-Kv1.3 Nanobodies in auto-immune diseases.

Example 13: In Vivo Proof-of-Concept and Benchmarking Study in a Delayed-Type Hypersensitivity (DTH) Rat Model The in vivo efficacy of an anti-Kv1.3 Nanobody (A019400029) on DNFB-induced delayed type hypersensitivity in Wistar rats was evaluated and compared with the anti-Kv1.3 peptide toxin ShK (*Stichodactyla* toxin). The study was designed to prove non-inferiority of the Nanobody versus ShK with 80% power, based on a non-inferiority margin which was derived from previously obtained results of the Nanobody and ShK in the same DTH model (see Example 12). The DTH response in the rats was elicited as follows (see FIG. 37): on day 0 (start of the in-life) and day 1, 100 µl of 1% (wt/vol) DNFB prepared in 4:1 acetone/olive oil was applied to the shaved dorsum for sensitization. On day 5, animals were challenged on both sides of the right ear pinnae of the animals with 50 µL of 0.5% (wt/vol) DNFB prepared in 4:1 acetone: olive oil. Animals (n=10 rats/group) received two subcutaneous (s.c.) injections of either vehicle, the benchmark compound ShK or the anti-Kv1.3 Nanobody at 12 hours and/or 1 hour preceding the challenge. As positive control, animals were treated with dexamethasone (topical, 0.75 mg at 1 hour and 6 hours post-challenge). On day 5 before DNFB challenge, the baseline right ear pinna thickness was measured, and the net ear swelling response was determined 24 hours after challenge with a spring-loaded micrometer.

The results of the experiments are shown in FIG. 39. The vehicle-treated control animals showed a mean increase in right ear thickness of 0.266±0.027 mm. Rats from the positive control group, treated with dexamethasone 1 h and 6 h post-challenge (topical), showed a pronounced reduction in the ear swelling response (mean increase in ear thickness of 0.018±0.016 mm). Two s.c. injections of 100 µg/kg of the reference compound ShK resulted in a statistical significant reduction of the ear swelling response versus vehicle (mean increase in ear thickness of 0.136±0.024 mm). Rats treated with an equimolar dose of the Nanobody (1.05 mg/kg) showed a comparable and significant reduction in ear swelling (mean increase in ear thickness of 0.120±0.022 mm). This response was statistically non-inferior compared to the benchmark ShK group. On the other hand, rats treated with a 5-fold higher dose of the Nanobody (5.25 mg/kg) showed statistical superiority on the 5% significance level in reducing the ear swelling response compared to the benchmark ShK group at 100 µg/kg (mean increase in ear thickness of 0.102±0.014 mm).

In conclusion, these results demonstrate that the anti-Kv1.3 Nanobody is superior compared to ShK for the treatment of the DTH response in rats, and highlight its immunosuppressant potential for the treatment of autoimmune diseases.

Example 14: Pharmacokinetics of Anti-Kv1.3 Nanobody in Delayed-Type Hypersensitivity (DTH) Rat Model The pharmacokinetics of the anti-Kv1.3 Nanobody A019400029 was determined in a DNFB-induced delayed type hypersensitivity model in Wistar rats (see Example 12 and Example 13). Animals were dosed with 0.105, 1.05 or 5.25 mg/kg Nanobody and plasma was isolated at multiple timepoints after challenge with DNFB (n=4). Total Nanobody concentrations in plasma were measured using Enzyme-linked Immunosorbent Assay (ELISA). In brief, 96-well microtiter plates (Maxisorp, Nunc, Wiesbaden, Germany) were coated overnight at 4° C. with 50 μL/well of an in-house purified anti-Nanobody Nanobody (0.5 μg/mL). Next, plates were aspirated and blocked for 1 hour at room temperature with PBS/1% casein. After washing the plates 3 times with PBS/0.05% Tween 20, samples were diluted 1/10 and 50 μL of the diluted sample was incubated on the plate for 1 hour at room temperature (RT) while shaking at 600 rpm. Plates were washed, and 50 μL/well of an in-house biotinylated anti-Nanobody Nanobody (0.05 μg/mL in PBS/0.1% casein) was added for 1 hour at RT while shaking. The biotinylated anti-Nanobody Nanobody was detected by addition of 50 μL/well Horse Radish Peroxidase—(HRP) labeled streptavidin (1 μg/mL in PBS/0.1% casein) for 0.5 hour at RT while shaking at 600 rpm. After a final washing step, 50 μL of the HRP-substrate enhanced soluble 3,3',5,5'-tetramethylbenzidine (esTMB, SDT, Brussels, Belgium) was added. The limit of detection (LOD) of the assay was 9.77 ng/mL.

FIG. 40 shows the plasma pharmacokinetic profiles of A019400029 in individual animals at different time points after challenge with DNFB. The average response of 2 replicate measures is reported. The highest reported plasma concentration was 149.4 ng/mL in the 0.105 mg/kg dosing group (12 hours post-challenge); 5629.3 ng/mL in the 1.05 mg/kg dosing group (12 hours post-challenge) and 17227 ng/mL in the 5.25 mg/kg dosing group (8 hours post-challenge).

In conclusion, these data confirm the exposure of animals in a delayed-type hypersensitivity rat model after dosing with A019400029, and demonstrate that this exposure is dose-dependent.

Example 15: Sequence Optimization of Anti-Kv1.3 Nanobody A0194009G09

15.1 Sequence Optimization: Sequence Analysis

Parental wild type Nanobody sequences were mutated to yield Nanobody sequences that are more identical to human VH3-JH germline consensus sequences. Specific amino acids in the framework regions that differ between the Nanobody and the human VH3-JH germline consensus were altered to the human counterpart in such a way that the protein structure, activity and stability were kept intact. Based on alignment of A0194009G09 and A0194020A06 sequence with VH3-23/JH5 human germline, amongst others, the 4 following variants were generated: A019400071, A019400072, A019400073 and A019400074 (SEQ ID NOs: 514 to 517 respectively). These variants include the 7 mutations L11V, A14P, G19R, T62S, A74S, K83R and V89L (numbering according to Kabat). In these variants, the methionine at position 53 was further substituted by glutamine (A019400071 and A019400072) or by alanine (A019400073 and A019400074). In addition, variants A019400071 and A019400073 carry the S94G mutation and variants A019400072 and A019400074 carry the T97E mutation. Corresponding amino acid sequences are shown in Table A-3 and Table A-9.

15.2 Evaluation of Four Selected Humanization Variants in Expression Profiling

Cloning, Copy Number Determination and Expression Analysis

In this example we describe cloning of the Nanobodies A019400071, A019400072, A019400073 and A019400074 into *Pichia pastoris* X33 using the commercially available system from Invitrogen/RTC, their copy number determination and expression levels after production in shake flasks and fed batch fermentation. The subunits in these trivalent Nanobodies are fused head-to-tail with $(GGGGS)_n$ linkers.

The genes encoding for the Nanobodies A019400071, A019400072, A019400073 and A019400074 were synthesized using gBlocks® (Integrated DNA Technologies) for *Pichia* expression. The Nanobody sequence was downstream of and in frame with the aMF signal peptide sequence (signal peptide from the *saccharomyces* Alpha mating factor for secretion into the medium). The Nanobodies in the pPICZa vectors were under the control of the AOX1 methanol inducible promoter.

Transformation of the X-33 strain was done with the obtained expression vectors in accordance with the 'User manual for pPicZalphaA, B and C' (version D, 110801, Manual part no. 25-0148; Invitrogen) and Methods in Molecular Biology 2007 (Humana Press Inc.) and clones were selected on zeocin containing plates. Clones were picked ad random and were streaked on a new zeocin plate. A qPCR was performed to rank the clones according to their copy numbers. For each Nanobody construct, clones with a low and high copy number were selected based on a qPCR copy number screening assay. Next, the respective clones of each construct were tested for their expression level in shake flask as shown in FIG. 41. This Figure shows the relative expression levels after SDS-Page analysis of a medium sample. Clones with a higher copy number for each construct showed higher expression levels in case of the sequence optimized formats (A019400071-74); for the parental clone (A019400031), there was an inverse correlation.

Production Via Fermentation at Medium Scale (2 L)

The different constructs were further evaluated for their expression level at 2 L fermentor scale using complex medium. Cell biomass was accumulated during the first batch and glycerol fed batch phase, followed by the MeOH induction phase, during which the Nanobody was secreted into the fermentation medium. The estimated expression titers of the 5 different constructs are shown in Table B-16. The set of inserted sequence optimization mutations clearly increases the estimated yield.

TABLE B-16

Overview of the estimated expression yields for the different Nanobody constructs after SDS-Page analysis

| Construct | Wet Cell Weight at end of fermentation (g/L) | Estimated yield (g/L cell free medium) |
|---|---|---|
| A019400031 | 430 | 0.04 |
| A019400071 | 361 | 1.4 |
| A019400072 | 368 | 0.8 |
| A019400073 | 383 | 1.1 |
| A019400074 | 436 | 0.9 |

Characterization of Four Selected Humanization Variants in Potency Assay

Variants A019400071, A019400072, A019400073 and A019400074 were compared with A019400031 and ShK toxin in a T-cell activation assay as described in Example 4.4. The effect was evaluated of introduced mutations on the ability to inhibit IFNγ production of CCR7–CD45RA– T cells after stimulation with anti-CD3. The assay was performed both in presence and absence of HSA (2.5 µM). IC50 values are shown in Table B-17. No clear effect of specific mutations was noticed both in absence and presence of HSA.

TABLE B-17

Potency analysis of selected variants measured in a T-cell activation assay

| Construct | IC50 (M) |
|---|---|
| A019400031 | 3.6E-11 |
| A019400031 + HSA | 1.9E-10 |
| A019400071 | 9.6E-11 |
| A019400071 + HSA | 4.1E-10 |
| A019400072 | 3.2E-10 |
| A019400072 + HSA | 6.7E-10 |
| A019400073 | 1.4E-10 |
| A019400073 + HSA | 4.6E-10 |
| A019400074 | 1.6E-10 |
| A019400074 + HSA | 5.7E-10 |
| Shk | 4.1E-11 |
| Shk + HSA | 1.3E-11 |

Tables

TABLE A-1

Amino acid sequences of monovalent anti-Kv1.3 Nanobodies ("ID" refers to the SEQ ID NO as used herein)

| Name | ID | Amino acid sequence |
|---|---|---|
| A0194009B01 | 1 | EVQLVESGGGLVQAGGSLRLSCSASGLLFSVNSAGWYRQAPGKQRDFVARIRS GGSTNYADSVKGRFTISRDKATNTVYLQMNSLKPEDTAVYYCSSWRTGAYEYW GQGTLVTVSS |
| A0194009B06 | 2 | EVQLVESGGGLVQAGGSLRLSCSASGLLFSVNSAGWYRQAPGKQRDFVARIRS GGSTNYADSVKGRFTISRDKATNTVYLQMNSLKPEDTAVYYCSSWRTGAYEYW GQGTQVTVSS |
| A0194009G09_1 | 3 | EVQLVESGGGLVQAGGSLGLSCSASGLLFSRNSAGWYRQAPGKQREFVARIRM GGSINYADTVKGRFTISRDNAKNTVYLQMNSLKPEDTAVYYCSSWRTGFYEYW GQGTQVTVSS |
| A0194009G09 | 495 | EVQLVESGGGLVQAGGSLGLSCSASGLLFSRNSAGWYRQAPGKQREFVARIRM GGSINYADTVKGRFTISRDNAKNTVYLQMNSLKPEDTAVYYCSSWRTGFYEYW GQGTLVTVSS |
| A0194016A05 | 4 | EVQLVESGGGLVQAGGSLRLSCSASGLLFSVNSAGWYRQAPGKQRDFVARIRS GGSTNYADSVKGRFTISRDKATNTVHLQMNSLKPEDTAVYYCGSWRTGAYEY WGQGTLVTVSS |
| A0194016B04 | 5 | EVQLVESGGGLVQAGGSLRLSCSASGLLFSVNSAGWYRQAPGKQRDFVARIRS GGSTNYADSVKGRFTISRDKATNTLYLQMNNLKPEDTAVYYCSSWRTEAYEYW GRGTLVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| A0194016B06 | 6 | EVQLVESGGGLVQAGGSLRLSCSASGLLFSVNSAGWYRQAPGKQRDFVARIRSGGSTNYADSVKGRFTISRDKATNTVYLQMNSLKPEDTAVYYCSSWRTGAYEHWGQGTLVTVSS |
| A0194016C03 | 7 | EVQLVESGGGLVQAGGSLRLSCSASGLLFSVNSAGWYRQAPGKQRDFVARIRSGGSTNYADSVKGRFTISRDKATNTLYLQVNNLKPEDTAVYYCSSWRTEAYEYWGRGTLVTVSS |
| A0194016C10 | 8 | EVQLVESGGGLVQAGGSLRLSCSASGLLFSVNSAGWYRQAPGKQRDFVARIRSSGSTNYADSVKGRFTISRDKATNTVYLQMNSLKPEDTAVYYCSSWRTGAYEYWGQGAQVTVSS |
| A0194016F09 | 9 | EVQLVESGGGLVQAGGSLGLSCSASGLLFSVNSAGWYRQAPGKQRDFVARIRSGGSTNYADSVKGRFTISRDKATNTVYLQMNSLKPEDTAVYYCSSWRTGAYEYWGQGTQVTVSS |
| A0194016F11 | 10 | EVQLVESGGGLVQAGGSLRLSCSASGLLFSVNSAGWYRQAPGKQRDLVARIRSGGSTNYADSVKGRFTISRDKATNTLYLQMNNLKPEDTAVYYCSSWRTEAYEYWGRGTQVTVSS |
| A0194016G07 | 11 | EVQLVESGGGLVQAGGSLELSCSASGLLFSRNSVGWYRQAPGKKRDFVARIRSGGSTNYADSVKGRFIISRDNAKNTLYLQMNALKPEDTGVYYCSSWRTGAYEYWGQGTLVTVSS |
| A0194016G08 | 12 | EVQLVESGGGLVQAGGSLRLSCSASGLLFSANSAGWYRQAPGKQRDFVARIRSGGSTNYADSVKGRFTVSRDNAKNTMYLQMNGLKPEDTAVYYCSSWRTGAYEYWGQGTQVTVSS |
| A0194020A06 | 13 | EVQLVESGGGLVQAGGSLGLSCSASGLLFSRNSAGWYRQAPGKRREFVARIRMGGSINYADSVKGRFTVSRDNAKNMMYLQMNDLKPEDTAVYFCSGWREGFYEYWGQGTLVTVSS |
| A0194020A07 | 14 | EVQLVESGGGLVQAGGSLGLSCSASGLLFSRNSAGWYRRAPGKQREFVARIRMGGSINYADSVKGRFTTSRDNAKNTIYLQMNSLKPEDTAVYYCSSWREGFYEYWGQGTLVTVSS |
| A0194020B10 | 15 | EVQLVESGGGLVQAGGSLRLSCSASGLLFSVNSVGWYRRAPGKQREFVARLRTTGSTNYAQSVKGRFTISRDNAKNTVYLQMNNLKPEDTAVYYCSAWRIEAYEYWGQGTQVTVSS |
| A0194020C03 | 16 | EVQLVESGGGLVQPGGSLGLSCSASGLLFSRNSAGWYRQAPGKQREFVARIRMGGSINYADSVKGRFTTSRDNAKNTIYLQMNSLKPEDTAVYYCSSWREGFYEYWGQGTLVTVSS |
| A0194020C04 | 17 | EVQLVESGGGLVQAGGSLGLSCSASGLLFSRNSAGWYRQAPGKQREFVARIRMGGSINYGDSVKGRFTVSRDIAKNTMYLQMNDLKPEDTAKYFCSSWREGFYEYWGQGTLVTVSS |
| A0194020F09 | 18 | EVQLVESGGGLVQAGGSLGLSCSASGLLFSRNSAGWYRQAPGKQREFVARIRMGGSINYADSVKGRFTTSRDNAKNTIYLQMNSLKPEDTAVYYCSSWREGFYEYWGQGTQVTVSS |
| 7257f0227ef9f636dc7630192ad6e1c2 | 19 | EVQLVESAGGLVQAGGSPGLSSSDSGLLFSRHSAGWYRPAPGKRREFVARIRMGGSINYADSVKGRFTVSRDNAKNMMYLQMNDLKPEDTAVYFCSGWREGFYEYWGQGTQVTVSS |
| 5e260b33fe6df6b5c8488d5a032f4852 | 20 | EVQLVESGGGLVQAGGSLGLSCSASGLLFSRNSAGWYRQAPGKRRELVARIRMGGSINYADSVKGRFTVSRDNAKNMMYLLMNDLNREYTAVYFCSGWREGFFEYWGQGTQVTVSS |
| afc519230558a133019113e9509a672d | 21 | EVQLVESGGGLVQAGGALGLPCSASGLLFIRNSASWYRQAPGKRREFVARIRMGGSINYADSVKGRFTVSRDNAKNMMYLQMIDLKPEDTTVYCCSGWREGFYEYWGQGTQVTVSS |
| 728cbff15841abbeb52d482b0016f638 | 22 | EVQLVESGGGLVQAGGSLGLSCSASGLLFSRNSAGWYRQAPGKQREFVARIRMGGSINYADSVKGRFTTSRDNAKNTIYLQMNSLKPEDTAVYYCSSWREGFYEYWGQVTQVTVSS |
| f678139d1aa501f05ed990e993ff2875 | 23 | EVQLVESGGGLAQAGGSLGLSCSASGLLFSRNSAGRYRQAPGKRPEFFARVRMGGSINYADSVKGRFTVSRDNAKNMMYLQMNDLKPEDTAVYFCSGWREGFYEYSGQGTQVTVSS |
| 46dd642501e86a0a2dd21551e7faf09d | 24 | EVQLVESGGGFVQAGGSLGHSCSASGLLSSCNTAGWYRQAPGKRREFVARIRMVGSINYADSVKGRFTVSRDNAKNMMYLQMNDLKPEDTAVYFCSGWREGFYGYWGQGTQVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| 7e991df80879caf6e5e247f65a8a8511 | 25 | EVQLVESGGGLVQAGGSLGASRSASGLPLSRNSAGWYRQGPGKRREFVARIRMGGSINYADSVKGRFTVSGDNAKNMMYLQMNDLKPEDTAGYFCSGWREGFYEYWGQGTQVTVSS |
| 9e441891a0fa341c41527504c05ed15b | 26 | EVQLVESGGGLVQAGGSLGLSCSAPGLLFSRNSAGWCRQAPGKRREFVARTRMGGSINYADSVKGRFTVSRDNAKNMMYLQMNGLKPEDTAVCLCSGWREGFYEYWRQGTQVTVSS |
| efd395f1c79fe9a34e97926be4a9338a | 27 | EVQLVESGGCLVQAGGSLGLSCSASLLFFSRNSARWYRQAPVKRREFVGRIRMGGSINYADSGKGRFTVSRDNAKNMMYLQMNDLKPEDTAVYFCSGWREGFYEYWGQGTQVTVSS |
| 343640744296c3de37b6202ce181a132 | 28 | EVQLVESGGGLVQAGGSLGLACSASGLLISRNSAGWYRHAPGKQRAFVARVRMGGSINYGDAVKGRFTASRDIAKNTMYLQMNDLKPEDTAIYFCSSWREGFYEYWGQGTQVTVSS |
| 4f9e2c0a8018ba1c7e16fe3b803d0f49 | 29 | EVQLVESGGGLVQAGGALGLSCSASGLLFSRNSAGWYRQAPGKKRDFVARIRMGGSINYGVSVKGRFTVSRDIAKNTMYPQMNDLKPEDAAKYFCSSWRKGFYEYWGQGTQVTVSS |
| 213bd8ef8a6baa96fc7d30be8aafff99 | 30 | EVQLVESGGGSAQPGESLRLSCSASGLLFSRNSAGWYRQAPGKQREFVARIRMGGSINYGDSVKGRFTVSRDIAKNTMYLQMNDLKPEDTAKYFCSSWREGFYEYWGQGTQVTVSS |
| c12bd10881dd3a7abf989d49cdf44468 | 31 | EVQLVESGGGLVQAGGALGFTCSDSRLLFSRNSAGWYRQAAGKQREFVARIRMGGSINYGDSVKGRFTVSRDIAKNTMYLRMNDLKPEDTAIYFCSSWREGFYEYWGQGTQVTVSS |
| 36af9242c324d9ba4c518859deec3094 | 32 | EVQLVESGGALVQAGGSLGLPCSAPGLLFSRNSAGWYRQAPGKQREFVAGVRMGGSINYGGSVKGRFTVSRDIAKNTMYLQMNDLKPEDTAVYFCSSWRGGFYEYWGQGTQVTVSS |
| f9bb0eb8f0f497fa30f6d5bc51778ee1 | 33 | EVQLVESGGGFDQAGGSLGLPCSAPGLLFSRNRVGWYRQAPGKQRDFVARIRMGGSTNYADSVKGRFTISRDNAKNMVYLQMNSLKPEDTAVYYCSSWRTGFYEYWGQGTQVTVSS |
| 74c0c7da4aae9a3f64407f504af93fa6 | 34 | EVQLVESGGDLVQAGGALGLSCPASGLLFSRNSAGWYRQAPGKQRELVACIRMGGSINYGDSVKGRFTVSRDIAKNTMYLQVDDLKPEDTAIYFCSSWREGFYEYWGQGTQVTVSS |
| cf31a849d3da18aeedc44dd4d393fef0 | 35 | EVQLVESGGGLVKAGGSLGLSCSASGLLFSRNSVGWYRQAPGKQREFVARIRMGGSINYGGSVKGRFTVSRDIAKNTMYLQMNDLKPEETAWYFCSSWREGFYEYWSQRTQVTVSS |
| b077a6b050fff43ea3758b7a56dafb9b | 36 | EVQLVESAGGLVQAGGSLGLSCSASGLLFSRNSAGWYRQAPGKQREFVARIRMGGSINYGDSVKGRFTVSRDIAKDTRYMQINDLKPEDTAKYFCRSWREGLYEYWGQGTQVTVSS |
| d800d638e066182304b00f51542faf38 | 37 | EVQLVESGGGLLQAGGSLGLSCSASGLLLSRNRARWYRQAPGKQREFVARIRMGGSMNDGDSVKGRFTVSRDIAKNTMYLQMNDLKPEDTAIYFCRSWREGFYEYWGQGTQVTVSS |
| 45e8d1be704b2eef9ed8156abc03c6d8 | 38 | EVQLVESGGGLVQAGGALGLSCSASGLLFSRNSAGWHRQAPGKQREFVARIRMGGSINYGDSVKGRFTVSRDIAKNTMYLQMNELKPEDTAKYLCRSWREGFYESWGRGTQVTVSS |
| 32a3666f797cfcd58659bc01153ccb38 | 39 | EVQLVESGGGLVQAGGSLGLSCSASGLLFSRNSAGWYRPAPGKQREFVARIRMGGSINYGDSVKGRFTVARDIAKNTMYLQMNDLKPEETAIYFCSSWREGVYKYGGKGTQVTVSS |
| 1584d2e29498ea04b8cefac5c34d263d | 40 | EVQLVESGGGLVQAGGRRGLSCSASGFLFRRPSAGWYRQDPGKQREFVARIRMGGSINYGDSVKGRFTVSRDIAKNTMYLQMNDVKPEDTAKYFCSSWREGFYEYWGQGTQVTVSS |
| 2b7789fd646b01f675945e09acc89530 | 41 | EVQLVESGGALVQAGGSLGLSCSASGLLFIRNSAGCYRQAPGKHREFVARIRMGGSINYGDSVKGRFTVSRDIAKNTVYLQMNDLKPEYTAIYFCSSWREGYYEYWGQGTQVTVSS |
| 97276e7c5dea225b4fbb58426d23b2e5 | 42 | EVQLVESGGGLVEAGGSLGLSCSASGLLFSRISAGWYREAPGQQRECVARIRMGGSINYGDSVKGRFTVSRDIAKNTMYLQMNDLKPEHTAKYLCSSWREGFYEYWGQGTQVTVSS |
| a0615e93638f77818f6936045f94977f | 43 | EVQLVESGEGLVQAGGSLGLSCSASGLLFSPNSAGWYRQAPGKQRKFVARIRRGGGINYGDSVKGRFTVSRDIAKNTMYLQMNDLKPEDTAIYFCSSWREGFDEYWAQGTQVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| 5f18d5599843f072a1eed218d2a74048 | 44 | EVQLVESGGGLVQAGGPLGLSCSASGLLFSRNSAGWYRQAPGKQLAFVGRIGMGGCINYGDSVKGRFTVSRDIAKNTMYLQMNGLKPEDTAKYFCSSWREGFYEYWGQGTQVTVSS |
| 0f4d6d2f274ddd6f2beb50c53e54d4f4 | 45 | EVQLVESGGGLVQAAGSLGLPCSASGLLFSRMSARWYRQAPGEQREFVARIRMGGSINYGDSVKGRFTVTRDIAKNTMYLQMNDLKPEDTAKYFCSSWREGFYEYWCQGTQVTVSS |
| 545db63aa3771946a230075631c4d56d | 46 | EVQLVESGEGLVPAGGSLGPSCSASGLLFSRYSAGWYRQAPGKQREFVARSRMGGSINYGDSVKGRFTVSRDIAKNTMYLQMNDLKPEDTAEYFCSSWREGFYEYWGIGTQVTVSS |
| aff17a29c9e12331adb924c5c79b1643 | 47 | EVQLVESGGALVQAGGPPGLSCSASGLLFSRNSAGWYRQAPGKQREFVARIRMGGSINDGDSVKGRFTVSRDIDKNTMYLQMNDLKPENTAKYFCSSWREGFYKYWGQGTQVTVSS |
| ef8dd380aee92f426ec4a6b86dcba935 | 48 | EVQLVESGGGLVQAGGSLRLSCSASGLLFSVNSAGWYRQAPGQKREFVARIRTGGSTNYADSVKGRFTVSRGNAKNTVYLQMNNLKPEDTAVYYCSSWRTGAYEYWGQGTQVTVSS |
| 6812576932a2c1e0f08ec106e0d0a04e | 49 | EVQLVESGGGLVQAGGSLGLSCSASGLLFSRNIAGWYRPAPGKQREFVARIRMGGSINYGDSVKGRFNGSRDIAKNTMYLQMDDLKPEDTAICFCSSGREGFYEYWGQGTQVTVSS |
| 01ebe14f074a754cc51561530766ead4 | 50 | EVQLVESAGGLVQAGGPLGLSCSSSGLLFSLNSAGCSRQPPGKQREFVARIRMGGSINYGDSVKGRFTVSRDIAKNTMYLQMNDLKPEDTAKYFCSSWREGFYEYWGQGTQVTVSS |
| eb93eef0aa2380097f9dc5733bc6dd43 | 51 | EVQLVESGGALMQAGGSLGPPCPASGPLFRRTRAGWYRQAPGKQREFVARIRMGGSINYGDSVKGRFTVSRDIAKNTMYLQMNDLKPEDTAKYFCSSWREGFYEYWGQGTQVTVSS |
| 28c4a7cd04f53076c4f5acb03236ef61 | 52 | EVQLVESGGCLVQAGGSLGLSCSAPGLLFSPNSAGWYRQAPGKQREFVARILMGGSINYGDSVKGRFTVSRDIAKNTMYLQMKDLKPEDTAKYFCSRWREGFYEYCGQGTQVTVSS |
| 8c06f7a5597c4192b17846077a8fce8a | 53 | EVQLVESGGGLVQAGGPLGLSCSASGIPFSRNSAGWYRQAPGKQREFVARIRMGGSRNYGDSVKGRFTVSGDIAKNTMYLQMNDLKPEDTAKDFGSSWREGFYEYWGQGTQVTVSS |
| 63394ed3c69537d64eb90d1f6971fc43 | 54 | EVQLVESGGGLVQTGGSLTLSCSASGLLFSVNSAGWYRQAPGKQRDFVARIRRGGDTNYAESVRGRFTVSRDKAKNTMYLQMNSLKPEDTAVYYCASWRTGSYEYWGQGTQVTVSS |
| fc796afb415f19e50d23537a96a99ae0 | 55 | EVQLVESGGGLVQAGGSLRLSCSASGLLFSVNSAGWYRQAPGKQRIFVARLRRGGDTNYADSVKGRFTISRDNAKNTVYLQMNSLKPEDTAVYYCSAWRAGTYEYWGQVTQVTVSS |
| af47752f179d4b7a61f3a0536bbf4cfc | 56 | EVQLVESGGGSVHPGGSLRLSCSASGLLFSVNSAGWYRQAPGKQRIFVARLRRGGDTNYADSVKGRFTISRDNAKNTVYLQMNSLKPEDTAVYYCSAWRAGTYEYWGQGTQVTVSS |
| 4738fe2c7cdba35563859b889c0914be | 57 | EVQLVESGGGLVQAGGSLRLSCSASGLLFSVNSVGWYRRAPGKQREFVARLRTTGSTNYAESVKGRFTISRDNAKNTVYLQMNNLKPEDTAVYYCSAWRIEAYEYWGQGTQVTVSS |
| 7ca2189f04d2906f692762b2d3820dd2 | 58 | EVQLVESGGGLEQAGGSLRLSCSASGLLFSVNSAGWYRQAPGKQRDFVARIRSGGSTNYADSVKGRSTVSRDNAKNTLYLQLYSLKPEDTAVYYCSSWRTGAYEYWGQWTQVTVSS |
| 3f009bd0371fd5a057e1dd514a697a0d | 59 | EVQLVESGGGLVKAGGSLRLSCSASGLLFRVNSVGWYRQAPGKQRDFVARIRRGGSTNYADTVKGRVTISRDNAKNTVYLQMNSLSPADTGVYYCSSWREGAYEYWGQGTQVTVSS |
| 8d7c16aaec812b89b63ecfe25917a02d | 60 | EVQLVESGGGLVQAGGSLRLSCSASGLLFSVNSAGWYRRAPGKQREFVARLRRGGETNYGDSVKGRFTISRDKATNTLYLQMNSLRTEDTAVYYCSSWRTGSYEYWGQGTQVTVSS |
| 0049b650b8e87b0381fc26f80b9c4525 | 61 | EVQLVESGGGLVQAGGSLRLSCSASGLLFRVNSAGWYRQAQGKQREFVARIRSGGSTNYADSVKGRFIISRDNAQNTLYLQMNNLSPEDTAAYYCSSWRIDAYEYWGQGTQVTVSS |
| a0f1f7e657eebacae2796f435e4e4fda | 62 | EVQLVESAGGLVPAGGSLRLPCSAPGLLFSVDSAGWYRQAPGKQRDFVARIRSGGSTNDADSVKGRFTVSRDNAKNTVYLQMNSLKPEDTAVYYCSSWRTGAYEYWGQGTQVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| d9f77b8d61469fbeacad1fffa6142a31 | 63 | EVQLVESGGGFVQAGGSLRLSCSASGLLFSVNSTVSYRQAPGKQRDCVARIRSGGSTNYADSVKGRFTVSRDNAKNTVYLQMNSLKHEDTAVYYCSSWRTGAYEYWGQGTQVTVSS |
| 2f69e44b1b5912bda2c7dee779e5c265 | 64 | EVQLVESGEGLVKAGESLRLSCSASGLLFSVDSTGWYRQAPGKQREFFARIRSGGSINYGDSVKGRFTISRDKATNTLYLQMSNLNPEDTAVYYCSSWRIGSYEYWGQGTQVTVSS |
| A0194003A02 | 65 | EVQLVESGGGLVQAGDSLSLSCTASRGTFRNFGMGWFRQAQGKEREFVAAISRSGGHKYYSDSVKGRFTISKDNAKNMVSLQMNSLKPEDTAVYYCAARFRFDDGTSYYQRAFYDFWGQGTLVTVSS |
| A0194003A04 | 66 | EVQLVESGGGLVQAGDSLSLSCTASRGTFRNFGMGWSRQAQGKEREFVAAISRSGGHKYYSDSVKGRFTISKDNAKNMVSLQMNSLKPEDTAVYYCAARFRFDDGTSYYQRAFYDFWGQGTLVTVSS |
| A0194003A08 | 67 | EVQLVESGGGLVQAGDSLSLSCTASAGTFRNFGMGWFRQARGEEREFVATISRSARHTYYSDSVKGRFTISRDNAKNMVSLQMNSLKPEDTAVYYCAARFRSDDGTYYYQRAFYDFWGQGTQVTVSS |
| A0194003A09 | 68 | EVQLVESGGGLVQAGGSLSLSCTASGGTFRNYGMGWFRQAQGKEREFVAAISRSAGRTYYSDSVKGRFTISKNNAKNIMSLQMNSLKPEDTAVYYCAARFRFDDGTYYYQRAFYDFWGQGTLVTVSS |
| A0194003A12 | 69 | EVQLVESGGGLVQAGGSLSLSCTASGGTFRNYGMGWFRQAQGKEREFVAAISRSASRTYYSDSVKGRFTISKNNAKNIMSLQMNSLKPEDTAVYYCAARFRFDDGTYYYQRAFYDFWGQGTQVTVSS |
| A0194003B01 | 70 | EVQLVESGGGLVQAGGSLSLSCTASGGTFRNFGMGWFRQAQGKEREFVAAISRSGGHIYYSDSVKGRFTIARANAKNMVSLQMNSLKPEDTAVYYCAARFRFDDGTYYYQRAFYDFWGQGTQVTVSS |
| A0194003B06 | 71 | EVQLVESGGGLVQAGGSLSLSCTVSGGNFRNFGMGWFRQAHGKEREFVAAISRSGGRTYYADSVKGRFTISRDNAKNMVSLQMNSLKPEDTAVYSCAARFRSDDGTYYYQRAFYDFWGQGTQVTVSS |
| A0194003B09 | 72 | EVQLVESGGGLVQAGGSLSLSCTASGGTFRNYGMGWFRQAQGKEREFVAAISRSAGRTYYSDSVKGRFTISKNNAKNVMSLQMNSLKPEDTAVYYCAARFRFDDGTYYYQRAFYDFWGQGTLVTVSS |
| A0194003B11 | 73 | EVQLVESGGGLVRAGGSLSLSCTSSSGTFRNFAMGWFRQAQGKEREFVATISRSGGHTYYSDSVKGRFTISRDNAKNLVSLQMNSLKPEDTAVYYCAARFRFDDDTYYYQRAFYDFWGQGTLVTVSS |
| A0194003C08 | 74 | EVQLVESGGGLVQAGGSLSLSCTASGGTFRNYGMGWFRQAQGKEREFVAAISRSGGRTYYSDSVKGRFTISKNNAKNIMSLQMNSLKPEDTAVYYCAARFRFDDGTYYYQRAFYDFWGQGTQVTVSS |
| A0194003F08 | 75 | EVQLVESGGGLVQAGGSLSLSCTASGGTFRNFGMGWFRQDGQEREFVAAISRSGGRTYFSDSVKGRFTISKDNAKNILSLQMNSLKPEDTAVYYCAARFRFDDGTYYYQRAFYDFWGQGTQVTVSS |
| A0194004F06 | 76 | EVQLVESGGGLVQAGGSLSLSCTASRGTFRNFGMGWFRQAQGKEREFVAAISRSAGHTYYSDSVKGRFTISRDNAKNMVSLQMDSLKPEDTAVYYCAARFRFDDGTYYYQRTFYDFWGQGTQVTVSS |
| A0194007A01 | 77 | EVQLVESGGGLAQAGGSLSLSCTASGGNFRNFGMGWFRQVQGTEREFVAAISRTGGRTYFSDSVKGRFTISRDNAKNMVSLQMNSLKPEDSAVYYCAARFRGDGTYYYQRNFYDFWGQGTQVTVSS |
| A0194007B04 | 78 | EVQLVESGGGLVQAGDSLSLSCTASRGTFRNFGMGWFRQAQGKEREFVAAISRSGGHKYYSDSVQGRFTISKDNAKNMVSLQMNSLKPEDTAVYYCAARFRFDDGTSYYQRAFYDFWGQGTQVTVSS |
| A0194007B09 | 79 | EVQLVESGGGLVQTGGSLSLSCTASGGTFRNYGMGWFRQAQGKEREFVAAISRSAGRTYYSDSVKGRFTISKNNAKNIMSLQMNSLKPEDTAVYYCAARFRFDDGTYYYQRAFYDFWGQGTQVTVSS |
| A0194007B12 | 80 | EVQLVESGGGLVQAGGSLSLSCTASGGTFRNYAMGWFRQAQGKEREFVATISRSGGYTYYSDSVKGRFTISRDNAKNMVSLQMNSLKPEDTAVYYCAARFRFGDGTYYYQRAFYDFWGQGTQVTVSS |
| A0194007C01 | 81 | EVQLVESGGGLVQAGGSLSLSCTASGGTFRNFGMGWFRQAQGKEREFVAAISRSGGRTYYSDSVKGRFTISKDNAKNIMSLQMNSLRPEDTAVYYCAARFRFDDGTYYYQRAFYDFWGQGTQVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| A0194007D01 | 82 | EVQLVESGGGSVQAGGSLSLSCTASRGTFRNFGMGWFRQAQGKEREFVAAISRTGGRTYYSDSVKGRFTISRDNAKNMVSLQMNSLKPEDTAIYYCAARFRFDDGTYYYQRAFYDFWGQGTLVTVSS |
| A0194007D10 | 83 | EVQLVESGGGLVQAGDSLSLSCTASAGTFRNFGMGWFRQARGEEREFVATISRSARHTYYSDSVKGRFTISRDNAKNMVSLQMNSLKPEDTAVYYCAARFRSDGGTYYYQRAFYDFWGQGTQVTVSS |
| A0194007D11 | 84 | EVQLVESGGGLVQAGGSLSLSCTASAGTFRNFGMGWFRQAQGKEREFVAAISRSGGHTYYSDSVKGRFTISKDNAKNMVSLKMNSLKPEDTADYYCAARFRFDDGTYYYQRAFYDFWGQGTQVTVSS |
| A0194007E04 | 85 | EVQLVESGGGLVQAGGSLSLSCTASGGTFRNFGMGWFRQVQGKEREFVAAISRSGGHIFYSDSVKGRFTISKDNAKNILFLQMNSLKPEDTAVYYCAARFRFDDGTYYYQRAFYDFWGQGTQVTVSS |
| A0194007E08 | 86 | EVQLVESGGGLVQAGGSLSLSCTASGGTFRNYGMGWFRQAQGKEREFVAAISRSAGRTYYSDSAKGRFTISKNNAKNIMSLQMNSLKPEDTAVYYCAARFRFDDGTYYYQRAFYDFWGQGTLVTVSS |
| A0194007E12 | 87 | EVQLVESGGGLVQAGGSLSLSCTASGGNFRNFGMGWFRQAQGKEREFVAAISRSGGHTYYSDSVKGRFTISRDNAKNMVSLQMNSLKPEDTAVYYCAARFRYGDGTYYYQRAFYDFWGQGTLVTVSS |
| A0194007F01 | 88 | EVQLVESGGGLVQAGDSLSLSCTASRGTFRNFGMGWFRQAQGKEREFVAAISRSGGRKYYSDSVKGRFTISKDNAKNMVSLQMNSLKPEDTAVYYCAARFRFDDGTSYYQRAFYDFWGQGTLVTVSS |
| A0194007G09 | 89 | EVQLVESGGGLVEAGGSLSLSCTASAGTFRNFGMGWFRQARGEEREFVATISRSARHTYYSDSVKGRFTISRDNAKNMVSLQMNSLKPEDTAVYYCAARFRSDDGTYYYQRAFYDFWGQGTQVTVSS |
| A0194008A01 | 90 | EVQLVESGGGLVQAGDSLSLSCTASAGTLRNFGMGWFRQARGEEREFVATISRSARHTYYSDSVKGRFTISRDNAKNMVSLQMNSLKPEDTAVYYCAARFRSDDGTYYYQRRFYDFWGQGTQVTVSS |
| A0194008A02 | 91 | EVQLVESGGGLVQAGDSLSLSCTASAGTLRNFGMGWFRQARGEEREFVATISRSARHTYYSDSVKGRFTISRDNAKNMVSLQMNSLKPEDTAVYYCAARFRSGDGTYYYQRAFYDFWGQGTQVTVSS |
| A0194008A09 | 92 | EVQLVESGGGLVQAGGSLSLSCTASGGTFRNYGMGWFRQAQGKEREFVAAISRTGGHTYYSDSVKGRFTISKNNAKNIMSLQMNSLKPEDTAVYYCAARFRFGDGTYYYQRAFYDFWGQGTLVTVSS |
| A0194008A11 | 93 | EVQLVESGGGLVQAGDSLSLSCTASAGTLRNFGMGWFRQARGEEREFVATISRSARHTYYSDSVKGRFTISRDNAKNMVSLQMNSLKPEDTAVYYCAARFRSDDGTYYYQRAFYDFWGQGTQVTVSS |
| A0194008B01 | 94 | EVQLVESGGGLVQAGGSLSLSCTSSKGTFRNFAMGWFRQAQGKEREFVATISRSGGHTYYSDSVKGRFAISRDNAKNLVSLQMNSLNAEDTAVYYCAARFRSDDDTYYYQRAFYDFWGQGTLVTVSS |
| A0194008C01 | 95 | EVQLVESGGGLVQAGGSLSLPCTASGGTFRNYGMGWFRQAQGKEREFVAAISRSAGRTYYSDSVKGRFTISKNNAKNIMSLQMNSLKPEDTAVYYCAARFRFDDGTYYYQRAFYDFWGQGTLVTVSS |
| A0194008C07 | 96 | EVQLVESGGGLVQAGGSLSLSCTASGGTFRNYGMGWFRQAQGKERDFVAAISRTNGHIYYSDSVKGRFTISKDNAKNILSLQMNSLKPEDTAVYYCAARFRFGDGTYYYQRTFYDFWGQGTLVTVSS |
| A0194008C08 | 97 | EVQLVESGGGLVQAGGSLSLSCTASGGTFRNFAMGWFRQAQGKEREFVATISRSGGHIYYSDSVKGRFTISRDNAKNMVSLQMNSLKPEDTAVYYCAARFRFDDGTSYYYQRAFYDFWGQGTLVTVSS |
| A0194008D08 | 98 | EVQLVESGGDLVQPGGSLRLSCTASGGTFRNYGMGWFRQAQGKEREFVAAISRTGGHTYYSDSVKGRFTISKDNAKNIVSLQMNSLKPEDTAVYYCAARFRFGDGTYYYQRNFYDFWGQGTQVTVSS |
| A0194008F05 | 99 | EVQLVESGGGLVQAGGPLSLSCTASGGTFRNYGMGWFRQAQGKEREFVAAISRSAGRTYYSDSVKGRFTISKNNAKNIMSLQMNSLKPEDTAVYYCAARFRFDDGTYYYQRAFYDFWGQGTLVTVSS |
| A0194008G10 | 100 | EVQLVESGGGSVQAGGSLRLVCAFSGGTFRNFAMGWFRQAQGKEREFVATISRSGGHTYYSDSVKGRFTISKDNAKNMVYLQMYSLKPEDTAVYYCAGRFRFGDGAYYYQRTFYDFWGQGTLVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| KV13BIIPMP026D09 | 101 | EVQLVESGGGLVQAGGSLSLSCTASRGTFRNFAMGWFRQAQGKEREFVATISRSGGHIYYSDSVKGRFTISKDNAKNMVSLQMNSLKPEDTAVYYCAARFRFDDGTSYYQRAFYDFWGQGTQVTVSS |
| KV13BIIPMP026F08 | 102 | EVQLVESGGGLVQAGGSLSLSCTASRGTFRNYAMGWFRQAQGKEREFVATISRSGGHIYYSDSVKGRFAISKDNAKNMMSLRMNSLKPEDTAVYYCAARFRFDDGTYFYQRAFYDFWGQGTQVTVSS |
| KV13BIIPMP027A11 | 103 | KVQLVESRGGLVQAGGSLRLSCTASGGTFRNYGMGWFRQAQGKEREFVAAVSRTGGRTYYSDSVKGRFTISRDNAKNMVSLQMNKLKPEDTAVYYCAARFRFDDGTYYYQRAFYDFWGQGTQVTVSS |
| KV13BIIPMP027B10 | 104 | EVQLVESGGGLVQAGGSLSLSCTASGGTFRSYGMGWFRQAQGKEREFVAAISRTGGHTYYSDSVKGRFTISKNNAKNIMSLQMNSLKPEDTAVYYCAARFRFGDGTYYYQRAFYDFWGQGTQVTVSS |
| KV13BIIPMP027B12 | 105 | EVQLVESGGGLVQAGGSLSLSCTASGGNFRNFGMGWFRQAQGTEREFVAAISRTGGRTYFSDSVKGRFTISRDNAKNMVSLQMNSLKPEDTAVYYCAARFRFDDGTYYYQRNFYDFWGQGAQVTVSS |
| KV13BIIPMP027D09 | 106 | EVQLVESGGGLVQAGGSLSLSCTASGGTFRNFAMGWFREAQGKEREFVATISRSGGHTYYSDSVKGRFTISRDNAKNMVALQMNSLKPEDTAVYYCAARFRFDDGTYYYQRAFYNLWGQGTQVTVSS |
| KV13BIIPMP027D10 | 107 | EVQLVESGGGLVQAGGSLSLSCTASGGTFRNYGMGWFRQAQGKEREFVAAISRTGGHTYYSDSVKGRFTISKDNAKNMVSLQMNSLKPEDTAVYYCAARFRFGDGTYYYQRNFYDFWGQGTQVTVSS |
| KV13BIIPMP027E08 | 108 | EVQLVESGGGLVQAGGSLSLSCTASVGNFRNFGMGWFRQAQGKEREFVAAISRSGGHTYYSDSVKGRFTISRDNAKNMVSLQMNSLKPEDTAVYYCAARFRFDDGTYYYQRAFYDFWGQGTQVTVSS |
| KV13BIIPMP027E11 | 109 | EVQLVESGGGLVQAGGSLSLSCTVSGGNFRNFGMGWFRQAHGKEREFVAAISRSGGRTYYADSVKGRFTVSRDNAKNMVSLQMNSLKPEDTAVYSCAARFRSDDGTYYYQRAFYDFWGQGTQVTVSS |
| A019400003 | 110 | EVQLVESGGGLVQAGGSLSLSCTASGGTFRNFGMGWFRQAQGKEREFVAAISRTGGHTYYQDSVKGRFTISKDNAKNILSLQMNSLKPEDTAVYYCAARFRFGDGTYYYQRAFYDFWGQGTQVTVSS |
| KV13BIIPMP027H08 | 111 | EVQLVESGGGLVQAGGSLSLSCTASGGTFRNFAMGWFRQAQGKEREFVATISRSGGHIFYSESVKGRFTISRDNAKNMVSLQMNSLKPEDTAVYYCAARFRSDDGTYYYQRIFYDFWGQGTQVTVSS |
| KV13BIIPMP027H09 | 112 | EVQLVESGGGLVQPGGSLSLSCTASAGTFRNFGMGWFRQARGEEREFVATISRSARHTYYSDSVKGRFTISRDNAKNMVSLQMNSLKPEDTAVYYCAARFRSDDGTYYYQRAFYDFWGQGTQVTVSS |
| KV13BIIPMP027H10 | 113 | EVQLVESGGGSVQAGGSLSLSCTASRGTFRNYGMGWFRQAQGKEREFVAAISRSGGHTYYSDSVKGRFTISKDNAKNIMSLQMNSLKPEDTAVYYCAARFRFDDGTYYYQRAFYDFWGQGTQVTVSS |
| KV13BIIPMP049B09 | 114 | EVQLVESGGGLVQAGGSLSLSCTVSGGNFRNFGVGWFRQAHGKEREFVAAISRAGGRTYYADSVKGRFAISRDNAKNMVSLQMNSLKPEDTAVYTCAARFRSGDGTSYYERAFYDFWGQGTQVTVSS |
| KV13BIIPMP049E10 | 115 | KVQLVESGGGLVQPGGSLSLSCTASAGTFRNFGMGWFRQAQGTEREFVAAISRSGGRTYFSDSVKGRFTISKDNAKNMLSLQMNSLKPEDTAVYYCAARFRSDDGTYYYQRAFYDFWGQGAQVTVSS |
| KV13BIIPMP050A07 | 116 | EVQLVESGGGLVQAGGSLSLSCTVSGGTFRNYGMGWFRQFQGKEREFVAAISRSGGHIFYSESVKGRFTISRDNAKNMVSLQMNSLKPEDTAVYYCAARFRSGDGTYYYQRAFYDFWGQGTQVTVSS |
| KV13BIIPMP050A09 | 117 | EVQLVESGGGLVQAGGSLSLSCTASAGTFRNFGMGWFRQARGEAREFVATISRSGGHIYYSDSVKGRFTISRDNAKNMVSLQMNSLKPEDTAVYYCAARFRSDDGTYYYQRAFYDFWGQGTQVTVSS |
| KV13BIIPMP050A10 | 118 | EVQLVESGGGLVRAGGSLSLSCTSSSGTFRNFAMGWFRQAQGKEREFVATISRSGGHTYYSRDNAKNLVSLQMSSLKPEDTAVYYCAARFRFDDDTYYQRAFYDFWGQGTQVTVSS |
| KV13BIIPMP050B11 | 119 | EVQLVESGGGSVQAGNSLSLSCTASGGTFRNYAMGWFRQAQGKEREFVATISRSGGHIYYSDSVKGRFTISRDNAKNMVSLQMNSLKPEDTAAYYCAARFRFGDGTYYYQRAFYDFWGQGTQVTVSS |

TABLE A-1-continued

Amino acid sequences of monovalent anti-Kv1.3 Nanobodies ("ID" refers to the SEQ ID NO as used herein)

| Name | ID | Amino acid sequence |
|---|---|---|
| KV13BIIPMP050C09 | 120 | EVQLVESGGGLVQAGDSLSLSCTASRGTFRNFGMGWFRQAQGKEREFVAAISR SGGHKYYSDSVKGRSTISKDNAKNMVSLQMNSLKPEDTAVYYCAARFRDDGT SYYQRAFYDFWGQGTQVTVSS |
| KV13BIIPMP050D09 | 121 | EVQLVESGGGLAQAGGSLSLSCTASGGNFRNFGMGWFRQVQGTEREFVAAIS RTGGRTYFSDSVKGRFTISRDNAKNMVSLQMNSLKPEDSAVYYCAARFRGDG TYYYQRNFYGFWGQGAQVTVSS |
| KV13BIIPMP050E12 | 122 | EVQLVESGGGLVQAGGSLSLSCTASGGTFRNYGMGWFRQAQGKEREFVAAIS RSAGHIYYLNSVKGRFTISKDNAKNILSLQMNSLKPEDTAVYYCAARFRDDGTY YYQRAFYDFWGQGTQVTVSS |
| KV13BIIPMP050F11 | 123 | EVQLVESGGGLVQAGNSLSLSCTASAGTLRNFGMGWFRQARGEEREFVATISR SARHTYYSDSVKGRFTISRDNAKNMVSLQMNSLKPEDTAVYYCAARFRSDDGT YYYQRAFYDFWGQGTQVTVSS |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | A0194009B01 | 124 | EVQLVESGGGLVQAGGSLRLSCSAS | 181 | GLLFSVNSAG | 227 | WYRQAPGKQRDFVA | 268 | RIRSGGSTN | 310 | YADSVKGRFTISRDKATNTVYLQMNSLKPEDTAVYYCSS | 393 | WRTGAYEY | 436 | WGQGTLVTVSS |
| 2 | A0194009B06 | 124 | EVQLVESGGGLVQAGGSLRLSCSAS | 181 | GLLFSVNSAG | 227 | WYRQAPGKQRDFVA | 268 | RIRSGGSTN | 310 | YADSVKGRFTISRDKATNTVYLQMNSLKPEDTAVYYCSS | 393 | WRTGAYEY | 437 | WGQGTQVTVSS |
| 3 | A0194009G09_1 | 125 | EVQLVESGGGLVQAGGSLGLSCSAS | 182 | GLLFSRNSAG | 228 | WYRQAPGKQREFVA | 269 | RIRMGGSIN | 311 | YADTVKGRFTISRDNAKNTVYLQMNSLKPEDTAVYYCSS | 394 | WRTGFYEY | 437 | WGQGTQVTVSS |
| 495 | A0194009G09 | 125 | EVQLVESGGGLVQAGGSLGLSCSAS | 182 | GLLFSRNSAG | 228 | WYRQAPGKQREFVA | 269 | RIRMGGSIN | 311 | YADTVKGRFTISRDNAKNTVYLQMNSLKPEDTAVYYCSS | 394 | WRTGFYEY | 436 | WGQGTLVTVSS |
| 4 | A0194016A05 | 124 | EVQLVESGGGLVQAGGSLRLSCSAS | 181 | GLLFSVNSAG | 227 | WYRQAPGKQRDFVA | 268 | RIRSGGSTN | 312 | YADSVKGRFTISRDKATNTVHLQMNSLKPEDTAVYYCGS | 393 | WRTGAYEY | 436 | WGQGTLVTVSS |
| 5 | A0194016B04 | 124 | EVQLVESGGGLVQAGGSLRLSCSAS | 181 | GLLFSVNSAG | 227 | WYRQAPGKQRDFVA | 268 | RIRSGGSTN | 313 | YADSVKGRFTISRDKATNTLYLQMNNLKPEDTAVYYCSS | 395 | WRTEAYEY | 438 | WGRGTLVTVSS |
| 6 | A0194016B06 | 124 | EVQLVESGGGLVQAGGSLRLSCSAS | 181 | GLLFSVNSAG | 227 | WYRQAPGKQRDFVA | 268 | RIRSGGSTN | 310 | YADSVKGRFTISRDKATNTVYLQMNSLKPEDTAVYYCSS | 396 | WRTGAYEH | 436 | WGQGTLVTVSS |
| 7 | A0194016C03 | 124 | EVQLVESGGGLVQAGGSLRLSCSAS | 181 | GLLFSVNSAG | 227 | WYRQAPGKQRDFVA | 268 | RIRSGGSTN | 314 | YADSVKGRFTISRDKATNTLYLQVNNLKPEDTAVYYCSS | 395 | WRTEAYEY | 438 | WGRGTLVTVSS |
| 8 | A0194016C10 | 124 | EVQLVESGGGLVQAGGSLRLSCSAS | 181 | GLLFSVNSAG | 227 | WYRQAPGKQRDFVA | 270 | RIRSSGSTN | 310 | YADSVKGRFTISRDKATNTVYLQMNSLKPEDTAVYYCSS | 393 | WRTGAYEY | 439 | WGQGAQVTVSS |
| 9 | A0194016F09 | 125 | EVQLVESGGGLVQAGGSLGLSCSAS | 181 | GLLFSVNSAG | 227 | WYRQAPGKQRDFVA | 268 | RIRSGGSTN | 310 | YADSVKGRFTISRDKATNTVYLQMNSLKPEDTAVYYCSS | 393 | WRTGAYEY | 437 | WGQGTQVTVSS |
| 10 | A0194016F11 | 124 | EVQLVESGGGLVQAGGSLRLSCSAS | 181 | GLLFSVNSAG | 229 | WYRQAPGKQRDLVA | 268 | RIRSGGSTN | 313 | YADSVKGRFTISRDKATNTLYLQMNNLKPEDTAVYYCSS | 395 | WRTEAYEY | 440 | WGRGTQVTVSS |
| 11 | A0194016G07 | 126 | EVQLVESGGGLVQAGGSLELSCSAS | 183 | GLLFSRNSVG | 230 | WYRQAPGKKRDFVA | 268 | RIRSGGSTN | 315 | YADSVKGRFIISRDNAKNTLYLQMNALKPEDTGVYYCSS | 393 | WRTGAYEY | 436 | WGQGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 12 | A0194016G08 | 124 | EVQLVESGGGLVQAGGSLRLSCSAS | 184 | GLLFSANSAG | 227 | WYRQAPGKQRDFVA | 268 | RIRSGGSTN | 316 | YADSVKGRFTVSRDNAKNTMYLQMNGLKPEDTAVYYCSS | 393 | WRTGAYEY | 437 | WGQGTQVTVSS |
| 13 | A0194020A06 | 125 | EVQLVESGGGLVQAGGSLGLSCSAS | 182 | GLLFSRNSAG | 231 | WYRQAPGKRREFVA | 269 | RIRMGGSIN | 317 | YADSVKGRFTTSRDNAKNMMYLQMNDLKPEDTAVYFCSG | 397 | WREGFYEY | 436 | WGQGTLVTVSS |
| 14 | A0194020A07 | 125 | EVQLVESGGGLVQAGGSLGLSCSAS | 182 | GLLFSRNSAG | 232 | WYRRAPGKQREFVA | 269 | RIRMGGSIN | 318 | YADSVKGRFTTSRDNAKNTIYLQMNSLKPEDTAVYYCSS | 397 | WREGFYEY | 436 | WGQGTLVTVSS |
| 15 | A0194020B10 | 124 | EVQLVESGGGLVQAGGSLRLSCSAS | 185 | GLLFSVNSVG | 232 | WYRRAPGKQREFVA | 271 | RLRTTGSTN | 319 | YAQSVKGRFTISRDNAKNTVYLQMNNLKPEDTAVYYCSA | 398 | WRIEAYEY | 437 | WGQGTQVTVSS |
| 16 | A0194020C03 | 127 | EVQLVESGGGLVQPGGSLGLSCSAS | 182 | GLLFSRNSAG | 228 | WYRQAPGKQREFVA | 269 | RIRMGGSIN | 318 | YADSVKGRFTTSRDNAKNTIYLQMNSLKPEDTAVYYCSS | 397 | WREGFYEY | 436 | WGQGTLVTVSS |
| 17 | A0194020C04 | 125 | EVQLVESGGGLVQAGGSLGLSCSAS | 182 | GLLFSRNSAG | 228 | WYRQAPGKQREFVA | 269 | RIRMGGSIN | 320 | YGDSVKGRFTVSRDIAKNTMYLQMNDLKPEDTAKYFCSS | 397 | WREGFYEY | 436 | WGQGTLVTVSS |
| 18 | A0194020F09 | 125 | EVQLVESGGGLVQAGGSLGLSCSAS | 182 | GLLFSRNSAG | 228 | WYRQAPGKQREFVA | 269 | RIRMGGSIN | 318 | YADSVKGRFTTSRDNAKNTIYLQMNSLKPEDTAVYYCSS | 397 | WREGFYEY | 437 | WGQGTQVTVSS |
| 19 | 7257f0227ef9f631286dc7630192ad6e1c2 | 128 | EVQLVESAGGLVQAGGSPGLSSSDS | 186 | GLLFSRHSAG | 233 | WYRPAPGKRREFVA | 269 | RIRMGGSIN | 317 | YADSVKGRFTVSRDNAKNMMYLQMNDLKPEDTAVYFCSG | 397 | WREGFYEY | 437 | WGQGTQVTVSS |
| 20 | 5e260b33fe6df6b5c8488d5a032f4852 | 125 | EVQLVESGGGLVQAGGSLGLSCSAS | 182 | GLLFSRNSAG | 234 | WYRQAPGKRRELVA | 269 | RIRMGGSIN | 321 | YADSVKGRFTVSRDNAKNMMYLLMNDLNREYTAVYFCSG | 399 | WREGFFEY | 437 | WGQGTQVTVSS |
| 21 | afc519230558a133019113e9509a672d | 129 | EVQLVESGGGLVQAGGALGLPCSAS | 187 | GLLFIRNSAS | 231 | WYRQAPGKRREFVA | 269 | RIRMGGSIN | 322 | YADSVKGRFTVSRDNAKNMMYLQMIDLKPEDTTVYCCSG | 397 | WREGFYEY | 437 | WGQGTQVTVSS |
| 22 | 728cbff15841abbeb52d482b0016f638 | 125 | EVQLVESGGGLVQAGGSLGLSCSAS | 182 | GLLFSRNSAG | 228 | WYRQAPGKQREFVA | 269 | RIRMGGSIN | 318 | YADSVKGRFTTSRDNAKNTIYLQMNSLKPEDTAVYYCSS | 397 | WREGFYEY | 441 | WGQVTQVTVSS |
| 23 | f678139d1aa501f05ed990e993ff2875 | 130 | EVQLVESGGGLAQAGGSLGLSCSAS | 188 | GLLFSRNSAG | 235 | RYRQAPGKRPEFFA | 272 | RVRMGGSIN | 317 | YADSVKGRFTVSRDNAKNMMYLQMNDLKPEDTAVYFCSG | 397 | WREGFYEY | 442 | SGQGTQVTVSS |
| 24 | 46dd642501e86a0a2dd21551e7faf09d | 131 | EVQLVESGGGFVQAGGSLGHSCSAS | 189 | GLLSSTCNAG | 231 | WYRQAPGKRREFVA | 273 | RIRMVGSIN | 317 | YADSVKGRFTVSRDNAKNMMYLQMNDLKPEDTAVYFCSG | 400 | WREGFYGY | 437 | WGQGTQVTVSS |
| 25 | 7e991df80879caf6e5e247f65a8a8511 | 132 | EVQLVESGGGLVQAGGSLGASRSAS | 190 | GLPLSRNSAG | 236 | WYRQGPGKRREFVA | 269 | RIRMGGSIN | 323 | YADSVKGRFTVSGDNAKNMMYLQMNDLKPEDTAGYFCSG | 397 | WREGFYEY | 437 | WGQGTQVTVSS |
| 26 | 9e441891a0fa341c41527504c05ed15b | 133 | EVQLVESGGGLVQAGGSLGLSCSAP | 182 | GLLFSRNSAG | 237 | WCRQAPGKRREFVA | 274 | RTRMGGSIN | 324 | YADSVKGRFTVSRDNAKNMMYLQMNGLKPEDTAVCLCSG | 397 | WREGFYEY | 443 | WRQGTQVTVSS |
| 27 | efd395f1c79fe9a13434e97926be4a9338a | 134 | EVQLVESGGCLVQAGGSLGLSCSAS | 191 | LLFSRNSAR | 238 | WYRQAPVKRREFVG | 269 | RIRMGGSIN | 325 | YADSGKGRFTVSRDNAKNMMYLQMNDLKPEDTAVYFCSG | 397 | WREGFYEY | 437 | WGQGTQVTVSS |
| 28 | 343640744296c3de37b6202ce181a132 | 135 | EVQLVESGGGLVQAGGSLGLACSAS | 192 | GLLISRNSAG | 239 | WYRHAPGKQRAFVA | 272 | RVRMGGSIN | 326 | YGDAVKGRFTASRDIAKNTMYLQMNDLKPEDTAIYFCSS | 397 | WREGFYEY | 437 | WGQGTQVTVSS |
| 29 | 4f9e2c0a8018ba1c7e16fe3b803d0f49 | 136 | EVQLVESGGGLVQAGGALGLSCSAS | 182 | GLLFSRNSAG | 230 | WYRQAPGKKRDFVA | 269 | RIRMGGSIN | 327 | YGVSVKGRFTVSRDIAKNTMYPQMNDLKPEDAAKYFCSS | 401 | WRKGFYEY | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 30 | 213bd8ef8a6baa96fc7d30be8aafff99 | 137 | EVQLVESGGGSAQPGESLRLSCSAS | 182 | GLLFSRNSAG | 228 | WYRQAPGKQREFVA | 269 | RIRMGGSIN | 320 | YGDSVKGRFTVSRDIAKNTMYLQMNDLKPEDTAKYFCSS | 397 | WREGFYEY | 437 | WGQGTQVTVSS |
| 31 | c12bd10881dd3a7abf989d49cdf44468 | 138 | EVQLVESGGGLVQAGGALGFTCSDS | 193 | RLLFSRNSAG | 240 | WYRQAAGKQREFVA | 269 | RIRMGGSIN | 328 | YGDSVKGRFTVSRDIAKNTMYLRMNDLKPEDTAIYFCSS | 397 | WREGFYEY | 437 | WGQGTQVTVSS |
| 32 | 36af9242c324d9ba4c518859deec3094 | 139 | EVQLVESGGALVQAGGSLGLPCSAP | 182 | GLLFSRNSAG | 228 | WYRQAPGKQREFVA | 275 | GVRMGGSIN | 329 | YGGSVKGRFTVSRDIAKNTMYLQMNDLKPEDTAVYFCSS | 402 | WRGGFYEY | 437 | WGQGTQVTVSS |
| 33 | f9bb0eb8f0f497fa30f6d5bc51778ee1 | 140 | EVQLVESGGGFDQAGGSLGLPCSAP | 194 | GLLFSRNRVG | 227 | WYRQAPGKQRDFVA | 276 | RIRMGGSTN | 330 | YADSVKGRFTISRDNAKNMVYLQMNSLKPEDTAVYYCSS | 394 | WRTGFYEY | 437 | WGQGTQVTVSS |
| 34 | 74c0c7da4aae9a3f64407f504af93fa6 | 141 | EVQLVESGGDLVQAGGALGLSCPAS | 182 | GLLFSRNSAG | 241 | WYRQAPGKQRELVA | 277 | CIRMGGSIN | 331 | YGDSVKGRFTVSRDIAKNTMYLQVDDLKPEDTAIYFCSS | 397 | WREGFYEY | 437 | WGQGTQVTVSS |
| 35 | cf31a849d3da18aeedc44dd4d393fef0 | 142 | EVQLVESGGGLVKAGGSLGLSCSAS | 183 | GLLFSRNSVG | 228 | WYRQAPGKQREFVA | 269 | RIRMGGSIN | 332 | YGGSVKGRFTVSRDIAKNTMYLQMNDLKPEETAWYFCSS | 397 | WREGFYEY | 444 | WSQRTQVTVSS |
| 36 | b077a6b050fff43ea3758b7a56dafb9b | 143 | EVQLVESAGGLVQAGGSLGLSCSAS | 182 | GLLFSRNSAG | 228 | WYRQAPGKQREFVA | 269 | RIRMGGSIN | 333 | YGDSVKGRFTVSRDIAKDTRYMQINDLKPEDTAKYFCRS | 403 | WREGLYEY | 437 | WGQGTQVTVSS |
| 37 | d800d638e066182304b00f51542faf38 | 144 | EVQLVESGGGLLQAGGSLGLSCSAS | 195 | GLLLSRNRAR | 228 | WYRQAPGKQREFVA | 278 | RIRMGGSMN | 334 | DGDSVKGRFTVSRDIAKNTMYLQMNDLKPEDTAIYFCRS | 397 | WREGFYEY | 437 | WGQGTQVTVSS |
| 38 | 45e8d1be704b2eef9ed8156abc03c6d8 | 136 | EVQLVESGGGLVQAGGALGLSCSAS | 182 | GLLFSRNSAG | 242 | WHRQAPGKQREFVA | 269 | RIRMGGSIN | 335 | YGDSVKGRFTVSRDIAKNTMYLQMNELKPEDTAKYLCRS | 404 | WREGFYES | 440 | WGRGTQVTVSS |
| 39 | 32a3666f797cfcd12558659bc01153ccb38 | | EVQLVESGGGLVQAGGSLGLSCSAS | 182 | GLLFSRNSAG | 243 | WYRPAPGKQREFVA | 269 | RIRMGGSIN | 336 | YGDSVKGRFTVARDIAKNTMYLQMNDLKPEETAIYFCSS | 405 | WREGVYKY | 445 | GGKGTQVTVSS |
| 40 | 1584d2e29498ea04b8cefac5c34d263d | 145 | EVQLVESGGGLVQAGGRRGLSCSAS | 196 | GFLFRRPSAG | 244 | WYRQDPGKQREFVA | 269 | RIRMGGSIN | 337 | YGDSVKGRFTVSRDIAKNTMYLQMNDVKPEDTAKYFCSS | 397 | WREGFYEY | 437 | WGQGTQVTVSS |
| 41 | 2b7789fd646b01f675945e09acc89530 | 146 | EVQLVESGGALVQAGGSLGLSCSAS | 197 | GLLFIRNSAG | 245 | CYRQAPGKHREFVA | 269 | RIRMGGSIN | 338 | YGDSVKGRFTVSRDIAKNTVYLQMNDLKPEYTAIYFCSS | 406 | WREGYYEY | 437 | WGQGTQVTVSS |
| 42 | 97276e7c5dea225b4fbb58426d23b2e5 | 147 | EVQLVESGGGLVEAGGSLGLSCSAS | 198 | GLLFSRISAG | 246 | WYREAPGQQRECVA | 269 | RIRMGGSIN | 339 | YGDSVKGRFTVSRDIAKNTMYLQMNDLKPEHTAKYLCSS | 397 | WREGFYEY | 437 | WGQGTQVTVSS |
| 43 | a0615e93638f77818f6936045f94977f | 148 | EVQLVESGEGLVQAGGSLGLSCSAS | 199 | GLLFSPNSAG | 247 | WYRQAPGKQRKFVA | 279 | RIRRGGGIN | 340 | YGDSVKGRFTVSRDIAKNTMYLQMNDLKPEDTAIYFCSS | 407 | WREGFDEY | 446 | WAQGTQVTVSS |
| 44 | 5f18d5599843f072a1eed218d2a74048 | 149 | EVQLVESGGGLVQAGGPLGLSCSAS | 182 | GLLFSRNSAG | 248 | WYRQAPGKQLAFVG | 280 | RIGMGGCIN | 341 | YGDSVKGRFTVSRDIAKNTMYLQMNGLKPEDTAKYFCSS | 397 | WREGFYEY | 437 | WGQGTQVTVSS |
| 45 | 0f4d6d2f274ddd6f2beb50c53e54d4f4 | 150 | EVQLVESGGGLVQAAGSLGLPCSAS | 200 | GLLFSRMSAR | 249 | WYRQAPGEQREFVA | 269 | RIRMGGSIN | 342 | YGDSVKGRFTVTRDIAKNTMYLQMNDLKPEDTAKYFCSS | 397 | WREGFYEY | 447 | WCQGTQVTVSS |
| 46 | 545db63aa3771946a230075631c4d56d | 151 | EVQLVESGEGLVPAGGSLGPSCRYSAG | 201 | GLLFS | 228 | WYRQAPGKQREFVA | 281 | RSRMGGSIN | 343 | YGDSVKGRFTVSRDIAKNTMYLQMNDLKPEDTAEYFCSS | 397 | WREGFYEY | 448 | WGIGTQVTVSS |
| 47 | aff17a29c9e12331adb924c5c79b1643 | 152 | EVQLVESGGALVQAGGPPGLSCSAS | 182 | GLLFSRNSAG | 228 | WYRQAPGKQREFVA | 269 | RIRMGGSIN | 344 | DGDSVKGRFTVSRDIDKNTMYLQMNDLKPENTAKYFCSS | 408 | WREGFYKY | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 48 | ef8dd380aee92f426ec4a6b86dcba935 | 124 | EVQLVESGGGLVQAGGSLRLSCSAS | 181 | GLLFSVNSAG | 250 | WYRQAPGQKREFVA | 282 | RIRTGGSTN | 345 | YADSVKGRFTVSRGNAKNTVYLQMNNLKPEDTAVYYCSS | 393 | WRTGAYEY | 437 | WGQGTQVTVSS |
| 49 | 6812576932a2c1e0f08ec106e0d0a04e | 125 | EVQLVESGGGLVQAGGSLGLSCSAS | 202 | GLLFSRNIAG | 243 | WYRPAPGKQREFVA | 269 | RIRMGGSIN | 346 | YGDSVKGRFNGSRDIAKNTMYLQMDDLKPEDTAICFCSS | 409 | GREGFYEY | 437 | WGQGTQVTVSS |
| 50 | 01ebe14f074a754cc51561530766ead4 | 153 | EVQLVESAGGLVQAGGPLGLSCSSS | 203 | GLLFSLNSAG | 251 | CSRQPPGKQREFVA | 269 | RIRMGGSIN | 320 | YGDSVKGRFTVSRDIAKNTMYLQMNDLKPEDTAKYFCSS | 397 | WREGFYEY | 437 | WGQGTQVTVSS |
| 51 | eb93eef0aa2380097f9dc5733bc6dd43 | 154 | EVQLVESGGALMQAGGSLGPPCPAS | 204 | GPLFRRTRAG | 228 | WYRQAPGKQREFVA | 269 | RIRMGGSIN | 320 | YGDSVKGRFTVSRDIAKNTMYLQMNDLKPEDTAKYFCSS | 397 | WREGFYEY | 437 | WGQGTQVTVSS |
| 52 | 28c4a7cd04f53076c4f5acb03236ef61 | 155 | EVQLVESGGCLVQAGGSLGLSCSAP | 199 | GLLFSPNSAG | 228 | WYRQAPGKQREFVA | 283 | RILMGGSIN | 347 | YGDSVKGRFTVSRDIAKNTMYLQMKDLKPEDTAKYFCSR | 397 | WREGFYEY | 449 | CGQGTQVTVSS |
| 53 | 8c06f7a5597c4192b17846077a8fce8a | 149 | EVQLVESGGGLVQAGGPLGLSCSAS | 205 | GIPFSRNSAG | 228 | WYRQAPGKQREFVA | 284 | RIRMGGSRN | 348 | YGDSVKGRFTVSGDIAKNTMYLQMNDLKPEDTAKDFGSS | 410 | WREGFYEY | 437 | WGQGTQVTVSS |
| 54 | 63394ed3c69537d64eb90d1f6971fc43 | 156 | EVQLVESGGGLVQTGGSLTLSCSAS | 181 | GLLFSVNSAG | 227 | WYRQAPGKQRDFVA | 285 | RIRRGGDTN | 349 | YAESVRGRFTVSRDKAKNTMYLQMNSLKPEDTAVYYCAS | 411 | WRTGSYEY | 437 | WGQGTQVTVSS |
| 55 | fc796afb415f19e150d23537a96a99ae0 | 124 | EVQLVESGGGLVQAGGSLRLSCSAS | 181 | GLLFSVNSAG | 252 | WYRQAPGKQRIFVA | 286 | RLRRGGDTN | 350 | YADSVKGRFTISRDNAKNTVYLQMNSLKPEDTAVYYCSA | 412 | WRAGTYEY | 441 | WGQVTQVTVSS |
| 56 | af47752f179d4b7a61f3a0536bbf4cfc | 157 | EVQLVESGGGSVHPGGSLRLSCSAS | 181 | GLLFSVNSAG | 252 | WYRQAPGKQRIFVA | 286 | RLRRGGDTN | 350 | YADSVKGRFTISRDNAKNTVYLQMNSLKPEDTAVYYCSA | 412 | WRAGTYEY | 437 | WGQGTQVTVSS |
| 57 | 4738fe2c7cdba355638596889c0914be | 124 | EVQLVESGGGLVQAGGSLRLSCSAS | 185 | GLLFSVNSVG | 232 | WYRRAPGKQREFVA | 271 | RLRTTGSTN | 351 | YAESVRGRFTISRDNAKNTVYLQMNNLKPEDTAVYYCSA | 398 | WRIEAYEY | 437 | WGQGTQVTVSS |
| 58 | 7ca2189f04d2906f692762b2d3820dd2 | 158 | EVQLVESGGGLEQAGGSLRLSCSAS | 181 | GLLFSVNSAG | 227 | WYRQAPGKQRDFVA | 268 | RIRSGGSTN | 352 | YADSVKGRSTVSRDNAKNTLYLQLYSLKPEDTAVYYCSS | 393 | WRTGAYEY | 450 | WGQVVTQVTVSS |
| 59 | 3f009bd0371fd5a057e1dd514a697a0d | 159 | EVQLVESGGGLVKAGGSLRLSCSAS | 206 | GLLFRVNSVG | 227 | WYRQAPGKQRDFVA | 287 | RIRRGGSTN | 353 | YADTVKGRVTISRDNAKNTVYLQMNSLSPADTGVYYCSS | 413 | WREGAYEY | 437 | WGQGTQVTVSS |
| 60 | 8d7c16aaec812b89b63ecfe25917a02d | 124 | EVQLVESGGGLVQAGGSLRLSCSAS | 181 | GLLFSVNSAG | 232 | WYRRAPGKQREFVA | 288 | RLRRGGETN | 354 | YGDSVKGRFTISRDKATNTLYLQMNSLRTEDTAVYYCSS | 411 | WRTGSYEY | 437 | WGQGTQVTVSS |
| 61 | 0049b650b8e87b0381fc26f80b9c4525 | 124 | EVQLVESGGGLVQAGGSLRLSCSAS | 207 | GLLFRVNSAG | 253 | WYRQAPGKQREFVA | 268 | RIRSGGSTN | 355 | YADSVKGRFIISRDNAQNTLYLQMNNLSPEDTAAYYCSS | 414 | WRIDAYEY | 437 | WGQGTQVTVSS |
| 62 | a0f1f7e657eebacae2796f435e4e4fda | 160 | EVQLVESAGGLVPAGGSLRLPCSAP | 208 | GLLFSVDSAG | 227 | WYRQAPGKQRDFVA | 268 | RIRSGGSTN | 356 | DADSVKGRFTVSRDNAKNTVYLQMNSLKPEDTAVYYCSS | 393 | WRTGAYEY | 437 | WGQGTQVTVSS |
| 63 | d9f77b8d61469fbeacad1fffa6142a31 | 161 | EVQLVESGGGFVQAGGSLRLSCSAS | 209 | GLLFSVNSTV | 254 | SYRQAPGKQRDCVA | 268 | RIRSGGSTN | 357 | YADSVKGRFTVSRDNAKNTVYLQMNSLKHEDTAVYYCSS | 393 | WRTGAYEY | 437 | WGQGTQVTVSS |
| 64 | 2f69e44b1b5912bda2c7dee779e5c265 | 162 | EVQLVESGEGLVKAGESLRLSCSAS | 210 | GLLFSVDSTG | 255 | WYRQAPGKQREFFA | 289 | RIRSGGSIN | 358 | YGDSVKGRFTISRDKATNTLYLQMSNLNPEDTAVYYCSS | 415 | WRIGSYEY | 437 | WGQGTQVTVSS |
| 65 | A0194003A02 | 163 | EVQLVESGGGLVQAGDSLSLSCTAS | 211 | RGTFRNFGMG | 256 | WFRQAGGKEREFVA | 290 | AISRSGGHKY | 359 | YSDSVKGRFTISKDNAKNMVSLQMNSLKPEDTAVYYCAA | 416 | RFRFDDGTSYYQRAFYDF | 436 | WGQGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 66 | A0194003A04 | 163 | EVQLVESGGGLVQAGDSLSLSCTAS | 211 | RGTFNFGMG | 257 | WSRQAQGKEREFVA | 290 | AISRSGGHKY | 359 | YSDSVKGRFTISKDNAKNMVSLQMNSLKPEDTAVYYCAA | 416 | RFRFDDGTSYYQRAFYDF | 436 | WGQGTLVTVSS |
| 67 | A0194003A08 | 163 | EVQLVESGGGLVQAGDSLSLSCTAS | 212 | AGTFNFGMG | 258 | WFRQARGEEREFVA | 291 | TISRSARHTY | 360 | YSDSVKGRFTISRDNAKNMVSLQMNSLKPEDTAVYYCAA | 417 | RFRSDDGTYYYQRAFYDF | 437 | WGQGTQVTVSS |
| 68 | A0194003A09 | 164 | EVQLVESGGGLVQAGGSLSLSCTAS | 213 | GGTFNYGMG | 256 | WFRQAQGKEREFVA | 292 | AISRSAGRTY | 361 | YSDSVKGRFTISKNNAKNIMSLQMNSLKPEDTAVYYCAA | 418 | RFRFDDGTYYYQRAFYDF | 436 | WGQGTLVTVSS |
| 69 | A0194003A12 | 164 | EVQLVESGGGLVQAGGSLSLSCTAS | 213 | GGTFNYGMG | 256 | WFRQAQGKEREFVA | 293 | AISRSASRTY | 361 | YSDSVKGRFTISKNNAKNIMSLQMNSLKPEDTAVYYCAA | 418 | RFRFDDGTYYYQRAFYDF | 437 | WGQGTQVTVSS |
| 70 | A0194003B01 | 164 | EVQLVESGGGLVQAGGSLSLSCTAS | 214 | GGTFNFGMG | 256 | WFRQAQGKEREFVA | 294 | AISRSGGHIY | 362 | YSDSVKGRFTIARANAKNMVSLQMNSLKPEDTAVYYCAA | 418 | RFRFDDGTYYYQRAFYDF | 437 | WGQGTQVTVSS |
| 71 | A0194003B06 | 165 | EVQLVESGGGLVQAGGSLSLSCTVS | 215 | GGNFNFGMG | 259 | WFRQAHGKEREFVA | 295 | AISRSGGRTY | 363 | YADSVKGRFTISRDNAKNMVSLQMNSLKPEDTAVYSCAA | 417 | RFRSDDGTYYYQRAFYDF | 437 | WGQGTQVTVSS |
| 72 | A0194003B09 | 164 | EVQLVESGGGLVQAGGSLSLSCTAS | 213 | GGTFNYGMG | 256 | WFRQAQGKEREFVA | 292 | AISRSAGRTY | 364 | YSDSVKGRFTISKNNAKNVMSLQMNSLKPEDTAVYYCAA | 418 | RFRFDDGTYYYQRAFYDF | 436 | WGQGTLVTVSS |
| 73 | A0194003B11 | 166 | EVQLVESGGGLVRAGGSLSLSCTSS | 216 | SGTFNFAMG | 256 | WFRQAQGKEREFVA | 296 | TISRSGGHTY | 365 | YSDSVKGRFTISRDNAKNLVSLQMNSLKPEDTAVYYCAA | 419 | RFRFDDDTYYYQRAFYDF | 436 | WGQGTLVTVSS |
| 74 | A0194003C08 | 164 | EVQLVESGGGLVQAGGSLSLSCTAS | 213 | GGTFNYGMG | 256 | WFRQAQGKEREFVA | 295 | AISRSGGRTY | 361 | YSDSVKGRFTISKNNAKNIMSLQMNSLKPEDTAVYYCAA | 418 | RFRFDDGTYYYQRAFYDF | 437 | WGQGTQVTVSS |
| 75 | A0194003F08 | 164 | EVQLVESGGGLVQAGGSLSLSCTAS | 214 | GGTFNFGMG | 260 | WFRQDQGQEREFVA | 295 | AISRSGGRTY | 366 | FSDSVKGRFTISKDNAKNILSLQMNSLKPEDTAVYYCAA | 418 | RFRFDDGTYYYQRAFYDF | 437 | WGQGTQVTVSS |
| 76 | A0194004F06 | 164 | EVQLVESGGGLVQAGGSLSLSCTAS | 211 | RGTFNFGMG | 256 | WFRQAQGKEREFVA | 297 | AISRSAGHTY | 367 | YSDSVKGRFTISRDNAKNMVSLQMDSLKPEDTAVYYCAA | 420 | RFRFDDGTYYYQRTFYDF | 437 | WGQGTQVTVSS |
| 77 | A0194007A01 | 167 | EVQLVESGGGLAQAGGSLSLSCTAS | 215 | GGNFNFGMG | 261 | WFRQVQGTEREFVA | 298 | AISRTGGRTY | 368 | FSDSVKGRFTISRDNAKNMVSLQMNSLKPEDSAVYYCAA | 421 | RFRFGDGTYYYQRNFYDF | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 78 | A0194007B04 | 163 | EVQLVESGGGLVQAGDSLSLSCTAS | 211 | RGTFRNFGMG | 256 | WFRQAQGEKREFVA | 290 | AISRSGGHKY | 369 | YSDSVQGRFTISKDNAKNMVSLQMNSLKPEDTAVYYCAA | 416 | RFRFDDGTSYYQRAFYDF | 437 | WGQGTQVTVSS |
| 79 | A0194007B09 | 168 | EVQLVESGGGLVQTGGSLSLSCTAS | 213 | GGTFRNYGMG | 256 | WFRQAQGKEREFVA | 292 | AISRSAGRTY | 361 | YSDSVKGRFTISKNNAKNIMSLQMNSLKPEDTAVYYCAA | 418 | RFRFDDGTYYYQRAFYDF | 437 | WGQGTQVTVSS |
| 80 | A0194007B12 | 164 | EVQLVESGGGLVQAGGSLSLSCTAS | 217 | GGTFRNYAMG | 256 | WFRQAQGKEREFVA | 299 | TISRSGGYTY | 360 | YSDSVKGRFTISRDNAKNMVSLQMNSLKPEDTAVYYCAA | 422 | RFRFGDGTYYYQRAFYDF | 437 | WGQGTQVTVSS |
| 81 | A0194007C01 | 164 | EVQLVESGGGLVQAGGSLSLSCTAS | 214 | GGTFRGNFMG | 256 | WFRQAQGEKREFVA | 295 | AISRSGGRTY | 370 | YSDSVKGRFTISKDNAKNIMSLQMNSLRPEDTAVYYCAA | 418 | RFRFDDGTYYYQRAFYDF | 437 | WGQGTQVTVSS |
| 82 | A0194007D01 | 169 | EVQLVESGGGSVQAGGSLSLSCTAS | 211 | RGTFRGNFMG | 256 | WFRQAQGKEREFVA | 298 | AISRTGGRTY | 371 | YSDSVKGRFTISRDNAKNMVSLQMNSLKPEDTAIYYCAA | 418 | RFRFDDGTYYYQRAFYDF | 436 | WGQGTLVTVSS |
| 83 | A0194007D10 | 163 | EVQLVESGGGLVQAGDSLSLSCTAS | 212 | AGTFRNFGMG | 258 | WFRQARGEEREFVA | 291 | TISRSARHTY | 360 | YSDSVKGRFTISRDNAKNMVSLQMNSLKPEDTAVYYCAA | 423 | RFRSDGGTYYYQRAFYDF | 437 | WGQGTQVTVSS |
| 84 | A0194007D11 | 164 | EVQLVESGGGLVQAGGSLSLSCTAS | 212 | AGTFRNFGMG | 256 | WFRQAQGKEREFVA | 300 | AISRSGGHTY | 372 | YSDSVKGRFTISKDNAKNMVSLKMNSLKPEDTADYYCAA | 418 | RFRFDDGTYYYQRAFYDF | 437 | WGQGTQVTVSS |
| 85 | A0194007E04 | 164 | EVQLVESGGGLVQAGGSLSLSCTAS | 214 | GGTFRNFGMG | 262 | WFRQVQGKEREFVA | 301 | AISRSGGHIF | 373 | YSDSVKGRFTISKDNAKNILFLQMNSLKPEDTAVYYCAA | 418 | RFRFDDGTYYYQRAFYDF | 437 | WGQGTQVTVSS |
| 86 | A0194007E08 | 164 | EVQLVESGGGLVQAGGSLSLSCTAS | 213 | GGTFRNYGMG | 256 | WFRQAQGKEREFVA | 292 | AISRSAGRTY | 374 | YSDSAKGRFTISKNNAKNIMSLQMNSLKPEDTAVYYCAA | 418 | RFRFDDGTYYYQRAFYDF | 436 | WGQGTLVTVSS |
| 87 | A0194007E12 | 164 | EVQLVESGGGLVQAGGSLSLSCTAS | 215 | GGNFRFNGMG | 256 | WFRQAQGKEREFVA | 300 | AISRSGGHTY | 360 | YSDSVKGRFTISRDNAKNMVSLQMNSLKPEDTAVYYCAA | 424 | RFRYGDGTYYYQRAFYDF | 436 | WGQGTLVTVSS |
| 88 | A0194007F01 | 163 | EVQLVESGGGLVQAGDSLSLSCTAS | 211 | RGTFRNFGMG | 256 | WFRQAQGKEREFVA | 302 | AISRSGGRKY | 359 | YSDSVKGRFTISKDNAKNMVSLQMNSLKPEDTAVYYCAA | 416 | RFRFDDGTSYYQRAFYDF | 436 | WGQGTLVTVSS |
| 89 | A0194007G09 | 170 | EVQLVESGGGLVEAGGSLSLSCTAS | 212 | AGTFRNFGMG | 258 | WFRQARGEEREFVA | 291 | TISRSARHTY | 360 | YSDSVKGRFTISRDNAKNMVSLQMNSLKPEDTAVYYCAA | 417 | RFRSDDGTYYYQRAFYDF | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 90 | A0194008A01 | 163 | EVQLVESGGGLVQAGDSLSLSCTAS | 218 | AGTLRNFGMG | 258 | WFRQARGEEREFVA | 291 | TISRSARHTY | 360 | YSDSVKGRFTISRDNAKNMVSLQMNSLKPEDTAVYYCAA | 425 | RFRSDDGTYYYQRRFYDF | 437 | WGQGTQVTVSS |
| 91 | A0194008A02 | 163 | EVQLVESGGGLVQAGDSLSLSCTAS | 218 | AGTLRNFGMG | 258 | WFRQARGEEREFVA | 291 | TISRSARHTY | 360 | YSDSVKGRFTISRDNAKNMVSLQMNSLKPEDTAVYYCAA | 426 | RFRSGDGTYYYQRAFYDF | 437 | WGQGTQVTVSS |
| 92 | A0194008A09 | 164 | EVQLVESGGGLVQAGGSLSLSCTAS | 213 | GGTFRNYGMG | 256 | WFRQAQGKEREFVA | 303 | AISRTGGHTY | 361 | YSDSVKGRFTISKNNAKNIMSLQMNSLKPEDTAVYYCAA | 422 | RFRFGDGTYYYQRAFYDF | 436 | WGQGTLVTVSS |
| 93 | A0194008A11 | 163 | EVQLVESGGGLVQAGDSLSLSCTAS | 218 | AGTLRNFGMG | 258 | WFRQARGEEREFVA | 291 | TISRSARHTY | 360 | YSDSVKGRFTISRDNAKNMVSLQMNSLKPEDTAVYYCAA | 417 | RFRSDDGTYYYQRAFYDF | 437 | WGQGTQVTVSS |
| 94 | A0194008B01 | 171 | EVQLVESGGGLVQAGGSLSLSCTSS | 219 | KGTFRNFAMG | 256 | WFRQAQGKEREFVA | 296 | TISRSGGHTY | 375 | YSDSVKGRFAISRDNAKNLVSLQMNSLNAEDTAVYYCAA | 427 | RFRSDDDTYYYQRAFYDF | 436 | WGQGTLVTVSS |
| 95 | A0194008C01 | 172 | EVQLVESGGGLVQAGGSLSLPCTAS | 213 | GGTFRNYGMG | 256 | WFRQAQGKEREFVA | 292 | AISRSAGRTY | 361 | YSDSVKGRFTISKNNAKNIMSLQMNSLKPEDTAVYYCAA | 418 | RFRFDDGTYYYQRAFYDF | 436 | WGQGTLVTVSS |
| 96 | A0194008C07 | 164 | EVQLVESGGGLVQAGGSLSLSCTAS | 213 | GGTFRNYGMG | 263 | WFRQAQGKERDFVA | 304 | AISRTNGHIY | 376 | YSDSVKGRFTISKDNAKNILSLQMNSLKPEDTAVYYCAA | 428 | RFRFGDGTYYYQRTFYDF | 436 | WGQGTLVTVSS |
| 97 | A0194008C08 | 164 | EVQLVESGGGLVQAGGSLSLSCTAS | 220 | GGTFRNFAMG | 256 | WFRQAQGKEREFVA | 305 | TISRSGGHIY | 360 | YSDSVKGRFTISRDNAKNMVSLQMNSLKPEDTAVYYCAA | 416 | RFRFDDGTSYYQRAFYDF | 436 | WGQGTLVTVSS |
| 98 | A0194008D08 | 173 | EVQLVESGGDLVQPGGSLRLSCTAS | 213 | GGTFRNYGMG | 256 | WFRQAQGKEREFVA | 303 | AISRTGGHTY | 377 | YSDSVKGRFTISKDNAKNIVSLQMNSLKPEDTAVYYCAA | 421 | RFRFGDGTYYYQRNFYDF | 437 | WGQGTQVTVSS |
| 99 | A0194008F05 | 174 | EVQLVESGGGLVQAGGPLSLSCTAS | 213 | GGTFRNYGMG | 256 | WFRQAQGKEREFVA | 292 | AISRSAGRTY | 361 | YSDSVKGRFTISKNNAKNIMSLQMNSLKPEDTAVYYCAA | 418 | RFRFDDGTYYYQRAFYDF | 436 | WGQGTLVTVSS |
| 100 | A0194008G10 | 175 | EVQLVESGGGSVQAGGSLRLVCAFS | 220 | GGTFRNFAMG | 256 | WFRQAQGKEREFVA | 296 | TISRSGGHTY | 378 | YSDSVKGRFTISKDNAKNMVYLQMYSLKPEDTAVYYCAG | 429 | RFRFGDGAYYYQRTFYDF | 436 | WGQGTLVTVSS |
| 101 | KV13BIIPMP026D09 | 164 | EVQLVESGGGLVQAGGSLSLSCTAS | 221 | RGTFRNFAMG | 256 | WFRQAQGKEREFVA | 305 | TISRSGGHIY | 359 | YSDSVKGRFTISKDNAKNMVSLQMNSLKPEDTAVYYCAA | 416 | RFRFDDGTSYYQRAFYDF | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 102 | KV13BIIPMP026F08 | 164 | EVQLVESGGGLVQAGGSLSLCTAS | 222 | RGTFRNYAMG | 256 | WFRQAQGKEREFVA | 305 | TISRSGGHIY | 379 | YSDSVKGRFAISKDNAKNMMSLRMNSLKPEDTAVYYCAA | 430 | RFRFDDGTYFYQRAFYDF | 437 | WGQGTQVTVSS |
| 103 | KV13BIIPMP027A11 | 176 | EVQLVESRGGLVQAGGSLRLSCTAS | 213 | GGTFRNYGMG | 256 | WFRQAQGKEREFVA | 306 | AVSRTGGRTY | 380 | YSDSVKGRFTISRDNAKNMVSLQMNKLKPEDTAVYYCAA | 418 | RFRFDDGTYYYQRAFYDF | 437 | WGQGTQVTVSS |
| 104 | KV13BIIPMP027B10 | 164 | EVQLVESGGGLVQAGGSLSLCTAS | 223 | GGTFRSYGMG | 256 | WFRQAQGKEREFVA | 303 | AISRTGGHTY | 361 | YSDSVKGRFTISKNNAKNIMSLQMNSLKPEDTAVYYCAA | 422 | RFRFGDGTYYYQRAFYDF | 437 | WGQGTQVTVSS |
| 105 | KV13BIIPMP027B12 | 164 | EVQLVESGGGLVQAGGSLSLCTAS | 215 | GGNFRNFGMG | 264 | WFRQAQGTEREFVA | 298 | AISRTGGRTY | 381 | FSDSVKGRFTISRDNAKNMVSLQMNSLKPEDTAVYYCAA | 431 | RFRFDDGTYYYQRNFYDF | 439 | WGQGAQVTVSS |
| 106 | KV13BIIPMP027D09 | 164 | EVQLVESGGGLVQAGGSLSLCTAS | 220 | GGTFRNFAMG | 265 | WFRQAQGKEREFVA | 296 | TISRSGGHTY | 382 | YSDSVKGRFTISRDNAKNMVALQMNSLKPEDTAVYCAA | 432 | RFRFDDGTYYYQRAFYNL | 437 | WGQGTQVTVSS |
| 107 | KV13BIIPMP027D10 | 164 | EVQLVESGGGLVQAGGSLSLCTAS | 213 | GGTFRNYGMG | 256 | WFRQAQGKEREFVA | 303 | AISRTGGHTY | 359 | YSDSVKGRFTISKDNAKNMVSLQMNSLKPEDTAVYYCAA | 421 | RFRFGDGTYYYQRNFYDF | 437 | WGQGTQVTVSS |
| 108 | KV13BIIPMP027E08 | 164 | EVQLVESGGGLVQAGGSLSLCTAS | 224 | VGNFRNFGMG | 256 | WFRQAQGKEREFVA | 300 | AISRSGGHTY | 360 | YSDSVKGRFTISRDNAKNMVSLQMNSLKPEDTAVYYCAA | 418 | RFRFDDGTYYYQRAFYDF | 437 | WGQGTQVTVSS |
| 109 | KV13BIIPMP027E11 | 165 | EVQLVESGGGLVQAGGSLSLCTVS | 215 | GGNFRNFGMG | 259 | WFRQAHGKEREFVA | 295 | AISRSGGRTY | 383 | YADSVKGRFTVSRDNAKNMVSLQMNSLKPEDTAVSCAA | 417 | RFRSDDGTYYYQRAFYDF | 437 | WGQGTQVTVSS |
| 110 | A019400003 | 164 | EVQLVESGGGLVQAGGSLSLCTAS | 214 | GGTFRNFGMG | 256 | WFRQAQGKEREFVA | 303 | AISRTGGHTY | 384 | YQDSVKGRFTISKDNAKNILSLQMNSLKPEDTAVYYCAA | 422 | RFRFGDGTYYYQRAFYDF | 437 | WGQGTQVTVSS |
| 111 | KV13BIIPMP027H08 | 164 | EVQLVESGGGLVQAGGSLSLCTAS | 220 | GGTFRNFAMG | 256 | WFRQAQGKEREFVA | 307 | TISRSGGHIF | 385 | YSESVKGRFTISRDNAKNMVSLQMNSLKPEDTAVYYCAA | 433 | RFRSDDGTYYYQRIFYDF | 437 | WGQGTQVTVSS |
| 112 | KV13BIIPMP027H09 | 177 | EVQLVESGGGLVQPGGSLSLCTAS | 212 | AGTFRNFGMG | 258 | WFRQARGEEREFVA | 291 | TISRSARHTY | 360 | YSDSVKGRFTISRDNAKNMVSLQMNSLKPEDTAVYYCAA | 417 | RFRSDDGTYYYQRAFYDF | 437 | WGQGTQVTVSS |
| 113 | KV13BIIPMP027H10 | 169 | EVQLVESGGGSVQAGGSLSLCTAS | 225 | RGTFRNYGMG | 256 | WFRQAQGKEREFVA | 300 | AISRSGGHTY | 386 | YSDSVKGRFTISKDNAKNIMSLQMNSLKPEDTAVYYCAA | 418 | RFRFDDGTYYYQRAFYDF | 437 | WGQGTQVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 114 | KV13BIIPMP049B09 | 165 | EVQLVESGGGLVQAGGSLSLSCTVS | 226 | GGNFRNFGVG | 259 | WFRQAHGKEREFVA | 308 | AISRAGGRTY | 387 | YADSVKGRFAISRDNAKNMVSLQMNSLKPEDTAVYTCAA | 434 | RFRSGDTSYYERAFYDF | 437 | WGQGTQVTVSS |
| 115 | KV13BIIPMP049E10 | 178 | KVQLVESGGGLVQPGGSLSLSCTAS | 212 | AGTFRNFGMG | 264 | WFRQAQGTEREFVA | 295 | AISRSGGRTY | 388 | FSDSVKGRFTISKDNAKNMLSLQMNSLKPEDTAVYYCAA | 417 | RFRSDDGTYYYQRAFYDF | 439 | WGQGAQVTVSS |
| 116 | KV13BIIPMP050A07 | 165 | EVQLVESGGGLVQAGGSLSLSCTVS | 213 | GGTFRNYGMG | 266 | WFRQFQGKEREFVA | 301 | AISRSGGHIF | 385 | YSESVKGRFTISRDNAKNMVSLQMNSLKPEDTAVYYCAA | 426 | RFRSGDTYYYQRAFYDF | 437 | WGQGTQVTVSS |
| 117 | KV13BIIPMP050A09 | 164 | EVQLVESGGGLVQAGGSLSLSCTAS | 212 | AGTFRNFGMG | 267 | WFRQARGAEREFVA | 305 | TISRSGGHIY | 360 | YSDSVKGRFTISRDNAKNMVSLQMNSLKPEDTAVYYCAA | 417 | RFRSDDGTYYYQRAFYDF | 437 | WGQGTQVTVSS |
| 118 | KV13BIIPMP050A10 | 166 | EVQLVESGGGLVRAGGSLSLSCTSS | 216 | SGTFRNFAMG | 256 | WFRQAQGEKREFVA | 296 | TISRSGGHTY | 389 | YSDSVKGRFTISRDNAKNLVSLQMSSLKPEDTAVYYCAA | 419 | RFRFDDDTYYYQRAFYDF | 437 | WGQGTQVTVSS |
| 119 | KV13BIIPMP050B11 | 179 | EVQLVESGGSVQAGNSLSLSCTAS | 217 | GGTFRNYAMG | 256 | WFRQAQGKEREFVA | 305 | TISRSGGHIY | 390 | YSDSVKGRFTISRDNAKNMVSLQMNSLKPEDTAAYYCAA | 422 | RFRFGDTYYYQRAFYDF | 437 | WGQGTQVTVSS |
| 120 | KV13BIIPMP050C09 | 163 | EVQLVESGGGLVQAGDSLSLSCTAS | 211 | RGTFRNFGMG | 256 | WFRQAQGKEREFVA | 290 | AISRSGGHKY | 391 | YSDSVKGRSTISKDNAKNMVSLQMNSLKPEDTAVYYCAA | 416 | RFRFDDGTSYYQRAFYDF | 437 | WGQGTQVTVSS |
| 121 | KV13BIIPMP050D09 | 167 | EVQLVESGGGLAQAGGSLSLSCTAS | 215 | GGNFRNFGMG | 261 | WFRQVQGTEREFVA | 298 | AISRTGGRTY | 368 | FSDSVKGRFTISRDNAKNMVSLQMNSLKPEDSAVYYCAA | 435 | RFRFGDTYYYQRNFYGF | 439 | WGQGAQVTVSS |
| 122 | KV13BIIPMP050E12 | 164 | EVQLVESGGGLVQAGGSLSLSCTAS | 213 | GGTFRNYGMG | 256 | WFRQAQGEKREFVA | 309 | AISRSAGHIY | 392 | YLNSVKGRFTISKDNAKNILSLQMNSLKPEDTAVYYCAA | 418 | RFRFDDGTYYYQRAFYDF | 437 | WGQGTQVTVSS |
| 123 | KV13BIIPMP050F11 | 180 | EVQLVESGGGLVQAGNSLSLSCTAS | 218 | AGTLRNFGMG | 258 | WFRQARGEEREFVA | 291 | TISRSRAHTY | 360 | YSDSVKGRFTISRDNAKNMVSLQMNSLKPEDTAVYYCAA | 417 | RFRSDDGTYYYQRAFYDF | 437 | WGQGTQVTVSS |
| 498 | A019400050 | 125 | EVQLVESGGGLVQAGGSLGLSCSAS | 182 | GLLFSRNSAG | 228 | WYRQAPGKQREFVA | 541 | RIRAGGSIN | 311 | YADTVKGRFTISRDNAKNTVYLQMNSLKPEDTAVYYCSS | 394 | WRTGFYEY | 436 | WGQGTLVTVSS |
| 499 | A019400051 | 125 | EVQLVESGGGLVQAGGSLGLSCSAS | 182 | GLLFSRNSAG | 228 | WYRQAPGKQREFVA | 542 | RIREGGSIN | 311 | YADTVKGRFTISRDNAKNTVYLQMNSLKPEDTAVYYCSS | 394 | WRTGFYEY | 436 | WGQGTLVTVSS |
| 500 | A019400052 | 125 | EVQLVESGGGLVQAGGSLGLSCSAS | 182 | GLLFSRNSAG | 228 | WYRQAPGKQREFVA | 543 | RIRFGGSIN | 311 | YADTVKGRFTISRDNAKNTVYLQMNSLKPEDTAVYYCSS | 394 | WRTGFYEY | 436 | WGQGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 501 | A019400053 | 125 | EVQLVESGGG LVQAGGSLGL SCSAS | 182 | GLLFS SRNAG | 228 | WYRQAPG KQREFVA | 544 | RIRGG GSIN | 311 | YADTVKGRFTISRDNAKN TVYLQMNSLKPEDTAVYY CSS | 394 | WRTG FYEY | 436 | WGQGTL VTVSS |
| 502 | A019400054 | 125 | EVQLVESGGG LVQAGGSLGL SCSAS | 182 | GLLFS RNSAG | 228 | WYRQAPG KQREFVA | 545 | RIRHG GSIN | 311 | YADTVKGRFTISRDNAKN TVYLQMNSLKPEDTAVYY CSS | 394 | WRTG FYEY | 436 | WGQGTL VTVSS |
| 503 | A019400055 | 125 | EVQLVESGGG LVQAGGSLGL SCSAS | 182 | GLLFS RNSAG | 228 | WYRQAPG KQREFVA | 546 | RIRKG GSIN | 311 | YADTVKGRFTISRDNAKN TVYLQMNSLKPEDTAVYY CSS | 394 | WRTG FYEY | 436 | WGQGTL VTVSS |
| 504 | A019400056 | 125 | EVQLVESGGG LVQAGGSLGL SCSAS | 182 | GLLFS RNSAG | 228 | WYRQAPG KQREFVA | 547 | RIRLG GSIN | 311 | YADTVKGRFTISRDNAKN TVYLQMNSLKPEDTAVYY CSS | 394 | WRTG FYEY | 436 | WGQGTL VTVSS |
| 505 | A019400057 | 125 | EVQLVESGGG LVQAGGSLGL SCSAS | 182 | GLLFS RNSAG | 228 | WYRQAPG KQREFVA | 548 | RIRPG GSIN | 311 | YADTVKGRFTISRDNAKN TVYLQMNSLKPEDTAVYY CSS | 394 | WRTG FYEY | 436 | WGQGTL VTVSS |
| 506 | A019400058 | 125 | EVQLVESGGG LVQAGGSLGL SCSAS | 182 | GLLFS RNSAG | 228 | WYRQAPG KQREFVA | 549 | RIRQG GSIN | 311 | YADTVKGRFTISRDNAKN TVYLQMNSLKPEDTAVYY CSS | 394 | WRTG FYEY | 436 | WGQGTL VTVSS |
| 507 | A019400059 | 125 | EVQLVESGGG LVQAGGSLGL SCSAS | 182 | GLLFS RNSAG | 228 | WYRQAPG KQREFVA | 550 | RIRRG GSIN | 311 | YADTVKGRFTISRDNAKN TVYLQMNSLKPEDTAVYY CSS | 394 | WRTG FYEY | 436 | WGQGTL VTVSS |
| 508 | A019400060 | 125 | EVQLVESGGG LVQAGGSLGL SCSAS | 182 | GLLFS RNSAG | 228 | WYRQAPG KQREFVA | 289 | RIRSG GSIN | 311 | YADTVKGRFTISRDNAKN TVYLQMNSLKPEDTAVYY CSS | 394 | WRTG FYEY | 436 | WGQGTL VTVSS |
| 509 | A019400061 | 125 | EVQLVESGGG LVQAGGSLGL SCSAS | 182 | GLLFS RNSAG | 228 | WYRQAPG QKREFVA | 551 | RIRTG GSIN | 311 | YADTVKGRFTISRDNAKN TVYLQMNSLKPEDTAVYY CSS | 394 | WRTG FYEY | 436 | WGQGTL VTVSS |
| 510 | A019400062 | 125 | EVQLVESGGG LVQAGGSLGL SCSAS | 182 | GLLFS RNSAG | 228 | WYRQAPG QREKFVA | 552 | RIRVG GSIN | 311 | YADTVKGRFTISRDNAKN TVYLQMNSLKPEDTAVYY CSS | 394 | WRTG FYEY | 436 | WGQGTL VTVSS |
| 511 | A019400063 | 125 | EVQLVESGGG LVQAGGSLGL SCSAS | 182 | GLLFS RNSAG | 228 | WYRQAPG QKREFVA | 553 | RIRWG GSIN | 311 | YADTVKGRFTISRDNAKN TVYLQMNSLKPEDTAVYY CSS | 394 | WRTG FYEY | 436 | WGQGTL VTVSS |
| 512 | A019400064 | 125 | EVQLVESGGG LVQAGGSLGL SCSAS | 182 | GLLFS RNSAG | 228 | WYRQAPG KQREFVA | 554 | RIRYG GSIN | 311 | YADTVKGRFTISRDNAKN TVYLQMNSLKPEDTAVYY CSS | 394 | WRTG FYEY | 436 | WGQGTL VTVSS |
| 513 | A019400065 | 125 | EVQLVESGGG LVQAGGSLGL SCSAS | 182 | GLLFS RNSAG | 228 | WYRQAPG QKREFVA | 555 | RIRIG GSIN | 311 | YADTVKGRFTISRDNAKN TVYLQMNSLKPEDTAVYY CSS | 394 | WRTG FYEY | 436 | WGQGTL VTVSS |
| 526 | A019400071_1 | 559 | DVQLVESGGGV VQPGGSLRLSC SAS | 182 | GLLFS RNSAG | 228 | WYRQAPG QKREFVA | 549 | RIRQG GSIN | 557 | YADSVKGRFTISRDNSKN TVYLQMNSLRPEDTALYY CSG | 394 | WRTG FYEY | 436 | WGQGTL VTVSS |
| 535 | A019400071_2 | 556 | EVQLVESGGGV VQPGGSLRLSC SAS | 182 | GLLFS RNSAG | 228 | WYRQAPG QKREFVA | 549 | RIRQG GSIN | 557 | YADSVKGRFTISRDNSKN TVYLQMNSLRPEDTALYY CSG | 394 | WRTG FYEY | 436 | WGQGTL VTVSS |
| 527 | A019400072_1 | 559 | DVQLVESGGGV VQPGGSLRLSC SAS | 182 | GLLFS RNSAG | 228 | WYRQAPG QRKEFVA | 549 | RIRQG GSIN | 558 | YADSVKGRFTISRDNSKN TVYLQMNSLRPEDTALYY CSS | 397 | WREG FYEY | 436 | WGQGTL VTVSS |
| 536 | A019400072_2 | 556 | EVQLVESGGGV VQPGGSLRLSC SAS | 182 | GLLFS RNSAG | 228 | WYRQAPG KQREFVA | 549 | RIRQG GSIN | 558 | YADSVKGRFTISRDNSKN TVYLQMNSLRPEDTALYY CSS | 397 | WREG FYEY | 436 | WGQGTL VTVSS |
| 523 | A019400073_1 | 559 | DVQLVESGGGV VQPGGSLRLSC SAS | 182 | GLLFS RNSAG | 228 | WYRQAPG KQREFVA | 541 | RIRAG GSIN | 557 | YADSVKGRFTISRDNSKN TVYLQMNSLRPEDTALYY CSG | 394 | WRTG FYEY | 436 | WGQGTL VTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 532 | A019400073_2 | 556 | EVQLVESGGGVVQPGGSLRLSCSAS | 182 | GLLFSRNSAG | 228 | WYRQAPGKQREFVA | 541 | RIRAG GSIN | 557 | YADSVKGRFTISRDNSKNTVYLQMNSLRPEDTALYYCSG | 394 | WRTGFYEY | 436 | WGQGTLVTVSS |
| 524 | A019400074_1 | 559 | DVQLVESGGGVVQPGGSLRLSCSAS | 182 | GLLFSRNSAG | 228 | WYRQAPGKQREFVA | 541 | RIRAG GSIN | 558 | YADSVKGRFTISRDNSKNTVYLQMNSLRPEDTALYYCSS | 397 | WREGFYEY | 436 | WGQGTLVTVSS |
| 533 | A019400074_2 | 556 | EVQLVESGGGVVQPGGSLRLSCSAS | 182 | GLLFSRNSAG | 228 | WYRQAPGKQKREFVA | 541 | RIRAG GSIN | 558 | YADSVKGRFTISRDNSKNTVYLQMNSLRPEDTALYYCSS | 397 | WREGFYEY | 436 | WGQGTLVTVSS |
| 525 | A019400075_1 | 559 | DVQLVESGGGVVQPGGSLRLSCSAS | 182 | GLLFSRNSAG | 228 | WYRQAPGKQREFVA | 541 | RIRAG GSIN | 557 | YADSVKGRFTISRDNSKNTVYLQMNSLRPEDTALYYCSG | 397 | WREGFYEY | 436 | WGQGTLVTVSS |
| 534 | A019400075_2 | 556 | EVQLVESGGGVVQPGGSLRLSCSAS | 182 | GLLFSRNSAG | 228 | WYRQAPGKQKREFVA | 541 | RIRAG GSIN | 557 | YADSVKGRFTISRDNSKNTVYLQMNSLRPEDTALYYCSG | 397 | WREGFYEY | 436 | WGQGTLVTVSS |
| 529 | A019400076_1 | 559 | DVQLVESGGGVVQPGGSLRLSCSAS | 182 | GLLFSRNSAG | 228 | WYRQAPGKQKREFVA | 554 | RIRYG GSIN | 557 | YADSVKGRFTISRDNSKNTVYLQMNSLRPEDTALYYGCS | 394 | WRTGFYEY | 436 | WGQGTLVTVSS |
| 538 | A019400076_2 | 556 | EVQLVESGGGVVQPGGSLRLSCSAS | 182 | GLLFSRNSAG | 228 | WYRQAPGKQKREFVA | 554 | RIRYG GSIN | 557 | YADSVKGRFTISRDNSKNTVYLQMNSLRPEDTALYYCSG | 394 | WRTGFYEY | 436 | WGQGTLVTVSS |
| 530 | A019400077_1 | 559 | DVQLVESGGGVVQPGGSLRLSCSAS | 182 | GLLFSRNSAG | 228 | WYRQAPGKQKREFVA | 554 | RIRYG GSIN | 558 | YADSVKGRFTISRDNSKNTVYLQMNSLRPEDTALYYCSS | 397 | WREGFYEY | 436 | WGQGTLVTVSS |
| 539 | A019400077_2 | 556 | EVQLVESGGGVVQPGGSLRLSCSAS | 182 | GLLFSRNSAG | 228 | WYRQAPGKQREFVA | 554 | RIRYG GSIN | 558 | YADSVKGRFTISRDNSKNTVYLQMNSLRPEDTALYYCSS | 397 | WREGFYEY | 436 | WGQGTLVTVSS |
| 531 | A019400078_1 | 559 | DVQLVESGGGVVQPGGSLRLSCSAS | 182 | GLLFSRNSAG | 228 | WYRQAPGKQREFVA | 554 | RIRYG GSIN | 557 | YADSVKGRFTISRDNSKNTVYLQMNSLRPEDTALYYCSG | 397 | WREGFYEY | 436 | WGQGTLVTVSS |
| 540 | A019400078_2 | 556 | EVQLVESGGGVVQPGGSLRLSCSAS | 182 | GLLFSRNSAG | 228 | WYRQAPGKQREFVA | 554 | RIRYG GSIN | 557 | YADSVKGRFTISRDNSKNTVYLQMNSLRPEDTALYYCSG | 397 | WREGFYEY | 436 | WGQGTLVTVSS |
| 528 | A019400079_1 | 559 | DVQLVESGGGVVQPGGSLRLSCSAS | 182 | GLLFSRNSAG | 228 | WYRQAPGKQREFVA | 549 | RIRQG GSIN | 557 | YADSVKGRFTISRDNSKNTVYLQMNSLRPEDTALYYCSG | 397 | WREGFYEY | 436 | WGQGTLVTVSS |
| 537 | A019400079_2 | 556 | EVQLVESGGGVVQPGGSLRLSCSAS | 182 | GLLFSRNSAG | 228 | WYRQAPGKQREFVA | 549 | RIRQG GSIN | 557 | YADSVKGRFTISRDNSKNTVYLQMNSLRPEDTALYYCSG | 397 | WREGFYEY | 436 | WGQGTLVTVSS |

TABLE A-3

Amino acid sequences of selected multivalent anti-Kv1.3 Nanobodies

| Name | ID | Amino acid sequence |
|---|---|---|
| A019400004 (A019400003-40GS-A019400003) | 451 | EVQLVESGGGLVQAGGSLSLSCTASGGTFRNFGMGWFRQAQGKEREFVAAISRTGGHTYYQDSVKGRFTISKDNAKNILSLQMNSLKPEDTAVYYCAARFRFGDGTYYYQRAFYDFWGQGTQVTVSSGGGGSGGGGSGGGGSGGGGSGGGGSGGGGSGGGGSGGGGSEVQLVESGGGLVQAGGSLSLSCTASGGTFRNFGMGWFRQAQGKEREFVAAISRTGGHTYYQDSVKGRFTISKDNAKNILSLQMNSLKPEDTAVYYCAARFRFGDGTYYYQRAFYDFWGQGTQVTVSS |
| A019400009 (A0194009G09-35GS-A0194009G09) | 452 | EVQLVESGGGLVQAGGSLGLSCSASGLLFSRNSAGWYRQAPGKQREFVARIRMGGSINYADTVKGRFTISRDNAKNTVYLQMNSLKPEDTAVYYCSSWRIGFYEYWGQGTLVTVSSGGGGSGGGGSGGGGSGGGGSGGGGSGGGGSGGGGSEVQLVESGGGLVQAGGSLGLSCSASGLLFSRNSAGWYRQAPGKQREFVARIRMGGSINYADTVKGRFTISRDNAKNTVYLQMNSLKPEDTAVYYCSSWRTGFYEYWGQGTLVTVSS |

TABLE A-3-continued

Amino acid sequences of selected multivalent anti-Kv1.3 Nanobodies

| Name | ID | Amino acid sequence |
|---|---|---|
| A019400010 (A0194009G09-35GS-A019400003) | 453 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLSLSCTASGGTFRNFGMGWFRQAQGKEREFVAAISRTGGHTYYQDS VKGRFTISKDNAKNILSLQMNSLKPEDTAVYYCAARFRFGDGTYYYQRAFYDFWGQGTLVTVSS |
| A019400011 (A019400003-35GS-A0194009G09) | 454 | EVQLVESGGGLVQAGGSLSLSCTASGGTFRNFGMGWFRQAQGKEREFVAAISRTGGHTYYQDSVKGRFTISKD NAKNILSLQMNSLKPEDTAVYYCAARFRFGDGTYYYQRAFYDFWGQGTLVTVSSGGGGSGGGGSGGGGSGG GGSGGGGSGGGGSGGGGSEVQLVESGGGLVQAGGSLGLSCSASGLLFSRNSAGWYRQAPGKQREFVARIRM GGSINYADTVKGRFTISRDNAKNTVYLQMNSLKPEDTAVYYCSSWRTGFYEYWGQGTLVTVSS |
| A019400012 (A0194009G09-35GS-A019400003) | 455 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLSLSCTASGGTFRNFGMGWFRQAQGKEREFVAAISRTGGHTYYQDS VKGRFTISKDNAKNILSLQMNSLKPEDTAVYYCAARFRFGDGTYYYQRAFYDFWGQGTLVTVSS |
| A019400013 (A0194009G09-35GS-A0194009G09) | 456 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLGLSCSASGLLFSRNSAGWYRQAPGKQREFVARIRMGGSINYADTVK GRFTISRDNAKNTVYLQMNSLKPEDTAVYYCSSWRTGFYEYWGQGTLVTVSS |
| A019400014 (A019400003-35GS-A0194009G09) | 457 | EVQLVESGGGLVQAGGSLSLSCTASGGTFRNFGMGWFRQAQGKEREFVAAISRTGGHTYYQDSVKGRFTISKD NAKNILSLQMNSLKPEDTAVYYCAARFRFGDGTYYYQRAFYDFWGQGTLVTVSSGGGGSGGGGSGGGGSGG GGSGGGGSGGGGSGGGGSEVQLVESGGGLVQAGGSLGLSCSASGLLFSRNSAGWYRQAPGKQREFVARIRM GGSINYADTVKGRFTISRDNAKNTVYLQMNSLKPEDTAVYYCSSWRTGFYEYWGQGTLVTVSS |
| A019400015 (A0194009G09-35GS-A0194009G09-35GS-A0194009G09) | 458 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLGLSCSASGLLFSRNSAGWYRQAPGKQREFVARIRMGGSINYADTVK GRFTISRDNAKNTVYLQMNSLKPEDTAVYYCSSWRTGFYEYWGQGTLVTVSSGGGGSGGGGSGGGGSGGGG SGGGGSGGGGSGGGGSEVQLVESGGGLVQAGGSLGLSCSASGLLFSRNSAGWYRQAPGKQREFVARIRMGG SINYADTVKGRFTISRDNAKNTVYLQMNSLKPEDTAVYYCSSWRTGFYEYWGQGTLVTVSS |
| A019400016 (A0194009G09-35GS-A0194009G09-35GS-A0194009G09-35GS-A0194009G09) | 459 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLGLSCSASGLLFSRNSAGWYRQAPGKQREFVARIRMGGSINYADTVK GRFTISRDNAKNTVYLQMNSLKPEDTAVYYCSSWRTGFYEYWGQGTLVTVSSGGGGSGGGGSGGGGSGGGG SGGGGSGGGGSGGGGSEVQLVESGGGLVQAGGSLGLSCSASGLLFSRNSAGWYRQAPGKQREFVARIRMGG SINYADTVKGRFTISRDNAKNTVYLQMNSLKPEDTAVYYCSSWRTGFYEYWGQGTLVTVSSGGGGSGGGGS GGGSGGGGSGGGGSGGGGSEVQLVESGGGLVQAGGSLGLSCSASGLLFSRNSAGWYRQAPGKQRE FVARIRMGGSINYADTVKGRFTISRDNAKNTVYLQMNSLKPEDTAVYYCSSWRTGFYEYWGQGTLVTVSS |
| A019400032 (A0194020A06-35GS-A0194020A06) | 460 | DVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQAGGSLGLSCSASGLLFSRNSAGWYRQAPGKRREFVARIRMGGSINYADS VKGRFTVSRDNAKNMMYLQMNDLKPEDTAVYFCSGWREGFYEYWGQGTLVTVSS |
| A019400023 (A0194020B10-35GS-A0194020B10-35GS-ALB11) | 461 | EVQLVESGGGLVQAGGSLRLSCSASGLLFSVNSVGWYRRAPGKQREFVARLRTTGSTNYAQSVKGRFTISRDNA KNTVYLQMNNLKPEDTAVYYCSAWRIEAYEYWGQGTLVTVSSGGGGSGGGGSGGGGSGGGGSGGGGSGG GGSGGGGSEVQLVESGGGLVQAGGSLRLSCSASGLLFSVNSVGWYRRAPGKQREFVARLRTTGSTNYAQSVK GRFTISRDNAKNTVYLQMNNLKPEDTAVYYCSAWRIEAYEYWGQGTLVTVSSGGGGSGGGGSGGGGSGGGG SGGGGSGGGGSGGGGSEVQLVESGGGLVQPGNSLRLSCAASGFTFSSFGMSWVRQAPGKGLEWVSSISGSG SDTLYADSVKGRFTISRDNAKTTLYLQMNSLRPEDTAVYYCTIGGSLSRSSQGTLVTVSS |
| A019400024 (A0194020A06-35GS-A0194020A06-35GS-ALB11) | 462 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQAGGSLGLSCSASGLLFSRNSAGWYRQAPGKRREFVARIRMGGSINYADS VKGRFTVSRDNAKNMMYLQMNDLKPEDTAVYFCSGWREGFYEYWGQGTLVTVSSGGGGSGGGGSGGGGS GGGGSGGGGSGGGGSGGGGSEVQLVESGGGLVQPGNSLRLSCAASGFTFSSFGMSWVRQAPGKGLEWVSSI SGSGSDTLYADSVKGRFTISRDNAKTTLYLQMNSLRPEDTAVYYCTIGGSLSRSSQGTLVTVSS |
| A019400025 (A0194020B10-9GS-ALB11-9GS-A0194020B10) | 463 | EVQLVESGGGLVQAGGSLRLSCSASGLLFSVNSVGWYRRAPGKQREFVARLRTTGSTNYAQSVKGRFTISRDNA KNTVYLQMNNLKPEDTAVYYCSAWRIEAYEYWGQGTLVTVSSGGGGSGGGSEVQLVESGGGLVQPGNSLRLS CAASGFTFSSFGMSWVRQAPGKGLEWVSSISGSGSDTLYADSVKGRFTISRDNAKTTLYLQMNSLRPEDTAVYY CTIGGSLSRSSQGTLVTVSSGGGGSGGGSEVQLVESGGGLVQAGGSLRLSCSASGLLFSVNSVGWYRRAPGKQ REFVARLRTTGSTNYAQSVKGRFTISRDNAKNTVYLQMNNLKPEDTAVYYCSAWRIEAYEYWGQGTLVTVSS |
| A019400026 (A0194009G09-9GS-ALB11-9GS-A0194009G09) | 464 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGSEVQLVESGGGLVQPGNSLRL SCAASGFTFSSFGMSWVRQAPGKGLEWVSSISGSGSDTLYADSVKGRFTISRDNAKTTLYLQMNSLRPEDTAVY YCTIGGSLSRSSQGTLVTVSSGGGGSGGGSEVQLVESGGGLVQAGGSLGLSCSASGLLFSRNSAGWYRQAPGK QREFVARIRMGGSINYADTVKGRFTISRDNAKNIVYLQMNSLKPEDTAVYYCSSWRTGFYEYWGQGTLVTVSS |
| A019400027 (A0194009G09-35GS-A0194009G09-35GS-ALB11) | 465 | EVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRTGFYEYWGQGTLVTVSSGGGGSGGGGSGGGGSGGGGSGGGGSGG GGSGGGGSEVQLVESGGGLVQAGGSLGLSCSASGLLFSRNSAGWYRQAPGKQREFVARIRMGGSINYADTVK GRFTISRDNAKNTVYLQMNSLKPEDTAVYYCSSWRTGFYEYWGQGTLVTVSSGGGGSGGGGSGGGGSGGGG |

US 11,149,086 B2

TABLE A-3-continued

Amino acid sequences of selected multivalent anti-Kv1.3 Nanobodies

| Name | ID | Amino acid sequence |
|---|---|---|
| | | SGGGGSGGGGSGGGGSEVQLVESGGGLVQPGNSLRLSCAASGFTFSSFGMSWVRQAPGKGLEWVSSISGSG SDTLYADSVKGRFTISRDNAKTTLYLQMNSLRPEDTAVYYCTIGGSLSRSSQGTLVTVSS |
| A019400028 (A0194020A06- 9GS-ALB11- 9GS-A0194020A06) | 466 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGSEVQLVESGGGLVQPGNSL RLSCAASGFTFSSFGMSWVRQAPGKGLEWVSSISGSGSDTLYADSVKGRFTISRDNAKTTLYLQMNSLRPEDTA VYYCTIGGSLSRSSQGTLVTVSSGGGGSGGGSEVQLVESGGGLVQAGGSLGLSCSASGLLFSRNSAGWYRQAP GKRREFVARIRMGGSINYADSVKGRFTVSRDNAKNMMYLQMNDLKPEDTAVYFCSGWREGFYEYWGQGTL VTVSS |
| A019400029_1 (A0194020A06- 35GS-A0194020A06- 35GS-ALB11) | 467 | DVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQAGGSLGLSCSASGLLFSRNSAGWYRQAPGKRREFVARIRMGGSINYADS VKGRFTVSRDNAKNMMYLQMNDLKPEDTAVYFCSGWREGFYEYWGQGTLVTVSSGGGGSGGGGSGGGGS GGGGSGGGGSGGGGSGGGGSEVQLVESGGGLVQPGNSLRLSCAASGFTFSSFGMSWVRQAPGKGLEWVSSI SGSGSDTLYADSVKGRFTISRDNAKTTLYLQMNSLRPEDTAVYYCTIGGSLSRSSQGTLVTVSS |
| A019400034 (A0194020A06- 9GS-A0194020A06- 35GS-ALB11) | 468 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGSEVQLVESGGGLVQAGGSL GLSCSASGLLFSRNSAGWYRQAPGKRREFVARIRMGGSINYADSVKGRFTVSRDNAKNMMYLQMNDLKPED TAVYFCSGWREGFYEYWGQGTLVTVSSGGGGSGGGGSGGGGSGGGGSGGGGSGGGGSGGGGSEVQLVES GGGLVQPGNSLRLSCAASGFTFSSFGMSWVRQAPGKGLEWVSSISGSGSDTLYADSVKGRFTISRDNAKTTLYL QMNSLRPEDTAVYYCTIGGSLSRSSQGTLVTVSS |
| A019400035 (A0194020A06- 15GS-A0194020A06- 35GD-ALB11) | 469 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSEVQLVESGGGL VQAGGSLGLSCSASGLLFSRNSAGWYRQAPGKRREFVARIRMGGSINYADSVKGRFTVSRDNAKNMMYLQM NDLKPEDTAVYFCSGWREGFYEYWGQGTLVTVSSGGGGSGGGGSGGGGSGGGGSGGGGSGGGGSGGGGS EVQLVESGGGLVQPGNSLRLSCAASGFTFSSFGMSWVRQAPGKGLEWVSSISGSGSDTLYADSVKGRFTISRDN AKTTLYLQMNSLRPEDTAVYYCTIGGSLSRSSQGTLVTVSS |
| A019400036 (A0194020A06- 20GS-A0194020A06- 35GS-ALB11) | 470 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSEVQLVE SGGGLVQAGGSLGLSCSASGLLFSRNSAGWYRQAPGKRREFVARIRMGGSINYADSVKGRFTVSRDNAKNM MYLQMNDLKPEDTAVYFCSGWREGFYEYWGQGTLVTVSSGGGGSGGGGSGGGGSGGGGSGGGGSGGGG SGGGGSEVQLVESGGGLVQPGNSLRLSCAASGFTFSSFGMSWVRQAPGKGLEWVSSISGSGSDTLYADSVKGR FTISRDNAKTTLYLQMNSLRPEDTAVYYCTIGGSLSRSSQGTLVTVSS |
| A019400037 (A0194020A06- 25GS-A0194020A06- 35GS-ALB11) | 471 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQPGNSLRLSCAASGFTFSSFGMSWVRQAPGKGLEWVSSISGSGSDTLYAD SVKGRFTISRDNAKTTLYLQMNSLRPEDTAVYYCTIGGSLSRSSQGTLVTVSS |
| A019400038 (A0194020A06- 40GS-A0194020A06- 35GS-ALB11) | 472 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSGGGGSEVQLVESGGGLVQAGGSLGLSCSASGLLFSRNSAGWYRQAPGKRREFVARIRMGGSI NYADSVKGRFTVSRDNAKNMMYLQMNDLKPEDTAVYFCSGWREGFYEYWGQGTLVTVSSGGGGSGGGGS GGGGSGGGGSGGGGSGGGGSGGGGSEVQLVESGGGLVQPGNSLRLSCAASGFTFSSFGMSWVRQAPGKGL EWVSSISGSGSDTLYADSVKGRFTISRDNAKTTLYLQMNSLRPEDTAVYYCTIGGSLSRSSQGTLVTVSS |
| A019400039 (A0194020A06- 35GS-ALB11- 35GS-A0194020A06) | 473 | EVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQPGNSLRLSCAASGFTFSSFGMSWVRQAPGKGLEWVSSISGSGSDTLYAD SVKGRFTISRDNAKTTLYLQMNSLRPEDTAVYYCTIGGSLSRSSQGTLVTVSSGGGGSGGGGSGGGGSGGGGS GGGGSGGGGSGGGGSEVQLVESGGGLVQAGGSLGLSCSASGLLFSRNSAGWYRQAPGKRREFVARIRMGGSI NYADSVKGRFTVSRDNAKNMMYLQMNDLKPEDTAVYFCSGWREGFYEYWGQGTLVTVSS |
| A019400029 (A0194020A06(E1D)- 35GS-A0194020A06- 35GS-ALB11-A) | 496 | DVQLVESGGGLVQAGGSLGLSCSASGLLFSRNSAGWYRQAPGKRREFVARIRMGGSINYADSVKGRFTVSRDN AKNMMYLQMNDLKPEDTAVYFCSGWREGFYEYWGQGTLVTVSSGGGGSGGGGSGGGGSGGGGSGGGGS GGGGSGGGGSEVQLVESGGGLVQAGGSLGLSCSASGLLFSRNSAGWYRQAPGKRREFVARIRMGGSINYADS VKGRFTVSRDNAKNMMYLQMNDLKPEDTAVYFCSGWREGFYEYWGQGTLVTVSSGGGGSGGGGSGGGGS GGGGSGGGGSGGGGSGGGGSEVQLVESGGGLVQPGNSLRLSCAASGFTFSSFGMSWVRQAPGKGLEWVSSI SGSGSDTLYADSVKGRFTISRDNAKTTLYLQMNSLRPEDTAVYYCTIGGSLSRSSQGTLVTVSSA |
| A019400031 (A0194009G09(E1D)- 35GS-A0194009G09- 35GS-ALB11-A) | 497 | DVQLVESGGGLVQAGGSLGLSCSASGLLFSRNSAGWYRQAPGKQREFVARIRMGGSINYADTVKGRFTISRDN AKNTVYLQMNSLKPEDTAVYYCSSWRIGFYEYWGQGTLVTVSSGGGGSGGGGSGGGGSGGGGSGGGGSGG GGSGGGGSEVQLVESGGGLVQAGGSLGLSCSASGLLFSRNSAGWYRQAPGKQREFVARIRMGGSINYADTVK GRFTISRDNAKNTVYLQMNSLKPEDTAVYYCSSWRTGFYEYWGQGTLVTVSSGGGGSGGGGSGGGGSGGGG SGGGGSGGGGSGGGGSEVQLVESGGGLVQPGNSLRLSCAASGFTFSSFGMSWVRQAPGKGLEWVSSISGSG SDTLYADSVKGRFTISRDNAKTTLYLQMNSLRPEDTAVYYCTIGGSLSRSSQGTLVTVSSA |
| A019400071 (A0194009G09(E1D, L11V, A14P, G19R, | 514 | DVQLVESGGGVVQPGGSLRLSCSASGLLFSRNSAGWYRQAPGKQREFVARIRQGGSINYADSVKGRFTISRDNS KNTVYLQMNSLRPEDTALYYCSGWRTGFYEYWGQGTLVTVSSGGGGSGGGGSGGGGSGGGGSGGGGSGG GGSGGGGSEVQLVESGGGVVQPGGSLRLSCSASGLLFSRNSAGWYRQAPGKQREFVARIRQGGSINYADSVK |

TABLE A-3-continued

Amino acid sequences of selected multivalent anti-Kv1.3 Nanobodies

| Name | ID | Amino acid sequence |
|---|---|---|
| M53Q, T62S, A74S, K83R, V89L, S94G)-35GS-A0194009G09 (L11V, A14P, G19R, M53Q, T62S, A74S, K83R, V89L, S94G)-35GS-ALB82-A) | | GRFTISRDNSKNTVYLQMNSLRPEDTALYYCSGWRTGFYEYWGQGTLVTVSSGGGGSGGGGSGGGGSGGGG<br>SGGGGSGGGGSGGGGSEVQLVESGGGVVQPGNSLRLSCAASGFTFSSFGMSWVRQAPGKGLEWVSSISGSG<br>SDTLYADSVKGRFTISRDNAKTTLYLQMNSLRPEDTALYYCTIGGSLSRSSQGTLVTVSSA |
| A0194000072 (A0194009G09 (E1D, L11V, A14P, G19R, M53Q, T62S, A74S, K83R, V89L, T97E)-35GS-A0194009G09 (L11V, A14P, G19R, M53Q, T62S, A74S, K83R, V89L, T97E)-35GS-ALB82-A) | 515 | DVQLVESGGGVVQPGGSLRLSCSASGLLFSRNSAGWYRQAPGKQREFVARIRQGGSINYADSVKGRFTISRDNS<br>KNTVYLQMNSLRPEDTALYYCSSWREGFYEYWGQGTLVTVSSGGGGSGGGGSGGGGSGGGGSGGGGSGGGG<br>GSGGGGGSEVQLVESGGGVVQPGGSLRLSCSASGLLFSRNSAGWYRQAPGKQREFVARIRQGGSINYADSVKG<br>RFTISRDNSKNTVYLQMNSLRPEDTALYYCSSWREGFYEYWGQGTLVTVSSGGGGSGGGGSGGGGSGGGGS<br>GGGGSGGGGSGGGGSEVQLVESGGGVVQPGNSLRLSCAASGFTFSSFGMSWVRQAPGKGLEWVSSISGSGS<br>DTLYADSVKGRFTISRDNAKTTLYLQMNSLRPEDTALYYCTIGGSLSRSSQGTLVTVSSA |
| A0194000073 (A0194009G09 (E1D, L11V, A14P, G19R, M53A, T62S, A74S, K83R, V89L, S94G)-35GS-A0194009G09 (L11V, A14P, G19R, M53A, T62S, A74S, K83R, V89L, S94G)-35GS-ALB82-A) | 516 | DVQLVESGGGVVQPGGSLRLSCSASGLLFSRNSAGWYRQAPGKQREFVARIRAGGSINYADSVKGRFTISRDNS<br>KNTVYLQMNSLRPEDTALYYCSGWRTGFYEYWGQGTLVTVSSGGGGSGGGGSGGGGSGGGGSGGGGSGGGG<br>GGSGGGGSEVQLVESGGGVVQPGGSLRLSCSASGLLFSRNSAGWYRQAPGKQREFVARIRAGGSINYADSVK<br>GRFTISRDNSKNTVYLQMNSLRPEDTALYYCSGWRTGFYEYWGQGTLVTVSSGGGGSGGGGSGGGGSGGGG<br>SGGGGSGGGGSGGGGSEVQLVESGGGVVQPGNSLRLSCAASGFTFSSFGMSWVRQAPGKGLEWVSSISGSG<br>SDTLYADSVKGRFTISRDNAKTTLYLQMNSLRPEDTALYYCTIGGSLSRSSQGTLVTVSSA |
| A0194000074 (A0194009G09 (E1D, L11V, A14P, G19R, M53A, T62S, A74S, K83R, V89L, T97E)-35GS-A0194009G09 (L11V, A14P, G19R, M53A, T62S, A74S, K83R, V89L, T97E)-35GS-ALB82-A) | 517 | DVQLVESGGGVVQPGGSLRLSCSASGLLFSRNSAGWYRQAPGKQREFVARIRAGGSINYADSVKGRFTISRDNS<br>KNTVYLQMNSLRPEDTALYYCSSWREGFYEYWGQGTLVTVSSGGGGSGGGGSGGGGSGGGGSGGGGSGGG<br>GSGGGGGSEVQLVESGGGVVQPGGSLRLSCSASGLLFSRNSAGWYRQAPGKQREFVARIRAGGSINYADSVKGR<br>FTISRDNSKNTVYLQMNSLRPEDTALYYCSSWREGFYEYWGQGTLVTVSSGGGGSGGGGSGGGGSGGGGSG<br>GGGSGGGGSEVQLVESGGGVVQPGNSLRLSCAASGFTFSSFGMSWVRQAPGKGLEWVSSISGSGSD<br>TLYADSVKGRFTISRDNAKTTLYLQMNSLRPEDTALYYCTIGGSLSRSSQGTLVTVSSA |
| A0194000075 (A0194009G09 (E1D, L11V, A14P, G19R, M53A, T62S, A74S, K83R, V89L, S94G, T97E)-35GS-0194009G09 (L11V, A14P, G19R, M53A, T62S, A74S, K83R, V89L, S94G, T97E)-35GS-ALB82-A) | 518 | DVQLVESGGGVVQPGGSLRLSCSASGLLFSRNSAGWYRQAPGKQREFVARIRAGGSINYADSVKGRFTISRDNS<br>KNTVYLQMNSLRPEDTALYYCSGWREGFYEYWGQGTLVTVSSGGGGSGGGGSGGGGSGGGGSGGGGSGG<br>GGSGGGGSEVQLVESGGGVVQPGGSLRLSCSASGLLFSRNSAGWYRQAPGKQREFVARIRAGGSINYADSVK<br>GRFTISRDNSKNTVYLQMNSLRPEDTALYYCSGWREGFYEYWGQGTLVTVSSGGGGSGGGGSGGGGSGGGG<br>SGGGGSGGGGSGGGGSEVQLVESGGGVVQPGNSLRLSCAASGFTFSSFGMSWVRQAPGKGLEWVSSISGSG<br>SDTLYADSVKGRFTISRDNAKTTLYLQMNSLRPEDTALYYCTIGGSLSRSSQGTLVTVSSA |
| A0194000076 (A0194009G09 (E1D, L11V, A14P, G19R, M53Y, T62S, A74S, K83R, V89L, S94G)-35GS-A0194009G09 (L11V, A14P, G19R, M53Y, T62S, A74S, K83R, V89L, S94G)-35GS-ALB82-A) | 519 | DVQLVESGGGVVQPGGSLRLSCSASGLLFSRNSAGWYRQAPGKQREFVARIRYGGSINYADSVKGRFTISRDNS<br>KNTVYLQMNSLRPEDTALYYCSGWRTGFYEYWGQGTLVTVSSGGGGSGGGGSGGGGSGGGGSGGGGSGGGG<br>GGSGGGGSEVQLVESGGGVVQPGGSLRLSCSASGLLFSRNSAGWYRQAPGKQREFVARIRYGGSINYADSVKG<br>RFTISRDNSKNTVYLQMNSLRPEDTALYYCSGWRTGFYEYWGQGTLVTVSSGGGGSGGGGSGGGGSGGGGS<br>GGGGSGGGGSGGGGSEVQLVESGGGVVQPGNSLRLSCAASGFTFSSFGMSWVRQAPGKGLEWVSSISGSGS<br>DTLYADSVKGRFTISRDNAKTTLYLQMNSLRPEDTALYYCTIGGSLSRSSQGTLVTVSSA |
| A0194000077 (A0194009G09 (E1D, L11V, A14P, G19R, M53Y, T62S, A74S, K83R, V89L, T97E)-35GS-A0194009G09 (L11V, A14P, G19R, M53Y, T62S, A74S, K83R, V89L, T97E)-35GS-ALB82-A) | 520 | DVQLVESGGGVVQPGGSLRLSCSASGLLFSRNSAGWYRQAPGKQREFVARIRYGGSINYADSVKGRFTISRDNS<br>KNTVYLQMNSLRPEDTALYYCSSWREGFYEYWGQGTLVTVSSGGGGSGGGGSGGGGSGGGGSGGGGSGGGG<br>GSGGGGSEVQLVESGGGVVQPGGSLRLSCSASGLLFSRNSAGWYRQAPGKQREFVARIRYGGSINYADSVKGR<br>FTISRDNSKNTVYLQMNSLRPEDTALYYCSSWREGFYEYWGQGTLVTVSSGGGGSGGGGSGGGGSGGGGSG<br>GGGSGGGGGSEVQLVESGGGVVQPGNSLRLSCAASGFTFSSFGMSWVRQAPGKGLEWVSSISGSGSD<br>TLYADSVKGRFTISRDNAKTTLYLQMNSLRPEDTALYYCTIGGSLSRSSQGTLVTVSSA |
| A0194000078 (A0194009G09 (E1D, | 521 | DVQLVESGGGVVQPGGSLRLSCSASGLLFSRNSAGWYRQAPGKQREFVARIRYGGSINYADSVKGRFTISRDNS<br>KNTVYLQMNSLRPEDTALYYCSGWREGFYEYWGQGTLVTVSSGGGGSGGGGSGGGGSGGGGSGGGGSGG |

TABLE A-3-continued

Amino acid sequences of selected multivalent anti-Kv1.3 Nanobodies

| Name | ID | Amino acid sequence |
|---|---|---|
| L11V, A14P, G19R, M53Y, T62S, A74S, K83R, V89L, S94G, T97E)-35GS-0194009G09 (L11V, A14P, G19R, M53Y, T62S, A74S, K83R, V89L, S94G, T97E)-35GS-ALB82-A) | | GGSGGGGSEVQLVESGGGVVQPGGSLRLSCSASGLLFSRNSAGWYRQAPGKQREFVARIRYGGSINYADSVKG RFTISRDNSKNTVYLQMNSLRPEDTALYYCSGWREGFYEYWGQGTLVTVSSGGGGSGGGGSGGGGSGGGGS GGGGSGGGGSGGGGSEVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSA |
| A019400079 (A0194009G09(E1D, L11V, A14P, G19R, M53Q, T62S, A74S, K83R, V89L, S94G, T97E)-35GS-0194009G09 (L11V, A14P, G19R, M53Q, T62S, A74S, K83R, V89L, S94G, T97E)-35GS-ALB82-A) | 522 | DVQLVESGGGVVQPGGSLRLSCSASGLLFSRNSAGWYRQAPGKQREFVARIRQGGSINYADSVKGRFTISRDNS KNTVYLQMNSLRPEDTALYYCSGWREGFYEYWGQGTLVTVSSGGGGSGGGGSGGGGSGGGGSGGGGSGG GGSGGGGSEVQLVESGGGVVQPGGSLRLSCSASGLLFSRNSAGWYRQAPGKQREFVARIRQGGSINYADSVK GRFTISRDNSKNTVYLQMNSLRPEDTALYYCSGWREGFYEYWGQGTLVTVSSGGGGSGGGGSGGGGSGGGG SGGGGSGGGGSGGGGSEVQLVESGGGVVQPGNSLRLSCAASGFTFSSFGMSWVRQAPGKGLEWVSSISGSG SDTLYADSVKGRFTISRDNAKTTLYLQMNSLRPEDTALYYCTIGGSLSRSSQGTLVTVSSA |

TABLE A-4

Sequence alignment of Kv1.3 Family 1 binders

| Kabat# | 10 | 20 | 30 | 40 | 50 | 60 | 70 | 80 | 90 | 100 abcdefghij | 110 abcdefghij |
|---|---|---|---|---|---|---|---|---|---|---|---|
| A01940003 | EVQLVESGGGLVQAGGSLVQAGGSLSLSCTASGGTFRNFGMGWFRQAQGKEREFVAAI | | | | | SRTGHTYYQDSVKGRFTISKDNAKNILSLQMNSLKPEDTAVYYCAARPFGDGTYYQRAFYDFWGQGTQVTVSS | | | | | |
| KV13BIIPMP027B10 | .......... | .......... | ...SY..... | .......... | .......... | .....S.... | ......N... | ....M..... | .......... | ...........N...... | ..........L....... |
| KV13BIIPMP027D10 | .......... | .......... | ....Y..... | .......... | .......... | .....S.... | ..........  | ....M..... | .......... | ...........N...... | .................. |
| A0194008A09 | .......... | .......... | .......... | .......... | .......... | .....S.... | ..........  | ....MV.... | .......... | ....D.............. | ..........L....... |
| A0194007C01 | .......... | .......... | .......... | .......... | .......... | .....S.... | ..........  | ....M..... | .........R | ....D.............. | .................. |
| A0194007E12 | .......... | .......... | ....Y..... | .......... | .......... | ...S.R.S.. | ..........  | ....MV.... | .......... | ....Y.............. | .................. |
| A0194003C08 | .......... | .......... | ....Y..... | .......... | .......... | ...S.R.S.. | ....N..... | ....M..... | .......... | ....D.............. | .................. |
| A0194008D08 | ....D..P.. | .......R.. | ....Y..... | .......... | .......... | .....N.I.S. | .......... | ....V..... | .......... | ....D.......N...... | .................. |
| A0194008C07 | .......... | .......... | ....Y..... | .......... | ....D..... | .....N.I.S. | .......... | ..........  | .......... | ..................T | ..........L....... |
| KV13BIIPMP027H10 | .......... | ......S... | ....R..... | .......... | .......... | .....S.... | .......... | ....M..... | .......... | ....D.............. | .................. |
| A0194007E04 | .......... | .......... | .......... | .......... | .......... | ...S.IF.S. | .......... | .....F.... | .......... | ....D.............. | .................. |
| A0194007B12 | .......... | .......... | ...YA..... | ......V... | .......... | .....S.Y.S. | ..........R. | ....MV.... | .......... | ....D.............. | .................. |
| A0194007F08 | .......... | .......... | .......... | ......D..Q. | .......... | .....S.R.FS. | .......... | .......... | .......... | ....D.............. | .................. |
| KV13BIIPMP050E12 | .......... | .......... | ....Y..... | .......... | .......... | ..SA..I.LN. | .......... | ..MV.K.... | .......... | ....D.............. | .................. |
| A0194007D11 | .......... | ......A... | .......... | .......... | .......... | .....S.... | ....ARA... | ..MV...... | .......... | ....D.............. | ..........L....... |
| A0194007B09 | .......T.. | .......... | ....Y..... | .......... | .......... | .....S.I.S. | ....N..... | ....M..... | .......... | ....D.............. | .................. |
| A0194003A12 | .......... | .......... | ....V.N... | .......... | .......... | ..SA.SR... | .......... | ....M..... | .......... | ....D.............. | .................. |
| A0194003A09 | .......... | .......... | ....Y..... | .......... | .......... | ..SA.R.S.. | ....N..... | ....M..... | .......... | ....D.............. | ..........L....... |
| A0194003B09 | .......... | .......... | ....Y..... | .......... | .......... | ..SA.R.S.. | ....N..... | ....VM.... | .......... | ....D.............. | ..........L....... |
| A0194004F06 | .......... | .......... | .......... | .......... | .......... | ..SA...S.A. | ..........R. | ....MV.... | .......D.. | ....D.............. | .................. |
| A0194007E08 | .......... | ......S... | ....R..... | .......... | .......... | ..SA.R.S.. | ....N..... | ....MV..D. | .......... | ....D.............T | ..........L....... |
| A0194007D01 | .......... | .......... | ....R..... | .......... | .......... | .....R.S.. | ....N..... | ....M..... | .......... | ....D.............. | ..........L....... |
| A0194008F05 | .......... | ......P... | ....Y..... | .......... | .......... | ..SA.R.S.. | ....N..... | ....M..... | .......... | ....D.............. | ..........L....... |
| A0194008C01 | .......... | .......P.. | .......... | .......... | .......... | .....R.S.. | ..........R. | ....MVA... | .......... | ....D............NL | ..........L....... |
| KV13BIIPMP027D09 | .......... | ......S.N. | .......... | .......A.. | ...T...E.. | .....S.... | ..........R. | ....MV.... | .........A | ....D.............. | .................. |
| KV13BIIPMP050B11 | .......... | .......... | ...YA..... | .......... | ...T...... | ...S.IF.S. | ..........R. | ....MV.... | .......... | ....S.............. | .................. |
| KV13BIIPMP050A07 | .......... | .......... | ....Y..... | .......F.. | .......... | ...S.IF.SE. | ..........R. | ....MV.K.. | .......... | ....D.............. | .................. |
| KV13BIIPMP027A11 | K........R. | .......... | ....V..... | .......... | ...V....... | ......R.FS. | .......... | ....MV.... | .......... | ....S.............. | .................. |
| A0194007A01 | ........A. | ......R... | ....N..... | ......V.T. | .......... | ......R.S.. | ..........A. | ....MM..R. | .......... | ....D.............F | ...I.............. |
| KV13BIIPMP026D09 | .......... | .......... | ....R..... | .......... | ...T...... | ...S...I.S. | .......... | ....MV.... | .......... | ....D..........S... | .................. |
| KV13BIIPMP027B12 | .......... | .......... | ....R..... | .......T.. | .......... | ...S.R.FS. | .......... | ....MV.... | .......... | ....D..........S... | ..........N....... |
| A0194008C08 | .......... | ......D... | .......... | .......... | .......... | ...S...I.S. | .......... | ....MV.... | .......... | ....D..........S... | .................. |
| A0194007B04 | .......... | ......D... | ....R..... | .......... | .......... | ...S.K..S.. | ..........Q. | ....MV.... | .......... | ....D.............. | ..........A....... |
| A0194003A02 | .......... | ......D... | ....R..... | .......... | ...T...... | ...S.R.A.. | ..........R. | ....MV.... | .......... | ....D.............. | ..........L....... |
| KV13BIIPMP050A10 | .......... | .....R.... | ...S.S.... | .......A.. | .......... | ...S.K..S.. | ..........S. | ....LV.... | .........S | ....D.D...........S | ..........L....... |
| KV13BIIPMP050C09 | .......... | ......D... | ...S.S.... | .......... | .......... | ...S.K.S.. | ..........R. | ....MV.... | .......... | ....D.............. | .................. |
| A0194003B11 | .......... | .....R.... | ...S.S.... | .......A.. | ...T...... | ...S...I.S. | ..........A. | ....LV.... | .......... | ....D.D...........S | ..........L....... |
| KV13BIIPMP026F08 | .......... | .......... | ....R..... | .......YA. | ...T...... | ...S.IF.SE. | ..........R. | ....MM..R. | .......... | ....D.............F | .................. |
| KV13BIIPMP027H08 | .......... | .......... | .......A.. | .......A.. | .......... | ...S.IF.SE. | .......... | ....MV.... | .......... | ....SD............. | ...I.............. |
| KV13BIIPMP050A09 | .......... | .......... | .......A.. | ...R.EA... | ...T...... | ...S.I.S.. | .......... | ....MV.... | .......... | ....SD............. | .................. |
| A0194003B06 | .......... | ....V..N.. | .......... | .......H.. | .......... | ...S.R.A.. | ..........R. | ....MV.... | .........S | ....SD............S | .................. |
| KV13BIIPMP049E10 | K........P. | .......A.. | .......... | .......H.. | .......... | ...S.R..A. | .......... | ....M..... | .......... | ....SD............S | ..........A....... |
| KV13BIIPMP027E11 | .......... | ......V..N. | .......... | .......... | .......... | ...S.R.A.. | ....V.R... | ....MV.... | .......... | ....SD............. | .................. |
| A0194003A04 | .......... | ......D... | ....R..... | .......... | .......... | ...S...K.S. | .......... | ....MV.... | .......... | ....D.............S | ..........L....... |
| A0194007F01 | .......... | ......D... | ....R..... | .......... | .......... | ...S.RK.S.. | .......... | ....MV.... | .......... | ....D.............S | .................. |
| KV13BIIPMP050D09 | ........A. | .......... | ....N..... | .......... | .......... | ......R.FS. | ..........R. | ....MV.... | .......... | ....SD............. | ........N..G....A. |
| A0194007G09 | .......... | .......E.. | ....A..... | ...V.T.... | ...T...R.E. | .....S.... | ..........R. | ....MV.... | .......... | ........SD......... | .................. |

TABLE A-4-continued

```
Kabat#              10        20        30        40        50        60       a 70        80        90   abc  100       110  abcdefghij
                    |         |         |         |         |         |         |         |         |    |    |         |    |
A0194000003       : EVQLVESGGGLVQAGGSLSLSCTASGGTFRNFGMGWFRQAQGKEREFVAAISRTGGHTYYQDSVKGRFTISKDNAKNILSLQMNSLKPEDTAVYYCAARRFGDGTYYQRAFYDFWGQGTQVTVSS
KV13BIIPMP027H09  : ..................P.............A.L............R.E.......T...SAR.......S...............R......MV............SD.................
A0194008A02       : .................................A.L............R.E.......T...SAR.......S...............R......MV............S..................
A0194003A08       : ..................D..............A..............R.E.......T...SAR.......S...............R......MV............SD.................
KV13BIIPMP050F11  : ..................N..............A.L............R.E.......T...SAR.......S...............R......MV............SD.................
A0194008A11       : ..................D..............A..............R.E.......T...SAR.......S...............R......MV............SD.................
A0194007D10       : ..................D..............A..............R.E.......T...SAR.......A...............R......MV............SDG................
KV13BIIPMP049B09  : .................V..N.........V..................H...........A.R..A.........A.R......MV....T.......S...S.E.....R..
A0194008A01       : ..................D..............A.L.............R.E.......T...SAR.......S...........A.R......MV............SD............R.....
A0194008B01       : ...................S.K..........A..................T...S.......S...........A.R......LV....NA........SD.D................L.
A0194008G10       : ...................R.V.AF.......A...................T...S.......S................MVY..Y.......G.....A....T...L.
```

TABLE A-5

Sequence alignment of Kv1.3 Family 12 binders

```
KABAT#              :                                                                   .ABC                                  |
                    :EVQLVESGGGLVQAGGSLGLSCSASGLLFSRNSAGWYRQAPGKRREFVARIRMGGSINYADSVKGRFTVSRDNAKNMMYLQMNDLKPEDTAVYFCSGWREGFYEYWGQGTLVTVSS
A0194020A06         :.................................................................................................................
A0194020C04         :.....................................R........................I..TI......S...............K..S..................
A0194020A07         :...............P................................................TI......S...Y..S..............................
A0194020C03         :..................................................T.............TI......S...Y..S..............................
A0194020F09         :..................................................T.............TI......S...Y..S..T............................
A0194009G09         :................................................................TV......G...Y..S..T..........................Q
A0194016G08         :...............R....................Q.D......S..T...............T..TL...A...Y..S..T..A........................Q
A0194016F09         :...............E....V...............K.D......S..T...............I..TV...S.G.Y..S..T..A........................
A0194009B01         :...............R....V...............Q.D......S..T...............I.KT.TV...S...Y..S..T..A......................Q
A0194016B06         :...............R....V...............Q.D......S..T...............I.KT.TV...S...Y..S..T..A..H...................
A0194009B06         :...............R....V...............Q.D......S..T...............I.KT.TV...S...Y.GS..T..A......................Q
A0194016A05         :...............R....V...............Q.D......S..T...............I.KT.TVH..S...Y..S..TEA.......................
A0194016B04         :...............R....V...............Q.D......SS.T...............I.KT.TL.V.N...Y..S..TEA.....................R.
A0194016C03         :...............R....V...............Q.D......S..T...............I.KT.TV...N...Y..S..T..A.....................R.
A0194016C10         :...............R....V............R..Q.DL.....S..LTT.T..Q........I.KT.TL...N...Y..S..T..AQ......................
A0194016F11         :...............R....V...............Q.Q.........................I.KT.TL........Y..A..TEA....................R.Q
A0194020B10         :...............R....V...............Q...........................I...TV........Y..A..IEA.......................Q
```

TABLE A-6

Representative multivalent formats

| Construct ID | VHH identity | Family | Linker | VHH identity | Family | Linker | VHH identity | Family |
|---|---|---|---|---|---|---|---|---|
| A019400004 | A019400003 | 1 | 40 GS | A019400003 | 1 | | | |
| A019400012 A019400010 | A0194009G09 | 12 | 35 GS | A019400003 | 1 | | | |
| A019400013 A019400009 | A0194009G09 | 12 | 35 GS | A0194009G09 | 12 | | | |
| A019400014 A019400011 | A019400003 | 1 | 35 GS | A0194009G09 | 12 | | | |
| A019400015 | A0194009G09 | 12 | 35 GS | A0194009G09 | 12 | 35 GS | A0194009G09 | 12 |
| A019400032 | A0194020A06 | 12 | 35 GS | A0194020A06 | 12 | | | |
| A019400023 | A0194020B10 | 12 | 35 GS | A0194020B10 | 12 | 35 GS | Alb11 | |
| A019400024 | A0194020A06 | 12 | 35 GS | A0194020A06 | 12 | 35 GS | Alb11 | |
| A019400025 | A0194020B10 | 12 | 9 GS | Alb11 | | 9 GS | A0194020B10 | 12 |
| A019400026 | A0194009G09 | 12 | 9 GS | Alb11 | | 9 GS | A0194009G09 | 12 |
| A019400027 | A0194009G09 | 12 | 35 GS | A0194009G09 | 12 | 35 GS | Alb11 | |
| A019400028 | A0194020A06 | 12 | 9 GS | Alb11 | | 9 GS | A0194020A06 | 12 |
| A019400029 | A0194020A06 | 12 | 35 GS | A0194020A06 | 12 | 35 GS | Alb11 | |

TABLE A-7

Kv1.3 sequences from various species ("ID" refers to the SEQ ID NO as used herein)

| Prot ID | Species | ID | Sequence |
|---|---|---|---|
| P22001 | Homo sapiens | 474 | MDERLSLLRSPPPPSARHRAHPPQRPASSGGAHTLVNHGYAEPAAGRELPPDMTVVPGDHLLEPEVADG GGAPPQGGCGGGGCDRYEPLPPSLPAAGEQDCCGERVVINISGLRFETQLKTLCQFPETLLGDPKRRMRY FDPLRNEYFFDRNRPSFDAILYYQSGGRIRRPVNVPIDIFSEEIRFYQLGEEAMEKFREDEGFLREEERPLPR RDFQRQVWLLFEYPESSGPARGIAIVSVLVILISIVIFCLETLPEFRDEKDYPASTSQDSFEAAGNSTSGSRAG ASSFSDPFFVVETLCIIWFSFELLVRFFACPSKATFSRNIMNLIDIVAIIPYFITLGTELAERQGNGQQAMSLAI LRVIRLVRVFRIFKLSRHSKGLQILGQTLKASMRELGLLIFFLFIGVILFSSAVYFAEADDPTSGFSSIPDAFWW AVVTMTTVGYGDMHPVTIGGKIVGSLCAIAGVLTIALPVPVIVSNFNYFYHRETEGEEQSQYMHVGSCQH LSSSAEELRKARSNSTLSKSEYMVIEEGGMNHSAFPQTPFKTGNSTATCTTNNNPNSCVNIKKIFTDV |
| P78352 | Rattus norvegicus | 475 | MTVVPGDHLLEPEAAGGGGDPPQGGCVSGGGCDRYEPLPPALPAAGEQDCCGERVVINISGLRFETQL KTLCQFPETLLGDPKRRMRYFDPLRNEYFFDRNRPSFDAILYYQSGGRIRRPVNVPIDIFSEEIRFYQLGEEA MEKFREDEGFLREEERPLPRRDFQRQVWLLFEYPESSGPARGIAIVSVLVILISIVIFCLETLPEFRDEKDYPAS PSQDVFEAANNSTSGASSGASSFSDPFFVVETLCIIWFSFELLVRFFACPSKATFSRNIMNLIDIVAIIPYFITL GTELAERQGNGQQAMSLAILRVIRLVRVFRIFKLSRHSKGLQILGQTLKASMRELGLLIFFLFIGVILFSSAVYF AEADDPSSGFNSIPDAFWWAVVTMTTVGYGDMHPVTIGGKIVGSLCAIAGVLTIALPVPVIVSNFNYFYH RETEGEEQAQYMHVGSCQHLSSSAEELRKARSNSTLSKSEYMVIEEGGMNHSAFPQTPFKTGNSTATCTT NNNPNSCVNIKKIFTDV |
| P16390 | Mus musculus | 476 | MTVVPGDHLLEPEAAGGGGDPPQGGCGSGGGGGCDRYEPLPPALPAAGEQDCCGERVVINISGLRF ETQLKTLCQFPETLLGDPKRRMRYFDPLRNEYFFDRNRPSFDAILYYQSGGRIRRPVNVPIDIFSEEIRFYQL GEEAMEKFREDEGFLREEERPLPRRDFQRQVWLLFEYPESSGPARGIAIVSVLVILISIVIFCLETLPEFRDEKD YPASPSQDVFEAANNSTSGAPSGASSFSDPFFVVETLCIIWFSFELLVRFFACPSKATFSRNIMNLIDIVAIIPY FITLGTELAERQGNGQQAMSLAILRVIRLVRVFRIFKLSRHSKGLQILGQTLKASMRELGLLIFFLFIGVILFSS AVYFAEADDPSSGFNSIPDAFWWAVVTMTTVGYGDMHPVTIGGKIVGSLCAIAGVLTIALPVPVIVSNFN YFYHRETEGEEQAQYMHVGSCQHLSSSAEELRKARSNSTLSKSEYMVIEEGGMNHSAFPQTPFKTGNSTA TCTTNNNPNSCVNIKKIFTDV |
| XP_005542459 | Macaca fascicularis | 477 | MDEHLSLLRSPPPPSARHRAHPAQRPASSGGAHTLVNPGYAEPAAGPELPPDMTVVPGDHLLEPEVADG GGAPPQGGCGGGGCDRYEPLPPSLPAAGEQDCCGERVVINISGLRFETQLKTLCQFPETLLGDPKRRMRY FDPLRNEYFFDRNRPSFDAILYYQSGGRIRRPVNVPIDIFSEEIRFYQLGEEAMEKFREDEGFLREEERPLPR RDFQRQVWLLFEYPESSGPARGIAIVSVLVILISIVIFCLETLPEFRDEKDYPASPSQDSFDAAGNSTSGAAAG ASSFSDPFFVVETLCIIWFSFELLVRFFACPSKATFSRNIMNLIDIVAIIPYFITLGTELAERQGNGQQAMSLAI LRVIRLVRVFRIFKLSRHSKGLQILGQTLKASMRELGLLIFFLFIGVILFSSAVYFAEADDPTSGFSSIPDAFWW AVVTMTTVGYGDMHPVTIGGKIVGSLCAIAGVLTIALPVPVIVSNFNYFYHRETEGEEQAQYMHVGSCQH LSSSAEELRKARSNSTLSKSEYMVIEEGGMNHSAFPQTPFKTGNSTATCTTNNNPNSCVNIKKIFTDV |
| AFH32312 | Macaca mulatta | 477 | MDEHLSLLRSPPPPSARHRAHPAQRPASSGGAHTLVNPGYAEPAAGPELPPDMTVVPGDHLLEPEVADG GGAPPQGGCGGGGCDRYEPLPPSLPAAGEQDCCGERVVINISGLRFETQLKTLCQFPETLLGDPKRRMRY FDPLRNEYFFDRNRPSFDAILYYQSGGRIRRPVNVPIDIFSEEIRFYQLGEEAMEKFREDEGFLREEERPLPR RDFQRQVWLLFEYPESSGPARGIAIVSVLVILISIVIFCLETLPEFRDEKDYPASPSQDSFDAAGNSTSGAAAG ASSFSDPFFVVETLCIIWFSFELLVRFFACPSKATFSRNIMNLIDIVAIIPYFITLGTELAERQGNGQQAMSLAI LRVIRLVRVFRIFKLSRHSKGLQILGQTLKASMRELGLLIFFLFIGVILFSSAVYFAEADDPTSGFSSIPDAFWW AVVTMTTVGYGDMHPVTIGGKIVGSLCAIAGVLTIALPVPVIVSNFNYFYHRETEGEEQAQYMHVGSCQH LSSSAEELRKARSNSTLSKSEYMVIEEGGMNHSAFPQTPFKTGNSTATCTTNNNPNSCVNIKKIFTDV |

TABLE A-8

| Name | ID | Amino acid sequence |
|---|---|---|
| Alb-11 | 478 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 5GS linker | 479 | GGGGS |
| 7GS linker | 480 | sggsggs |
| 8GS linker | 481 | ggggcgggs |
| 9GS linker | 482 | GGGGSGGGS |
| 10GS linker | 483 | GGGGSGGGGS |
| 15GS linker | 484 | GGGGSGGGGSGGGGS |
| 18GS linker | 485 | GGGGSGGGGSGGGGGGS |
| 20GS linker | 486 | GGGGSGGGGSGGGGSGGGGS |
| 25GS linker | 487 | GGGGSGGGGSGGGGSGGGGSGGGGS |
| 30GS linker | 488 | GGGGSGGGGSGGGGSGGGGSGGGGSGGGGS |
| 35GS linker | 489 | GGGGSGGGGSGGGGSGGGGSGGGGSGGGGSGGGGS |
| 40GS linker | 490 | GGGGSGGGGSGGGGSGGGGSGGGGSGGGGSGGGGSGGGGS |
| G1 hinge | 491 | EPKSCDKTHTCPPCP |
| 9GS-G1 hinge | 492 | GGGGSGGGSEPKSCDKTHTCPPCP |
| Llama upper long hinge region | 493 | epktpkpqpaaa |
| G3 hinge | 494 | ELKTPLGDTTHTCPRCPEPKSCDTPPPCPRCPEPKSCDTPPPCPRCPEPKSCDTPPPCPRCP |

TABLE A-9

Amino acid sequences of monovalent sequence optimized anti-Kv1.3 Nanobodies ("ID" refers to the SEQ ID NO as used herein)

| Name | ID | Amino acid sequence |
|---|---|---|
| A019400050 | 498 | EVQLVESGGGLVQAGGSLGLSCSASGLLFSRNSAGWYRQAPGKQREFVARIRAGGSINYADTVKGRFTISRDNAKNTVYLQMNSLKPEDTAVYYCSSWRTGFYEYWGQGTLVTVSS |
| A019400051 | 499 | EVQLVESGGGLVQAGGSLGLSCSASGLLFSRNSAGWYRQAPGKQREFVARIREGGSINYADTVKGRFTISRDNAKNTVYLQMNSLKPEDTAVYYCSSWRTGFYEYWGQGTLVTVSS |
| A019400052 | 500 | EVQLVESGGGLVQAGGSLGLSCSASGLLFSRNSAGWYRQAPGKQREFVARIRFGGSINYADTVKGRFTISRDNAKNTVYLQMNSLKPEDTAVYYCSSWRTGFYEYWGQGTLVTVSS |
| A019400053 | 501 | EVQLVESGGGLVQAGGSLGLSCSASGLLFSRNSAGWYRQAPGKQREFVARIRGGGSINYADTVKGRFTISRDNAKNTVYLQMNSLKPEDTAVYYCSSWRTGFYEYWGQGTLVTVSS |
| A019400054 | 502 | EVQLVESGGGLVQAGGSLGLSCSASGLLFSRNSAGWYRQAPGKQREFVARIRHGGSINYADTVKGRFTISRDNAKNTVYLQMNSLKPEDTAVYYCSSWRTGFYEYWGQGTLVTVSS |
| A019400055 | 503 | EVQLVESGGGLVQAGGSLGLSCSASGLLFSRNSAGWYRQAPGKQREFVARIRKGGSINYADTVKGRFTISRDNAKNTVYLQMNSLKPEDTAVYYCSSWRTGFYEYWGQGTLVTVSS |
| A019400056 | 504 | EVQLVESGGGLVQAGGSLGLSCSASGLLFSRNSAGWYRQAPGKQREFVARIRLGGSINYADTVKGRFTISRDNAKNTVYLQMNSLKPEDTAVYYCSSWRTGFYEYWGQGTLVTVSS |
| A019400057 | 505 | EVQLVESGGGLVQAGGSLGLSCSASGLLFSRNSAGWYRQAPGKQREFVARIRPGGSINYADTVKGRFTISRDNAKNTVYLQMNSLKPEDTAVYYCSSWRTGFYEYWGQGTLVTVSS |
| A019400058 | 506 | EVQLVESGGGLVQAGGSLGLSCSASGLLFSRNSAGWYRQAPGKQREFVARIRQGGSINYADTVKGRFTISRDNAKNTVYLQMNSLKPEDTAVYYCSSWRTGFYEYWGQGTLVTVSS |

TABLE A-9-continued

Amino acid sequences of monovalent sequence optimized anti-Kv1.3 Nanobodies ("ID" refers to the SEQ ID NO as used herein)

| Name | ID | Amino acid sequence |
|---|---|---|
| A019400059 | 507 | EVQLVESGGGLVQAGGSLGLSCSASGLLFSRNSAGWYRQAPGKQREFVARIRRGGSINYADTVKGRFTISRDNAKNTVYLQMNSLKPEDTAVYYCSSWRTGFYEYWGQGTLVTVSS |
| A019400060 | 508 | EVQLVESGGGLVQAGGSLGLSCSASGLLFSRNSAGWYRQAPGKQREFVARIRSGGSINYADTVKGRFTISRDNAKNTVYLQMNSLKPEDTAVYYCSSWRTGFYEYWGQGTLVTVSS |
| A019400061 | 509 | EVQLVESGGGLVQAGGSLGLSCSASGLLFSRNSAGWYRQAPGKQREFVARIRTGGSINYADTVKGRFTISRDNAKNTVYLQMNSLKPEDTAVYYCSSWRTGFYEYWGQGTLVTVSS |
| A019400062 | 510 | EVQLVESGGGLVQAGGSLGLSCSASGLLFSRNSAGWYRQAPGKQREFVARIRVGGSINYADTVKGRFTISRDNAKNTVYLQMNSLKPEDTAVYYCSSWRTGFYEYWGQGTLVTVSS |
| A019400063 | 511 | EVQLVESGGGLVQAGGSLGLSCSASGLLFSRNSAGWYRQAPGKQREFVARIRWGGSINYADTVKGRFTISRDNAKNTVYLQMNSLKPEDTAVYYCSSWRTGFYEYWGQGTLVTVSS |
| A019400064 | 512 | EVQLVESGGGLVQAGGSLGLSCSASGLLFSRNSAGWYRQAPGKQREFVARIRYGGSINYADTVKGRFTISRDNAKNTVYLQMNSLKPEDTAVYYCSSWRTGFYEYWGQGTLVTVSS |
| A019400065 | 513 | EVQLVESGGGLVQAGGSLGLSCSASGLLFSRNSAGWYRQAPGKQREFVARIRIGGSINYADTVKGRFTISRDNAKNTVYLQMNSLKPEDTAVYYCSSWRTGFYEYWGQGTLVTVSS |
| A019400073_1 A0194009G09E1D, L11V, A14P, G19R, M53A, T62S, A74S, K83R, V89L, S94G | 523 | DVQLVESGGGVVQPGGSLRLSCSASGLLFSRNSAGWYRQAPGKQREFVARIRAGGSINYADSVKGRFTISRDNSKNTVYLQMNSLRPEDTALYYCSGWRTGFYEYWGQGTLVTVSS |
| A019400074_1 A0194009G09E1D, L11V, A14P, G19R, M53A, T62S, A74S, K83R, V89L, T97E | 524 | DVQLVESGGGVVQPGGSLRLSCSASGLLFSRNSAGWYRQAPGKQREFVARIRAGGSINYADSVKGRFTISRDNSKNTVYLQMNSLRPEDTALYYCSSWREGFYEYWGQGTLVTVSS |
| A019400075_1 A0194009G09E1D, L11V, A14P, G19R, M53A, T62S, A74S, K83R, V89L, S94G, T97E | 525 | DVQLVESGGGVVQPGGSLRLSCSASGLLFSRNSAGWYRQAPGKQREFVARIRAGGSINYADSVKGRFTISRDNSKNTVYLQMNSLRPEDTALYYCSGWREGFYEYWGQGTLVTVSS |
| A019400071_1 A0194009G09E1D, L11V, A14P, G19R, M53Q, T62S, A74S, K83R, V89L, S94G | 526 | DVQLVESGGGVVQPGGSLRLSCSASGLLFSRNSAGWYRQAPGKQREFVARIRQGGSINYADSVKGRFTISRDNSKNTVYLQMNSLRPEDTALYYCSGWRTGFYEYWGQGTLVTVSS |
| A019400072_1 A0194009G09E1D, L11V, A14P, G19R, M53Q, T62S, A74S, K83R, V89L, T97E | 527 | DVQLVESGGGVVQPGGSLRLSCSASGLLFSRNSAGWYRQAPGKQREFVARIRQGGSINYADSVKGRFTISRDNSKNTVYLQMNSLRPEDTALYYCSSWREGFYEYWGQGTLVTVSS |
| A019400079_1 A0194009G09E1D, L11V, A14P, G19R, M53Q, T62S, A74S, K83R, V89L, S94G, T97E | 528 | DVQLVESGGGVVQPGGSLRLSCSASGLLFSRNSAGWYRQAPGKQREFVARIRQGGSINYADSVKGRFTISRDNSKNTVYLQMNSLRPEDTALYYCSGWREGFYEYWGQGTLVTVSS |
| A019400076_1 A0194009G09E1D, L11V, A14P, G19R, M53Y, T62S, A74S, K83R, V89L, S94G | 529 | DVQLVESGGGVVQPGGSLRLSCSASGLLFSRNSAGWYRQAPGKQREFVARIRYGGSINYADSVKGRFTISRDNSKNTVYLQMNSLRPEDTALYYCSGWRTGFYEYWGQGTLVTVSS |
| A019400077_1 A0194009G09E1D, L11V, A14P, G19R, M53Y, T62S, A74S, K83R, V89L, T97E | 530 | DVQLVESGGGVVQPGGSLRLSCSASGLLFSRNSAGWYRQAPGKQREFVARIRYGGSINYADSVKGRFTISRDNSKNTVYLQMNSLRPEDTALYYCSSWREGFYEYWGQGTLVTVSS |
| A019400078_1 A0194009G09E1D, L11V, A14P, G19R, M53Y, T62S, A74S, K83R, V89L, S94G, T97E | 531 | DVQLVESGGGVVQPGGSLRLSCSASGLLFSRNSAGWYRQAPGKQREFVARIRYGGSINYADSVKGRFTISRDNSKNTVYLQMNSLRPEDTALYYCSGWREGFYEYWGQGTLVTVSS |

TABLE A-9-continued

Amino acid sequences of monovalent sequence optimized anti-Kv1.3 Nanobodies ("ID" refers to the SEQ ID NO as used herein)

| Name | ID | Amino acid sequence |
|---|---|---|
| A019400073_2<br>A0194009G09L11V, A14P,<br>G19R, M53A, T62S, A74S,<br>K83R, V89L, S94G | 532 | EVQLVESGGGVVQPGGSLRLSCSASGLLFSRNSAGWYRQAPGKQREFVARIRA<br>GGSINYADSVKGRFTISRDNSKNTVYLQMNSLRPEDTALYYCSGWRTGFYEYW<br>GQGTLVTVSS |
| A019400074_2<br>A0194009G09L11V, A14P,<br>G19R, M53A, T62S, A74S,<br>K83R, V89L, T97E | 533 | EVQLVESGGGVVQPGGSLRLSCSASGLLFSRNSAGWYRQAPGKQREFVARIRA<br>GGSINYADSVKGRFTISRDNSKNTVYLQMNSLRPEDTALYYCSSWREGFYEYWG<br>QGTLVTVSS |
| A019400075_2<br>A0194009G09L11V, A14P,<br>G19R, M53A, T62S, A74S,<br>K83R, V89L, S94G, T97E | 534 | EVQLVESGGGVVQPGGSLRLSCSASGLLFSRNSAGWYRQAPGKQREFVARIRA<br>GGSINYADSVKGRFTISRDNSKNTVYLQMNSLRPEDTALYYCSGWREGFYEYW<br>GQGTLVTVSS |
| A019400071_2<br>A0194009G09L11V, A14P,<br>G19R, M53Q, T62S, A74S,<br>K83R, V89L, S94G | 535 | EVQLVESGGGVVQPGGSLRLSCSASGLLFSRNSAGWYRQAPGKQREFVARIRQ<br>GGSINYADSVKGRFTISRDNSKNTVYLQMNSLRPEDTALYYCSGWRTGFYEYW<br>GQGTLVTVSS |
| A019400072_2<br>A0194009G09L11V, A14P,<br>G19R, M53Q, T62S, A74S,<br>K83R, V89L, T97E | 536 | EVQLVESGGGVVQPGGSLRLSCSASGLLFSRNSAGWYRQAPGKQREFVARIRQ<br>GGSINYADSVKGRFTISRDNSKNTVYLQMNSLRPEDTALYYCSSWREGFYEYWG<br>QGTLVTVSS |
| A019400079_2<br>A0194009G09L11V, A14P,<br>G19R, M53Q, T62S, A74S,<br>K83R, V89L, S94G, T97E | 537 | EVQLVESGGGVVQPGGSLRLSCSASGLLFSRNSAGWYRQAPGKQREFVARIRQ<br>GGSINYADSVKGRFTISRDNSKNTVYLQMNSLRPEDTALYYCSGWREGFYEYW<br>GQGTLVTVSS |
| A019400076_2<br>A0194009G09L11V, A14P,<br>G19R, M53Y, T62S, A74S,<br>K83R, V89L, S94G | 538 | EVQLVESGGGVVQPGGSLRLSCSASGLLFSRNSAGWYRQAPGKQREFVARIRY<br>GGSINYADSVKGRFTISRDNSKNTVYLQMNSLRPEDTALYYCSGWRTGFYEYW<br>GQGTLVTVSS |
| A019400077_2<br>A0194009G09L11V, A14P,<br>G19R, M53Y, T62S, A74S,<br>K83R, V89L, T97E | 539 | EVQLVESGGGVVQPGGSLRLSCSASGLLFSRNSAGWYRQAPGKQREFVARIRY<br>GGSINYADSVKGRFTISRDNSKNTVYLQMNSLRPEDTALYYCSSWREGFYEYWG<br>QGTLVTVSS |
| A019400078_2<br>A0194009G09L11V, A14P,<br>G19R, M53Y, T62S, A74S,<br>K83R, V89L, S94G, T97E | 540 | EVQLVESGGGVVQPGGSLRLSCSASGLLFSRNSAGWYRQAPGKQREFVARIRY<br>GGSINYADSVKGRFTISRDNSKNTVYLQMNSLRPEDTALYYCSGWREGFYEYW<br>GQGTLVTVSS |

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. An immunoglobulin single variable domain that specifically binds to the EL1 extracellular loop of potassium channel 3 (Kv1.3) comprising amino acid residues 254-294 of SEQ ID NO: 474, wherein the immunoglobulin single variable domain modulates the activity of Kv1.3 by reducing or totally inhibiting the efflux of potassium ions from T-cells, as determined in Patch Clamp assay, wherein the immunoglobulin single variable domain has the structure FR1-CDR1-FR2-CDR2-FR3-CDR3-FR4, in which CDR1, CDR2 and CDR3 are complementarity determining regions, and FR1, FR2, FR3 and FR4 are framework regions, in which:
  i) CDR1 consists of the amino acid sequence of any one of SEQ ID NOs: 181-210 or an amino acid sequence having 2 or 1 amino acid(s) substitution with the amino acid sequence of SEQ ID NO: 182; wherein
    at position 3 the L has been changed into P;
    at position 4 the F has been changed into L;
    at position 5 the S has been changed into I or R;
    at position 6 the R has been changed into P or V;
    at position 7 the N has been changed into D;
    at position 8 the S has been changed into R;
    at position 9 the A has been changed into V or T; and/or
    at position 10 the G has been changed into R; and
  ii) CDR2 consists of the amino acid sequence of any one of SEQ ID NOs: 268-289 and SEQ ID NOs: 541-555 or an amino acid sequence having 2 or 1 amino acid(s) substitution with the amino acid sequence of SEQ ID NO: 269; wherein
    at position 2 the I has been changed into V or L;
    at position 4 the M has been changed into S, R, A, Q or T;
    at position 5 the G has been changed into T;
    at position 7 the S has been changed into D; and/or
    at position 8 the I has been changed into T; and
  iii) CDR3 consists of the amino acid sequence of any one of SEQ ID NOs: 393-415 or an amino acid sequence having 2 or 1 amino acid(s) substitution with the amino acid sequence of SEQ ID NO: 397; wherein
    at position 3 the E has been changed into T or I;
    at position 4 the G has been changed into E;
    at position 5 the F has been changed into A, T or S; and/or
    at position 7 the E has been changed into K.

2. The immunoglobulin single variable domain according to claim 1, in which:
  i) CDR1 consists of the amino acid sequence of any one of SEQ ID NOs: 181-210 or an amino acid sequence having 2 or 1 amino acid(s) substitution with the amino acid sequence of SEQ ID NO: 182, wherein
    at position 5 the S has been changed into R;
    at position 6 the R has been changed into V;
    at position 8 the S has been changed into R;
    at position 9 the A has been changed into V; and/or
    at position 10 the G has been changed into R; and
  ii) CDR2 consists of the amino acid sequence of any one of SEQ ID NOs: 268-289 and SEQ ID NOs: 541-555 or an amino acid sequence having 2 or 1 amino acid(s) substitution with the amino acid sequence of SEQ ID NO: 269, wherein
    at position 2 the I has been changed into V or L;
    at position 4 the M has been changed into S, R, A, or T;
    at position 7 the S has been changed into D; and/or
    at position 8 the I has been changed into T; and
  iii) CDR3 consists of the amino acid sequence of any one of SEQ ID NOs: 393-415 or an amino acid sequence having 2 or 1 amino acid(s) substitution with the amino acid sequence of SEQ ID NO: 397, wherein
    at position 3 the E has been changed into T or I;
    at position 4 the G has been changed into E; and/or
    at position 5 the F has been changed into A or S.

3. The immunoglobulin single variable domain according to claim 1, wherein said immunoglobulin single variable domain is chosen from the group of polypeptides, wherein:
  CDR1 is SEQ ID NO: 182, CDR2 is SEQ ID NO: 549, and CDR3 is SEQ ID NO: 397;
  CDR1 is SEQ ID NO: 182, CDR2 is SEQ ID NO: 269, and CDR3 is SEQ ID NO: 397;
  CDR1 is SEQ ID NO: 182, CDR2 is SEQ ID NO: 269, and CDR3 is SEQ ID NO: 394;
  CDR1 is SEQ ID NO: 181, CDR2 is SEQ ID NO: 268, and CDR3 is SEQ ID NO: 393;
  CDR1 is SEQ ID NO: 181, CDR2 is SEQ ID NO: 268, and CDR3 is SEQ ID NO: 395;
  CDR1 is SEQ ID NO: 181, CDR2 is SEQ ID NO: 268, and CDR3 is SEQ ID NO: 396;
  CDR1 is SEQ ID NO: 181, CDR2 is SEQ ID NO: 270, and CDR3 is SEQ ID NO: 393;
  CDR1 is SEQ ID NO: 183, CDR2 is SEQ ID NO: 268, and CDR3 is SEQ ID NO: 393;
  CDR1 is SEQ ID NO: 184, CDR2 is SEQ ID NO: 268, and CDR3 is SEQ ID NO: 393;
  CDR1 is SEQ ID NO: 185, CDR2 is SEQ ID NO: 271, and CDR3 is SEQ ID NO: 398;
  CDR1 is SEQ ID NO: 182, CDR2 is SEQ ID NO: 541, and CDR3 is SEQ ID NO: 394;
  CDR1 is SEQ ID NO: 182, CDR2 is SEQ ID NO: 541, and CDR3 is SEQ ID NO: 397; and
  CDR1 is SEQ ID NO: 182, CDR2 is SEQ ID NO: 549, and CDR3 is SEQ ID NO: 394.

4. The immunoglobulin single variable domain according to claim 1, wherein said immunoglobulin single variable domain essentially consists of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation; and wherein said immunoglobulin single variable domain is chosen from the group consisting of immunoglobulin single variable domains with SEQ ID NOs: 1-64, 495, 498-513 and 523-540 or immunoglobulin single variable domains that have a sequence identity of more than 85% with SEQ ID NOs: 1-64, 495, 498-513 and 523-540.

5. A polypeptide that comprises or essentially consists of one or more immunoglobulin single variable domains according to claim 1.

6. The polypeptide according to claim 5, wherein said polypeptide is chosen from the group of polypeptides with SEQ ID NOs: 451-473 or polypeptides that have a sequence identity of more than 85% with SEQ ID NOs: 451-473.

7. A compound or construct that comprises or essentially consists of an immunoglobulin single variable domain according to claim 1, and which further comprises one or more other groups, residues, moieties or binding units, optionally linked via one or more peptidic linkers.

8. The compound or construct according to claim 7, in which said one or more other groups, residues, moieties or binding units provide the polypeptide with increased half-life, compared to the corresponding immunoglobulin single variable domain without the one or more other groups, residues, moieties or binding units.

9. The compound or construct according to claim 8, in which said one or more other groups, residues, moieties or binding units that provide the immunoglobulin single variable domain or polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

10. The compound or construct according to claim 9, wherein said compound or construct is chosen from the group consisting of compounds or constructs with SEQ ID NOs: 461-473 or compounds or constructs that have a sequence identity of more than 85% with SEQ ID NOs: 461-473.

11. The immunoglobulin single variable domain according to claim 1, in which:
  i) CDR1 consists of the amino acid sequence of any one of SEQ ID NOs: 181-210 or an amino acid sequence having 2 or 1 amino acid(s) substitution with the amino acid sequence of SEQ ID NO: 182; wherein
    at position 6 the R has been changed into V; and/or
    at position 9 the A has been changed into V; and
  ii) CDR2 consists of the amino acid sequence of any one of SEQ ID NOs: 268-289 and SEQ ID NOs: 541-555 or an amino acid sequence having 2 or 1 amino acid(s) substitution with the amino acid sequence of SEQ ID NO: 269; wherein
    at position 2 the I has been changed into L;
    at position 4 the M has been changed into S, A or Q; and/or
    at position 8 the I has been changed into T; and
  iii) CDR3 consists of the amino acid sequence of any one of SEQ ID NOs: 393-415 or an amino acid sequence having 2 or 1 amino acid(s) substitution with the amino acid sequence of SEQ ID NO: 397; wherein
    at position 3 the E has been changed into T or I;
    at position 4 the G has been changed into E; and/or
    at position 5 the F has been changed into A.

* * * * *